US009988424B2

(12) United States Patent
Haynes et al.

(10) Patent No.: US 9,988,424 B2
(45) Date of Patent: Jun. 5, 2018

(54) IMMUNOGENS COMPRISING HUMAN IMMUNODEFICIENCY VIRUS V1/V2 POLYPEPTIDES

(71) Applicants: DUKE UNIVERSITY, Durham, NC (US); THE UNITED STATES OF AMERICA, AS REPRESENTED BY THE SECRETARY OF THE ARMY, Washington, DC (US); NEW YORK UNIVERSITY, New York, NY (US)

(72) Inventors: Barton F. Haynes, Durham, NC (US); Huaxin Liao, Durham, NC (US); Jerome Kim, Fort Detrick, MD (US); Nelson Michael, Fort Detrick, MD (US); Susan B. Zolla-Pazner, New York, NY (US)

(73) Assignees: DUKE UNIVERSITY, Durham, NC (US); U.S. ARMY MEDICAL RESEARCH AND MATERIEL COMMAND, Fort Detrick, MD (US); NEW YORK UNIVERSITY, New York, NY (US)

( * ) Notice: Subject to any disclaimer, the term of this patent is extended or adjusted under 35 U.S.C. 154(b) by 222 days.

(21) Appl. No.: 14/363,131

(22) PCT Filed: Dec. 5, 2012

(86) PCT No.: PCT/US2012/000570
§ 371 (c)(1),
(2) Date: Jun. 5, 2014

(87) PCT Pub. No.: WO2013/085550
PCT Pub. Date: Jun. 13, 2013

(65) Prior Publication Data
US 2014/0335126 A1    Nov. 13, 2014

Related U.S. Application Data

(60) Provisional application No. 61/566,884, filed on Dec. 5, 2011, provisional application No. 61/580,475, filed on Dec. 27, 2011, provisional application No. 61/613,222, filed on Mar. 20, 2012.

(51) Int. Cl.
| | |
|---|---|
| *C07K 14/16* | (2006.01) |
| *C07K 14/005* | (2006.01) |
| *C07K 16/10* | (2006.01) |
| *A61K 39/21* | (2006.01) |
| *A61K 39/12* | (2006.01) |

(52) U.S. Cl.
CPC ............ *C07K 14/005* (2013.01); *A61K 39/12* (2013.01); *A61K 39/21* (2013.01); *C07K 14/162* (2013.01); *C07K 16/1063* (2013.01); *C07K 2317/34* (2013.01); *C07K 2317/55* (2013.01); *C07K 2317/76* (2013.01); *C07K 2317/92* (2013.01); *C12N 2710/24043* (2013.01); *C12N 2740/16034* (2013.01); *C12N 2740/16122* (2013.01); *C12N 2740/16134* (2013.01)

(58) Field of Classification Search
CPC ................. C07K 14/162; A61K 39/21; C12N 2740/16134; C12N 2740/16122
See application file for complete search history.

(56) References Cited

U.S. PATENT DOCUMENTS

| | | |
|---|---|---|
| 5,855,866 A | 1/1999 | Thorpe et al. |
| 5,877,289 A | 3/1999 | Thorpe et al. |
| 5,965,132 A | 10/1999 | Thorpe et al. |
| 6,004,555 A | 12/1999 | Thorpe et al. |
| 6,093,399 A | 7/2000 | Thorpe et al. |
| 6,261,535 B1 | 7/2001 | Thorpe et al. |
| 6,815,201 B2 | 11/2004 | Pinter |
| 7,078,491 B1 | 7/2006 | Harrington |
| 7,417,125 B2 | 8/2008 | Goddard et al. |
| 2003/0105282 A1 | 6/2003 | Pinter |
| 2011/0044994 A1 | 2/2011 | Chan-Hui et al. |
| 2014/0248311 A1 | 9/2014 | Kim et al. |
| 2014/0341949 A1 | 11/2014 | Haynes et al. |

FOREIGN PATENT DOCUMENTS

| | | |
|---|---|---|
| WO | 1998/045331 | 10/1998 |
| WO | 2010107939 | 9/2010 |
| WO | WO 2010-107939 | 9/2010 |
| WO | 2011/106100 | 9/2011 |
| WO | 2013/039792 | 3/2013 |

OTHER PUBLICATIONS

Vaccari, M., et al., 2010, Phase III HIV vaccine trial in Thailand: a step toward a protective vaccine for HIV, Expert Rev. Vaccines 9(9):997-1005.*
International Search Report for PCT/US2012/000570, dated Jun. 25, 2013, Choi, Sung Hee.
Written Opinion of the International Searching Authority for PCT/US2012/000570, dated Jun. 25, 2013, Choi, Sung Hee, 8 pages.
NCBI GenBank Accession No. AAA80332, (Nov. 1, 1995).
Bonsignori, M. et al., "Analysis of a clonal lineage of HIV-1 envelope V2/V3 conformational epitope-specific broadly neutralizing antibodies and their inferred unmutated common ancestors", Journal of Virology, vol. 85, No. 19, (Jul. 27, 2011), (E-pub), pp. 9998-10009.
Ferrari, G. et al., "An HIV-1 gp120 envelope human monoclonal antibody that recognizes a C1 conformational epitope mediates potent antibody-dependent cellular cytotoxicity (ADCC) activity and defines a common ADCC epitope in human HIV-1 serum", Journal of Virology, vol. 85, No. 14, (May 4, 011), pp. 7029-7036.
McLellan, J.S. et al., "V1/V2-directed antibodies elicited in RV144 vaccinees bind to a structurally polymorphic site", Retrovirology, vol. 9, Suppl. 2, (Sep. 13, 2012), p. 107.
International Preliminary Report on Patentability dated Jun. 10, 2014, issued in connection with PCT/US2012/000570.

(Continued)

*Primary Examiner* — Jeffrey Parkin
(74) *Attorney, Agent, or Firm* — Baker Donelson

(57) ABSTRACT

The invention is generally directed to V1V2 immunogens.

20 Claims, 173 Drawing Sheets

(56) References Cited

OTHER PUBLICATIONS

Adachi et al, "Production of acquired immunodeficiency syndrome-associated retrovirus in human and nonhuman cells transfected with an infectious molecular clone," J. Virol. 59(2):284-291 (1986).

Adams et al, "PHENIX: building new software for automated crystallographic structure determination" Acta Crystallogr D Biol Crystallogr. Nov. 2002;58(Pt 11):1948-54. Epub Oct. 21, 2002.

Alam et al, "Differential reactivity of germ line allelic variants of a broadly neutralizing HIV-1 antibody to a gp41 fusion intermediate conformation," J Virol. Nov. 2011;85(22):11725-31. doi: 10.1128/JVI.05680-11. Epub Sep. 14, 2011.

Alam et al, "The role of antibody polyspecificity and lipid reactivity in binding of broadly neutralizing anti-HIV-1 envelope human monoclonal antibodies 2F5 and 4E10 to glycoprotein 41 membrane proximal envelope epitopes," J. Immunol. 178(7):4424-35 (2007).

Alam et al, "Role of HIV membrane in neutralization by two broadly neutralizing antibodies," Proc Natl Acad Sci U S A. Dec. 1, 2009;106(48):20234-9. doi: 10.1073/pnas.0908713106. Epub Nov. 11, 2009.

Alam et al, "Human immunodeficiency virus type 1 gp41 antibodies that mask membrane proximal region epitopes: antibody binding kinetics, induction, and potential for regulation in acute infection," J Virol. Jan. 2008;82(1):115-25. Epub Oct. 17, 2007.

Barefoot et al. "Comparison of multiple vaccine vectors in a single heterologous prime-boost trial," Vaccine. Nov. 11, 2008;26(48):6108-18. doi: 10.1016/j.vaccine.2008.09.007. Epub Sep. 20, 2008.

Barouch et al, "Mosaic HIV-1 vaccines expand the breadth and depth of cellular immune responses in rhesus monkeys," Nat Med. Mar. 2010;16(3):319-23. doi: 10.1038/nm.2089. Epub Feb. 21, 2010.

Zolla-Pazner and Cardozo, "Structure-function relationships of HIV-1 envelope sequence-variable regions refocus vaccine design," Nat Rev Immunol. Jul. 2010;10(7):527-35. doi: 10.1038/nri2801.

Yu et al, "Recombinant *Mycobacterium bovis* bacillus Calmette-Guerin elicits human immunodeficiency virus type 1 envelope-specific T lymphocytes at mucosal sites," Clin Vaccine Immunol. Jul. 2007;14(7):886-93. Epub May 16, 2007.
Bonsignori et al, "Analysis of a clonal lineage of HIV-1 envelope V2/V3 conformational epitope-specific broadly neutralizing antibodies and their inferred unmutated common ancestors," J Virol. Oct. 2011;85(19):9998-10009. doi: 10.1128/JVI.05045-11. Epub Jul. 2, 2011.
Bonsignori et al, "HIV-1 envelope induces memory B cell responses that correlate with plasma antibody levels after envelope gp120 protein vaccination or HIV-1 infection," J Immunol. Aug. 15, 2009;183(4):2708-17. doi: 10.4049/immunol.0901068. Epub Jul. 22, 2009.
Burrer et al, "Neutralizing as well as non-neutralizing polyclonal immunoglobulin (lg)G from infected patients capture HIV-1 via antibodies directed against the principal immunodominant domain of gp41," Virology 333:102-113 (2005).
Changela et al, "Crystal structure of human antibody 2909 reveals conserved features of quaternary structure-specific antibodies that potently neutralize HIV-1," J Virol. Mar. 2011;85(6):2524-35. doi: 10.1128/JVI.02335-10. Epub Dec. 29, 2010.
Chohan et al, "Selection for human immunodeficiency virus type 1 envelope glycosylation variants with shorter V1-V2 loop sequences occurs during transmission of certain genetic subtypes and may impact viral RNA levels," J. Virol. 79(10):6528-31 (2005).
Dal Porto et al, "Very low affinity B cells form germinal centers, become memory B cells, and participate in secondary immune responses when higher affinity competition is reduced," J Exp Med. May 6, 2002;195(9):1215-21.
DeVico et al, "Antibodies to CD4-induced sites in HIV gp120 correlate with the control of SHIV challenge in macaques vaccinated with subunit immunogens," Proc. Nal Acad. Sci. USA 104:17477-82 (2007).
Doria-Rose et al, "A short segment of the HIV-1 gp120 V1/V2 region is a major determinant of resistance to V1/V2 neutralizing antibodies," J Virol. Aug. 2012;86(15):8319-23. doi: 10.1128/JVI.00696-12. Epub May 23, 2012.
Droit et al, "rMAT—an R/Bioconductor package for analyzing ChIP-chip experiments," Bioinformatics. Mar. 1, 2010;26(5):678-9. doi: 10.1093/bioinformatics/btq023. Epub Jan. 19, 2010.
Yu et al, "Generation of mucosal anti-human immunodeficiency virus type 1 T-cell responses by recombinant *Mycobacterium smegmatis*," Clin Vaccine Immunol. Nov. 2006;13(11):1204-11. Epub Aug. 30, 2006.
Wei et al, "Emergence of resistant human immunodeficiency virus type 1 in patients receiving fusion inhibitor (T-20) monotherapy," Antimicrob. Agents Chemother. 46(6):1896-905 (2002).
Edmonds et al., "Replication competent molecular clones of HIV-1 expressing Renilla luciferase facilitate the analysis of antibody inhibition in PBMC," Virology. Dec. 5, 2010;408(1):1-13. doi: 10.1016/j.virol.2010.08.028. Epub Sep. 21, 2010.
Emsley & Cowtan, "Coot: model-building tools for molecular graphic," Acta Crystallogr D Biol Crystallogr. Dec. 2004;60(Pt 12 Pt 1):2126-32. Epub Nov. 26, 2004.
Esparza et al. Coordinating Committee of the Global HIV/AIDS Vaccine Enterprise, "The Global HIV/AIDS Vaccine Enterprise: Scientific Strategic Plan" PLoS Med. Feb. 2005; 2(2): e25. Published online Jan. 18, 2005. doi: 10.1371/journal.pmed.0020025.
Ferrari et al, "An HIV-1 gp120 envelope human monoclonal antibody that recognizes a C1 conformational epitope mediates potent antibody-dependent cellular cytotoxicity (ADCC) activity and defines a common ADCC epitope in human HIV-1 serum," J Virol. Jul. 2011;85(14):7029-36. doi: 10.1128/JVI.00171-11. Epub May 4, 2011.
Finney, "Bioassay and the practice of statistical inference," International Statistical Review/Revue Internationale de Statistique 47:1-12 (1979).
Folks et al, "Characterization of a continuous T-cell line susceptible to the cytopathic effects of the acquired immunodeficiency syndrome (AIDS)-associated retrovirus," Proc. Natl. Acad. Sci. USA 82(13):4539-43 (1985).
Flynn et al., "Immunization with HIV Gag targeted to dendritic cells followed by recombinant New York vaccinia virus induces robust T-cell immunity in nonhuman primates," Proc Natl Acad Sci U S A. Apr. 26, 2011;108(17):7131-6. doi: 10.1073/pnas.1103869108. Epub Apr. 5, 2011.
Gilbert et al, "Correlation between immunologic responses to a recombinant glycoprotein 120 vaccine and incidence of HIV-1 infection in a phase 3 HIV-1 preventive vaccine trial," J Infect Dis. Mar. 1, 2005;191(5):666-77. Epub Jan. 27, 2005.
Gilbert et al, "Commentary on "Principal Stratification—a Goal or a Tool?" by Judea Pearl," Int J Biostat. Jan. 1, 2011; 7(1): 36. Published online Sep. 20, 2011. doi: 10.2202/1557-4679.1341.
Gorny et al, "Human anti-V2 monoclonal antibody that neutralizes primary but not laboratory isolates of human immunodeficiency virus type 1," J. Virol. 68(12):8312-8320 (1994).
Gorny et al., "Identification of a new quaternary neutralizing epitope on human immunodeficiency virus type 1 virus particles." J Virol. Apr. 2005;79(8):5232-7.
Gorny et al., "Functional and immunochemical cross-reactivity of V2-specific monoclonal antibodies from HIV-1-infected individuals," Virology. Jun. 5, 2012;427(2):198-207. doi: 10.1016/j.virol.2012.02.003. Epub Mar. 7, 2012.
Haynes et al, "B-cell-lineage immunogen design in vaccine development with HIV-1 as a case study," Nat Biotechnol. May 7, 2012;30(5):423-33. doi: 10.1038/nbt.2197.
Holm, Scandinavian Journal of Statistics 6(2):65-70 (1979).
Horton et al, "Optimization and validation of an 8-color intracellular cytokine staining (ICS) assay to quantify antigen-specific T cells induced by vaccination," J. Immunol. Methods 323(1):39-54 (2007).
Huang et al, "Simultaneous Evaluation of the Magnitude and Breadth of a Left and Right Censored Multivariate Response, with Application to HIV Vaccine Development," Development Stat. Biopyharm. Res. 1(1):81-91 (2009).

(56) References Cited

OTHER PUBLICATIONS

Yates et al, "Multiple HIV-1-specific IgG3 responses decline during acute HIV-1: implications for detection of incident HIV infection," AIDS. Nov. 13, 2011;25(17):2089-97. doi: 10.1097/QAD. 0b013e32834b348e.
Kasturi et al, "Programming the magnitude and persistence of antibody responses with innate immunity," Nature. Feb. 24, 2011;470(7335):543-7. doi: 10.1038/nature09737.
Keele et al, "Identification and characterization of transmitted and early founder virus envelopes in primary HIV-1 infection," Proc. Natl Acad Sci U S A. May 27, 2008;105(21):7552-7. doi: 10.1073/pnas.0802203105. Epub May 19, 2008.
Langer et al, "Automated macromolecular model building for X-ray crystallography using ARP/wARP version 7," Nat Protoc 3(7):1171-1179 (2008).
Leaman et al, "In-solution virus capture assay helps deconstruct heterogeneous antibody recognition of human immunodeficiency virus type 1," J Virol. Apr. 2010;84(7):3382-95. doi: 10.1128/JVI. 02363-09. Epub Jan. 20, 2010.
Leaver-Fay et al, "ROSETTA3: an object-oriented software suite for the simulation and design of macromolecules," Methods Enzymol 487:545-574 (2011).
Li et al, "Human immunodeficiency virus type 1 env clones from acute and early subtype B infections for standardized assessments of vaccine-elicited neutralizing antibodies," J. Virol. 79(16):10108-25 (2005).
Liao et al, "Initial antibodies binding to HIV-1 gp41 in acutely infected subjects are polyreactive and highly mutated," J Exp Med. Oct. 24, 2011;208(11):2237-49. doi: 10.1084/jem.20110363. Epub Oct. 10, 2011.
Liao et al, "High-throughput isolation of immunoglobulin genes from single human B cells and expression as monoclonal antibodies," J Virol Methods. Jun. 2009;158(1-2):171-9. doi: 10.1016/j. jviromet.2009.02.014. Epub Feb. 21, 2009.
Liao et al, "A group M consensus envelope glycoprotein induces antibodies that neutralize subsets of subtype B and C HIV-1 primary viruses," Virology 353(2):268-82 (2006).
Yagita et al, "A novel natural killer cell line (KHYG-1) from a patient with aggressive natural killer cell leukemia carrying a p53 point mutation," Leukemia 14(5):922-30 (2000).
Ma et al, "Envelope deglycosylation enhances antigenicity of HIV-1 gp41 epitopes for both broad neutralizing antibodies and their unmutated ancestor antibodies," PLoS Pathog. Sep. 2011;7(9):e1002200. doi: 10.1371/journal.ppat.1002200. Epub Sep. 1, 2011.
McLinden et al., "Detection of HIV-1 neutralizing antibodies in a human CD4?/CXCR4?/CCR5? T-lymphoblastoid cell assay system," PLoS One. Nov. 28, 2013;8(11):e77756. doi: 10.1371/journal. pone.0077756. eCollection 2013.
Xiao et al, "Maturation Pathways of Cross-Reactive HIV-1 Neutralizing Antibodies," Viruses. Dec. 2009;1(3):802-17. doi: 10.3390/v1030802. Epub Nov. 6, 2009.
Montefiori, J. et al., "Magnitude and breadth of the neutralizing antibody response in the RV144 and Vax003 HIV-1 vaccine efficacy trials," J Infect Dis. Aug. 1, 2012;206(3):431-41. doi: 10.1093/infdis/jis367. Epub May 25, 2012.
Nawaz et al, "The genotype of early-transmitting HIV gp120s promotes a (4) ß(7)-reactivity, revealing a (4) ß(7) +/CD4 + T cells as key targets in mucosal transmission," PLoS Pathog. Feb. 2011;7(2):e1001301. doi: 10.1371/journal.ppat.1001301. Epub Feb. 24, 2011.
O'Doherty et al., "Human immunodeficiency virus type 1 spinoculation enhances infection through virus binding," J. Virol. 74(21):10074-80 (2000).
Wu et al, "Focused evolution of HIV-1 neutralizing antibodies revealed by structures and deep sequencing," Science. Sep. 16, 2011;333(6049):1593-602. doi: 10.1126/science.1207532. Epub Aug. 11, 2011.

Pitisuttithum et al, "Phase I/II study of a candidate vaccine designed against the B and E subtypes of HIV-1," J Acquir Immune Defic Syndr. Sep. 1, 2004;37(1):1160-5.
Platt et al, "Effects of CCR5 and CD4 cell surface concentrations on infections by macrophagetropic isolates of human immunodeficiency virus type 1," J. Virol. 72(4):2855-64 (1998).
Plotkin & Gilbert, "Nomenclature for immune correlates of protection after vaccination," Clin Infect Dis. Jun. 2012;54(11):1615-7. doi: 10.1093/cid/cis238. Epub Mar. 20, 2012.
Plotkin, "Vaccines: correlates of vaccine-induced immunity," Clin Infect Dis. Aug. 1, 2008;47(3):401-9. doi: 10.1086/589862.
Plotkin, "Correlates of protection induced by vaccination," Clin Vaccine Immunol. Jul. 2010;17(7):1055-65. doi: 10.1128/CVI. 00131-10. Epub May 12, 2010.
Pollara et al, "High-throughput quantitative analysis of HIV-1 and SIV-specific ADCC-mediating antibody responses," Cytometry A. Aug. 2011;79(8):603-12. doi: 10.1002/cyto.a.21084. Epub Jul. 6, 2011.
Qin et al, "A framework for assessing immunological correlates of protection in vaccine trials," J. Infect. Dis. J Infect Dis. Nov. 1, 2007;196(9):1304-12. Epub Oct. 2, 2007.
Quan et al, "Human amniotic IgA inhibits natural IgG autoantibodies of maternal or unrelated origin." Eur. J. Immunol. 28(12):4001-9 (1998).
Rubin, Donald B. 1996. "Multiple Imputation after 18 Years." Journal of the American Statistical Association 91(434):473-89.
Schwickert et al, "A dynamic T cell-limited checkpoint regulates affinity-dependent B cell entry into the germinal center," J Exp Med. Jun. 6, 2011;208(6):1243-52. doi: 10.1084/jem.20102477. Epub May 16, 2011.
Rerks-Ngarm et al, "Vaccination with ALVAC and AIDSVAX to prevent HIV-1 infection in Thailand," N Engl J Med. Dec. 3, 2009;361(23):2209-20. doi: 10.1056/NEJMoa0908492. Epub Oct. 20, 2009.
Ritz and Streibig, "Bioassay Analysis using R," Journal of Statistical Software 12:1-22 (2005).
Rolland et al., "Genetic impact of vaccination on breakthrough HIV-1 sequences from the STEP trial," Nat Med. Mar. 2011;17(3):366-71. doi: 10.1038/nm.2316. Epub Feb. 2, 2011.
Rolland et al, "Increased HIV-1 vaccine efficacy against viruses with genetic signatures in Env V2," Nature. Oct. 18, 2012;490(7420):417-20. doi: 10.1038/nature11519. Epub Sep. 10, 2012.
Rothman, "No adjustments are needed for multiple comparisons," Epidemiology 1(1):43-6 (1990).
Santra et al, "Mosaic vaccines elicit CD8+ T lymphocyte responses that confer enhanced immune coverage of diverse HIV strains in monkeys," Nat Med. Mar. 2010;16(3):324-8. doi: 10.1038/nm. 2108. Epub Feb. 21, 2010.
Seaman et al, "Tiered categorization of a diverse panel of HIV-1 Env pseudoviruses for assessment of neutralizing antibodies," J Virol. Feb. 2010;84(3):1439-52. doi: 10.1128/JVI.02108-09. Epub Nov. 25, 2009.
Tomaras et al, "Initial B-cell responses to transmitted human immunodeficiency virus type 1: virion-binding immunoglobulin M (IgM) and IgG antibodies followed by plasma anti-gp41 antibodies with ineffective control of initial viremia," J Virol. Dec. 2008;82(24):12449-63. doi: 10.1128/JVI.01708-08. Epub Oct. 8, 2008.
Torrieri-Dramard et al., "Intranasal DNA vaccination induces potent mucosal and systemic immune responses and cross-protective immunity against influenza viruses," Mol Ther. Mar. 2011;19(3):602-11. doi: 10.1038/mt.2010.222. Epub Oct. 19, 2010.
Trkola et al, "A cell line-based neutralization assay for primary human immunodeficiency virus type 1 isolates that use either the CCR5 or the CXCR4 coreceptor" J. Virol. 73(11):8966-8974 (1999).
Volpe et al, "SoDA: implementation of a 3D alignment algorithm for inference of antigen receptor recombinations," Bioinformatics. Feb. 15, 2006;22(4):438-44. Epub Dec. 15, 2005.
GenBank Accession No. AF2699954.
EPO Supplemental Search Report and opinion dated Jul. 3, 2015.

(56) References Cited

OTHER PUBLICATIONS

Granados-Gonzalez Viviana et al: "[Role of the HIV-1 gp120 V1IV2 domains in the induction of neutralizing antibodies].", Enfermedades Infecciosas Y Microbiologfa Clinica Nov. 2009, vol. 27, No. 9, Nov. 2009 (Nov. 2009), pp. 523-530.

Haynes et al., "Immune-correlates analysis of an HIV-1 vaccine efficacy trial," N Engl J Med. Apr. 5, 2012;366(14):1275-86. doi: 10.1056/NEJMoa1113425.

Karasavvas et al., "The Thai Phase III HIV Type 1 Vaccine trial (RV144) regimen induces antibodies that target conserved regions within the V2 loop of gp120," AIDS Res Hum Retroviruses. Nov. 2012;28(11):1444-57. doi: 10.1089/aid.2012.0103. Epub Oct. 4, 2012.

McLellan et al., "Structure of HIV-1 gp120 V1/V2 domain with broadly neutralizing antibody PG9," Nature. Nov. 23, 2011;480(7377):336-43. doi: 10.1038/nature10696.

Pinter et al., "Potent neutralization of primary HIV-1 isolates by antibodies directed against epitopes present in the V1/V2 domain of HIV-1 gp120," Vaccine. Nov. 1998;16(19):1803-11.

Pinter et al., "The C108g epitope in the V2 domain of gp120 functions as a potent neutralization target when introduced into envelope proteins derived from human immunodeficiency virus type 1 primary isolates," J Virol. Jun. 2005;79(11):6909-17.

Walker et al., "Broad and potent neutralizing antibodies from an African donor reveal a new HIV-1 vaccine target," Science. Oct. 9, 2009;326(5950):285-9. doi: 10.1126/science.1178746. Epub Sep. 3, 2009.

Zolla-Pazner et al., "Vaccine-induced IgG antibodies to V1V2 regions of multiple HIV-1 subtypes correlate with decreased risk of HIV-1 infection," PLoS One. Feb. 4, 2014;9(2):e87572. doi: 10.1371/journal.pone.0087572.eCollection 2014.

European Examination Report dated Feb. 7, 2017.

Arthos et al, "HIV-1 envelope protein binds to and signals through integrin alpha4beta7, the gut mucosal homing receptor for peripheral T cells," Nat Immunol. Mar. 2008;9(3):301-9. doi: 10.1038/ni1566. Epub Feb. 10, 2008.

Benjamini and Hochberg. "Controlling the false discovery rate: a practical and powerful approach to multiple testing." Journal of the royal statistical society. Series B (Methodological) (1995): 289-300.

Bonsignori et al, "Antibody-dependent cellular cytotoxicity-mediating antibodies from an HIV-1 vaccine efficacy trial target multiple epitopes and preferentially use the VH1 gene family," J Virol. Nov. 2012;86(21):11521-32. doi: 10.1128/JVI.01023-12. Epub Aug. 15, 2012.

Borgan et al, "Exposure stratified case-cohort designs," Lifetime Data Anal. 6(1):39-58 (2000).

Breslow et al, "Maximum Likelihood Estimation of Logistic Regression Parameters under Two-phase, Outcome-dependent Sampling," Journal of the Royal Statistical Society Series B, Statistical Methodology 59(2):447-61 (1997).

Durbin et al. Biological sequence analysis: probabilistic models of proteins and nucleic acids. Cambridge university press, 1998.

Edlefsen et al, AIDS Vaccine 2011, Abstract No. S07.04:47 Bangkok, Thailand, Sep. 12-14, 2011.

Karlsson et al, "The challenges of eliciting neutralizing antibodies to HIV-1 and to influenza virus," Nat Rev Microbial 6(2):143-155 (2008).

Klausner et al, "Medicine. The need for a global HIV vaccine enterprise," Science. Jun. 27, 2003;300(5628):2036-39.

Liu et al. "Dynamic antibody specificities and virion concentrations in circulating immune complexes in acute to chronic HIV-1 infection." Journal of virology 85.21 (2011): 11196-11207.

Ngo et al, "Identification and testing of control peptides for antigen microarrays," J Immunol Methods. Apr. 15, 2009;343(2):68-78. doi: 10.1016/j.jim2008.12.004. Epub Jan. 20, 2009.

Otwinowski & Minor, Processing of X-ray diffraction data collected in oscillation mode, Methods Enzymol 276:307-326 (1997).

Pancera et al, "Crystal structure of PG16 and chimeric dissection with somatically related PG9: structure-function analysis of two quaternary-specific antibodies that effectively neutralize HIV-1," J Virol. Aug. 2010;84(16):8098-110. doi 10.1128/JVI.00966-10. Epub Jun. 10, 2010.

Safsten et al, "Screening antibody-antigen interactions in parallel using Biacore A100," Anal Biochem. Jun. 15, 2006;353(2):181-90. Epub Feb. 14, 2006.

Sandberg et al, "New chemical descriptors relevant for the design of biologically active peptides. A multivariate characterization of 87 amino acids," J. Med. Chem. 41(14):2481-91 (1998).

Shih et al, "Role of BCR affinity in T cell dependent antibody responses in vivo," Nat Immunol. Jun. 2002;3(6):570-5. Epub May 20, 2002.

Zolla-Pazner et al, AIDS Research and Human Retroviruses, Abstract No. 27:A21 (2011).

* cited by examiner

>A244_V1V2
METDTLLIWVLLLWVPGSTGDQVKLTPPCVTLHCTNANLTKANLTNVNNRTNVSNII
GNITDEVRNCSFNMTTELRDKKQKVHALFYKLDIVPIEDNNDSSEYRLINCNTSVIK
QP

AE.A244 V1V2_Tags_N156QN160Q

>A244_V1V2_Tags_N156QN160Q
METDTLLLWVLLLWVPGSTGDQVKLTPPCVTLHCTNANLTKANLTNVNNRTNVSNII
GNITDEVRQCSFQMTTELRDKKQKVHALFYKLDIVPIEDNNDSSEYRLINCNTSVIK
QPGLNDIFEAQKIEWHELEVLFQGPGHHHHHH AE.A244 V1V2_Tags_deltaN7D >A244_V1V2_Tags-deltaN7D
METDTLLLWVLLLWVPGSTGDQVKLTPPCVTLHCTNADLTKADLTNVNDRTDVSNII
GDITDEVRNCSFNMTTELRDKKQKVHALFYKLDIVPIEDNDDSSEYRLINCDTSVIK
QPGLNDIFEAQKIEWHELEVLFQGPGHHHHHH

AE.A244 V1V2_deltaN7D

>A244_V1V2_Tags-deltaN7D
METDTL

Fig. 6

Alignment of V1V2 Loops of Different HIV-1 Envs

```
A.9004SS_V1V2      VKLTPLCVTL NCSQYVSSHV NNHN.NSSHN VSSHSGNITS ..DMKICSFN TTTEVRDKKQ
A.Q23_V1V2         ---------- H-TNV..... .T-VNT TGDRE-.... ...L-N---- M---L---R-
AE.92Th023_V1V2    ---------- --TNANVTN. ....VKNIT- -PNII----D ...EVRN--- M---L-----
AE.A244_V1V2       ------P--- H-TNANLTKA -LT-V-NRT- --NII----D ..EVRN---- M---L-----
B.63521_V1V2       ---------- --TDVTNAT. ...I-ATNI NN-SG-..VE SGEI-N---- I---S----V-
B.CaseA_V1V2       ---------- --IDLRNATN ATS-S-TTNT T--SG-LMME QGEI-N---- I--SI----V-
B.HXB2_V1V2        --------S- K-TDLK.... ......-DTNT N--SGRM-ME KGEI-N---- IS-SI-G-V-
B.MN_V1V2          ---------- --TDLRNTT. ....NTN--TD- NN-K-EGTIK GGE--N---- I--SIG---M-
C.1086C_V1V2       ---------- --TNVK.... ......GNESD T-EV...... ...-N---K A---LK---H
D.9009SA_V1V2      ---------- --TT...... ....-TNF AN-TGKD--- ..E-QD---- I---I---QK A.9004SS_V1V2      KVYSLFYKLD VVPISNDS.. ....SQYRLI NCNTSAITQA
A.Q23_V1V2         ------R--- I---NENQG- -----E---- ----------
AE.92Th023_V1V2    --HA------ I---EDNTS- S-----E--- -----V-K--
AE.A244_V1V2       --HA------ I---EDNND- S-----E--- -----V-K-P
B.63521_V1V2       -E-A------ I---T-E--- -----K---- S-----VL--
B.CaseA_V1V2       -E-A------ I---D-PKN- S-----TN-- S-----V---
B.HXB2_V1V2        -E-AF----- II---D--T- -----TS-K-T S-----V---
B.MN_V1V2          -E-A-L---- IE---D---- -----TS--- S---------
C.1086C_V1V2       --HA------ --LNGN-S-- SSG-.E---- ----------
D.9009SA_V1V2      --HA------ I-Q-D-NTEA NANYTS---- ----------
```

HCDR3 Alignment of PG9, CH58 and CH59

```
              10        20
        ....|....|....|....|....
PG9     EAGGPDYRNGYNYYDFYDGYYNYHYMDV
CH58    -LGG----R---Y-YHD-SSGYY---YLDY
CH59    ----------------DSPRGEL---PLNY
```

Variable Region Sequences of CH58, CH59, CH58_RUA and CH59RUA Heavy and Light Chain Genes >CH58_VH.pep
VHEVQLVQSGAEVKKPGESLKISCKGSGYRFTSYWIVWVRQMPGKGLEWMGIIYPGDFDTKYSPSFQGQVTISADKSISTAYLQWSS
LKASDTAMYYCARLGGRYYHDSSGYYYLDYWGQGTLVTVSS >CH58_VL.pep
NFMLTQPHSVSESPGKTVTISCTRSSGSVASDYVQWYQQRPGSAPTTVVYEDNQRPSGVPDRFSGSIDSSSNSASLTISGLKTEDEA
DYYCQSYDNSSWVFGGGTKLTVL >CH59_VH.pep
VHEVQLVESGGGLVQPGRSLRLSCAASGFTFDDGAMHWVRQAPGKGLEWVSGISWNSNIIAYADSVKGRFTISRDNAKNSLYLEMNS
LRVEDTALYYCAKDSPRGELPLNYWGQGTLVTVSS >CH59_VL.pep
SYELTQPPSVSVSPGQTARITCSGDALPKNYAYWYQQKSGQAPVLVIYEDSKRPSGIPERFSGSSSGTMATLTISGAQVEDEADYYC
YSTDSSGNHRVFGGGTKLTVL >CH58VH_RUA.pep
EVQLVQSGAEVKKPGESLKISCKGSGYSFTSYWIGWVRQMPGKGLEWMGIIYPGDSDTRYSPSFQGQVTISADKSISTAYLQWSSLK
ASDTAMYYCARLGGRYYYDSSGYYYFDYWGQGTLVTVSS >CH58VL_RUA.pep
NFMLTQPHSVSESPGKTVTISCTRSSGSIASNYVQWYQQRPGSSPTTVIYEDNQRPSGVPDRFSGSIDSSSNSASLTISGLKTEDEA
DYYCQSYDNSSWVFGGGTKLTVL >CH59VH_RUA.pep
EVQLVESGGGLVQPGRSLRLSCAASGFTFDDYAMHWVRQAPGKGLEWVSGISWNSGSIGYADSVKGRFTISRDNAKNSLYLQMNSLR
AEDTALYYCAKDSPRGELPFDYWGQGTLVTVSS >CH59VL_RUA.pep
SYELTQPPSVSVSPGQTARITCSGDALPKKYAYWYQQKSGQAPVLVIYEDSKRPSGIPERFSGSSSGTMATLTISGAQVEDEADYYC
YSTDSSGNHRVFGGGTKLTVL

Fig. 12

Fig. 13
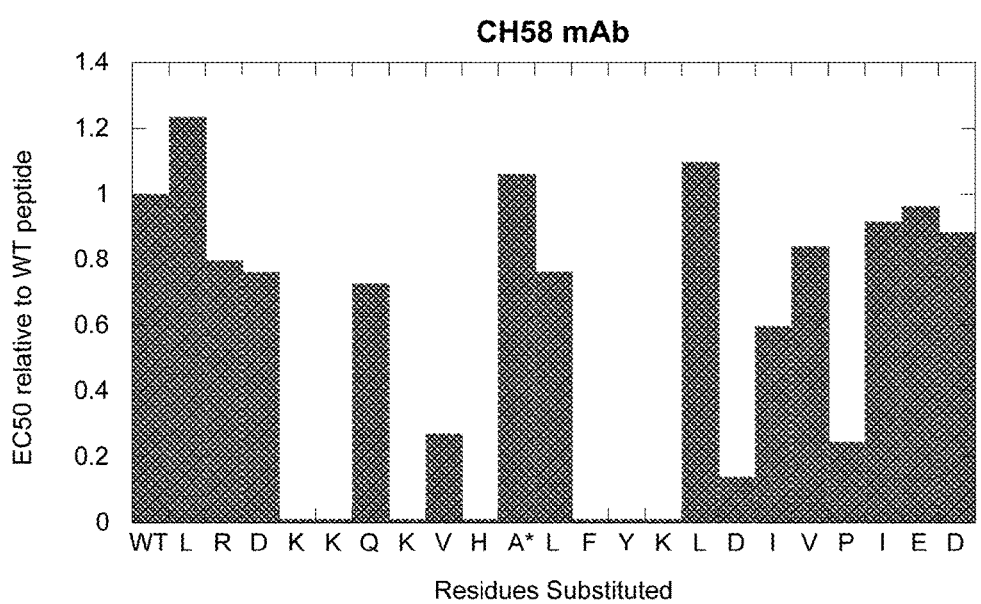
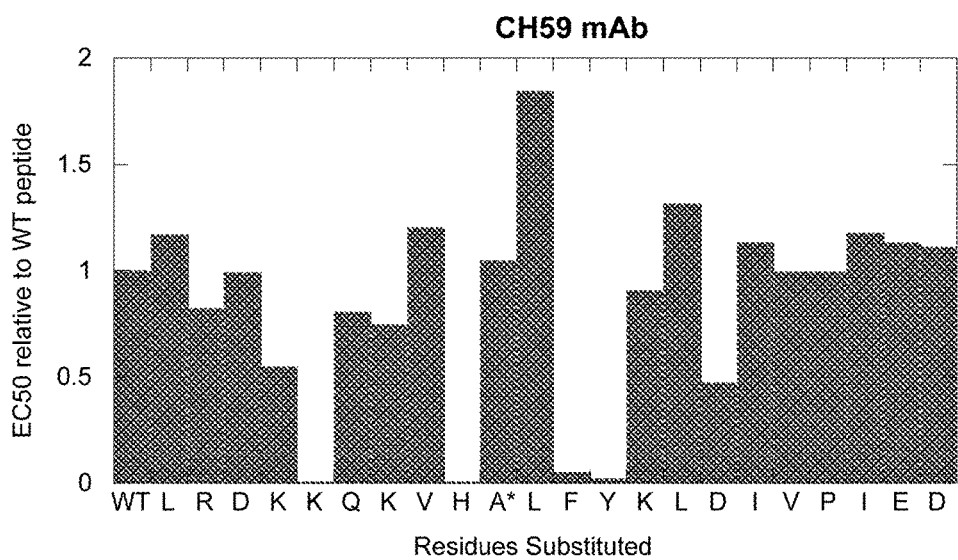

Fig. 14

New RV144 V2 Human MAbs

- CH58: ELRDKKQKVHALFYKLDIVPIED
- CH59: ELRDKKQKVHALFYKLDIVPIED 169 181

Both CH58, CH59 neutralize Tier 1 AE.92TH023 but not Tier 2 AE.CM244

Both medidate ADCC against CM235 infected CD4 T cell targets

Mattia Bonisgnori, Kwan-Ki Hwang, Rob Parks, Guido Ferrari, David Montefiori, Georgia Tomaras Hua-Xin Liao

Reactivity of CH01 and RUA Antibodies To Various HIV-1 Envs (48)

Fig. 17

1. Codon-optimized DNA sequence of HIV-1 Env V1V2_tags design:

>HV1300055 (C.1086C_V1_V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCAACGTGAAGGGCAACGAGTCCGACACCTCCGAGGTGATGA
AGAACTGCTCCTTCAAGGCCACCACCGAGCTGAAGGACAAGAAGCACAAGGTGCACGCCCTGTTCTACAAGCTGGACGTG
GTGCCCCTGAACGGCAACTCCTCCTCCTCCGGCGAGTACCGCCTGATCAACTGCAACACCTCCGCCATCACCCAGGCCTA
Gggatcctctaga
>HV1300056 (A.9004SS_V1_V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCTCCCAGTACGTGTCCTCCACGTGAACAACCACAACAACTCCT
CCCACAACGTGTCCTCCCACTCCGGCAACATCACCTCCGACATGAAGATCTGCTCCTTCAACACCACCACCGAGGTGCGC
GACAAGAAGCAGAAGGTGTACTCCCTGTTCTACAAGCTGGACGTGGTGCCCATCTCCAACGACTCCTCCCAGTACCGCCT
GATCAACTGCAACACCTCCGCCATCACCCAGGCCTAGggatcctctaga
>HV1300057 (B.63521_V1_V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCGACGTGACCAACGCCACCAACATCAACGCCACCAACATCA
ACAACTCCTCCGGCGGCGTGGAGTCCGGCGAGATCAAGAACTGCTCCTTCAACATCACCACCTCCGTGCGCGACAAGGTG
CAGAAGGAGTACGCCCTGTTCTACAAGCTGGACATCGTGCCCATCACCAACGAGTCCTCCAAGTACCGCCTGATCTCCTG
CAACACCTCCGTGCTGACCCAGGCCTAGggatcctctaga
>HV1300058 (D.9009SA_V1_V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCACCAACTCCACCAACTTCGCCAACTCCACCGGCAAGGACA
TCGAGATGCAGGACTGCTCCTTCAACATCACCACCGAGATCCGCGACAAGCAGAAGAAGGTGCACGCCCTGTTCTACAAG
CTGGACATCGTGCAGATCGACAACAACACCGAGGCCAACGCCAACTACACCTCCTACCGCCTGATCAACTGCAACACCTC
CGCCATCACCCAGGCC
>HV1300059 (A.Q23_V1_V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGCACTGCACCAACGTGACCTCCGTGAACACCACCGGCGACCGCGAGGGCC
TGAAGAACTGCTCCTTCAACATGACCACCGAGCTGCGCGACAAGCGCCAGAAGGTGTACTCCCTGTTCTACCGCCTGGAC
ATCGTGCCCATCAACGAGAACCAGGGCTCCGAGTACCGCCTGATCAACTGCAACACCTCCGCCATCACCCAGGCCTAGgg
atcctctaga
>HV1300060 (AE.A244_V1_V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCCTGCGTGACCCTGCACTGCACCAACGCCAACCTGACCAAGGCCAACCTGACCAACGTGAACA
ACCGCACCAACGTGTCCAACATCATCGGCAACATCACCGACGAGGTGCGCAACTGCTCCTTCAACATGACCACCGAGCTG
CGCGACAAGAAGCAGAAGGTGCACGCCCTGTTCTACAAGCTGGACATCGTGCCCATCGAGGACAACAACGACTCCTCCGA
GTACCGCCTGATCAACTGCAACACCTCCGTGATCAAGCAGCCCTAGggatcctctaga
>HV1300061 (B.CaseA_V1_V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCATCGACCTGCGCAACGCCACCAACGCCACCTCCAACTCCAACA
CCACCAACACCACCTCCTCCTCCGGCGGCCTGATGATGGAGCAGGGCGAGATCAAGAACTGCTCCTTCAACATCACCACC
TCCATCCGCGACAAGGTGCAGAAGGAGTACGCCCTGTTCTACAAGCTGGACATCGTGCCCATCGACAACCCCAAGAACTC
CACCAACTACCGCCTGATCTCCTGCAACACCTCCGTGATCACCCAGGCCTAGggatcctctaga
>HV1300062 (B.HXB2_V1-V2)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGCCCTGAAGTGCACCGACCTGAAGAACGACACCAACACCAACTCCTCCTCCGGCC
GCATGATCATGGAGAAGGGCGAGATCAAGAACTGCTCCTTCAACATCTCCACCTCCATCCGCGGCAAGGTGCAGAAGGAG
TACGCCTTCTTCTACAAGCTGGACATCATCCCCATCGACAACGACACCACCTCCTACAAGCTGACCTCCTGCAACACCTC
CGTGATCACCCAGGCCTAGggatcctctaga
>RV144_356272_V1V2.opt
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGGAGTGCACCAACGCCAACCTGAAGGAGGACAACAAGACCACCGACTCCC
CCATCCGCATCGGCAACATCTCCGACGAGGTGCGCAACTGCTCCTTCAACATCACCACCGAGATCAAGGACAAGAAGCAG
CAGGTGCAGGCCCTGTTCTACCGCCTGGACATCGTGCAGATGGGCAACGACTCCCGCTACCGCCTGATCAACTGCAACAC
CTCCGTGATCAAGCAGTAGggatcctctaga
>RV144_427299_V1V2.opt
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAAGTGCACCGCCAACATCACCATCACCAACGCCACCACCCGCACCGAGA
ACACCACCAAGGAGAACCTGATCGGCAACATCACCGACGAGCTGCGCAACTGCTCCTTCAACGTCACCACCGAGCTGCGC
GACCGCCAGCGCAAGGCCTACGCCCTGTTCTACAAGCTGGACATCGTGCCCATCAACAACGAGGCCAACTCCTCCGAGTA
CCGCCTGATCAACTGCAACACCTCCGTGATCAAGCAGTAGggatcctctaga 1 continued. Codon-optimized DNA sequence of HIV-1 Env V1V2_tags design:

>HV1300063 (C.1086C_V1_V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCAACGTGAAGGGCAACGAGTCCGACACCTCCGAGGTGATGA
AGAACTGCTCCTTCAAGGCCACCACCGAGCTGAAGGACAAGAAGCACAAGGTGCACGCCCTGTTCTACAAGCTGGACGTG

Fig. 17 cont'd-1

```
GTGCCCCTGAACGGCAACTCCTCCTCCTCCGGCGAGTACCGCCTGATCAACTGCAACACCTCCGCCATCACCCAGGCCGG
CCTGAACGACATCTTCGAGGCCCAGAAGATCGAGTGGCACGAGCTGGAGGTGCTGTTCCAGGGCCCCGGCCACCATCACC
ATCACCACTAGggatcctctaga
>HV1300064 (A.9004SS_V1_V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCTCCCAGTACGTGTCCTCCCACGTGAACAACCACAACAACTCCT
CCCACAACGTGTCCTCCCACTCCGGCAACATCACCTCCGACATGAAGATCTGCTCCTTCAACACCACCACCGAGGTGCGC
GACAAGAAGCAGAAGGTGTACTCCCTGTTCTACAAGCTGGACGTGGTGCCCATCTCCAACGACTCCTCCCAGTACCGCCT
GATCAACTGCAACACCTCCGCCATCACCCAGGCCGGCCTGAACGACATCTTCGAGGCCCAGAAGATCGAGTGGCACGAGC
TGGAGGTGCTGTTCCAGGGCCCCGGCCACCATCACCATCACCACTAGggatcctctaga
>HV1300065 (B.63521_V1_V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCGACGTGACCAACGCCACCAACATCAACGCCACCAACATCA
ACAACTCCTCCGGCGGCGTGGAGTCCGGCGAGATCAAGAACTGCTCCTTCAACATCACCACCTCCGTGCGCGACAAGGTG
CAGAAGGAGTACGCCCTGTTCTACAAGCTGGACATCGTGCCCATCACCAACGAGTCCTCCAAGTACCGCCTGATCTCCTG
CAACACCTCCGTGCTGACCCAGGCCGGCCTGAACGACATCTTCGAGGCCCAGAAGATCGAGTGGCACGAGCTGGAGGTGC
TGTTCCAGGGCCCCGGCCACCACCATCACCATCACCACTAGggatcctctaga
>HV1300066 (D.9009SA_V1_V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCACCAACTCCACCAACTTCGCCAACTCCACCGGCAAGGACA
TCGAGATGCAGGACTGCTCCTTCAACATCACCACCGAGATCCGCGACAAGCAGAAGAAGGTGCACGCCCTGTTCTACAAG
CTGGACATCGTGCAGATCGACAACAACACCGAGGCAACGCCAACTACACCTCCTACCGCCTGATCAACTGCAACACCTC
CGCCATCACCCAGGCCGGCCTGAACGACATCTTCGAGGCCCAGAAGATCGAGTGGCACGAGCTGGAGGTGCTGTTCCAGG
GCCCCGGCCACCATCACCATCACCACTAGggatcctctaga
>HV1300067 (A.Q23_V1_V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGCACTGCACCAACGTGACCTCCGTGAACACCACCGGCGACCGCGAGGGCC
TGAAGAACTGCTCCTTCAACATGACCACCGAGCTGCGCGACAAGCGCCAGAAGGTGTACCTGTTCTACCGCCTGGAC
ATCGTGCCCATCAACGAGAACCAGGGCTCCGAGTACCGCCTGATCAACTGCAACACCTCCGCCATCACCCAGGCCGGCCT
GAACGACATCTTCGAGGCCCAGAAGATCGAGTGGCACGAGCTGGAGGTGCTGTTCCAGGGCCCCGGCCACCATCACCATC
ACCACTAGggatcctctaga
>HV1300068 (AE.A244_V1_V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCCCTGCGTGACCCTGCACTGCACCAACGCCAACCTGACCAAGGCCAACCTGACCAACGTGAACA
ACCGCACCAACGTGTCCAACATCATCGGCAACATCACCGACGAGGTGCGCAACTGCTCCTTCAACATGACCACCGAGCTG
CGCGACAAGAAGCAGAAGGTGCACGCCCTGTTCTACAAGCTGGACATCGTGCCCATCGAGGACAACAACGACTCCTCCGA
GTACCGCCTGATCAACTGCAACACCTCCGTGATCAAGCAGCCCGGCCTGAACGACATCTTCGAGGCCCAGAAGATCGAGT
GGCACGAGCTGGAGGTGCTGTTCCAGGGCCCCGGCCACCATCACCATCACCACTAGggatcctctaga
>HV1300069 (B.CaseA_V1_V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCATCGACCTGCGCAACGCCACCAACGCCACCTCCAACTCCAACA
CCACCAACACCACCTCCTCCTCCGGCGGCCTGATGATGGAGCAGGGCGAGATCAAGAACTGCTCCTTCAACATCACCACC
TCCATCCGCGACAAGGTGCAGAAGGAGTACGCCCTGTTCTACAAGCTGGACATCGTGCCCATCGACAACCCCAAGAACTC
CACCAACTACCGCCTGATCTCCTGCAACACCTCCGTGATCACCCAGGCCGGCCTGAACGACATCTTCGAGGCCCAGAAGA
TCGAGTGGCACGAGCTGGAGGTGCTGTTCCAGGGCCCCGGCCACCACCATCACCATCACCACTAGggatcctctaga
>HV1300070 (B.HXB2_V1-V2_Tags)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGTCCCTGAAGTGCACCGACCTGAAGAACGACACCAACACCAACTCCTCCTCCGGCC
GCATGATCATGGAGAAGGGCGAGATCAAGAACTGCTCCTTCAACATCTCCATCCGCGGCAAGGTGCAGAAGGAG
TACGCCTTCTTCTACAAGCTGGACATCATCCCCATCGACAACGACACCACCTCCTACAAGCTGACCTCCTGCAACACCTC
CGTGATCACCCAGGCCGGCCTGAACGACATCTTCGAGGCCCAGAAGATCGAGTGGCACGAGCTGGAGGTGCTGTTCCAGG
GCCCCGGCCACCATCACCATCACCACTAGggatcctctaga
>HV1300078 (B.MNV1V2_tags.opt)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCGACCTGCGCAACACCACCAACACCAACAACTCCACCGACA
ACAACAACTCCAAGTCCGAGGGCACCATCAAGGGCGGCGAGATGAAGAACTGCTCCTTCAACATCACCACCTCCATCGGC
GACAAGATGCAGAAGGAGTACGCCCTGCTGTACAAGCTGGACATCGAGCCCATCGACAACGACTCCACCTCCTACCGCCT
GATCTCCTGCAACACCTCCGTGATCACCCAGGCCGGCCTGAACGACATCTTCGAGGCCCAGAAGATCGAGTGGCACGAGC
TGGAGGTGCTGTTCCAGGGCCCCGGCCACCACCACCACCACCACTAGggatcctctaga
>HV1300079 (AE.92TH023V1V2_tags.opt)
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAACTGCACCAACGCCAACGTGACCAACGTGAAGAACATCACCAACGTGC
CCAACATCATCGGCAACATCACCGACGAGGTGCGCAACTGCTCCTTCAACATGACCACCGAGCTGCGCGACAAGAAGCAG
AAGGTGCACGCCCTGTTCTACAAGCTGGACATCGTGCCCATCGAGGACAACACCTCCTCCTCCGAGTACCGCCTGATCAA
CTGCAACACCTCCGTGATCAAGCAGGCCGGCCTGAACGACATCTTCGAGGCCCAGAAGATCGAGTGGCACGAGCTGGAGG
TGCTGTTCCAGGGCCCCGGCCACCACCACCACCACCACTAGggatcctctaga aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGGAGTGCACCAACGCCAACCTGAAGGAGGACAACAAGACCACCGACTCCC
CCATCCGCATCGGCAACATCTCCGACGAGGTGCGCAACTGCTCCTTCAACATCACCACCGAGATCAAGGACAAGAAGCAG
```

Fig. 17 cont'd-2

```
CAGGTGCAGGCCCTGTTCTACCGCCTGGACATCGTGCAGATGGGCAACGACTCCCGCTACCGCCTGATCAACTGCAACAC
CTCCGTGATCAAGCAGGGCCTGAACGACATCTTCGAGGCCCAGAAGATCGAGTGGCACGAGCTGGAGGTGCTGTTCCAGG
GCCCCGGCCACCACCACCACCACCACTAGggatcctctaga
>RV144_427299_V1V2_Tags.opt
aagcttgtcgacaccATGGAGACCGACACCCTGCTGCTGTGGGTGCTGCTGCTGTGGGTGCCCGGCTCCACCGGCGACCA
GGTGAAGCTGACCCCCCTGTGCGTGACCCTGAAGTGCACCGCCAACATCACCATCACCAACGCCACCACCCGCACCGAGA
CACCACCAAGGAGAACCTGATCGGCAACATCACCGACGAGCTGCGCAACTGCTCCTTCAACGTGACCACCGAGCTGCGC
GACCGCCAGCGCAAGGCCTACGCCCTGTTCTACAAGCTGGACATCGTGCCCATCAACAACGAGGCCAACTCCTCCGAGTA
CCGCCTGATCAACTGCAACACCTCCGTGATCAAGCAGGGCCTGAACGACATCTTCGAGGCCCAGAAGATCGAGTGGCACG
AGCTGGAGGTGCTGTTCCAGGGCCCCGGCCACCACCACCACCACCACTAGggatcctctaga
```

Amino acid sequence of HIV-1 Env V1V2 design:

```
>C.1086C_V1_V2
METDTLLLWVLLLWVPGSTGDQVKLTPLCVTLNCTNVKGNESDTSEVMKNCSFKATTELKDKKHKVHALFYKLDVVPLNG
NSSSSGEYRLINCNTSAITQA
>A.9004SS_V1_V2
METDTLLLWVLLLWVPGSTGDQVKLTPLCVTLNCSQYVSSHVNNHNNSSHNVSSHSGNITSDMKICSFNTTTEVRDKKQK
VYSLFYKLDVVPISNDSSQYRLINCNTSAITQA
>B.63521_V1_V2
METDTLLLWVLLLWVPGSTGDQVKLTPLCVTLNCTDVTNATNINATNINNSSGGVESGEIKNCSFNITTSVRDKVQKEYA
LFYKLDIVPITNESSKYRLISCNTSVLTQA
>D.9009SA_V1_V2
METDTLLLWVLLLWVPGSTGDQVKLTPLCVTLNCTTNSTNFANSTGKDIEMQDCSFNITTEIRDKQKKVHALFYKLDIVQ
IDNNTEANANYTSYRLINCNTSAITQA
>A.Q23_V1_V2
METDTLLLWVLLLWVPGSTGDQVKLTPLCVTLHCTNVTSVNTTGDREGLKNCSFNMTTELRDKRQKVYSLFYRLDIVPIN
ENQGSEYRLINCNTSAITQA
>AE.A244_V1_V2
METDTLLLWVLLLWVPGSTGDQVKLTPPCVTLHCTNANLTKANLTNVNNRTNVSNIIGNITDEVRNCSFNMTTELRDKKQ
KVHALFYKLDIVPIEDNNDSSEYRLINCNTSVIKQP
>B.CaseA_V1_V2
METDTLLLWVLLLWVPGSTGDQVKLTPLCVTLNCIDLRNATNATSNSNTTNTTSSSGGLMMEQGEIKNCSFNITTSIRDK
VQKEYALFYKLDIVPIDNPKNSTNYRLISCNTSVITQA
>B.HXB2_V1-V2
METDTLLLWVLLLWVPGSTGDQVKLTPLCVSLKCTDLKNDTNTNSSSGRMIMEKGEIKNCSFNISTSIRGKVQKEYAFFY
KLDIIPIDNDTTSYKLTSCNTSVITQA
>B.MNV1V2
METDTLLLWVLLLWVPGSTGDQVKLTPLCVTLNCTDLRNTTNTNNSTDNNNSKSEGTIKGGEMKNCSFNITTSIGDKMQK
EYALLYKLDIEPIDNDSTSYRLISCNTSVITQA
>AE.92TH023V1V2
METDTLLLWVLLLWVPGSTGDQVKLTPLCVTLNCTNANVTNVKNITNVPNIIGNITDEVRNCSFNMTTELRDKKQKVHAL
FYKLDIVPIEDNTSSSEYRLINCNTSVIKQA
>RV144_356272_V1V2
METDTLLLWVLLLWVPGSTGDQVKLTPLCVTLECTNANLKEDNKTTDSPIRIGNISDEVRNCSFNITTEIKDKKQQVQAL
FYRLDIVQMGNDSRYRLINCNTSVIKQ
>RV144_427299_V1V2
METDTLLLWVLLLWVPGSTGDQVKLTPLCVTLKCTANITITNATTRTENTTKENLIGNITDELRNCSFNVTTELRDRQRK
AYALFYKLDIVPINNEANSSEYRLINCNTSVIKQ
```

Amino acid sequence of HIV-1 Env V1V2_Tags design:

```
>C.1086C_V1_V2_Tags
METDTLLLWVLLLWVPGSTGDQVKLTPLCVTLNCTNVKGNESDTSEVMKNCSFKATTELKDKKHKVHALFYKLDVVPLNG
NSSSSGEYRLINCNTSAITQAGLNDIFEAQKIEWHELEVLFQGPGHHHHHH
> A.9004SS_V1_V2_Tags
METDTLLLWVLLLWVPGSTGDQVKLTPLCVTLNCSQYVSSHVNNHNNSSHNVSSHSGNITSDMKICSFNTTTEVRDKKQK
VYSLFYKLDVVPISNDSSQYRLINCNTSAITQAGLNDIFEAQKIEWHELEVLFQGPGHHHHHH
> B.63521_V1_V2_Tags
METDTLLLWVLLLWVPGSTGDQVKLTPLCVTLNCTDVTNATNINATNINNSSGGVESGEIKNCSFNITTSVRDKVQKEYA
LFYKLDIVPITNESSKYRLISCNTSVLTQAGLNDIFEAQKIEWHELEVLFQGPGHHHHHH
> D.9009SA_V1_V2_Tags
METDTLLLWVLLLWVPGSTGDQVKLTPLCVTLNCTTNSTNFANSTGKDIEMQDCSFNITTEIRDKQKKVHALFYKLDIVQ
IDNNTEANANYTSYRLINCNTSAITQAGLNDIFEAQKIEWHELEVLFQGPGHHHHHH
> A.Q23_V1_V2_Tags
METDTLLLWVLLLWVPGSTGDQVKLTPLCVTLHCTNVTSVNTTGDREGLKNCSFNMTTELRDKRQKVYSLFYRLDIVPIN
ENQGSEYRLINCNTSAITQAGLNDIFEAQKIEWHELEVLFQGPGHHHHHH
> AE.A244_V1_V2_Tags
```

Fig. 17 cont'd-3

```
METDTLLLWVLLLWVPGSTGDQVKLTPPCVTLHCTNANLTKANLTNVNNRTNVSNIIGNITDEVRNCSFNMTTELRDKKQ
KVHALFYKLDIVPIEDNNDSSEYRLINCNTSVIKQPGLNDIFEAQKIEWHELEVLFQGPGHHHHHH
> B.CaseA_V1_V2_Tags
METDTLLLWVLLLWVPGSTGDQVKLTPLCVTLNCIDLRNATNATSNSNTTNTTSSSGGLMMEQGEIKNCSFNITTSIRDK
VQKEYALFYKLDIVPIDNPKNSTNYRLISCNTSVITQAGLNDIFEAQKIEWHELEVLFQGPGHHHHHH
>B.HXB2_V1-V2_Tags
METDTLLLWVLLLWVPGSTGDQVKLTPLCVSLKCTDLKNDTNTNSSSGRMIMEKGEIKNCSFNISTSIRGKVQKEYAFFY
KLDIIPIDNDTTSYKLTSCNTSVITQAGLNDIFEAQKIEWHELEVLFQGPGHHHHHH
>B.MNV1V2_tags
METDTLLLWVLLLWVPGSTGDQVKLTPLCVTLNCTDLRNTTNTNNSTDNNNSKSEGTIKGGEMKNCSFNITTSIGDKMQK
EYALLYKLDIEPIDNDSTSYRLISCNTSVITQAGLNDIFEAQKIEWHELEVLFQGPGHHHHHH
>AE.92TH023V1V2_tags
METDTLLLWVLLLWVPGSTGDQVKLTPLCVTLNCTNANVTNVKNITNVPNIIGNITDEVRNCSFNMTTELRDKKQKVHAL
FYKLDIVPIEDNTSSSEYRLINCNTSVIKQAGLNDIFEAQKIEWHELEVLFQGPGHHHHHH
>RV144_356272_V1V2-Tags
METDTLLLWVLLLWVPGSTGDQVKLTPLCVTLECTNANLKEDNKTTDSPIRIGNISDEVRNCSFNITTEIKDKKQQVQAL
FYRLDIVQMGNDSRYRLINCNTSVIKQGLNDIFEAQKIEWHELEVLFQGPGHHHHHH
>RV144_427299_V1V2_Tags
METDTLLLWVLLLWVPGSTGDQVKLTPLCVTLKCTANITITNATTRTENTTKENLIGNITDELRNCSFNVTTELRDRQRK
AYALFYKLDIVPINNEANSSEYRLINCNTSVIKQGLNDIFEAQKIEWHELEVLFQGPGHHHHHH Design of minimally glycosylated HIV-1 V1V2 Env protein using A244
V1V2 as example:

>A244V1V2_Tags_delta7N
aagcttgtcgacaccATGGAGACCGACACCCTGCTGCTGTGGGTGCTGCTGCTGTGGGTGCCCGGCTCCACCGGCGACCA
GGTGAAGCTGACCCCCCCCTGCGTGACCCTGCACTGCACCAACGCCGACCTGACCAAGGCCGACCTGACCAACGTGAACG
ACCGCACCGACGTGTCCAACATCATCGGCGACATCACCGACGAGGTGCGCAACTGCTCCTTCAACATGACCACCGAGCTG
CGCGACAAGAAGCAGAAGGTGCACGCCCTGTTCTACAAGCTGGACATCGTGCCCATCGAGGACAACGACGACTCCTCCGA
GTACCGCCTGATCAACTGCGACACCTCCGTGATCAAGCAGCCCGGCCTGAACGACATCTTCGAGGCCCAGAAGATCGAGT
GGCACGAGCTGGAGGTGCTGTTCCAGGGCCCCGGCCACCATCACCATCACCACTAGggatcctctaga
>Amino acid encoded by A244V1V2_Tags_delta7N
METDTLLLWVLLLWVPGSTGDQVKLTPPCVTLHCTNADLTKADLTNVNDRTDVSNIIGDITDEVRNCSFNMTTELRDKKQ
KVHALFYKLDIVPIEDNDDSSEYRLINCDTSVIKQPGLNDIFEAQKIEWHELEVLFQGPGHHHHHH >A244V1V2_delta7N
aagcttgtcgacaccATGGAGACCGACACCCTGCTGCTGTGGGTGCTGCTGCTGTGGGTGCCCGGCTCCACCGGCGACCA
GGTGAAGCTGACCCCCCCCTGCGTGACCCTGCACTGCACCAACGCCGACCTGACCAAGGCCGACCTGACCAACGTGAACG
ACCGCACCGACGTGTCCAACATCATCGGCGACATCACCGACGAGGTGCGCAACTGCTCCTTCAACATGACCACCGAGCTG
CGCGACAAGAAGCAGAAGGTGCACGCCCTGTTCTACAAGCTGGACATCGTGCCCATCGAGGACAACGACGACTCCTCCGA
GTACCGCCTGATCAACTGCGACACCTCCGTGATCAAGCAGCCCTAGggatcctctaga
>Amino acid encoded by A244V1V2_delta7N
METDTLLLWVLLLWVPGSTGDQVKLTPPCVTLHCTNADLTKADLTNVNDRTDVSNIIGDITDEVRNCSFNMTTELRDKKQ
KVHALFYKLDIVPIEDNDDSSEYRLINCDTSVIKQP
```

Fig. 19
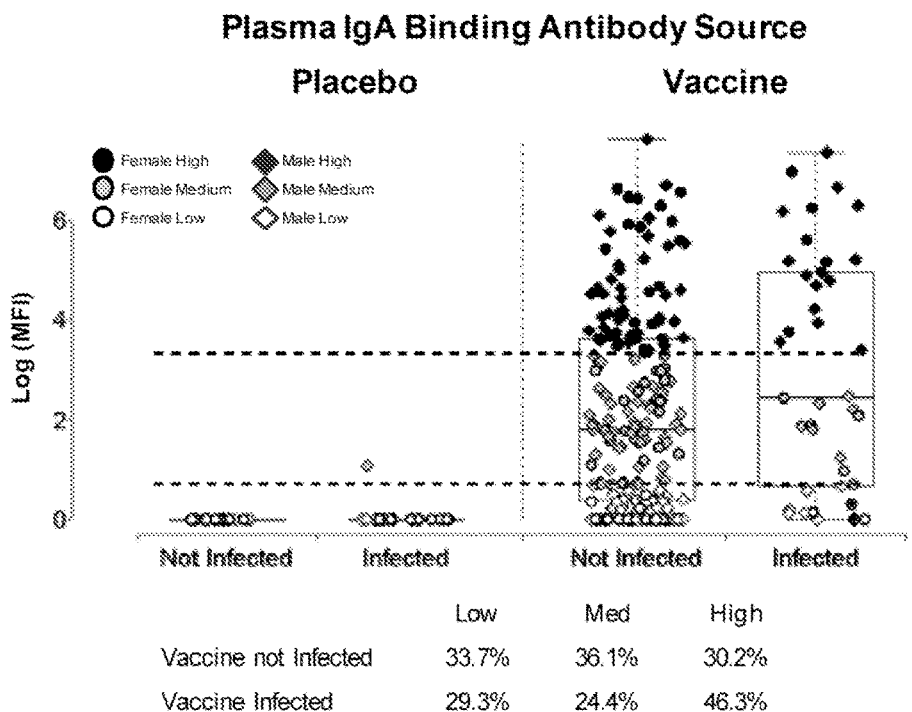
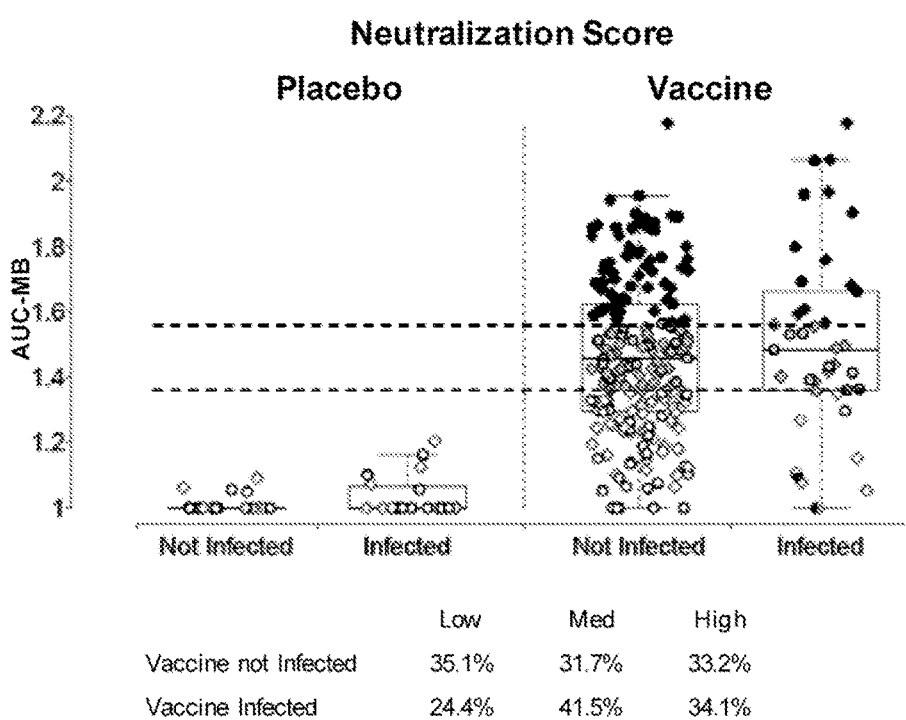

Fig. 19 cont'd-1
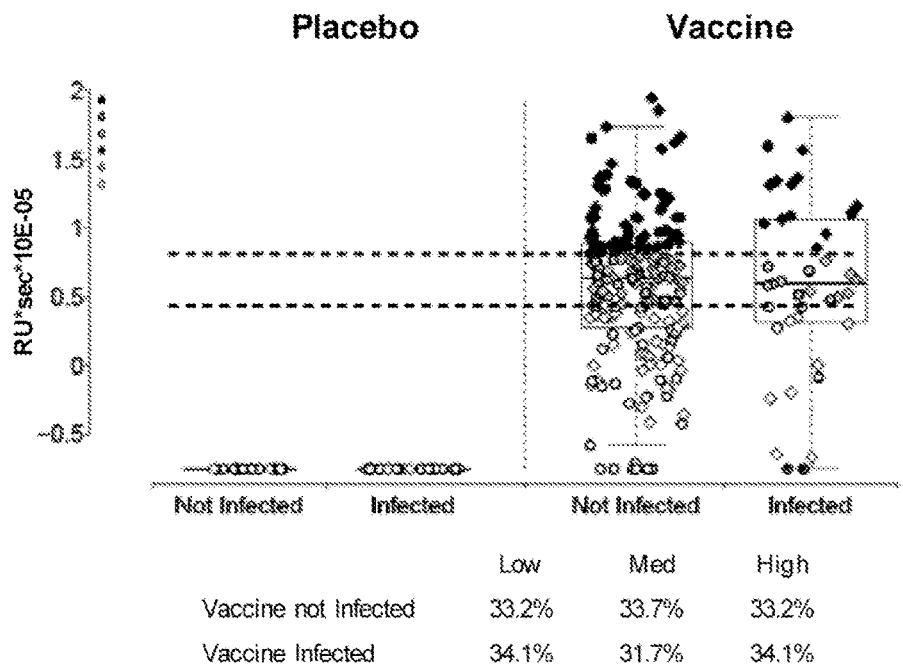
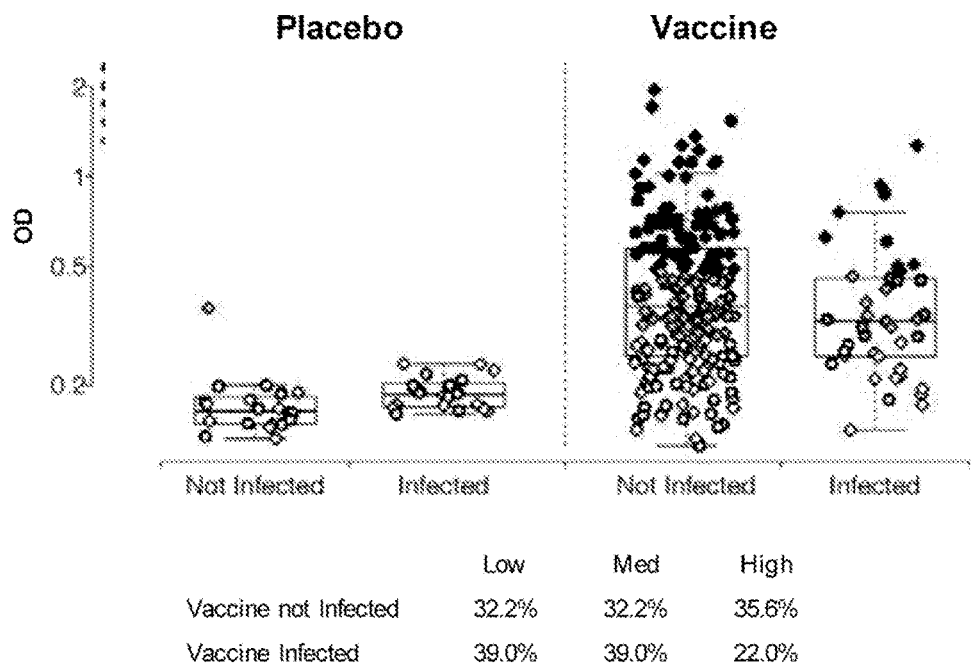

Fig. 19 cont'd-2
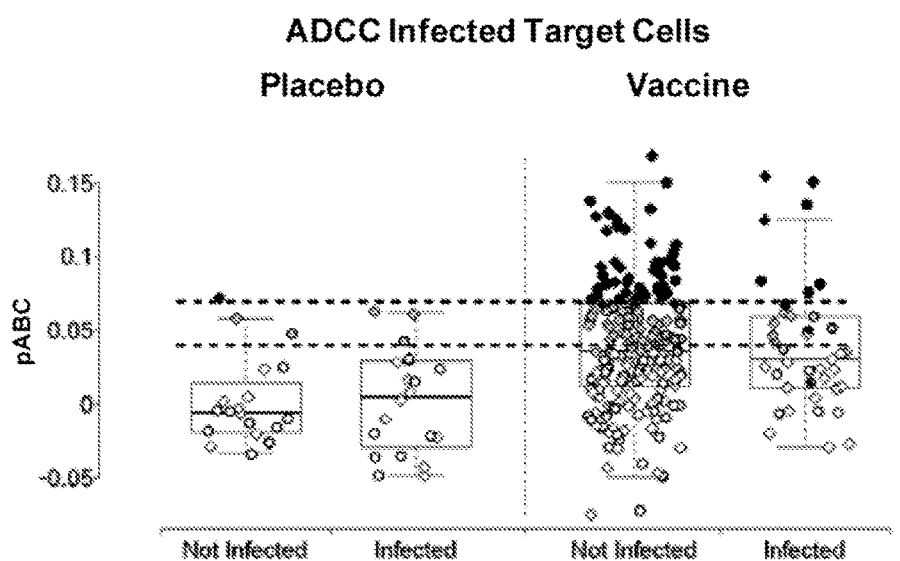
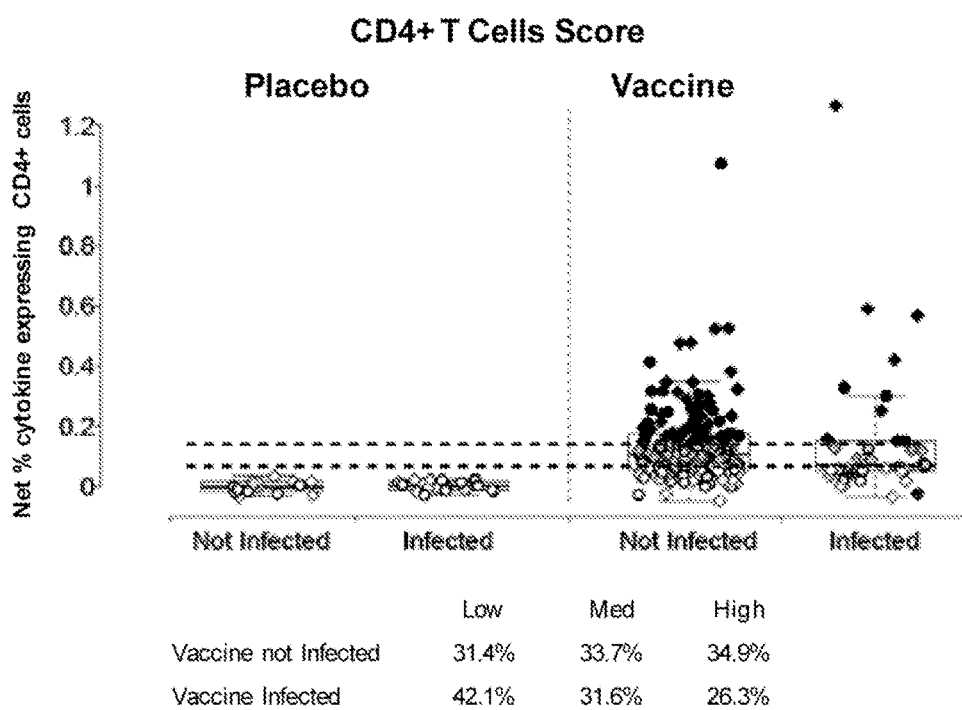

Fig. 20
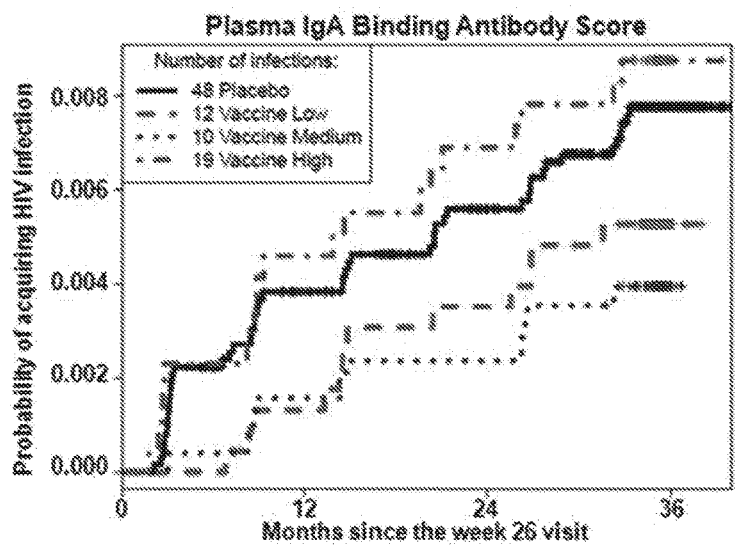
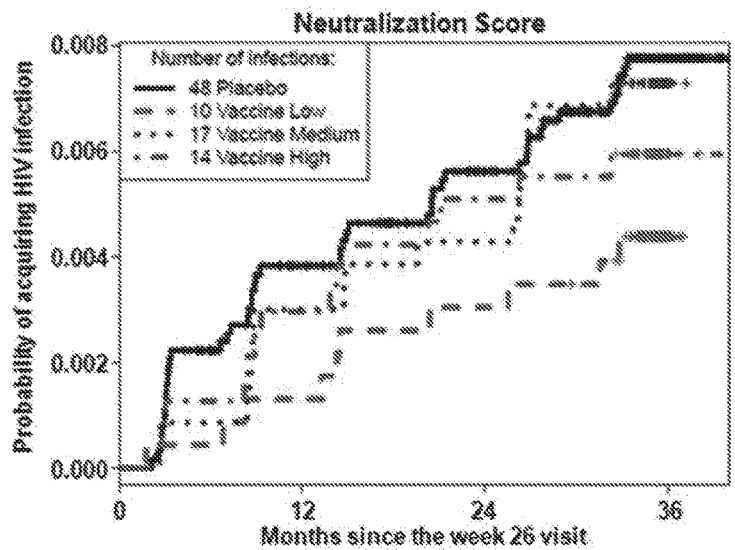

Fig. 20 cont'd-1
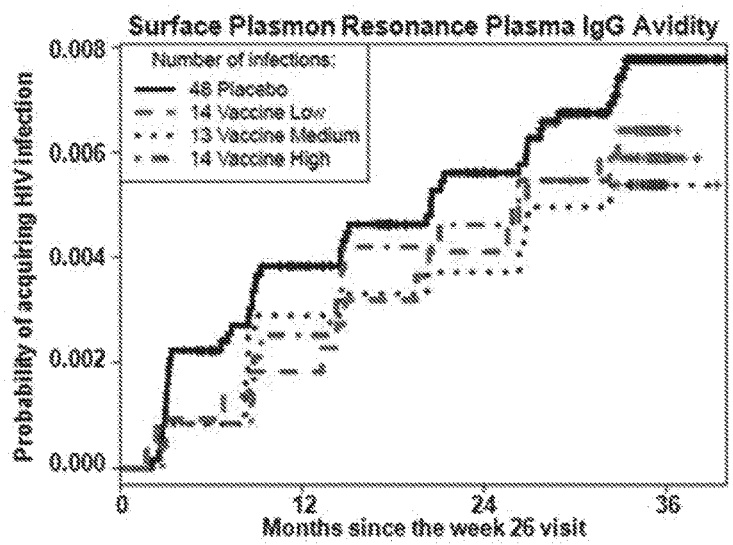
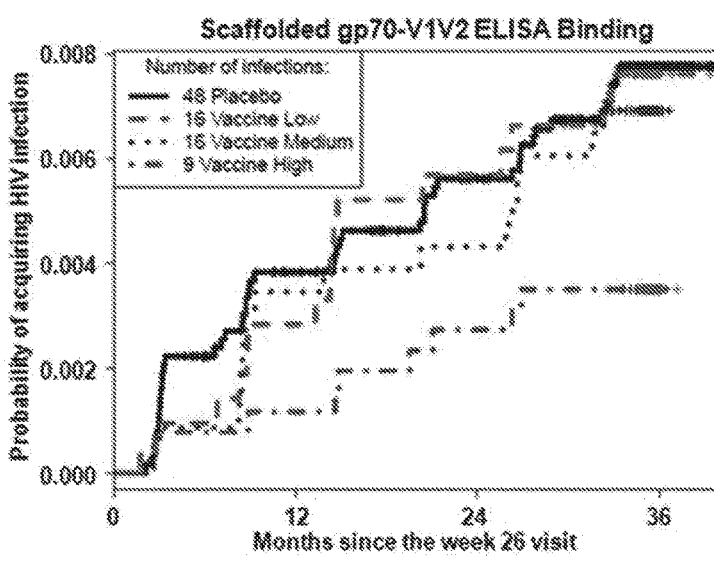

Fig. 20 cont'd-2
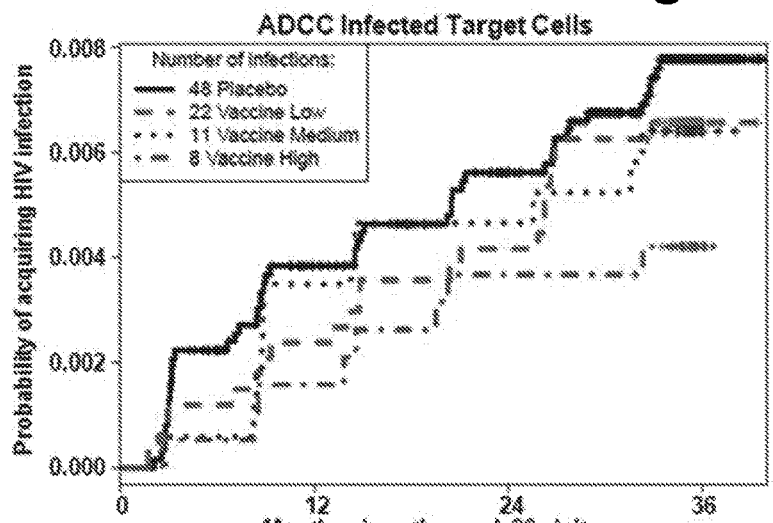
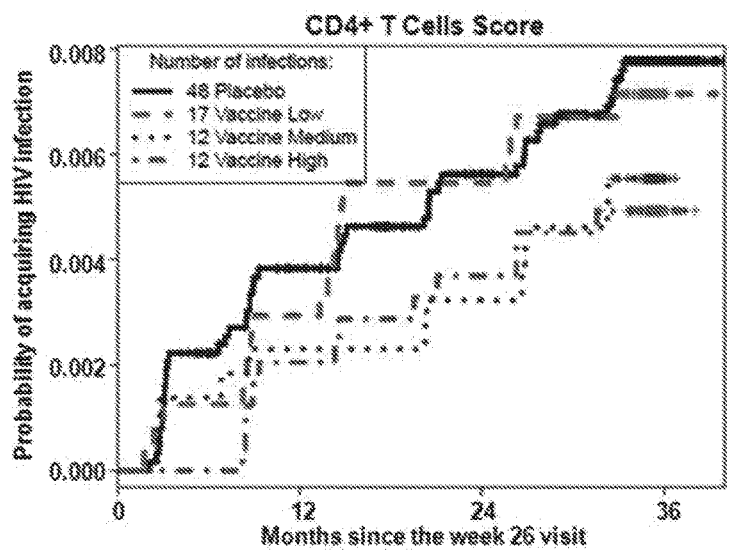

Fig. 23 Scatterplots and Spearman rank correlation values (r) for all pairs of the 6 primary variables.

Fig. 25
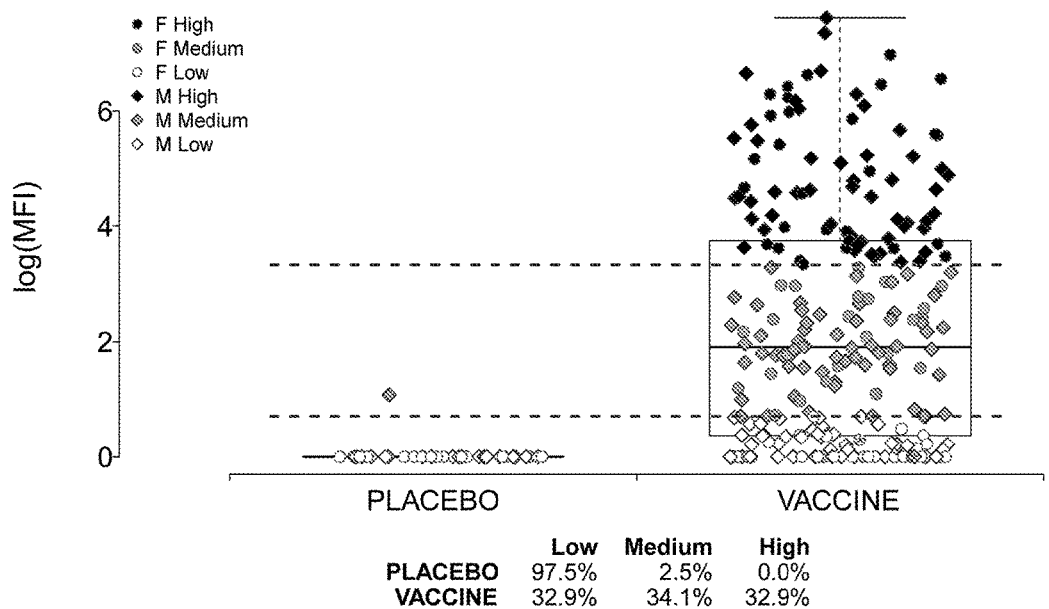
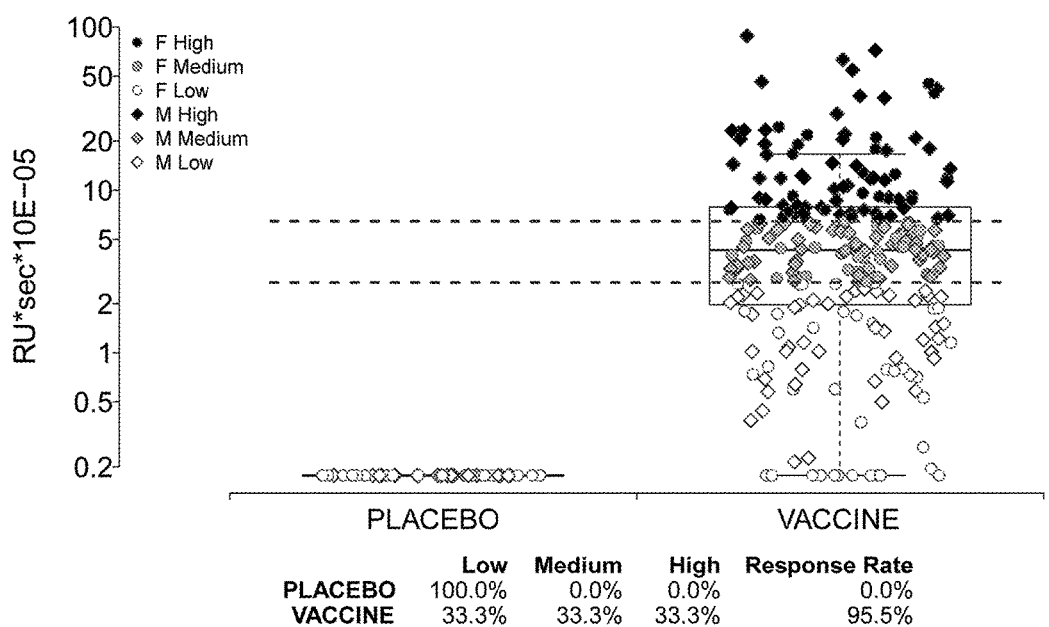

Fig. 26
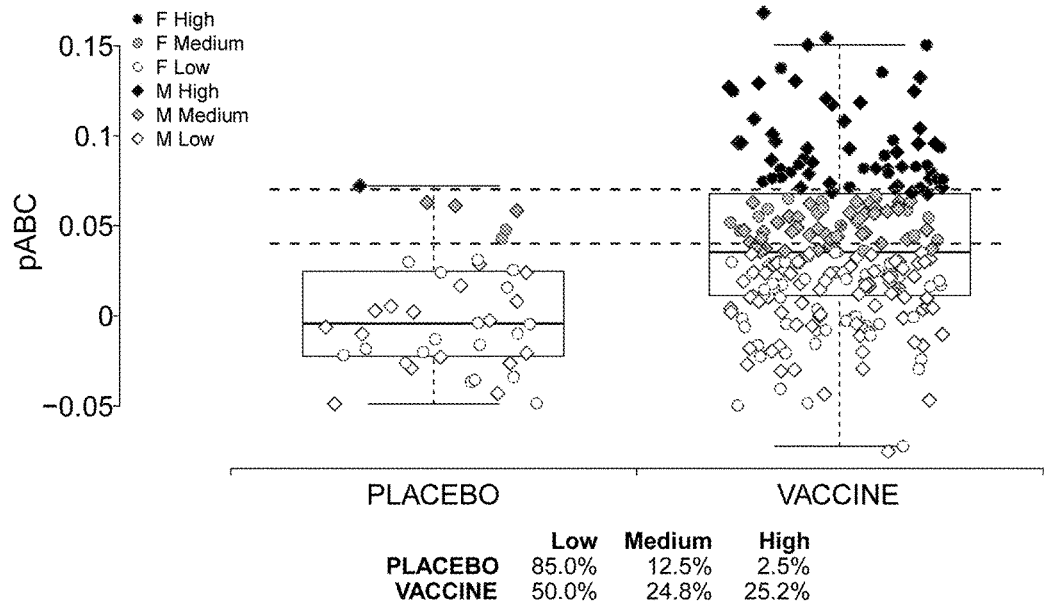
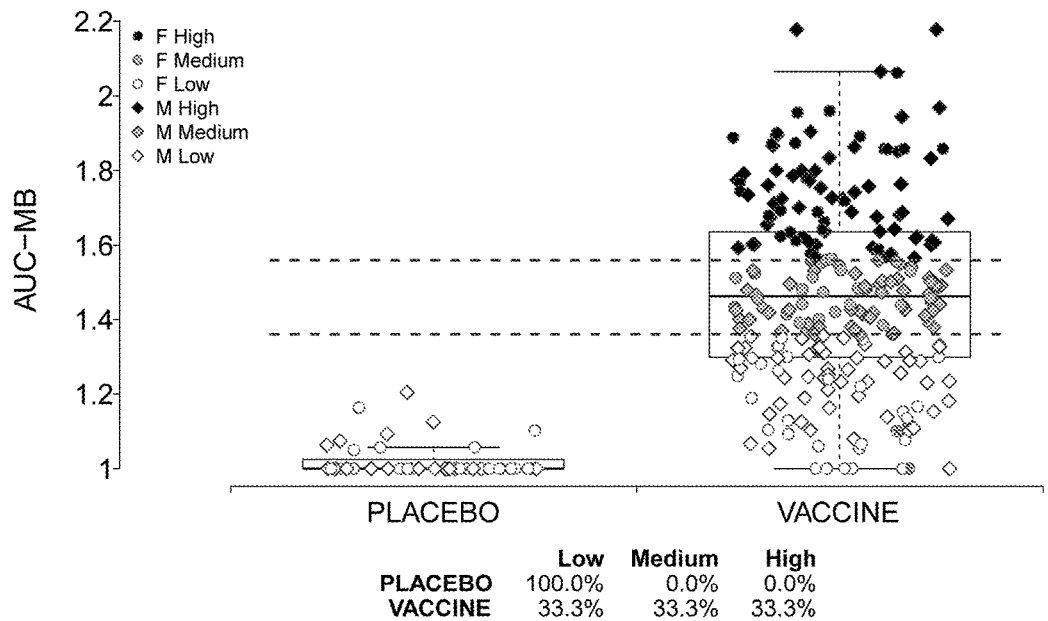

Fig. 27
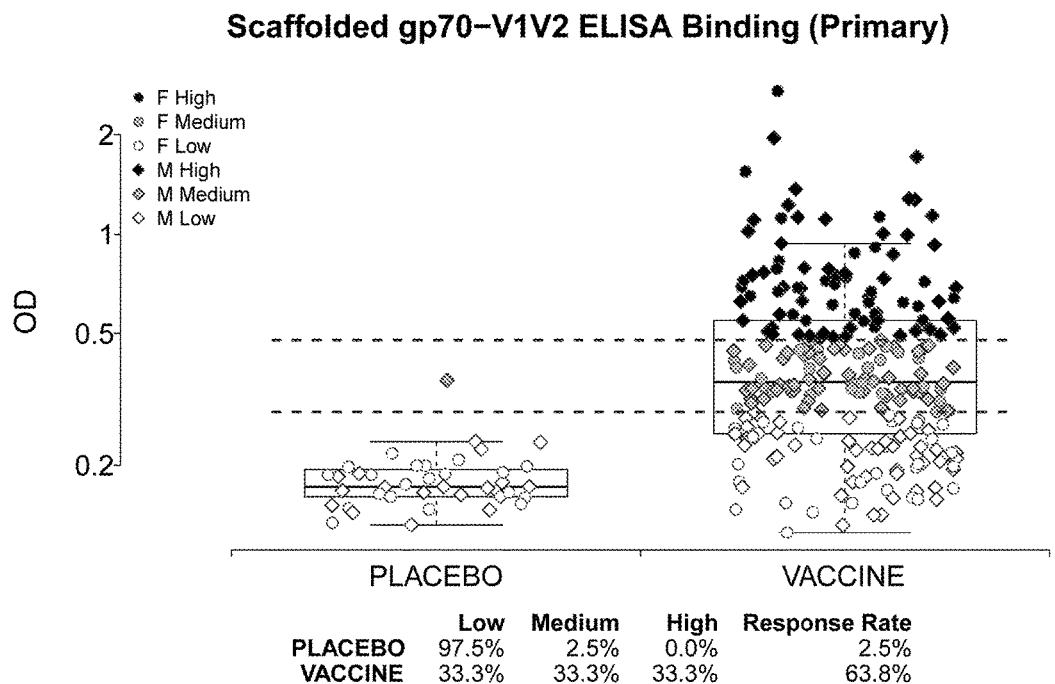
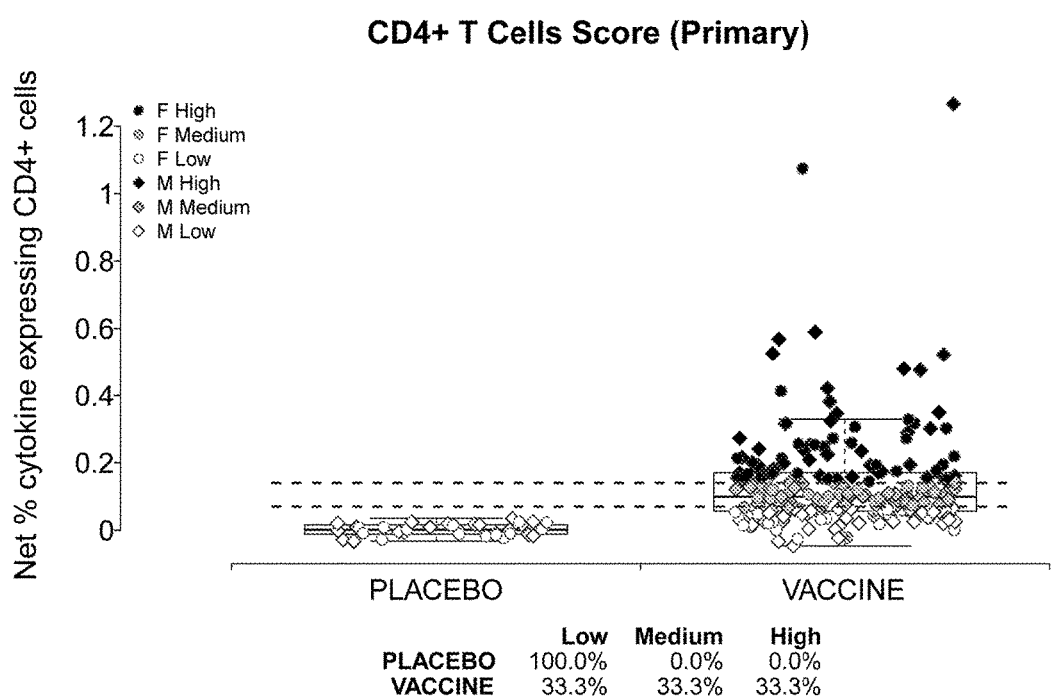

Fig. 28
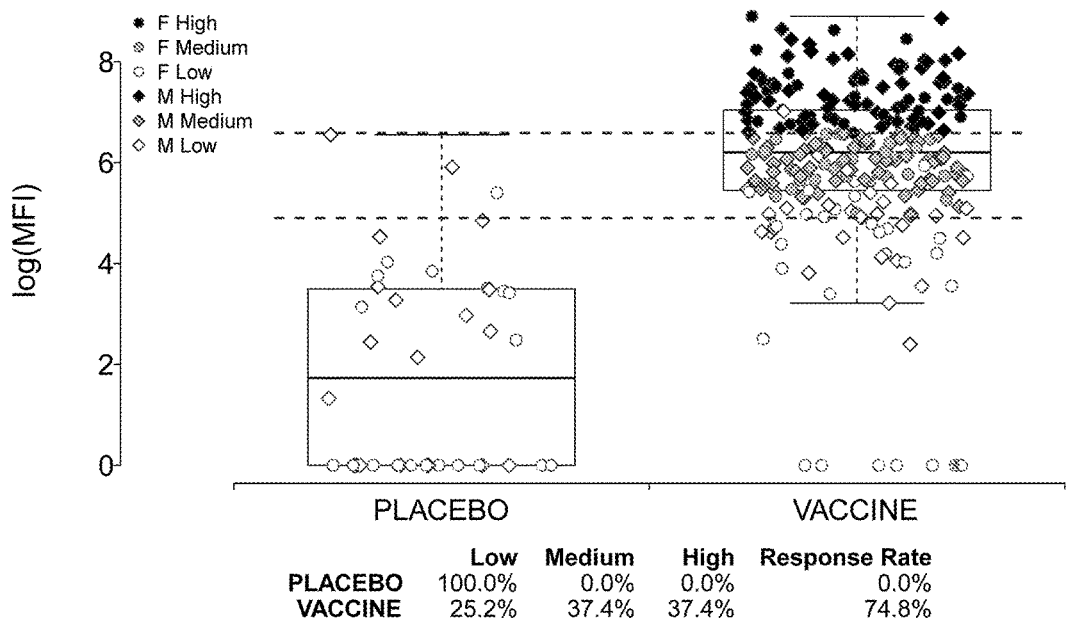
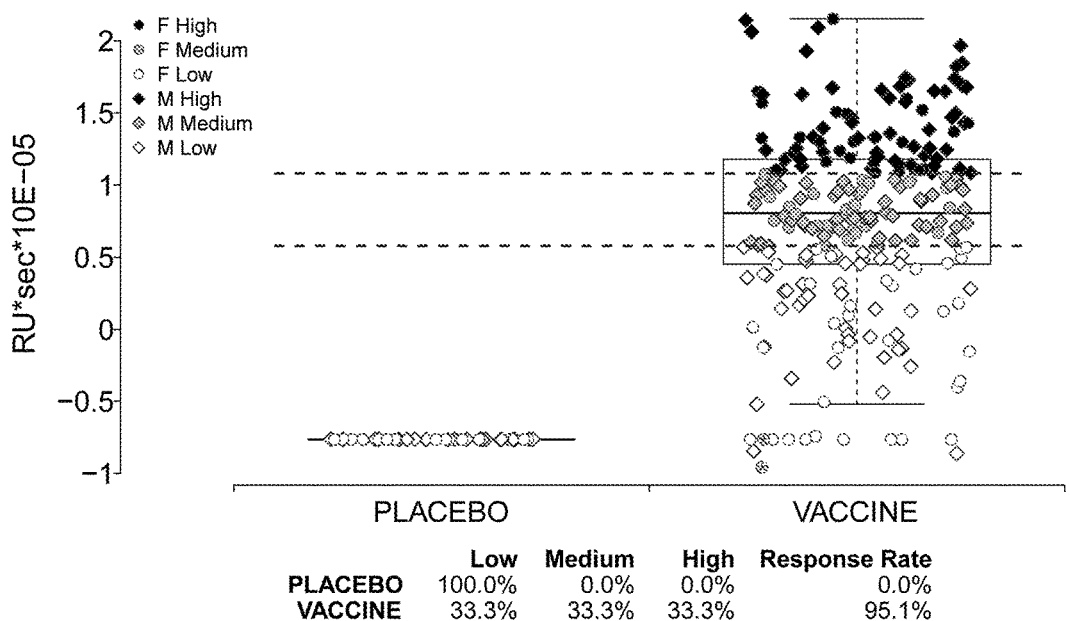

Fig. 29
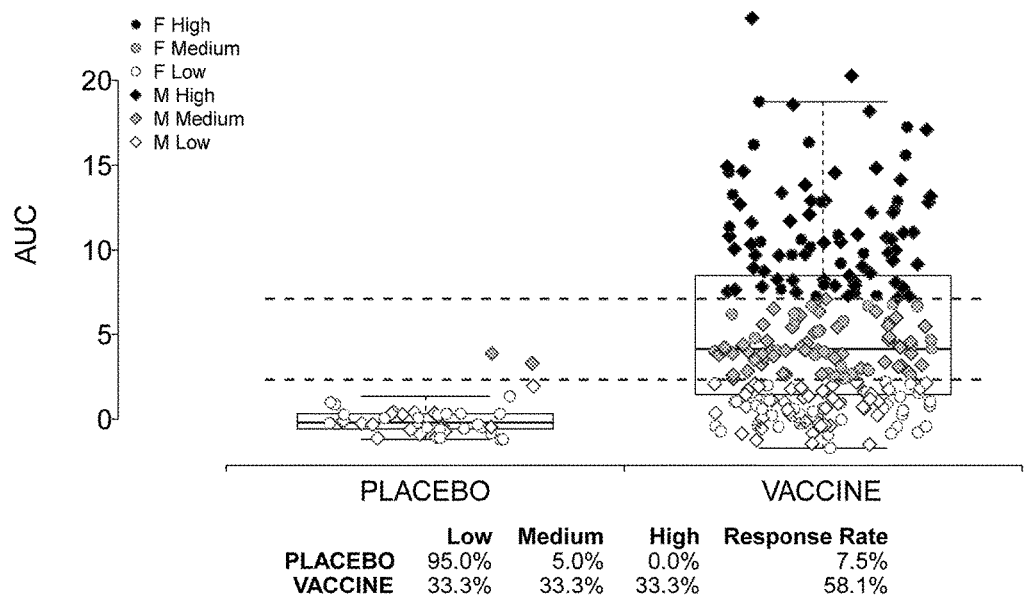
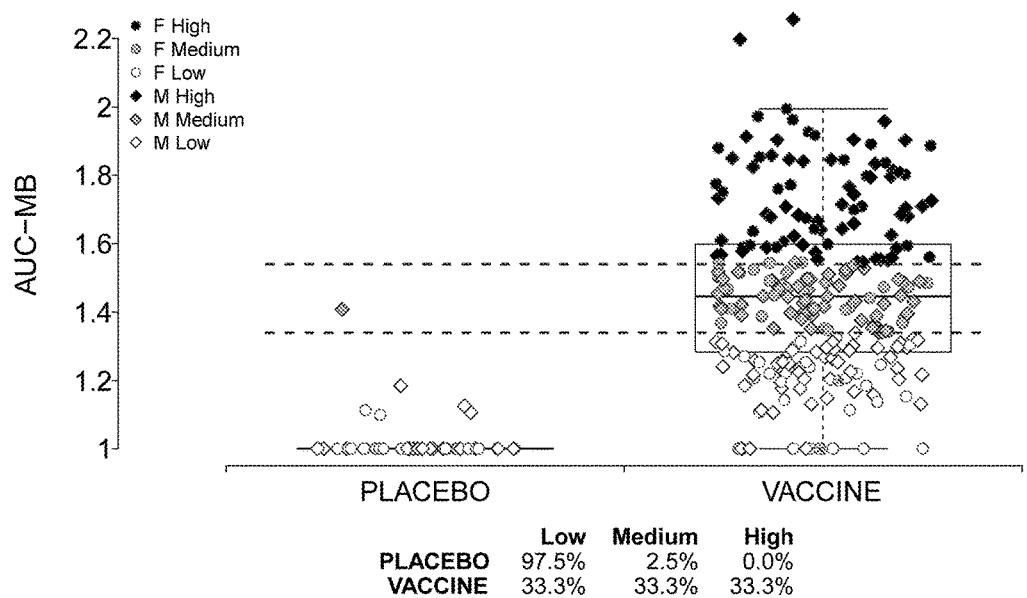

Fig. 30
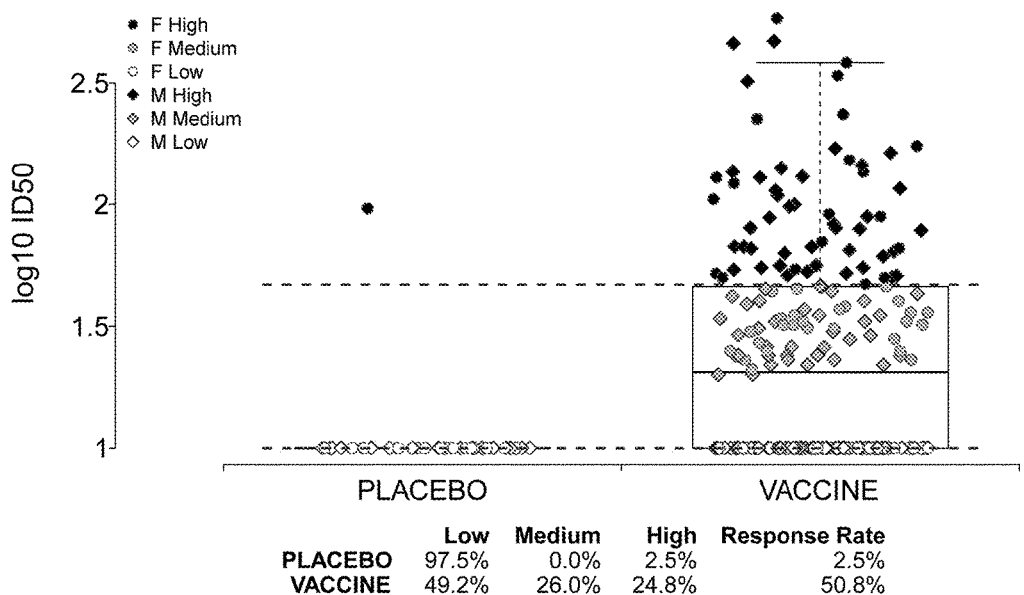
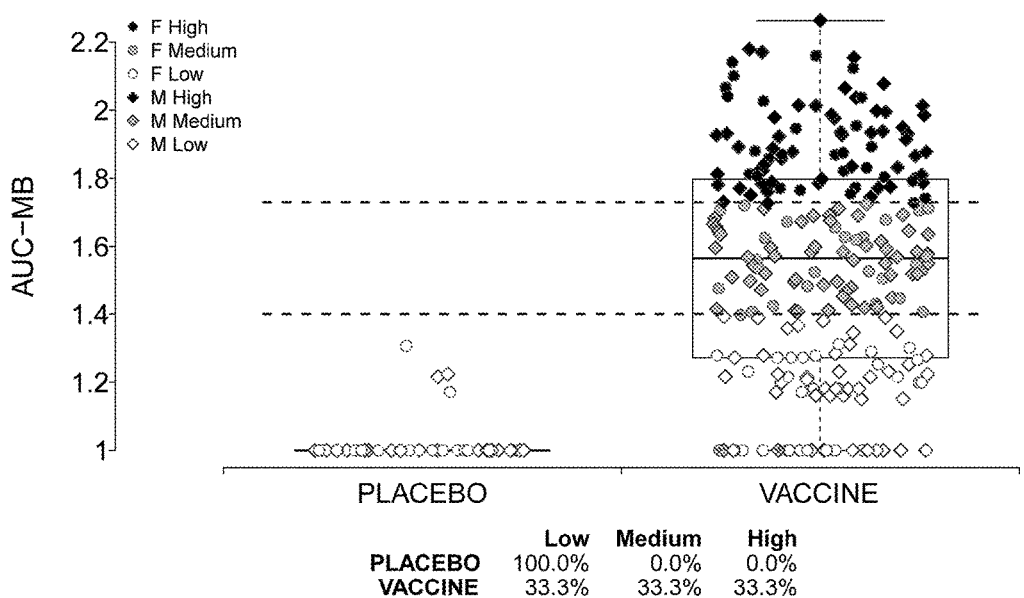

Fig. 31
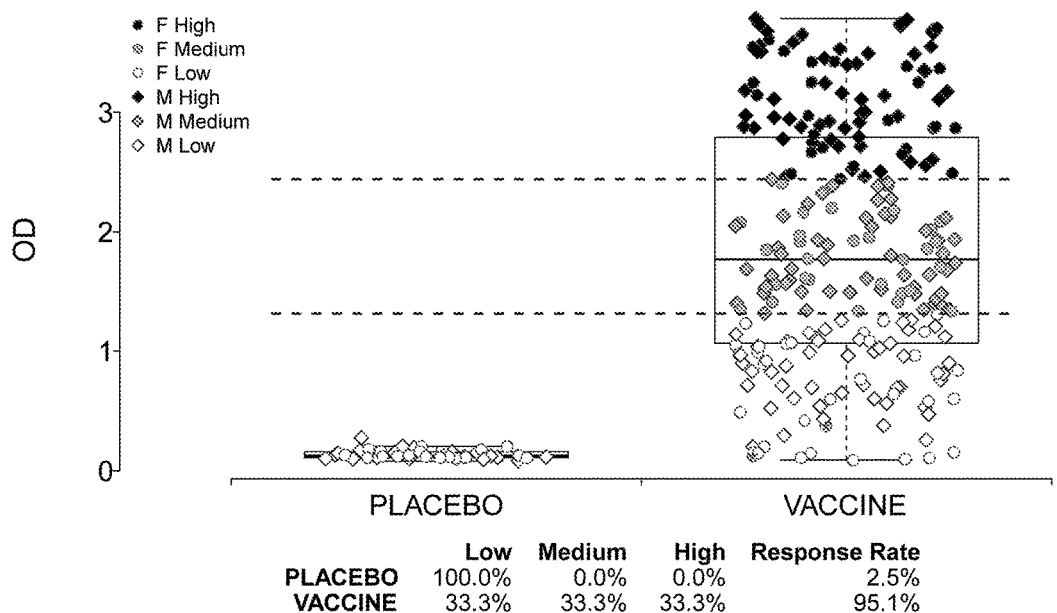
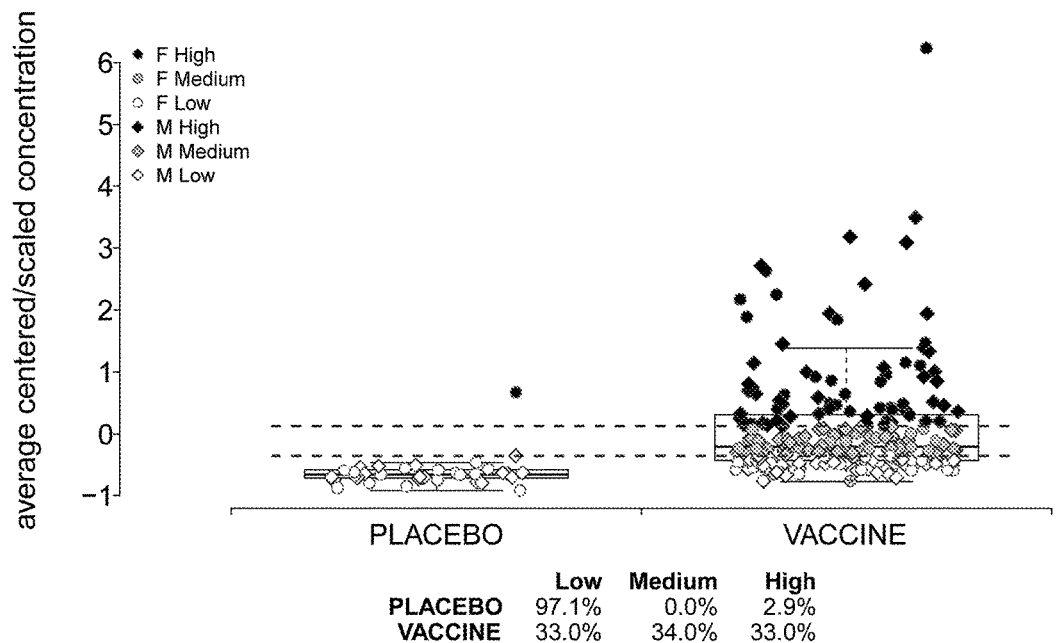

Fig. 33
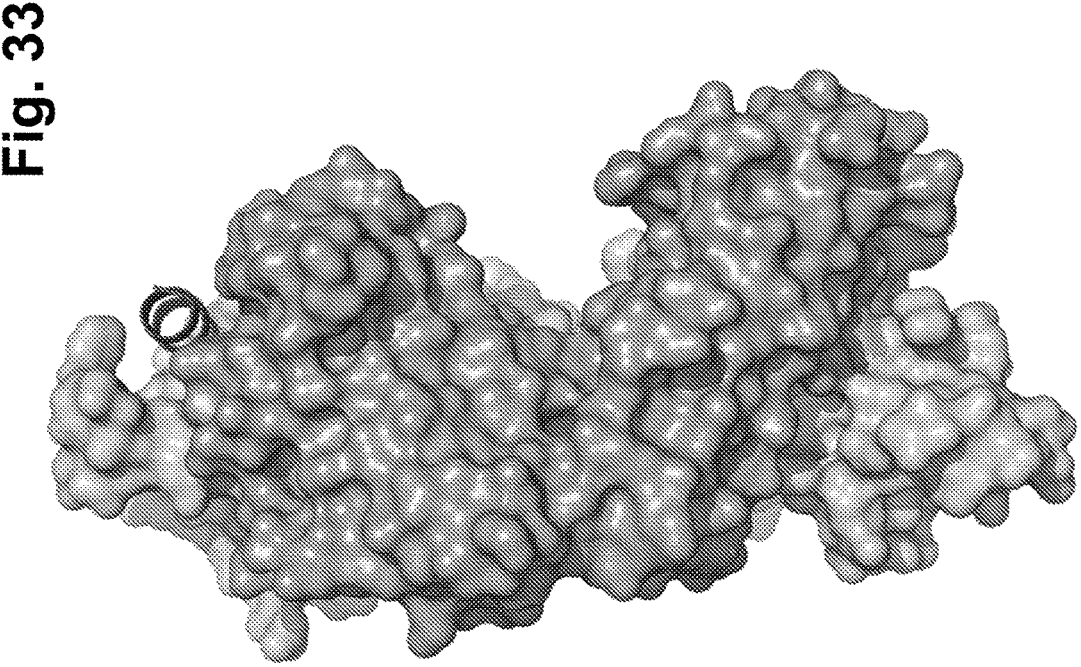
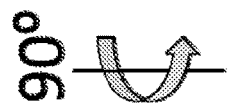
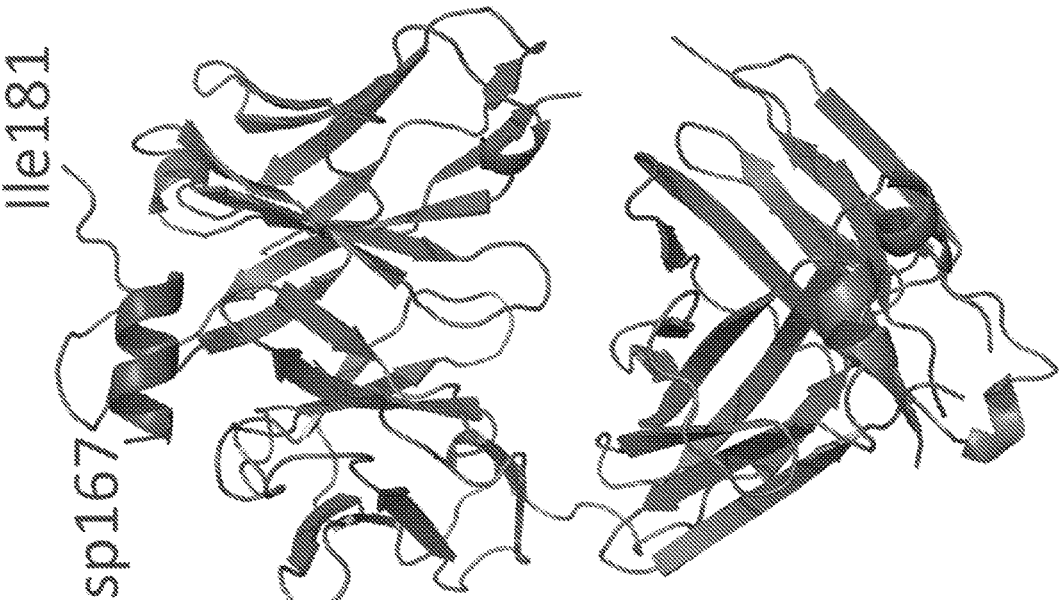

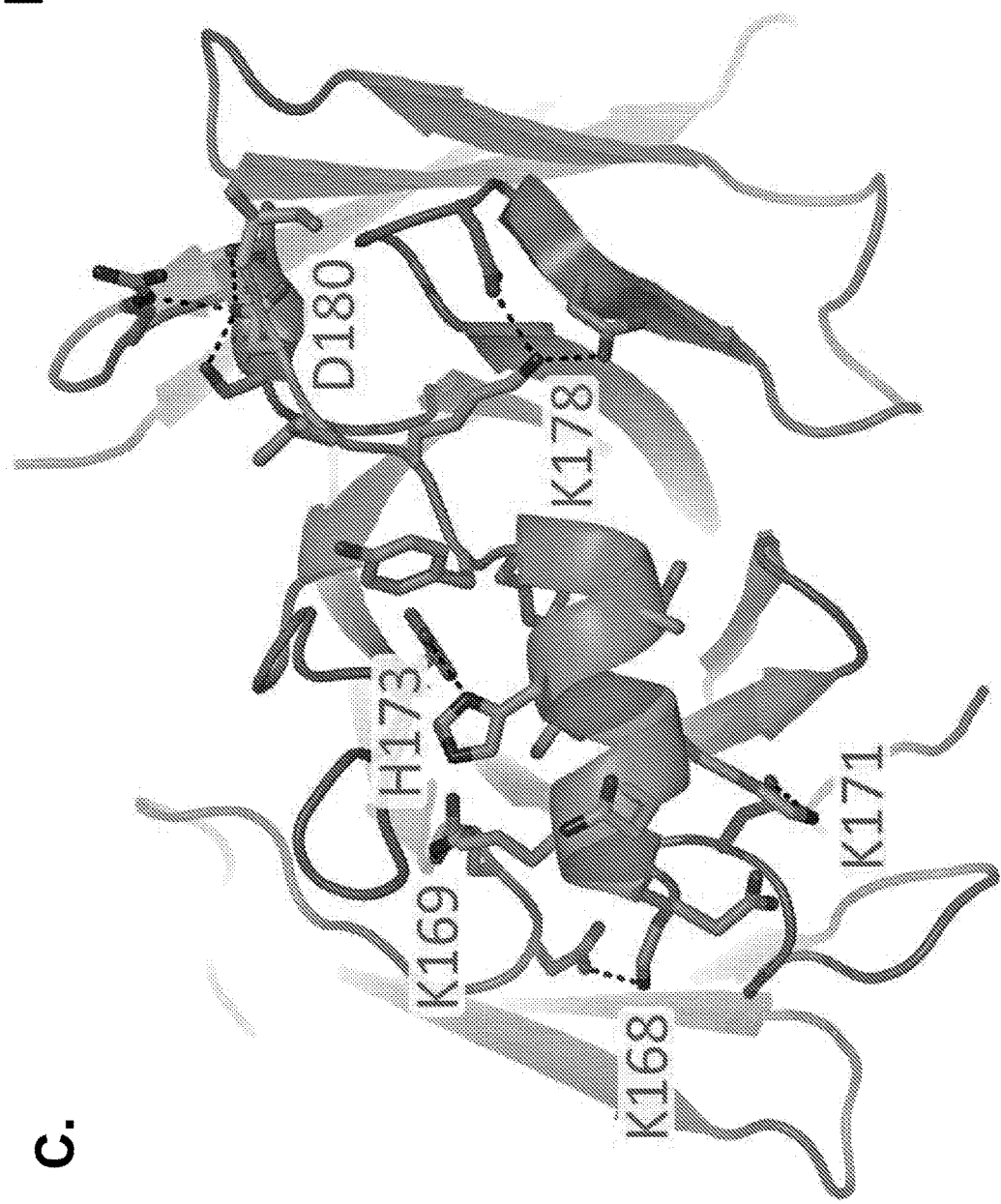

Fig. 34

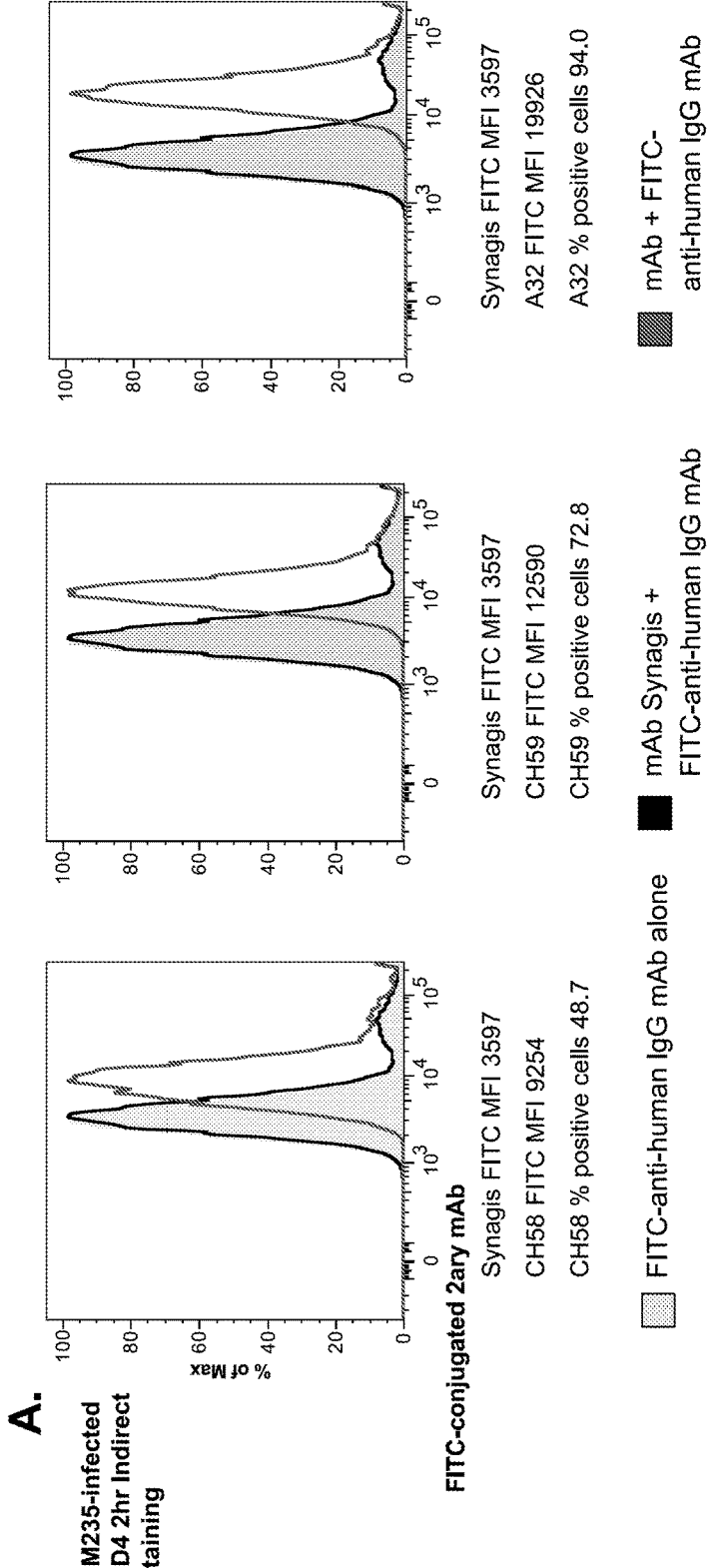

Fig. 35 – Binding of anti-V2 mAb CH58 and CH59 to infected cells. The histograms report the staining of activated PB CD4+ T cells infected with Infectious Molecular Clone CM235 using the CH58 (left), CH59 (middle), and A32 (right) mAb. One-two hundred thousand CD4+ T cells were stained with 10μg/ml of each mAb. The gating strategy included identification of p24+ cells out of the singlets and viable cell population. The Synagis® and A32 mAbs were used as negative and positive controls, respectively. The overlaying histograms represent the staining of HIV-1 infected CD4+ T cells after incubation with no Ab (unstained; gray area), with the secondary Ab alone (Secondary Ab Alone; black curve), and with primary and secondary Ab (primary Ab+ secondary Ab; green curve). Under each histogram, the table report the Median Fluorescence Intensity (MFI) of the staining of each mAb and the percentage of p24+ cells recognized by each mAb (% positive cells). The MFI of the Synagis is reported as reference, and the background staining for this mAb was 11% of p24+ cells.

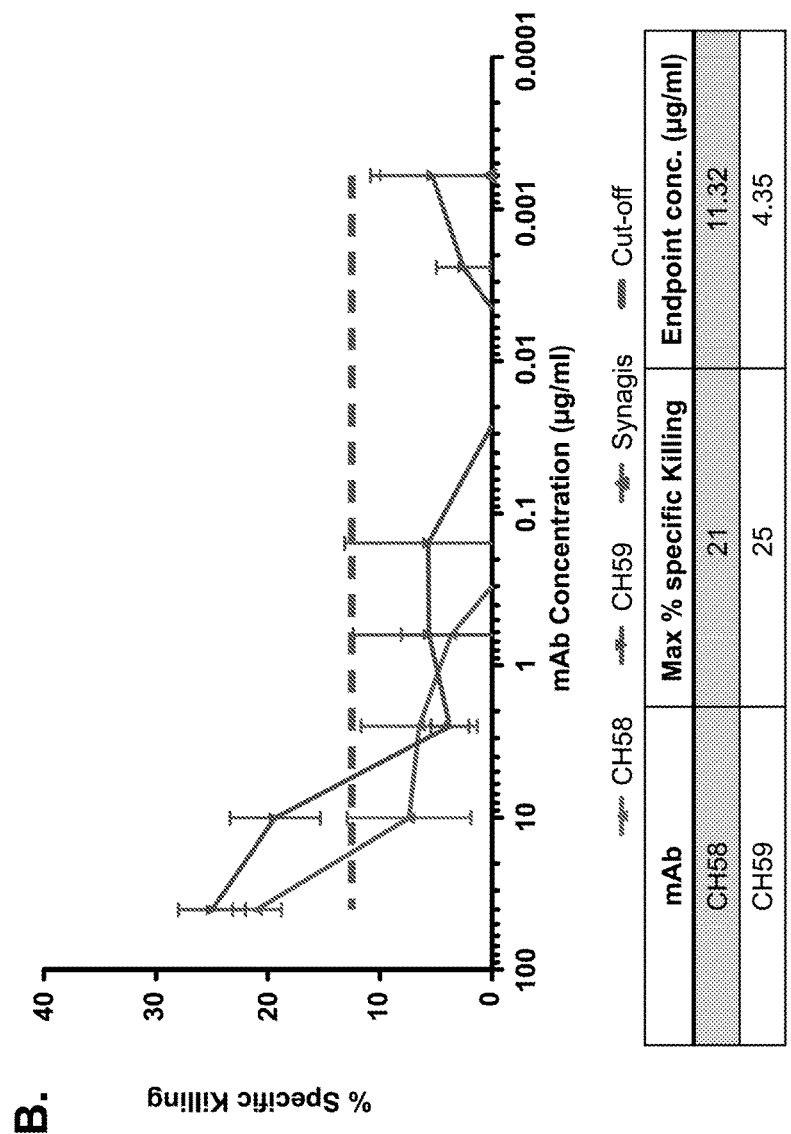

Fig. 35 – ADCC activity mediated by anti-V2 mAbs CH58 and CH59. The percentage of specific killing mediated by the CH358 (red line) and CH59 (blue line) using IMC$_{CM235}$-infected CEM.NKR$_{CCR5}$ is reported. Each mAb was tested starting at 40μg/ml in a 4 fold dilution series. The Synagis® (orange line) mAbs were used as positive and negative controls, respectively. The green line represents the cut-off for positivity. The curves represent the average of three independent experiments; the error bars represent the standard deviations. The maximum % Specific Killing and the Endpoint Concentration for the CH58 and CH59 mAbs are reported in the table below the graph.

Fig. 36

- Binding of conformational V2 (697D) and V2V3 mAbs (PG9, PG16, CH01) but not of A32 (C1) or b12 (CD4 bs) to A244 gp120 is blocked by mAbs CH58 (A) and CH59 (B). Binding of the Env gp120 to V3 mAb 19b (C) did not block binding of any of the tested mAbs. Inset in C shows binding data from C rescaled for the binding of CH01, PG9 and PG16 (on 19b surface) and overlayed with curves for the same mAbs showing no binding to gp120 captured on CH58 and CH59 immobilized surfaces. Equivalent amounts of A244 gp120 proteins were captured on each mAb immobilized surfaces and each of the mAbs were injected at 50ug/mL, with Synagis as a negative control mAb.

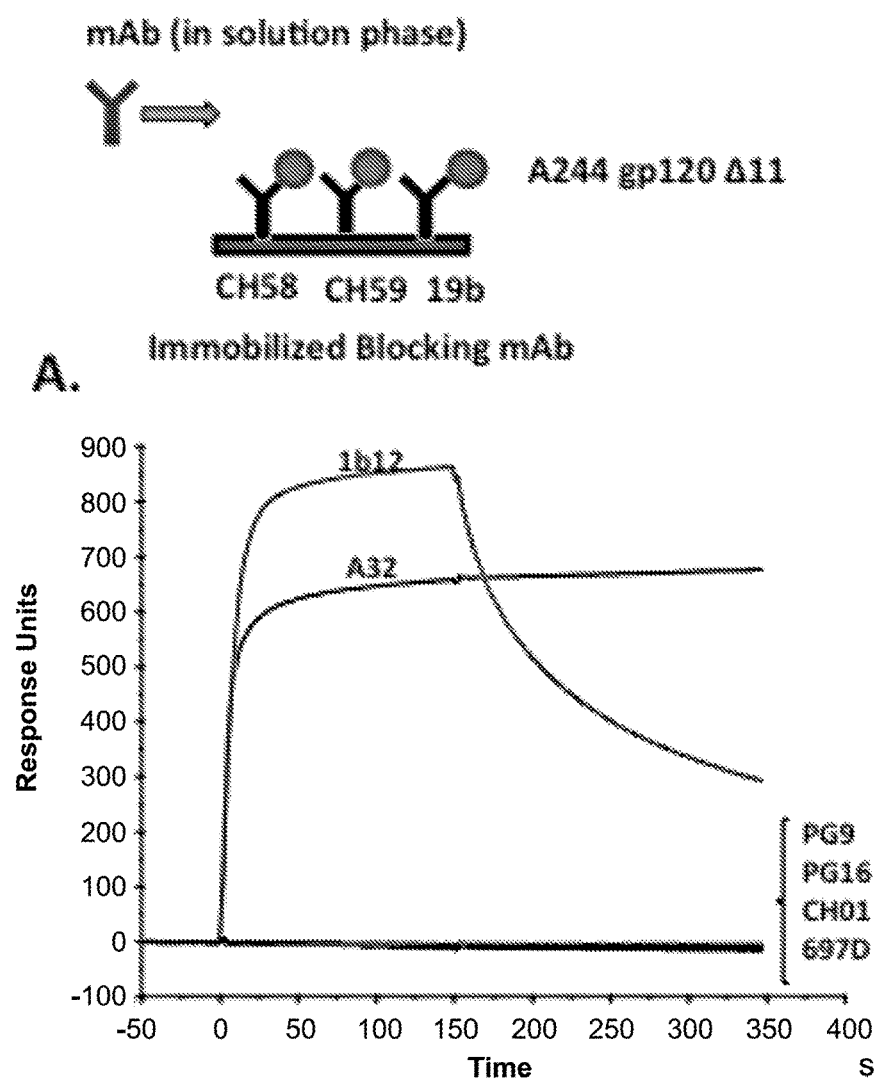

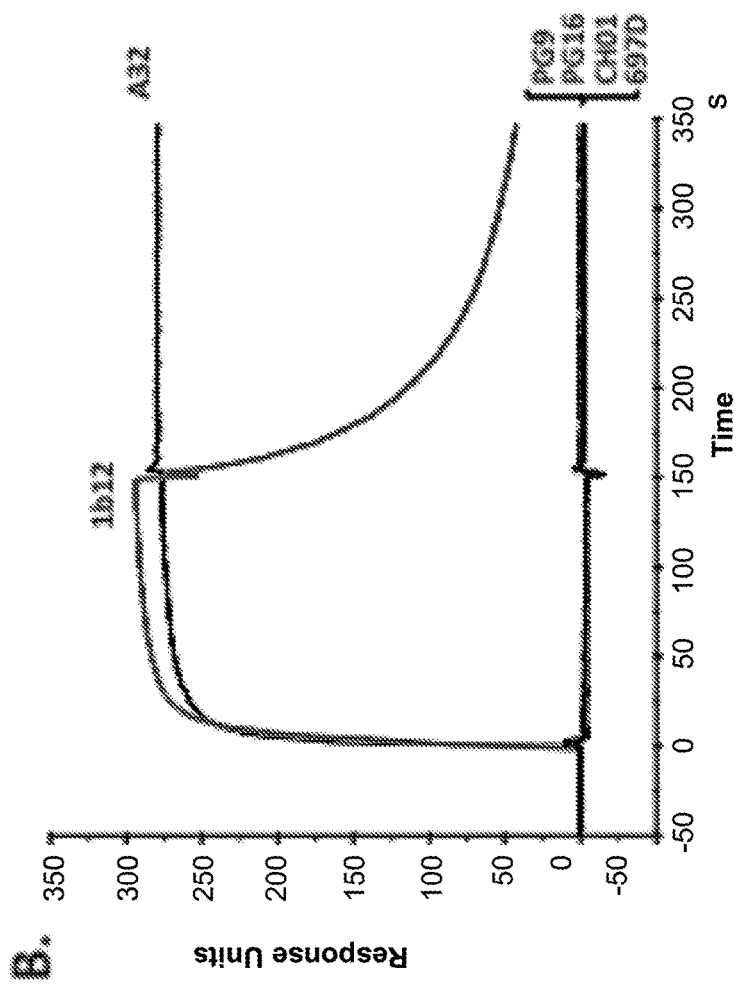

Fig. 36 – Binding of conformational V2 (697D) and V2V3 mAbs (PG9, PG16, CH01) but not of A32 (C1) or b12 (CD4 bs) to A244 gp120 is blocked by mAbs CH58 (A) and CH59 (B). Binding of the Env gp120 to V3 mAb 19b (C) did not block binding of any of the tested mAbs. Inset in C shows binding data from C rescaled for the binding of CH01, PG9 and PG16 (on 19b surface) and overlayed with curves for the same mAbs showing no binding to gp120 captured on CH58 and CH59 immobilized surfaces. Equivalent amounts of A244 gp120 proteins were captured on each mAb immobilized surfaces and each of the mAbs were injected at 50ug/mL, with Synagis as a negative control mAb.

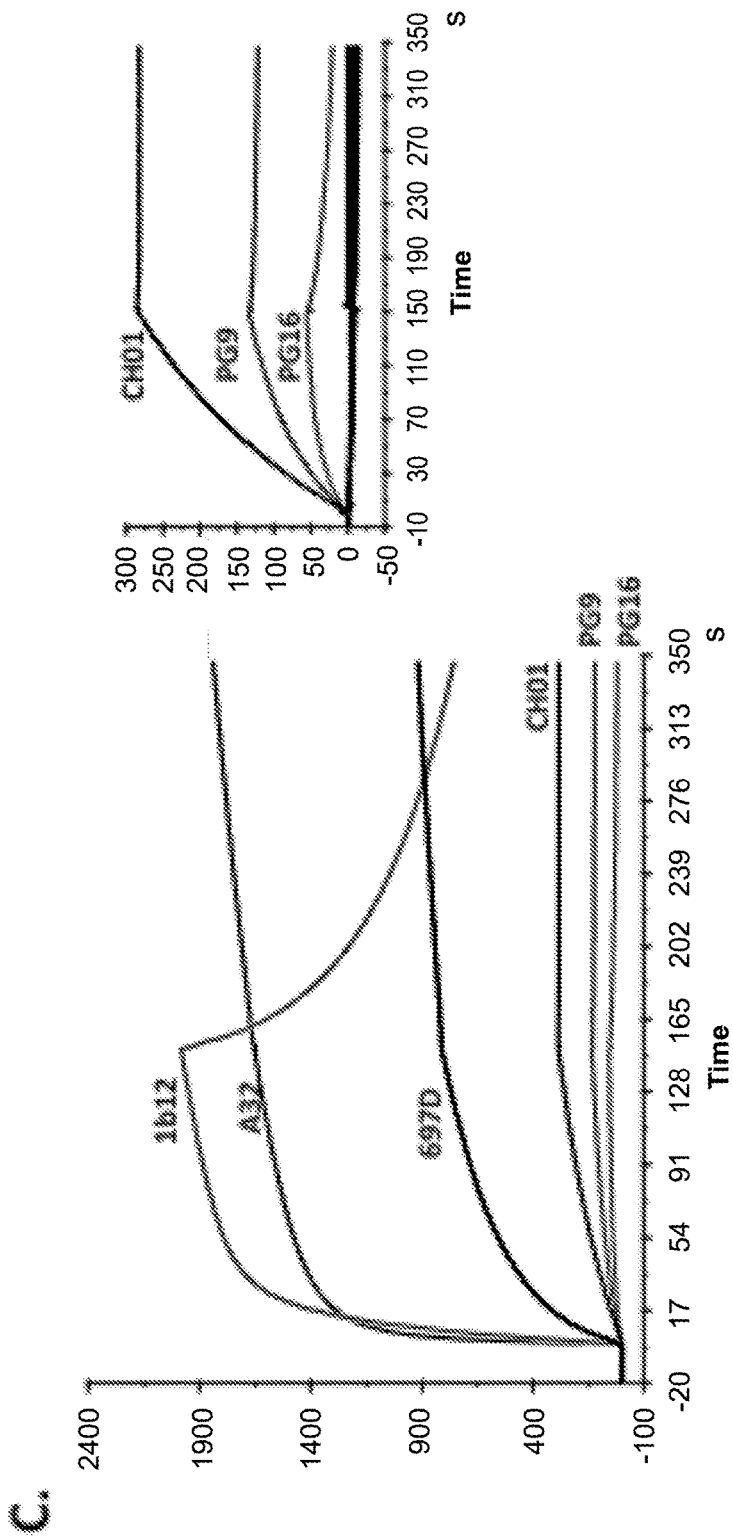

Fig. 36 – Binding of conformational V2 (697D) and V2V3 mAbs (PG9, PG16, CH01) but not of A32 (C1) or b12 (CD4 bs) to A244 gp120 is blocked by mAbs CH58 (A) and CH59 (B). Binding of the Env gp120 to V3 mAb 19b (C) did not block binding of any of the tested mAbs. Inset in C shows binding data from C rescaled for the binding of CH01, PG9 and PG16 (on 19b surface) and overlayed with curves for the same mAbs showing no binding to gp120 captured on CH58 and CH59 immobilized surfaces. Equivalent amounts of A244 gp120 proteins were captured on each mAb immobilized surfaces and each of the mAbs were injected at 50ug/mL, with Synagis as a negative control mAb.

Fig. 37 – Alignment of the HCDR3 sequence of mAbs PG9, PG16, CH58, CH59, CH01 and 697D and their RUAs.

The amino acid sequences of the CDR H3 regions of mAbs PG16, CH58, CH59, 697D and CH01 and their RUSAs were aligned to that of mAb PG9. Each sequence was aligned independently to PG9 (paired alignment) using Clustal W and final adjustment was made manually. Gaps are indicated with dots. Amino acids conserved between PG9 and either CH58 or CH59 sequences are highlighted in red. The number of amino acids shared with PG9 over the total is reported on the right for each mAb

```
                                                      Similarity to
                                                      PG9  CDRH3

PG9:       EAGGPDYRNGYNYYDFYDGYYNYHYMDV              28/28  100%
PG16:      EAGGPIWHDDVKYYDFNDGYYNYHYMDV              20/28  71.4%
CH58:      .LGG...R..Y.YHD.SSGYY...YLDY              11/17  64.7%
CH59:      ..DSP.R.G...EL.......PLNY                  5/11  45.5%
697D:      .TSG....VGLHF....GY.....FDY                5/12  41.7%
CH01:      ...GTDYTIDDAGIHY.QGSGTFWYFDL               7/24  29.2%

PG9RUA:    EAGGPDYRNGXNYYDFWSGYYNYYMDV               28/28  100%
PG16RUA:   EAGGPIWHDDVKYYDFNDGYYYYYMDV               19/28  67.9%
CH58RUA:   .LGG...R..Y.YYD.SSGYY...YFDY              11/17  64.7
CH59RUA:   ..DSP.R.G...EL.......PFDY                  5/11  45.5%
697DRUA:   .TSG....VGLHF....GY.....FDY                5/12  41.7%
CH01RUA1:  ...GTDYTIDDQGIR.YQGSGTFWYFDL               7/24  29.2%
```

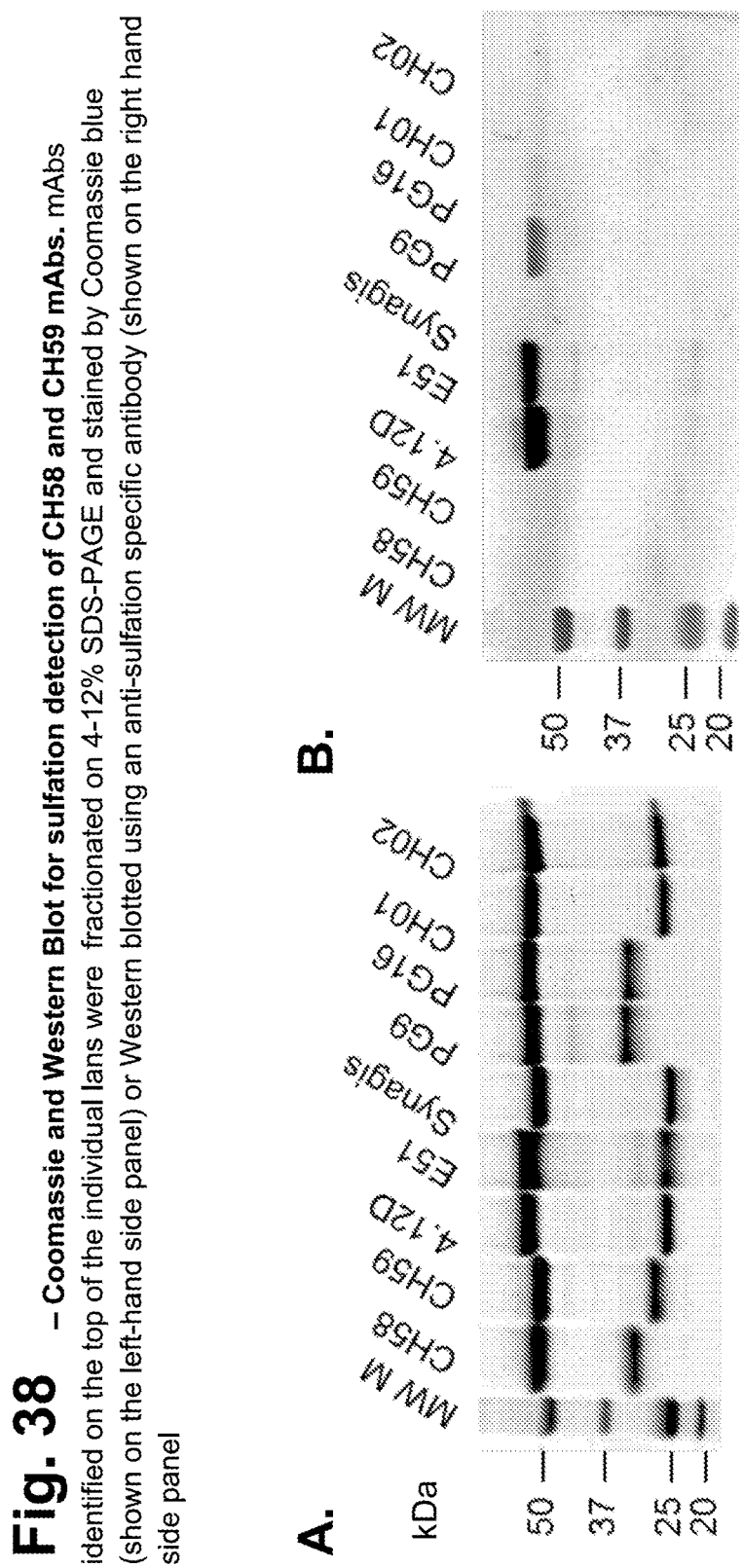
Fig. 38 – Coomassie and Western Blot for sulfation detection of CH58 and CH59 mAbs. mAbs identified on the top of the individual lans were fractionated on 4-12% SDS-PAGE and stained by Coomassie blue (shown on the left-hand side panel) or Western blotted using an anti-sulfation specific antibody (shown on the right hand side panel

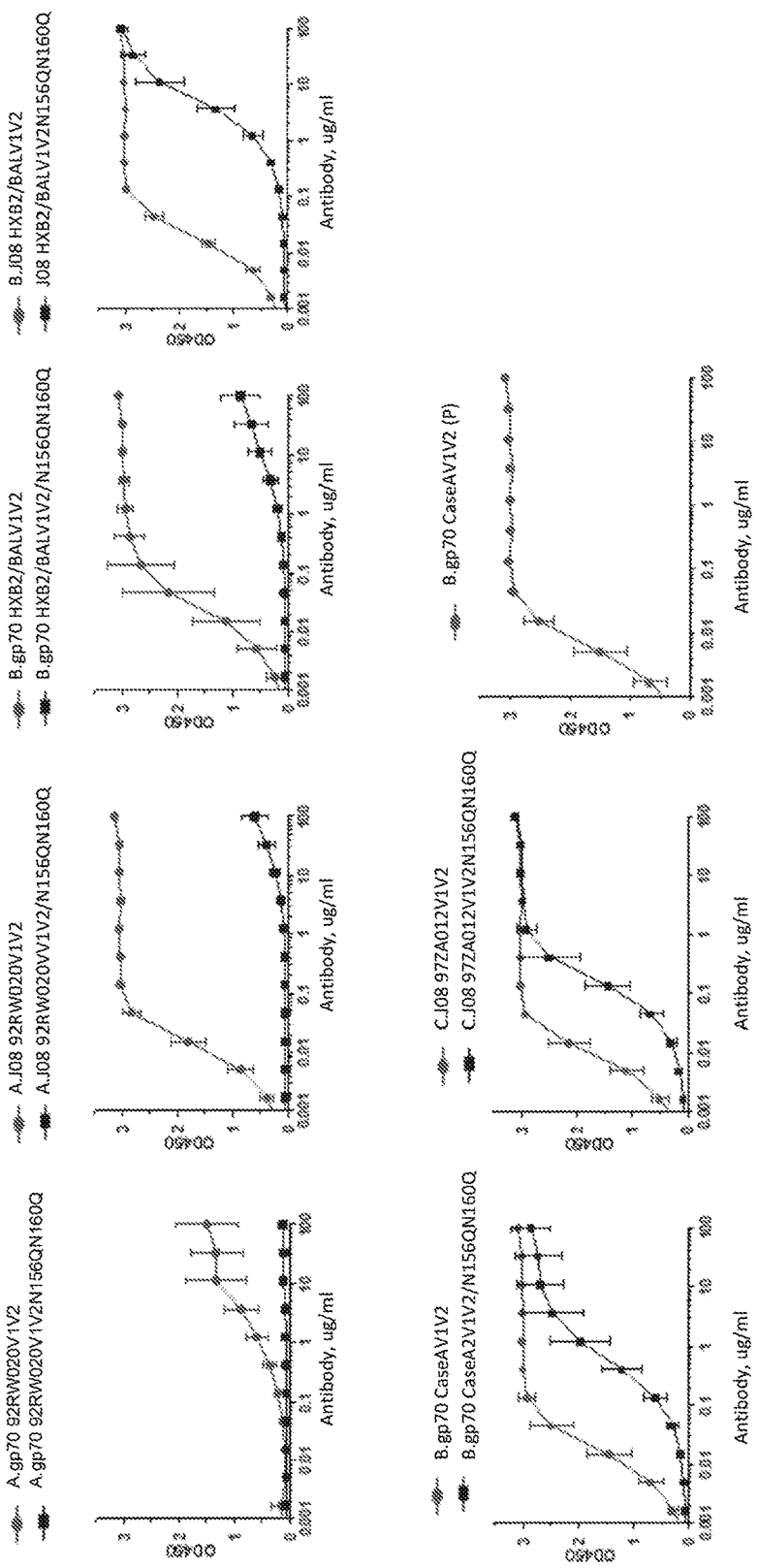

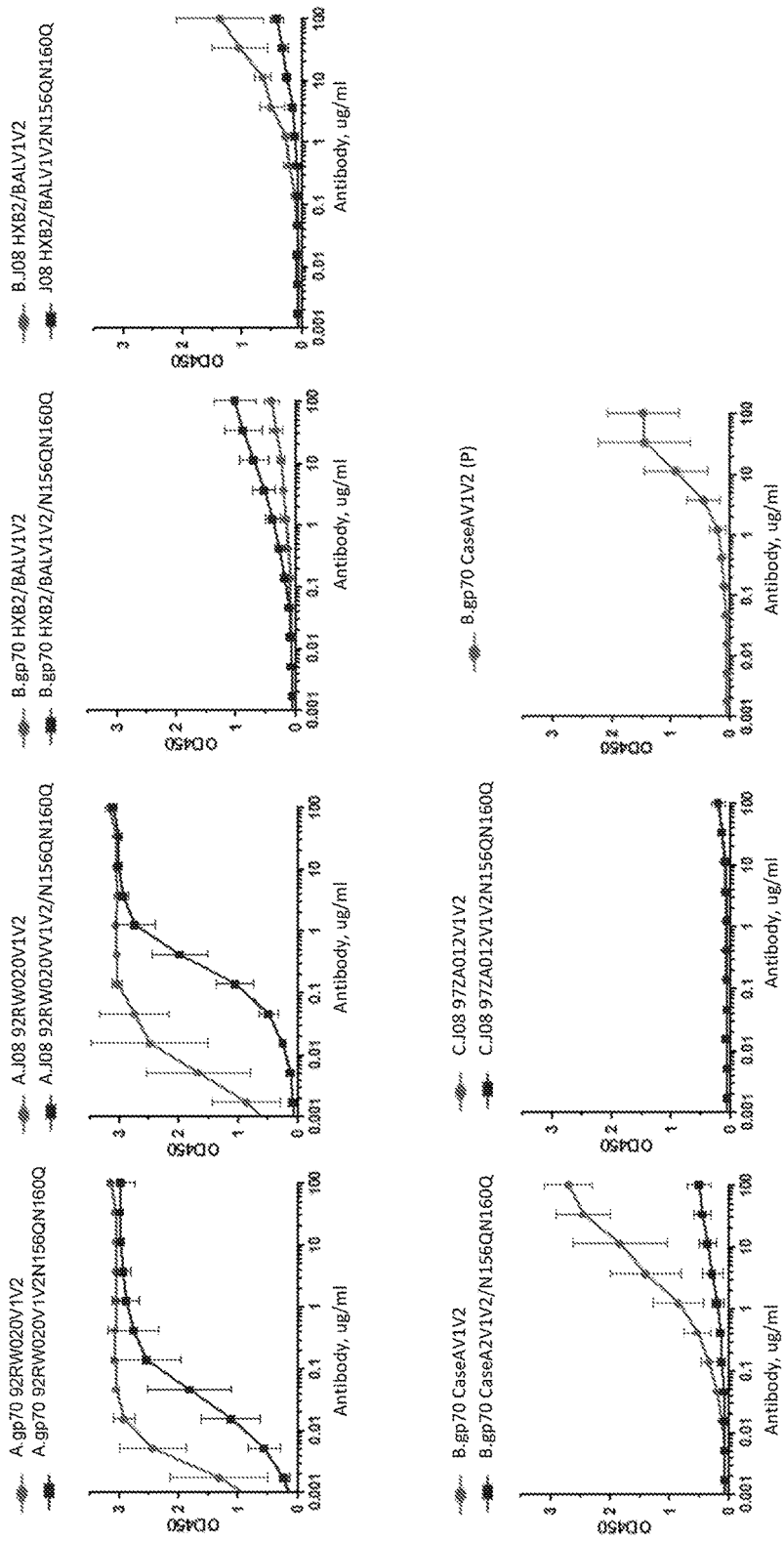
Fig. 40 — Binding of CH58 mAb to V2 constructs. Serial dilutions ranging from 100 μg/ml to 0.001 μg/ml of mAb CH58 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

Fig. 41 – Binding of CH59 mAb to V2 constructs. Serial dilutions ranging from 100 µg/ml to 0.001 µg/ml of mAb CH59 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

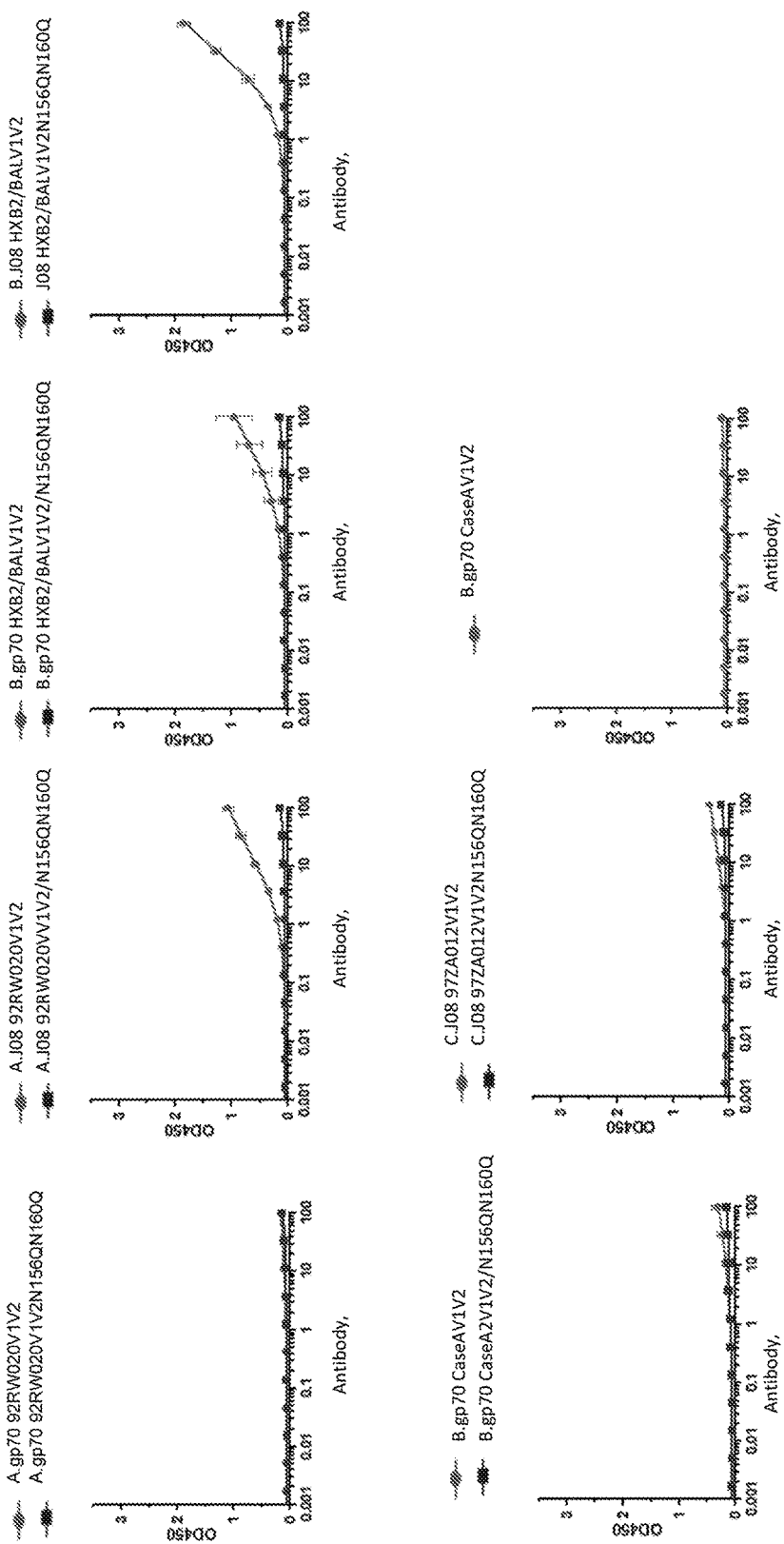
Fig. 42 – Binding of PG9 mAb to V2 constructs. Serial dilutions ranging from 100 μg/ml to 0.001 μg/ml of mAb PG9 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

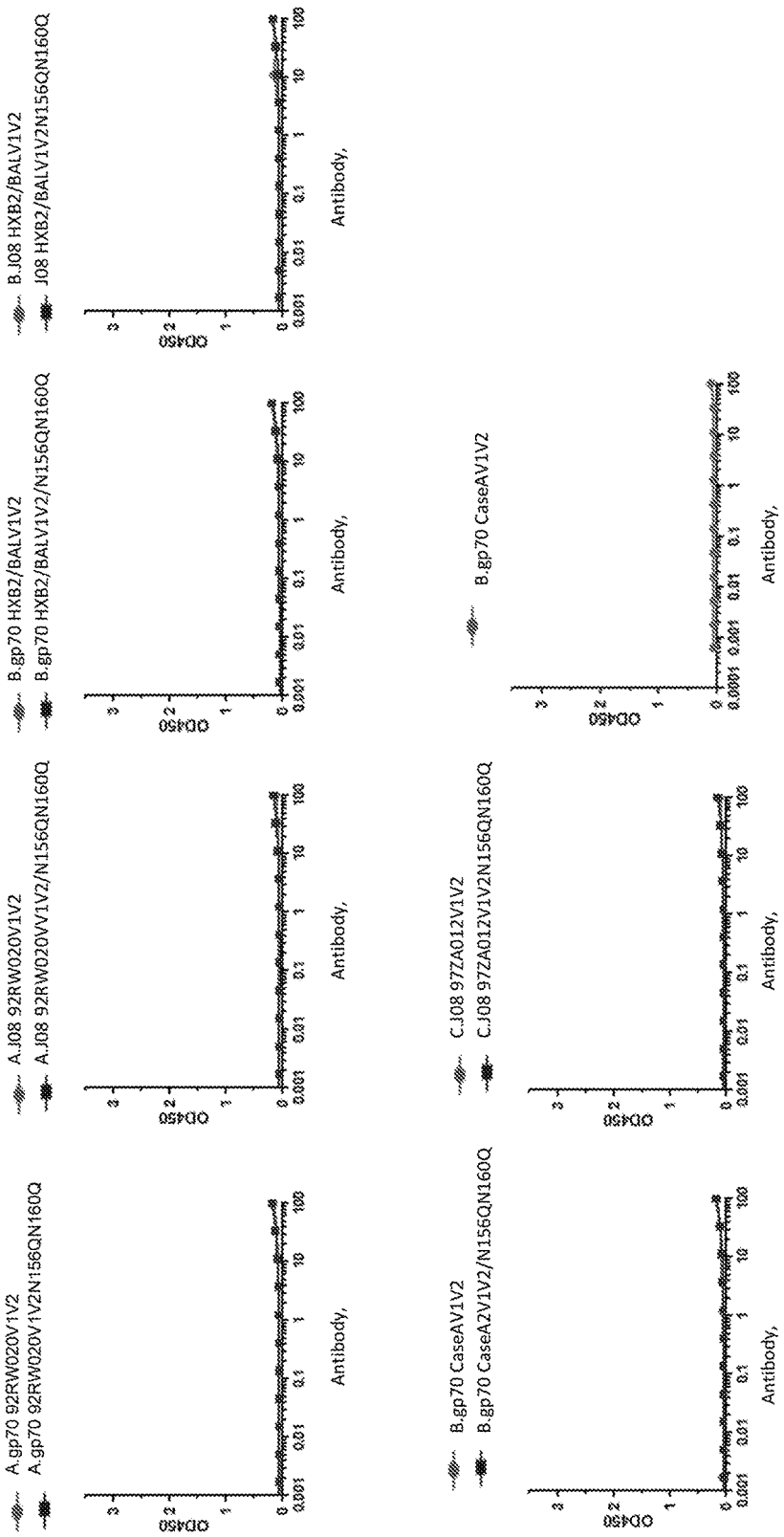
Fig. 43 – Binding of PG16 mAb to V2 constructs. Serial dilutions ranging from 100 µg/ml to 0.001 µg/ml of mAb PG16 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

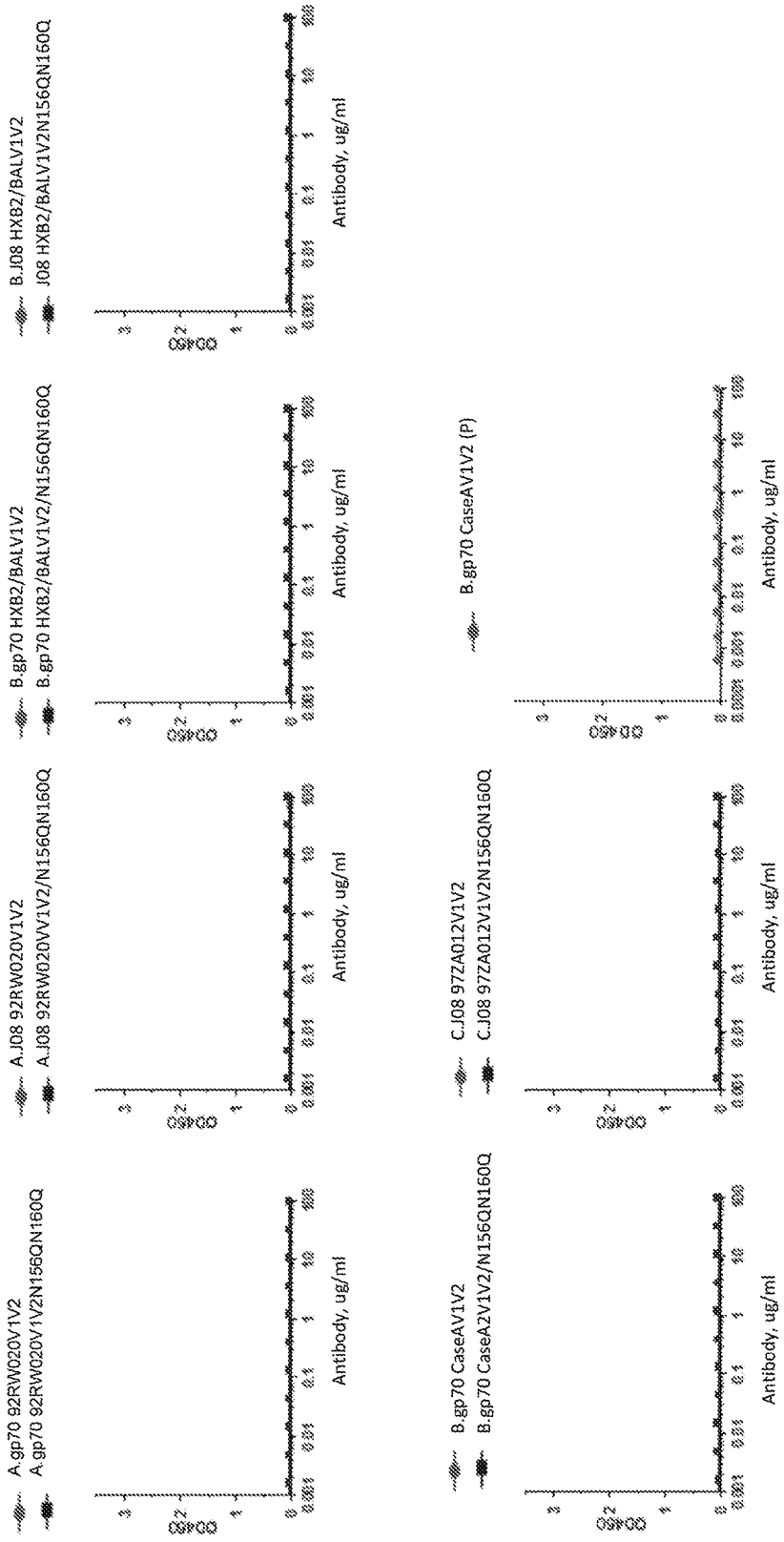
Fig. 44 – Binding of CH01 mAb to V2 constructs. Serial dilutions ranging from 100 μg/ml to 0.001 μg/ml of mAb CH01 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

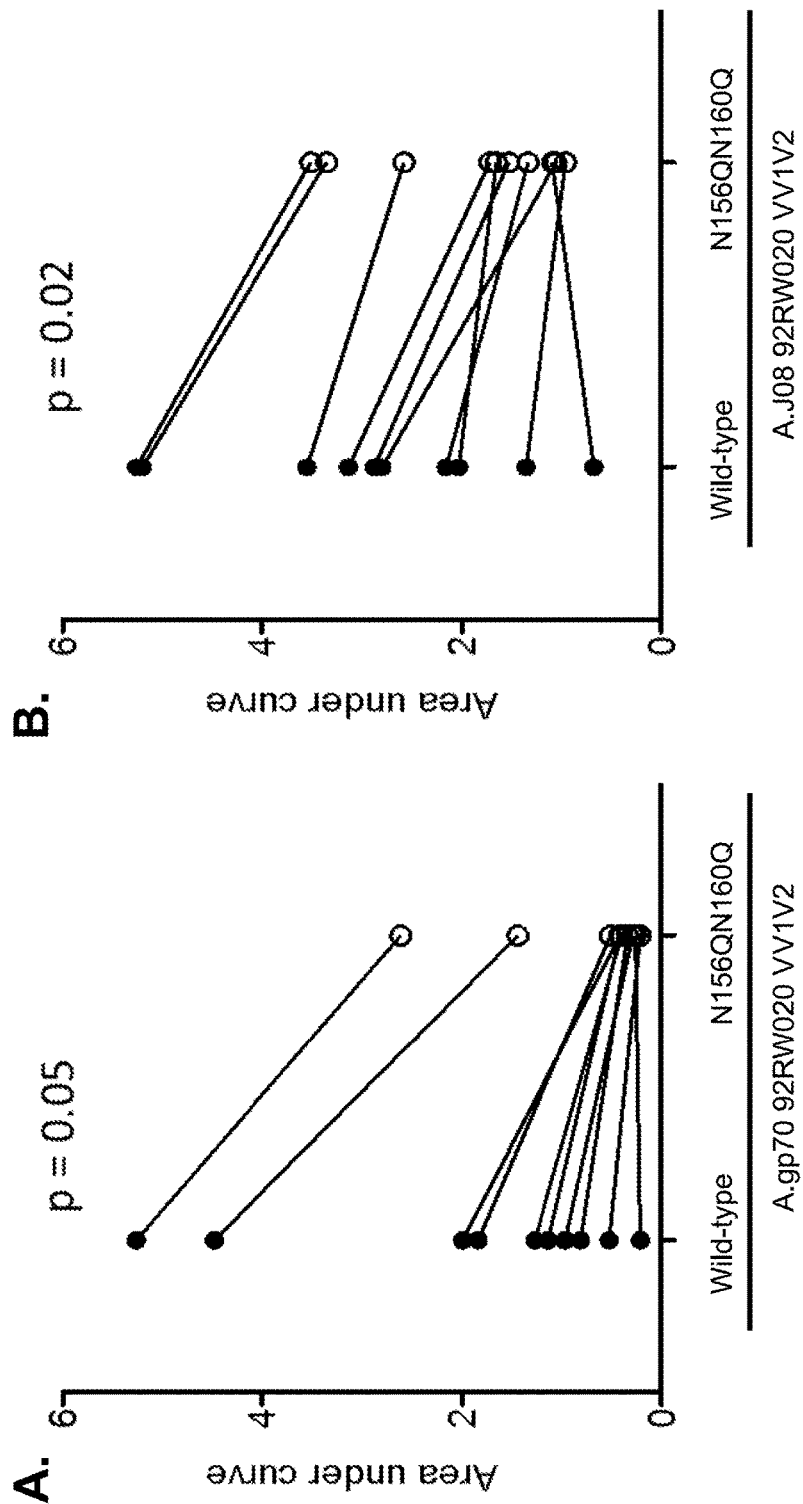

Fig. 45 Anti-HIV-1 V1V2 responses in rhesus macaques raised by immunization with E.A244 gp120 protein. Plasma samples from rhesus macaques immunized with E.A44 gp120 were tested for binding to recombinant HIV-1 clade A (92RW020 V1V2 protein scaffold on either gp70 (A) and J08 (B) and the same V1V2 mutant proteins with N156Q and N160Q mutations. The reactivity of the plasma plotted as area under curve is shown on the y axis.

Binding of RV144 mAbs CH58 and CH58_RUA to HIV-1 Envs. Serial dilutions ranging from 100 µg/ml to 0.001 µg/ml of mAb CH58 and CH58_RUA were tested for binding to a panel of 43 HIV-1 Envs indicted on the y axis in ELISA. Shown is the binding of mAbs CH58 and CGH58_RUA (indicated on the top of the graphs) expressed as OD405 nm reading at 10ug/ml (x axis). Data shown are the representative of three experiments.

Binding of RV144 mAbs CH58 and CH58_RUA to HIV-1 Envs. Serial dilutions ranging from 100 µg/ml to 0.001 µg/ml of mAb CH58 and CH58_RUA were tested for binding to a panel of 43 HIV-1 Envs indicted on the y axis in ELISA. Shown is the binding of mAbs CH58 and CGH58_RUA (indicated on the top of the graphs) expressed as OD405 nm reading at 10ug/ml (x axis). Data shown are the representative of three experiments.

Binding of RV144 mAbs CH59 and CH59_RUA to HIV-1 Envs. Serial dilutions ranging from 100 µg/ml to 0.001 µg/ml of mAb CH59 and CH59_RUA were tested for binding to a panel of 43 HIV-1 Envs indicted on the y axis in ELISA. Shown is the binding of mAbs CH59 and CH59_RUA (indicated on the top of the graphs) expressed as OD405 nm reading at 10ug/ml (x axis). Data shown are the representative of three experiments."

Binding of RV144 mAbs CH59 and CH59_RUA to HIV-1 Envs. Serial dilutions ranging from 100 µg/ml to 0.001 µg/ml of mAb CH59 and CH59_RUA were tested for binding to a panel of 43 HIV-1 Envs indicted on the y axis in ELISA. Shown is the binding of mAbs CH59 and CH59_RUA (indicated on the top of the graphs) expressed as OD405 nm reading at 10ug/ml (x axis). Data shown are the representative of three experiments."

Binding of RV144 mAbs CH01 and CH01_RUA to HIV-1 Envs. Serial dilutions ranging from 100 μg/ml to 0.001 μg/ml of mAb CH01 and CH01_RUA were tested for binding to a panel of 43 HIV-1 Envs indicted on the y axis in ELISA. Shown is the binding of mAbs CH01 and CH01_RUA (indicated on the top of the graphs) expressed as OD405 nm reading at 10ug/ml (x axis). Data shown are the representative of three experiments."

OD 405nm

Binding of RV144 mAbs CH01 and CH01_RUA to HIV-1 Envs. Serial dilutions ranging from 100 µg/ml to 0.001 µg/ml of mAb CH01 and CH01_RUA were tested for binding to a panel of 43 HIV-1 Envs indicted on the y axis in ELISA. Shown is the binding of mAbs CH01 and CH01_RUA (indicated on the top of the graphs) expressed as OD405 nm reading at 10ug/ml (x axis). Data shown are the representative of three experiments."

Binding of RV144 mAbs PG9 and PG9_RUA to HIV-1 Envs. Serial dilutions ranging from 100 µg/ml to 0.001 µg/ml of mAb PG19 and PG9_RUA were tested for binding to a panel of 43 HIV-1 Envs indicted on the y axis in ELISA. Shown is the binding of mAbs PG19 and PG9_RUA (indicated on the top of the graphs) expressed as OD405 nm reading at 10ug/ml (x axis). Data shown are the representative of three experiments."

Binding of RV144 mAbs PG9 and PG9_RUA to HIV-1 Envs. Serial dilutions ranging from 100 µg/ml to 0.001 µg/ml of mAb PG19 and PG9_RUA were tested for binding to a panel of 43 HIV-1 Envs indicted on the y axis in ELISA. Shown is the binding of mAbs PG19 and PG9_RUA (indicated on the top of the graphs) expressed as OD405 nm reading at 10ug/ml (x axis). Data shown are the representative of three experiments."

Binding of RV144 mAbs PG16 and PG116_RUA to HIV-1 Envs. Serial dilutions ranging from 100 µg/ml to 0.001 µg/ml of mAb PG16 and PG16_RUA were tested for binding to a panel of 43 HIV-1 Envs indicted on the y axis in ELISA. Shown is the binding of mAbs PG16 and PG16_RUA (indicated on the top of the graphs) expressed as OD405 nm reading at 10ug/ml (x axis). Data shown are the representative of three experiments."

Binding of RV144 mAbs PG16 and PG116_RUA to HIV-1 Envs. Serial dilutions ranging from 100 µg/ml to 0.001 µg/ml of mAb PG16 and PG16_RUA were tested for binding to a panel of 43 HIV-1 Envs indicted on the y axis in ELISA. Shown is the binding of mAbs PG16 and PG16_RUA (indicated on the top of the graphs) expressed as OD405 nm reading at 10ug/ml (x axis). Data shown are the representative of three experiments."

Binding of RV144 mAbs 697D and 697D_RUA to HIV-1 Envs. Serial dilutions ranging from 100 µg/ml to 0.001 µg/ml of mAb 697D and 697D_RUA were tested for binding to a panel of 43 HIV-1 Envs indicted on the y axis in ELISA. Shown is the binding of mAbs 697D and 697D_RUA (indicated on the top of the graphs) expressed as OD405 nm reading at 10ug/ml (x axis). Data shown are the representative of three experiments."

Binding of RV144 mAbs 697D and 697D_RUA to HIV-1 Envs. Serial dilutions ranging from 100 µg/ml to 0.001 µg/ml of mAb 697D and 697D_RUA were tested for binding to a panel of 43 HIV-1 Envs indicted on the y axis in ELISA. Shown is the binding of mAbs 697D and 697D_RUA (indicated on the top of the graphs) expressed as OD405 nm reading at 10ug/ml (x axis). Data shown are the representative of three experiments."

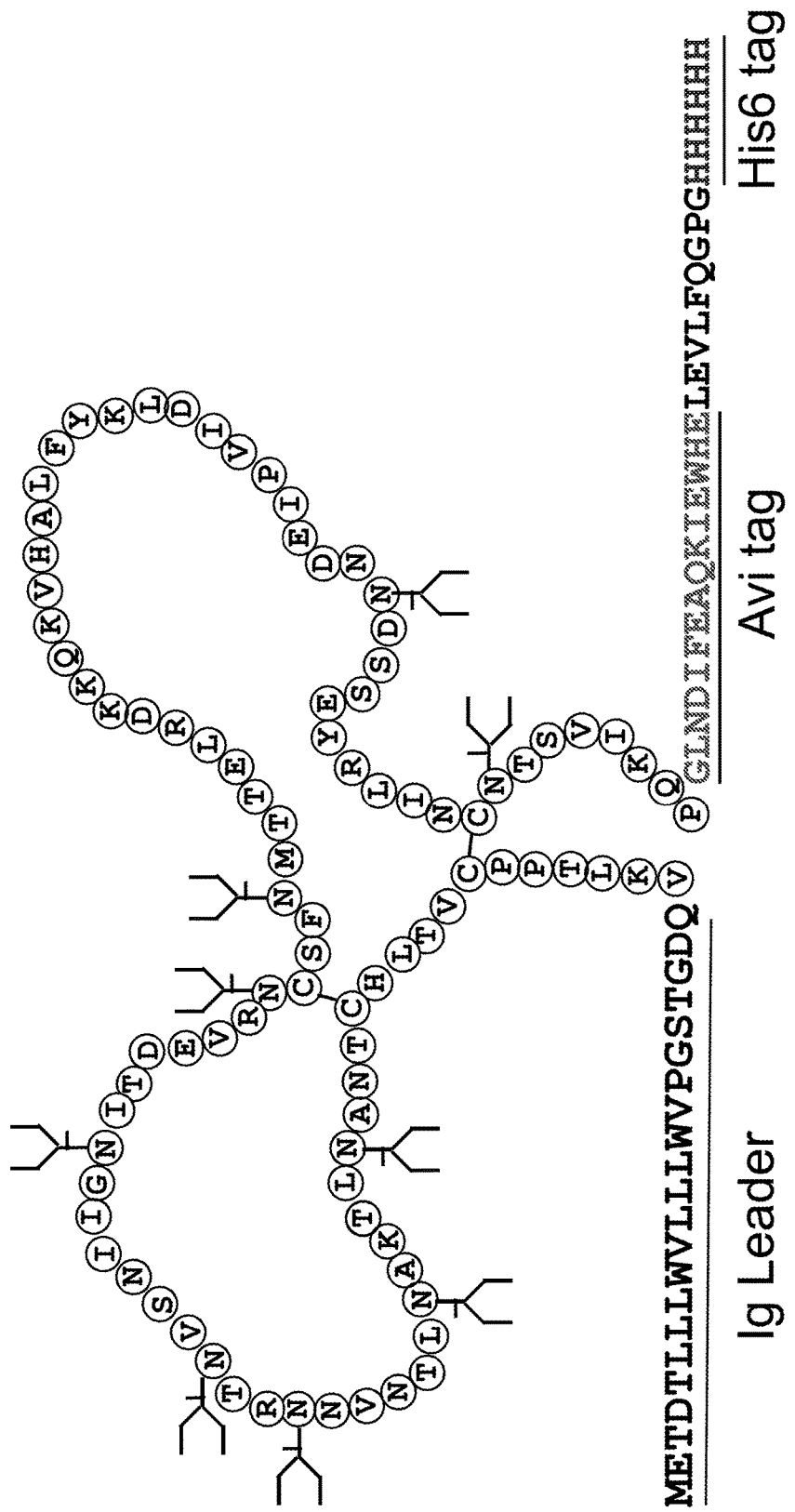
Fig. 47 Schematic representation of the design of HIV-1 Env V1V2_Tags. Gene constructs of HIV-1 V1V2-Tags were made

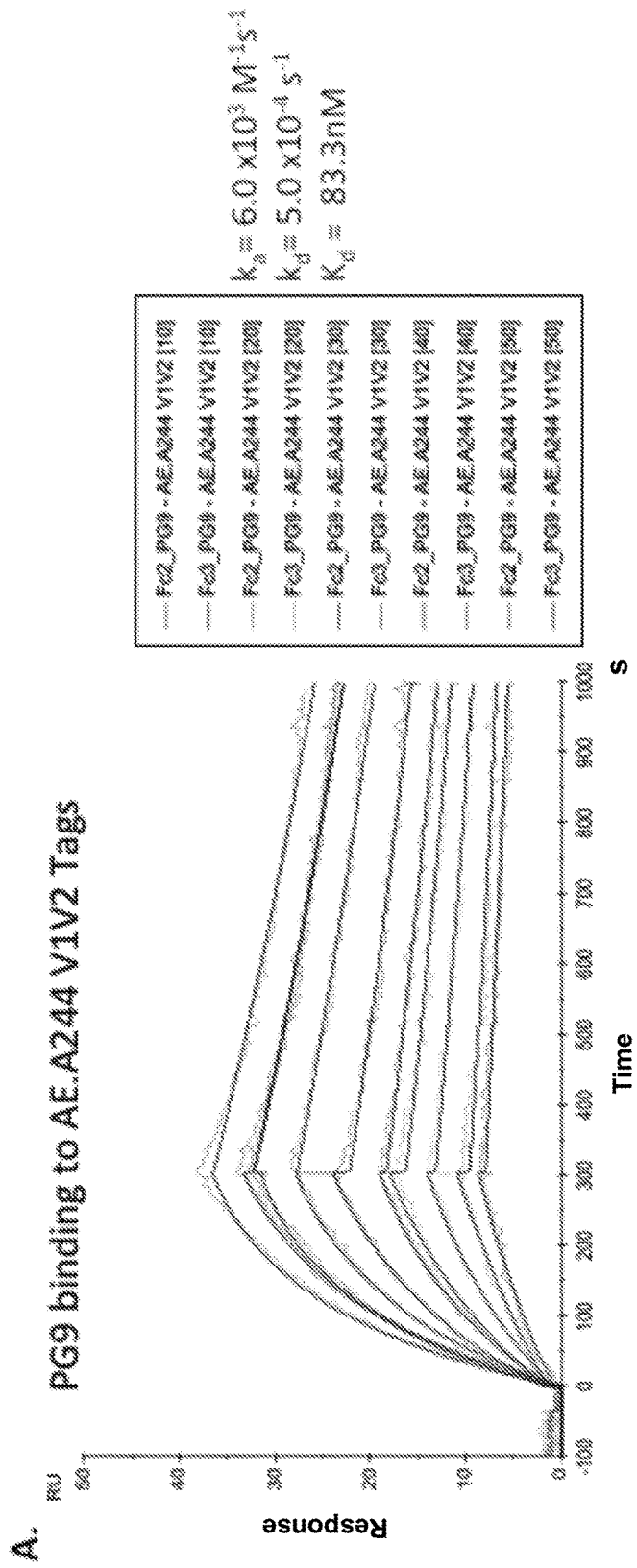

Fig. 48 Binding of V2 and V2V3 conformational mAbs PG9 and CH58 to AE.A244 V1V2 Tags protein.
Each of the mAbs was captured on an anti-Fc antibody immobilized sensor surface to about 100-125 RU. AE.A244 V1V2 tags protein was injected as analyte at concentrations ranging from 0.5 - 3ug/mL (CH58), or 10-50 ug/mL (PG9). A negative control mAb (Synagis) was used with each mAb to subtract non-specific binding. Curve fitting to a 1:1 Langmuir model included binding data from two independent flow cells with the same mAb captured.

Slower on-rate (~40-fold) of PG9 likely due to additional requirement of glycan interactions

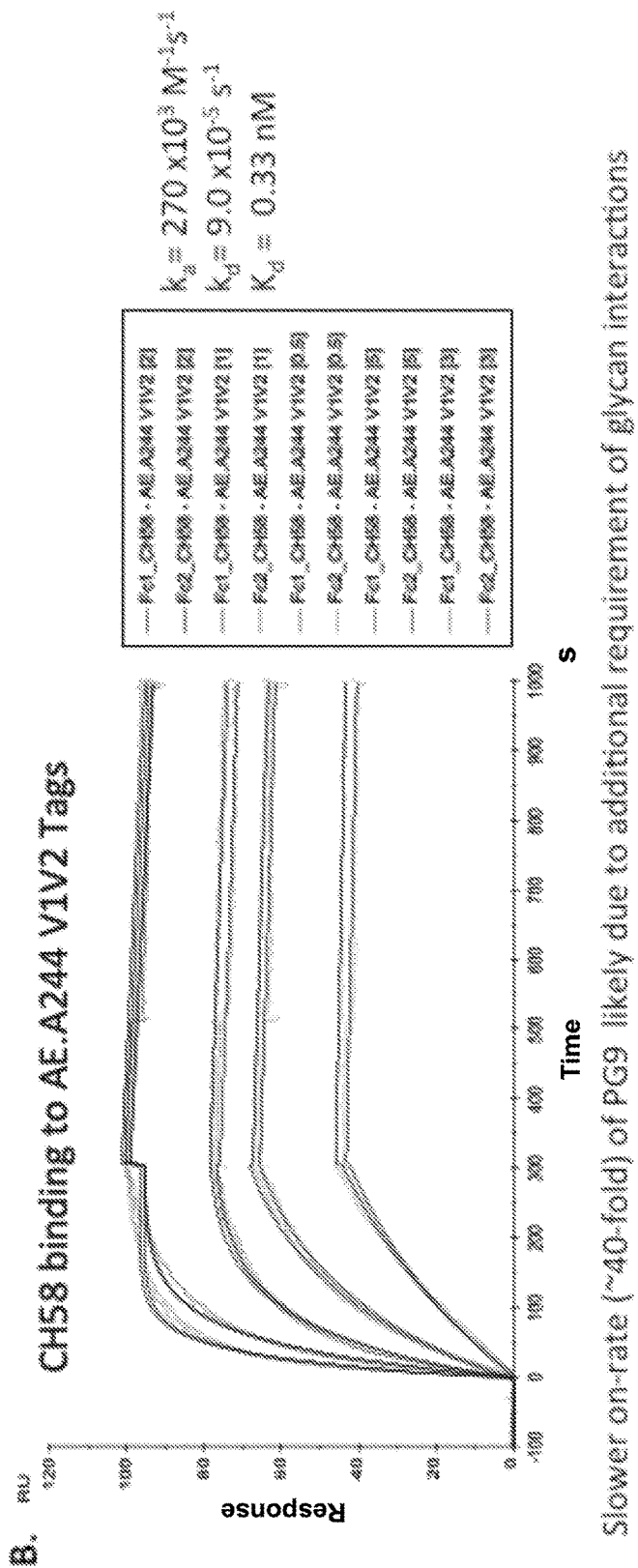

Fig. 48 Binding of V2 and V2V3 conformational mAbs PG9 and CH58 to AE.A244 V1V2 Tags protein. Each of the mAbs was captured on an anti-Fc antibody immobilized sensor surface to about 100-125 RU. AE.A244 V1V2 tags protein was injected as analyte at concentrations ranging from 0.5 - 3ug/mL (CH58), or 10-50 ug/mL (PG9). A negative control mAb (Synagis) was used with each mAb to subtract non-specific binding. Curve fitting to a 1:1 Langmuir model included binding data from two independent flow cells with the same mAb captured.

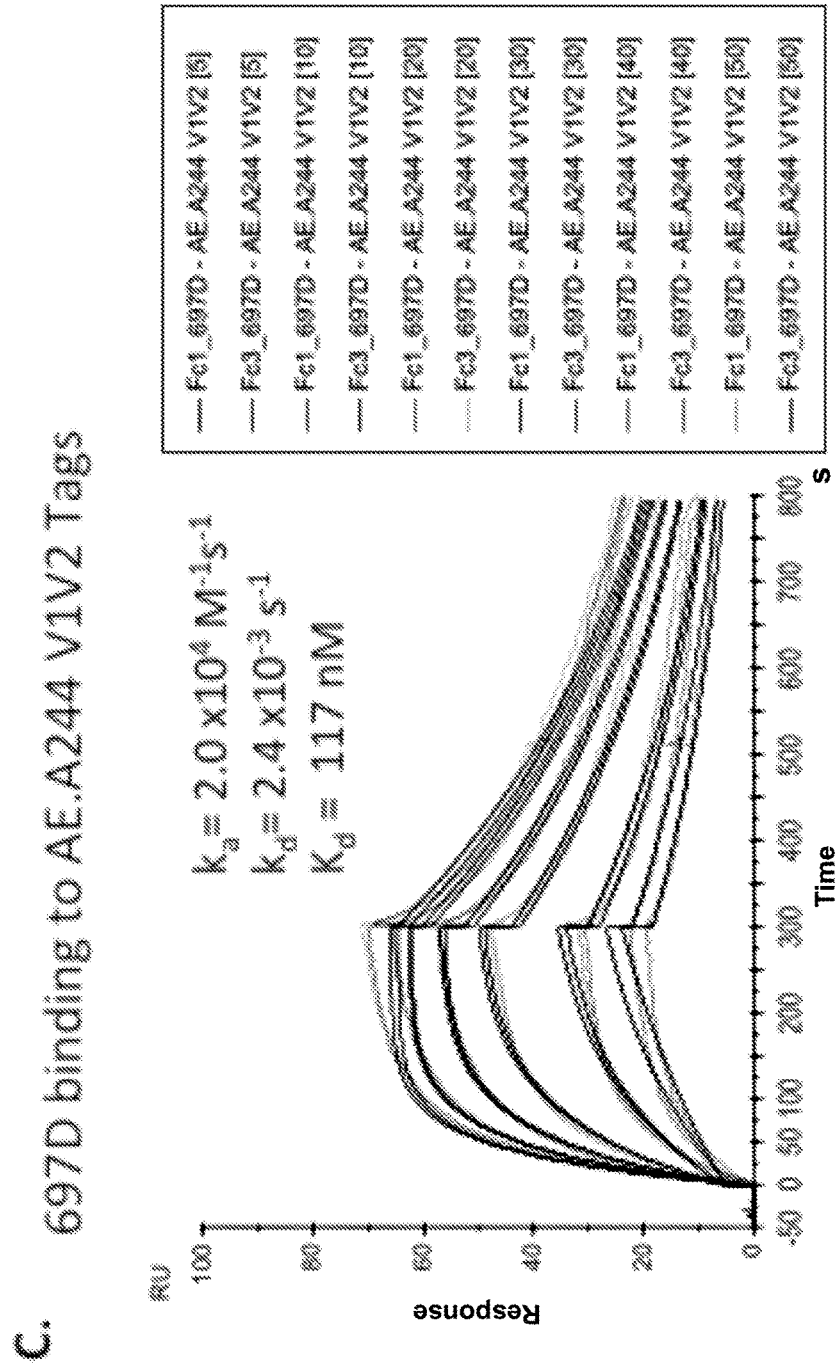

Fig. 48 Binding of mAbs 697D and CH01 to AE.A244 V1V2 Tags protein. Each of the mAbs was captured on an anti-Fc antibody immobilized sensor surface to about 100-125 RU. AE.A244 V1V2 tags protein was injected as analyte at concentrations ranging from 0.5 - 3ug/ml (CH58), or 10-50 ug/mL (CH01). A negative control mAb (Synagis) was used with each mAb to subtract non-specific binding. Curve fitting to a 1:1 Langmuir model included binding data from two independent flow cells with the same mAb captured.

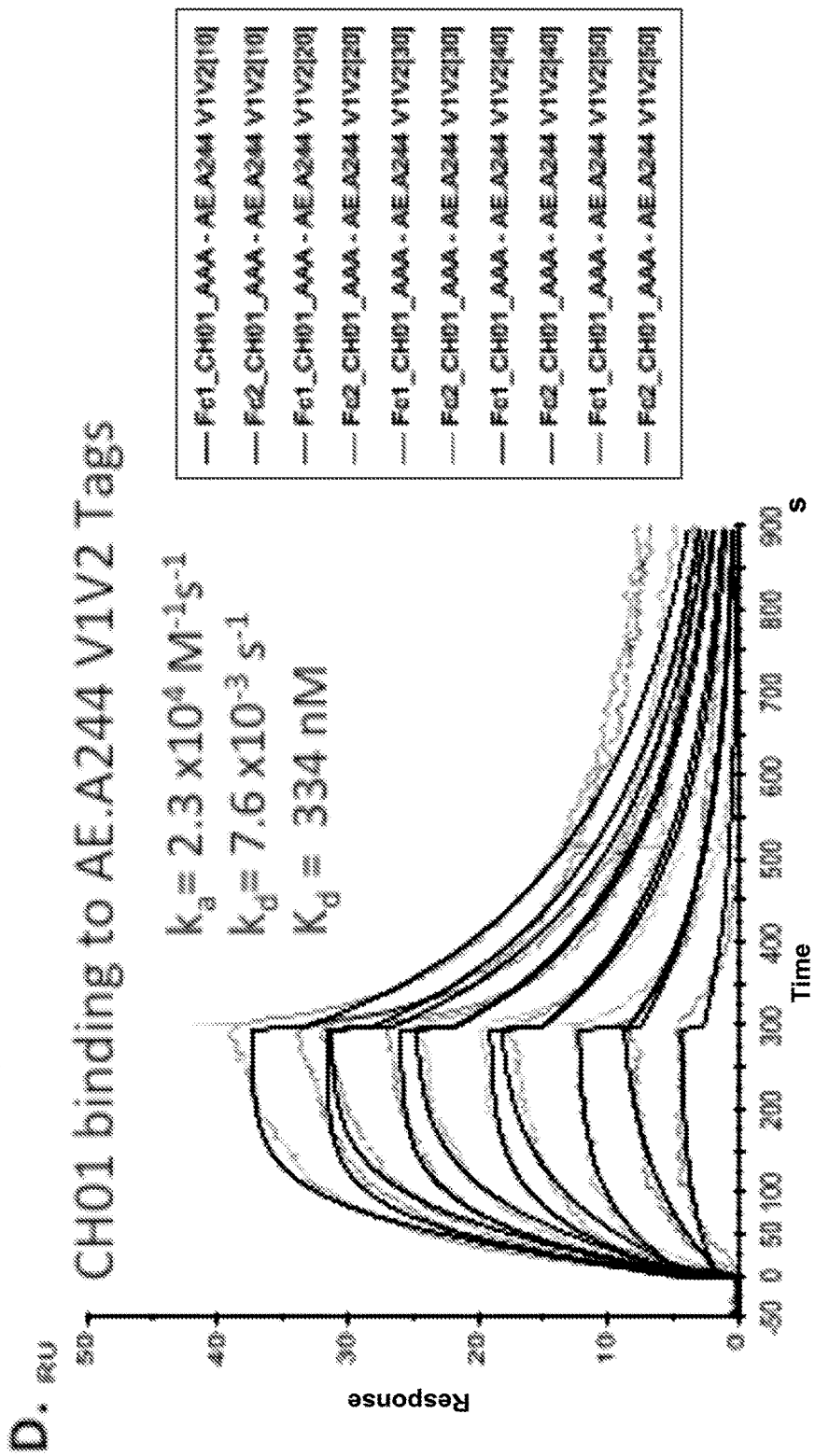

Fig. 48 Binding of mAbs 697D and CH01 to AE.A244 V1V2 Tags protein. Each of the mAbs was captured on an anti-Fc antibody immobilized sensor surface to about 100-125 RU. AE.A244 V1V2 tags protein was injected as analyte at concentrations ranging from 0.5 - 3ug/mL (CH58), or 10-50 ug/mL (CH01). A negative control mAb (Synagis) was used with each mAb to subtract non-specific binding. Curve fitting to a 1:1 Langmuir model included binding data from two independent flow cells with the same mAb captured.

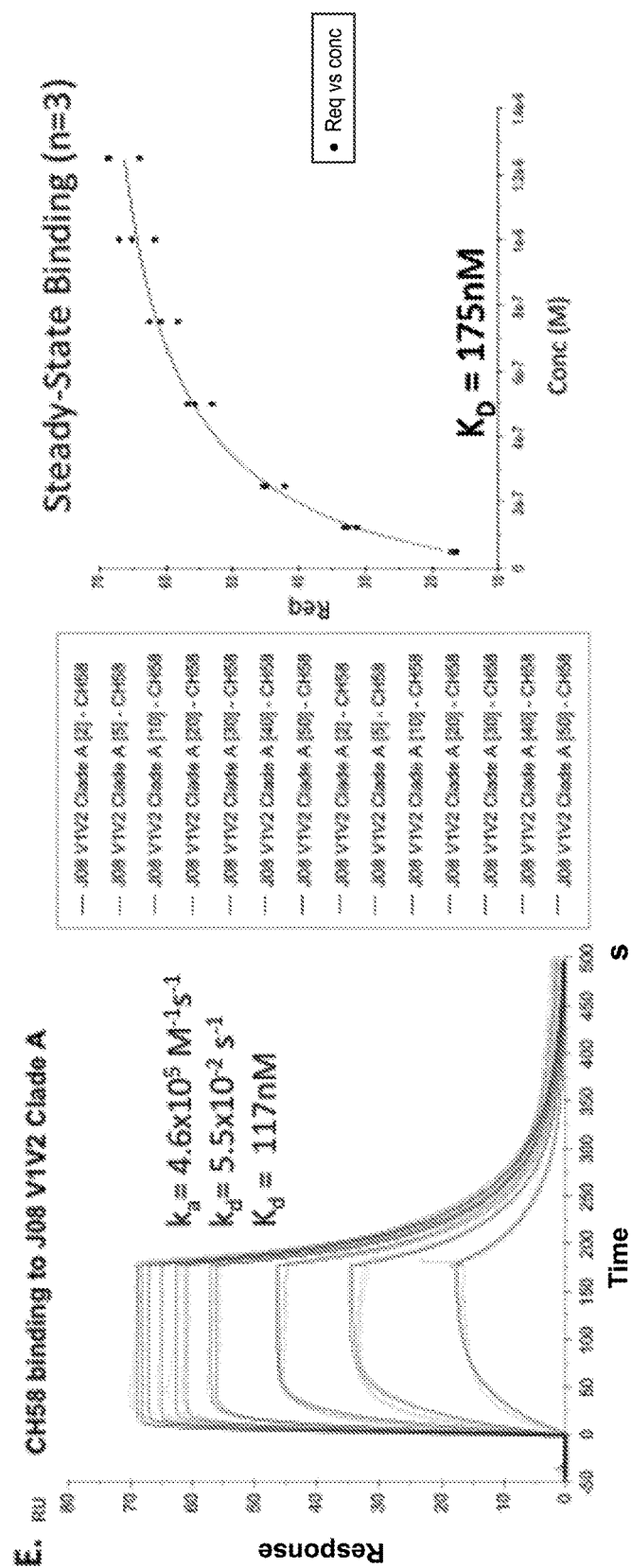

Fig. 48 Binding of mAb CH58 to J08 A.92RW020V1V2 and J08 A.92RW020V1V2 N156QN160Q proteins. mAb CH58 was captured on an anti-Fc antibody immobilized sensor surface to about 100-125 RU. J08 A.92RW020V1V2 and J08 A.92RW020V1V2 N156QN160Q proteins were injected as analyte at concentrations ranging from 0.5 - 3ug/mL. A negative control mAb (Synagis) was used with each mAb to subtract non-specific binding. Curve fitting to a 1:1 Langmuir model included binding data from two independent flow cells with the same mAb captured.

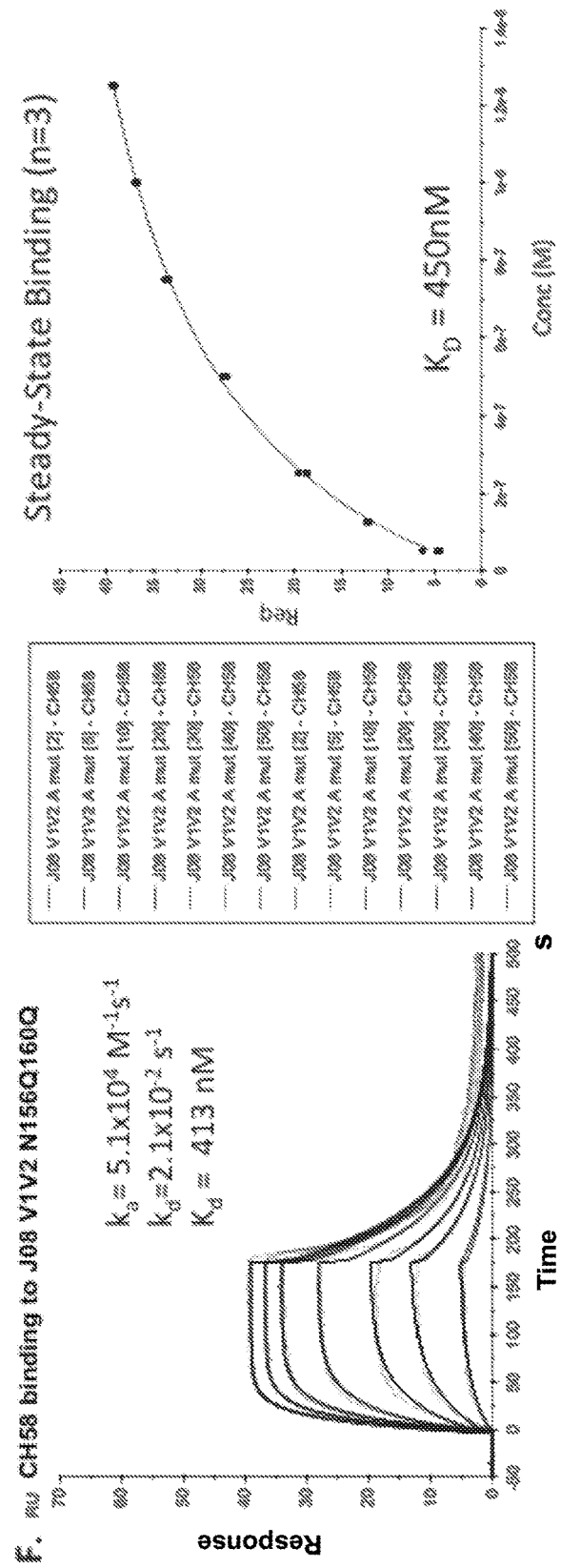

Fig. 48 Binding of mAb CH58 to J08 A.92RW020V1V2 and J08 A.92RW020V1V2 N156QN160Q proteins. mAb CH58 was captured on an anti-Fc antibody immobilized sensor surface to about 100-125 RU. J08 A.92RW020V1V2 and J08 A.92RW020V1V2 N156QN160Q proteins were injected as analyte at concentrations ranging from 0.5 - 3ug/mL. A negative control mAb (Synagis) was used with each mAb to subtract non-specific binding. Curve fitting to a 1:1 Langmuir model included binding data from two independent flow cells with the same mAb captured.

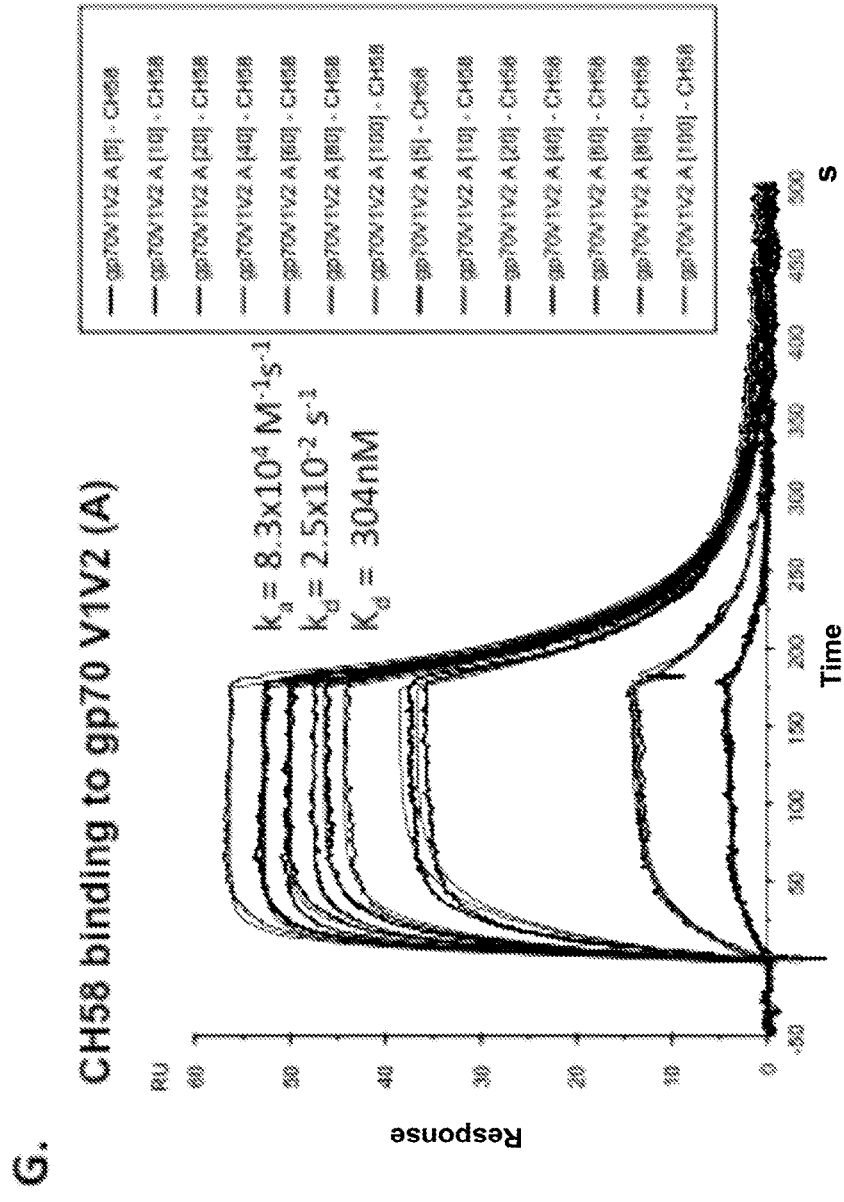
Fig. 48 Binding of V2 mAb CH58 to gp70 A.92RW020V

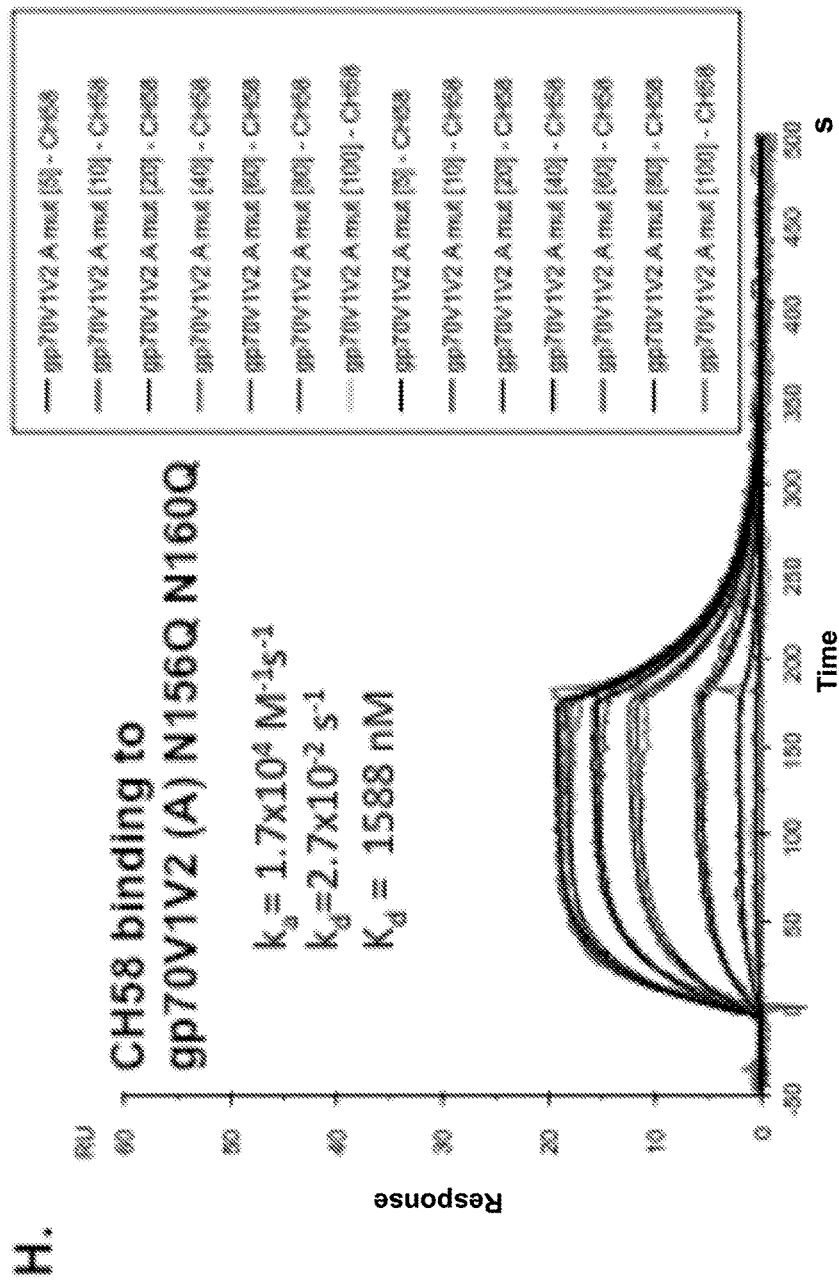

Fig. 48 Binding of V2 mAb CH58 to gp70 A.92RW020V1V2 and gp70 A.92RW020V1V2 N156QN160Q proteins. CH58 was captured on an anti-Fc antibody immobilized sensor surface to about 100-125 RU. gp70 A.92RW020V1V2 and gp70 A.92RW020V1V2N156QN160Q proteins were injected as analyte at concentrations ranging from 0.5 - 3ug/mL. A negative control mAb (Synagis) was used with each mAb to subtract non-specific binding. Curve fitting to a 1:1 Langmuir model included binding data from two independent flow cells with the same mAb captured.

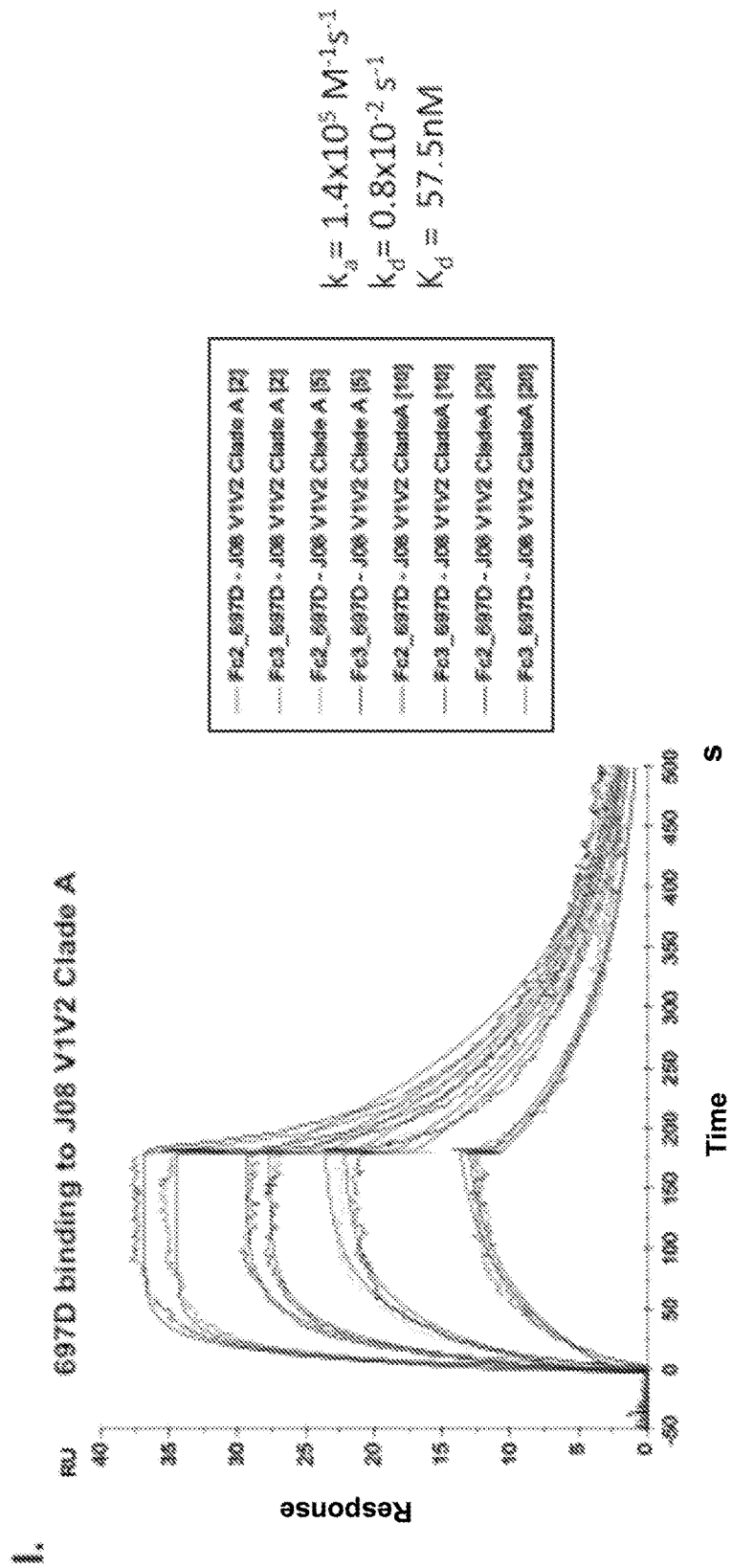
Fig. 48 Binding of V2 mAb 697D to J08 A.92RW020V1V2 and gp70 C

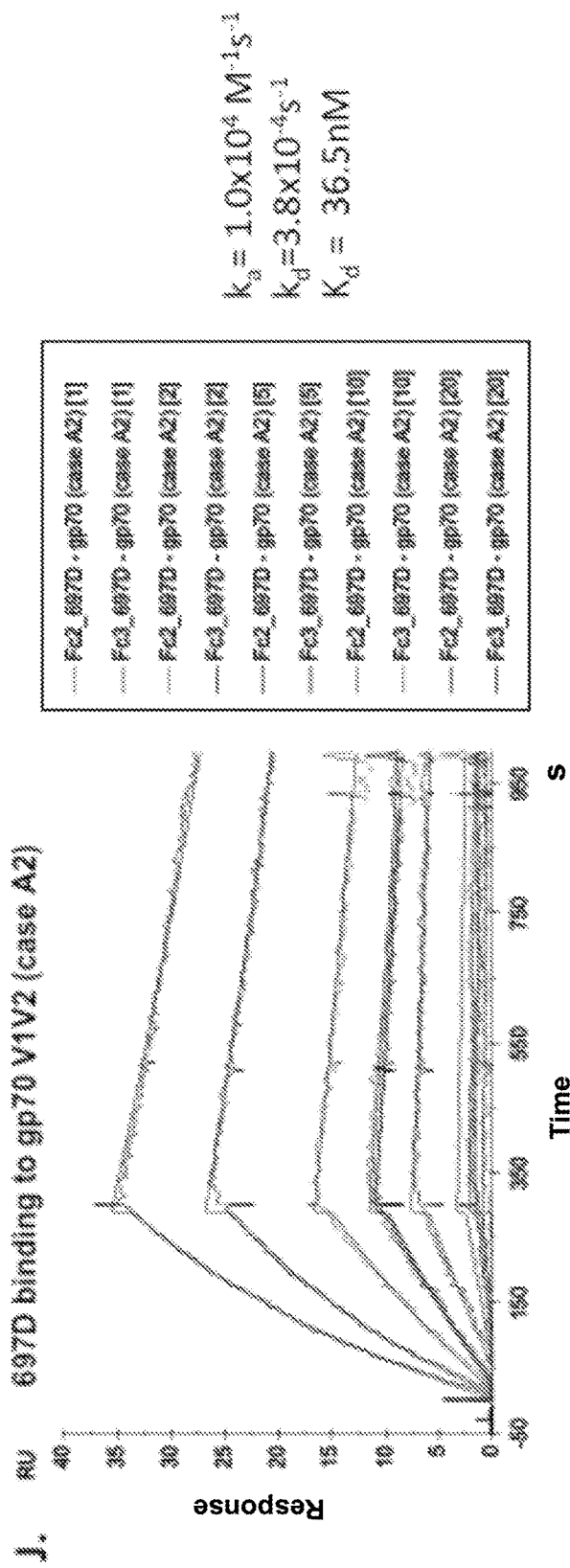

Fig. 48  Binding of V2 mAb 697D to J08 A.92RW020V1V2 and gp70 CaseA2 V1V2. mAb697D was captured on an anti-Fc antibody immobilized sensor surface to about 100-125 RU. J08 A.92RW020V1V2 proteins were injected as analyte at concentrations ranging from 5-50ug/mL. A negative control mAb (Synagis) was used with each mAb to subtract non-specific binding. Curve fitting to a 1:1 Langmuir model included binding data from two independent flow cells with the same mAb captured.

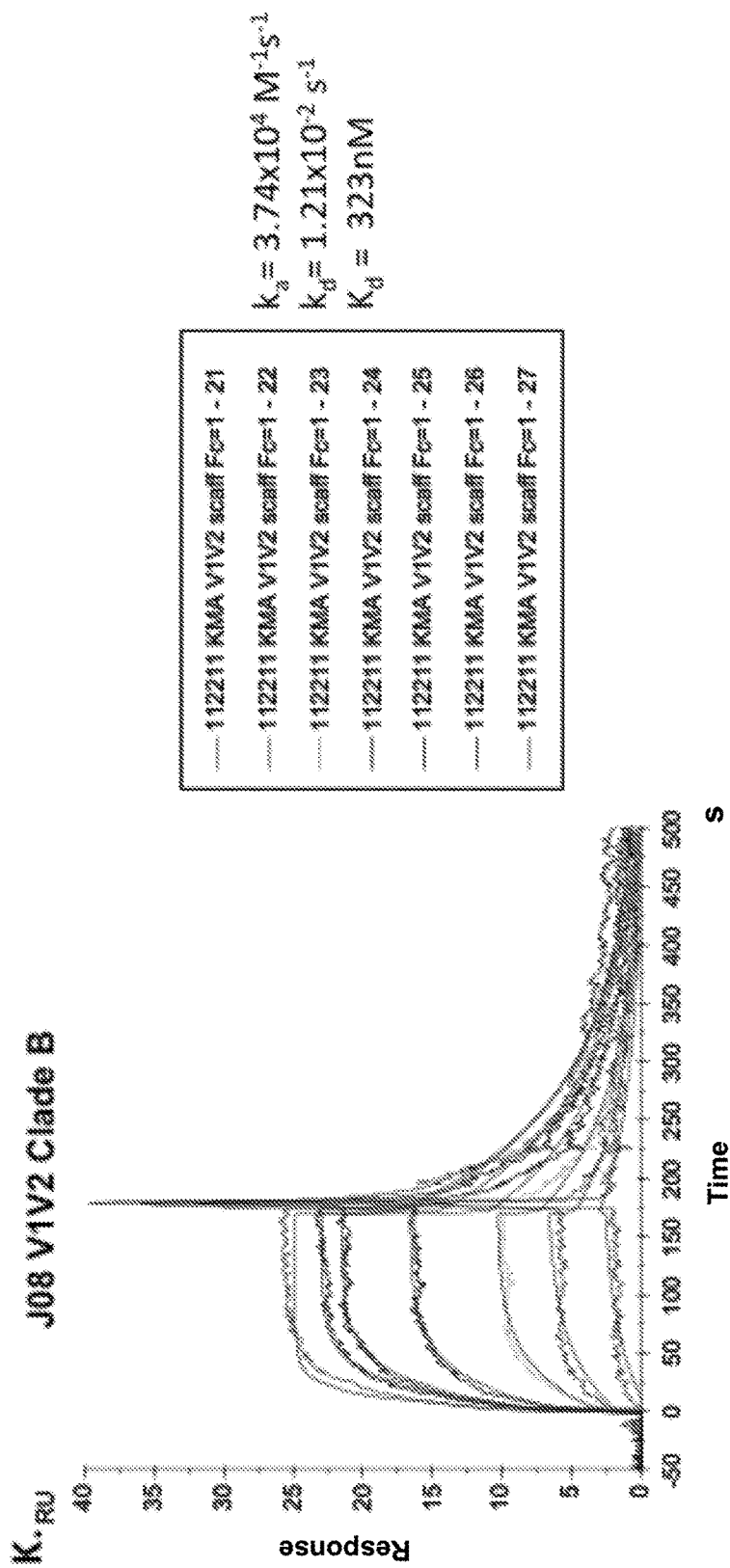

Fig. 48 Binding of mAb CH58 to J08.A.92RW020V1V2 and J08.A.92RW020V1V2 N156N160Q Tags proteins. mAb CH58 was captured on an anti-Fc antibody immobilized sensor surface to about 100-125 RU. J08.A.92RW020V1V2 and J08.A.92RW020V1V2 N156N160Q Tags were injected as analyte at concentrations ranging from 0.5 - 3ug/mL. negative control mAb (Synagis) was used to subtract non-specific binding. Curve fitting to a 1:1 Langmuir model included binding data from two independent flow cells with the same mAb captured.

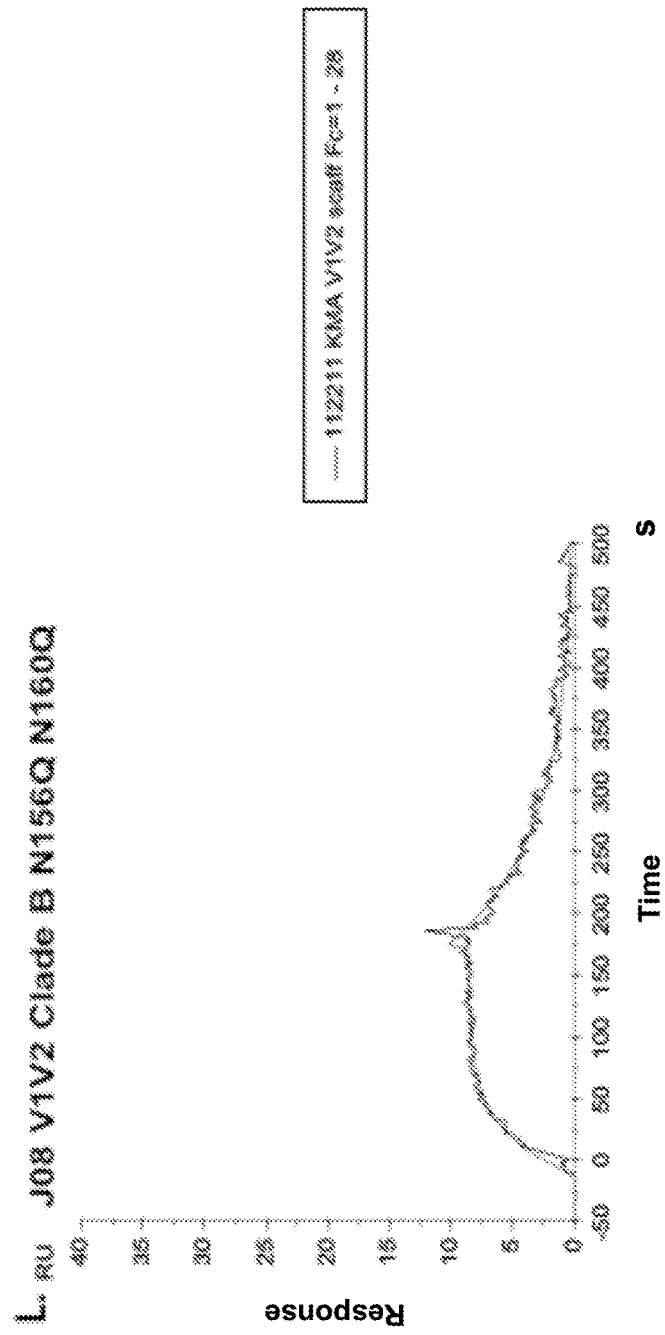
Fig. 48 Binding of mAb CH58 to J08.A.92RW020V1V2 and J08.A.92RW020V1V2 N156N160Q Tags proteins. mAb CH58 was captured on an anti-Fc antibody immobilized sensor surface to about 100-125 RU. J08.A.92RW020V1V2 and J08.A.92RW020V1V2 N156N160Q Tags were injected as analyte at concentrations ranging from 0.5 - 3ug/mL. negative control mAb (Synagis) was used to

Impact of ALVAC gp120 AE/B Immunogenicity and Correlates

Follow-up Studies: RV144 Vaccine Elicited Antibodies

- Is there evidence that the RV144 Env IgA correlate involves interactions of antibodies with affinities for different Fc receptors?

- Does the vaccine elicited IgG subclass profile, specifically IgG3 indicate a potentially protective response?

HIV VACCINE
TRIALS NETWORK

The HIV Vaccine Trials Network is supported through a cooperative agreement with the National Institute of Allergy and Infectious Diseases.

Fig. 49 cont'd-2

IgA and ADCC Correlates of Risk in RV144

- IgA levels of Env binding antibodies directly correlated with infection risk (higher IgA, higher risk of infection).

- ADCC activity alone did not correlate with infection risk.

- High ADCC with low IgA did inversely correlate with infection risk (high ADCC, low IgA, low infection risk).

HIV VACCINE
TRIALS NETWORK

The HIV Vaccine Trials Network is supported through a cooperative agreement with the National Institute of Allergy and Infectious Diseases.

Fig. 49 cont'd-3

Hypothesis: Monomeric Plasma IgA gp120 Antibodies block IgG ADCC

<u>Rationale</u>

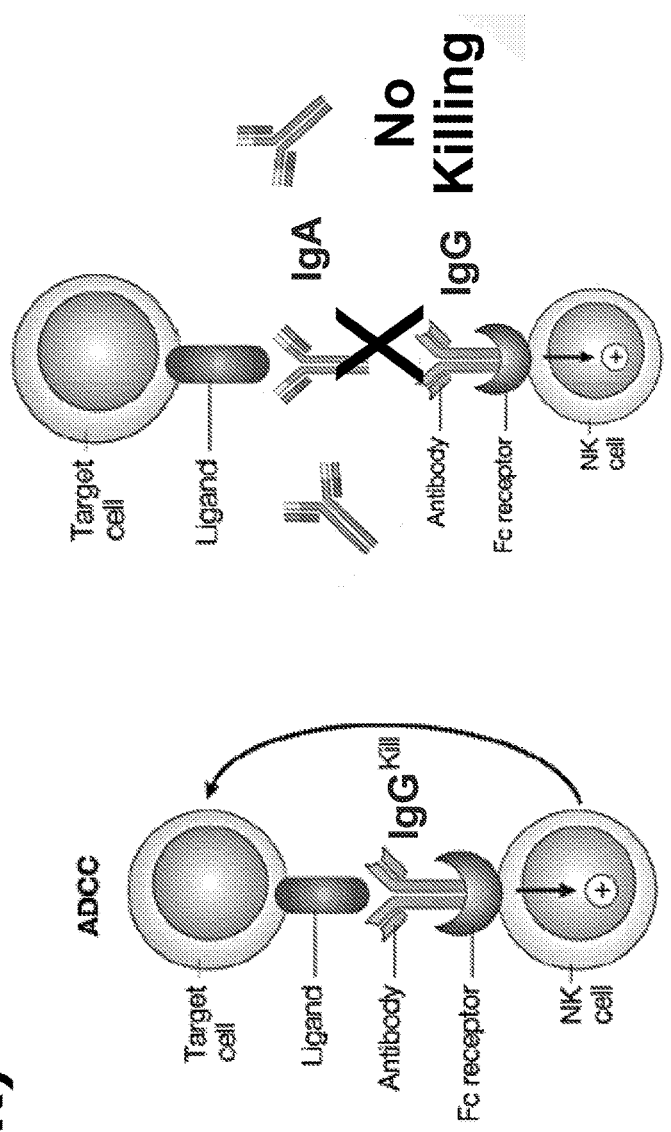
Fig. 49 cont'd-4. Model of Monomeric Plasma IgA gp120 Antibodies blocking IgG ADCC (via NK)

Fig. 49 cont'd-5

Prior Reports of IgA Blocking Functional IgG Activity

- IgA inhibits IgG phagocytosis (Russell J.Leuko Bio 1995) (Wilton, CEI 1978).

- Blocks IgG mediated complement dependent bacteriolysis N. Meningitidis (Griffis JI, 1975, 1983).

- Serum IgA (from nasopharyngeal carcinoma) block IgG mediated ADCC (Pearson 1981 Int. J. Cancer).

HIV VACCINE
TRIALS NETWORK

The HIV Vaccine Trials Network is supported through a cooperative agreement with the National Institute of Allergy and Infectious Diseases.

Fig. 49 cont'd-6

How to test the hypothesis that some HIV-1 specific IgAs can block IgG function?

HIV VACCINE
TRIALS NETWORK

The HIV Vaccine Trials Network is supported through a cooperative agreement with the National Institute of Allergy and Infectious Diseases.

Fig. 49 cont'd-7

Experiments to test the hypothesis

- Determine relative levels of Env specific IgA vs. IgG in plasma.

- Determine whether there are differences in affinity of Env specific IgA and IgG monoclonal antibodies from RV144.

- Determine whether RV144 IgA mAbs can inhibit ADCC (via NK cells) by IgG mAbs of similar specificity.

HIV VACCINE
TRIALS NETWORK

The HIV Vaccine Trials Network is supported through a cooperative agreement with the National Institute of Allergy and Infectious Diseases.

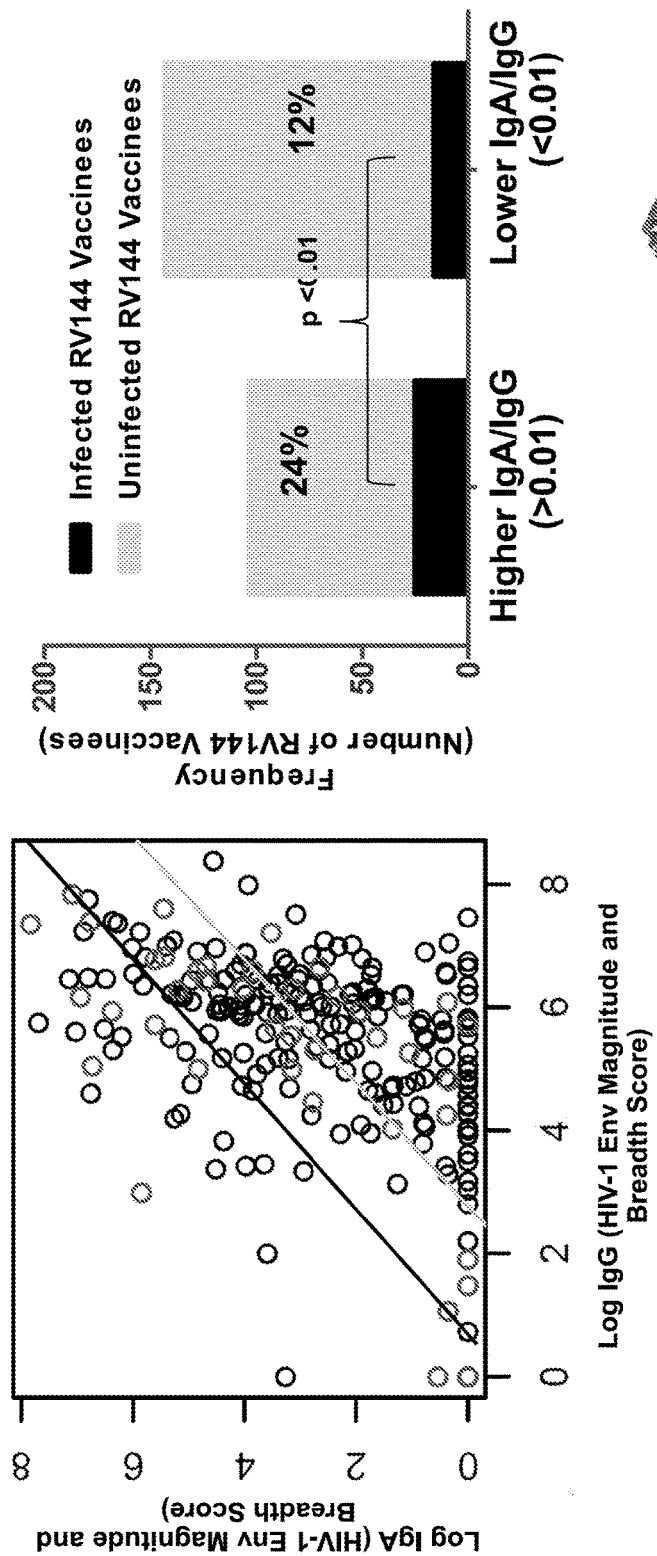
Fig. 49 cont'd-8
Enrichment of Higher Env IgA/IgG Ratio in Infected RV144 Vaccinees
The HIV Vaccine Trials Network is supported through a cooperative agreement with the National Institute of Allergy and Infectious Diseases.

Does the ratio of Env specific IgA/IgG provide additional information about relative risk of infection?

HIV V

Fig. 49 cont'd-10

Odds Ratio for Env IgA binding alone or relative to Env IgG (IgA/IgG ratio)

| Clade | Envelope Protein/Peptide | Odds Ratio | | | p-value | | |
|---|---|---|---|---|---|---|---|
| | | IgA | IgG | IgA/IgG | IgA | IgG | IgA/IgG |
| CRF01 AE | C1 Peptide | 1.69 | 0.85 | 1.79 | 0.0004 | 0.3503 | 0.0004 |
| Clade A | A1ConEnv gp140 | 1.57 | 0.87 | 1.66 | 0.0020 | 0.4316 | 0.0028 |
| Multi-Clade[1] | Breadth 14 HIV-1 Env Panel IgA Primary Score[3] | 1.39 | 0.78 | 1.62 | 0.0507 | 0.3884 | 0.0086 |
| Multi-Clade[1] | Unweighted Breadth 14 Env Panel Score | 1.36 | 0.83 | 1.61 | 0.0782 | 0.2922 | 0.0074 |
| Clade AE Vaccine Strain[1] | A244gD-(mon) gp120 | 1.28 | 0.72 | 1.58 | 0.1427 | 0.0318 | 0.0074 |
| Clade AE[1] | 97CNGX2F gp140 | 1.27 | 0.76 | 1.50 | 0.1331 | 0.0855 | 0.0142 |
| Clade G[1] | GConEnv gp140 | 1.31 | 0.81 | 1.49 | 0.0891 | 0.2162 | 0.0190 |
| Clade B gp120 | Con6 gp120 | 1.01 | 0.90 | 1.06 | 0.9520 | 0.6008 | 0.7264 |
| Non-HIV[2] | HSV gD peptide | 1.01 | 1.02 | 1.01 | 0.9366 | 0.9334 | 0.9549 |

The HIV Vaccine Trials Network is supported through a cooperative agreement with the National Institute of Allergy and Infectious Diseases.

HIV VACCINE TRIALS NETWORK

Fig. 49 cont'd-11

IgA Env Mabs and ADCC Mediating Mabs from RV144 vaccinees

- Two IgA HIV-1 binding mAbs from RV144
  - CH38- IgA2 and CH29- IgA2
- IgG ADCC mAbs from RV144
  - CH54, CH57-IgG (same donor as CH38), and CH80-IgG (same donor as CH29)
  - These mAbs are specific for the C1 region of gp120.
- C1 Region gp120 mAbs block binding of CH38 IgA and CH29 IgA mAbs

HIV VACCINE
TRIALS NETWORK

Liao, Alam, Bonsignori, Moody, Haynes

The HIV Vaccine Trials Network is supported through a cooperative agreement with the National Institute of Allergy and Infectious Diseases.

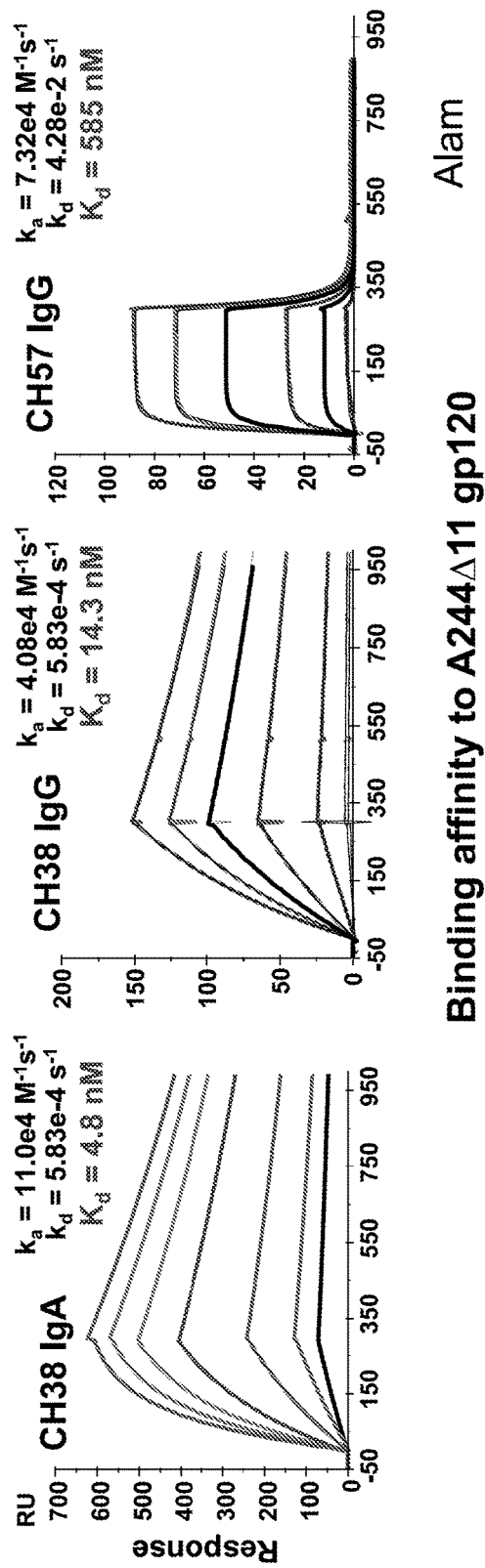
Fig. 49 cont'd-12
RV144 IgA mAb binds with two logs greater affinity to HIV-1 Env than IgG mAb of similar specificity

Fig. 49 cont'd-13
RV144 Purified mIgA inhibition of ADCC mediating A32 mAb
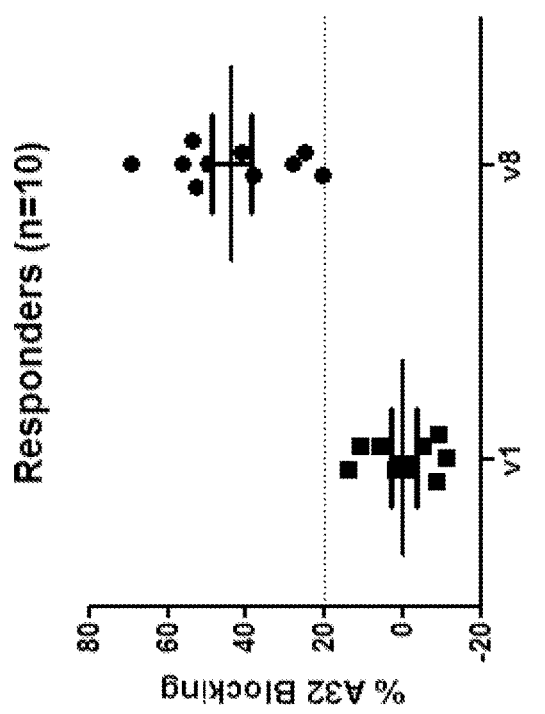
Shaunna Shen
The HIV Vaccine Trials Network is supported through a cooperative agreement with the National Institute of Allergy and Infectious Diseases.

CH38 IgG mAb but not CH38 IgA mAb mediates ADCC

CH38 IgA Inhibits ADCC of CM235 Infected Target Cells by R

Fig. 49 cont'd-16

Conclusions

- There is a diverse range of IgA epitope specificities elicited by RV144 vaccination. Purified plasma IgA antibodies from some vaccinees can bind infectious virions (heterologous T/F viruses).

- Infected RV144 Vaccinees are enriched for higher HIV-1 Env IgA/IgG plasma ratios for some Env specificities.

- CH38 IgA mAb has ~2 logs higher avidity for HIV-1 Env than CH57 IgG mAb (same Env specificity from same vaccinee).

- Purified RV144 Plasma IgA from some vaccinees are C1 region specific- similar to ADCC Ab generated from RV144.

- CH38 IgA mAb can block IgG mAb mediated ADCC (via NK cells).

HIV VACCINE
TRIALS NETWORK

The HIV Vaccine Trials Network is supported through a cooperative agreement with the National Institute of Allergy and Infectious Diseases.

Fig. 49 cont'd-17

Summary

- There are numerous HIV-1 specificities elicited by vaccination- all with potentially different effector functions (and different IgA forms). Not all HIV-1 Env IgA specificities correlated with increased risk of infection.

- The ratios of vaccine-elicited Env IgA/ IgG can correlate with infection risk representing either an interaction of some IgA and IgG antibodies or representing different levels of protective antibodies or other factors that associate with these ratios

- A fraction of these IgA specificities (C1 region specific) are capable of inhibiting IgG and NK mediated ADCC Next step is to test these mAbs alone and in combination in NHP protection studies.

**HIV V

Comparison Study of VAX003 vs. RV144 and Follow-up Correlates Analysis

HIV VACCINE
TRIALS NETWORK

The HIV Vaccine Trials Network is supported through a cooperative agreement with the National Institute of Allergy and Infectious Diseases.

Did RV144 elicit a different magnitude and quality of response than VAX003?

HIV VACCINE
TRIALS NETWORK

The HIV Vaccine Trials Network is supported through a cooperative agreement with the National Institute of Allergy and Infectious Diseases.

Fig. 49 cont'd-20

Previous Work

- Montefiori et al. (JID 2012) demonstrated that neutralizing antibodies were lower in RV144 vs. VAX003.

- Prime boost protein (gp160/gp120) vaccination elicited high levels of Env IgG4 (Gorse et al. ARHR1999); whereas, the ALVACvcp152 prime with MNgp120 boost elicited lower Env IgG4 relative to IgG1 and IgG3 responses (Banerjee et al. ARHR 2010).

HIV VACCINE
TRIALS NETWORK

The HIV Vaccine Trials Network is supported through a cooperative agreement with the National Institute of Allergy and Infectious Diseases.

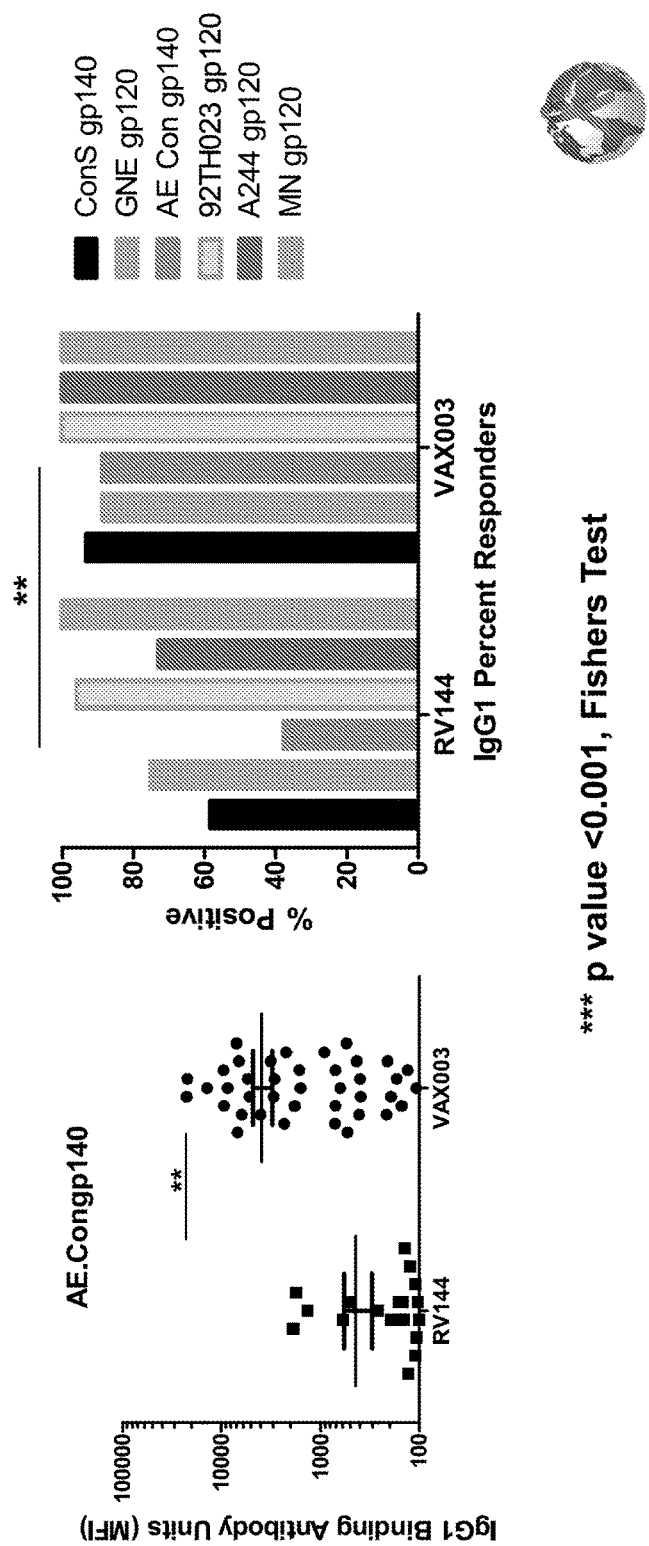
Fig. 49 cont'd-21

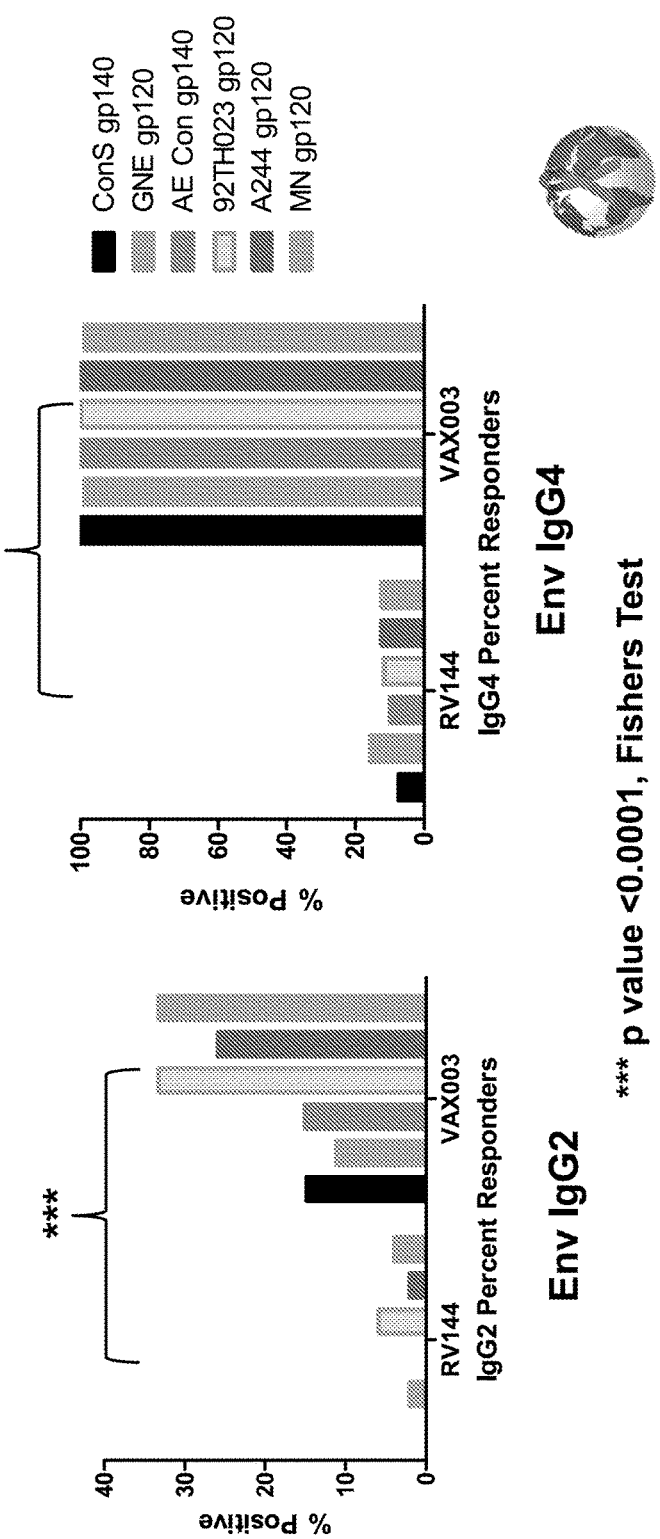

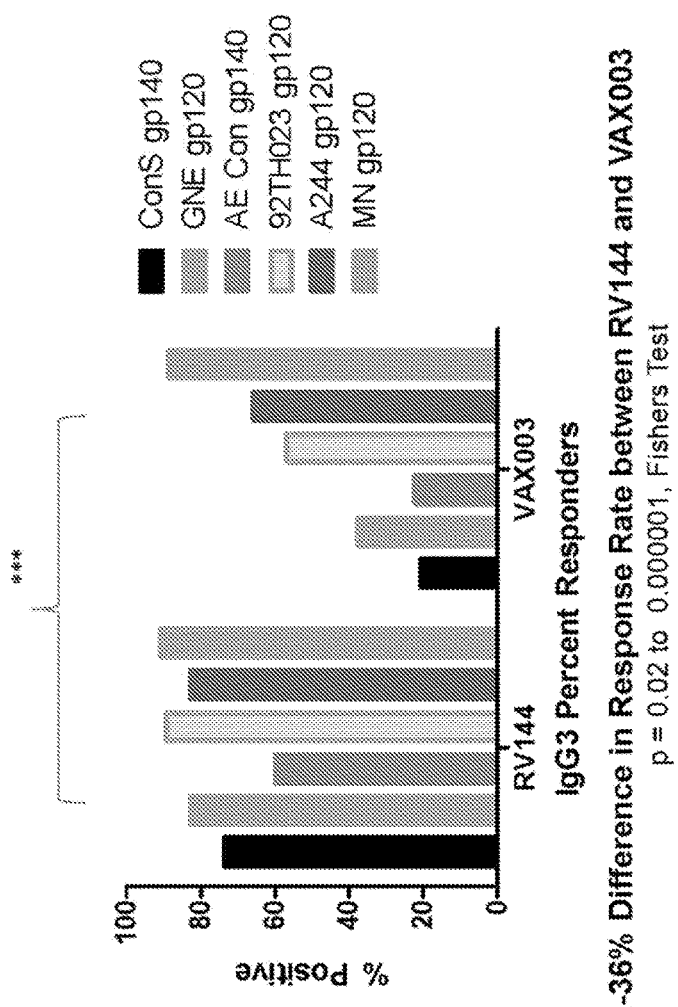
Fig. 49 cont'd-23

Fig. 49 cont'd-24

Env IgG3 Responses Higher in RV144 vs. VAX003

| Type of Env Protein | HIV-1 Env Protein | p-value[A] | % Difference RV144-VAX003[B] |
|---|---|---|---|
| Group M Consensus Envelope Protein | ConS gp140 | <0.000001 | 35.54 |
| RV144 Vaccine Prime Protein | GNE8 gp120 | 0.000002 | 33.60 |
| Circulating Strain in Thailand (AE) | AE Consensus gp140 | 0.0005 | 24.53 |
| RV144 Vaccine Prime | 92Th023 gp120 | 0.002 | 21.76 |
| RV144 and VAX003 Vaccine Boost | A244 gp120 | 0.24 | 8.86 |
| RV144 and VAX003 Vaccine Boost | MN gp120 | 0.83 | 1.94 |

HIV VACCINE
TRIALS NETWORK

The HIV Vaccine Trials Network is supported through a cooperative agreement with the National Institute of Allergy and Infectious Diseases.

Fig. 49 cont'd-25

IgG3 Subclass as a Biomarker of Immune Control

- IgG3 antibodies to MSP3 was associated with long-term control of falciparum malaria (Druilhe et al. PLoS Med 2007).

- IgG3 antibodies were associated with clearance and long-term clinical protection of Chikungunya virus (Kam et al. JID 2012).

HIV VACCINE
TRIALS NETWORK

The HIV Vaccine Trials Network is supported through a cooperative agreement with the National Institute of Allergy and Infectious Diseases.

Fig. 49 cont'd-26

V1V2 IgG Correlate in RV144

- V1V2 IgG Correlated with decreased risk of infection in RV144 (Haynes et al. NEJM 2012).

Increased vaccine efficacy at viruses matching the vaccine at position 169 (K169)(Rolland, Kim et al. Nature 2012).

V2 mAbs (e.g. CH58) were isolated from RV144 that had the ability to mediate immune pressure at position 169 (Liao, Haynes et al. 2012).

HIV VACCINE
TRIALS NETWORK

The HIV Vaccine Trials Network is supported through a cooperative agreement with the National Institute of Allergy and Infectious Diseases.

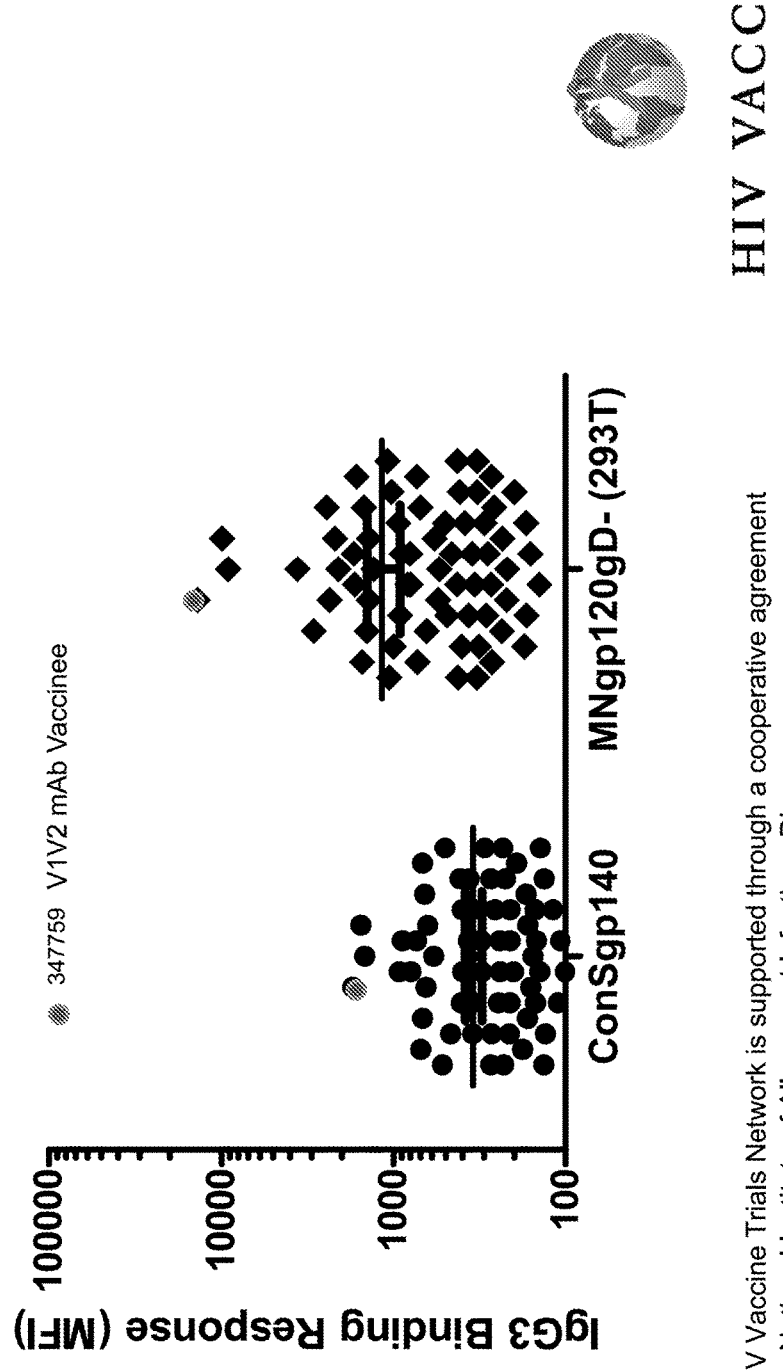

Were V1V2 IgG3 Responses Higher in RV144 compared to VAX003?

HIV VACCINE
TRIALS NETWORK

The HIV Vaccine Trials Network is supported through a cooperative agreement with the National Institute of Allergy and Infectious Diseases.

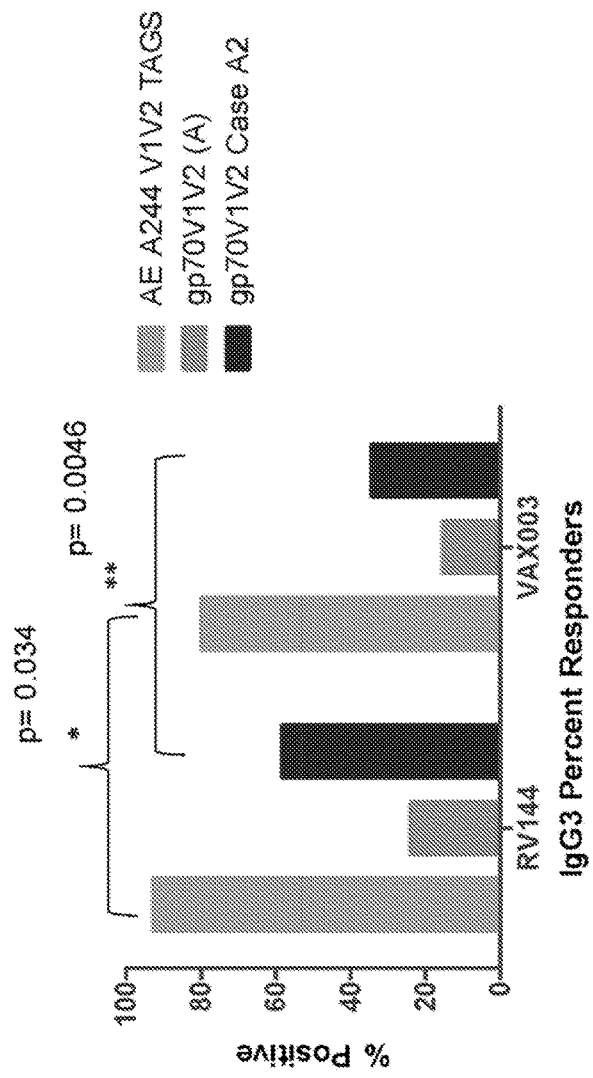

Do V1V2 IgG3 Responses Correlate with Decreased Risk of Infection in the RV144 Case Control Study?

HIV VACCINE
TRIALS NETWORK

The HIV Vaccine Trials Network is supported through a cooperative agreement with the National Institute of Allergy and Infectious Diseases.

Fig. 49 cont'd-31

Methods for Assessing V1V2 IgG3 in a Follow-up Case Control Study

IgG3 responses to V1V2 were measured (blinded) in 205 RV144 vaccinees and 41 infected vaccinees and 40 placebos with the binding antibody multiplex assay (BAMA).

V1V2 Proteins (Liao, Haynes) including the same protein in the RV144 case control study (gp70V1V2 caseA2) and also with a mutation that matches to the CRF01AE circulating strain (gp70V1V2.169K).

The HIV Vaccine Trials Network is supported through a cooperative agreement with the National Institute of Allergy and Infectious Diseases.

Fig. 49 cont'd-32

Higher IgG3 Response Rate to gp70V1V2169K Correlates with Decreased Risk of Infection

| Var encoding | Responder/Non-resp | | | |
|---|---|---|---|---|
| Model | Univariate | | IgA adj. | |
| | OR | p-val | OR | p-val |
| AEA244V1V2Tags293F | 0.796 | 0.162 | 0.738 | 0.075 |
| C1086C_V1_V2Tags | 0.775 | 0.142 | 0.743 | 0.093 |
| gp70_BCaseA_V1_V2 | 0.746 | 0.131 | 0.676 | 0.054 |
| gp70_BCaseA2V1V2169K | 0.595 | 0.006 | 0.563 | 0.003 |

RV144 V1V2 antigen with mutation that matches circulating strains in Thailand

HIV VACCINE
TRIALS NETWORK

The HIV Vaccine Trials Network is supported through a cooperative agreement with the National Institute of Allergy and Infectious Diseases.

Fig. 49 cont'd-33

Higher IgG3 Magnitude to V1V2 antigens, when adjusted for IgA responses, Correlates with Decreased Risk of Infection

| Var encoding | Continuous | | | |
|---|---|---|---|---|
| Model | Univariate | | IgA adj. | |
| | OR | p-val | OR | p-val |
| AEA244V1V2Tags293F | 0.791 | 0.185 | 0.682 | 0.045 |
| gp70V1V2CaseA2 | 0.753 | 0.104 | 0.703 | 0.049 |
| gp70V1V2C | 0.749 | 0.088 | 0.689 | 0.034 |

HIV VACCINE
TRIALS NETWORK

The HIV Vaccine Trials Network is supported through a cooperative agreement with the National Institute of Allergy and Infectious Diseases.

Fig. 49 cont'd-34

Summary

- In a comparison study of RV144 and VAX003, HIV-1 Env IgG3 responses were higher in RV144.

- One of the IgG3 Env specificities that was higher in RV144 than VAX003 was gp70V1V2 Case A2 IgG3.

- V1V2 IgG3 responses significantly correlated with decreased risk of infection in a follow-up study to the RV144 correlates. Response rate and magnitude of the V1V2 IgG3 response correlated with decreased risk of infection.

HIV VACCINE
TRIALS NETWORK

The HIV Vaccine Trials Network is supported through a cooperative agreement with the National Institute of Allergy and Infectious Diseases.

Fig. 49 cont'd-35

Relevance for HIV-1 Vaccine Evaluation

The IgG3 finding in <u>both studies</u> (VAX003 vs RV144 comparison study and the follow-up RV144 Case Control Study) provides rationale that IgG3 antibodies to the HIV-1 Env (and to V1V2) may be a hypothesis to test as a biomarker of a potentially protective response.

HIV VACCINE
TRIALS NETWORK

The HIV Vaccine Trials Network is supported through a cooperative agreement with the National Institute of Allergy and Infectious Diseases.

V1V2 IgG and IgA Breadth in HVTN 204

HVTN 204 and HVTN 505

- The phase II DNA prime, rAd5 boost vaccine (HVTN 204) exhibited sufficient safety and immunogenicity to advance into a phase IIb efficacy trial (Churchyard et al. PLoS ONE 2011; 6 (8): e21225).

- The vaccine regimen for HVTN 204 (phase II) and HVTN 505 (phase IIb efficacy) are both multi-clade (A,B,C) DNA prime (m 0,1,2) and multi-clade (A,B,C) rAd5 boost (m 6).

- HVTN 505 was restricted to Ad5 seronegative volunteers in the U.S.; whereas HVTN 204 was in both Ad5+ and Ad5- volunteers in Latin America, South Africa and the U.S.

HIV VACCINE
TRIALS NETWORK

The HIV Vaccine Trials Network is supported through a cooperative agreement with the National Institute of Allergy and Infectious Diseases.

Fig. 50 cont'd-2

Talk Outline

- Follow-up RV144 V1V2 IgG correlates analysis to formally test another assay (BAMA) and multiple forms of V1V2 antigens (Zolla-Pazner, Tomaras, Haynes, Montefiori, Nabel, Liao, Gilbert, DeCamp, Fong et al.).

- Measure V1V2 IgG and IgA Env responses (RV144 Correlates) in HVTN 204 in similar strategies.

- Determine other potentially protective responses in HVTN 204 that were not measured as part of the RV144 correlates analysis (e.g. gp41Ab and virion capture antibodies).

HIV VACCINE
TRIALS NETWORK

The HIV Vaccine Trials Network is supported through a cooperative agreement with the National Institute of Allergy and Infectious Diseases.

Fig. 50 cont'd-3

Methods for Assessing V1V2 IgG in a Follow-up Case Control Study

IgG responses to V1V2 were measured (blinded) in 205 RV144 vaccinees and 41 infected vaccinees and 40 placebos with the binding antibody multiplex assay (BAMA).

Robustness of the V1V2 measurement V1V2 proteins made in multiple labs (Liao, Haynes, Pinter) were tested.

Ongoing analyses and studies to test different clades and forms (gp70, tags, peptides).

HIV VACCINE
TRIALS NETWORK

The HIV Vaccine Trials Network is supported through a cooperative agreement with the National Institute of Allergy and Infectious Diseases.

Results of Follow-up Case Control Study

| | ELISA Zolla-Pazner | | BAMA Tomaras | |
|---|---|---|---|---|
| | OR | p-value | OR | p-value |
| gp70.B.caseA2.V169K.LL | 0.57 | 0.0046 | 0.52 | 0.0002 |
| gp70.B.caseA2.APorig | 0.62 | 0.0149 | 0.6 | 0.0059 |
| gp70.B.caseA2.LL | 0.60 | 0.0084 | 0.59 | 0.0031 |

Adjusted for IgA

OR of 0.52 is a 48% risk reduction

HIV VACCINE
TRIALS NETWORK

The HIV Vaccine Trials Network is supported through a cooperative agreement with the National Institute of Allergy and Infectious Diseases.

Fig. 50 cont'd-5

Were gp70V1V2 IgG Responses Elicited in HVTN 204?

HIV VACCINE
TRIALS NETWORK

The HIV Vaccine Trials Network is supported through a cooperative agreement with the National Institute of Allergy and Infectious Diseases.

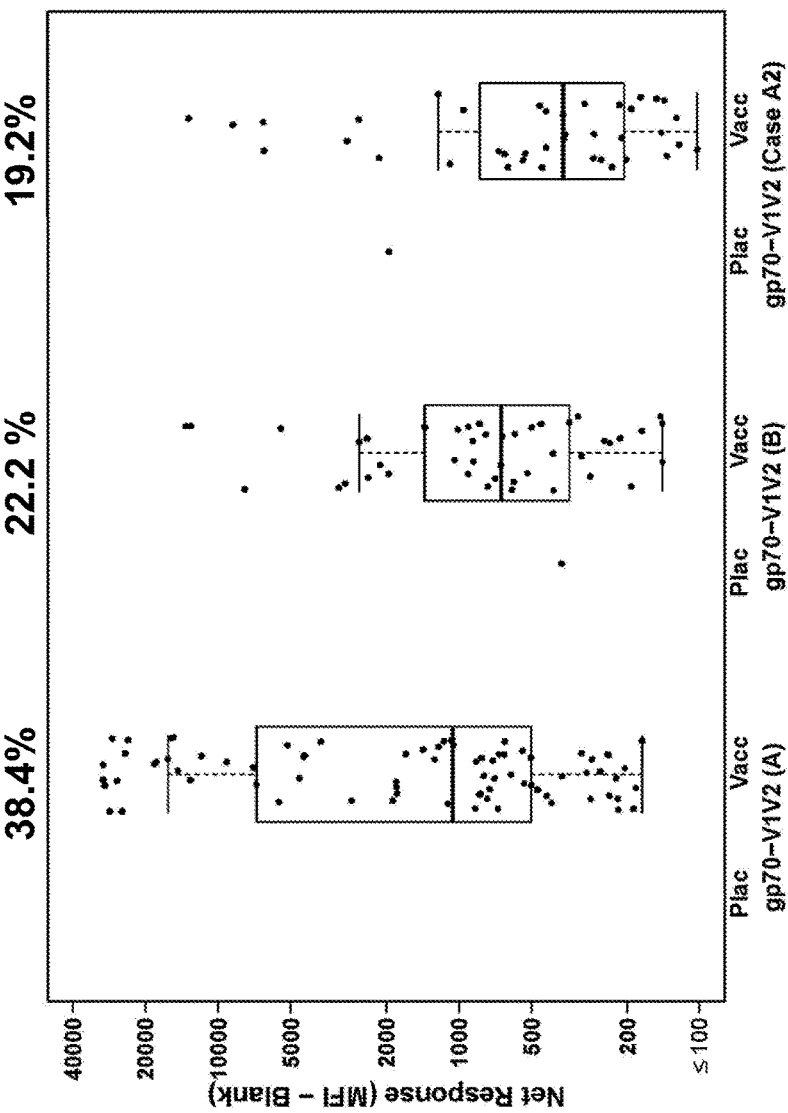
Fig. 50 cont'd-6

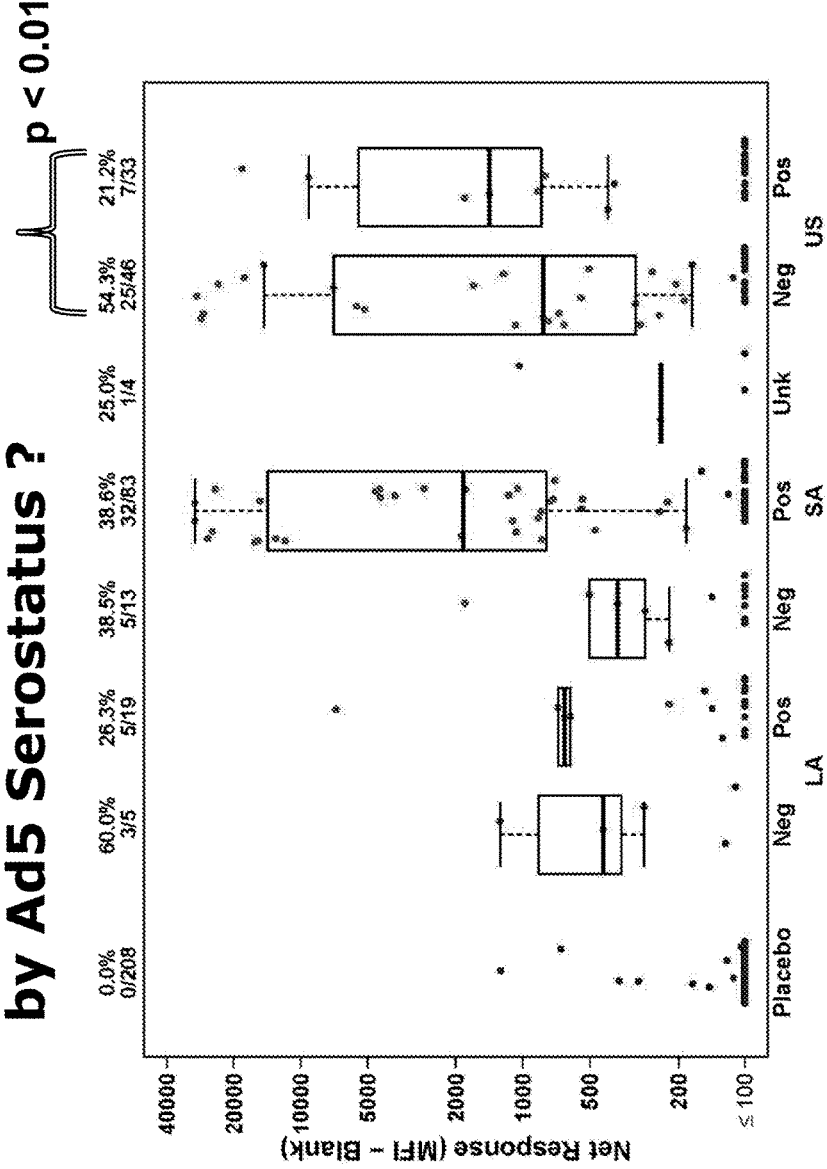
Fig. 50 cont'd-9

How does Env IgA compare between RV144 and HVTN 204?

HIV VACCINE
TRIALS NETWORK

The HIV Vaccine Trials Network is supported through a cooperative agreement with the National Institute of Allergy and Infectious Diseases.

Fig. 50 cont'd-11

Methods for Assessing Env IgA in HVTN 204

Env IgA breadth panel (multiple clades) was performed (blinded) in ~200 HVTN 204 vaccinees with the binding antibody multiplex assay.

Analysis was identical analysis to that performed for RV144 (Grove, Fong, Gilbert et al).

HIV VACCINE
TRIALS NETWORK

The HIV Vaccine Trials Network is supported through a cooperative agreement with the National Institute of Allergy and Infectious Diseases.

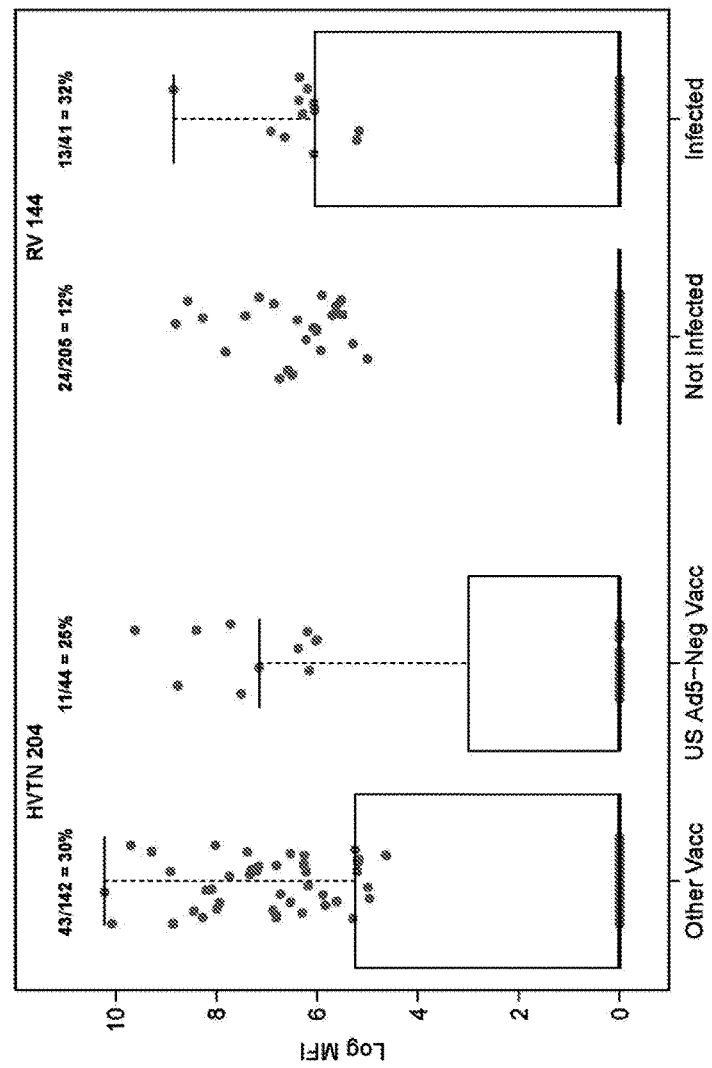
Fig. 50 cont'd-13
IgA Env Response to A1ConEnv is significantly higher in HVTN 204 than RV144; although similar magnitude
** p <0.001

HVTN 204 Cross-clade Binding Responses Including gp41 Ab

| CONS gp140 | Clade C DU123 | VRC-A | VRC-B | gp41 | p55Gag |
|---|---|---|---|---|---|
| 94.6% | 93.1% | 83.7% | 94.6% | 93.1% | 45.5% |

HIV VACCINE
TRIALS NETWORK

The HIV Vaccine Trials Network is supported through a cooperative agreement with the National Institute of Allergy and Infectious Diseases.

What other Ab responses were elicited in HVTN 204?

HIV VACCINE
TRIALS NETWORK

The HIV Vaccine Trials Network is supported through a cooperative agreement with the National Institute of Allergy and Infectious Diseases.

Fig. 50 cont'd-16

Gp41 Env Specific Antibodies

- Conformational gp41 IgG Ab correlating with protection in NHP study (Haase et al.).

- Proof of concept study with gp41 IgG that can capture virions: F240 IgG. (Modest protection) (Burton and Moore *et al.* PNAS 2011)

The HIV Vaccine Trials Network is supported through a cooperative agreement with the National Institute of Allergy and Infectious Diseases.

HIV VACCINE
TRIALS NETWORK

Fig. 50 cont'd-17

Generation of Monoclonal Antibodies from HVTN 204 Vaccinees

| mAb ID | VH | Mut. Freq. (%) | Isotype | Specificity |
|---|---|---|---|---|
| CH69 | 1-69 | 3.2 | G1 | Bind gp140 and gp41 Conformational (not to ID) |
| CH70 | 1-69 | 4.7 | G1 | |
| CH71 | 1-69 | 4.2 | G1 | |

K. Jones, W. Williams, B. Haynes *et al.*
HVTN young investigators

HIV VACCINE
TRIALS NETWORK

The HIV Vaccine Trials Network is supported through a cooperative agreement with the National Institute of Allergy and Infectious Diseases.

Fig. 50 cont'd-18

Antibody Quality: Infectious Virion Capture

- Antibodies that can capture infectious virions may represent a functional antibody response that can prevent HIV-acquisition.

- Relative amounts of Ab capture of infectious vs. non-infectious virions can be calculated. (Liu ,Tomaras JV 2011)

The HIV Vaccine Trials Network is supported through a cooperative agreement with the National Institute of Allergy and Infectious Diseases.

HIV VACCINE
TRIALS NETWORK

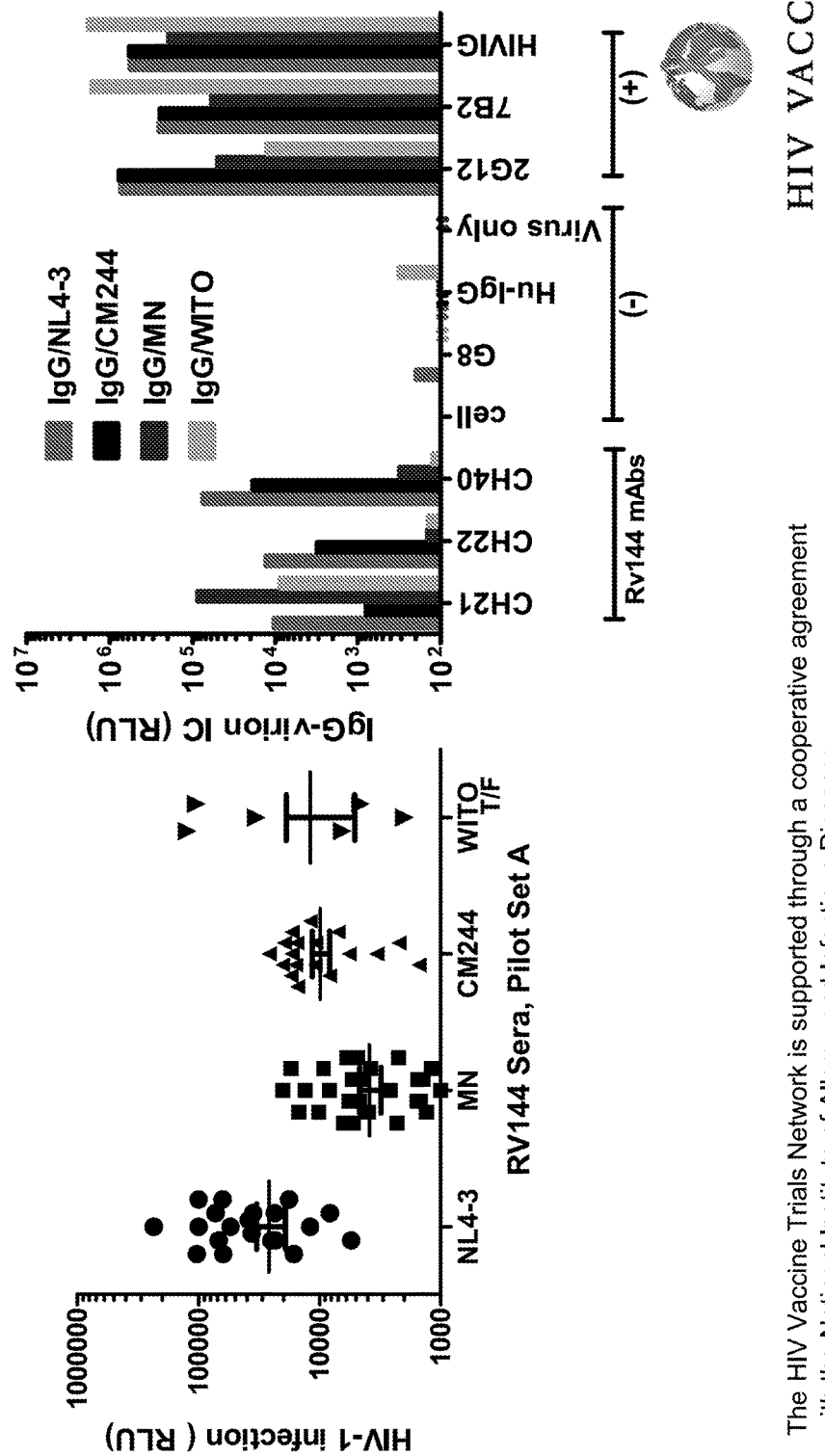

HVTN 204 elicited gp41 antibodies (mAb analysis) capture infectious T/F virus

Fig. 50 cont'd-21

Summary

- V1/V2 IgG antibodies (gp70 V1V2 CaseA2/Clade A) were elicited in HVTN 204, along with multiple other epitope specificities, including gp41 IgG antibodies that can capture infectious virions.

- V1V2 IgG antibody response was higher in Ad5 seronegatives and indicates that HVTN505 could have the opportunity to test the V1V2 IgG correlate should there be efficacy.

- Env IgA antibody primary RV144 correlate was lower in HVTN 204. However the Env IgA response to individual Envs, in particular for clade A, was in some cases higher than RV144.

HIV VACCINE
TRIALS NETWORK

The HIV Vaccine Trials Network is supported through a cooperative agreement with the National Institute of Allergy and Infectious Diseases.

Fig. 50 cont'd-22

Conclusions

- HVTN 505 phase IIb efficacy study has an opportunity to examine the role of V1V2 IgG responses, the impact of Env IgA, and as well other immune responses like gp41 specific virion capture antibodies.

HIV VACCINE
TRIALS NETWORK

The HIV Vaccine Trials Network is supported through a cooperative agreement with the National Institute of Allergy and Infectious Diseases.

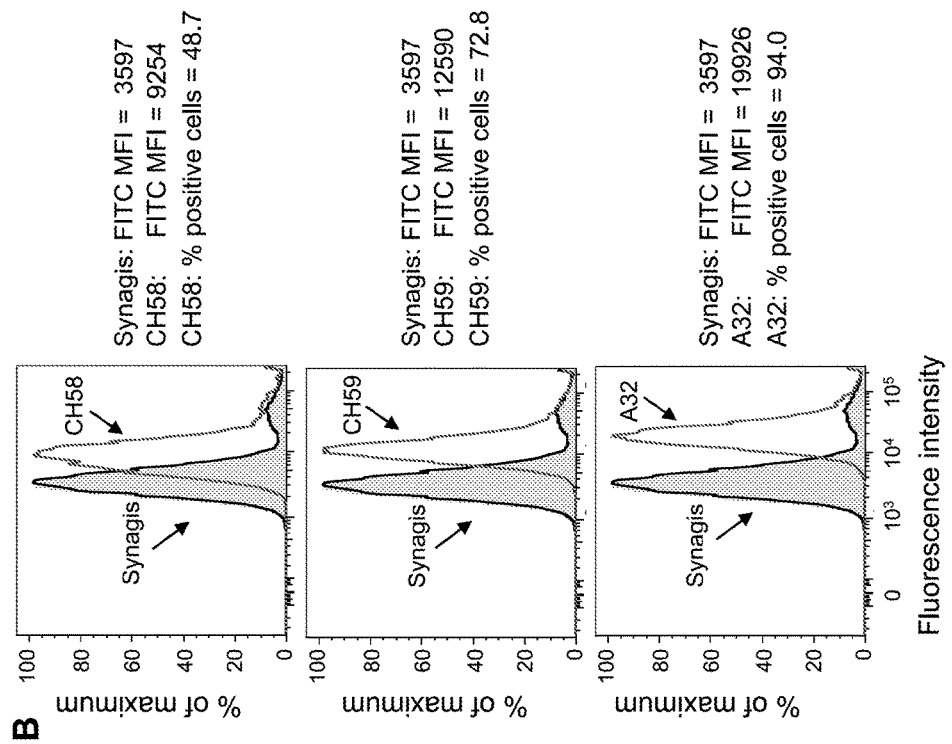
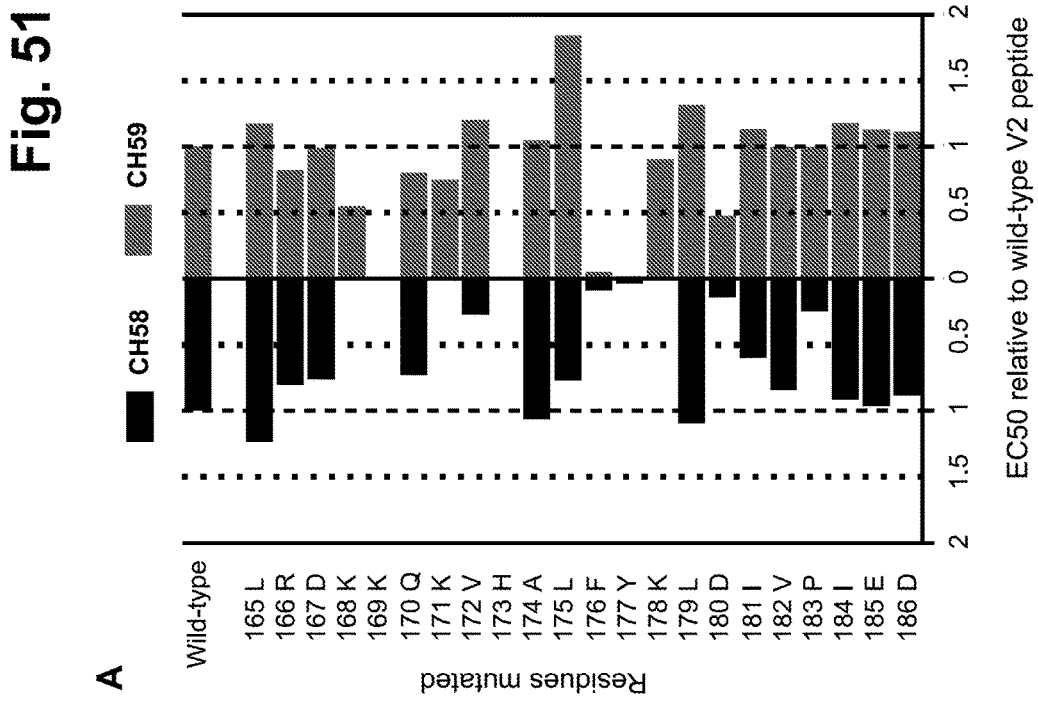
Fig. 51

Fig. 53
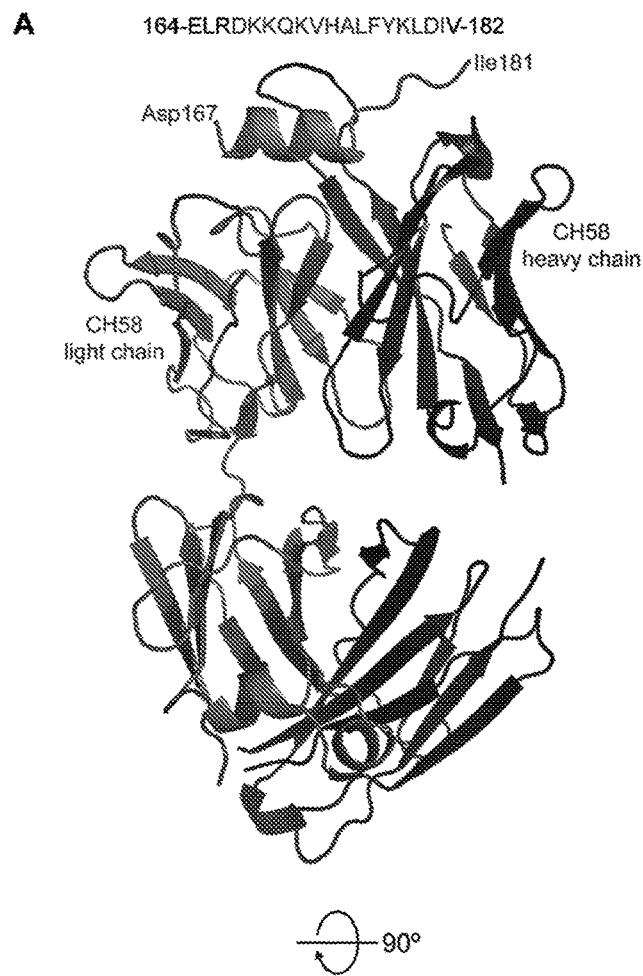
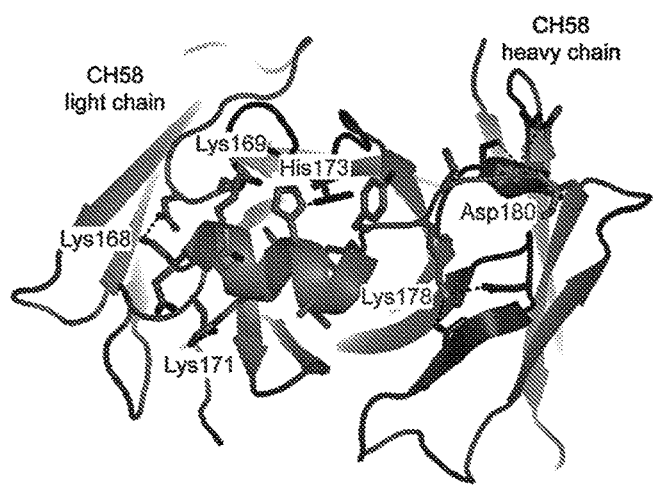

Fig. 53
B     164-ELRDKKQKVHALFYKLDIV-182
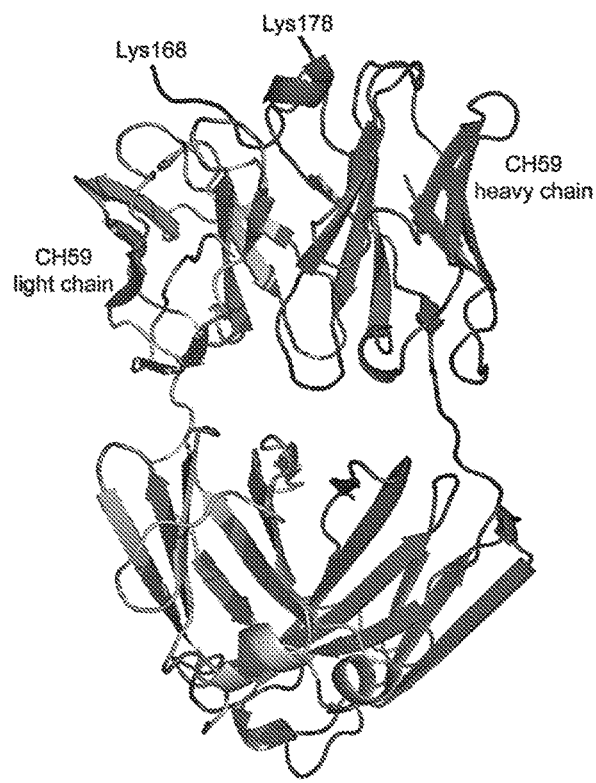
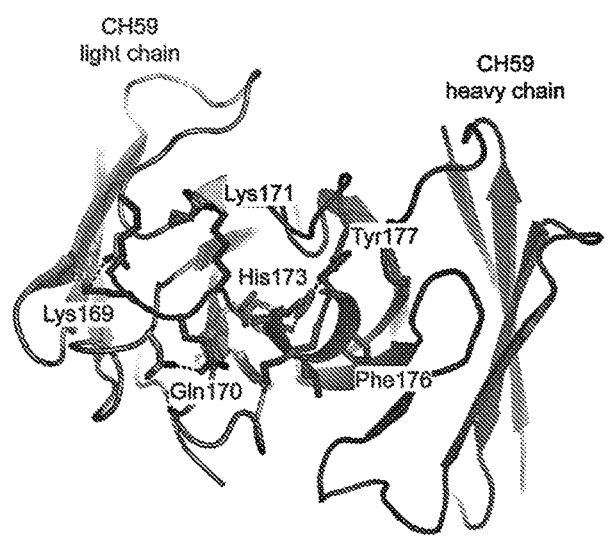

Fig. 53
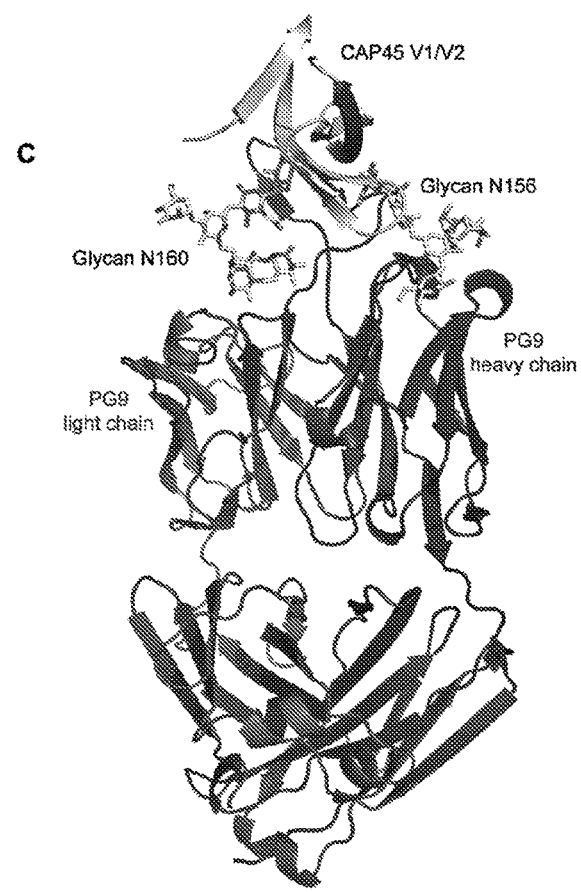
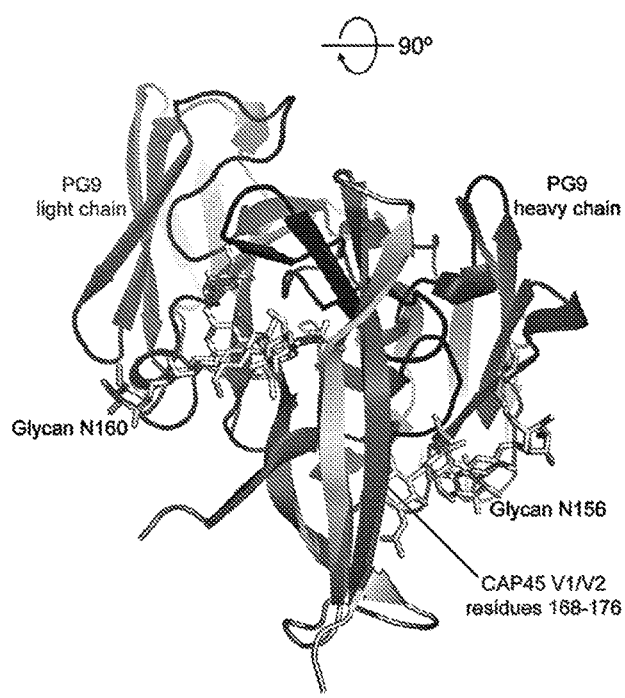

Data collection and refinement statistics (molecular replacement)

|  | CH58 Fab | CH58 w/ V2 peptide | CH59 w/ V2 peptide |
|---|---|---|---|
| PDB ID | 4HQQ | 4HPO | 4HPY |
| Data collection | | | |
| Space group | $P2_12_12_1$ | C2 | $P2_12_12_1$ |
| Cell dimensions | | | |
| $a, b, c$ (Å) | 63.0, 70.4, 135.8 | 140.6, 75.8, 54.7 | 41.9, 79.2, 127.1 |
| $\alpha, \beta, \gamma$ (°) | 90.0, 90.0, 90.0 | 90.0, 112.0, 90.0 | 90.0, 90.0, 90.0 |
| Resolution (Å) | 50.0-2.4 (2.44-2.40)* | 50.0-1.7 (1.73-1.70)* | 20.0-1.5 (1.53-1.50)* |
| $R_{sym}$ or $R_{merge}$ (%) | 13.6 (50.6) | 9.6 (38.7) | 11.8 (87.4) |
| $I / \sigma I$ | 18.2 (2.0) | 19.5 (1.9) | 21.2 (3.7) |
| Completeness (%) | 97.7 (82.8) | 90.7 (56.1) | 100 (100) |
| Redundancy | 6.3 (3.3) | 3.3 (2.2) | 7.0 (5.6) |
| | | | |
| Refinement | | | |
| Resolution (Å) | 25.8-2.40 | 24.8-1.69 | 19.9-1.50 |
| No. reflections | 23,681 | 53,364 | 68,657 |
| $R_{work} / R_{free}$ | 0.183/0.225 | 0.185/0.211 | 0.171/0.187 |
| No. atoms | | | |
|   Protein | 3,232 | 3,413 | 3,344 |
|   Ligand/ion | - | 24 | 12 |
|   Water | 191 | 403 | 521 |
| B-factors | | | |
|   Protein | 52.8 | 42.1 | 16.5 |
|   Ligand/ion | - | 92.7 | 22.1 |
|   Water | 49.1 | 42.4 | 32.1 |
| R.m.s. deviations | | | |
|   Bond lengths (Å) | 0.004 | 0.007 | 0.004 |
|   Bond angles (°) | 0.87 | 1.11 | 1.00 |

*Values in parentheses are for highest-resolution shell.

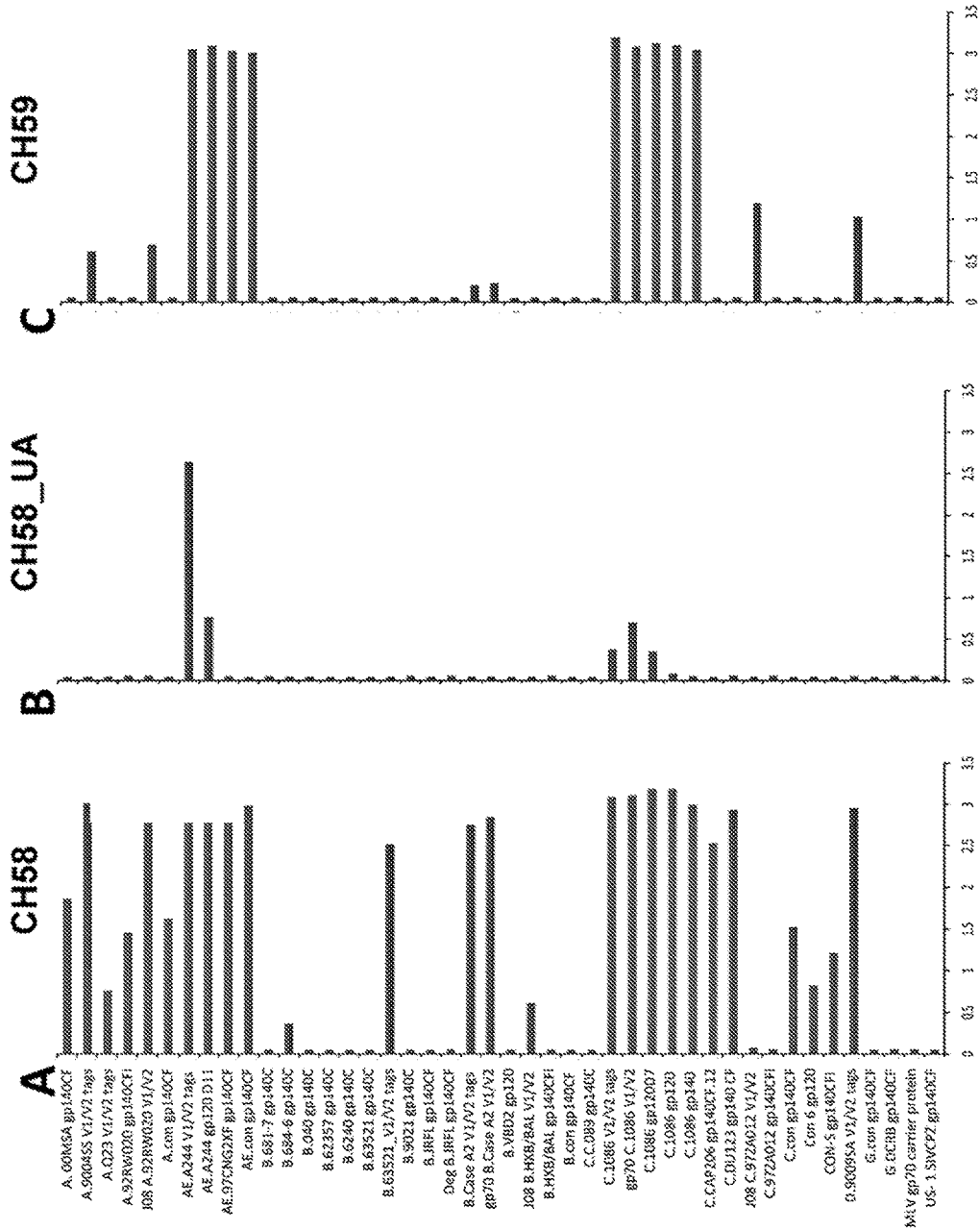

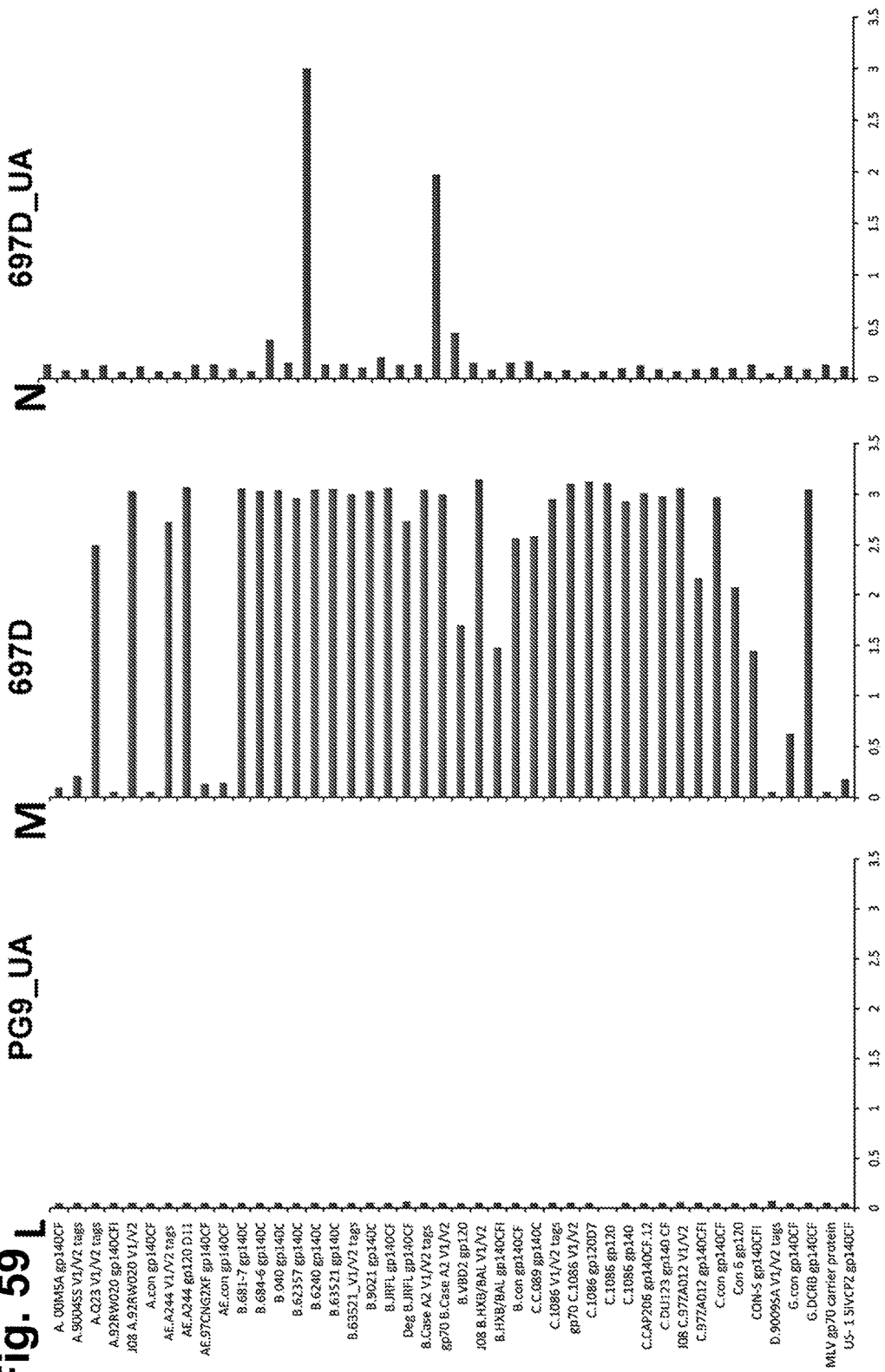

| Subject ID | mAb ID | Heavy chain | | | | | | Light chain | | | |
|---|---|---|---|---|---|---|---|---|---|---|---|
| | | V | D | J | Mutation frequency | CDR3 length | Isotype | V | J | Mutation frequency | CDR3 length |
| 347759 | CH58 | 5-51 | 3-22 | 4 | 1.90% | 19 | IgG1 | L6-57 | 3 | 1.80% | 9 |
| 347759 | CH59 | 3-9 | 1-26 | 4 | 2.80% | 13 | IgG1 | L3-10 | 3 | 0.90% | 11 |
| 200134 | HG107 | 3-9 | 2-2 | 4 | 2.30% | 14 | IgG1 | L3-10 | 1 | 0.90% | 10 |
| 302689 | HG120 | 3-23 | 5-5 | 4 | 1.60% | 13 | IgG1 | L3-10 | 2 | 0.30% | 10 |

B

```
>HG107VH
GAGGTGCAGCTGGTGGAGTCTGGGGGAGACTTGGTACAGCCTGGCAGGTCCCTGAGACTCTCCTGTGCAGC
CTCTGGATTCACCTTTGATGATTATGCCATGCACTGGGTCCGGCAAGCTCCAGGGAAGGGCCTGGAGTGGA
TCTCAGGTATTAGTGGGAATAGTGGTAGCAGAGGCTATGCGGACTCTGTGAAGGGCCGATTCACCATCTCC
AGAGACAACGCCAAGAACTCCCTGTATCTGCAAATGAACAGTCTGAGAGCTGAGGACACGGCCTTGTATTA
CTGTGCAACAGATGGAGACAGATCTGGCACTACGCCTCTTGACCATTGGGGCCAGGGAACCCGGGTCACCG
TCTCCTCA
>HG107VL
TCCTATGAGCTGACACAGCCACCCTCGGTGTCAGTGTCCCCAGGACAAACGGCCAGGATCACCTGCTCTGG
AGATGCATTGCCAAAAAATTATGCTTATTGGTACCAGCAGAAGTCAGGCCAGGCCCCTGCGTTGGTCATCT
ATGAGGACAGCAAACGACCCTCCGGGATCCCTGAGAGATTCTCTGGCTCCAGCTCAGGGACAATGGCCACC
TTGACTATCAGTGGGGCCCAGGTGGAGGATGAAGCTGACTACTACTGTTACTCAACAGACAGCAGTGGTAC
TCCCTCCTTCGGAACTGGGACCAAGGTCACCGTCCTA

>HG120VH
GAGGTGCAGCTGGTGGAGTCTGGGGGAGGCTTGGTACAGCCTGGGGGGTCCCTGAGACTCTCCTGTGCAGC
CTCTGGATTCACCTTTAGCAGTTATGCCATGAGGTGGGTCCGCCAGGCTCCAGGGAAGGGGCTGGAGTGGG
TCTCAGGTATTAGTGGTAGTGGTGGTAGCACATACTACGCAGACTCCGTGAAGGGCCGGTTCACCATCTCC
AGAGACAATTCCAAGATCACGCTGTATCTGCAAATGGACAGCCTGAGAGTCGAGGACACGGCCGTATATTA
CTGTGCGACAGCGCCCCTCAGCTATGATTCCTCCACGGACTACTGGGGCCAGGGAACCCTGGTCACCGTCT
CCTCA
>HG120VL
TCCTATGAGCTGACACAGCCACCCTCGGTGTCAGTGTCCCCAGGACAAACGGCCAGGATCACCTGCTCTGG
AGATGCATTGCCAAAAAATATGCTTATTGGTACCAGCAGAAGTCAGGCCAGGCCCCTGTGCTGGTCATCT
ATGAGGACAGCAAACGACCCTCCGGGATCCCTGAGAGATTCTCTGGCTCCAGCTCAGGGACAATGGCCACC
TTGACTATCAGTGGGGCCCAGGTGGAGGATGAAGCTGACTACTACTGTTACTCAACAGACAGCAGTGGTAA
TCCCCGATTCGGCAGAGGGACCAAGCTGACCGTCCTA
```

C

```
CH59VL    SYELTQPPSV SVSPGQTARI TCS..GDALP KNYAYWYQQK SGQAPVLVIY  SKRPSGIP
HG107VL   ---------- ---------- ---..----- ---------- -----A----  --------
HG120VL   ---------- ---------- ---..----- -K-------- ----------  --------
CH58VL    NFM----H-- -E---K-VT- S-TRSSGSVA SD-VQ----R P-S--TT-V-  NQ----V-  60

CH59VL    ERFSGS..SS GTMATLTISG AQVEDEADYY CYSTDSSGNH RVFGGGTKLT VL
HG107VL   ------..-- ---------- ---------- --------TP .S--T---V- --
HG120VL   ------..-- ---------- ---------- ---------P .R--R----- --
CH58VL    D-----ID-- SNS-S----- LKT------- -Q-Y-N..SS W---------  --112
```

Fig. 60
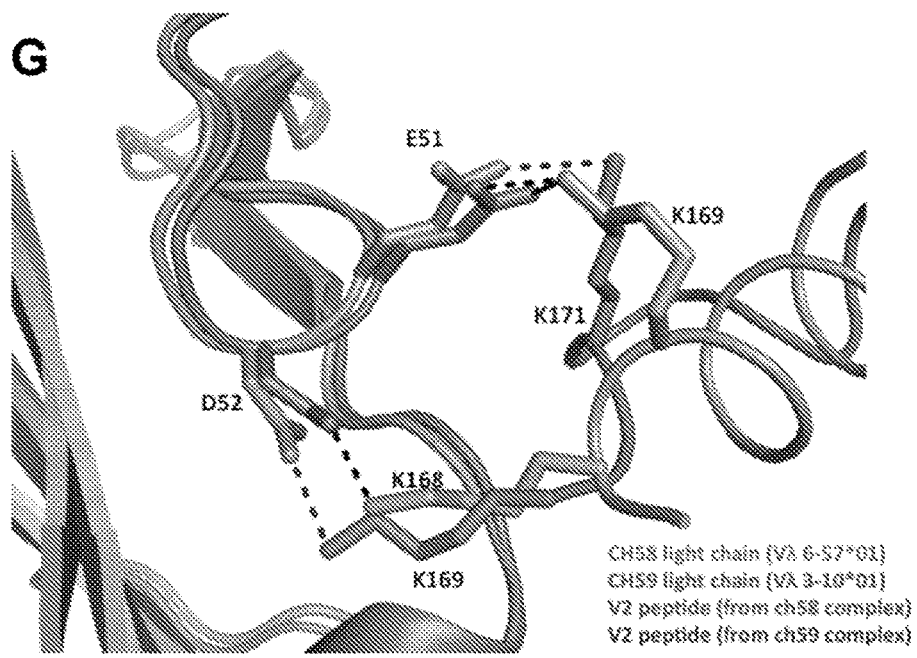
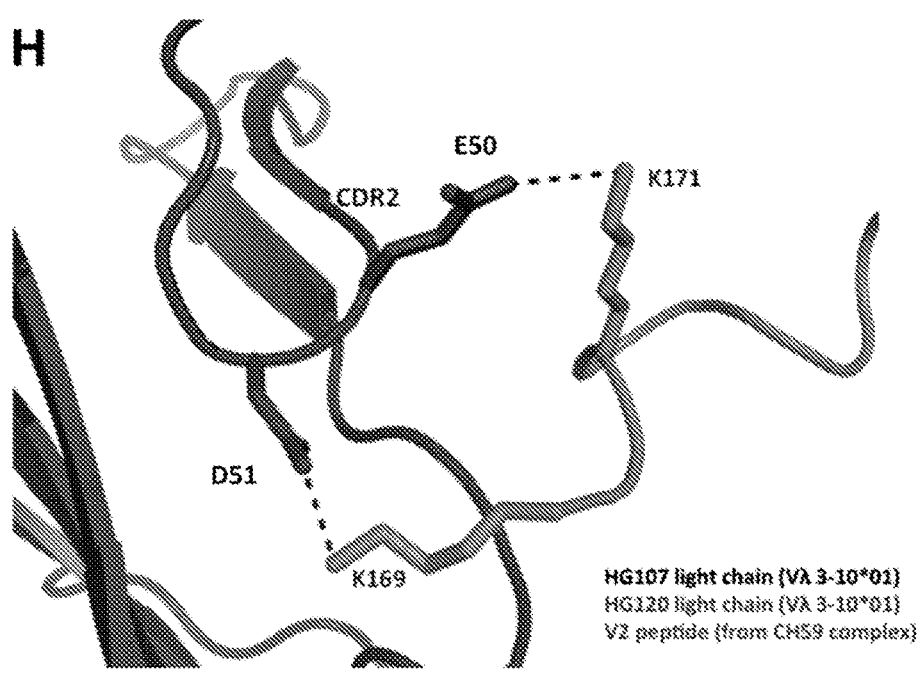

*AE.703359 gp20/Mut3 = AE.703359 gp120/Q169K/R170Q/Q173H; AE.427299 gp120/Mut 4 = AE.427299 gp120/R168K/Q169K/Y173H/A174V.

SEQUENCE LISTING

<160> NUMBER OF SEQ ID NOS: 243

<210> SEQ ID NO 1
<211> LENGTH: 21
<212> TYPE: PRT
<213> ORGANISM: Human immunodeficiency virus 1

<400> SEQUENCE: 1

Lys Lys Lys Val His Ala Leu Phe Tyr Lys Leu Asp Ile Val Pro Ile
1               5                   10                  15

Glu Asp Lys Lys Lys
            20

<210> SEQ ID NO 2
<211> LENGTH: 42
<212> TYPE: PRT
<213> ORGANISM: Human immunodeficiency virus 1

<400> SEQUENCE: 2

Cys Ser Phe Asn Met Thr Thr Glu Leu Arg Asp Lys Lys Gln Lys Val
1               5                   10                  15

His Ala Leu Phe Tyr Lys Leu Asp Ile Val Pro Ile Glu Asp Asn Thr
            20                  25                  30

Ser Ser Ser Glu Tyr Arg Leu Ile Asn Cys
        35                  40

<210> SEQ ID NO 3
<211> LENGTH: 14
<212> TYPE: PRT
<213> ORGANISM: Human immunodeficiency virus 1

<400> SEQUENCE: 3

Leu Arg Asp Lys Lys Gln Arg Val Tyr Ser Leu Phe Tyr Lys
1               5                   10

<210> SEQ ID NO 4
<211> LENGTH: 23
<212> TYPE: PRT
<213> ORGANISM: Human immunodeficiency virus 1

<400> SEQUENCE: 4

Ile Thr Thr Ser Ile Gly Asp Lys Met Gln Lys Glu Tyr Ala Leu Leu
1               5                   10                  15

Tyr Lys Leu Asp Ile Glu Pro
            20

<210> SEQ ID NO 5
<211> LENGTH: 21
<212> TYPE: PRT
<213> ORGANISM: Human immunodeficiency virus 1

<400> SEQUENCE: 5

Ser Phe Asn Met Thr Thr Glu Leu Arg Asp Lys Lys Gln Lys Val His
1               5                   10                  15

Ala Leu Phe Tyr Lys
            20

<210> SEQ ID NO 6
<211> LENGTH: 24
<212> TYPE: PRT
<213> ORGANISM: Human immunodeficiency virus 1

<400> SEQUENCE: 6

-continued

```
Met Gln Glu Asp Val Ile Ser Leu Trp Asp Gln Ser Leu Lys Pro Cys
1               5                   10                  15

Val Lys Leu Thr Pro Leu Cys Val
            20

<210> SEQ ID NO 7
<211> LENGTH: 32
<212> TYPE: PRT
<213> ORGANISM: Herpes simplex virus

<400> SEQUENCE: 7

Lys Tyr Ala Leu Val Asp Ala Ser Leu Lys Met Ala Asp Pro Asn Arg
1               5                   10                  15

Phe Arg Gly Lys Asp Leu Pro Val Leu Asp Gln Leu Thr Asp Pro Pro
            20                  25                  30

<210> SEQ ID NO 8
<211> LENGTH: 21
<212> TYPE: PRT
<213> ORGANISM: Human immunodeficiency virus 1

<400> SEQUENCE: 8

Lys Lys Lys Glu Tyr Arg Leu Ile Asn Cys Asn Thr Ser Val Ile Lys
1               5                   10                  15

Gln Ala Lys Lys Lys
            20

<210> SEQ ID NO 9
<211> LENGTH: 21
<212> TYPE: PRT
<213> ORGANISM: Unknown
<220> FEATURE:
<223> OTHER INFORMATION: Description of Unknown: Ig leader
      peptide

<400> SEQUENCE: 9

Met Glu Thr Asp Thr Leu Leu Leu Trp Val Leu Leu Leu Trp Val Pro
1               5                   10                  15

Gly Ser Thr Gly Asp
            20

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 22
<212> TYPE: PRT
<213> ORGANISM: Human immunodeficiency virus 1

<400> SEQUENCE: 11

Leu Arg Asp Lys Lys Gln Lys Val His Ala Leu Phe Tyr Lys Leu Asp
1               5                   10                  15

Ile Val Pro Ile Glu Asp
            20
```

-continued

<210> SEQ ID NO 12
<211> LENGTH: 19
<212> TYPE: PRT
<213> ORGANISM: Human immunodeficiency virus 1

<400> SEQUENCE: 12

Glu Leu Arg Asp Lys Lys Gln Lys Val His Ala Leu Phe Tyr Lys Leu
1               5                   10                  15

Asp Ile Val

<210> SEQ ID NO 13
<211> LENGTH: 14
<212> TYPE: PRT
<213> ORGANISM: Human immunodeficiency virus 1

<400> SEQUENCE: 13

Lys Lys Lys Val His Ala Leu Phe Tyr Lys Leu Asp Ile Val
1               5                   10

<210> SEQ ID NO 14
<211> LENGTH: 378
<212> TYPE: DNA
<213> ORGANISM: Homo sapiens

<400> SEQUENCE: 14
gaggtgcagc tggtgcagtc tggagcagag gtgaaaaagc ccggggagtc tctgaagatc      60
tcctgtaagg gttctggata caggtttacc agttactgga tcgtctgggt gcgccagatg     120
cccgggaaag gcctggagtg gatggggatc atctatcctg gtgactttga taccaaatac     180
agcccgtcct tccaaggcca ggtcaccatc tcagccgaca gtccatcag caccgcctac     240 ctacagtgga gcagcctgaa ggcctcggac accgccatgt attactgtgc gagacttggc     300
ggcagatatt accatgatag tagtggttat tactaccttg actactgggg ccagggaacc     360
ctggtcaccg tctcctca                                                   378

<210> SEQ ID NO 15
<211> LENGTH: 330
<212> TYPE: DNA
<213> ORGANISM: Homo sapiens

<400> SEQUENCE: 15
aattttatgc tgactcagcc ccactctgtg tcggagtctc cggggaagac ggtaaccatc      60
tcctgcaccc gcagcagtgg cagcgttgcc agcgactatg tgcagtggta ccagcagcgc     120
ccgggcagtg cccccaccac tgtggtctat gaggataacc aaagaccctc tggggtccct     180
gatcgattct ctggctccat cgacagctcc tccaactctg cctccctcac catctctgga     240
ctgaagactg aggacgaggc tgactactac tgtcagtctt atgataacag ctcttgggtg     300
ttcggcggag ggaccaagct gaccgtccta                                      330

<210> SEQ ID NO 16
<211> LENGTH: 360
<212> TYPE: DNA
<213> ORGANISM: Homo sapiens

<400> SEQUENCE: 16
gaagtgcagc tggtggagtc tgggggaggc ttggtacagc ctggcaggtc cctgagactc      60
tcctgtgcag cctctggatt cacctttgat gatggtgcca tgcactgggt ccggcaagct     120

```
ccagggaagg gcctggagtg ggtctcaggt attagttgga atagtaatat catagcctat    180
gcggactctg tgaagggccg attcaccatc tccagagaca acgccaagaa ctccctgtat    240
ttagaaatga acagtctgag agttgaggac acggccttgt attactgtgc aaaagattct    300 ccgcggggg agctacccct tgaactactgg ggccagggaa ccctggtcac cgtctcctca    360
```

```
<210> SEQ ID NO 17
<211> LENGTH: 324
<212> TYPE: DNA
<213> ORGANISM: Homo sapiens

<400> SEQUENCE: 17
```

```
tcctatgagc tgacacagcc accctcggtg tcagtgtccc caggacaaac ggccaggatc     60
acctgctctg gagatgcatt gccaaaaaac tatgcttatt ggtaccagca gaagtcaggc    120
caggcccctg tgttggtcat ctatgaggac agcaaacgac cctccgggat ccctgagaga    180
ttctctggct ccagctcagg gacaatggcc accttgacta tcagtggggc ccaggttgag    240
gatgaagctg actactactg ttactcaaca gacagcagtg gtaatcatag ggtgttcggc    300
ggagggacca agctgaccgt ccta                                           324
```

```
<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18
```

Ala Arg Asp Lys Lys Gln Lys Val His Ala Leu Phe Tyr Lys Leu Asp
1               5                   10                  15

Ile Val Pro Ile Glu Asp
            20

```
<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

Leu Ala Asp Lys Lys Gln Lys Val His Ala Leu Phe Tyr Lys Leu Asp
1               5                   10                  15

Ile Val Pro Ile Glu Asp
            20

```
<210> SEQ ID NO 20
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

Leu Arg Ala Lys Lys Gln Lys Val His Ala Leu Phe Tyr Lys Leu Asp
1               5                   10                  15

Ile Val Pro Ile Glu Asp
            20

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Arg Asp Ala Lys Gln Lys Val His Ala Leu Phe Tyr Lys Leu Asp
1               5                   10                  15

Ile Val Pro Ile Glu Asp
            20

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Arg Asp Lys Ala Gln Lys Val His Ala Leu Phe Tyr Lys Leu Asp
1               5                   10                  15

Ile Val Pro Ile Glu Asp
            20

<210> SEQ ID NO 23
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Arg Asp Lys Lys Ala Lys Val His Ala Leu Phe Tyr Lys Leu Asp
1               5                   10                  15

Ile Val Pro Ile Glu Asp
            20

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Arg Asp Lys Lys Gln Ala Val His Ala Leu Phe Tyr Lys Leu Asp
1               5                   10                  15

Ile Val Pro Ile Glu Asp
            20

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Arg Asp Lys Lys Gln Lys Ala His Ala Leu Phe Tyr Lys Leu Asp
1               5                   10                  15

Ile Val Pro Ile Glu Asp
            20

<210> SEQ ID NO 26
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Arg Asp Lys Lys Gln Lys Val Ala Ala Leu Phe Tyr Lys Leu Asp
1               5                   10                  15

Ile Val Pro Ile Glu Asp
            20

<210> SEQ ID NO 27
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Leu Arg Asp Lys Lys Gln Lys Val His Glu Leu Phe Tyr Lys Leu Asp
1               5                   10                  15

Ile Val Pro Ile Glu Asp
            20

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Arg Asp Lys Lys Gln Lys Val His Ala Ala Phe Tyr Lys Leu Asp
1               5                   10                  15

Ile Val Pro Ile Glu Asp
            20

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Arg Asp Lys Lys Gln Lys Val His Ala Leu Ala Tyr Lys Leu Asp
1               5                   10                  15

Ile Val Pro Ile Glu Asp
            20

<210> SEQ ID NO 30
<211> LENGTH: 22
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 30

Leu Arg Asp Lys Lys Gln Lys Val His Ala Leu Phe Ala Lys Leu Asp
1               5                   10                  15

Ile Val Pro Ile Glu Asp
            20

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Arg Asp Lys Lys Gln Lys Val His Ala Leu Phe Tyr Ala Leu Asp
1               5                   10                  15

Ile Val Pro Ile Glu Asp
            20

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Arg Asp Lys Lys Gln Lys Val His Ala Leu Phe Tyr Lys Ala Asp
1               5                   10                  15

Ile Val Pro Ile Glu Asp
            20

<210> SEQ ID NO 33
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg Asp Lys Lys Gln Lys Val His Ala Leu Phe Tyr Lys Leu Ala
1               5                   10                  15

Ile Val Pro Ile Glu Asp
            20

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Leu Arg Asp Lys Lys Gln Lys Val His Ala Leu Phe Tyr Lys Leu Asp
1               5                   10                  15

Ala Val Pro Ile Glu Asp
            20
```

<210> SEQ ID NO 35
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Arg Asp Lys Lys Gln Lys Val His Ala Leu Phe Tyr Lys Leu Asp
1               5                   10                  15

Ile Ala Pro Ile Glu Asp
            20

<210> SEQ ID NO 36
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Arg Asp Lys Lys Gln Lys Val His Ala Leu Phe Tyr Lys Leu Asp
1               5                   10                  15

Ile Val Ala Ile Glu Asp
            20

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Arg Asp Lys Lys Gln Lys Val His Ala Leu Phe Tyr Lys Leu Asp
1               5                   10                  15

Ile Val Pro Ala Glu Asp
            20

<210> SEQ ID NO 38
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Arg Asp Lys Lys Gln Lys Val His Ala Leu Phe Tyr Lys Leu Asp
1               5                   10                  15

Ile Val Pro Ile Ala Asp
            20

<210> SEQ ID NO 39
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

-continued

```
Leu Arg Asp Lys Lys Gln Lys Val His Ala Leu Phe Tyr Lys Leu Asp
1               5                   10                  15

Ile Val Pro Ile Glu Ala
            20

<210> SEQ ID NO 40
<211> LENGTH: 14
<212> TYPE: PRT
<213> ORGANISM: Human immunodeficiency virus 1

<400> SEQUENCE: 40

Asp Lys Lys Gln Lys Val His Ala Leu Phe Tyr Lys Leu Asp
1               5                   10

<210> SEQ ID NO 41
<211> LENGTH: 4
<212> TYPE: PRT
<213> ORGANISM: Human immunodeficiency virus 1

<400> SEQUENCE: 41

Lys Lys Gln Lys
1

<210> SEQ ID NO 42
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Val Lys Leu Thr Pro Leu Cys Val Thr Leu Asn Cys Ile Asp Leu Arg
1               5                   10                  15

Asn Ala Thr Asn Ala Thr Ser Asn Ser Asn Thr Thr Asn Thr Thr Ser
            20                  25                  30

Ser Ser Gly Gly Leu Met Met Glu Gln Gly Glu Ile Lys Asn Cys Ser
        35                  40                  45

Phe Asn Ile Thr Thr Ser Ile Arg Asp Lys Val Gln Lys Glu Tyr Ala
    50                  55                  60

Leu Phe Tyr Lys Leu Asp Ile Val Pro Ile Asp Asn Pro Lys Asn Ser
65                  70                  75                  80

Thr Asn Tyr Arg Leu Ile Ser Cys Asn Thr Ser Val Ile Thr Gln Ala
                85                  90                  95

<210> SEQ ID NO 43
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Leu Lys Pro Cys Val Lys Leu Thr Pro Leu Cys Val Thr Leu Asp Cys
1               5                   10                  15

Asn Ala Thr Ala Ser Asn Val Thr Asn Glu Met Arg Asn Cys Ser Phe
            20                  25                  30

Asn Ile Thr Thr Glu Leu Lys Asp Lys Lys Gln Gln Val Tyr Ser Leu
        35                  40                  45

Phe Tyr Lys Leu Asp Val Val Gln Ile Asn Glu Lys Asn Glu Thr Asp
```

```
            50                  55                  60
Lys Tyr Arg Leu Ile Asn Cys Asn Thr Ser Ala Ile Thr Gln Ala
 65                  70                  75

<210> SEQ ID NO 44
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Lys Pro Cys Val Lys Leu Thr Pro Leu Cys Val Ser Leu Lys Cys
  1               5                  10                  15

Thr Asp Leu Lys Asn Asp Thr Asn Thr Asn Ser Ser Ser Gly Arg Met
             20                  25                  30

Ile Met Glu Lys Gly Glu Ile Lys Asn Cys Ser Phe Asn Ile Ser Thr
         35                  40                  45

Ser Ile Arg Gly Lys Val Gln Lys Glu Tyr Ala Phe Phe Tyr Lys Leu
     50                  55                  60

Asp Ile Ile Pro Ile Asp Asn Asp Thr Thr Ser Tyr Ser Leu Thr Ser
 65                  70                  75                  80

Cys Asn Thr Ser Val Ile Thr Gln Ala
                 85

<210> SEQ ID NO 45
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Leu Lys Pro Cys Val Lys Leu Thr Pro Leu Cys Val Thr Leu His Cys
  1               5                  10                  15

Thr Asn Ala Thr Phe Lys Asn Asn Val Thr Asn Asp Met Asn Lys Glu
             20                  25                  30

Ile Arg Asn Cys Ser Phe Asn Thr Thr Thr Glu Ile Arg Asp Lys Lys
         35                  40                  45

Gln Gln Gly Tyr Ala Leu Phe Tyr Arg Pro Asp Ile Val Leu Leu Lys
     50                  55                  60

Glu Asn Arg Asn Asn Ser Asn Asn Ser Glu Tyr Ile Leu Ile Asn Cys
 65                  70                  75                  80

Asn Ala Ser Thr Ile Thr Gln Ala
                 85

<210> SEQ ID NO 46
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Cys Val Thr Leu Asn Cys Thr Ser Pro Ala Ala His Asn Glu Ser Glu
  1               5                  10                  15

Thr Arg Val Lys His Cys Ser Phe Asn Ile Thr Thr Asp Val Lys Asp
             20                  25                  30
```

Arg Lys Gln Lys Val Asn Ala Thr Phe Tyr Asp Leu Asp Ile Val Pro
         35                   40                   45

Leu Ser Ser Ser Asp Asn Ser Ser Asn Ser Ser Leu Tyr Arg Leu Ile
 50                    55                   60

Ser Cys
 65

<210> SEQ ID NO 47
<211> LENGTH: 94
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 47

Val Lys Leu Thr Pro Pro Cys Val Thr Leu His Cys Thr Asn Ala Asn
1               5                 10               15

Leu Thr Lys Ala Asn Leu Thr Asn Val Asn Asn Arg Thr Asn Val Ser
         20                   25                   30

Asn Ile Ile Gly Asn Ile Thr Asp Glu Val Arg Asn Cys Ser Phe Asn
        35                   40                   45

Met Thr Thr Glu Leu Arg Asp Lys Lys Gln Lys Val His Ala Leu Phe
 50                    55                   60

Tyr Lys Leu Asp Ile Val Pro Ile Glu Asp Asn Asn Asp Ser Ser Glu
65                 70                 75                 80

Tyr Arg Leu Ile Asn Cys Asn Thr Ser Val Ile Lys Gln Pro
        85                   90

<210> SEQ ID NO 48
<211> LENGTH: 400
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 48

Met Ala Cys Ser Thr Leu Pro Lys Ser Pro Lys Asp Lys Ile Asp Pro
1               5                 10               15

Arg Asp Leu Leu Ile Pro Leu Ile Leu Phe Leu Ser Leu Lys Gly Ala
         20                   25                   30

Arg Ser Ala Ala Pro Gly Ser Ser Pro His His His His His His Gln
        35                   40                   45

Val Tyr Asn Ile Thr Trp Glu Val Thr Asn Gly Asp Arg Glu Thr Val
 50                    55                   60

Trp Ala Ile Ser Gly Asn His Pro Leu Trp Thr Trp Trp Pro Val Leu
65                 70                 75                 80

Thr Pro Asp Leu Cys Met Leu Ala Leu Ser Gly Pro Pro His Trp Gly
               85                 90               95

Leu Glu Tyr Gln Ala Pro Tyr Ser Ser Pro Pro Gly Pro Pro Cys Cys
              100                 105                110

Ser Gly Ser Ser Gly Ser Ser Ala Gly Cys Ser Arg Asp Cys Asp Glu
         115                  120                 125

Pro Leu Thr Ser Leu Thr Pro Arg Cys Asn Thr Ala Trp Asn Arg Leu
     130                  135                 140

Lys Leu Asp Gln Val Thr His Lys Ser Ser Glu Gly Phe Tyr Val Cys
145               150                155               160

```
Pro Gly Ser His Arg Pro Arg Glu Ala Lys Ser Cys Gly Gly Pro Asp
                165                 170                 175

Ser Phe Tyr Cys Ala Ser Trp Gly Cys Glu Thr Thr Gly Arg Val Tyr
            180                 185                 190

Trp Lys Pro Ser Ser Ser Trp Asp Tyr Ile Thr Val Asp Asn Asn Leu
        195                 200                 205

Thr Thr Ser Gln Ala Val Gln Val Cys Lys Asp Asn Lys Trp Cys Asn
    210                 215                 220

Pro Leu Ala Ile Gln Phe Thr Asn Ala Gly Lys Gln Val Thr Ser Trp
225                 230                 235                 240

Thr Thr Gly His Tyr Trp Gly Leu Arg Leu Tyr Val Ser Gly Arg Asp
                245                 250                 255

Pro Gly Leu Thr Phe Gly Ile Arg Leu Arg Tyr Gln Asn Leu Gly Pro
            260                 265                 270

Arg Val Pro Ile Gly Pro Asn Pro Val Leu Ala Asp Gln Leu Ser Leu
        275                 280                 285

Pro Arg Pro Asn Pro Leu Pro Lys Pro Ala Lys Ser Pro Pro Ala Ser
    290                 295                 300

Val Lys Leu Thr Pro Leu Cys Val Thr Leu Asn Cys Ile Asp Leu Arg
305                 310                 315                 320

Asn Ala Thr Asn Ala Thr Ser Asn Ser Asn Thr Thr Asn Thr Thr Ser
                325                 330                 335

Ser Ser Gly Gly Leu Met Met Glu Gln Gly Glu Ile Lys Asn Cys Ser
            340                 345                 350

Phe Asn Ile Thr Thr Ser Ile Arg Asp Lys Val Gln Lys Glu Tyr Ala
        355                 360                 365

Leu Phe Tyr Lys Leu Asp Ile Val Pro Ile Asp Asn Pro Lys Asn Ser
    370                 375                 380

Thr Asn Tyr Arg Leu Ile Ser Cys Asn Thr Ser Val Ile Thr Gln Ala
385                 390                 395                 400

<210> SEQ ID NO 49
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His His His His His Gln
        35                  40                  45

Val Tyr Asn Ile Thr Trp Glu Val Thr Asn Gly Asp Arg Glu Thr Val
    50                  55                  60

Trp Ala Ile Ser Gly Asn His Pro Leu Trp Thr Trp Pro Val Leu
65                  70                  75                  80

Thr Pro Asp Leu Cys Met Leu Ala Leu Ser Gly Pro His Trp Gly
                85                  90                  95

Leu Glu Tyr Gln Ala Pro Tyr Ser Ser Pro Gly Pro Pro Cys Cys
            100                 105                 110

Ser Gly Ser Ser Gly Ser Ser Ala Gly Cys Ser Arg Asp Cys Asp Glu
```

```
                  115                 120                 125
Pro Leu Thr Ser Leu Thr Pro Arg Cys Asn Thr Ala Trp Asn Arg Leu
    130                 135                 140

Lys Leu Asp Gln Val Thr His Lys Ser Ser Glu Gly Phe Tyr Val Cys
145                 150                 155                 160

Pro Gly Ser His Arg Pro Arg Glu Ala Lys Ser Cys Gly Gly Pro Asp
                165                 170                 175

Ser Phe Tyr Cys Ala Ser Trp Gly Cys Glu Thr Thr Gly Arg Val Tyr
            180                 185                 190

Trp Lys Pro Ser Ser Ser Trp Asp Tyr Ile Thr Val Asp Asn Asn Leu
        195                 200                 205

Thr Thr Ser Gln Ala Val Gln Val Cys Lys Asp Asn Lys Trp Cys Asn
    210                 215                 220

Pro Leu Ala Ile Gln Phe Thr Asn Ala Gly Lys Gln Val Thr Ser Trp
225                 230                 235                 240

Thr Thr Gly His Tyr Trp Gly Leu Arg Leu Tyr Val Ser Gly Arg Asp
                245                 250                 255

Pro Gly Leu Thr Phe Gly Ile Arg Leu Arg Tyr Gln Asn Leu Gly Pro
            260                 265                 270

Arg Val Pro Ile Gly Pro Asn Pro Val Leu Ala Asp Gln Leu Ser Leu
        275                 280                 285

Pro Arg Pro Asn Pro Leu Pro Lys Pro Ala Lys Ser Pro Pro Ala Ser
    290                 295                 300

Val Lys Leu Thr Pro Leu Cys Val Thr Leu Asn Cys Thr Asn Val Lys
305                 310                 315                 320

Gly Asn Glu Ser Asp Thr Ser Glu Val Met Lys Asn Cys Ser Phe Lys
                325                 330                 335

Ala Thr Thr Glu Leu Lys Asp Lys Lys His Lys Val His Ala Leu Phe
            340                 345                 350

Tyr Lys Leu Asp Val Val Pro Leu Asn Gly Asn Ser Ser Ser Ser Gly
        355                 360                 365

Glu Tyr Arg Leu Ile Asn Cys Asn Thr Ser Ala Ile Thr Gln Ala
    370                 375                 380

<210> SEQ ID NO 50
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His His His His His His Gln
        35                  40                  45

Val Tyr Asn Ile Thr Trp Glu Val Thr Asn Gly Asp Arg Glu Thr Val
    50                  55                  60

Trp Ala Ile Ser Gly Asn His Pro Leu Trp Thr Trp Pro Val Leu
65                  70                  75                  80

Thr Pro Asp Leu Cys Met Leu Ala Leu Ser Gly Pro Pro His Trp Gly
                85                  90                  95
```

```
Leu Glu Tyr Gln Ala Pro Tyr Ser Ser Pro Gly Pro Cys Cys
            100                 105                 110

Ser Gly Ser Ser Gly Ser Ser Ala Gly Cys Ser Arg Asp Cys Asp Glu
        115                 120                 125

Pro Leu Thr Ser Leu Thr Pro Arg Cys Asn Thr Ala Trp Asn Arg Leu
        130                 135                 140

Lys Leu Asp Gln Val Thr His Lys Ser Ser Glu Gly Phe Tyr Val Cys
145                 150                 155                 160

Pro Gly Ser His Arg Pro Arg Glu Ala Lys Ser Cys Gly Gly Pro Asp
                165                 170                 175

Ser Phe Tyr Cys Ala Ser Trp Gly Cys Glu Thr Thr Gly Arg Val Tyr
            180                 185                 190

Trp Lys Pro Ser Ser Ser Trp Asp Tyr Ile Thr Val Asp Asn Asn Leu
            195                 200                 205

Thr Thr Ser Gln Ala Val Gln Val Cys Lys Asp Asn Lys Trp Cys Asn
210                 215                 220

Pro Leu Ala Ile Gln Phe Thr Asn Ala Gly Lys Gln Val Thr Ser Trp
225                 230                 235                 240

Thr Thr Gly His Tyr Trp Gly Leu Arg Leu Tyr Val Ser Gly Arg Asp
            245                 250                 255

Pro Gly Leu Thr Phe Gly Ile Arg Leu Arg Tyr Gln Asn Leu Gly Pro
            260                 265                 270

Arg Val Pro Ile Gly Pro Asn Pro Val Leu Ala Asp Gln Leu Ser Leu
            275                 280                 285

Pro Arg Pro Asn Pro Leu Pro Lys Pro Ala Lys Ser Pro Pro Ala Ser
            290                 295                 300

<210> SEQ ID NO 51
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Ser Gln Tyr Val Ser Ser His Val Asn Asn His Asn Ser
        35                  40                  45

Ser His Asn Val Ser Ser His Ser Gly Asn Ile Thr Ser Asp Met Lys
50                  55                  60

Ile Cys Ser Phe Asn Thr Thr Thr Glu Val Arg Asp Lys Lys Gln Lys
65                  70                  75                  80

Val Tyr Ser Leu Phe Tyr Lys Leu Asp Val Val Pro Ile Ser Asn Asp
                85                  90                  95

Ser Ser Gln Tyr Arg Leu Ile Asn Cys Asn Thr Ser Ala Ile Thr Gln
            100                 105                 110

Ala Gly Leu Asn Asp Ile Phe Glu Ala Gln Lys Ile Glu Trp His Glu
        115                 120                 125

Leu Glu Val Leu Phe Gln Gly Pro Gly His His His His His His
    130                 135                 140

<210> SEQ ID NO 52
```

<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

His Cys Thr Asn Val Thr Ser Val Asn Thr Thr Gly Asp Arg Glu Gly
        35                  40                  45

Leu Lys Asn Cys Ser Phe Asn Met Thr Thr Glu Leu Arg Asp Lys Arg
    50                  55                  60

Gln Lys Val Tyr Ser Leu Phe Tyr Arg Leu Asp Ile Val Pro Ile Asn
65                  70                  75                  80

Glu Asn Gln Gly Ser Glu Tyr Arg Leu Ile Asn Cys Asn Thr Ser Ala
                85                  90                  95

Ile Thr Gln Ala Gly Leu Asn Asp Ile Phe Glu Ala Gln Lys Ile Glu
            100                 105                 110

Trp His Glu Leu Glu Val Leu Phe Gln Gly Pro Gly His His His His
        115                 120                 125

His His
    130

<210> SEQ ID NO 53
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asn Leu Thr Lys Ala Asn Leu Thr Asn Val Asn
        35                  40                  45

Asn Arg Thr Asn Val Ser Asn Ile Ile Gly Asn Ile Thr Asp Glu Val
    50                  55                  60

Arg Asn Cys Ser Phe Asn Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asn Asp Ser Ser Glu Tyr Arg Leu Ile Asn Cys Asn Thr Ser Val
            100                 105                 110

Ile Lys Gln Pro Gly Leu Asn Asp Ile Phe Glu Ala Gln Lys Ile Glu
        115                 120                 125

Trp His Glu Leu Glu Val Leu Phe Gln Gly Pro Gly His His His His
    130                 135                 140

His His
145

<210> SEQ ID NO 54

<211> LENGTH: 140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asp Val Thr Asn Ala Thr Asn Ile Asn Ala Thr Asn Ile
        35                  40                  45

Asn Asn Ser Ser Gly Gly Val Glu Ser Gly Glu Ile Lys Asn Cys Ser
    50                  55                  60

Phe Asn Ile Thr Thr Ser Val Arg Asp Lys Val Gln Lys Glu Tyr Ala
65                  70                  75                  80

Leu Phe Tyr Lys Leu Asp Ile Val Pro Ile Thr Asn Glu Ser Ser Lys
                85                  90                  95

Tyr Arg Leu Ile Ser Cys Asn Thr Ser Val Leu Thr Gln Ala Gly Leu
            100                 105                 110

Asn Asp Ile Phe Glu Ala Gln Lys Ile Glu Trp His Glu Leu Glu Val
        115                 120                 125

Leu Phe Gln Gly Pro Gly His His His His His
    130                 135                 140
```

<210> SEQ ID NO 55
<211> LENGTH: 148
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Ile Asp Leu Arg Asn Ala Thr Asn Ala Thr Ser Asn Ser Asn
        35                  40                  45

Thr Thr Asn Thr Thr Ser Ser Ser Gly Gly Leu Met Met Glu Gln Gly
    50                  55                  60

Glu Ile Lys Asn Cys Ser Phe Asn Ile Thr Thr Ser Ile Arg Asp Lys
65                  70                  75                  80

Val Gln Lys Glu Tyr Ala Leu Phe Tyr Lys Leu Asp Ile Val Pro Ile
                85                  90                  95

Asp Asn Pro Lys Asn Ser Thr Asn Tyr Arg Leu Ile Ser Cys Asn Thr
            100                 105                 110

Ser Val Ile Thr Gln Ala Gly Leu Asn Asp Ile Phe Glu Ala Gln Lys
        115                 120                 125

Ile Glu Trp His Glu Leu Glu Val Leu Phe Gln Gly Pro Gly His His
    130                 135                 140

His His His His
145
```

<210> SEQ ID NO 56

<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Glu Thr Asp Thr Leu Leu Leu Trp Val Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Thr Asn Ser Thr Asn Phe Ala Asn Ser Thr Gly Lys Asp
        35                  40                  45

Ile Glu Met Gln Asp Cys Ser Phe Asn Ile Thr Thr Glu Ile Arg Asp
50                  55                  60

Lys Gln Lys Lys Val His Ala Leu Phe Tyr Lys Leu Asp Ile Val Gln
65                  70                  75                  80

Ile Asp Asn Asn Thr Glu Ala Asn Ala Asn Tyr Thr Ser Tyr Arg Leu
                85                  90                  95

Ile Asn Cys Asn Thr Ser Ala Ile Thr Gln Ala Gly Leu Asn Asp Ile
            100                 105                 110

Phe Glu Ala Gln Lys Ile Glu Trp His Glu Leu Glu Val Leu Phe Gln
        115                 120                 125

Gly Pro Gly His His His His His His
    130                 135

<210> SEQ ID NO 57
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Gly Ala Met Gly Ile Gln Met Asn Trp Gln Asn Leu Trp Arg Trp
1               5                   10                  15

Gly Thr Met Ile Leu Gly Met Leu Ile Ile Cys Ser Val Ala Glu Lys
            20                  25                  30

Ser Trp Val Thr Val Tyr Tyr Gly Val Pro Val Trp Arg Asp Ala Glu
        35                  40                  45

Thr Thr Leu Phe Cys Ala Ser Asp Ala Lys Ala His Asp Lys Glu Val
        50                  55                  60

His Asn Val Trp Ala Thr His Ala Cys Val Pro Thr Asp Pro Asn Pro
65                  70                  75                  80

Gln Glu Met Ile Leu Glu Asn Val Thr Glu Asp Phe Asn Met Trp Lys
                85                  90                  95

Asn Ser Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asp Ser Asn Ile Thr Ser Asn Ser Thr Ser Asn Ser Thr
    130                 135                 140

Lys Asp Ser Ala Thr Leu Asp Met Lys Ser Glu Ile Gln Asn Cys Ser
145                 150                 155                 160

Phe Asn Met Thr Thr Glu Leu Arg Asp Lys Lys Gln Lys Val Tyr Ser
                165                 170                 175

-continued

```
Leu Phe Tyr Arg Leu Asp Val Val Gln Ile Asn Glu Asn Ser Ser Asp
                180                 185                 190

Tyr Arg Leu Ile Asn Cys Asn Thr Ser Ala Ile Thr Gln Ala Cys Pro
            195                 200                 205

Lys Val Thr Phe Glu Pro Ile Pro Ile His Tyr Cys Ala Pro Ala Gly
        210                 215                 220

Phe Ala Ile Leu Lys Cys Asn Asp Lys Lys Phe Asn Gly Thr Gly Pro
225                 230                 235                 240

Cys Thr Asn Val Ser Thr Val Gln Cys Thr His Gly Ile Lys Pro Val
                245                 250                 255

Val Thr Thr Gln Leu Leu Leu Asn Gly Ser Leu Ala Glu Glu Glu Val
                260                 265                 270

Met Ile Arg Ser Glu Asn Ile Thr Glu Asn Ala Lys Asn Ile Ile Val
            275                 280                 285

Gln Phe Lys Glu Pro Val Gln Ile Ile Cys Ile Arg Pro Gly Asn Asn
        290                 295                 300

Thr Arg Lys Ser Val His Ile Gly Pro Gly Gln Ala Phe Tyr Ala Thr
305                 310                 315                 320

Gly Asp Ile Ile Gly Asp Ile Arg Gln Ala His Cys Asn Val Ser Arg
                325                 330                 335

Glu Leu Trp Asn Lys Thr Leu Gln Glu Val Ala Thr Gln Leu Arg Lys
            340                 345                 350

His Phe Arg Asn Asn Thr Lys Ile Ile Phe Thr Asn Ser Ser Gly Gly
        355                 360                 365

Asp Val Glu Ile Thr Thr His Ser Phe Asn Cys Gly Gly Glu Phe Phe
        370                 375                 380

Tyr Cys Asp Thr Ser Gly Leu Phe Asn Ser Ser Trp Thr Ala Ser Asn
385                 390                 395                 400

Asp Ser Met Gln Glu Ala His Ser Thr Glu Ser Asn Ile Thr Leu Gln
                405                 410                 415

Cys Arg Ile Lys Gln Ile Ile Asn Met Trp Gln Arg Ala Gly Gln Ala
            420                 425                 430

Met Tyr Ala Pro Pro Ile Pro Gly Ile Ile Arg Cys Glu Ser Asn Ile
        435                 440                 445

Thr Gly Leu Ile Leu Thr Arg Asp Gly Gly Glu Gly Asn Asn Ser Thr
        450                 455                 460

Asn Glu Thr Phe Arg Pro Val Gly Gly Asn Met Arg Asp Asn Trp Arg
465                 470                 475                 480

Ser Glu Leu Tyr Lys Tyr Lys Val Val Lys Val Glu Pro Leu Gly Val
                485                 490                 495

Ala Pro Thr Lys Ser Arg Thr Leu Thr Val Gln Ala Arg Gln Leu Leu
            500                 505                 510

Ser Gly Ile Val Gln Gln Gln Ser Asn Leu Leu Arg Ala Ile Glu Ala
        515                 520                 525

Gln Gln His Leu Leu Lys Leu Thr Val Trp Gly Ile Lys Gln Leu Gln
        530                 535                 540

Ala Arg Val Leu Ala Val Glu Arg Tyr Leu Arg Asp Gln Gln Leu Leu
545                 550                 555                 560

Gly Ile Trp Gly Cys Ser Gly Lys Leu Ile Cys Thr Thr Asn Val Pro
                565                 570                 575

Trp Asn Ser Ser Trp Ser Asn Lys Ser Leu Asp Glu Ile Trp Glu Asn
            580                 585                 590
```

```
Met Thr Trp Met Gln Trp Asp Lys Glu Val Ser Asn Tyr Thr Gln Met
            595                 600                 605

Ile Tyr Asn Leu Leu Glu Glu Ser Gln Asn Gln Glu Lys Asn Glu
    610                 615                 620

Gln Glu Leu Leu Ala Leu Asp Lys Trp Ala Asn Leu Trp Asn Trp Phe
625                 630                 635                 640

Asn Ile Ser Asn Trp Leu Trp
                645

<210> SEQ ID NO 58
<211> LENGTH: 601
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Arg Val Arg Gly Ile Gln Thr Ser Trp Gln Asn Leu Trp Arg Trp
1               5                   10                  15

Gly Thr Met Ile Leu Gly Met Leu Val Ile Tyr Ser Ala Ala Glu Asn
            20                  25                  30

Leu Trp Val Ala Val Tyr Tyr Gly Val Pro Val Trp Lys Asp Ala Glu
        35                  40                  45

Thr Thr Leu Phe Cys Ala Ser Asp Ala Lys Ala Tyr Asp Thr Glu Val
    50                  55                  60

His Asn Val Trp Glu Thr His Ala Cys Val Pro Thr Asp Pro Asn Pro
65                  70                  75                  80

Gln Glu Ile His Leu Glu Asn Val Thr Glu Asp Phe Asn Met Trp Arg
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asp Cys Asn Ala Thr Ala Ser Asn Val Thr Asn Glu Met Arg Asn Cys
    130                 135                 140

Ser Phe Asn Ile Thr Thr Glu Leu Lys Asp Lys Lys Gln Gln Val Tyr
145                 150                 155                 160

Ser Leu Phe Tyr Lys Leu Asp Val Gln Ile Asn Glu Lys Asn Glu
                165                 170                 175

Thr Asp Lys Tyr Arg Leu Ile Asn Cys Asn Thr Ser Ala Ile Thr Gln
            180                 185                 190

Ala Cys Pro Lys Val Ser Phe Glu Pro Ile Pro Ile His Tyr Cys Ala
        195                 200                 205

Pro Ala Gly Phe Ala Ile Leu Lys Cys Lys Asp Thr Glu Phe Asn Gly
    210                 215                 220

Thr Gly Pro Cys Lys Asn Val Ser Thr Val Gln Cys Thr His Gly Ile
225                 230                 235                 240

Arg Pro Val Ile Ser Thr Gln Leu Leu Leu Asn Gly Ser Leu Ala Glu
                245                 250                 255

Glu Gly Ile Gln Ile Arg Ser Glu Asn Ile Thr Asn Asn Ala Lys Thr
            260                 265                 270

Ile Ile Val Gln Leu Asp Lys Ala Val Lys Ile Asn Cys Thr Arg Pro
        275                 280                 285

Asn Asn Asn Thr Arg Lys Gly Val Arg Ile Gly Pro Gly Gln Ala Phe
    290                 295                 300
```

```
Tyr Ala Thr Gly Gly Ile Ile Gly Asp Ile Arg Gln Ala His Cys His
305                 310                 315                 320

Val Ser Arg Ala Lys Trp Asn Asp Thr Leu Arg Gly Val Ala Lys Lys
                325                 330                 335

Leu Arg Glu His Phe Lys Asn Lys Thr Ile Ile Phe Gly Lys Ser Ser
            340                 345                 350

Gly Gly Asp Ile Glu Ile Thr Thr His Ser Phe Ile Cys Gly Gly Glu
        355                 360                 365

Phe Phe Tyr Cys Asn Thr Ser Gly Leu Phe Asn Ser Thr Trp Glu Ser
    370                 375                 380

Asn Ser Thr Glu Ser Asn Asn Thr Thr Ser Asn Asp Thr Ile Thr Leu
385                 390                 395                 400

Thr Cys Arg Ile Lys Gln Ile Ile Asn Met Trp Gln Lys Val Gly Gln
                405                 410                 415

Ala Met Tyr Pro Pro Pro Ile Gln Gly Val Ile Arg Cys Glu Ser Asn
            420                 425                 430

Ile Thr Gly Leu Leu Leu Thr Arg Asp Gly Gly Asn Asn Ser Thr Asn
        435                 440                 445

Glu Ile Phe Arg Pro Gly Gly Gly Asn Met Arg Asp Asn Trp Arg Ser
    450                 455                 460

Glu Leu Tyr Lys Tyr Lys Val Val Lys Ile Glu Pro Leu Gly Val Ala
465                 470                 475                 480

Pro Ser Arg Ala Lys Leu Thr Ala Gln Ala Arg Gln Leu Leu Ser Gly
                485                 490                 495

Ile Val Gln Gln Gln Ser Asn Leu Leu Arg Ala Ile Glu Ala Gln Gln
            500                 505                 510

His Met Leu Lys Leu Thr Val Trp Gly Ile Lys Gln Leu Gln Ala Arg
        515                 520                 525

Val Leu Ala Val Glu Arg Tyr Leu Lys Asp Gln Gln Leu Glu Ile Trp
    530                 535                 540

Asp Asn Met Thr Trp Leu Gln Trp Asp Lys Glu Ile Ser Asn Tyr Thr
545                 550                 555                 560

Gln Ile Ile Tyr Asn Leu Ile Glu Glu Ser Gln Asn Gln Gln Glu Lys
                565                 570                 575

Asn Glu Gln Asp Leu Leu Ala Leu Asp Lys Trp Ala Ser Leu Trp Asn
            580                 585                 590

Trp Phe Asp Ile Ser Arg Trp Leu Trp
        595                 600

<210> SEQ ID NO 59
<211> LENGTH: 629
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Arg Val Met Gly Ile Gln Arg Asn Cys Gln His Leu Leu Arg Trp
1               5                   10                  15

Gly Thr Met Ile Leu Gly Met Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Met
```

-continued

```
                50                  55                  60
His Asn Val Trp Ala Thr His Ala Cys Val Pro Thr Asp Pro Asn Pro
 65                  70                  75                  80

Gln Glu Ile His Leu Glu Asn Val Thr Glu Phe Asn Met Trp Lys
                 85                  90                  95

Asn Asn Met Val Glu Gln Met His Thr Asp Ile Ile Ser Leu Trp Asp
                100                 105                 110

Gln Ser Leu Lys Pro Cys Val Lys Leu Thr Pro Leu Cys Val Thr Leu
                115                 120                 125

Asn Cys Ser Asn Val Asn Val Thr Asn Asn Thr Thr Asn Thr His Glu
                130                 135                 140

Glu Glu Ile Lys Asn Cys Ser Phe Asn Met Thr Thr Glu Leu Arg Asp
145                 150                 155                 160

Lys Lys Gln Lys Val Tyr Ser Leu Phe Tyr Arg Leu Asp Val Val Gln
                165                 170                 175

Ile Asn Glu Asn Asn Ser Asn Ser Ser Tyr Arg Leu Ile Asn Cys Asn
                180                 185                 190

Thr Ser Ala Ile Thr Gln Ala Cys Pro Lys Val Ser Phe Glu Pro Ile
                195                 200                 205

Pro Ile His Tyr Cys Ala Pro Ala Gly Phe Ala Ile Leu Lys Cys Lys
    210                 215                 220

Asp Lys Glu Phe Asn Gly Thr Gly Pro Cys Lys Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Val Ile Ile Arg Ser Glu Asn Ile
            260                 265                 270

Thr Asn Asn Ala Lys Thr Ile Ile Val Gln Leu Thr Lys Pro Val Lys
                275                 280                 285

Ile Asn Cys Thr Arg Pro Asn Asn Asn Thr Arg Lys Ser Ile Arg Ile
    290                 295                 300

Gly Pro Gly Gln Ala Phe Tyr Ala Thr Gly Asp Ile Ile Gly Asp Ile
305                 310                 315                 320

Arg Gln Ala His Cys Asn Val Ser Arg Ser Glu Trp Asn Lys Thr Leu
                325                 330                 335

Gln Lys Val Ala Lys Gln Leu Arg Lys Tyr Phe Lys Asn Lys Thr Ile
                340                 345                 350

Ile Phe Thr Asn Ser Ser Gly Gly Asp Leu Glu Ile Thr Thr His Ser
    355                 360                 365

Phe Asn Cys Gly Gly Glu Phe Phe Tyr Cys Asn Thr Ser Gly Leu Phe
    370                 375                 380

Asn Ser Thr Trp Asn Gly Thr Met Lys Asn Thr Ile Thr Leu Pro
385                 390                 395                 400

Cys Arg Ile Lys Gln Ile Ile Asn Met Trp Gln Arg Ala Gly Gln Ala
                405                 410                 415

Met Tyr Ala Pro Pro Ile Gln Gly Val Ile Arg Cys Glu Ser Asn Ile
                420                 425                 430

Thr Gly Leu Leu Leu Thr Arg Asp Gly Gly Asn Asn Thr Asn Glu
                435                 440                 445

Thr Phe Arg Pro Gly Gly Gly Asp Met Arg Asp Asn Trp Arg Ser Glu
                450                 455                 460

Leu Tyr Lys Tyr Lys Val Val Lys Ile Glu Pro Leu Gly Val Ala Pro
465                 470                 475                 480
```

```
Thr Arg Ala Lys Thr Leu Thr Val Gln Ala Arg Gln Leu Leu Ser Gly
            485                 490                 495

Ile Val Gln Gln Gln Ser Asn Leu Leu Arg Ala Ile Glu Ala Gln Gln
        500                 505                 510

His Leu Leu Lys Leu Thr Val Trp Gly Ile Lys Gln Leu Gln Ala Arg
    515                 520                 525

Val Leu Ala Val Glu Arg Tyr Leu Lys Asp Gln Gln Leu Leu Gly Ile
530                 535                 540

Trp Gly Cys Ser Gly Lys Leu Ile Cys Thr Thr Asn Val Pro Trp Asn
545                 550                 555                 560

Ser Ser Trp Ser Asn Lys Ser Gln Asn Glu Ile Trp Asp Asn Met Thr
                565                 570                 575

Trp Leu Gln Trp Asp Lys Glu Ile Ser Asn Tyr Thr His Ile Ile Tyr
            580                 585                 590

Asn Leu Ile Glu Glu Ser Gln Asn Gln Gln Glu Lys Asn Glu Gln Asp
        595                 600                 605

Leu Leu Ala Leu Asp Lys Trp Ala Asn Leu Trp Asn Trp Phe Asp Ile
    610                 615                 620

Ser Asn Trp Leu Trp
625

<210> SEQ ID NO 60
<211> LENGTH: 630
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Arg
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Asn Trp Thr Asn Ser Asn Thr Thr Asn Gly
    130                 135                 140

Pro Asn Lys Ile Gly Asn Ile Thr Asp Glu Val Lys Asn Cys Thr Phe
145                 150                 155                 160

Asn Met Thr Thr Glu Leu Lys Asp Lys Gln Lys Val His Ala Leu
                165                 170                 175

Phe Tyr Lys Leu Asp Ile Val Gln Ile Asn Ser Ser Glu Tyr Arg Leu
            180                 185                 190

Ile Asn Cys Asn Thr Ser Val Ile Lys Gln Ala Cys Pro Lys Ile Ser
```

|     |     |     | 195 |     |     |     | 200 |     |     |     | 205 |     |     |     |
| --- | --- | --- | --- | --- | --- | --- | --- | --- | --- | --- | --- | --- | --- | --- |

Phe Asp Pro Ile Pro Ile His Tyr Cys Thr Pro Ala Gly Tyr Ala Ile
210                     215                     220

Leu Lys Cys Asn Asp Lys Asn Phe Asn Gly Thr Gly Pro Cys Lys Asn
225                     230                     235                     240

Val Ser Ser Val Gln Cys Thr His Gly Ile Lys Pro Val Val Ser Thr
                        245                     250                     255

Gln Leu Leu Leu Asn Gly Ser Leu Ala Glu Glu Ile Ile Ile Arg
                260                     265                     270

Ser Glu Asn Leu Thr Asn Asn Ala Lys Thr Ile Ile Val His Leu Asn
            275                     280                     285

Lys Ser Val Glu Ile Asn Cys Thr Arg Pro Ser Asn Asn Thr Arg Thr
290                     295                     300

Ser Ile Thr Met Gly Pro Gly Gln Val Phe Tyr Arg Thr Gly Asp Ile
305                     310                     315                     320

Ile Gly Asp Ile Arg Lys Ala Tyr Cys Glu Ile Asn Gly Ile Lys Trp
                        325                     330                     335

Asn Glu Val Leu Val Gln Val Thr Gly Lys Leu Lys Glu His Phe Asn
                340                     345                     350

Lys Thr Ile Ile Phe Gln Pro Pro Ser Gly Gly Asp Leu Glu Ile Ile
            355                     360                     365

Thr His His Phe Ser Cys Arg Gly Glu Phe Phe Tyr Cys Asn Thr Thr
370                     375                     380

Lys Leu Phe Asn Asn Thr Cys Ile Gly Asn Thr Ser Met Glu Gly Cys
385                     390                     395                     400

Asn Asn Thr Ile Ile Leu Pro Cys Lys Ile Lys Gln Ile Ile Asn Met
                        405                     410                     415

Trp Gln Gly Val Gly Gln Ala Met Tyr Ala Pro Pro Ile Ser Gly Arg
                420                     425                     430

Ile Asn Cys Val Ser Asn Ile Thr Gly Ile Leu Leu Thr Arg Asp Gly
            435                     440                     445

Gly Ala Asp Asn Asn Thr Thr Asn Glu Thr Phe Arg Pro Gly Gly Gly
450                     455                     460

Asn Ile Lys Asp Asn Trp Arg Ser Glu Leu Tyr Lys Tyr Lys Val Val
465                     470                     475                     480

Glu Ile Glu Pro Leu Gly Ile Ala Pro Thr Arg Ala Arg Thr Leu Thr
                        485                     490                     495

Val Gln Ala Arg Gln Leu Leu Ser Gly Ile Val Gln Gln Ser Asn
                500                     505                     510

Leu Leu Arg Ala Ile Glu Ala Gln Gln His Leu Leu Gln Leu Thr Val
            515                     520                     525

Trp Gly Ile Lys Gln Leu Gln Ala Arg Val Leu Ala Val Glu Arg Tyr
530                     535                     540

Leu Lys Asp Gln Lys Phe Leu Gly Leu Trp Gly Cys Ser Gly Lys Ile
545                     550                     555                     560

Ile Cys Thr Thr Ala Val Pro Trp Asn Ser Ser Trp Ser Asn Lys Ser
                        565                     570                     575

Phe Glu Glu Ile Trp Asp Asn Met Thr Trp Ile Glu Trp Glu Arg Glu
                580                     585                     590

Ile Ser Asn Tyr Thr Ser Gln Ile Tyr Glu Ile Leu Thr Glu Ser Gln
            595                     600                     605

Asn Gln Gln Asp Arg Asn Glu Lys Asp Leu Leu Glu Leu Asp Lys Trp
610                     615                     620

```
Ala Ser Leu Trp Asn Trp
625                 630

<210> SEQ ID NO 61
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Val Pro Val
                20                  25                  30

Trp Lys Glu Ala Asp Thr Thr Leu Phe Cys Ala Ser Asp Ala Lys Ala
            35                  40                  45

His Glu Thr Glu Val His Asn Val Trp Ala Thr His Ala Cys Val Pro
    50                  55                  60

Thr Asp Pro Asn Pro Gln Glu Ile Asp Leu Glu Asn Val Thr Glu Asn
65                  70                  75                  80

Phe Asn Met Trp Lys Asn Asn Met Val Glu Gln Met Gln Glu Asp Val
                85                  90                  95

Ile Ser Leu Trp Asp Gln Ser Leu Lys Pro Cys Val Lys Leu Thr Pro
            100                 105                 110

Pro Cys Val Thr Leu His Cys Thr Asn Ala Asn Leu Thr Lys Ala Asn
        115                 120                 125

Leu Thr Asn Val Asn Asn Arg Thr Asn Val Ser Asn Ile Ile Gly Asn
    130                 135                 140

Ile Thr Asp Glu Val Arg Asn Cys Ser Phe Asn Met Thr Thr Glu Leu
145                 150                 155                 160

Arg Asp Lys Lys Gln Lys Val His Ala Leu Phe Tyr Lys Leu Asp Ile
                165                 170                 175

Val Pro Ile Glu Asp Asn Asn Asp Ser Ser Glu Tyr Arg Leu Ile Asn
            180                 185                 190

Cys Asn Thr Ser Val Ile Lys Gln Pro Cys Pro Lys Ile Ser Phe Asp
        195                 200                 205

Pro Ile Pro Ile His Tyr Cys Thr Pro Ala Gly Tyr Ala Ile Leu Lys
    210                 215                 220

Cys Asn Asp Lys Asn Phe Asn Gly Thr Gly Pro Cys Lys Asn Val Ser
225                 230                 235                 240

Ser Val Gln Cys Thr His Gly Ile Lys Pro Val Val Ser Thr Gln Leu
                245                 250                 255

Leu Leu Asn Gly Ser Leu Ala Glu Glu Ile Ile Arg Ser Glu
            260                 265                 270

Asn Leu Thr Asn Asn Ala Lys Thr Ile Ile Val His Leu Asn Lys Ser
        275                 280                 285

Val Val Ile Asn Cys Thr Arg Pro Ser Asn Asn Thr Arg Thr Ser Ile
    290                 295                 300

Thr Ile Gly Pro Gly Gln Val Phe Tyr Arg Thr Gly Asp Ile Ile Gly
305                 310                 315                 320

Asp Ile Arg Lys Ala Tyr Cys Glu Ile Asn Gly Thr Glu Trp Asn Lys
                325                 330                 335

Ala Leu Lys Gln Val Thr Glu Lys Leu Lys Glu His Phe Asn Asn Lys
```

```
                340             345             350
Pro Ile Ile Phe Gln Pro Pro Ser Gly Gly Asp Leu Glu Ile Thr Met
            355                 360                 365

His His Phe Asn Cys Arg Gly Glu Phe Phe Tyr Cys Asn Thr Thr Arg
    370                 375                 380

Leu Phe Asn Asn Thr Cys Ile Ala Asn Gly Thr Ile Glu Gly Cys Asn
385                 390                 395                 400

Gly Asn Ile Thr Leu Pro Cys Lys Ile Lys Gln Ile Ile Asn Met Trp
                405                 410                 415

Gln Gly Ala Gly Gln Ala Met Tyr Ala Pro Pro Ile Ser Gly Thr Ile
            420                 425                 430

Asn Cys Val Ser Asn Ile Thr Gly Ile Leu Leu Thr Arg Asp Gly Gly
        435                 440                 445

Ala Thr Asn Asn Thr Asn Asn Glu Thr Phe Arg Pro Gly Gly Gly Asn
        450                 455                 460

Ile Lys Asp Asn Trp Arg Asn Glu Leu Tyr Lys Tyr Lys Val Val Gln
465                 470                 475                 480

Ile Glu Pro Leu Gly Val Ala Pro Thr Arg Ala Lys Arg Arg Val Val
                485                 490                 495

Glu Arg Glu Lys Arg
            500

<210> SEQ ID NO 62
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
                20                  25                  30

Leu Trp Val Thr Val Tyr Tyr Gly Val Pro Val Trp Lys Glu Ala Asp
            35                  40                  45

Thr Thr Leu Phe Cys Ala Ser Asp Ala Lys Ala His Glu Thr Glu Val
        50                  55                  60

His Asn Val Trp Ala Thr His Ala Cys Val Pro Thr Asp Pro Asn Pro
65                  70                  75                  80

Gln Glu Ile Asp Leu Glu Asn Val Thr Glu Asn Phe Asn Met Trp Lys
                85                  90                  95

Asn Asn Met Val Glu Gln Met Gln Glu Asp Val Ile Ser Leu Trp Asp
                100                 105                 110

Gln Ser Leu Lys Pro Cys Val Lys Leu Thr Pro Pro Cys Val Thr Leu
            115                 120                 125

His Cys Thr Asn Ala Asn Leu Thr Lys Ala Asn Leu Thr Asn Val Asn
        130                 135                 140

Asn Arg Thr Asn Val Ser Asn Ile Ile Gly Asn Ile Thr Asp Glu Val
145                 150                 155                 160

Arg Asn Cys Ser Phe Asn Met Thr Thr Glu Leu Arg Asp Lys Lys Gln
                165                 170                 175

Lys Val His Ala Leu Phe Tyr Lys Leu Asp Ile Val Pro Ile Glu Asp
            180                 185                 190
```

Asn Asn Asp Ser Ser Glu Tyr Arg Leu Ile Asn Cys Asn Thr Ser Val
            195                 200                 205

Ile Lys Gln Pro Cys Pro Lys Ile Ser Phe Asp Pro Ile Pro Ile His
    210                 215                 220

Tyr Cys Thr Pro Ala Gly Tyr Ala Ile Leu Lys Cys Asn Asp Lys Asn
225                 230                 235                 240

Phe Asn Gly Thr Gly Pro Cys Lys Asn Val Ser Ser Val Gln Cys Thr
                245                 250                 255

His Gly Ile Lys Pro Val Val Ser Thr Gln Leu Leu Leu Asn Gly Ser
            260                 265                 270

Leu Ala Glu Glu Glu Ile Ile Ile Arg Ser Glu Asn Leu Thr Asn Asn
        275                 280                 285

Ala Lys Thr Ile Ile Val His Leu Asn Lys Ser Val Val Ile Asn Cys
    290                 295                 300

Thr Arg Pro Ser Asn Asn Thr Arg Thr Ser Ile Thr Ile Gly Pro Gly
305                 310                 315                 320

Gln Val Phe Tyr Arg Thr Gly Asp Ile Ile Gly Asp Ile Arg Lys Ala
                325                 330                 335

Tyr Cys Glu Ile Asn Gly Thr Glu Trp Asn Lys Ala Leu Lys Gln Val
            340                 345                 350

Thr Glu Lys Leu Lys Glu His Phe Asn Asn Lys Pro Ile Ile Phe Gln
        355                 360                 365

Pro Pro Ser Gly Gly Asp Leu Glu Ile Thr Met His His Phe Asn Cys
    370                 375                 380

Arg Gly Glu Phe Phe Tyr Cys Asn Thr Thr Arg Leu Phe Asn Asn Thr
385                 390                 395                 400

Cys Ile Ala Asn Gly Thr Ile Glu Gly Cys Asn Gly Asn Ile Thr Leu
                405                 410                 415

Pro Cys Lys Ile Lys Gln Ile Ile Asn Met Trp Gln Gly Ala Gly Gln
            420                 425                 430

Ala Met Tyr Ala Pro Pro Ile Ser Gly Thr Ile Asn Cys Val Ser Asn
        435                 440                 445

Ile Thr Gly Ile Leu Leu Thr Arg Asp Gly Gly Ala Thr Asn Asn Thr
    450                 455                 460

Asn Asn Glu Thr Phe Arg Pro Gly Gly Gly Asn Ile Lys Asp Asn Trp
465                 470                 475                 480

Arg Asn Glu Leu Tyr Lys Tyr Lys Val Val Gln Ile Glu Pro Leu Gly
                485                 490                 495

Val Ala Pro Thr Arg Ala Lys Arg Arg Val Val Glu Arg Glu Lys Arg
            500                 505                 510

<210> SEQ ID NO 63
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Ser Asp Asn
            20                  25                  30

Leu Trp Val Thr Val Tyr Tyr Gly Val Pro Val Trp Arg Asp Ala Asp
        35                  40                  45

```
Thr Thr Leu Phe Cys Ala Ser Asp Ala Lys Ala His Glu Thr Glu Val
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Asn Phe Asn Met Trp Lys
                85                  90                  95

Asn Asn Met Val Glu Gln Met Gln Glu Asp Val Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Asn Leu Thr Asn Val Asn Ile Thr Asn Val
    130                 135                 140

Ser Asn Ile Ile Gly Asn Ile Thr Asn Glu Val Arg Asn Cys Ser Phe
145                 150                 155                 160

Asn Met Thr Thr Glu Leu Arg Asp Lys Lys Gln Lys Val His Ala Leu
                165                 170                 175

Phe Tyr Lys Leu Asp Ile Val Gln Ile Glu Asp Asn Asn Ser Tyr Arg
            180                 185                 190

Leu Ile Asn Cys Asn Thr Ser Val Ile Lys Gln Ala Cys Pro Lys Ile
        195                 200                 205

Ser Phe Asp Pro Ile Pro Ile His Tyr Cys Thr Pro Ala Gly Tyr Ala
210                 215                 220

Ile Leu Lys Cys Asn Asp Lys Asn Phe Asn Gly Thr Gly Pro Cys Lys
225                 230                 235                 240

Asn Val Ser Ser Val Gln Cys Thr His Gly Ile Lys Pro Val Val Ser
                245                 250                 255

Thr Gln Leu Leu Leu Asn Gly Ser Leu Ala Glu Glu Ile Ile Ile
            260                 265                 270

Arg Ser Glu Asn Leu Thr Asn Asn Ala Lys Thr Ile Ile Val His Leu
        275                 280                 285

Asn Lys Ser Val Glu Ile Asn Cys Thr Arg Pro Ser Asn Asn Thr Arg
    290                 295                 300

Thr Ser Ile Thr Ile Gly Pro Gly Gln Val Phe Tyr Arg Thr Gly Asp
305                 310                 315                 320

Ile Ile Gly Asp Ile Arg Lys Ala Tyr Cys Glu Ile Asn Gly Thr Lys
                325                 330                 335

Trp Asn Glu Val Leu Lys Gln Val Thr Glu Lys Leu Lys Glu His Phe
            340                 345                 350

Asn Asn Lys Thr Ile Ile Phe Gln Pro Pro Ser Gly Gly Asp Leu Glu
        355                 360                 365

Ile Thr Met His His Phe Asn Cys Arg Gly Glu Phe Phe Tyr Cys Asn
    370                 375                 380

Thr Thr Lys Leu Phe Asn Asn Thr Cys Ile Gly Asn Glu Thr Met Glu
385                 390                 395                 400

Gly Cys Asn Gly Thr Ile Ile Leu Pro Cys Lys Ile Lys Gln Ile Ile
                405                 410                 415

Asn Met Trp Gln Gly Ala Gly Gln Ala Met Tyr Ala Pro Pro Ile Ser
            420                 425                 430

Gly Arg Ile Asn Cys Val Ser Asn Ile Thr Gly Ile Leu Leu Thr Arg
        435                 440                 445

Asp Gly Gly Ala Asn Asn Thr Asn Glu Thr Phe Arg Pro Gly Gly Gly
    450                 455                 460
```

Asn Ile Lys Asp Asn Trp Arg Ser Glu Leu Tyr Lys Tyr Lys Val Val
465                 470                 475                 480

Gln Ile Glu Pro Leu Gly Ile Ala Pro Thr Arg Ala Lys Thr Leu Thr
            485                 490                 495

Val Gln Ala Arg Gln Leu Leu Ser Gly Ile Val Gln Gln Ser Asn
        500                 505                 510

Leu Leu Arg Ala Ile Glu Ala Gln Gln His Leu Leu Gln Leu Thr Val
        515                 520                 525

Trp Gly Ile Lys Gln Leu Gln Ala Arg Val Leu Ala Val Glu Arg Tyr
    530                 535                 540

Leu Lys Asp Gln Lys Phe Leu Gly Leu Trp Gly Cys Ser Gly Lys Ile
545                 550                 555                 560

Ile Cys Thr Thr Ala Val Pro Trp Asn Ser Thr Trp Ser Asn Arg Ser
            565                 570                 575

Phe Glu Glu Ile Trp Asn Asn Met Thr Trp Ile Glu Trp Glu Arg Glu
            580                 585                 590

Ile Ser Asn Tyr Thr Asn Gln Ile Tyr Glu Ile Leu Thr Glu Ser Gln
    595                 600                 605

Asn Gln Gln Asp Arg Asn Glu Lys Asp Leu Leu Glu Leu Asp Lys Trp
610                 615                 620

Ala Ser Leu Trp Asn Trp Phe Asp Ile Thr Asn Trp Leu Trp
625                 630                 635

<210> SEQ ID NO 64
<211> LENGTH: 702
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Met Arg Val Met Gly Thr Arg Arg Asn Cys Gln His Leu Trp Lys Trp
1               5                   10                  15

Gly Ile Met Leu Leu Gly Met Leu Met Ile Cys Ser Ala Thr Glu Gln
            20                  25                  30

Leu Trp Val Thr Val Tyr Tyr Gly Val Pro Val Trp Lys Asp Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Pro Leu Val Asn Val Thr Glu Lys Phe Asp Ile Trp Lys
                85                  90                  95

Asn Asn Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Thr Ile Thr Asn Glu Val Thr Ala Thr Val Ala
    130                 135                 140

Thr Ala Thr Ser Ser Lys Thr Ile Ser Pro Ala Ile Ser Pro Glu Met
145                 150                 155                 160

Lys Asn Cys Ser Phe Asn Thr Asn Ala Ile Leu Gln Asp Lys Val Ser
                165                 170                 175

Lys Asp Tyr Ala Leu Phe Tyr Asn Leu Asp Ile Val Gln Ile Glu Asp
            180                 185                 190

-continued

Lys Asp Asn Lys Thr Asn Asn Asp Ser Lys Thr Tyr Asp Ser Tyr Arg
            195                 200                 205

Leu Ile Ser Cys Asn Thr Ser Val Ile Thr Gln Ala Cys Pro Lys Thr
210                 215                 220

Ser Phe Lys Pro Ile Pro Ile His Tyr Cys Ala Pro Ala Gly Phe Ala
225                 230                 235                 240

Ile Leu Lys Cys Asn Asp Arg Asn Phe Asn Gly Thr Glu Pro Cys Lys
            245                 250                 255

Asn Val Ser Thr Val Gln Cys Thr His Gly Ile Arg Pro Val Val Ser
            260                 265                 270

Thr Gln Leu Leu Leu Asn Gly Ser Leu Ala Glu Asp Glu Val Val Ile
            275                 280                 285

Arg Ser Ser Asn Phe Ser Asn Asn Ala Arg Thr Ile Leu Val Gln Leu
            290                 295                 300

Lys Asp Pro Val Thr Ile Asn Cys Thr Arg Pro Asn Asn Asn Thr Arg
305                 310                 315                 320

Arg Ser Ile Asn Ile Gly Pro Gly Arg Ala Phe Tyr Ala Thr Gly Glu
            325                 330                 335

Ile Ile Gly Asn Ile Arg Gln Ala His Cys Asn Ile Ser Met Ala Asn
            340                 345                 350

Trp Thr Asn Thr Leu Lys Gln Ile Ala Gly Lys Leu Gly Lys Gln Phe
            355                 360                 365

Asp His Lys Thr Ile Val Phe Asn His Ser Ser Gly Gly Asp Pro Glu
            370                 375                 380

Ile Val Met His Thr Phe Asn Cys Gly Gly Glu Phe Phe Tyr Cys Asn
385                 390                 395                 400

Thr Ser Gly Leu Phe Asn Ser Thr Trp Thr Trp Asn Ser Thr Gly Asn
            405                 410                 415

Tyr Tyr Ser Ser Asn Ser Ser Gly Ser Gly Thr Asn Asn Thr Ile
            420                 425                 430

Ile Leu Gln Cys Arg Ile Lys Gln Ile Ile Asn Met Trp Gln Thr Val
            435                 440                 445

Gly Lys Ala Met Tyr Ala Pro Pro Ile Arg Gly Lys Ile Ser Cys Val
450                 455                 460

Ser Asn Ile Thr Gly Leu Leu Leu Val Arg Asp Gly Gly Asp Asn Asn
465                 470                 475                 480

Ser Ser Glu Glu Ile Phe Arg Pro Ala Gly Gly Asp Met Arg Asp Asn
            485                 490                 495

Trp Arg Ser Glu Leu Tyr Lys Tyr Lys Val Val Lys Ile Glu Pro Leu
            500                 505                 510

Gly Ile Ala Pro Thr Lys Ala Arg Glu Arg Val Gln Arg Glu Lys
            515                 520                 525

Glu Ala Val Gly Ile Gly Ala Leu Phe Leu Gly Phe Leu Gly Ala Ala
            530                 535                 540

Gly Ser Thr Met Gly Ala Ala Ser Ile Ala Leu Thr Val Gln Ala Arg
545                 550                 555                 560

Gln Leu Leu Ser Gly Ile Val Gln Gln Asn Asn Leu Leu Arg Ala
            565                 570                 575

Ile Glu Ala Gln Gln His Met Leu Gln Leu Thr Val Trp Gly Ile Lys
            580                 585                 590

Gln Leu Gln Ala Arg Val Leu Ala Val Glu Arg Tyr Leu Arg Asp Gln
            595                 600                 605

Gln Leu Leu Gly Ile Trp Gly Cys Ser Gly Lys His Ile Cys Thr Thr
610                 615                 620

Asn Val Pro Trp Asn Ala Ser Trp Ser Asn Asn Arg Asn Leu Ser Gln
625                 630                 635                 640

Ile Trp Asp Asn Leu Thr Trp Met Gln Trp Glu Lys Glu Ile Asp Asn
            645                 650                 655

Tyr Thr Ser Leu Ile Tyr Ser Leu Ile Glu Glu Ser Gln Ile Gln Gln
            660                 665                 670

Glu Lys Asn Glu Gln Asp Leu Leu Ala Leu Asp Lys Trp Asp Ser Leu
        675                 680                 685

Trp Asn Trp Phe Asn Ile Thr His Trp Leu Trp Tyr Ile Lys
690                 695                 700

<210> SEQ ID NO 65
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Lys Val Lys Gly Ile Met Lys Asn Cys Gln Asn Ser Trp Ser Gly
1               5                   10                  15

Gly Ile Leu Leu Leu Gly Met Leu Met Ile Cys Ser Ala Ala Glu Asp
            20                  25                  30

Lys Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Ser Thr Glu Arg
50                  55                  60

His Asn Ile Trp Ala Thr His Ala Cys Val Pro Thr Asp Pro Ser Pro
65                  70                  75                  80

Gln Glu Ile Val Met Gly Asn Val Thr Glu Asp Phe Asn Met Trp Lys
                85                  90                  95

Asn Glu Met Ala Val Gln Met His Glu Asp Val Ile Ser Leu Trp Asp
            100                 105                 110

Gln Ser Leu Lys Pro Cys Val Lys Leu Thr Pro Leu Cys Val Ser Leu
        115                 120                 125

Asp Cys Thr Asn Val Asn Ile Thr Asn His Asn Ser Thr Asn Pro Glu
130                 135                 140

Glu Gln Met Lys Glu Gly Glu Ile Lys Asn Cys Ser Phe Asn Phe Thr
145                 150                 155                 160

Thr Asn Ile Lys Asp Lys Ile Gln Lys Thr Tyr Ala Leu Phe Tyr Lys
                165                 170                 175

Leu Asp Leu Val Pro Ile Asp Asp Glu Asn Asn Thr Asn Thr Ser Tyr
            180                 185                 190

Arg Leu Ile Ser Cys Asn Thr Ser Val Ile Thr Gln Ala Cys Pro Lys
        195                 200                 205

Val Thr Phe Glu Pro Ile Pro Ile His Tyr Cys Ala Pro Ala Gly Phe
210                 215                 220

Ala Ile Leu Lys Cys Asn Asn Lys Thr Phe Asn Gly Thr Gly Pro Cys
225                 230                 235                 240

Thr Asn Val Ser Thr Val Gln Cys Thr His Gly Ile Lys Pro Val Val
                245                 250                 255

Ser Thr Gln Leu Leu Leu Asn Gly Ser Leu Ala Glu Glu Glu Ile Ile
            260                 265                 270

```
Ile Arg Ser Glu Asn Ile Thr Asp Asn Thr Lys Asn Ile Ile Val His
            275                 280                 285

Leu Asn Lys Ser Val Gln Ile Asn Cys Ile Arg Pro Asn Asn Asn Thr
        290                 295                 300

Arg Lys Gly Ile His Ile Gly Pro Gly Ala Phe Trp Ala Thr Gly Glu
305                 310                 315                 320

Ile Ile Gly Asp Ile Arg Gln Ala His Cys Asn Val Ser Arg Glu Asp
                325                 330                 335

Trp Asn Lys Thr Leu Arg Arg Ile Ser Lys Lys Leu Arg Asp Ile Phe
            340                 345                 350

Asn Lys Thr Ile Asn Phe Thr Ser Ser Gly Gly Asp Pro Glu Ile
        355                 360                 365

Val Met His Ser Phe Asn Cys Gly Gly Glu Phe Phe Tyr Cys Asn Ser
            370                 375                 380

Thr Pro Leu Phe Asn Ser Ser Trp Tyr Gly Asn Glu Thr Asp Val Ser
385                 390                 395                 400

Asn Ser Thr Glu Asn Ser Thr Arg Gly Glu Ile Thr Leu Pro Cys Arg
                405                 410                 415

Ile Lys Gln Ile Ile Asn Met Trp Gln Glu Val Gly Lys Ala Met Tyr
            420                 425                 430

Ala Pro Pro Ile Ser Gly Pro Ile Ser Cys Ser Ser Asn Ile Thr Gly
            435                 440                 445

Leu Ile Leu Thr Arg Asp Gly Gly Asn Asn Ser Ser Asn Thr Glu Ile
        450                 455                 460

Phe Arg Pro Gly Gly Gly Asn Met Met Asp Asn Trp Arg Ser Glu Leu
465                 470                 475                 480

Tyr Lys Tyr Lys Val Val Gln Leu Glu Pro Leu Gly Ile Ala Pro Ser
                485                 490                 495

Arg Ala Arg Glu Arg Val Val Gln Arg Glu Lys Glu Ala Val Gly Phe
                500                 505                 510

Gly Ala Leu Leu Leu Gly Phe Leu Gly Thr Ala Gly Ser Thr Met Gly
            515                 520                 525

Ala Val Ser Leu Thr Leu Thr Val Gln Ala Arg Gln Leu Leu Ser Gly
            530                 535                 540

Ile Val Gln Gln Gln Asn Asn Leu Leu Arg Ala Ile Glu Ala Gln Gln
545                 550                 555                 560

His Met Leu Gln Leu Thr Val Trp Gly Ile Lys Gln Leu Gln Ala Arg
                565                 570                 575

Val Leu Ala Val Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
            595                 600                 605

Asp Ser Trp Ser Asn Arg Ser Leu Thr Asp Ile Trp Asp Asn Met Thr
        610                 615                 620

Trp Met Gln Trp Glu Lys Glu Ile Asp Asn Tyr Thr Gly Leu Ile Tyr
625                 630                 635                 640

Thr Leu Ile Glu Glu Ser Gln Phe Gln Gln Glu Lys Asn Glu Gln Asp
                645                 650                 655

Leu Leu Ala Leu Asp Lys Trp Ala Ser Leu Trp Asn Trp Phe Asp Ile
            660                 665                 670

Thr Lys Trp Leu Trp Tyr Ile Lys
        675                 680
```

```
<210> SEQ ID NO 66
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
                20                  25                  30

Tyr Tyr Gly Val Pro Val Trp Lys Glu Ala Thr Thr Thr Leu Phe Cys
            35                  40                  45

Ala Ser Asp Ala Lys Ala Tyr Asp Thr Glu Val His Asn Val Trp Ala
        50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Ile Arg Asp Glu
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365
```

```
Gly Gly Glu Phe Phe Tyr Cys Asn Ser Thr Gln Leu Phe Asn Ser Thr
        370                 375                 380

Trp Asn Asn Asn Thr Glu Gly Ser Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
                420                 425                 430

Ser Asn Ile Thr Gly Leu Leu Leu Thr Arg Asp Gly Gly Ile Asn Glu
            435                 440                 445

Asn Gly Thr Glu Ile Phe Arg Pro Gly Gly Gly Asp Met Arg Asp Asn
        450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Thr Leu Thr Val Gln Ala Arg Leu
                485                 490                 495

Leu Leu Ser Gly Ile Val Gln Gln Gln Asn Asn Leu Leu Arg Ala Ile
            500                 505                 510

Glu Ala Gln Gln Arg Met Leu Gln Leu Thr Val Trp Gly Ile Lys Gln
        515                 520                 525

Leu Gln Ala Arg Val Leu Ala Val Glu Arg Tyr Leu Gly Asp Gln Gln
        530                 535                 540

Leu Leu Gly Ile Trp Gly Cys Ser Gly Lys Leu Ile Cys Thr Thr Ala
545                 550                 555                 560

Val Pro Trp Asn Ala Ser Trp Ser Asn Lys Ser Leu Asp Arg Ile Trp
                565                 570                 575

Asn Asn Met Thr Trp Met Glu Trp Glu Arg Glu Ile Asp Asn Tyr Thr
            580                 585                 590

Ser Glu Ile Tyr Thr Leu Ile Glu Gly Ser Gln Asn Gln Gln Glu Lys
        595                 600                 605

Asn Glu Gln Glu Leu Leu Glu Leu Asp Lys Trp Ala Ser Leu Trp Asn
610                 615                 620

Trp Phe Asp Ile Thr Lys Trp Leu Trp
625                 630

<210> SEQ ID NO 67
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Arg Val Met Gly Ile Arg Lys Asn Tyr Gln His Leu Trp Arg Glu
1               5                   10                  15

Gly Ile Leu Leu Leu Gly Ile Leu Met Ile Cys Ser Ala Ala Asp Asn
            20                  25                  30

Leu Trp Val Thr Val Tyr Tyr Gly Val Pro Val Trp Arg Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Glu Leu Lys Asn Val Thr Glu Asn Phe Asn Met Trp Glu
```

-continued

```
                85                  90                  95
Asn Asn Met Val Glu Gln Met His Glu Asp Ile Ile Ser Leu Trp Asp
                100                 105                 110
Gln Ser Leu Lys Pro Cys Val Lys Leu Thr Pro Leu Cys Val Thr Leu
            115                 120                 125
Asn Cys Thr Asp Leu Gly Asn Val Thr Asn Thr Asn Ser Asn Gly
            130                 135                 140
Glu Met Met Glu Lys Gly Glu Val Lys Asn Cys Ser Phe Lys Ile Thr
145                 150                 155                 160
Thr Asp Ile Lys Asp Arg Thr Arg Lys Glu Tyr Ala Leu Phe Tyr Lys
                165                 170                 175
Leu Asp Val Val Pro Ile Asn Asp Thr Arg Tyr Arg Leu Val Ser Cys
            180                 185                 190
Asn Thr Ser Val Ile Thr Gln Ala Cys Pro Lys Val Ser Phe Glu Pro
            195                 200                 205
Ile Pro Ile His Tyr Cys Ala Pro Ala Gly Phe Ala Ile Leu Lys Cys
            210                 215                 220
Asn Asp Lys Gln Phe Ile Gly Thr Gly Pro Cys Thr Asn Val Ser Thr
225                 230                 235                 240
Val Gln Cys Thr His Gly Ile Arg Pro Val Val Ser Thr Gln Leu Leu
                245                 250                 255
Leu Asn Gly Ser Leu Ala Glu Glu Val Val Ile Arg Ser Val Asn
            260                 265                 270
Phe Ser Asp Asn Ala Lys Thr Ile Ile Val Gln Leu Asn Lys Ser Val
            275                 280                 285
Glu Ile Thr Cys Thr Arg Pro Asn Asn Asn Thr Arg Lys Ser Ile Pro
            290                 295                 300
Met Gly Pro Gly Lys Ala Phe Tyr Ala Arg Gly Asp Ile Thr Gly Asp
305                 310                 315                 320
Ile Arg Lys Ala Tyr Cys Glu Ile Asn Gly Thr Glu Trp His Ser Thr
                325                 330                 335
Leu Lys Leu Val Val Glu Lys Leu Arg Glu Gln Tyr Asn Lys Thr Ile
            340                 345                 350
Val Phe Asn Arg Ser Ser Gly Gly Asp Pro Glu Ile Val Met Tyr Ser
            355                 360                 365
Phe Asn Cys Gly Gly Glu Phe Phe Tyr Cys Asn Ser Thr Lys Leu Phe
            370                 375                 380
Asn Ser Thr Trp Pro Trp Asn Asp Thr Lys Gly Ser His Asp Thr Asn
385                 390                 395                 400
Gly Thr Leu Ile Leu Pro Cys Lys Ile Lys Gln Ile Ile Asn Met Trp
                405                 410                 415
Gln Gly Val Gly Lys Ala Met Tyr Ala Pro Pro Ile Glu Gly Lys Ile
            420                 425                 430
Arg Cys Ser Ser Asn Ile Thr Gly Leu Leu Leu Thr Arg Asp Gly Gly
            435                 440                 445
Tyr Glu Ser Asn Glu Thr Asp Glu Ile Phe Arg Pro Gly Gly Gly Asp
            450                 455                 460
Met Arg Asp Asn Trp Arg Ser Glu Leu Tyr Lys Tyr Lys Val Val Lys
465                 470                 475                 480
Ile Glu Pro Leu Gly Val Ala Pro Thr Lys Ala Lys Glu Arg Val Val
                485                 490                 495
Gln Arg Glu Lys Glu Ala Phe Gly Leu Gly Ala Val Phe Leu Gly Phe
            500                 505                 510
```

```
Leu Gly Ala Ala Gly Ser Thr Met Gly Ala Ser Ile Thr Leu Thr
            515                 520                 525

Val Gln Ala Arg Gln Leu Leu Ser Gly Ile Val Gln Gln Asn Asn
530                 535                 540

Leu Leu Arg Ala Ile Glu Ala Gln Gln His Leu Leu Gln Leu Thr Val
545                 550                 555                 560

Trp Gly Ile Lys Gln Leu Gln Ala Arg Val Leu Ala Val Glu Arg Tyr
                565                 570                 575

Leu Lys Asp Gln Gln Leu Leu Gly Ile Trp Gly Cys Ser Gly Lys Leu
            580                 585                 590

Ile Cys Thr Thr Thr Val Pro Trp Asn Thr Ser Trp Ser Asn Lys Ser
        595                 600                 605

Leu Glu Gln Ile Trp Asp Asn Met Thr Trp Met Glu Trp Glu Arg Glu
    610                 615                 620

Ile Asp Asn Tyr Thr Gly Tyr Ile Tyr Gln Leu Ile Glu Ser Gln
625                 630                 635                 640

Asn Gln Gln Glu Lys Asn Glu Gln Glu Leu Leu Ala Leu Asp Lys Trp
                645                 650                 655

Ala Ser Leu Trp Asn Trp Phe Asp Ile Thr Asn Trp Leu Trp Tyr Ile
            660                 665                 670

Lys

<210> SEQ ID NO 68
<211> LENGTH: 673
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Arg Val Arg Glu Ile Arg Arg Asn Tyr Gln His Leu Trp Lys Trp
1               5                   10                  15

Gly Ile Met Leu Leu Gly Ile Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Asp Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Glu Ser Leu Lys Pro Cys Val Lys Leu Thr Pro Leu Cys Val Thr Leu
        115                 120                 125

Asn Cys Thr Asn Ala Thr Ser Thr Asn Phe Thr Ala Lys Asn Glu Gly
    130                 135                 140

Gly Ile Lys Asn Cys Ser Phe Asn Ile Thr Thr Glu Arg Arg Gly Arg
145                 150                 155                 160

Lys Lys Thr Glu Tyr Ala Thr Phe Tyr Glu Thr Asp Leu Val Leu Ile
                165                 170                 175

Asn Asp Asp Asn Thr Thr Ser Tyr Arg Leu Ile Ser Cys Asn Thr Ser
            180                 185                 190
```

-continued

```
Val Ile Lys Gln Ala Cys Pro Lys Val Thr Phe Glu Pro Ile Pro Ile
        195                 200                 205

His Tyr Cys Ala Pro Ala Gly Phe Ala Ile Leu Lys Cys Lys Asp Lys
    210                 215                 220

Lys Phe Asn Gly Thr Gly Ala Cys Thr Asn Val Ser Thr Val Gln Cys
225                 230                 235                 240

Thr His Gly Ile Arg Pro Val Val Ser Thr Gln Leu Leu Asn Gly
                245                 250                 255

Ser Leu Ala Glu Glu Val Val Arg Ser Lys Phe Ala Asn
            260                 265                 270

Asn Ala Lys Ile Ile Val Gln Leu Asn Glu Ser Val Glu Ile Asn
        275                 280                 285

Cys Thr Arg Pro Asn Asn Asn Thr Arg Lys Ser Ile His Ile Gly Pro
    290                 295                 300

Gly Gln Ala Phe Tyr Thr Thr Gly Ala Ile Ile Gly Asp Ile Arg Gln
305                 310                 315                 320

Ala Tyr Cys Asn Ile Ser Arg Ala Lys Trp Asn Asp Thr Leu Lys Gln
                325                 330                 335

Ile Ala Ile Lys Leu Arg Glu Lys Phe Gly Asn Asn Lys Thr Ile Val
            340                 345                 350

Phe Asn Gln Ser Ser Gly Gly Asp Pro Glu Val Val Met His Ile Ser
        355                 360                 365

Asn Cys Gly Gly Glu Phe Phe Tyr Cys Asn Thr Thr Lys Leu Phe Asn
    370                 375                 380

Asn Thr Trp Asn Ser Asn Asp Thr Trp Thr Asn Thr Glu Glu Ser Asn
385                 390                 395                 400

Glu Thr Glu Ile Arg Leu Pro Cys Arg Ile Lys Gln Ile Ile Asn Met
                405                 410                 415

Trp Gln Glu Val Gly Lys Ala Met Tyr Ala Pro Pro Ile Gln Gly Gln
            420                 425                 430

Ile Arg Cys Ser Ser Asn Ile Thr Gly Leu Leu Leu Thr Arg Asp Gly
        435                 440                 445

Gly Asn Asn Thr Asn Asn Thr Glu Val Phe Arg Pro Gly Gly Gly Asp
    450                 455                 460

Met Arg Asp Asn Trp Arg Ser Glu Leu Tyr Lys Tyr Lys Val Val Lys
465                 470                 475                 480

Ile Glu Pro Leu Gly Val Ala Pro Thr Lys Ala Lys Glu Arg Val Val
                485                 490                 495

Gln Arg Glu Lys Glu Ala Val Gly Leu Gly Ala Leu Phe Leu Gly Phe
            500                 505                 510

Leu Gly Ala Ala Gly Ser Thr Met Gly Ala Ala Ser Val Thr Leu Thr
        515                 520                 525

Val Gln Ala Arg Gln Leu Leu Ser Gly Ile Val Gln Gln Gln Ser Asn
    530                 535                 540

Leu Leu Arg Ala Ile Glu Ala Gln Gln His Leu Leu Gln Leu Thr Val
545                 550                 555                 560

Trp Gly Ile Lys Gln Leu Gln Ala Arg Val Leu Ala Val Glu Arg Tyr
                565                 570                 575

Leu Lys Asp Gln Gln Leu Leu Gly Ile Trp Gly Cys Ser Gly Lys Leu
            580                 585                 590

Ile Cys Thr Thr Ala Val Pro Trp Asn Ala Ser Trp Ser Asn Lys Ser
        595                 600                 605
```

Leu Asn Asp Ile Trp Asn Asn Met Thr Trp Met Glu Trp Glu Arg Glu
    610                 615                 620

Ile Asn Asn Tyr Thr Ser Leu Ile Tyr Asn Leu Ile Glu Glu Ser Gln
625                 630                 635                 640

Asn Gln Gln Glu Lys Asn Glu Leu Glu Leu Leu Glu Leu Asp Lys Trp
                645                 650                 655

Ala Ser Leu Trp Asn Trp Phe Asp Ile Thr Asn Trp Leu Trp Tyr Ile
            660                 665                 670

Lys

<210> SEQ ID NO 69
<211> LENGTH: 693
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Met Arg Val Lys Gly Ile Arg Lys Asn Tyr Gln His Leu Trp Arg Trp
1               5                   10                  15

Gly Ile Trp Arg Trp Gly Ile Met Leu Leu Gly Thr Leu Met Ile Cys
            20                  25                  30

Ser Ala Thr Glu Lys Leu Trp Val Thr Val Tyr Tyr Gly Val Pro Val
            35                  40                  45

Trp Lys Glu Ala Thr Thr Thr Leu Phe Cys Ala Ser Asp Ala Lys Ala
    50                  55                  60

Tyr Ser Pro Glu Lys His Asn Ile Trp Ala Thr His Ala Cys Val Pro
65                  70                  75                  80

Thr Asp Pro Asn Pro Gln Glu Leu Val Leu Gly Asn Val Thr Glu Asp
                85                  90                  95

Phe Asn Met Trp Lys Asn Asn Met Val Glu Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu Asn Cys Thr Asp Leu Lys Asn Ser Ala Thr Asp
    130                 135                 140

Thr Asn Gly Thr Ser Gly Thr Asn Asn Arg Thr Val Glu Gln Gly Met
145                 150                 155                 160

Glu Thr Glu Ile Lys Asn Cys Ser Phe Asn Ile Thr Thr Gly Ile Gly
                165                 170                 175

Asn Lys Met Gln Lys Glu Tyr Ala Leu Phe Tyr Lys Leu Asp Val Val
            180                 185                 190

Pro Ile Asp Ser Asn Asn Asn Ser Asp Asn Thr Ser Tyr Arg Leu Ile
        195                 200                 205

Ser Cys Asn Thr Ser Val Val Thr Gln Ala Cys Pro Lys Thr Ser Phe
    210                 215                 220

Glu Pro Ile Pro Ile His Tyr Cys Ala Pro Ala Gly Phe Ala Ile Leu
225                 230                 235                 240

Lys Cys Asn Asn Lys Thr Phe Ser Gly Lys Gly Pro Cys Lys Asn Val
                245                 250                 255

Ser Thr Val Gln Cys Thr His Gly Ile Arg Pro Val Val Ser Thr Gln
            260                 265                 270

Leu Leu Leu Asn Gly Ser Leu Ala Glu Glu Ile Val Ile Arg Ser
        275                 280                 285

-continued

```
Glu Asn Phe Thr Asn Asn Ala Lys Thr Ile Ile Val Gln Leu Asn Glu
    290                 295                 300
Ser Val Ile Ile Asn Cys Thr Arg Pro Asn Asn Asn Thr Arg Lys Gly
305                 310                 315                 320
Ile His Ile Gly Leu Gly Arg Ala Leu Tyr Ala Thr Gly Asp Ile Ile
                325                 330                 335
Gly Asp Ile Arg Gln Ala His Cys Asn Leu Ser Ser Lys Ser Trp Asn
            340                 345                 350
Lys Thr Leu Gln Gln Val Val Arg Lys Leu Arg Glu Gln Phe Gly Asn
        355                 360                 365
Lys Thr Ile Ala Phe Asn Gln Ser Ser Gly Gly Asp Gln Glu Ile Val
370                 375                 380
Lys His Ser Phe Asn Cys Gly Gly Glu Phe Phe Tyr Cys Asp Thr Thr
385                 390                 395                 400
Gln Leu Phe Asn Ser Thr Trp Ser Ser Asn Asp Thr Trp Asn Ser Thr
                405                 410                 415
Gly Val Gln Asp Asn Asn Ile Thr Leu Pro Cys Arg Ile Lys Gln Ile
            420                 425                 430
Ile Asn Met Trp Gln Glu Val Gly Lys Ala Met Tyr Ala Pro Pro Ile
        435                 440                 445
Gln Gly Leu Ile Ser Cys Ser Ser Asn Ile Thr Gly Leu Leu Leu Thr
450                 455                 460
Arg Asp Gly Gly Thr Asn Asn Thr Asn Ala Thr Glu Ile Phe Arg Pro
465                 470                 475                 480
Gly Gly Gly Asp Met Arg Asp Asn Trp Arg Ser Glu Leu Tyr Lys Tyr
                485                 490                 495
Lys Val Val Lys Ile Glu Pro Leu Gly Ile Ala Pro Thr Lys Ala Lys
            500                 505                 510
Glu Arg Val Val Gln Arg Glu Lys Glu Ala Val Gly Leu Gly Ala Val
        515                 520                 525
Phe Ile Gly Phe Leu Gly Ala Ala Gly Ser Thr Met Gly Ala Ala Ser
530                 535                 540
Val Thr Leu Thr Val Gln Ala Arg Gln Leu Leu Ser Gly Ile Val Gln
545                 550                 555                 560
Gln Gln Asn Asn Leu Leu Arg Ala Ile Glu Ala Gln Gln His Met Leu
                565                 570                 575
Gln Leu Thr Val Trp Gly Ile Lys Gln Leu Gln Ala Arg Ile Leu Ala
            580                 585                 590
Val Glu Arg Tyr Leu Lys Asp Gln Gln Ile Leu Gly Ile Trp Gly Cys
        595                 600                 605
Ser Gly Lys Leu Ile Cys Pro Thr Ala Val Pro Trp Asn Ala Ser Trp
610                 615                 620
Ser Asn Lys Ser Leu Thr Ala Ile Trp Asn Asn Met Thr Trp Met Glu
625                 630                 635                 640
Trp Glu Arg Glu Ile Asp Asn Tyr Thr Gly Leu Ile Tyr Ser Leu Ile
                645                 650                 655
Glu Glu Ser Gln Ile Gln Gln Glu Gln Asn Glu Lys Glu Leu Leu Glu
            660                 665                 670
Leu Asp Lys Trp Ala Ser Leu Trp Asn Trp Phe Asp Ile Thr Lys Trp
        675                 680                 685
Leu Trp Tyr Ile Lys
        690
```

<210> SEQ ID NO 70
<211> LENGTH: 693
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Met Arg Val Lys Gly Ile Arg Lys Asn Tyr Gln His Leu Trp Arg Trp
1               5                   10                  15

Gly Thr Met Leu Leu Gly Ile Leu Met Ile Cys Ser Ala Ala Ala Gln
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Leu Val Leu Ala Asn Val Thr Glu Asn Phe Asn Met Trp Asn
                85                  90                  95

Asn Thr Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Thr Asn Ala Thr Asn Ile Asn Ala Thr Asn Ile
    130                 135                 140

Asn Asn Ser Ser Gly Gly Val Glu Ser Gly Glu Ile Lys Asn Cys Ser
145                 150                 155                 160

Phe Asn Ile Thr Thr Ser Val Arg Asp Lys Val Gln Lys Glu Tyr Ala
                165                 170                 175

Leu Phe Tyr Lys Leu Asp Ile Val Pro Ile Thr Asn Glu Ser Ser Lys
            180                 185                 190

Tyr Arg Leu Ile Ser Cys Asn Thr Ser Val Leu Thr Gln Ala Cys Pro
        195                 200                 205

Lys Val Ser Phe Glu Pro Ile Pro Ile His Tyr Cys Ala Pro Ala Gly
    210                 215                 220

Phe Ala Ile Leu Lys Cys Asn Asn Glu Thr Phe Asn Gly Lys Gly Pro
225                 230                 235                 240

Cys Ile Asn Val Ser Thr Val Gln Cys Thr His Gly Ile Arg Pro Val
                245                 250                 255

Val Ser Thr Gln Leu Leu Leu Asn Gly Ser Leu Ala Glu Lys Glu Val
            260                 265                 270

Ile Ile Arg Ser Asp Asn Phe Ser Asp Asn Ala Lys Asn Ile Ile Val
        275                 280                 285

Gln Leu Lys Glu Tyr Val Lys Ile Asn Cys Thr Arg Pro Asn Asn Asn
    290                 295                 300

Thr Arg Lys Ser Ile His Ile Gly Pro Gly Arg Ala Phe Tyr Ala Thr
305                 310                 315                 320

Gly Glu Ile Ile Gly Asn Ile Arg Gln Ala His Cys Asn Ile Ser Arg
                325                 330                 335

Ser Lys Trp Asn Asp Thr Leu Lys Gln Ile Ala Ala Lys Leu Gly Glu
            340                 345                 350

Gln Phe Arg Asn Lys Thr Ile Val Phe Asn Pro Ser Ser Gly Gly Asp
        355                 360                 365
```

Leu Glu Ile Val Thr His Ser Phe Asn Cys Gly Gly Glu Phe Phe Tyr
    370                 375                 380

Cys Asn Thr Thr Lys Leu Phe Asn Ser Thr Trp Ile Arg Glu Gly Asn
385                 390                 395                 400

Asn Gly Thr Trp Asn Gly Thr Ile Gly Leu Asn Asp Thr Ala Gly Asn
                405                 410                 415

Asp Thr Ile Ile Leu Pro Cys Lys Ile Lys Gln Ile Ile Asn Met Trp
            420                 425                 430

Gln Glu Val Gly Lys Ala Met Tyr Ala Pro Pro Ile Arg Gly Gln Ile
                435                 440                 445

Arg Cys Ser Ser Asn Ile Thr Gly Leu Ile Leu Thr Arg Asp Gly Gly
450                 455                 460

Lys Asp Asp Ser Asn Gly Ser Glu Ile Leu Glu Ile Phe Arg Pro Gly
465                 470                 475                 480

Gly Gly Asp Met Arg Asp Asn Trp Arg Ser Glu Leu Tyr Lys Tyr Lys
                485                 490                 495

Val Val Arg Ile Glu Pro Leu Gly Val Ala Pro Thr Arg Ala Arg Glu
                500                 505                 510

Arg Val Val Gln Lys Glu Lys Glu Ala Val Gly Leu Gly Ala Met Phe
            515                 520                 525

Leu Gly Phe Leu Gly Ala Ala Gly Ser Ala Met Gly Ala Ala Ser Met
    530                 535                 540

Thr Leu Thr Val Gln Ala Arg Gln Leu Leu Ser Gly Ile Val Gln Gln
545                 550                 555                 560

Gln Asn Asn Leu Leu Arg Ala Ile Glu Ala Gln Gln His Met Leu Gln
                565                 570                 575

Leu Thr Val Trp Gly Ile Lys Gln Leu Gln Ala Arg Val Leu Ala Val
            580                 585                 590

Glu Arg Tyr Leu Lys Asp Gln Gln Leu Leu Gly Ile Trp Gly Cys Ser
                595                 600                 605

Gly Lys Leu Ile Cys Thr Thr Asp Val Pro Trp Asp Thr Ser Trp Ser
    610                 615                 620

Asn Lys Thr Leu Asp Asp Ile Trp Gly Ser Asn Met Thr Trp Met Glu
625                 630                 635                 640

Trp Glu Arg Glu Ile Asp Asn Tyr Thr Ser Thr Ile Tyr Thr Leu Leu
                645                 650                 655

Glu Glu Ala Gln Tyr Gln Gln Glu Lys Asn Glu Lys Glu Leu Leu Glu
                660                 665                 670

Leu Asp Lys Trp Ala Ser Leu Trp Asn Trp Phe Asp Ile Thr Asn Trp
            675                 680                 685

Leu Trp Tyr Ile Arg
    690

<210> SEQ ID NO 71
<211> LENGTH: 690
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Met Arg Val Lys Gly Ile Arg Lys Asn Cys Gln Gln His Leu Trp Arg
1               5                   10                  15

Trp Gly Thr Met Leu Leu Gly Ile Leu Met Ile Cys Ser Ala Ala Glu
                20                  25                  30

```
Asn Leu Trp Val Thr Val Tyr Tyr Gly Val Pro Val Trp Lys Glu Ala
             35                  40                  45

Thr Thr Thr Leu Phe Cys Ala Ser Asp Ala Lys Ala Tyr Asp Thr Glu
 50                  55                  60

Val His Asn Val Trp Ala Thr His Ala Cys Val Pro Thr Asp Pro Asn
 65                  70                  75                  80

Pro Gln Glu Met Val Leu Glu Asn Val Thr Glu Tyr Phe Asn Met Trp
                 85                  90                  95

Lys Asn Asn Met Val Glu Gln Met His Glu Asp Ile Ile Ser Leu Trp
                100                 105                 110

Asp Gln Ser Leu Lys Pro Cys Val Lys Leu Thr Pro Leu Cys Val Thr
            115                 120                 125

Leu Thr Cys Thr Asp Tyr Glu Trp Asn Cys Thr Gly Ile Arg Asn Ser
        130                 135                 140

Ile Cys Lys Tyr Asn Asn Met Thr Asn Asn Ser Ser Ser Gly Asn Tyr
145                 150                 155                 160

Thr Gly Trp Glu Arg Gly Glu Ile Lys Asn Cys Ser Phe Asn Ser Thr
                165                 170                 175

Ile Ser Gly Ile Arg Asp Lys Val Arg Lys Glu Tyr Ala Leu Leu Tyr
            180                 185                 190

Lys Ile Asp Leu Val Ser Ile Asp Gly Ser Asn Thr Ser Tyr Arg Met
        195                 200                 205

Ile Ser Cys Asn Thr Ser Val Ile Thr Gln Ser Cys Pro Lys Ile Ser
210                 215                 220

Phe Glu Pro Ile Pro Leu His Tyr Cys Thr Pro Ala Gly Phe Ala Leu
225                 230                 235                 240

Leu Lys Cys Asn Asp Lys Lys Phe Asn Gly Thr Gly Leu Cys His Asn
                245                 250                 255

Val Ser Thr Val Gln Cys Thr His Gly Ile Lys Pro Val Val Ser Thr
            260                 265                 270

Gln Leu Leu Leu Asn Gly Ser Leu Ala Glu Glu Val Val Ile Arg
        275                 280                 285

Ser Lys Asn Phe Thr Asp Asn Ala Lys Ile Ile Ile Val Gln Leu Asn
290                 295                 300

Glu Thr Val Glu Ile Asn Cys Thr Arg Pro Gly Asn Asn Thr Arg Lys
305                 310                 315                 320

Ser Ile His Ile Ala Pro Gly Arg Thr Phe Tyr Ala Thr Gly Glu Ile
                325                 330                 335

Ile Gly Asp Ile Arg Arg Ala His Cys Asn Ile Ser Arg Glu Lys Trp
            340                 345                 350

Asn Thr Thr Leu His Arg Ile Ala Thr Lys Leu Arg Glu Gln Tyr Asn
        355                 360                 365

Lys Thr Ile Val Phe Asn Gln Ser Ser Gly Gly Asp Pro Glu Ile Val
    370                 375                 380

Met His Ser Val Asn Cys Gly Gly Glu Phe Phe Tyr Cys Asn Thr Ser
385                 390                 395                 400

Lys Leu Phe Asn Ser Thr Trp Asn Ser Thr Gly Gly Ser Ile Ser Glu
                405                 410                 415

Asp Ser Glu Asn Ile Thr Leu Pro Cys Arg Ile Lys Gln Ile Val Asn
            420                 425                 430

Met Trp Gln Glu Val Gly Lys Ala Met Tyr Ala Pro Pro Ile Arg Gly
        435                 440                 445
```

```
Gln Ile Arg Cys Ser Ser Asn Ile Thr Gly Leu Leu Leu Thr Arg Asp
    450                 455                 460
Gly Gly Ile Asn Gln Ser Ile Ser Glu Thr Phe Arg Pro Gly Gly Gly
465                 470                 475                 480
Asp Met Arg Asp Asn Trp Arg Ser Glu Leu Tyr Lys Tyr Lys Val Val
                485                 490                 495
Lys Ile Glu Pro Leu Gly Ile Ala Pro Thr Lys Ala Arg Glu Arg Val
            500                 505                 510
Val Gln Arg Glu Lys Glu Ala Val Gly Ile Gly Ala Val Phe Leu Gly
        515                 520                 525
Phe Leu Gly Ala Ala Gly Ser Thr Met Gly Ala Ala Ser Leu Thr Leu
    530                 535                 540
Thr Val Gln Ala Arg Leu Leu Leu Ser Gly Ile Val Gln Gln Gln Asn
545                 550                 555                 560
Asn Leu Leu Arg Ala Ile Glu Ala Gln Gln His Met Leu Gln Leu Thr
                565                 570                 575
Val Trp Gly Ile Lys Gln Leu Gln Ala Arg Val Leu Ala Leu Glu Arg
            580                 585                 590
Tyr Leu Arg Asp Gln Gln Leu Met Gly Ile Trp Gly Cys Ser Gly Lys
        595                 600                 605
Leu Ile Cys Thr Thr Ala Val Pro Trp Asn Ala Ser Trp Ser Asn Lys
    610                 615                 620
Ser Leu Asn Asp Ile Trp Asn Asn Met Thr Trp Met Gln Trp Glu Arg
625                 630                 635                 640
Glu Ile Asp Asn Tyr Thr Gly Leu Ile Tyr Ser Leu Leu Glu Glu Ser
                645                 650                 655
Gln Asn Gln Gln Glu Lys Asn Glu Gln Asp Leu Leu Ala Leu Asp Lys
            660                 665                 670
Trp Ala Asn Leu Trp Thr Trp Phe Asp Ile Ser Asn Trp Leu Trp Tyr
        675                 680                 685
Ile Lys
    690

<210> SEQ ID NO 72
<211> LENGTH: 632
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Arg Val Lys Gly Ile Arg Lys Asn Tyr Gln His Leu Trp Arg Trp
1               5                   10                  15
Gly Thr Met Leu Leu Gly Met Leu Met Ile Cys Ser Ala Ala Glu Lys
                20                  25                  30
Leu Trp Val Thr Val Tyr Tyr Gly Val Pro Val Trp Lys Glu Ala Thr
            35                  40                  45
Thr Thr Leu Phe Cys Ala Ser Asp Ala Lys Ala Tyr Asp Thr Glu Val
        50                  55                  60
His Asn Val Trp Ala Thr His Ala Cys Val Pro Thr Asp Pro Asn Pro
65                  70                  75                  80
Gln Glu Val Val Leu Glu Asn Val Thr Glu Asn Phe Asn Met Trp Lys
                85                  90                  95
Asn Asn Met Val Glu Gln Met His Glu Asp Ile Ile Ser Leu Trp Asp
            100                 105                 110
```

```
Gln Ser Leu Lys Pro Cys Val Lys Leu Thr Pro Leu Cys Val Thr Leu
    115                 120                 125

Asn Cys Thr Asp Leu Met Asn Ala Thr Asn Thr Asn Thr Thr Ile Ile
130                 135                 140

Tyr Arg Trp Arg Gly Glu Ile Lys Asn Cys Ser Phe Asn Ile Thr Thr
145                 150                 155                 160

Ser Ile Arg Asp Lys Val Gln Lys Glu Tyr Ala Leu Phe Tyr Lys Leu
                165                 170                 175

Asp Val Val Pro Ile Asp Asn Asp Asn Thr Ser Tyr Arg Leu Ile Ser
                180                 185                 190

Cys Asn Thr Ser Val Ile Thr Gln Ala Cys Pro Lys Val Ser Phe Glu
            195                 200                 205

Pro Ile Pro Ile His Tyr Cys Ala Pro Ala Gly Phe Ala Ile Leu Lys
        210                 215                 220

Cys Asn Asp Lys Lys Phe Asn Gly Thr Gly Pro Cys Thr Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Glu Val Val Ile Arg Ser Glu
            260                 265                 270

Asn Phe Thr Asp Asn Ala Lys Thr Ile Ile Val Gln Leu Asn Glu Ser
        275                 280                 285

Val Glu Ile Asn Cys Thr Arg Pro Asn Asn Asn Thr Arg Lys Ser Ile
    290                 295                 300

His Ile Gly Pro Gly Arg Ala Phe Tyr Thr Thr Gly Glu Ile Ile Gly
305                 310                 315                 320

Asp Ile Arg Gln Ala His Cys Asn Ile Ser Arg Ala Lys Trp Asn Asn
                325                 330                 335

Thr Leu Lys Gln Ile Val Lys Lys Leu Arg Glu Gln Phe Gly Asn Lys
            340                 345                 350

Thr Ile Val Phe Asn Gln Ser Ser Gly Gly Asp Pro Glu Ile Val Met
        355                 360                 365

His Ser Phe Asn Cys Gly Gly Glu Phe Phe Tyr Cys Asn Thr Thr Gln
370                 375                 380

Leu Phe Asn Ser Thr Trp Asn Gly Thr Trp Asn Asn Thr Glu Gly Asn
385                 390                 395                 400

Ile Thr Leu Pro Cys Arg Ile Lys Gln Ile Ile Asn Met Trp Gln Glu
                405                 410                 415

Val Gly Lys Ala Met Tyr Ala Pro Pro Ile Arg Gly Gln Ile Arg Cys
                420                 425                 430

Ser Ser Asn Ile Thr Gly Leu Leu Leu Thr Arg Asp Gly Gly Asn Asn
            435                 440                 445

Glu Thr Glu Ile Phe Arg Pro Gly Gly Gly Asp Met Arg Asp Asn Trp
        450                 455                 460

Arg Ser Glu Leu Tyr Lys Tyr Lys Val Val Lys Ile Glu Pro Leu Gly
465                 470                 475                 480

Val Ala Pro Thr Lys Ala Lys Thr Leu Thr Val Gln Ala Arg Gln Leu
                485                 490                 495

Leu Ser Gly Ile Val Gln Gln Asn Asn Leu Leu Arg Ala Ile Glu
            500                 505                 510

Ala Gln Gln His Leu Leu Gln Leu Thr Val Trp Gly Ile Lys Gln Leu
        515                 520                 525
```

```
Gln Ala Arg Val Leu Ala Val Glu Arg Tyr Leu Lys Asp Gln Gln Leu
        530                 535                 540

Leu Gly Ile Trp Gly Cys Ser Gly Lys Leu Ile Cys Thr Thr Ala Val
545                 550                 555                 560

Pro Trp Asn Ala Ser Trp Ser Asn Lys Ser Leu Asp Glu Ile Trp Asp
                565                 570                 575

Asn Met Thr Trp Met Glu Trp Glu Arg Glu Ile Asp Asn Tyr Thr Ser
                580                 585                 590

Leu Ile Tyr Thr Leu Ile Glu Glu Ser Gln Asn Gln Gln Glu Lys Asn
        595                 600                 605

Glu Gln Glu Leu Leu Glu Leu Asp Lys Trp Ala Ser Leu Trp Asn Trp
610                 615                 620

Phe Asp Ile Thr Asn Trp Leu Trp
625                 630

<210> SEQ ID NO 73
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
                20                  25                  30

Tyr Tyr Gly Val Pro Val Trp Lys Glu Ala Thr Thr Thr Leu Phe Cys
            35                  40                  45

Ala Ser Asp Ala Lys Ala Tyr Asp Thr Glu Val His Asn Val Trp Ala
        50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
130                 135                 140

Glu Ile Lys Asn Cys Ser Phe Asn Ile Thr Thr Ser Ile Arg Asp Glu
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255
```

Leu Ala Glu Glu Val Val Ile Arg Ser Asp Asn Phe Thr Asn Asn
                260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Thr Leu Thr Val Gln Ala Arg Leu
                485                 490                 495

Leu Leu Ser Gly Ile Val Gln Gln Gln Asn Asn Leu Leu Arg Ala Ile
            500                 505                 510

Glu Ala Gln Gln Arg Met Leu Gln Leu Thr Val Trp Gly Ile Lys Gln
        515                 520                 525

Leu Gln Ala Arg Val Leu Ala Val Glu Arg Tyr Leu Gly Asp Gln Gln
    530                 535                 540

Leu Leu Gly Ile Trp Gly Cys Ser Gly Lys Leu Ile Cys Thr Thr Ala
545                 550                 555                 560

Val Pro Trp Asn Ala Ser Trp Ser Asn Lys Ser Leu Asp Arg Ile Trp
                565                 570                 575

Asn Asn Met Thr Trp Met Glu Trp Glu Arg Glu Ile Asp Asn Tyr Thr
            580                 585                 590

Ser Glu Ile Tyr Thr Leu Ile Glu Glu Ser Gln Asn Gln Gln Glu Lys
        595                 600                 605

Asn Glu Gln Glu Leu Leu Glu Leu Asp Lys Trp Ala Ser Leu Trp Asn
    610                 615                 620

Trp Phe Asp Ile Thr Lys Trp Leu Trp
625                 630

<210> SEQ ID NO 74
<211> LENGTH: 618
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 74

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Leu Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asp Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Ser
            180                 185                 190

Leu Thr Ser Cys Asn Thr Ser Val Ile Thr Gln Ala Cys Pro Lys Val
        195                 200                 205

Ser Phe Glu Pro Ile Pro Asn His Tyr Cys Ala Pro Ala Gly Phe Ala
    210                 215                 220

Ile Leu Lys Cys Lys Asp Lys Lys Phe Asn Gly Lys Gly Pro Cys Thr
225                 230                 235                 240

Asn Val Ser Thr Val Gln Cys Thr His Gly Ile Arg Pro Val Val Ser
                245                 250                 255

Thr Gln Leu Leu Val Thr Gly Asn Leu Ala Glu Glu Val Val Ile
            260                 265                 270

Arg Ser Ala Asn Phe Ala Asp Asn Ala Lys Val Ile Ile Val Gln Leu
        275                 280                 285

Asn Glu Ser Val Glu Ile Asn Cys Thr Arg Pro Asn Asn Thr Arg
    290                 295                 300

Lys Ser Ile His Ile Gly Pro Gly Arg Ala Phe Tyr Thr Thr Gly Glu
305                 310                 315                 320

Ile Ile Gly Asp Ile Arg Gln Ala His Cys Asn Leu Ser Arg Ala Lys
                325                 330                 335

Trp Asn Asp Thr Leu Asn Lys Ile Val Ile Lys Leu Arg Glu Gln Phe
            340                 345                 350

Gly Asn Lys Thr Ile Val Phe Lys His Ser Ser Gly Gly Asp Pro Glu
        355                 360                 365

Ile Val Thr His Ser Phe Asn Cys Gly Gly Glu Phe Phe Tyr Cys Asn
    370                 375                 380

Ser Thr Gln Leu Phe Asn Ser Thr Trp Phe Asn Ser Thr Trp Ser Thr
385                 390                 395                 400

```
Glu Gly Ser Asn Asn Thr Gly Ser Asp Thr Ile Thr Leu Pro Cys
                405                 410                 415

Arg Ile Lys Gln Ile Ile Asn Met Trp Gln Lys Val Gly Lys Ala Met
            420                 425                 430

Tyr Ala Pro Pro Ile Ser Gly Gln Ile Arg Cys Ser Ser Asn Ile Thr
            435                 440                 445

Gly Leu Leu Leu Thr Arg Asp Gly Gly Asn Ser Asn Asn Glu Ser Glu
        450                 455                 460

Ile Phe Arg Leu Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Leu Thr Val Gln Ala Arg Gln Leu Leu Ser Gly Ile
            500                 505                 510

Val Gln Gln Gln Asn Asn Leu Leu Arg Ala Ile Glu Ala Gln Gln His
        515                 520                 525

Leu Leu Gln Leu Thr Val Trp Gly Ile Lys Gln Leu Gln Ala Arg Thr
        530                 535                 540

Leu Ala Val Glu Arg Tyr Leu Lys Asp Gln Gln Leu Leu Glu Gln Ile
545                 550                 555                 560

Trp Asn His Thr Thr Trp Met Glu Trp Asp Arg Glu Ile Asn Asn Tyr
                565                 570                 575

Thr Ser Leu Ile His Ser Leu Ile Glu Glu Ser Gln Asn Gln His Glu
            580                 585                 590

Lys Asn Glu Gln Glu Leu Leu Glu Leu Asp Lys Trp Ala Ser Leu Trp
        595                 600                 605

Asn Trp Phe Asn Ile Thr Asn Trp Leu Trp
        610                 615

<210> SEQ ID NO 75
<211> LENGTH: 682
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Arg Val Arg Gly Met Leu Arg Asn Cys Gln Gln Trp Trp Ile Trp
1               5                   10                  15

Gly Ile Leu Gly Phe Trp Met Leu Met Ile Cys Ser Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Arg Ala Tyr Glu Arg Glu Val
    50                  55                  60

His Asn Val Trp Ala Thr His Ala Cys Val Pro Thr Asp Pro Asn Pro
65                  70                  75                  80

Gln Glu Met Val Leu Val Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Ile Leu
        115                 120                 125

Glu Cys Asn Asn Ala Asn Gly Thr Thr Asn Asn Gly Ser Val Ile Val
```

```
            130                 135                 140
Val Asn Glu Asn Ser Thr Met Tyr Gly Glu Ile Gln Asn Cys Ser Phe
145                 150                 155                 160

Lys Val Asn Ser Glu Ile Lys Gly Lys Lys Gln Asp Val Tyr Ala Leu
                165                 170                 175

Phe Asn Ser Leu Asp Ile Val Lys Leu Tyr Asn Asn Gly Thr Ser Gln
                180                 185                 190

Tyr Arg Leu Ile Asn Cys Asn Thr Ser Thr Leu Thr Gln Ala Cys Pro
            195                 200                 205

Lys Val Ser Phe Asp Pro Ile Pro Ile His Tyr Cys Ala Pro Ala Gly
            210                 215                 220

Tyr Ala Ile Leu Lys Cys Asn Asn Lys Thr Phe Asn Gly Thr Gly Pro
225                 230                 235                 240

Cys Asn Asn Val Ser Thr Val Gln Cys Thr His Gly Ile Lys Pro Val
                245                 250                 255

Val Ser Thr Gln Leu Leu Leu Asn Gly Ser Leu Ala Glu Gly Glu Ile
                260                 265                 270

Ile Ile Arg Ser Lys Asn Leu Thr Asp Asn Thr Lys Thr Ile Ile Val
            275                 280                 285

His Leu Asn Glu Ser Ile Lys Ile Asn Cys Ile Arg Pro Asn Asn Asn
            290                 295                 300

Thr Arg Arg Ser Ile Arg Ile Gly Pro Gly Gln Ala Phe Tyr Ala Ala
305                 310                 315                 320

Asn Gly Ile Val Gly Asn Ile Arg Gln Ala His Cys Asn Ile Ser Glu
                325                 330                 335

Gly Glu Trp Asn Lys Thr Leu Tyr Arg Val Ser Arg Lys Leu Ala Glu
                340                 345                 350

His Phe Pro Gly Lys Glu Ile Lys Phe Lys Pro His Ser Gly Gly Asp
            355                 360                 365

Leu Glu Ile Thr Thr His Ser Phe Asn Cys Arg Gly Glu Phe Phe Tyr
            370                 375                 380

Cys Asn Thr Ser Lys Leu Phe Asn Gly Thr Tyr Asn Gly Thr Tyr Thr
385                 390                 395                 400

Asn Asn Asp Thr Asn Ser Thr Ile Ile Leu Pro Cys Arg Ile Lys Gln
                405                 410                 415

Ile Ile Asn Met Trp Gln Glu Val Gly Gln Ala Met Tyr Ala Pro Pro
                420                 425                 430

Ile Glu Gly Ile Ile Ala Cys Asn Ser Thr Ile Thr Gly Leu Leu Leu
            435                 440                 445

Thr Arg Asp Gly Gly Asp Lys Asn Gly Ser Lys Pro Glu Ile Phe Arg
450                 455                 460

Pro Gly Gly Gly Asp Met Arg Asp Asn Trp Arg Ser Glu Leu Tyr Lys
465                 470                 475                 480

Tyr Lys Val Val Glu Ile Lys Pro Leu Gly Ile Ala Pro Thr Lys Ala
                485                 490                 495

Lys Glu Arg Val Val Glu Lys Glu Lys Thr Ile Gln Lys Glu Ala Val
                500                 505                 510

Gly Ile Gly Ala Val Phe Leu Gly Phe Leu Gly Ala Ala Gly Ser Thr
            515                 520                 525

Met Gly Ala Ala Ser Ile Thr Leu Thr Val Gln Ala Arg Gln Leu Leu
            530                 535                 540

Ser Gly Ile Val Gln Gln Gln Ser Asn Leu Leu Arg Ala Ile Glu Ala
545                 550                 555                 560
```

Gln Gln His Met Leu Gln Leu Thr Val Trp Gly Ile Lys Gln Leu Gln
                565                 570                 575

Ala Arg Val Leu Ala Met Glu Arg Tyr Leu Gln Asp Gln Gln Leu Leu
            580                 585                 590

Gly Ile Trp Gly Cys Ser Gly Lys Leu Ile Cys Thr Thr Ala Val Pro
        595                 600                 605

Trp Asn Ser Ser Trp Ser Asn Lys Thr Leu Glu Tyr Ile Trp Gly Asn
    610                 615                 620

Met Thr Trp Met Gln Trp Asp Arg Glu Ile Asp Asn Tyr Thr Gly Ile
625                 630                 635                 640

Ile Tyr Asp Leu Leu Glu Asp Ser Gln Ile Gln Gln Glu Lys Asn Glu
                645                 650                 655

Lys Asp Leu Leu Ala Leu Asp Ser Trp Lys Asn Leu Trp Ser Trp Phe
            660                 665                 670

Ser Ile Thr Asn Trp Leu Trp Tyr Ile Lys
        675                 680

<210> SEQ ID NO 76
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Trp Val Thr
            20                  25                  30

Val Tyr Tyr Gly Val Pro Val Trp Lys Glu Ala Lys Thr Thr Leu Phe
        35                  40                  45

Cys Ala Ser Asp Ala Lys Ala Tyr Glu Lys Glu Val His Asn Val Trp
    50                  55                  60

Ala Thr His Ala Cys Val Pro Thr Asp Pro Asn Pro Gln Glu Met Val
65                  70                  75                  80

Leu Ala Asn Val Thr Glu Asn Phe Asn Met Trp Lys Asn Asp Met Val
                85                  90                  95

Glu Gln Met His Glu Asp Ile Ile Ser Leu Trp Asp Glu Ser Leu Lys
            100                 105                 110

Pro Cys Val Lys Leu Thr Pro Leu Cys Val Thr Leu Asn Cys Thr Asn
        115                 120                 125

Val Lys Gly Asn Glu Ser Asp Thr Ser Glu Val Met Lys Asn Cys Ser
    130                 135                 140

Phe Lys Ala Thr Thr Glu Leu Lys Asp Lys Lys His Lys Val His Ala
145                 150                 155                 160

Leu Phe Tyr Lys Leu Asp Val Val Pro Leu Asn Gly Asn Ser Ser Ser
                165                 170                 175

Ser Gly Glu Tyr Arg Leu Ile Asn Cys Asn Thr Ser Ala Ile Thr Gln
            180                 185                 190

Ala Cys Pro Lys Val Ser Phe Asp Pro Ile Pro Leu His Tyr Cys Ala
        195                 200                 205

Pro Ala Gly Phe Ala Ile Leu Lys Cys Asn Asn Lys Thr Phe Asn Gly
    210                 215                 220

Thr Gly Pro Cys Arg Asn Val Ser Thr Val Gln Cys Thr His Gly Ile

```
            225                 230                 235                 240
Lys Pro Val Val Ser Thr Gln Leu Leu Leu Asn Gly Ser Leu Ala Glu
                245                 250                 255
Glu Glu Ile Ile Ile Arg Ser Glu Asn Leu Thr Asn Asn Ala Lys Thr
                260                 265                 270
Ile Ile Val His Leu Asn Glu Ser Val Asn Ile Val Cys Thr Arg Pro
                275                 280                 285
Asn Asn Asn Thr Arg Lys Ser Ile Arg Ile Gly Pro Gly Gln Thr Phe
290                 295                 300
Tyr Ala Thr Gly Asp Ile Ile Gly Asn Ile Arg Gln Ala His Cys Asn
305                 310                 315                 320
Ile Asn Glu Ser Lys Trp Asn Asn Thr Leu Gln Lys Val Gly Glu Glu
                325                 330                 335
Leu Ala Lys His Phe Pro Ser Lys Thr Ile Lys Phe Glu Pro Ser Ser
                340                 345                 350
Gly Gly Asp Leu Glu Ile Thr Thr His Ser Phe Asn Cys Arg Gly Glu
                355                 360                 365
Phe Phe Tyr Cys Asn Thr Ser Asp Leu Phe Asn Gly Thr Tyr Arg Asn
        370                 375                 380
Gly Thr Tyr Asn His Thr Gly Arg Ser Ser Asn Gly Thr Ile Thr Leu
385                 390                 395                 400
Gln Cys Lys Ile Lys Gln Ile Ile Asn Met Trp Gln Glu Val Gly Arg
                405                 410                 415
Ala Ile Tyr Ala Pro Pro Ile Glu Gly Glu Ile Thr Cys Asn Ser Asn
                420                 425                 430
Ile Thr Gly Leu Leu Leu Arg Asp Gly Gly Gln Ser Asn Glu Thr
        435                 440                 445
Asn Asp Thr Glu Thr Phe Arg Pro Gly Gly Gly Asp Met Arg Asp Asn
        450                 455                 460
Trp Arg Ser Glu Leu Tyr Lys Tyr Lys Val Val Glu Ile Lys Pro Leu
465                 470                 475                 480
Gly Val Ala Pro Thr Glu Ala Lys Glu Arg Val Val Glu Arg Glu Lys
                485                 490                 495
Glu

<210> SEQ ID NO 77
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Met Arg Val Arg Gly Ile Trp Lys Asn Trp Pro Gln Trp Leu Ile Trp
1               5                   10                  15
Ser Ile Leu Gly Phe Trp Ile Gly Asn Met Glu Gly Ser Val Pro Val
                20                  25                  30
Trp Lys Glu Ala Lys Thr Thr Leu Phe Cys Ala Ser Asp Ala Lys Ala
        35                  40                  45
Tyr Glu Lys Glu Val His Asn Val Trp Ala Thr His Ala Cys Val Pro
    50                  55                  60
Thr Asp Pro Asn Pro Gln Glu Met Val Leu Ala Asn Val Thr Glu Asn
65                  70                  75                  80
Phe Asn Met Trp Lys Asn Asp Met Val Glu Gln Met His Glu Asp Ile
```

```
                85                  90                  95
Ile Ser Leu Trp Asp Glu Ser Leu Lys Pro Cys Val Lys Leu Thr Pro
            100                 105                 110

Leu Cys Val Thr Leu Asn Cys Thr Asn Val Lys Gly Asn Glu Ser Asp
        115                 120                 125

Thr Ser Glu Val Met Lys Asn Cys Ser Phe Lys Ala Thr Thr Glu Leu
    130                 135                 140

Lys Asp Lys Lys His Lys Val His Ala Leu Phe Tyr Lys Leu Asp Val
145                 150                 155                 160

Val Pro Leu Asn Gly Asn Ser Ser Ser Gly Glu Tyr Arg Leu Ile
            165                 170                 175

Asn Cys Asn Thr Ser Ala Ile Thr Gln Ala Cys Pro Lys Val Ser Phe
            180                 185                 190

Asp Pro Ile Pro Leu His Tyr Cys Ala Pro Ala Gly Phe Ala Ile Leu
            195                 200                 205

Lys Cys Asn Asn Lys Thr Phe Asn Gly Thr Gly Pro Cys Arg Asn Val
        210                 215                 220

Ser Thr Val Gln Cys Thr His Gly Ile Lys Pro Val Val Ser Thr Gln
225                 230                 235                 240

Leu Leu Leu Asn Gly Ser Leu Ala Glu Glu Ile Ile Arg Ser
            245                 250                 255

Glu Asn Leu Thr Asn Asn Ala Lys Thr Ile Ile Val His Leu Asn Glu
            260                 265                 270

Ser Val Asn Ile Val Cys Thr Arg Pro Asn Asn Asn Thr Arg Lys Ser
        275                 280                 285

Ile Arg Ile Gly Pro Gly Gln Thr Phe Tyr Ala Thr Gly Asp Ile Ile
        290                 295                 300

Gly Asn Ile Arg Gln Ala His Cys Asn Ile Asn Glu Ser Lys Trp Asn
305                 310                 315                 320

Asn Thr Leu Gln Lys Val Gly Glu Glu Leu Ala Lys His Phe Pro Ser
            325                 330                 335

Lys Thr Ile Lys Phe Glu Pro Ser Ser Gly Gly Asp Leu Glu Ile Thr
            340                 345                 350

Thr His Ser Phe Asn Cys Arg Gly Glu Phe Phe Tyr Cys Asn Thr Ser
            355                 360                 365

Asp Leu Phe Asn Gly Thr Tyr Arg Asn Gly Thr Tyr Asn His Thr Gly
        370                 375                 380

Arg Ser Ser Asn Gly Thr Ile Thr Leu Gln Cys Lys Ile Lys Gln Ile
385                 390                 395                 400

Ile Asn Met Trp Gln Glu Val Gly Arg Ala Ile Tyr Ala Pro Pro Ile
            405                 410                 415

Glu Gly Glu Ile Thr Cys Asn Ser Asn Ile Thr Gly Leu Leu Leu Leu
            420                 425                 430

Arg Asp Gly Gly Gln Ser Asn Glu Thr Asn Asp Thr Glu Thr Phe Arg
        435                 440                 445

Pro Gly Gly Gly Asp Met Arg Asp Asn Trp Arg Ser Glu Leu Tyr Lys
        450                 455                 460

Tyr Lys Val Val Glu Ile Lys Pro Leu Gly Val Ala Pro Thr Glu Ala
465                 470                 475                 480

Lys Arg Arg Val Val Glu Arg Glu Lys Arg
            485                 490

<210> SEQ ID NO 78
```

<211> LENGTH: 669
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Met Arg Val Arg Gly Ile Trp Lys Asn Trp Pro Gln Trp Leu Ile Trp
1               5                   10                  15

Ser Ile Leu Gly Phe Trp Ile Gly Asn Met Glu Gly Ser Trp Val Thr
            20                  25                  30

Val Tyr Tyr Gly Val Pro Val Trp Lys Glu Ala Lys Thr Thr Leu Phe
        35                  40                  45

Cys Ala Ser Asp Ala Lys Ala Tyr Glu Lys Glu Val His Asn Val Trp
    50                  55                  60

Ala Thr His Ala Cys Val Pro Thr Asp Pro Asn Pro Gln Glu Met Val
65                  70                  75                  80

Leu Ala Asn Val Thr Glu Asn Phe Asn Met Trp Lys Asn Asp Met Val
                85                  90                  95

Glu Gln Met His Glu Asp Ile Ile Ser Leu Trp Asp Glu Ser Leu Lys
            100                 105                 110

Pro Cys Val Lys Leu Thr Pro Leu Cys Val Thr Leu Asn Cys Thr Asn
        115                 120                 125

Val Lys Gly Asn Glu Ser Asp Thr Ser Glu Val Met Lys Asn Cys Ser
    130                 135                 140

Phe Lys Ala Thr Thr Glu Leu Lys Asp Lys Lys His Lys Val His Ala
145                 150                 155                 160

Leu Phe Tyr Lys Leu Asp Val Val Pro Leu Asn Gly Asn Ser Ser Ser
                165                 170                 175

Ser Gly Glu Tyr Arg Leu Ile Asn Cys Asn Thr Ser Ala Ile Thr Gln
            180                 185                 190

Ala Cys Pro Lys Val Ser Phe Asp Pro Ile Pro Leu His Tyr Cys Ala
        195                 200                 205

Pro Ala Gly Phe Ala Ile Leu Lys Cys Asn Asn Lys Thr Phe Asn Gly
    210                 215                 220

Thr Gly Pro Cys Arg Asn Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Ile Ile Ile Arg Ser Glu Asn Leu Thr Asn Asn Ala Lys Thr
            260                 265                 270

Ile Ile Val His Leu Asn Glu Ser Val Asn Ile Val Cys Thr Arg Pro
        275                 280                 285

Asn Asn Asn Thr Arg Lys Ser Ile Arg Ile Gly Pro Gly Gln Thr Phe
    290                 295                 300

Tyr Ala Thr Gly Asp Ile Ile Gly Asn Ile Arg Gln Ala His Cys Asn
305                 310                 315                 320

Ile Asn Glu Ser Lys Trp Asn Asn Thr Leu Gln Lys Val Gly Glu Glu
                325                 330                 335

Leu Ala Lys His Phe Pro Ser Lys Thr Ile Lys Phe Glu Pro Ser Ser
            340                 345                 350

Gly Gly Asp Leu Glu Ile Thr Thr His Ser Phe Asn Cys Arg Gly Glu
        355                 360                 365

Phe Phe Tyr Cys Asn Thr Ser Asp Leu Phe Asn Gly Thr Tyr Arg Asn
```

```
                370                 375                 380
Gly Thr Tyr Asn His Thr Gly Arg Ser Ser Asn Gly Thr Ile Thr Leu
385                 390                 395                 400

Gln Cys Lys Ile Lys Gln Ile Ile Asn Met Trp Gln Glu Val Gly Arg
                405                 410                 415

Ala Ile Tyr Ala Pro Pro Ile Glu Glu Ile Thr Cys Asn Ser Asn
                420                 425                 430

Ile Thr Gly Leu Leu Leu Arg Asp Gly Gln Ser Asn Glu Thr
            435                 440                 445

Asn Asp Thr Glu Thr Phe Arg Pro Gly Gly Gly Asp Met Arg Asp Asn
            450                 455                 460

Trp Arg Ser Glu Leu Tyr Lys Tyr Lys Val Val Glu Ile Lys Pro Leu
465                 470                 475                 480

Gly Val Ala Pro Thr Glu Ala Lys Glu Arg Val Val Glu Arg Glu Lys
                485                 490                 495

Glu Ala Val Gly Ile Gly Ala Val Phe Leu Gly Phe Leu Gly Ala Ala
                500                 505                 510

Gly Ser Thr Met Gly Ala Ala Ser Met Thr Leu Thr Val Gln Ala Arg
            515                 520                 525

Gln Leu Leu Ser Gly Ile Val Gln Gln Gln Ser Asn Leu Leu Arg Ala
            530                 535                 540

Ile Glu Ala Gln Gln His Met Leu Gln Leu Thr Val Trp Gly Ile Lys
545                 550                 555                 560

Gln Leu Gln Ala Arg Val Leu Ala Ile Glu Arg Tyr Leu Lys Asp Gln
                565                 570                 575

Gln Leu Leu Gly Met Trp Gly Cys Ser Gly Lys Leu Ile Cys Thr Thr
            580                 585                 590

Ala Val Pro Trp Asn Ser Ser Trp Ser Asn Lys Ser Gln Asn Glu Ile
            595                 600                 605

Trp Gly Asn Met Thr Trp Met Gln Trp Asp Arg Glu Ile Asn Asn Tyr
            610                 615                 620

Thr Asn Thr Ile Tyr Arg Leu Leu Glu Asp Ser Gln Asn Gln Gln Glu
625                 630                 635                 640

Lys Asn Glu Lys Asp Leu Leu Ala Leu Asp Ser Trp Lys Asn Leu Trp
                645                 650                 655

Asn Trp Phe Asp Ile Ser Lys Trp Leu Trp Tyr Ile Lys
            660                 665

<210> SEQ ID NO 79
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
                20                  25                  30

Asn Cys Thr Asn Val Lys Gly Asn Glu Ser Asp Thr Ser Glu Val Met
            35                  40                  45

Lys Asn Cys Ser Phe Lys Ala Thr Thr Glu Leu Lys Asp Lys Lys His
        50                  55                  60
```

```
Lys Val His Ala Leu Phe Tyr Lys Leu Asp Val Pro Leu Asn Gly
 65                  70                  75                  80

Asn Ser Ser Ser Gly Glu Tyr Arg Leu Ile Asn Cys Asn Thr Ser
                 85                  90                  95

Ala Ile Thr Gln Ala Gly Leu Asn Asp Ile Phe Glu Ala Gln Lys Ile
            100                 105                 110

Glu Trp His Glu Leu Glu Val Leu Phe Gln Gly Pro Gly His His His
        115                 120                 125

His His His
    130

<210> SEQ ID NO 80
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Arg Val Arg Gly Ile Pro Arg Asn Trp Pro Gln Trp Trp Met Trp
1               5                   10                  15

Gly Ile Leu Gly Phe Trp Met Ile Ile Cys Arg Val Val Gly Asn
            20                  25                  30

Met Trp Val Thr Val Tyr Tyr Gly Val Pro Val Trp Thr Asp Ala Lys
            35                  40                  45

Thr Thr Leu Phe Cys Ala Ser Asp Thr Lys Ala Tyr Asp Arg Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Ala Thr Phe Lys Asn Asn Val Thr Asn Asp Met Asn
    130                 135                 140

Lys Glu Ile Arg Asn Cys Ser Phe Asn Thr Thr Thr Glu Ile Arg Asp
145                 150                 155                 160

Lys Lys Gln Gln Gly Tyr Ala Leu Phe Tyr Arg Pro Asp Ile Val Leu
                165                 170                 175

Leu Lys Glu Asn Arg Asn Asn Ser Asn Ser Glu Tyr Ile Leu Ile
            180                 185                 190

Asn Cys Asn Ala Ser Thr Ile Thr Gln Ala Cys Pro Lys Val Asn Phe
        195                 200                 205

Asp Pro Ile Pro Ile His Tyr Cys Ala Pro Ala Gly Tyr Ala Ile Leu
    210                 215                 220

Lys Cys Asn Asn Lys Thr Phe Ser Gly Lys Gly Pro Cys Asn Asn Val
225                 230                 235                 240

Ser Thr Val Gln Cys Thr His Gly Ile Lys Pro Val Ser Thr Gln
                245                 250                 255

Leu Leu Leu Asn Gly Ser Leu Ala Glu Lys Glu Ile Ile Ile Arg Ser
            260                 265                 270

Glu Asn Leu Thr Asp Asn Val Lys Thr Ile Ile Val His Leu Asn Lys
        275                 280                 285
```

Ser Val Glu Ile Val Cys Thr Arg Pro Asn Asn Thr Arg Lys Ser
    290                 295                 300

Met Arg Ile Gly Pro Gly Gln Thr Phe Tyr Ala Thr Gly Asp Ile Ile
305                 310                 315                 320

Gly Asp Ile Arg Gln Ala Tyr Cys Asn Ile Ser Gly Ser Lys Trp Asn
                325                 330                 335

Glu Thr Leu Lys Arg Val Lys Glu Lys Leu Gln Glu Asn Tyr Asn Asn
            340                 345                 350

Asn Lys Thr Ile Lys Phe Ala Pro Ser Ser Gly Gly Asp Leu Glu Ile
        355                 360                 365

Thr Thr His Ser Phe Asn Cys Arg Gly Glu Phe Phe Tyr Cys Asn Thr
    370                 375                 380

Thr Arg Leu Phe Asn Asn Asn Ala Thr Glu Asp Glu Thr Ile Thr Leu
385                 390                 395                 400

Pro Cys Arg Ile Lys Gln Ile Ile Asn Met Trp Gln Gly Val Gly Arg
                405                 410                 415

Ala Met Tyr Ala Pro Pro Ile Ala Gly Asn Ile Thr Cys Lys Ser Asn
            420                 425                 430

Ile Thr Gly Leu Leu Leu Val Arg Asp Gly Gly Glu Asp Asn Lys Thr
        435                 440                 445

Glu Glu Ile Phe Arg Pro Gly Gly Gly Asn Met Lys Asp Asn Trp Arg
    450                 455                 460

Ser Glu Leu Tyr Lys Tyr Lys Val Ile Glu Leu Lys Pro Leu Gly Ile
465                 470                 475                 480

Ala Pro Thr Gly Ala Lys Leu Thr Val Gln Ala Arg Gln Leu Leu Ser
                485                 490                 495

Ser Ile Val Gln Gln Gln Ser Asn Leu Leu Arg Ala Ile Glu Ala Gln
            500                 505                 510

Gln His Met Leu Gln Leu Thr Val Trp Gly Ile Lys Gln Leu Gln Thr
        515                 520                 525

Arg Val Leu Ala Ile Glu Arg Tyr Leu Lys Asp Gln Gln Leu Glu Ile
    530                 535                 540

Trp Asn Asn Met Thr Trp Met Glu Trp Asp Arg Glu Ile Ser Asn Tyr
545                 550                 555                 560

Thr Asp Thr Ile Tyr Arg Leu Leu Glu Asp Ser Gln Thr Gln Gln Glu
                565                 570                 575

Lys Asn Glu Lys Asp Leu Leu Ala Leu Asp Ser Trp Lys Asn Leu Trp
            580                 585                 590

Ser Trp Phe Asp Ile Ser Asn Trp Leu Trp
        595                 600

<210> SEQ ID NO 81
<211> LENGTH: 665
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Arg Val Arg Gly Ile Pro Arg Asn Trp Pro Gln Trp Trp Ile Trp
1               5                   10                  15

Gly Leu Leu Gly Phe Trp Val Ile Ile Thr Cys Arg Val Val Gly Gln
            20                  25                  30

Leu Trp Val Thr Val Tyr Tyr Gly Val Pro Val Trp Thr Glu Ala Lys

```
            35                  40                  45
Thr Thr Leu Phe Cys Ala Ser Asp Ala Lys Ala Tyr Asp Lys Glu Val
 50                  55                  60

His Asn Val Trp Ala Thr His Ala Cys Val Pro Thr Asp Pro Asn Pro
 65                  70                  75                  80

Gln Glu Ile Val Leu Glu Asn Ile Thr Glu Asn Phe Asn Met Trp Lys
                     85                  90                  95

Asn Asp Met Val Asp Gln Met His Glu Asp Ile Ile Ser Leu Trp Asp
                100                 105                 110

Gln Ser Leu Lys Pro Cys Val Lys Leu Thr Pro Leu Cys Val Thr Leu
                115                 120                 125

Asn Cys Thr Asn Ala Asn Ile Asn Val Thr Ser Val Ser Asn Asp Ser
                130                 135                 140

Arg Ile Met Asn Glu Ile Lys Asn Cys Ser Phe Asn Thr Thr Thr
145                 150                 155                 160

Glu Ile Arg Asp Lys Lys Gln Arg Val Tyr Ala Leu Phe Tyr Arg Ser
                165                 170                 175

Asp Val Val Pro Leu Asn Ser Ser Glu Tyr Ile Leu Ile Asn Cys Asn
                180                 185                 190

Thr Ser Thr Ile Thr Gln Ala Cys Pro Lys Val Thr Phe Asp Pro Ile
                195                 200                 205

Pro Leu His Tyr Cys Ala Pro Ala Gly Tyr Ala Ile Leu Lys Cys Asn
210                 215                 220

Asn Lys Thr Phe Asn Gly Ala Gly Pro Cys Leu Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Ile Ile Ile Lys Ser Lys Asn Leu
                260                 265                 270

Thr Asp Asp Thr Asn Thr Ile Ile Val His Leu Asn Lys Ser Ile Glu
                275                 280                 285

Ile Val Cys Thr Arg Pro Gly Asn Asn Thr Arg Lys Ser Ile Arg Ile
290                 295                 300

Gly Pro Gly Gln Thr Phe Phe Ala Thr Gly Asp Ile Ile Gly Asp Ile
305                 310                 315                 320

Arg Glu Ala His Cys Asn Leu Ser Lys Asp Ala Trp Asn Lys Thr Leu
                325                 330                 335

Glu Gln Ile Lys Gly Lys Leu Lys Glu His Phe Ser Gly Lys Glu Ile
                340                 345                 350

Lys Phe Ala Pro Ser Ser Gly Gly Asp Pro Glu Val Ala Thr His Ser
                355                 360                 365

Phe Asn Cys Arg Gly Glu Phe Phe Tyr Cys Asn Thr Thr Lys Leu Phe
                370                 375                 380

Asn Glu Thr Tyr Thr Arg Ser Asn Asn Ser Asn Glu Thr Ile Ile Leu
385                 390                 395                 400

Pro Cys Arg Ile Lys Gln Ile Ile Asn Met Trp Gln Glu Val Gly Arg
                405                 410                 415

Ala Met Tyr Ala Pro Pro Ile Ala Gly Asn Ile Thr Cys Asn Ser Ser
                420                 425                 430

Ile Thr Gly Leu Leu Leu Thr Arg Asp Pro Gly His Asn Asn Thr Glu
                435                 440                 445

Thr Phe Arg Pro Thr Gly Gly Asn Met Lys Asp Asn Trp Arg Asn Glu
450                 455                 460
```

-continued

```
Leu Tyr Lys Tyr Lys Val Val Glu Ile Lys Pro Leu Gly Val Ala Pro
465                 470                 475                 480

Thr Asn Ala Lys Glu Arg Val Val Glu Arg Glu Lys Glu Ala Val Gly
                485                 490                 495

Ile Gly Ala Val Leu Leu Gly Phe Leu Gly Ala Ala Gly Ser Thr Met
            500                 505                 510

Gly Ala Ala Ser Ile Thr Leu Thr Val Gln Ala Arg Gln Leu Leu Ser
            515                 520                 525

Gly Ile Val Gln Gln Gln Ser Asn Leu Leu Arg Ala Ile Glu Ala Gln
        530                 535                 540

Gln His Met Leu Gln Leu Thr Val Trp Gly Ile Lys Gln Leu Gln Thr
545                 550                 555                 560

Arg Val Leu Ala Ile Glu Arg Tyr Leu Lys Asp Gln Gln Leu Leu Gly
                565                 570                 575

Leu Trp Gly Cys Ser Gly Arg Leu Ile Cys Thr Thr Asn Val Pro Trp
            580                 585                 590

Asn Ser Ser Trp Ser Asn Lys Ser Gln Glu Asp Ile Trp Gly Asn Met
            595                 600                 605

Thr Trp Met Gln Trp Asp Arg Glu Ile Ser Asn Tyr Thr Ser Thr Ile
        610                 615                 620

Tyr Arg Leu Leu Glu Asp Ser Gln Asn Gln Gln Glu Lys Asn Glu Lys
625                 630                 635                 640

Asp Leu Leu Ala Leu Asp Ser Trp Lys Asn Leu Trp Asn Trp Phe Asp
                645                 650                 655

Ile Thr Lys Trp Leu Trp Tyr Ile Arg
            660                 665

<210> SEQ ID NO 82
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Arg Val Arg Gly Ile Leu Arg Asn Cys Gln Gln Trp Trp Ile Trp
1               5                   10                  15

Gly Ile Leu Gly Phe Trp Met Leu Met Ile Cys Asn Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Thr Asn Ala Thr Asn Thr Met Gly Glu Ile Lys
    130                 135                 140

Asn Cys Ser Phe Asn Ile Thr Thr Glu Leu Arg Asp Lys Lys Gln Lys
```

-continued

```
            145                 150                 155                 160
Val Tyr Ala Leu Phe Tyr Arg Leu Asp Ile Val Pro Leu Asn Glu Asn
                    165                 170                 175

Asn Ser Tyr Arg Leu Ile Asn Cys Asn Thr Ser Ala Ile Thr Gln Ala
            180                 185                 190

Cys Pro Lys Val Ser Phe Asp Pro Ile Pro Ile His Tyr Cys Ala Pro
        195                 200                 205

Ala Gly Tyr Ala Ile Leu Lys Cys Asn Asn Lys Thr Phe Asn Gly Thr
    210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Glu
                245                 250                 255

Glu Ile Ile Ile Arg Ser Glu Asn Leu Thr Asn Asn Ala Lys Thr Ile
            260                 265                 270

Ile Val His Leu Asn Glu Ser Val Glu Ile Val Cys Thr Arg Pro Asn
        275                 280                 285

Asn Asn Thr Arg Lys Ser Ile Arg Ile Gly Pro Gly Gln Thr Phe Tyr
    290                 295                 300

Ala Thr Gly Asp Ile Ile Gly Asp Ile Arg Gln Ala His Cys Asn Ile
305                 310                 315                 320

Ser Glu Asp Lys Trp Asn Lys Thr Leu Gln Lys Val Ser Lys Lys Leu
                325                 330                 335

Lys Glu His Phe Pro Asn Lys Thr Ile Lys Phe Glu Pro Ser Ser Gly
            340                 345                 350

Gly Asp Leu Glu Ile Thr Thr His Ser Phe Asn Cys Arg Gly Glu Phe
        355                 360                 365

Phe Tyr Cys Asn Thr Ser Lys Leu Phe Asn Ser Thr Tyr Asn Ser Thr
    370                 375                 380

Asn Ser Thr Ile Thr Leu Pro Cys Arg Ile Lys Gln Ile Ile Asn Met
385                 390                 395                 400

Trp Gln Glu Val Gly Arg Ala Met Tyr Ala Pro Pro Ile Ala Gly Asn
                405                 410                 415

Ile Thr Cys Lys Ser Asn Ile Thr Gly Leu Leu Leu Thr Arg Asp Gly
            420                 425                 430

Gly Lys Asn Asn Thr Glu Thr Phe Arg Pro Gly Gly Gly Asp Met Arg
        435                 440                 445

Asp Asn Trp Arg Ser Glu Leu Tyr Lys Tyr Lys Val Val Glu Ile Lys
    450                 455                 460

Pro Leu Gly Ile Ala Pro Thr Lys Ala Lys Thr Leu Thr Val Gln Ala
465                 470                 475                 480

Arg Gln Leu Leu Ser Gly Ile Val Gln Gln Ser Asn Leu Leu Arg
                485                 490                 495

Ala Ile Glu Ala Gln Gln His Met Leu Gln Leu Thr Val Trp Gly Ile
            500                 505                 510

Lys Gln Leu Gln Thr Arg Val Leu Ala Ile Glu Arg Tyr Leu Lys Asp
        515                 520                 525

Gln Gln Leu Leu Gly Ile Trp Gly Cys Ser Gly Lys Leu Ile Cys Thr
    530                 535                 540

Thr Ala Val Pro Trp Asn Ser Ser Trp Ser Asn Lys Ser Gln Glu Asp
545                 550                 555                 560

Ile Trp Asp Asn Met Thr Trp Met Gln Trp Asp Arg Glu Ile Ser Asn
                565                 570                 575
```

Tyr Thr Asp Thr Ile Tyr Arg Leu Leu Glu Asp Ser Gln Asn Gln Gln
            580                 585                 590

Glu Lys Asn Glu Lys Asp Leu Leu Ala Leu Asp Ser Trp Lys Asn Leu
        595                 600                 605

Trp Asn Trp Phe Asp Ile Thr Asn Trp Leu Trp
610                 615

<210> SEQ ID NO 83
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Arg Val Lys Gly Ile Gln Arg Asn Trp Pro Gln Trp Trp Ile Trp
1               5                   10                  15

Gly Ile Leu Gly Phe Trp Met Ile Ile Cys Arg Val Val Gly Asn
            20                  25                  30

Leu Trp Val Thr Val Tyr Tyr Gly Val Pro Val Trp Thr Glu Ala Lys
        35                  40                  45

Thr Thr Leu Phe Cys Ala Ser Asp Ala Lys Ala Tyr Glu Arg Glu Val
    50                  55                  60

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

Asn Asp Met Val Asp Gln Met His Glu Asp Ile Ile Ser Ile Trp Asp
            100                 105                 110

Gln Ser Leu Lys Pro Cys Val Lys Leu Thr Pro Leu Cys Val Thr Leu
        115                 120                 125

Asn Cys Thr Asp Val Lys Val Asn Ala Thr Ser Asn Gly Thr Thr Thr
    130                 135                 140

Tyr Asn Asn Ser Ile Asp Ser Met Asn Gly Glu Ile Lys Asn Cys Ser
145                 150                 155                 160

Phe Asn Ile Thr Thr Glu Ile Arg Asp Lys Lys Gln Lys Val Tyr Ala
                165                 170                 175

Leu Phe Tyr Arg Pro Asp Val Val Pro Leu Asn Glu Asn Ser Ser Ser
            180                 185                 190

Tyr Ile Leu Ile Asn Cys Asn Thr Ser Thr Thr Thr Gln Ala Cys Pro
        195                 200                 205

Lys Val Ser Phe Asp Pro Ile Pro Ile His Tyr Cys Ala Pro Ala Gly
    210                 215                 220

Tyr Ala Ile Leu Lys Cys Asn Asn Lys Thr Phe Asn Gly Thr Gly Pro
225                 230                 235                 240

Cys His Asn Val Ser Thr Val Gln Cys Thr His Gly Ile Lys Pro Val
                245                 250                 255

Val Ser Thr Gln Leu Leu Leu Asn Gly Ser Leu Ala Glu Glu Glu Ile
            260                 265                 270

Ile Ile Arg Ser Glu Asn Leu Thr Asn Asn Ala Lys Thr Ile Ile Val
        275                 280                 285

His Leu Asn Glu Ser Ile Glu Ile Val Cys Thr Arg Pro Asn Asn Asn
    290                 295                 300

Thr Arg Lys Ser Ile Arg Ile Gly Pro Gly Gln Thr Val Tyr Ala Thr

```
            305                 310                 315                 320
Asn Asp Ile Ile Gly Asp Ile Arg Gln Ala His Cys Asn Ile Ser Lys
                325                 330                 335

Thr Lys Trp Asn Thr Thr Leu Glu Lys Val Lys Glu Lys Leu Lys Glu
                340                 345                 350

His Phe Pro Ser Lys Ala Ile Thr Phe Gln Pro His Ser Gly Gly Asp
                355                 360                 365

Leu Glu Val Thr Thr His Ser Phe Asn Cys Arg Gly Glu Phe Phe Tyr
            370                 375                 380

Cys Asp Thr Thr Lys Leu Phe Asn Glu Ser Asn Leu Asn Thr Thr Asn
385                 390                 395                 400

Thr Thr Thr Leu Thr Leu Pro Cys Arg Ile Lys Gln Ile Val Asn Met
                405                 410                 415

Trp Gln Gly Val Gly Arg Ala Met Tyr Ala Pro Pro Val Glu Gly Asn
                420                 425                 430

Ile Thr Cys Asn Ser Ser Ile Thr Gly Leu Leu Leu Val Arg Asp Gly
                435                 440                 445

Gly Asn Thr Ser Asn Ser Thr Pro Glu Ile Phe Arg Pro Gly Gly Gly
            450                 455                 460

Asn Met Lys Asp Asn Trp Arg Ser Glu Leu Tyr Lys Tyr Lys Val Val
465                 470                 475                 480

Glu Ile Lys Pro Leu Gly Val Ala Pro Thr Lys Ala Lys Thr Leu Thr
                485                 490                 495

Val Gln Ala Arg Gln Leu Leu Ser Gly Ile Val Gln Gln Gln Ser Asn
                500                 505                 510

Leu Leu Arg Ala Ile Glu Ala Gln Gln His Met Leu Gln Leu Thr Val
                515                 520                 525

Trp Gly Ile Lys Gln Leu Gln Ala Arg Val Leu Ala Ile Glu Arg Tyr
            530                 535                 540

Leu Lys Asp Gln Gln Leu Leu Gly Leu Trp Gly Cys Ser Gly Lys Leu
545                 550                 555                 560

Ile Cys Pro Thr Thr Val Pro Trp Asn Ser Ser Trp Ser Asn Lys Ser
                565                 570                 575

Gln Thr Asp Ile Trp Asp Asn Met Thr Trp Met Gln Trp Asp Arg Glu
                580                 585                 590

Ile Ser Asn Tyr Thr Gly Thr Ile Tyr Lys Leu Leu Glu Glu Ser Gln
            595                 600                 605

Asn Gln Gln Glu Lys Asn Glu Lys Asp Leu Leu Ala Leu Asp Ser Trp
610                 615                 620

Lys Asn Leu Trp Ser Trp Phe Asp Ile Thr Asn Trp Leu Trp
625                 630                 635

<210> SEQ ID NO 84
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Arg Val Met Gly Ile Gln Arg Asn Cys Gln His Leu Trp Arg Trp
1               5                   10                  15

Gly Thr Met Ile Leu Gly Met Leu Met Ile Cys Ser Ala Ala Glu Asn
                20                  25                  30
```

```
Leu Trp Val Thr Val Tyr Tyr Gly Val Pro Val Trp Lys Glu Ala Asn
            35                  40                  45

Thr Thr Leu Phe Cys Ala Ser Asp Ala Lys Ala Tyr Asp Thr Glu Val
 50                  55                  60

His Asn Val Trp Ala Thr His Ala Cys Val Pro Thr Asp Pro Asn Pro
 65                  70                  75                  80

Gln Glu Ile Val Leu Glu Asn Val Thr Glu Asn Phe Asn Met Trp Lys
                 85                  90                  95

Asn Asn Met Val Glu Gln Met His Glu Asp Ile Ile Ser Leu Trp Asp
             100                 105                 110

Gln Ser Leu Lys Pro Cys Val Lys Leu Thr Pro Leu Cys Val Thr Leu
         115                 120                 125

Asn Cys Thr Asn Val Arg Asn Val Ser Ser Asn Gly Thr Glu Thr Asp
130                 135                 140

Asn Glu Glu Ile Lys Asn Cys Ser Phe Asn Ile Thr Thr Glu Leu Arg
145                 150                 155                 160

Asp Lys Lys Gln Lys Val Tyr Ala Leu Phe Tyr Arg Leu Asp Val Val
                165                 170                 175

Pro Ile Asp Asp Lys Asn Ser Ser Glu Ile Ser Gly Lys Asn Ser Ser
             180                 185                 190

Glu Tyr Tyr Arg Leu Ile Asn Cys Asn Thr Ser Ala Ile Thr Gln Ala
         195                 200                 205

Cys Pro Lys Val Ser Phe Glu Pro Ile Pro Ile His Tyr Cys Ala Pro
210                 215                 220

Ala Gly Phe Ala Ile Leu Lys Cys Asn Asp Lys Lys Phe Asn Gly Thr
225                 230                 235                 240

Gly Pro Cys Lys Asn Val Ser Thr Val Gln Cys Thr His Gly Ile Lys
                245                 250                 255

Pro Val Val Ser Thr Gln Leu Leu Leu Asn Gly Ser Leu Ala Glu Glu
             260                 265                 270

Glu Ile Ile Ile Arg Ser Glu Asn Ile Thr Asn Asn Ala Lys Thr Ile
         275                 280                 285

Ile Val Gln Leu Asn Glu Ser Val Glu Ile Asn Cys Thr Arg Pro Asn
290                 295                 300

Asn Asn Thr Arg Lys Ser Ile His Ile Gly Pro Gly Gln Ala Phe Tyr
305                 310                 315                 320

Ala Thr Gly Glu Ile Ile Gly Asp Ile Arg Gln Ala His Cys Asn Ile
                325                 330                 335

Ser Arg Thr Lys Trp Asn Lys Thr Leu Gln Gln Val Ala Lys Lys Leu
             340                 345                 350

Arg Glu His Phe Asn Asn Lys Thr Ile Ile Phe Lys Pro Ser Ser Gly
         355                 360                 365

Gly Asp Leu Glu Ile Thr Thr His Ser Phe Asn Cys Gly Gly Glu Phe
370                 375                 380

Phe Tyr Cys Asn Thr Ser Gly Leu Phe Asn Ser Thr Trp Met Phe Asn
385                 390                 395                 400

Gly Thr Tyr Met Phe Asn Gly Thr Lys Asp Asn Ser Glu Thr Ile Thr
                405                 410                 415

Leu Pro Cys Arg Ile Lys Gln Ile Ile Asn Met Trp Gln Gly Val Gly
             420                 425                 430

Gln Ala Met Tyr Ala Pro Pro Ile Glu Gly Lys Ile Thr Cys Lys Ser
         435                 440                 445

Asn Ile Thr Gly Leu Leu Leu Thr Arg Asp Gly Gly Asn Asn Ser Asn
```

```
                450                 455                 460
Lys Asn Lys Thr Glu Thr Phe Arg Pro Gly Gly Gly Asp Met Arg Asp
465                 470                 475                 480

Asn Trp Arg Ser Glu Leu Tyr Lys Tyr Lys Val Val Lys Ile Glu Pro
                485                 490                 495

Leu Gly Val Ala Pro Thr Lys Ala Lys Arg Arg Val Val Glu Arg Glu
            500                 505                 510

Lys Arg

<210> SEQ ID NO 85
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Thr Val Tyr Tyr Gly Val Pro Val Trp Lys Glu Ala Asn
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Val Asn Val Thr Asn Thr Thr Asn Asn Thr Glu Glu
    130                 135                 140

Lys Gly Glu Ile Lys Asn Cys Ser Phe Asn Ile Thr Thr Glu Ile Arg
145                 150                 155                 160

Asp Lys Lys Gln Lys Val Tyr Ala Leu Phe Tyr Arg Leu Asp Val Val
                165                 170                 175

Pro Ile Asp Asp Asn Asn Asn Ser Ser Asn Tyr Arg Leu Ile Asn
            180                 185                 190

Cys Asn Thr Ser Ala Ile Thr Gln Ala Cys Pro Lys Val Ser Phe Glu
        195                 200                 205

Pro Ile Pro Ile His Tyr Cys Ala Pro Ala Gly Phe Ala Ile Leu Lys
    210                 215                 220

Cys Asn Asp Lys Lys Phe Asn Gly Thr Gly Pro Cys Lys Asn Val Ser
225                 230                 235                 240

Thr Val Gln Cys Thr His Gly Ile Lys Pro Val Val Ser Thr Gln Leu
                245                 250                 255

Leu Leu Asn Gly Ser Leu Ala Glu Glu Ile Ile Arg Ser Glu
            260                 265                 270

Asn Ile Thr Asn Asn Ala Lys Thr Ile Ile Val Gln Leu Asn Glu Ser
        275                 280                 285

Val Glu Ile Asn Cys Thr Arg Pro Asn Asn Asn Thr Arg Lys Ser Ile
```

-continued

```
                290                 295                 300
Arg Ile Gly Pro Gly Gln Ala Phe Tyr Ala Thr Gly Asp Ile Ile Gly
305                 310                 315                 320

Asp Ile Arg Gln Ala His Cys Asn Ile Ser Gly Thr Lys Trp Asn Lys
                325                 330                 335

Thr Leu Gln Gln Val Ala Lys Lys Leu Arg Glu His Phe Asn Asn Lys
                340                 345                 350

Thr Ile Ile Phe Lys Pro Ser Ser Gly Gly Asp Leu Glu Ile Thr Thr
                355                 360                 365

His Ser Phe Asn Cys Arg Gly Glu Phe Phe Tyr Cys Asn Thr Ser Gly
                370                 375                 380

Leu Phe Asn Ser Thr Trp Ile Gly Asn Gly Thr Lys Asn Asn Asn Asn
385                 390                 395                 400

Thr Asn Asp Thr Ile Thr Leu Pro Cys Arg Ile Lys Gln Ile Ile Asn
                405                 410                 415

Met Trp Gln Gly Val Gly Gln Ala Met Tyr Ala Pro Pro Ile Glu Gly
                420                 425                 430

Lys Ile Thr Cys Lys Ser Asn Ile Thr Gly Leu Leu Leu Thr Arg Asp
                435                 440                 445

Gly Gly Asn Asn Thr Asn Glu Thr Glu Ile Phe Arg Pro Gly Gly
                450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Lys Ala Lys Leu Thr
                485                 490                 495

Val Gln Ala Arg Gln Leu Leu Ser Gly Ile Val Gln Gln Gln Ser Asn
                500                 505                 510

Leu Leu Arg Ala Ile Glu Ala Gln Gln His Leu Leu Gln Leu Thr Val
                515                 520                 525

Trp Gly Ile Lys Gln Leu Gln Ala Arg Val Leu Ala Val Glu Arg Tyr
                530                 535                 540

Leu Lys Asp Gln Gln Leu Glu Ile Trp Asp Asn Met Thr Trp Met Glu
545                 550                 555                 560

Trp Glu Arg Glu Ile Asn Asn Tyr Thr Asp Ile Ile Tyr Ser Leu Ile
                565                 570                 575

Glu Glu Ser Gln Asn Gln Gln Glu Lys Asn Glu Gln Glu Leu Leu Ala
                580                 585                 590

Leu Asp Lys Trp Ala Ser Leu Trp Asn Trp Phe Asp Ile Thr Asn Trp
                595                 600                 605

Leu Trp
    610

<210> SEQ ID NO 86
<211> LENGTH: 626
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Arg Val Lys Gly Ile Gln Arg Asn Trp Gln His Leu Trp Lys Trp
1               5                   10                  15

Gly Thr Leu Ile Leu Gly Leu Val Ile Ile Cys Ser Ala Ser Asn Asn
                20                  25                  30
```

```
Leu Trp Val Thr Val Tyr Tyr Gly Val Pro Val Trp Glu Asp Ala Asp
             35                  40                  45

Thr Thr Leu Phe Cys Ala Ser Asp Ala Lys Ala Tyr Ser Thr Glu Arg
 50                  55                  60

His Asn Val Trp Ala Thr His Ala Cys Val Pro Thr Asp Pro Asn Pro
 65                  70                  75                  80

Gln Glu Ile Thr Leu Glu Asn Val Thr Glu Asn Phe Asn Met Trp Lys
                 85                  90                  95

Asn Asn Met Val Glu Gln Met His Glu Asp Ile Ile Ser Leu Trp Asp
            100                 105                 110

Glu Ser Leu Lys Pro Cys Val Lys Leu Thr Pro Leu Cys Val Thr Leu
        115                 120                 125

Asn Cys Thr Asp Val Asn Val Thr Asn Asn Thr Asn Asn Thr Lys
130                 135                 140

Lys Glu Ile Lys Asn Cys Ser Phe Asn Ile Thr Glu Ile Arg Asp
145                 150                 155                 160

Lys Lys Lys Lys Glu Tyr Ala Leu Phe Tyr Arg Leu Asp Val Val Pro
                165                 170                 175

Ile Asn Asp Asn Gly Asn Ser Ser Ile Tyr Arg Leu Ile Asn Cys Asn
            180                 185                 190

Val Ser Thr Ile Lys Gln Ala Cys Pro Lys Val Thr Phe Asp Pro Ile
        195                 200                 205

Pro Ile His Tyr Cys Ala Pro Ala Gly Phe Ala Ile Leu Lys Cys Arg
    210                 215                 220

Asp Lys Lys Phe Asn Gly Thr Gly Pro Cys Lys Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Ile Ile Ile Arg Ser Glu Asn Ile
            260                 265                 270

Thr Asp Asn Thr Lys Val Ile Ile Val Gln Leu Asn Glu Thr Ile Glu
        275                 280                 285

Ile Asn Cys Thr Arg Pro Asn Asn Asn Thr Arg Lys Ser Ile Arg Ile
    290                 295                 300

Gly Pro Gly Gln Ala Phe Tyr Ala Thr Gly Asp Ile Ile Gly Asp Ile
305                 310                 315                 320

Arg Gln Ala His Cys Asn Val Ser Arg Thr Lys Trp Asn Glu Met Leu
                325                 330                 335

Gln Lys Val Lys Ala Gln Leu Lys Lys Ile Phe Asn Lys Ser Ile Thr
            340                 345                 350

Phe Asn Ser Ser Ser Gly Gly Asp Leu Glu Ile Thr Thr His Ser Phe
        355                 360                 365

Asn Cys Arg Gly Glu Phe Phe Tyr Cys Asn Thr Ser Gly Leu Phe Asn
    370                 375                 380

Asn Ser Leu Leu Asn Ser Thr Asn Ser Thr Ile Thr Leu Pro Cys Lys
385                 390                 395                 400

Ile Lys Gln Ile Val Arg Met Trp Gln Arg Val Gly Gln Ala Met Tyr
                405                 410                 415

Ala Pro Pro Ile Ala Gly Asn Ile Thr Cys Arg Ser Asn Ile Thr Gly
            420                 425                 430

Leu Leu Leu Thr Arg Asp Gly Gly Asn Asn Thr Glu Thr Phe Arg
        435                 440                 445

Pro Gly Gly Gly Asp Met Arg Asp Asn Trp Arg Ser Glu Leu Tyr Lys
```

450                 455                 460
Tyr Lys Ile Val Lys Ile Lys Pro Leu Gly Val Ala Pro Thr Arg Ala
465                 470                 475                 480

Arg Thr Leu Thr Val Gln Val Arg Gln Leu Leu Ser Gly Ile Val Gln
                    485                 490                 495

Gln Gln Ser Asn Leu Leu Arg Ala Ile Glu Ala Gln Gln His Leu Leu
                500                 505                 510

Gln Leu Thr Val Trp Gly Ile Lys Gln Leu Gln Ala Arg Val Leu Ala
                515                 520                 525

Val Glu Arg Tyr Leu Lys Asp Gln Gln Leu Leu Gly Ile Trp Gly Cys
                530                 535                 540

Ser Gly Lys Leu Ile Cys Thr Thr Asn Val Pro Trp Asn Thr Ser Trp
545                 550                 555                 560

Ser Asn Lys Ser Tyr Asn Glu Ile Trp Asp Asn Met Thr Trp Ile Glu
                565                 570                 575

Trp Glu Arg Glu Ile Ser Asn Tyr Thr Gln Gln Ile Tyr Ser Leu Ile
                580                 585                 590

Glu Glu Ser Gln Asn Gln Gln Glu Lys Asn Glu Gln Asp Leu Leu Ala
                595                 600                 605

Leu Asp Lys Trp Ala Ser Leu Trp Asn Trp Phe Asp Ile Thr Lys Trp
610                 615                 620

Leu Trp
625

<210> SEQ ID NO 87
<211> LENGTH: 630
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Arg Val Lys Gly Ile Gln Arg Asn Trp Gln His Leu Trp Asn Trp
1               5                   10                  15

Gly Ile Leu Ile Leu Gly Leu Val Ile Ile Cys Ser Ala Glu Lys Leu
                20                  25                  30

Trp Val Thr Val Tyr Tyr Gly Val Pro Val Trp Glu Asp Ala Asn Ala
                35                  40                  45

Pro Leu Phe Cys Ala Ser Asp Ala Lys Ala His Ser Thr Glu Ser His
            50                  55                  60

Asn Ile Trp Ala Thr His Ala Cys Val Pro Thr Asp Pro Ser Pro Gln
65                  70                  75                  80

Glu Ile Asn Met Arg Asn Val Thr Glu Asn Phe Asn Met Trp Lys Asn
                85                  90                  95

Asn Met Val Glu Gln Met His Glu Asp Ile Ile Ser Leu Trp Asp Glu
                100                 105                 110

Ser Leu Lys Pro Cys Val Lys Leu Thr Pro Leu Cys Val Thr Leu Asn
                115                 120                 125

Cys Thr Glu Ile Asn Asn Asn Ser Thr Arg Asn Ile Thr Glu Glu Tyr
            130                 135                 140

Arg Met Thr Asn Cys Ser Phe Asn Met Thr Thr Glu Leu Arg Asp Lys
145                 150                 155                 160

Lys Lys Ala Glu Tyr Ala Leu Phe Tyr Arg Thr Asp Val Val Pro Ile
                165                 170                 175

-continued

Asn Glu Met Asn Asn Glu Asn Gly Thr Asn Ser Thr Trp Tyr Arg
            180                 185                 190

Leu Thr Asn Cys Asn Val Ser Thr Ile Lys Gln Ala Cys Pro Lys Val
        195                 200                 205

Thr Phe Glu Pro Ile Pro Ile His Tyr Cys Ala Pro Ala Gly Phe Ala
    210                 215                 220

Ile Leu Lys Cys Val Asp Lys Lys Phe Asn Gly Thr Gly Thr Cys Asn
225                 230                 235                 240

Asn Val Ser Thr Val Gln Cys Thr His Gly Ile Lys Pro Val Val Ser
            245                 250                 255

Thr Gln Leu Leu Leu Asn Gly Ser Leu Ala Glu Lys Asp Ile Ile Ile
        260                 265                 270

Ser Ser Glu Asn Ile Ser Asp Asn Ala Lys Val Ile Ile Val His Leu
    275                 280                 285

Asn Arg Ser Val Glu Ile Asn Cys Thr Arg Pro Asn Asn Asn Thr Arg
        290                 295                 300

Arg Ser Val Ala Ile Gly Pro Gly Gln Ala Phe Tyr Thr Thr Gly Glu
305                 310                 315                 320

Val Ile Gly Asp Ile Arg Lys Ala His Cys Asn Val Ser Trp Thr Lys
            325                 330                 335

Trp Asn Glu Thr Leu Arg Asp Val Gln Ala Lys Leu Gln Glu Tyr Phe
        340                 345                 350

Ile Asn Lys Ser Ile Glu Phe Asn Ser Ser Gly Gly Asp Leu Glu
    355                 360                 365

Ile Thr Thr His Ser Phe Asn Cys Gly Gly Glu Phe Phe Tyr Cys Asn
    370                 375                 380

Thr Ser Gly Leu Phe Asn Asn Ser Ile Leu Lys Ser Asn Ile Ser Glu
385                 390                 395                 400

Asn Asn Asp Thr Ile Thr Leu Asn Cys Lys Ile Lys Gln Ile Val Arg
            405                 410                 415

Met Trp Gln Arg Val Gly Gln Ala Met Tyr Ala Pro Pro Ile Ala Gly
        420                 425                 430

Asn Ile Thr Cys Arg Ser Asn Ile Thr Gly Leu Ile Leu Thr Arg Asp
    435                 440                 445

Gly Gly Asp Asn Asn Ser Thr Ser Glu Ile Phe Arg Pro Gly Gly Gly
450                 455                 460

Asp Met Lys Asn Asn Trp Arg Ser Glu Leu Tyr Lys Tyr Lys Thr Val
465                 470                 475                 480

Lys Ile Lys Ser Leu Gly Ile Ala Pro Thr Arg Ala Arg Thr Leu Thr
            485                 490                 495

Val Gln Val Arg Gln Leu Leu Ser Gly Ile Val Gln Gln Ser Asn
        500                 505                 510

Leu Leu Arg Ala Ile Glu Ala Gln Gln His Leu Leu Gln Leu Thr Val
    515                 520                 525

Trp Gly Ile Lys Gln Leu Arg Ala Arg Val Leu Ala Leu Glu Arg Tyr
    530                 535                 540

Leu Lys Asp Gln Gln Leu Leu Gly Ile Trp Gly Cys Ser Gly Lys Leu
545                 550                 555                 560

Ile Cys Thr Thr Asn Val Pro Trp Asn Thr Ser Trp Ser Asn Lys Ser
            565                 570                 575

Tyr Asn Glu Ile Trp Glu Asn Met Thr Trp Ile Glu Trp Glu Arg Glu
        580                 585                 590

Ile Asp Asn Tyr Thr Tyr His Ile Tyr Ser Leu Ile Glu Gln Ser Gln

```
                595                 600                 605
Ile Gln Gln Glu Lys Asn Glu Gln Asp Leu Leu Ala Leu Asp Gln Trp
            610                 615                 620

Ala Ser Leu Trp Ser Trp
625             630

<210> SEQ ID NO 88
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Lys Val Met Glu Lys Lys Arg Leu Trp Leu Ser Tyr Cys Leu
1               5                   10                  15

Leu Ser Ser Leu Ile Ile Pro Gly Leu Ser Ser Leu Trp Ala Thr Val
                20                  25                  30

Tyr Tyr Gly Val Pro Val Trp Arg Asp Val Glu Thr Thr Leu Phe Cys
            35                  40                  45

Ala Ser Asp Ala Lys Ala Tyr Lys Gln Glu Ala His Asn Ile Trp Ala
50                  55                  60

Thr Gln Ala Cys Val Pro Thr Asp Pro Asn Pro Gln Glu Val His Leu
65                  70                  75                  80

Pro Asn Val Thr Glu Lys Phe Asp Met Trp Glu Asn Asn Met Ala Glu
                85                  90                  95

Gln Met Gln Glu Asp Ile Ile Ser Leu Trp Asp Gln Ser Leu Lys Pro
            100                 105                 110

Cys Ile Lys Leu Thr Pro Leu Cys Val Thr Met Thr Cys Leu Asn Pro
        115                 120                 125

Asp Ser Asn Ser Ser Ala Val Asn Thr Thr Asp Ile Met Arg Asn Cys
130                 135                 140

Ser Phe Asn Ile Thr Thr Glu Leu Arg Asp Lys Lys Lys Gln Val Tyr
145                 150                 155                 160

Ser Leu Phe Tyr Val Asp Asp Leu Ala His Ile Asn Asn Asn Thr Tyr
                165                 170                 175

Arg Leu Ile Asn Cys Asn Thr Thr Ala Ile Thr Gln Ala Cys Pro Lys
            180                 185                 190

Thr Ser Phe Glu Pro Ile Pro Ile His Tyr Cys Ala Pro Pro Gly Phe
        195                 200                 205

Ala Ile Leu Lys Cys Asn Glu Lys Asp Phe Lys Gly Lys Gly Glu Cys
210                 215                 220

Lys Asn Val Ser Thr Val Gln Cys Thr His Gly Ile Lys Pro Val Val
225                 230                 235                 240

Thr Thr Gln Leu Ile Ile Asn Gly Ser Leu Ala Thr Lys Asn Val Thr
                245                 250                 255

Val Arg Ser Lys Asn Phe Ala Asp Ile Ile Leu Val Gln Phe Ser Glu
            260                 265                 270

Gly Val Asn Met Thr Cys Ile Arg Pro Gly Asn Asn Thr Val Gly Asn
        275                 280                 285

Val Gln Leu Gly Pro Gly Met Thr Phe Tyr Asn Ile Pro Lys Ile Val
290                 295                 300

Gly Asp Val Arg Glu Ala His Cys Asn Ile Ser Lys Leu Thr Trp Glu
305                 310                 315                 320
```

-continued

```
Lys Gln Arg Lys Tyr Thr Leu Glu Ile Ile Lys Lys Glu Ala Asn Leu
                325                 330                 335
Thr Lys Val Glu Leu Ile Pro Asn Ala Gly Gly Asp Pro Glu Val Val
            340                 345                 350
Asn Met Met Leu Asn Cys Gly Gly Glu Phe Phe Tyr Cys Asn Thr Ile
        355                 360                 365
Pro Leu Phe Asn Met Thr Tyr Asn Asn Thr Asp Asn Thr Thr Ile Thr
    370                 375                 380
Leu Lys Cys Arg Ile Arg Gln Ile Val Asn Gln Trp Met Arg Val Gly
385                 390                 395                 400
Lys Gly Ile Phe Ala Pro Pro Ile Lys Gly Val Leu Ser Cys Asn Ser
                405                 410                 415
Asn Ile Thr Gly Met Ile Leu Asp Ile Ser Ile Ser Ala Val Asn Asn
            420                 425                 430
Asp Ser Arg Asn Ile Thr Val Met Pro Thr Gly Gly Asp Met Thr Ala
        435                 440                 445
Leu Trp Lys Asn Glu Leu His Lys Tyr Lys Val Ser Ile Glu Pro
    450                 455                 460
Ile Gly Val Ala Pro Gly Lys Ala Lys Val Leu Thr Val Gln Ala Arg
465                 470                 475                 480
Gln Leu Leu Ser Gly Ile Val Gln Gln Asn Asn Leu Leu Arg Ala
                485                 490                 495
Ile Glu Ala Gln Gln His Leu Leu Gln Leu Ser Val Trp Gly Ile Lys
            500                 505                 510
Gln Leu Gln Ala Arg Val Leu Ala Val Glu Arg Tyr Leu Lys Asp Gln
        515                 520                 525
Gln Ile Leu Gly Leu Trp Gly Cys Ser Gly Lys Thr Ile Cys Tyr Thr
    530                 535                 540
Thr Val Pro Trp Asn Asp Thr Trp Ser Asn Asn Leu Ser Tyr Asp Ala
545                 550                 555                 560
Ile Trp Gly Asn Leu Thr Trp Gln Glu Trp Asp Arg Lys Val Arg Asn
                565                 570                 575
Tyr Ser Gly Thr Ile Phe Ser Leu Ile Glu Gln Ala Gln Glu Gln Gln
            580                 585                 590
Asn Thr Asn Glu Lys Ser Leu Leu Glu Leu Asp Gln Trp Ser Ser Leu
        595                 600                 605
Trp Asn Trp Phe Asp Ile Thr Asn Trp Leu Trp
    610                 615
```

<210> SEQ ID NO 89
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
gaggtgcagc tggtgcagtc tggagcagag gtgaaaaagc cggggagtc tctgaagatc      60 tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca agtccatcag caccgcctac    240
ctgcagtgga gcagctgaa ggcctcggac accgccatgt attactgtgc gagacttggc    300
ggcaggtatt actatgatag tagtggttat tactactttg actactgggg ccagggaacc    360
```
ctggtcaccg tctcctca                                                378

<210> SEQ ID NO 90
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90
aattttatgc tgactcagcc ccactctgtg tcggagtctc cggggaagac ggtaaccatc      60
tcctgcaccc gcagcagtgg cagcattgcc agcaactatg tgcagtggta ccagcagcgc    120
ccgggcagtt cccccaccac tgtgatctat gaggataacc aaagaccctc tggggtccct    180
gatcggttct ctggctccat cgacagctcc tccaactctg cctccctcac catctctgga    240
ctgaagactg aggacgaggc tgactactac tgtcagtctt atgatagcag ctcttgggtg    300
ttcggcggag ggaccaagct gaccgtccta                                     330

<210> SEQ ID NO 91
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gaagtgcagc tggtggagtc tgggggaggc ttggtacagc ctggcaggtc cctgagactc      60
tcctgtgcag cctctggatt cacctttgat gattatgcca tgcactgggt ccggcaagct    120
ccagggaagg gcctggagtg ggtctcaggt attagttgga atagtggtag cataggctat    180
gcggactctg tgaagggccg attcaccatc tccagagaca cgccaagaa ctccctgtat     240 ctgcaaatga acagtctgag agctgaggac acggccttgt attactgtgc aaaagattct    300
ccgcgggggg agctacccct tgactactgg ggccagggaa ccctggtcac cgtctcctca    360

<210> SEQ ID NO 92
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
tcctatgagc tgacacagcc accctcggtg tcagtgtccc caggacaaac ggccaggatc      60
acctgctctg gagatgcatt gccaaaaaaa tatgcttatt ggtaccagca gaagtcaggc    120
caggcccctg tgctggtcat ctatgaggac agcaaacgac cctccgggat ccctgagaga    180
ttctctggct ccagctcagg gacaatggcc accttgacta tcagtggggc ccaggtggag    240
gatgaagctg actactactg ttactcaaca gacagcagtg gtaatcatag ggtgttcggc    300
ggagggacca agctgaccgt ccta                                           324

<210> SEQ ID NO 93
<211> LENGTH: 363
<212> TYPE: DNA
<213> ORGANISM: Artificial Sequence
<220> FEATURE:
<223> OTHER INFORMATION: Description of Artificial Sequence: Synthetic -continued polynucleotide

<400> SEQUENCE: 93

```
caggtccagc tggtgcaatc tggggctgag gtgaagaagc ctgggtcctc ggtgaaggtc      60
tcctgcaagg cttctggagg caccttcagc agctatacta tcagctgggt gcgacaggcc     120
cctggacaag ggcttgagtg gatgggaagg atcatcccta tccttggtat agcaaactac     180
gcacagaagt tccagggcag agtcacgatt accgcggaca atccacgag cacagcctac      240
atggagctga gcagcctgag atctgaggac acggccgtgt attactgtgc gacatctggg     300
gtgggactac acttcggcta ctttgactac tggggccagg gaaccctggt caccgtctcc     360
tca                                                                  363
```

<210> SEQ ID NO 94
<211> LENGTH: 333
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94

```
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatggtaaca gcaatcggcc ctcagggatc     180
cctgaccgat tctctggctc caagtctggc acctcagcct ccctggccat cactgggctc     240
caggctgagg atgaggctga ttattactgc cagtcctatg acagcagcct gagtggttat     300
gtcttcggaa ctgggaccaa ggtcaccgtc cta                                  333
```

<210> SEQ ID NO 95
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
gaggtgcagc tggtggagtc tgggggaggt gtggtacggc ctgggggtc cctgagactc       60
tcctgtgcag cctctggatt cacctttgat gattatggca tgagctgggt ccgccaagct     120
ccagggaagg ggctggagtg gtctctggt attaattgga atggtggtag cacaggttat      180
gcagactctg tgaagggccg attcaccatc tccagagaca acgccaagaa ctccctgtat     240
ctgcaaatga acagtctgag agccgaggac acggccttgt attactgtgc gagagggacc     300
gattacacta ttgacgacca ggggatccgt tatcaaggtt cggggaccttc tggtacttc     360
gatctctggg gccgtggcac cctggtcact gtctcctca                            399
```

<210> SEQ ID NO 96
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96

```
gaggtgcagc tggtggagtc tgggggaggt gtggtacggc ctgggggtc cctgagactc       60
```

```
tcctgtgcag cctctggatt cacctttgat gattatggca tgagctgggt ccgccaagct    120
ccagggaagg ggctggagtg ggtctctggt attaattgga atggtggtag cacaggttat    180
gcagactctg tgaagggccg attcaccatc tccagagaca cgccaagaa ctccctgtat     240 ctgcaaatga acagtctgag agccgaggac acggccttgt attactgtgc gagagggacc    300
gattacacta ttgacgacca ggggatcctt tatcaaggtt cggggacctt ctggtacttc    360
gatctctggg gccgtggcac cctggtcact gtctcctca                           399
```

<210> SEQ ID NO 97  
<211> LENGTH: 399  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 97

```
gaggtgcagc tggtggagtc tgggggaggt gtggtacggc ctgggggtc cctgagactc     60 tcctgtgcag cctctggatt cacctttgat gattatggca tgagctgggt ccgccaagct    120
ccagggaagg ggctggagtg ggtctctggt attaattgga atggtggtag cacaggttat    180
gcagactctg tgaagggccg attcaccatc tccagagaca cgccaagaa ctccctgtat     240 ctgcaaatga acagtctgag agccgaggac acggccttgt atcactgtgc gagagggacc    300
gattacacta ttgacgacca ggggatccat tactatggtt cggggaccta ctggtacttc    360
gatctctggg gccgtggcac cctggtcact gtctcctca                           399
```

<210> SEQ ID NO 98  
<211> LENGTH: 324  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 98

```
gaaattgtgt tgacgcagtc tccaggcacc ctgtctttgt ctccagggga aagagccacc    60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctccccgta cacgttcggc    300
caagggacca aggtggaaat caaa                                           324
```

<210> SEQ ID NO 99  
<211> LENGTH: 411  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 99

```
caggtgcagc tggtggagtc tgggggaggc gtggtccagc ctggggaggtc cctgagactc    60 tcctgtgcag cgtctggatt cacctttcagt agctatggca tgcactgggt ccgccaggct   120
ccaggcaagg ggctggagtg ggtggcagtt atatcatatg atggaagtaa taaatactat    180
gcagactccg tgaagggccg attcaccatc tccagagaca attccaagaa cacgctgtat    240
```

```
ctgcaaatga acagcctgag agccgaggac acggctgtgt attactgtgc gagagaggct    300
ggtgggcccg actaccgtaa tgggtacaac tattacgatt tttggagtgg ttattataac    360
tactactaca tggacgtctg gggcaaaggg accacggtca ccgtctcctc a             411
```

<210> SEQ ID NO 100
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
cagtctgccc tgactcagcc tgcctccgtg tctgggtctc ctggacagtc gatcaccatc     60
tcctgcactg gaaccagcag tgatgttggg agttataacc ttgtctcctg gtaccaacag    120
cacccaggca agcccccaa actcatgatt tatgaggtca gtaagcggcc ctcaggggtt     180
tctaatcgct tctctggctc caagtctggc aacacggcct ccctgacaat ctctgggctc    240
caggctgagg acgaggctga ttattactgc tgctctctga agcacgagac gttgggtg      300 ttcggcggag ggaccaagct gaccgtccta                                     330
```

<210> SEQ ID NO 101
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
caggtgcagc tggtggagtc tgggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagaggct    300
ggtgggccaa tctggcatga cgacgtcaaa tattacgatt ttaatgacgg ctactactac    360
tactactaca tggacgtctg gggcaaaggg accacggtca ccgtctcctc a             411
```

<210> SEQ ID NO 102
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102

```
cagtctgccc tgactcagcc tgcctccgtg tctgggtctc ctggacagtc gatcaccatc     60
tcctgcactg gaaccagcag tgatgttggg agttataacc ttgtctcctg gtaccaacag    120
cacccaggca agcccccaa actcatgatt tatgaggtca gtaagcggcc ctcaggggtt     180
tctaatcgct tctctggctc caagtctggc aacacggcct ccctgacaat ctctgggctc    240
caggctgagg acgaggctga ttattactgc tgctcactga cagacagaag ccatcgcata    300
ttcggcggag ggaccaagct gaccgtccta                                     330
```

<210> SEQ ID NO 103

<211> LENGTH: 126
<212> TYPE: PRT
<213> ORGANISM: Homo sapiens

<400> SEQUENCE: 103

| Glu | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |

| Ser | Leu | Lys | Ile | Ser | Cys | Lys | Gly | Ser | Gly | Tyr | Arg | Phe | Thr | Ser | Tyr |
|---|---|---|---|---|---|---|---|---|---|---|---|---|---|---|---|
| | | | 20 | | | | | 25 | | | | | 30 | | |

| Trp | Ile | Val | Trp | Val | Arg | Gln | Met | Pro | Gly | Lys | Gly | Leu | Glu | Trp | Met |
|---|---|---|---|---|---|---|---|---|---|---|---|---|---|---|---|
| | | 35 | | | | | 40 | | | | | 45 | | | |

| Gly | Ile | Ile | Tyr | Pro | Gly | Asp | Phe | Asp | Thr | Lys | Tyr | Ser | Pro | Ser | Phe |
|---|---|---|---|---|---|---|---|---|---|---|---|---|---|---|---|
| 50 | | | | | 55 | | | | | 60 | | | | | |

| Gln | Gly | Gln | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Leu | Gln | Trp | Ser | Ser | Leu | Lys | Ala | Ser | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Leu | Gly | Gly | Arg | Tyr | Tyr | His | Asp | Ser | Ser | Gly | Tyr | Tyr | Tyr |
|---|---|---|---|---|---|---|---|---|---|---|---|---|---|---|---|
| | | | 100 | | | | | 105 | | | | | 110 | | |

| Leu | Asp | Tyr | Trp | Gly | Gln | Gly | Thr | Leu | Val | Thr | Val | Ser | Ser |
|---|---|---|---|---|---|---|---|---|---|---|---|---|---|
| | | 115 | | | | | 120 | | | | | 125 | |

<210> SEQ ID NO 104
<211> LENGTH: 126
<212> TYPE: PRT
<213> ORGANISM: Homo sapiens

<400> SEQUENCE: 104

| Glu | Val | Gln | Leu | Val | Gln | Ser | Gly | Ala | Glu | Val | Lys | Lys | Pro | Gly | Glu |
|---|---|---|---|---|---|---|---|---|---|---|---|---|---|---|---|
| 1 | | | | 5 | | | | | 10 | | | | | 15 | |

| Ser | Leu | Lys | Ile | Ser | Cys | Lys | Gly | Ser | Gly | Tyr | Ser | Phe | Thr | Ser | Tyr |
|---|---|---|---|---|---|---|---|---|---|---|---|---|---|---|---|
| | | | 20 | | | | | 25 | | | | | 30 | | |

| Trp | Ile | Gly | Trp | Val | Arg | Gln | Met | Pro | Gly | Lys | Gly | Leu | Glu | Trp | Met |
|---|---|---|---|---|---|---|---|---|---|---|---|---|---|---|---|
| | | 35 | | | | | 40 | | | | | 45 | | | |

| Gly | Ile | Ile | Tyr | Pro | Gly | Asp | Ser | Asp | Thr | Arg | Tyr | Ser | Pro | Ser | Phe |
|---|---|---|---|---|---|---|---|---|---|---|---|---|---|---|---|
| 50 | | | | | 55 | | | | | 60 | | | | | |

| Gln | Gly | Gln | Val | Thr | Ile | Ser | Ala | Asp | Lys | Ser | Ile | Ser | Thr | Ala | Tyr |
|---|---|---|---|---|---|---|---|---|---|---|---|---|---|---|---|
| 65 | | | | | 70 | | | | | 75 | | | | | 80 |

| Leu | Gln | Trp | Ser | Ser | Leu | Lys | Ala | Ser | Asp | Thr | Ala | Met | Tyr | Tyr | Cys |
|---|---|---|---|---|---|---|---|---|---|---|---|---|---|---|---|
| | | | | 85 | | | | | 90 | | | | | 95 | |

| Ala | Arg | Leu | Gly | Gly | Arg | Tyr | Tyr | Tyr | Asp | Ser | Ser | Gly | Tyr | Tyr | Tyr |
|---|---|---|---|---|---|---|---|---|---|---|---|---|---|---|---|
| | | | 100 | | | | | 105 | | | | | 110 | | |

| Phe | Asp | Tyr | Trp | Gly | Gln | Gly | Thr | Leu | Val | Thr | Val | Ser | Ser |
|---|---|---|---|---|---|---|---|---|---|---|---|---|---|
| | | 115 | | | | | 120 | | | | | 125 | |

<210> SEQ ID NO 105
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

| Glu | Val | Gln | Leu | Val | Glu | Ser | Gly | Gly | Gly | Leu | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Asp | Asp | Gly |
|---|---|---|---|---|---|---|---|---|---|---|---|---|---|---|---|
| | | | 20 | | | | | 25 | | | | | 30 | | |

Ala Met His Trp Val Arg Gln Ala Pro Gly Lys Gly Leu Glu Trp Val
            35                  40                  45

Ser Gly Ile Ser Trp Asn Ser Asn Ile Ile Ala Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Val Glu Asp Thr Ala Leu Tyr Tyr Cys
                85                  90                  95

Ala Lys Asp Ser Pro Arg Gly Glu Leu Pro Leu Asn Tyr Trp Gly Gln
            100                 105                 110

Gly Thr Leu Val Thr Val Ser Ser
        115                 120

<210> SEQ ID NO 106
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ser Pro Arg Gly Glu Leu Pro Phe Asp Tyr Trp Gly Gln
            100                 105                 110

Gly Thr Leu Val Thr Val Ser Ser
        115                 120

<210> SEQ ID NO 107
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Gly Asn Phe Asn Thr Tyr
            20                  25                  30

Thr Ile Ser Trp Val Arg Gln Ala Pro Gly Gln Gly Leu Glu Trp Met
            35                  40                  45

Gly Arg Ile Ile Pro Ile Phe Gly Ile Val Asn Pro Ala Gln Lys Phe
 50                  55                  60

Pro Gly Arg Val Thr Ile Asn Val Asp Lys Ser Thr Asn Thr Ala Tyr
65                  70                  75                  80

-continued

Met Glu Leu Ser Ser Leu Arg Ser Glu Asp Thr Ala Val Tyr Tyr Cys
            85                  90                  95

Ala Thr Ser Gly Val Gly Leu His Phe Gly Tyr Phe Asp Tyr Trp Gly
        100                 105                 110

Gln Gly Thr Gln Val Thr Val Ser Ser
        115                 120

<210> SEQ ID NO 108
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Thr Ser Gly Val Gly Leu His Phe Gly Tyr Phe Asp Tyr Trp Gly
        100                 105                 110

Gln Gly Thr Leu Val Thr Val Ser Ser
        115                 120

<210> SEQ ID NO 109
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Ala Asn Val Val Arg Pro Gly Gly
1               5                   10                  15

Ser Leu Arg Leu Ser Cys Lys Ala Ser Gly Phe Ile Phe Glu Asn Phe
            20                  25                  30

Gly Phe Ser Trp Val Arg Gln Ala Pro Gly Lys Gly Leu Gln Trp Val
        35                  40                  45

Ala Gly Leu Asn Trp Asn Gly Gly Asp Thr Arg Tyr Ala Asp Ser Val
    50                  55                  60

Lys Gly Arg Phe Arg Met Ser Arg Asp Asn Ser Arg Asn Phe Val Tyr
65                  70                  75                  80

Leu Asp Met Asp Lys Val Gly Val Asp Thr Ala Phe Tyr Tyr Cys
            85                  90                  95

Ala Arg Gly Thr Asp Tyr Thr Ile Asp Asp Ala Gly Ile His Tyr Gln
        100                 105                 110

Gly Ser Gly Thr Phe Trp Tyr Phe Asp Leu Trp Gly Arg Gly Thr Leu
        115                 120                 125

Val Ser Val Ser Ser
    130

<210> SEQ ID NO 110
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Thr Asp Tyr Thr Ile Asp Asp Gln Gly Ile Arg Tyr Gln
            100                 105                 110

Gly Ser Gly Thr Phe Trp Tyr Phe Asp Leu Trp Gly Arg Gly Thr Leu
        115                 120                 125

Val Thr Val Ser Ser
    130

<210> SEQ ID NO 111
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Thr Asp Tyr Thr Ile Asp Asp Gln Gly Ile Leu Tyr Gln
            100                 105                 110

Gly Ser Gly Thr Phe Trp Tyr Phe Asp Leu Trp Gly Arg Gly Thr Leu
        115                 120                 125

Val Thr Val Ser Ser
    130

<210> SEQ ID NO 112
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Gly Thr Asp Tyr Thr Ile Asp Asp Gln Gly Ile His Tyr Tyr
            100                 105                 110

Gly Ser Gly Thr Tyr Trp Tyr Phe Asp Leu Trp Gly Arg Gly Thr Leu
        115                 120                 125

Val Thr Val Ser Ser
    130

<210> SEQ ID NO 113
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Gln Arg Leu Val Glu Ser Gly Gly Val Val Gln Pro Gly Ser Ser
1               5                   10                  15

Leu Arg Leu Ser Cys Ala Ala Ser Gly Phe Asp Phe Ser Arg Gln Gly
            20                  25                  30

Met His Trp Val Arg Gln Ala Pro Gly Gln Gly Leu Glu Trp Val Ala
        35                  40                  45

Phe Ile Lys Tyr Asp Gly Ser Glu Lys Tyr His Ala Asp Ser Val Trp
    50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser
    130                 135

<210> SEQ ID NO 114
<211> LENGTH: 137

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Glu Gln Leu Val Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
            20                  25                  30

Gly Met His Trp Val Arg Gln Ala Pro Gly Lys Gly Leu Glu Trp Val
        35                  40                  45

Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser
    130                 135

<210> SEQ ID NO 115
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Gly Pro Asp Tyr Arg Asn Gly Tyr Asn Tyr Tyr
            100                 105                 110

Asp Phe Trp Ser Gly Tyr Tyr Asn Tyr Tyr Met Asp Val Trp Gly
        115                 120                 125

Lys Gly Thr Thr Val Thr Val Ser Ser
    130                 135

<210> SEQ ID NO 116
<211> LENGTH: 137
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 116

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Tyr Tyr Tyr Met Asp Val Trp Gly
        115                 120                 125

Lys Gly Thr Thr Val Thr Val Ser Ser
        130                 135

<210> SEQ ID NO 117
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Met Ala Cys Ser Thr Leu Pro Lys Ser Pro Leu Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His His His His His His Gln
        35                  40                  45

Val Tyr Asn Ile Thr Trp Glu Val Thr Asn Gly Asp Arg Glu Thr Val
    50                  55                  60

Trp Ala Ser Gly Asn His Pro Leu Trp Thr Trp Trp Pro Val Leu Thr
65                  70                  75                  80

Pro Asp Leu Cys Met Leu Ala Leu Ser Gly Pro Pro His Trp Gly Leu
                85                  90                  95

Glu Tyr Gln Ala Pro Tyr Ser Ser Pro Pro Gly Pro Pro Cys Cys Ser
            100                 105                 110

Gly Ser Ser Gly Ser Ser Ala Gly Cys Ser Arg Asp Cys Asp Glu Pro
        115                 120                 125

Leu Thr Ser Leu Thr Pro Arg Cys Asn Thr Ala Trp Asn Arg Leu Lys
    130                 135                 140

Leu Asp Gln Val Thr His Lys Ser Ser Glu Gly Phe Tyr Val Cys Pro
145                 150                 155                 160

Gly Ser His Arg Pro Arg Glu Ala Lys Ser Cys Gly Gly Pro Asp Ser
                165                 170                 175

Phe Tyr Cys Ala Ser Trp Gly Cys Glu Thr Thr Gly Arg Val Tyr Trp
            180                 185                 190

```
Lys Pro Ser Ser Trp Asp Tyr Ile Thr Val Asp Asn Asn Leu Thr
        195                 200                 205

Thr Ser Gln Ala Val Gln Val Cys Lys Asp Asn Lys Trp Cys Asn Pro
    210                 215                 220

Leu Ala Ile Gln Phe Thr Asn Ala Gly Lys Gln Val Thr Ser Trp Thr
225                 230                 235                 240

Thr Gly His Tyr Trp Gly Leu Arg Leu Tyr Val Ser Gly Arg Asp Pro
                245                 250                 255

Gly Leu Thr Phe Gly Ile Arg Leu Arg Tyr Gln Asn Leu Gly Pro Arg
            260                 265                 270

Val Pro Ile Gly Pro Asn Pro Val Leu Ala Asp Gln Leu Ser Leu Pro
        275                 280                 285

Arg Pro Asn Pro Leu Pro Lys Pro Ala Lys Ser Pro Pro Ala Ser
    290                 295                 300

<210> SEQ ID NO 118
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Arg Val Lys Glu Thr Gln Met Asn Trp Pro Asn Leu Trp Lys Trp
1               5                   10                  15

Gly Thr Leu Ile Leu Gly Leu Val Ile Cys Ser Ala Val Pro Val
            20                  25                  30

Trp Lys Glu Ala Asp Thr Thr Leu Phe Cys Ala Ser Asp Ala Lys Ala
        35                  40                  45

His Glu Thr Glu Val His Asn Val Trp Ala Thr His Ala Cys Val Pro
    50                  55                  60

Thr Asp Pro Asn Pro Gln Glu Ile Asp Leu Glu Asn Val Thr Glu Asn
65                  70                  75                  80

Phe Asn Met Trp Lys Asn Asn Met Val Glu Gln Met Gln Glu Asp Val
                85                  90                  95

Ile Ser Leu Trp Asp Gln Ser Leu Lys Pro Cys Val Lys Leu Thr Pro
            100                 105                 110

Pro Cys Val Thr Leu His Cys Thr Asn Ala Asn Leu Thr Lys Ala Asn
        115                 120                 125

Leu Thr Asn Val Asn Asn Arg Thr Asn Val Ser Asn Ile Ile Gly Asn
    130                 135                 140

Ile Thr Asp Glu Val Arg Asn Cys Ser Phe Asn Met Thr Thr Glu Leu
145                 150                 155                 160

Arg Asp Lys Val Gln Lys Val His Ala Leu Phe Tyr Lys Leu Asp Ile
                165                 170                 175

Val Pro Ile Glu Asp Asn Asn Asp Ser Ser Glu Tyr Arg Leu Ile Asn
            180                 185                 190

Cys Asn Thr Ser Val Ile Lys Gln Pro Cys Pro Lys Ile Ser Phe Asp
        195                 200                 205

Pro Ile Pro Ile His Tyr Cys Thr Pro Ala Gly Tyr Ala Ile Leu Lys
    210                 215                 220

Cys Asn Asp Lys Asn Phe Asn Gly Thr Gly Pro Cys Lys Asn Val Ser
225                 230                 235                 240

Ser Val Gln Cys Thr His Gly Ile Lys Pro Val Val Ser Thr Gln Leu
                245                 250                 255
```

```
Leu Leu Asn Gly Ser Leu Ala Glu Glu Ile Ile Ile Arg Ser Glu
            260                 265                 270

Asn Leu Thr Asn Asn Ala Lys Thr Ile Ile Val His Leu Asn Lys Ser
        275                 280                 285

Val Val Ile Asn Cys Thr Arg Pro Ser Asn Asn Thr Arg Thr Ser Ile
290                 295                 300

Thr Ile Gly Pro Gly Gln Val Phe Tyr Arg Thr Gly Asp Ile Ile Gly
305                 310                 315                 320

Asp Ile Arg Lys Ala Tyr Cys Glu Ile Asn Gly Thr Glu Trp Asn Lys
                325                 330                 335

Ala Leu Lys Gln Val Thr Glu Lys Leu Lys Glu His Phe Asn Asn Lys
            340                 345                 350

Pro Ile Ile Phe Gln Pro Pro Ser Gly Gly Asp Leu Glu Ile Thr Met
        355                 360                 365

His His Phe Asn Cys Arg Gly Glu Phe Phe Tyr Cys Asn Thr Thr Arg
370                 375                 380

Leu Phe Asn Asn Thr Cys Ile Ala Asn Gly Thr Ile Glu Gly Cys Asn
385                 390                 395                 400

Gly Asn Ile Thr Leu Pro Cys Lys Ile Lys Gln Ile Ile Asn Met Trp
                405                 410                 415

Gln Gly Ala Gly Gln Ala Met Tyr Ala Pro Pro Ile Ser Gly Thr Ile
            420                 425                 430

Asn Cys Val Ser Asn Ile Thr Gly Ile Leu Leu Thr Arg Asp Gly Gly
        435                 440                 445

Ala Thr Asn Asn Thr Asn Asn Glu Thr Phe Arg Pro Gly Gly Gly Asn
    450                 455                 460

Ile Lys Asp Asn Trp Arg Asn Glu Leu Tyr Lys Tyr Lys Val Val Gln
465                 470                 475                 480

Ile Glu Pro Leu Gly Val Ala Pro Thr Arg Ala Lys Arg Arg Val Val
                485                 490                 495

Glu Arg Glu Lys Arg
            500

<210> SEQ ID NO 119
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Met Arg Val Lys Glu Thr Gln Met Asn Trp Pro Asn Leu Trp Lys Trp
1               5                   10                  15

Gly Thr Leu Ile Leu Gly Leu Val Ile Ile Cys Ser Ala Val Pro Val
            20                  25                  30

Trp Lys Glu Ala Asp Thr Thr Leu Phe Cys Ala Ser Asp Ala Lys Ala
        35                  40                  45

His Glu Thr Glu Val His Asn Val Trp Ala Thr His Ala Cys Val Pro
    50                  55                  60

Thr Asp Pro Asn Pro Gln Glu Ile Asp Leu Glu Asn Val Thr Glu Asn
65                  70                  75                  80

Phe Asn Met Trp Lys Asn Asn Met Val Glu Gln Met Gln Glu Asp Val
                85                  90                  95

Ile Ser Leu Trp Asp Gln Ser Leu Lys Pro Cys Val Lys Leu Thr Pro
```

```
                100             105             110
Pro Cys Val Thr Leu His Cys Thr Asn Ala Asn Leu Thr Lys Ala Asn
            115                 120                 125

Leu Thr Asn Val Asn Asn Arg Thr Asn Val Ser Asn Ile Ile Gly Asn
130                 135                 140

Ile Thr Asp Glu Val Arg Asn Cys Ser Phe Asn Met Thr Thr Glu Leu
145                 150                 155                 160

Arg Asp Lys Val Gln Lys Glu Tyr Ala Leu Phe Tyr Lys Leu Asp Ile
            165                 170                 175

Val Pro Ile Glu Asp Asn Asn Asp Ser Ser Glu Tyr Arg Leu Ile Asn
            180                 185                 190

Cys Asn Thr Ser Val Ile Lys Gln Pro Cys Pro Lys Ile Ser Phe Asp
            195                 200                 205

Pro Ile Pro Ile His Tyr Cys Thr Pro Ala Gly Tyr Ala Ile Leu Lys
            210                 215                 220

Cys Asn Asp Lys Asn Phe Asn Gly Thr Gly Pro Cys Lys Asn Val Ser
225                 230                 235                 240

Ser Val Gln Cys Thr His Gly Ile Lys Pro Val Val Ser Thr Gln Leu
            245                 250                 255

Leu Leu Asn Gly Ser Leu Ala Glu Glu Ile Ile Arg Ser Glu
            260                 265                 270

Asn Leu Thr Asn Asn Ala Lys Thr Ile Ile Val His Leu Asn Lys Ser
            275                 280                 285

Val Val Ile Asn Cys Thr Arg Pro Ser Asn Asn Thr Arg Thr Ser Ile
            290                 295                 300

Thr Ile Gly Pro Gly Gln Val Phe Tyr Arg Thr Gly Asp Ile Ile Gly
305                 310                 315                 320

Asp Ile Arg Lys Ala Tyr Cys Glu Ile Asn Gly Thr Glu Trp Asn Lys
            325                 330                 335

Ala Leu Lys Gln Val Thr Glu Lys Leu Lys Glu His Phe Asn Asn Lys
            340                 345                 350

Pro Ile Ile Phe Gln Pro Pro Ser Gly Gly Asp Leu Glu Ile Thr Met
            355                 360                 365

His His Phe Asn Cys Arg Gly Glu Phe Phe Tyr Cys Asn Thr Thr Arg
            370                 375                 380

Leu Phe Asn Asn Thr Cys Ile Ala Asn Gly Thr Ile Glu Gly Cys Asn
385                 390                 395                 400

Gly Asn Ile Thr Leu Pro Cys Lys Ile Lys Gln Ile Ile Asn Met Trp
            405                 410                 415

Gln Gly Ala Gly Gln Ala Met Tyr Ala Pro Pro Ile Ser Gly Thr Ile
            420                 425                 430

Asn Cys Val Ser Asn Ile Thr Gly Ile Leu Leu Thr Arg Asp Gly Gly
            435                 440                 445

Ala Thr Asn Asn Thr Asn Asn Glu Thr Phe Arg Pro Gly Gly Gly Asn
            450                 455                 460

Ile Lys Asp Asn Trp Arg Asn Glu Leu Tyr Lys Tyr Lys Val Val Gln
465                 470                 475                 480

Ile Glu Pro Leu Gly Val Ala Pro Thr Arg Ala Lys Arg Arg Val Val
            485                 490                 495

Glu Arg Glu Lys Arg
            500

<210> SEQ ID NO 120
```

<211> LENGTH: 500
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

```
Met Arg Val Lys Glu Thr Gln Arg Asn Trp Pro Asn Leu Trp Lys Trp
1               5                   10                  15
Gly Thr Leu Ile Leu Gly Leu Val Ile Ile Cys Ser Ala Val Pro Val
            20                  25                  30
Trp Lys Asp Ala Asn Thr Thr Leu Phe Cys Ala Ala Asp Ala Lys Ala
        35                  40                  45
His Glu Thr Glu Val His Asn Val Trp Ala Thr His Thr Cys Val Pro
    50                  55                  60
Thr Asp Pro Asn Pro Gln Glu Ile His Met Glu Asn Val Thr Glu Asn
65                  70                  75                  80
Phe Asn Met Trp Lys Asn Met Val Glu Gln Met His Glu Asp Val
                85                  90                  95
Ile Ser Leu Trp Asp Gln Ser Leu Lys Pro Cys Ile Lys Val Thr Pro
            100                 105                 110
Leu Cys Val Thr Leu Asn Cys Thr Asp Ala Lys Phe Asp Ser Asn Lys
        115                 120                 125
Thr Tyr Ala Asn Ser Thr Val Glu Asn Ile Thr Ile Glu Asn Ile Thr
    130                 135                 140
Asp Glu Val Arg Asn Cys Ser Phe Asn Ile Thr Thr Glu Leu Arg Asp
145                 150                 155                 160
Lys Gln Arg Lys Val Gln Ala Leu Phe Tyr Arg Leu Asp Ile Ile Gln
                165                 170                 175
Thr Glu Asn Arg Ser Ser Gly Ile Asn Gly Ser Phe Gln Glu Tyr Arg
            180                 185                 190
Leu Ile Asn Cys Asn Thr Ser Val Ile Lys Gln Ala Cys Pro Lys Ile
        195                 200                 205
Ser Phe Asp Pro Ile Pro Ile His Tyr Cys Thr Pro Ala Gly Tyr Ala
    210                 215                 220
Ile Leu Lys Cys Asn Asp Lys Lys Phe Asn Gly Thr Gly Pro Cys Lys
225                 230                 235                 240
Asn Val Ser Ser Val Gln Cys Thr His Gly Ile Lys Pro Val Ile Ser
                245                 250                 255
Thr Gln Leu Leu Leu Asn Gly Ser Ile Ala Glu Glu Lys Ile Ile Ile
            260                 265                 270
Arg Ser Glu Asn Ile Thr Asn Asn Ala Lys Thr Ile Ile Val His Leu
        275                 280                 285
Asn Arg Thr Ile Ile Ile Asn Cys Thr Arg Pro Ser Asn Asn Thr Arg
    290                 295                 300
Thr Ser Ile Asn Ile Gly Pro Gly Gln Met Leu Phe Tyr Lys Pro Gly
305                 310                 315                 320
Asp Ile Ile Gly Asp Ile Arg Lys Ala Tyr Cys Glu Ile Asn Gly Thr
                325                 330                 335
Lys Trp Lys Lys Thr Leu Asp Gln Val Lys Arg Glu Leu Glu Glu His
            340                 345                 350
Phe Pro Asn Lys Thr Ile Thr Phe Gln Pro Ser Ser Gly Gly Asp Pro
        355                 360                 365
Glu Ile Thr Met His His Phe Asn Cys Arg Gly Glu Phe Phe Tyr Cys
```

```
            370                 375                 380
Asn Thr Thr Gln Leu Phe Asn Met Thr Gln Leu Asn Glu Thr Leu Asn
385                 390                 395                 400

Glu Thr Ile Ile Leu Pro Cys Arg Ile Lys Gln Ile Ile Asn Met Trp
                405                 410                 415

Gln Arg Val Gly Gln Ala Met Tyr Asn Pro Val Gln Gly His Ile
            420                 425                 430

Asn Cys Val Ser Asn Ile Thr Gly Ile Leu Leu Thr Arg Asp Gly Gly
            435                 440                 445

Ala Asn Glu Thr Asn Gly Thr Glu Thr Phe Arg Pro Glu Gly Gly Asn
450                 455                 460

Ile Lys Asp Asn Trp Arg Ser Glu Leu Tyr Lys Tyr Lys Val Val Gln
465                 470                 475                 480

Ile Glu Pro Leu Gly Val Ala Pro Thr Arg Ala Lys Glu Arg Val Val
            485                 490                 495

Glu Arg Gln Glu
            500

<210> SEQ ID NO 121
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Arg Val Lys Glu Thr Gln Arg Asn Trp Pro Asn Leu Trp Lys Trp
1               5                   10                  15

Gly Thr Leu Ile Leu Gly Leu Val Ile Ile Cys Ser Ala Val Pro Val
            20                  25                  30

Trp Lys Asp Ala Asn Thr Thr Leu Phe Cys Ala Ala Asp Ala Lys Ala
        35                  40                  45

His Glu Thr Glu Val His Asn Val Trp Ala Thr His Thr Cys Val Pro
50                  55                  60

Thr Asp Pro Asn Pro Gln Glu Ile His Met Glu Asn Val Thr Glu Asn
65                  70                  75                  80

Phe Asn Met Trp Lys Asn Asn Met Val Glu Gln Met His Glu Asp Val
                85                  90                  95

Ile Ser Leu Trp Asp Gln Ser Leu Lys Pro Cys Ile Lys Val Thr Pro
            100                 105                 110

Leu Cys Val Thr Leu Asn Cys Thr Asp Ala Lys Phe Asp Ser Asn Lys
        115                 120                 125

Thr Tyr Ala Asn Ser Thr Val Glu Asn Ile Thr Ile Glu Asn Ile Thr
    130                 135                 140

Asp Glu Val Arg Asn Cys Ser Phe Asn Ile Thr Thr Glu Leu Arg Asp
145                 150                 155                 160

Lys Lys Arg Lys Val Gln Ala Leu Phe Tyr Arg Leu Asp Ile Ile Gln
                165                 170                 175

Thr Glu Asn Arg Ser Ser Gly Ile Asn Gly Ser Phe Gln Glu Tyr Arg
            180                 185                 190

Leu Ile Asn Cys Asn Thr Ser Val Ile Lys Gln Ala Cys Pro Lys Ile
        195                 200                 205

Ser Phe Asp Pro Ile Pro Ile His Tyr Cys Thr Pro Ala Gly Tyr Ala
    210                 215                 220
```

```
Ile Leu Lys Cys Asn Asp Lys Lys Phe Asn Gly Thr Gly Pro Cys Lys
225                 230                 235                 240

Asn Val Ser Ser Val Gln Cys Thr His Gly Ile Lys Pro Val Ile Ser
            245                 250                 255

Thr Gln Leu Leu Leu Asn Gly Ser Ile Ala Glu Glu Lys Ile Ile Ile
        260                 265                 270

Arg Ser Glu Asn Ile Thr Asn Asn Ala Lys Thr Ile Ile Val His Leu
    275                 280                 285

Asn Arg Thr Ile Ile Ile Asn Cys Thr Arg Pro Ser Asn Asn Thr Arg
290                 295                 300

Thr Ser Ile Asn Ile Gly Pro Gly Gln Met Leu Phe Tyr Lys Pro Gly
305                 310                 315                 320

Asp Ile Ile Gly Asp Ile Arg Lys Ala Tyr Cys Glu Ile Asn Gly Thr
                325                 330                 335

Lys Trp Lys Lys Thr Leu Asp Gln Val Lys Arg Glu Leu Glu Glu His
            340                 345                 350

Phe Pro Asn Lys Thr Ile Thr Phe Gln Pro Ser Ser Gly Gly Asp Pro
        355                 360                 365

Glu Ile Thr Met His His Phe Asn Cys Arg Gly Glu Phe Phe Tyr Cys
    370                 375                 380

Asn Thr Thr Gln Leu Phe Asn Met Thr Gln Leu Asn Glu Thr Leu Asn
385                 390                 395                 400

Glu Thr Ile Ile Leu Pro Cys Arg Ile Lys Gln Ile Ile Asn Met Trp
                405                 410                 415

Gln Arg Val Gly Gln Ala Met Tyr Asn Pro Pro Val Gln Gly His Ile
            420                 425                 430

Asn Cys Val Ser Asn Ile Thr Gly Ile Leu Leu Thr Arg Asp Gly Gly
        435                 440                 445

Ala Asn Glu Thr Asn Gly Thr Glu Thr Phe Arg Pro Glu Gly Gly Asn
    450                 455                 460

Ile Lys Asp Asn Trp Arg Ser Glu Leu Tyr Lys Tyr Lys Val Val Gln
465                 470                 475                 480

Ile Glu Pro Leu Gly Val Ala Pro Thr Arg Ala Lys Glu Arg Val Val
                485                 490                 495

Glu Arg Gln Glu
            500

<210> SEQ ID NO 122
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Met Arg Val Lys Glu Thr Gln Arg Asn Trp Pro Asn Leu Trp Lys Trp
1               5                   10                  15

Gly Thr Leu Ile Leu Gly Leu Val Ile Ile Cys Ser Ala Val Pro Val
            20                  25                  30

Trp Lys Asp Ala Asn Thr Thr Leu Phe Cys Ala Ala Asp Ala Lys Ala
        35                  40                  45

His Glu Thr Glu Val His Asn Val Trp Ala Thr His Thr Cys Val Pro
    50                  55                  60

Thr Asp Pro Asn Pro Gln Glu Ile His Met Glu Asn Val Thr Glu Asn
65                  70                  75                  80
```

-continued

```
Phe Asn Met Trp Lys Asn Asn Met Val Glu Gln Met His Glu Asp Val
                 85                  90                  95
Ile Ser Leu Trp Asp Gln Ser Leu Lys Pro Cys Ile Lys Val Thr Pro
            100                 105                 110
Leu Cys Val Thr Leu Asn Cys Thr Asp Ala Lys Phe Asp Ser Asn Lys
            115                 120                 125
Thr Tyr Ala Asn Ser Thr Val Glu Asn Ile Thr Ile Glu Asn Ile Thr
    130                 135                 140
Asp Glu Val Arg Asn Cys Ser Phe Asn Ile Thr Thr Glu Leu Arg Asp
145                 150                 155                 160
Lys Lys Gln Lys Val His Ala Leu Phe Tyr Arg Leu Asp Ile Ile Gln
                165                 170                 175
Thr Glu Asn Arg Ser Ser Gly Ile Asn Gly Ser Phe Gln Glu Tyr Arg
            180                 185                 190
Leu Ile Asn Cys Asn Thr Ser Val Ile Lys Gln Ala Cys Pro Lys Ile
            195                 200                 205
Ser Phe Asp Pro Ile Pro Ile His Tyr Cys Thr Pro Ala Gly Tyr Ala
    210                 215                 220
Ile Leu Lys Cys Asn Asp Lys Lys Phe Asn Gly Thr Gly Pro Cys Lys
225                 230                 235                 240
Asn Val Ser Ser Val Gln Cys Thr His Gly Ile Lys Pro Val Ile Ser
                245                 250                 255
Thr Gln Leu Leu Leu Asn Gly Ser Ile Ala Glu Lys Ile Ile Ile
            260                 265                 270
Arg Ser Glu Asn Ile Thr Asn Asn Ala Lys Thr Ile Ile Val His Leu
            275                 280                 285
Asn Arg Thr Ile Ile Ile Asn Cys Thr Arg Pro Ser Asn Asn Thr Arg
    290                 295                 300
Thr Ser Ile Asn Ile Gly Pro Gly Gln Met Leu Phe Tyr Lys Pro Gly
305                 310                 315                 320
Asp Ile Ile Gly Asp Ile Arg Lys Ala Tyr Cys Glu Ile Asn Gly Thr
                325                 330                 335
Lys Trp Lys Lys Thr Leu Asp Gln Val Lys Arg Glu Leu Glu Glu His
            340                 345                 350
Phe Pro Asn Lys Thr Ile Thr Phe Gln Pro Ser Ser Gly Gly Asp Pro
            355                 360                 365
Glu Ile Thr Met His His Phe Asn Cys Arg Gly Glu Phe Phe Tyr Cys
    370                 375                 380
Asn Thr Thr Gln Leu Phe Asn Met Thr Gln Leu Asn Glu Thr Leu Asn
385                 390                 395                 400
Glu Thr Ile Ile Leu Pro Cys Arg Ile Lys Gln Ile Ile Asn Met Trp
                405                 410                 415
Gln Arg Val Gly Gln Ala Met Tyr Asn Pro Pro Val Gln Gly His Ile
            420                 425                 430
Asn Cys Val Ser Asn Ile Thr Gly Ile Leu Leu Thr Arg Asp Gly Gly
            435                 440                 445
Ala Asn Glu Thr Asn Gly Thr Glu Thr Phe Arg Pro Glu Gly Gly Asn
    450                 455                 460
Ile Lys Asp Asn Trp Arg Ser Glu Leu Tyr Lys Tyr Lys Val Val Gln
465                 470                 475                 480
Ile Glu Pro Leu Gly Val Ala Pro Thr Arg Ala Lys Glu Arg Val Val
                485                 490                 495
```

Glu Arg Gln Glu
            500

<210> SEQ ID NO 123
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Met Arg Val Lys Glu Thr Gln Arg Ser Trp Pro Asn Leu Trp Lys Trp
1               5                   10                  15

Gly Thr Leu Ile Leu Gly Leu Val Ile Met Cys Asn Ala Val Pro Val
            20                  25                  30

Trp Arg Asp Ala Asp Thr Thr Leu Phe Cys Ala Ser Asp Ala Gln Ala
        35                  40                  45

His Val Thr Glu Val His Asn Ile Trp Ala Thr His Ala Cys Val Pro
    50                  55                  60

Thr Asp Pro Asn Pro Gln Glu Ile His Leu Glu Asn Val Thr Glu Asn
65                  70                  75                  80

Phe Asn Met Trp Lys Asn Asn Met Ala Glu Gln Met Gln Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Lys Cys Thr Ala Asn Ile Thr Ile Thr Asn Ala
        115                 120                 125

Thr Thr Arg Thr Glu Asn Thr Thr Lys Glu Asn Leu Ile Gly Asn Ile
130                 135                 140

Thr Asp Glu Leu Arg Asn Cys Ser Phe Asn Val Thr Thr Glu Leu Arg
145                 150                 155                 160

Asp Arg Gln Arg Lys Ala Tyr Ala Leu Phe Tyr Lys Leu Asp Ile Val
                165                 170                 175

Pro Ile Asn Asn Glu Ala Asn Ser Ser Glu Tyr Arg Leu Ile Asn Cys
            180                 185                 190

Asn Thr Ser Val Ile Lys Gln Ala Cys Pro Lys Val Ser Phe Asp Pro
        195                 200                 205

Ile Pro Ile His Tyr Cys Thr Pro Ala Gly Tyr Ala Ile Leu Lys Cys
    210                 215                 220

Asn Asp Lys Asn Phe Asn Gly Thr Gly Pro Cys Lys Asn Val Ser Ser
225                 230                 235                 240

Val Gln Cys Thr His Gly Ile Lys Pro Val Val Ser Thr Gln Leu Leu
                245                 250                 255

Leu Asn Gly Ser Leu Ala Glu Asp Glu Ile Ile Arg Ser Glu Asn
            260                 265                 270

Leu Thr Asp Asn Ser Lys Asn Ile Ile Val His Leu Asn Glu Ser Val
        275                 280                 285

Val Ile Asn Cys Thr Arg Pro Ser Asn Asn Thr Val Lys Ser Ile Arg
    290                 295                 300

Ile Gly Pro Gly Gln Thr Phe Tyr Arg Thr Gly Asp Ile Ile Gly Asp
305                 310                 315                 320

Ile Arg Gln Ala Tyr Cys Asn Val Asn Gly Thr Lys Trp Tyr Glu Val
                325                 330                 335

Leu Arg Asn Val Thr Lys Lys Leu Lys Glu His Phe Asn Asn Lys Thr
            340                 345                 350

-continued

Ile Val Phe Gln Gln Pro Pro Gly Gly Asp Leu Glu Ile Thr Thr
        355                 360                 365

His His Phe Asn Cys Arg Gly Glu Phe Phe Tyr Cys Asn Thr Thr Glu
    370                 375                 380

Leu Phe Asn Asn Thr Cys Val Asn Glu Thr Ile Asn Asn Gly Thr Glu
385                 390                 395                 400

Gly Trp Cys Lys Gly Asp Ile Ile Leu Pro Cys Arg Ile Lys Gln Ile
                405                 410                 415

Ile Asn Leu Trp Gln Glu Val Gly Gln Ala Met Tyr Ala Pro Pro Val
            420                 425                 430

Ser Gly Gln Ile Arg Cys Ile Ser Asn Ile Thr Gly Ile Ile Leu Thr
                435                 440                 445

Arg Asp Gly Gly Asn Gly Lys Asn Gly Thr Leu Asn Asn Glu Thr Phe
450                 455                 460

Arg Pro Gly Gly Gly Asn Met Lys Asp Asn Trp Arg Ser Glu Leu Tyr
465                 470                 475                 480

Lys Tyr Lys Val Val Glu Ile Glu Pro Leu Gly Ile Ala Pro Ser Arg
                485                 490                 495

Ala Lys Glu Arg Val Val Glu Met Lys Arg Glu Lys Glu
                500                 505

<210> SEQ ID NO 124
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Arg Val Lys Glu Thr Gln Arg Ser Trp Pro Asn Leu Trp Lys Trp
1               5                   10                  15

Gly Thr Leu Ile Leu Gly Leu Val Ile Met Cys Asn Ala Val Pro Val
            20                  25                  30

Trp Arg Asp Ala Asp Thr Thr Leu Phe Cys Ala Ser Asp Ala Gln Ala
        35                  40                  45

His Val Thr Glu Val His Asn Ile Trp Ala Thr His Ala Cys Val Pro
    50                  55                  60

Thr Asp Pro Asn Pro Gln Glu Ile His Leu Glu Asn Val Thr Glu Asn
65                  70                  75                  80

Phe Asn Met Trp Lys Asn Asn Met Ala Glu Gln Met Gln Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Lys Cys Thr Ala Asn Ile Thr Ile Thr Asn Ala
        115                 120                 125

Thr Thr Arg Thr Glu Asn Thr Thr Lys Glu Asn Leu Ile Gly Asn Ile
    130                 135                 140

Thr Asp Glu Leu Arg Asn Cys Ser Phe Asn Val Thr Thr Glu Leu Arg
145                 150                 155                 160

Asp Arg Lys Arg Lys Ala Tyr Ala Leu Phe Tyr Lys Leu Asp Ile Val
                165                 170                 175

Pro Ile Asn Asn Glu Ala Asn Ser Ser Glu Tyr Arg Leu Ile Asn Cys
            180                 185                 190

Asn Thr Ser Val Ile Lys Gln Ala Cys Pro Lys Val Ser Phe Asp Pro

```
            195                 200                 205
Ile Pro Ile His Tyr Cys Thr Pro Ala Gly Tyr Ala Ile Leu Lys Cys
210                 215                 220

Asn Asp Lys Asn Phe Asn Gly Thr Gly Pro Cys Lys Asn Val Ser Ser
225                 230                 235                 240

Val Gln Cys Thr His Gly Ile Lys Pro Val Val Ser Thr Gln Leu Leu
                245                 250                 255

Leu Asn Gly Ser Leu Ala Glu Asp Glu Ile Ile Arg Ser Glu Asn
            260                 265                 270

Leu Thr Asp Asn Ser Lys Asn Ile Ile Val His Leu Asn Glu Ser Val
        275                 280                 285

Val Ile Asn Cys Thr Arg Pro Ser Asn Asn Thr Val Lys Ser Ile Arg
290                 295                 300

Ile Gly Pro Gly Gln Thr Phe Tyr Arg Thr Gly Asp Ile Ile Gly Asp
305                 310                 315                 320

Ile Arg Gln Ala Tyr Cys Asn Val Asn Gly Thr Lys Trp Tyr Glu Val
                325                 330                 335

Leu Arg Asn Val Thr Lys Lys Leu Lys Glu His Phe Asn Asn Lys Thr
            340                 345                 350

Ile Val Phe Gln Gln Pro Pro Gly Gly Asp Leu Glu Ile Thr Thr
        355                 360                 365

His His Phe Asn Cys Arg Gly Glu Phe Phe Tyr Cys Asn Thr Thr Glu
        370                 375                 380

Leu Phe Asn Asn Thr Cys Val Asn Glu Thr Ile Asn Asn Gly Thr Glu
385                 390                 395                 400

Gly Trp Cys Lys Gly Asp Ile Ile Leu Pro Cys Arg Ile Lys Gln Ile
                405                 410                 415

Ile Asn Leu Trp Gln Glu Val Gly Gln Ala Met Tyr Ala Pro Pro Val
            420                 425                 430

Ser Gly Gln Ile Arg Cys Ile Ser Asn Ile Thr Gly Ile Ile Leu Thr
        435                 440                 445

Arg Asp Gly Gly Asn Gly Lys Asn Gly Thr Leu Asn Asn Glu Thr Phe
450                 455                 460

Arg Pro Gly Gly Gly Asn Met Lys Asp Asn Trp Arg Ser Glu Leu Tyr
465                 470                 475                 480

Lys Tyr Lys Val Val Glu Ile Glu Pro Leu Gly Ile Ala Pro Ser Arg
                485                 490                 495

Ala Lys Glu Arg Val Val Glu Met Lys Arg Glu Lys Glu
            500                 505

<210> SEQ ID NO 125
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Arg Val Lys Glu Thr Gln Arg Ser Trp Pro Asn Leu Trp Lys Trp
1               5                   10                  15

Gly Thr Leu Ile Leu Gly Leu Val Ile Met Cys Asn Ala Val Pro Val
            20                  25                  30

Trp Arg Asp Ala Asp Thr Thr Leu Phe Cys Ala Ser Asp Ala Gln Ala
        35                  40                  45
```

-continued

His Val Thr Glu Val His Asn Ile Trp Ala Thr His Ala Cys Val Pro
    50                  55                  60

Thr Asp Pro Asn Pro Gln Glu Ile His Leu Glu Asn Val Thr Glu Asn
65                  70                  75                  80

Phe Asn Met Trp Lys Asn Asn Met Ala Glu Gln Met Gln Glu Asp Val
                85                  90                  95

Ile Ser Leu Trp Asp Gln Ser Leu Lys Pro Cys Val Lys Leu Thr Pro
            100                 105                 110

Leu Cys Val Thr Leu Lys Cys Thr Ala Asn Ile Thr Ile Thr Asn Ala
            115                 120                 125

Thr Thr Arg Thr Glu Asn Thr Thr Lys Glu Asn Leu Ile Gly Asn Ile
        130                 135                 140

Thr Asp Glu Leu Arg Asn Cys Ser Phe Asn Val Thr Thr Glu Leu Arg
145                 150                 155                 160

Asp Lys Lys Arg Lys Ala His Val Leu Phe Tyr Lys Leu Asp Ile Val
                165                 170                 175

Pro Ile Asn Asn Glu Ala Asn Ser Ser Glu Tyr Arg Leu Ile Asn Cys
            180                 185                 190

Asn Thr Ser Val Ile Lys Gln Ala Cys Pro Lys Val Ser Phe Asp Pro
        195                 200                 205

Ile Pro Ile His Tyr Cys Thr Pro Ala Gly Tyr Ala Ile Leu Lys Cys
    210                 215                 220

Asn Asp Lys Asn Phe Asn Gly Thr Gly Pro Cys Lys Asn Val Ser Ser
225                 230                 235                 240

Val Gln Cys Thr His Gly Ile Lys Pro Val Val Ser Thr Gln Leu Leu
                245                 250                 255

Leu Asn Gly Ser Leu Ala Glu Asp Glu Ile Ile Ile Arg Ser Glu Asn
            260                 265                 270

Leu Thr Asp Asn Ser Lys Asn Ile Ile Val His Leu Asn Glu Ser Val
        275                 280                 285

Val Ile Asn Cys Thr Arg Pro Ser Asn Asn Thr Val Lys Ser Ile Arg
    290                 295                 300

Ile Gly Pro Gly Gln Thr Phe Tyr Arg Thr Gly Asp Ile Ile Gly Asp
305                 310                 315                 320

Ile Arg Gln Ala Tyr Cys Asn Val Asn Gly Thr Lys Trp Tyr Glu Val
                325                 330                 335

Leu Arg Asn Val Thr Lys Lys Leu Lys Glu His Phe Asn Asn Lys Thr
            340                 345                 350

Ile Val Phe Gln Gln Pro Pro Gly Gly Asp Leu Glu Ile Thr Thr
        355                 360                 365

His His Phe Asn Cys Arg Gly Glu Phe Phe Tyr Cys Asn Thr Thr Glu
    370                 375                 380

Leu Phe Asn Asn Thr Cys Val Asn Glu Thr Ile Asn Asn Gly Thr Glu
385                 390                 395                 400

Gly Trp Cys Lys Gly Asp Ile Ile Leu Pro Cys Arg Ile Lys Gln Ile
                405                 410                 415

Ile Asn Leu Trp Gln Glu Val Gly Gln Ala Met Tyr Ala Pro Pro Val
            420                 425                 430

Ser Gly Gln Ile Arg Cys Ile Ser Asn Ile Thr Gly Ile Ile Leu Thr
        435                 440                 445

Arg Asp Gly Gly Asn Gly Lys Asn Gly Thr Leu Asn Asn Glu Thr Phe
450                 455                 460

Arg Pro Gly Gly Gly Asn Met Lys Asp Asn Trp Arg Ser Glu Leu Tyr

```
                465                 470                 475                 480
Lys Tyr Lys Val Val Glu Ile Glu Pro Leu Gly Ile Ala Pro Ser Arg
                        485                 490                 495
Ala Lys Glu Arg Val Val Glu Met Lys Arg Glu Lys Glu
                500                 505

<210> SEQ ID NO 126
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Met Ala Cys Ser Thr Leu Pro Lys Ser Pro Lys Asp Lys Ile Asp Pro
1               5                   10                  15
Arg Asp Leu Leu Ile Pro Leu Ile Leu Phe Leu Ser Leu Lys Gly Ala
                20                  25                  30
Arg Ser Ala Ala Pro Gly Ser Ser Pro His His His His His His Gln
            35                  40                  45
Val Tyr Asn Ile Thr Trp Glu Val Thr Asn Gly Asp Arg Glu Thr Val
        50                  55                  60
Trp Ala Ile Ser Gly Asn His Pro Leu Trp Thr Trp Trp Pro Val Leu
65                  70                  75                  80
Thr Pro Asp Leu Cys Met Leu Ala Leu Ser Gly Pro Pro His Trp Gly
                85                  90                  95
Leu Glu Tyr Gln Ala Pro Tyr Ser Ser Pro Pro Gly Pro Pro Cys Cys
                100                 105                 110
Ser Gly Ser Ser Gly Ser Ser Ala Gly Cys Ser Arg Asp Cys Asp Glu
            115                 120                 125
Pro Leu Thr Ser Leu Thr Pro Arg Cys Asn Thr Ala Trp Asn Arg Leu
        130                 135                 140
Lys Leu Asp Gln Val Thr His Lys Ser Ser Glu Gly Phe Tyr Val Cys
145                 150                 155                 160
Pro Gly Ser His Arg Pro Arg Glu Ala Lys Ser Cys Gly Gly Pro Asp
                165                 170                 175
Ser Phe Tyr Cys Ala Ser Trp Gly Cys Glu Thr Thr Gly Arg Val Tyr
                180                 185                 190
Trp Lys Pro Ser Ser Ser Trp Asp Tyr Ile Thr Val Asp Asn Asn Leu
            195                 200                 205
Thr Thr Ser Gln Ala Val Gln Val Cys Lys Asp Asn Lys Trp Cys Asn
        210                 215                 220
Pro Leu Ala Ile Gln Phe Thr Asn Ala Gly Lys Gln Val Thr Ser Trp
225                 230                 235                 240
Thr Thr Gly His Tyr Trp Gly Leu Arg Leu Tyr Val Ser Gly Arg Asp
                245                 250                 255
Pro Gly Leu Thr Phe Gly Ile Arg Leu Arg Tyr Gln Asn Leu Gly Pro
                260                 265                 270
Arg Val Pro Ile Gly Pro Asn Pro Val Leu Ala Asp Gln Leu Ser Leu
            275                 280                 285
Pro Arg Pro Asn Pro Leu Pro Lys Pro Ala Lys Ser Pro Pro Ala Ser
        290                 295                 300
Val Lys Leu Thr Pro Leu Cys Val Thr Leu Asn Cys Ile Asp Leu Arg
305                 310                 315                 320
```

Asn Ala Thr Asn Ala Thr Ser Asn Ser Asn Thr Thr Asn Thr Thr Ser
            325                 330                 335

Ser Ser Gly Gly Leu Met Met Glu Gln Gly Glu Ile Lys Asn Cys Ser
        340                 345                 350

Phe Asn Ile Thr Thr Ser Ile Arg Asp Lys Lys Gln Lys Glu Tyr Ala
            355                 360                 365

Leu Phe Tyr Lys Leu Asp Ile Val Pro Ile Asp Asn Pro Lys Asn Ser
370                 375                 380

Thr Asn Tyr Arg Leu Ile Ser Cys Asn Thr Ser Val Ile Thr Gln Ala
385                 390                 395                 400

<210> SEQ ID NO 127
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
            20                  25                  30

Arg Ser Ala Ala Pro Gly Ser Ser Pro His His His His His His Gln
        35                  40                  45

Val Tyr Asn Ile Thr Trp Glu Val Thr Asn Gly Asp Arg Glu Thr Val
    50                  55                  60

Trp Ala Ile Ser Gly Asn His Pro Leu Trp Thr Trp Trp Pro Val Leu
65                  70                  75                  80

Thr Pro Asp Leu Cys Met Leu Ala Leu Ser Gly Pro Pro His Trp Gly
                85                  90                  95

Leu Glu Tyr Gln Ala Pro Tyr Ser Ser Pro Pro Gly Pro Pro Cys Cys
            100                 105                 110

Ser Gly Ser Ser Gly Ser Ser Ala Gly Cys Ser Arg Asp Cys Asp Glu
        115                 120                 125

Pro Leu Thr Ser Leu Thr Pro Arg Cys Asn Thr Ala Trp Asn Arg Leu
    130                 135                 140

Lys Leu Asp Gln Val Thr His Lys Ser Ser Glu Gly Phe Tyr Val Cys
145                 150                 155                 160

Pro Gly Ser His Arg Pro Arg Glu Ala Lys Ser Cys Gly Gly Pro Asp
                165                 170                 175

Ser Phe Tyr Cys Ala Ser Trp Gly Cys Glu Thr Thr Gly Arg Val Tyr
            180                 185                 190

Trp Lys Pro Ser Ser Ser Trp Asp Tyr Ile Thr Val Asp Asn Asn Leu
        195                 200                 205

Thr Thr Ser Gln Ala Val Gln Val Cys Lys Asp Asn Lys Trp Cys Asn
    210                 215                 220

Pro Leu Ala Ile Gln Phe Thr Asn Ala Gly Lys Gln Val Thr Ser Trp
225                 230                 235                 240

Thr Thr Gly His Tyr Trp Gly Leu Arg Leu Tyr Val Ser Gly Arg Asp
                245                 250                 255

Pro Gly Leu Thr Phe Gly Ile Arg Leu Arg Tyr Gln Asn Leu Gly Pro
            260                 265                 270

Arg Val Pro Ile Gly Pro Asn Pro Val Leu Ala Asp Gln Leu Ser Leu
        275                 280                 285

```
Pro Arg Pro Asn Pro Leu Pro Lys Pro Ala Lys Ser Pro Pro Ala Ser
    290                 295                 300

Val Lys Leu Thr Pro Leu Cys Val Thr Leu Asn Cys Ile Asp Leu Arg
305                 310                 315                 320

Asn Ala Thr Asn Ala Thr Ser Asn Ser Asn Thr Thr Asn Thr Thr Ser
                325                 330                 335

Ser Ser Gly Gly Leu Met Met Glu Gln Gly Glu Ile Lys Asn Cys Ser
            340                 345                 350

Phe Asn Ile Thr Thr Ser Ile Arg Asp Lys Lys Gln Lys Val His Ala
        355                 360                 365

Leu Phe Tyr Lys Leu Asp Ile Val Pro Ile Asp Asn Pro Lys Asn Ser
    370                 375                 380

Thr Asn Tyr Arg Leu Ile Ser Cys Asn Thr Ser Val Ile Thr Gln Ala
385                 390                 395                 400

<210> SEQ ID NO 128
<211> LENGTH: 323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
tcctatgagc tgacacagcc accctcggtg tcagtgtccc caggacaaac ggccaggatc      60
acctgctctg gagatgcatt gccaaaaaac tatgcttatt ggtaccagca gaagtcaggc     120
caggcccctg tgttggtcat ctatgaggac agcaaacgac cctccgggat ccctgagaga     180
ttctctggct ccagctcagg gacaatggcc accttgacta tcagtggggc ccaggttgag     240
gatgaagctg actactactg ttactcaaca gacagcagtg gtaatcatag ggtgttcggc     300
ggagggacca agctgaccgt cct                                             323

<210> SEQ ID NO 129
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asn Leu Thr Lys Ala Asn Leu Thr Asn Val Asn
        35                  40                  45

Asn Arg Thr Asn Val Ser Asn Ile Ile Gly Asn Ile Thr Asp Glu Val
    50                  55                  60

Arg Asn Cys Ser Phe Asn Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asn Asp Ser Ser Glu Tyr Arg Leu Ile Asn Cys Asn Thr Ser Val
            100                 105                 110

Ile Lys Gln Pro
        115
```

<210> SEQ ID NO 130
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Glu Thr Asp Thr Leu Leu Leu Trp Val Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asn Leu Thr Lys Ala Asn Leu Thr Asn Val Asn
        35                  40                  45

Asn Arg Thr Asn Val Ser Asn Ile Ile Gly Asn Ile Thr Asp Glu Val
    50                  55                  60

Arg Gln Cys Ser Phe Gln Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asn Asp Ser Ser Glu Tyr Arg Leu Ile Asn Cys Asn Thr Ser Val
            100                 105                 110

Ile Lys Gln Pro Gly Leu Asn Asp Ile Phe Glu Ala Gln Lys Ile Glu
        115                 120                 125

Trp His Glu Leu Glu Val Leu Phe Gln Gly Pro Gly His His His His
    130                 135                 140

His His
145

<210> SEQ ID NO 131
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Val Lys Leu Thr Pro Pro Cys Val Thr Leu His Cys Thr Asn Ala Asn
1               5                   10                  15

Leu Thr Lys Ala Asn Leu Thr Asn Val Asn Asn Arg Thr Asn Val Ser
            20                  25                  30

Asn Ile Ile Gly Asn Ile Thr Asp Glu Val Arg Gln Cys Ser Phe Gln
        35                  40                  45

Met Thr Thr Glu Leu Arg Asp Lys Lys Gln Lys Val His Ala Leu Phe
    50                  55                  60

Tyr Lys Leu Asp Ile Val Pro Ile Glu Asp Asn Asn Asp Ser Ser Glu
65                  70                  75                  80

Tyr Arg Leu Ile Asn Cys Asn Thr Ser Val Ile Lys Gln Pro
                85                  90

<210> SEQ ID NO 132
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asp Leu Thr Lys Ala Asp Leu Thr Asn Val Asn
        35                  40                  45

Asp Arg Thr Asp Val Ser Asn Ile Ile Gly Asp Ile Thr Asp Glu Val
    50                  55                  60

Arg Asn Cys Ser Phe Asn Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asp Asp Ser Ser Glu Tyr Arg Leu Ile Asn Cys Asp Thr Ser Val
            100                 105                 110

Ile Lys Gln Pro Gly Leu Asn Asp Ile Phe Glu Ala Gln Lys Ile Glu
            115                 120                 125

Trp His Glu Leu Glu Val Leu Phe Gln Gly Pro Gly His His His His
    130                 135                 140

His His
145

<210> SEQ ID NO 133
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Asp or Asn
<220> FEATURE:
<221> NAME/KEY: MOD_RES
<222> LOCATION: (21)..(21)
<223> OTHER INFORMATION: Asp or Asn
<220> FEATURE:
<221> NAME/KEY: MOD_RES
<222> LOCATION: (27)..(27)
<223> OTHER INFORMATION: Asp or Asn
<220> FEATURE:
<221> NAME/KEY: MOD_RES
<222> LOCATION: (30)..(30)
<223> OTHER INFORMATION: Asp or Asn
<220> FEATURE:
<221> NAME/KEY: MOD_RES
<222> LOCATION: (37)..(37)
<223> OTHER INFORMATION: Asp or Asn
<220> FEATURE:
<221> NAME/KEY: MOD_RES
<222> LOCATION: (76)..(76)
<223> OTHER INFORMATION: Asp or Asn
<220> FEATURE:
<221> NAME/KEY: MOD_RES
<222> LOCATION: (87)..(87)
<223> OTHER INFORMATION: Asp or Asn

<400> SEQUENCE: 133

Val Lys Leu Thr Pro Pro Cys Val Thr Leu His Cys Thr Asn Ala Xaa
1               5                   10                  15

Leu Thr Lys Ala Xaa Leu Thr Asn Val Asn Xaa Arg Thr Xaa Val Ser
            20                  25                  30

Asn Ile Ile Gly Xaa Ile Thr Asp Glu Val Arg Asn Cys Ser Phe Asn

-continued

```
                35                  40                  45

Met Thr Thr Glu Leu Arg Asp Lys Lys Gln Lys Val His Ala Leu Phe
 50                  55                  60

Tyr Lys Leu Asp Ile Val Pro Ile Glu Asp Asn Xaa Asp Ser Ser Glu
65                  70                  75                  80

Tyr Arg Leu Ile Asn Cys Xaa Thr Ser Val Ile Lys Gln Pro
                85                  90

<210> SEQ ID NO 134
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
                20                  25                  30

His Cys Thr Asn Ala Asp Leu Thr Lys Ala Asp Leu Thr Asn Val Asn
                35                  40                  45

Asp Arg Thr Asp Val Ser Asn Ile Ile Gly Asp Ile Thr Asp Glu Val
 50                  55                  60

Arg Asn Cys Ser Phe Asn Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asp Asp Ser Ser Glu Tyr Arg Leu Ile Asn Cys Asp Thr Ser Val
                100                 105                 110

Ile Lys Gln Pro
        115

<210> SEQ ID NO 135
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Val Lys Leu Thr Pro Leu Cys Val Thr Leu Asn Cys Ser Gln Tyr Val
1               5                   10                  15

Ser Ser His Val Asn Asn His Asn Ser Ser His Asn Val Ser Ser
                20                  25                  30

His Ser Gly Asn Ile Thr Ser Asp Met Lys Ile Cys Ser Phe Asn Thr
                35                  40                  45

Thr Thr Glu Val Arg Asp Lys Lys Gln Lys Val Tyr Ser Leu Phe Tyr
 50                  55                  60

Lys Leu Asp Val Val Pro Ile Ser Asn Asp Ser Ser Gln Tyr Arg Leu
65                  70                  75                  80

Ile Asn Cys Asn Thr Ser Ala Ile Thr Gln Ala
                85                  90

<210> SEQ ID NO 136
<211> LENGTH: 77
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 136

Val Lys Leu Thr Pro Leu Cys Val Thr Leu His Cys Thr Asn Val Thr
1               5                   10                  15

Ser Val Asn Thr Thr Gly Asp Arg Glu Gly Leu Lys Asn Cys Ser Phe
            20                  25                  30

Asn Met Thr Thr Glu Leu Arg Asp Lys Arg Lys Val Tyr Ser Leu Phe
        35                  40                  45

Tyr Arg Leu Asp Ile Val Pro Ile Asn Glu Asn Gln Gly Ser Glu Tyr
50                  55                  60

Arg Leu Ile Asn Cys Asn Thr Ser Ala Ile Thr Gln Ala
65                  70                  75

<210> SEQ ID NO 137
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Val Lys Leu Thr Pro Leu Cys Val Thr Leu Asn Cys Thr Asn Ala Asn
1               5                   10                  15

Val Thr Asn Val Lys Asn Ile Thr Asn Val Pro Asn Ile Ile Gly Asn
            20                  25                  30

Ile Thr Asp Glu Val Arg Asn Cys Ser Phe Asn Met Thr Thr Glu Leu
        35                  40                  45

Arg Asp Lys Lys Gln Lys Val His Ala Leu Phe Tyr Lys Leu Asp Ile
    50                  55                  60

Val Pro Ile Glu Asp Asn Thr Ser Ser Ser Glu Tyr Arg Leu Ile Asn
65                  70                  75                  80

Cys Asn Thr Ser Val Ile Lys Gln Ala
                85

<210> SEQ ID NO 138
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Val Lys Leu Thr Pro Leu Cys Val Thr Leu Asn Cys Thr Asp Val Thr
1               5                   10                  15

Asn Ala Thr Asn Ile Asn Ala Thr Asn Ile Asn Ser Ser Gly Gly
            20                  25                  30

Val Glu Ser Gly Glu Ile Lys Asn Cys Ser Phe Asn Ile Thr Thr Ser
        35                  40                  45

Val Arg Asp Lys Val Gln Lys Glu Tyr Ala Leu Phe Tyr Lys Leu Asp
    50                  55                  60

Ile Val Pro Ile Thr Asn Glu Ser Ser Lys Tyr Arg Leu Ile Ser Cys
65                  70                  75                  80

Asn Thr Ser Val Leu Thr Gln Ala
                85

<210> SEQ ID NO 139
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Val Lys Leu Thr Pro Leu Cys Val Ser Leu Lys Cys Thr Asp Leu Lys
1               5                   10                  15

Asn Asp Thr Asn Thr Asn Ser Ser Ser Gly Arg Met Ile Met Glu Lys
            20                  25                  30

Gly Glu Ile Lys Asn Cys Ser Phe Asn Ile Ser Thr Ser Ile Arg Gly
        35                  40                  45

Lys Val Gln Lys Glu Tyr Ala Phe Phe Tyr Lys Leu Asp Ile Ile Pro
    50                  55                  60

Ile Asp Asn Asp Thr Thr Ser Tyr Lys Leu Thr Ser Cys Asn Thr Ser
65                  70                  75                  80

Val Ile Thr Gln Ala
                85

<210> SEQ ID NO 140
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Val Lys Leu Thr Pro Leu Cys Val Thr Leu Asn Cys Thr Asp Leu Arg
1               5                   10                  15

Asn Thr Thr Asn Thr Asn Asn Ser Thr Asp Asn Asn Ser Lys Ser
            20                  25                  30

Glu Gly Thr Ile Lys Gly Gly Glu Met Lys Asn Cys Ser Phe Asn Ile
        35                  40                  45

Thr Thr Ser Ile Gly Asp Lys Met Gln Lys Glu Tyr Ala Leu Leu Tyr
    50                  55                  60

Lys Leu Asp Ile Glu Pro Ile Asp Asn Asp Ser Thr Ser Tyr Arg Leu
65                  70                  75                  80

Ile Ser Cys Asn Thr Ser Val Ile Thr Gln Ala
                85                  90

<210> SEQ ID NO 141
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Val Lys Leu Thr Pro Leu Cys Val Thr Leu Asn Cys Thr Asn Val Lys
1               5                   10                  15

Gly Asn Glu Ser Asp Thr Ser Glu Val Met Lys Asn Cys Ser Phe Lys
            20                  25                  30

Ala Thr Thr Glu Leu Lys Asp Lys Lys His Lys Val His Ala Leu Phe
        35                  40                  45

```
Tyr Lys Leu Asp Val Val Pro Leu Asn Gly Asn Ser Ser Ser Gly
    50                  55                  60

Glu Tyr Arg Leu Ile Asn Cys Asn Thr Ser Ala Ile Thr Gln Ala
65                  70                  75
```

<210> SEQ ID NO 142
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Val Lys Leu Thr Pro Leu Cys Val Thr Leu Asn Cys Thr Thr Asn Ser
1               5                   10                  15

Thr Asn Phe Ala Asn Ser Thr Gly Lys Asp Ile Glu Met Gln Asp Cys
                20                  25                  30

Ser Phe Asn Ile Thr Thr Glu Ile Arg Asp Lys Gln Lys Lys Val His
            35                  40                  45

Ala Leu Phe Tyr Lys Leu Asp Ile Val Gln Ile Asp Asn Asn Thr Glu
        50                  55                  60

Ala Asn Ala Asn Tyr Thr Ser Tyr Arg Leu Ile Asn Cys Asn Thr Ser
65                  70                  75                  80

Ala Ile Thr Gln Ala
                85
```

<210> SEQ ID NO 143
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Glu Ala Gly Gly Pro Asp Tyr Arg Asn Gly Tyr Asn Tyr Tyr Asp Phe
1               5                   10                  15

Tyr Asp Gly Tyr Tyr Asn Tyr His Tyr Met Asp Val
                20                  25
```

<210> SEQ ID NO 144
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Glu Leu Gly Gly Pro Asp Tyr Arg Asn Gly Tyr Asn Tyr His Asp Phe
1               5                   10                  15

Ser Ser Gly Tyr Tyr Asn Tyr His Tyr Leu Asp Tyr
                20                  25
```

<210> SEQ ID NO 145
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Glu Ala Gly Gly Pro Asp Tyr Arg Asn Gly Tyr Asn Tyr Tyr Asp Ser
1               5                   10                  15

Pro Arg Gly Glu Leu Asn Tyr His Pro Leu Asn Tyr
            20                  25

<210> SEQ ID NO 146
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Val His Glu Val Gln Leu Val Gln Ser Gly Ala Glu Val Lys Lys Pro
1               5                   10                  15

Gly Glu Ser Leu Lys Ile Ser Cys Lys Gly Ser Gly Tyr Arg Phe Thr
            20                  25                  30

Ser Tyr Trp Ile Val Trp Val Arg Gln Met Pro Gly Lys Gly Leu Glu
        35                  40                  45

Trp Met Gly Ile Ile Tyr Pro Gly Asp Phe Asp Thr Lys Tyr Ser Pro
50                  55                  60

Ser Phe Gln Gly Gln Val Thr Ile Ser Ala Asp Lys Ser Ile Ser Thr
65                  70                  75                  80

Ala Tyr Leu Gln Trp Ser Ser Leu Lys Ala Ser Asp Thr Ala Met Tyr
                85                  90                  95

Tyr Cys Ala Arg Leu Gly Gly Arg Tyr Tyr His Asp Ser Ser Gly Tyr
            100                 105                 110

Tyr Tyr Leu Asp Tyr Trp Gly Gln Gly Thr Leu Val Thr Val Ser Ser
        115                 120                 125

<210> SEQ ID NO 147
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Val Ala Ser Asp
            20                  25                  30

Tyr Val Gln Trp Tyr Gln Gln Arg Pro Gly Ser Ala Pro Thr Thr Val
        35                  40                  45

Val Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Asn
                85                  90                  95

Ser Ser Trp Val Phe Gly Gly Gly Thr Lys Leu Thr Val Leu
            100                 105                 110

<210> SEQ ID NO 148
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Val His Glu Val Gln Leu Val Glu Ser Gly Gly Leu Val Gln Pro
1               5                   10                  15

Gly Arg Ser Leu Arg Leu Ser Cys Ala Ala Ser Gly Phe Thr Phe Asp
            20                  25                  30

Asp Gly Ala Met His Trp Val Arg Gln Ala Pro Gly Lys Gly Leu Glu
        35                  40                  45

Trp Val Ser Gly Ile Ser Trp Asn Ser Asn Ile Ile Ala Tyr Ala Asp
50                  55                  60

Ser Val Lys Gly Arg Phe Thr Ile Ser Arg Asp Asn Ala Lys Asn Ser
65                  70                  75                  80

Leu Tyr Leu Glu Met Asn Ser Leu Arg Val Glu Asp Thr Ala Leu Tyr
                85                  90                  95

Tyr Cys Ala Lys Asp Ser Pro Arg Gly Glu Leu Pro Leu Asn Tyr Trp
            100                 105                 110

Gly Gln Gly Thr Leu Val Thr Val Ser Ser
        115                 120
```

<210> SEQ ID NO 149
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Asn Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Arg Val Phe Gly Gly Gly Thr Lys Leu Thr Val Leu
            100                 105
```

<210> SEQ ID NO 150
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

```
Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Leu Gly Gly Arg Tyr Tyr Tyr Asp Ser Ser Gly Tyr Tyr Tyr
            100                 105                 110

Phe Asp Tyr Trp Gly Gln Gly Thr Leu Val Thr Val Ser Ser
        115                 120                 125

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Ser Trp Val Phe Gly Gly Gly Thr Lys Leu Thr Val Leu
            100                 105                 110

<210> SEQ ID NO 152
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95
```

```
Ala Lys Asp Ser Pro Arg Gly Glu Leu Pro Phe Asp Tyr Trp Gly Gln
            100                 105                 110

Gly Thr Leu Val Thr Val Ser Ser
        115                 120

<210> SEQ ID NO 153
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn His
                85                  90                  95

Arg Val Phe Gly Gly Gly Thr Lys Leu Thr Val Leu
            100                 105

<210> SEQ ID NO 154
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Thr Thr Phe Lys Leu Ala Ala Cys Val Thr Leu Ala Cys Thr Ser
1               5                   10                  15

Pro Ala Ala His Ala Glu Ser Glu Thr Arg Val Lys His Cys Ser Phe
            20                  25                  30

Asn Ile Thr Thr Asp Val Lys Asp Arg Lys Gln Lys Val Asn Ala Thr
        35                  40                  45

Phe Tyr Asp Leu Asp Ile Val Pro Leu Ser Ser Ser Asp Ala Ser Ser
50                  55                  60

Ala Ser Ser Leu Tyr Arg Leu Ile Ser Cys Gln Thr Thr Thr Thr Glu
65                  70                  75                  80

Ala Val Asp Ala Ala Thr Ala Ala Lys Val Phe Lys Gln Tyr Ala Asn
                85                  90                  95

Asp Asn Gly Ile Asp Gly Glu Trp Thr Tyr Asp Asp Ala Thr Lys Thr
            100                 105                 110

Phe Thr Val Thr Glu Gly Leu Glu Val Leu Phe Gln
        115                 120

<210> SEQ ID NO 155
<211> LENGTH: 124
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 155

Met Thr Thr Phe Lys Leu Ala Ala Cys Val Thr Leu Arg Cys Thr Asn
1               5                   10                  15

Ala Thr Ile Asn Gly Ser Leu Thr Glu Val Lys Asn Cys Ser Phe
            20                  25                  30

Asn Ile Thr Thr Glu Leu Arg Asp Lys Lys Gln Lys Ala Tyr Ala Leu
        35                  40                  45

Phe Tyr Arg Pro Asp Val Val Pro Leu Asn Lys Asn Ser Pro Ser Gly
    50                  55                  60

Asn Ser Ser Glu Tyr Ile Leu Ile Asn Cys Gln Thr Thr Thr Thr Glu
65                  70                  75                  80

Ala Val Asp Ala Ala Thr Ala Ala Lys Val Phe Lys Gln Tyr Ala Asn
                85                  90                  95

Asp Asn Gly Ile Asp Gly Glu Trp Thr Tyr Asp Asp Ala Thr Lys Thr
            100                 105                 110

Phe Thr Val Thr Glu Gly Leu Glu Val Leu Phe Gln
        115                 120

<210> SEQ ID NO 156
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Glu Leu Arg Asp Lys Lys Gln Lys Val His Ala Leu Phe Tyr Lys Leu
1               5                   10                  15

Asp Ile Val Pro Ile Glu Asp
            20

<210> SEQ ID NO 157
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 157
aagcttgtcg acaccatgga gaccgacacc ctgctgctgt gggtgctgct gctgtgggtg     60
cccggctcca ccggcgacca ggtgaagctg acccccctgt gcgtgaccct gaactgcacc    120
aacgtgaagg gcaacgagtc cgacacctcc gaggtgatga agaactgctc cttcaaggcc    180
accaccgagc tgaaggacaa gaagcacaag gtgcacgccc tgttctacaa gctggacgtg    240
gtgcccctga cggcaactc ctcctcctcc ggcgagtacc gcctgatcaa ctgcaacacc    300
tccgccatca cccaggccta gggatcctct aga                                 333

<210> SEQ ID NO 158
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 158

```
aagcttgtcg acaccatgga gaccgacacc ctgctgctgt gggtgctgct gctgtgggtg    60
cccggctcca ccggcgacca ggtgaagctg accccctgt gcgtgaccct gaactgctcc    120
cagtacgtgt cctcccacgt gaacaaccac aacaactcct cccacaacgt gtcctcccac    180
tccggcaaca tcacctccga catgaagatc tgctccttca acaccaccac cgaggtgcgc    240
gacaagaagc agaaggtgta ctccctgttc tacaagctgg acgtggtgcc catctccaac    300
gactcctccc agtaccgcct gatcaactgc aacacctccg ccatcaccca ggcctaggga    360
tcctctaga                                                           369
```

<210> SEQ ID NO 159
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159

```
aagcttgtcg acaccatgga gaccgacacc ctgctgctgt gggtgctgct gctgtgggtg    60
cccggctcca ccggcgacca ggtgaagctg accccctgt gcgtgaccct gaactgcacc    120
gacgtgacca acgccaccaa catcaacgcc accaacatca caactcctc cggcggcgtg    180 gagtccggcg agatcaagaa ctgctccttc aacatcacca cctccgtgcg cgacaaggtg    240
cagaaggagt acgccctgtt ctacaagctg gacatcgtgc ccatcaccaa cgagtcctcc    300
aagtaccgcc tgatctcctg caacacctcc gtgctgaccc aggcctaggg atcctctaga    360
```

<210> SEQ ID NO 160
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160

```
aagcttgtcg acaccatgga gaccgacacc ctgctgctgt gggtgctgct gctgtgggtg    60
cccggctcca ccggcgacca ggtgaagctg accccctgt gcgtgaccct gaactgcacc    120
accaactcca ccaacttcgc caactccacc ggcaaggaca tcgagatgca ggactgctcc    180
ttcaacatca ccaccgagat ccgcgacaag cagaagaagg tgcacgccct gttctacaag    240
ctggacatcg tgcagatcga caacaacacc gaggccaacg ccaactacac ctcctaccgc    300
ctgatcaact gcaacacctc cgccatcacc caggcc                              336
```

<210> SEQ ID NO 161
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161

```
aagcttgtcg acaccatgga gaccgacacc ctgctgctgt gggtgctgct gctgtgggtg    60
cccggctcca ccggcgacca ggtgaagctg accccctgt gcgtgaccct gcactgcacc    120
aacgtgacct ccgtgaacac caccggcgac cgcgagggcc tgaagaactg ctccttcaac    180
atgaccaccg agctgcgcga caagcgccag aaggtgtact ccctgttcta ccgcctggac    240
```

```
atcgtgccca tcaacgagaa ccagggctcc gagtaccgcc tgatcaactg caacacctcc    300
gccatcaccc aggcctaggg atcctctaga                                     330
```

<210> SEQ ID NO 162
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162

```
aagcttgtcg acaccatgga gaccgacacc ctgctgctgt gggtgctgct gctgtgggtg    60
cccggctcca ccggcgacca ggtgaagctg acccccccct gcgtgaccct gcactgcacc   120
aacgccaacc tgaccaaggc caacctgacc aacgtgaaca accgcaccaa cgtgtccaac   180
atcatcggca acatcaccga cgaggtgcgc aactgctcct tcaacatgac caccgagctg   240
cgcgacaaga agcagaaggt gcacgccctg ttctacaagc tggacatcgt gcccatcgag   300
gacaacaacg actcctccga gtaccgcctg atcaactgca cacctccgt gatcaagcag   360 ccctagggat cctctaga                                                  378
```

<210> SEQ ID NO 163
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163

```
aagcttgtcg acaccatgga gaccgacacc ctgctgctgt gggtgctgct gctgtgggtg    60
cccggctcca ccggcgacca ggtgaagctg acccccctgt gcgtgaccct gaactgcatc   120
gacctgcgca acgccaccaa cgccacctcc aactccaaca ccaccaacac cacctcctcc   180
tccggcggcc tgatgatgga gcagggcgag atcaagaact gctccttcaa catcaccacc   240
tccatccgcg acaaggtgca gaaggagtac gccctgttct acaagctgga catcgtgccc   300
atcgacaacc ccaagaactc caccaactac cgcctgatct cctgcaacac ctccgtgatc   360
acccaggcct agggatcctc taga                                           384
```

<210> SEQ ID NO 164
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164

```
aagcttgtcg acaccatgga gaccgacacc ctgctgctgt gggtgctgct gctgtgggtg    60
cccggctcca ccggcgacca ggtgaagctg acccccctgt gcgtgtccct gaagtgcacc   120
gacctgaaga acgacaccaa caccaactcc tcctccggcc gcatgatcat ggagaagggc   180
gagatcaaga actgctcctt caacatctcc acctccatcc gcggcaaggt gcagaaggag   240
tacgccttct tctacaagct ggacatcatc cccatcgaca acgacaccac ctcctacaag   300
ctgacctcct gcaacacctc cgtgatcacc caggcctagg gatcctctag a             351
```

```
<210> SEQ ID NO 165
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 165
aagcttgtcg acaccatgga gaccgacacc ctgctgctgt gggtgctgct gctgtgggtg      60
cccggctcca ccggcgacca ggtgaagctg acccccctgt gcgtgaccct ggagtgcacc     120
aacgccaacc tgaaggagga caacaagacc accgactccc ccatccgcat cggcaacatc     180
tccgacgagg tgcgcaactg ctccttcaac atcaccaccg agatcaagga caagaagcag     240
caggtgcagg ccctgttcta ccgcctggac atcgtgcaga tgggcaacga ctcccgctac     300
cgcctgatca actgcaacac ctccgtgatc aagcagtagg gatcctctag a              351

<210> SEQ ID NO 166
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
aagcttgtcg acaccatgga gaccgacacc ctgctgctgt gggtgctgct gctgtgggtg      60
cccggctcca ccggcgacca ggtgaagctg acccccctgt gcgtgaccct gaagtgcacc     120
gccaacatca ccatcaccaa cgccaccacc cgcaccgaga caccaccaa ggagaacctg      180 atcggcaaca tcaccgacga gctgcgcaac tgctccttca acgtgaccac cgagctgcgc     240
gaccgccagc gcaaggccta cgccctgttc tacaagctgg acatcgtgcc catcaacaac     300
gaggccaact cctccgagta ccgcctgatc aactgcaaca cctccgtgat caagcagtag     360
ggatcctcta ga                                                         372

<210> SEQ ID NO 167
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 167
aagcttgtcg acaccatgga gaccgacacc ctgctgctgt gggtgctgct gctgtgggtg      60
cccggctcca ccggcgacca ggtgaagctg acccccctgt gcgtgaccct gaactgcacc     120
aacgtgaagg gcaacgagtc cgacacctcc gaggtgatga gaactgctc cttcaaggcc     180 accaccgagc tgaaggacaa gaagcacaag gtgcacgccc tgttctacaa gctggacgtg     240
gtgcccctga cggcaactc ctcctcctcc ggcgagtacc gcctgatcaa ctgcaacacc      300
tccgccatca cccaggccgg cctgaacgac atcttcgagg cccagaagat cgagtggcac     360
gagctggagg tgctgttcca gggccccggc caccatcacc atcaccacta gggatcctct     420
aga                                                                   423

<210> SEQ ID NO 168
<211> LENGTH: 459
<212> TYPE: DNA
<213> ORGANISM: Artificial Sequence
```

<220> FEATURE:
<223> OTHER INFORMATION: Description of Artificial Sequence: Synthetic
    polynucleotide

<400> SEQUENCE: 168

```
aagcttgtcg acaccatgga gaccgacacc ctgctgctgt gggtgctgct gctgtgggtg      60
cccggctcca ccggcgacca ggtgaagctg accccctgt gcgtgaccct gaactgctcc     120
cagtacgtgt cctcccacgt gaacaaccac aacaactcct cccacaacgt gtcctcccac    180
tccggcaaca tcacctccga catgaagatc tgctccttca acaccaccac cgaggtgcgc    240
gacaagaagc agaaggtgta ctccctgttc tacaagctgg acgtggtgcc catctccaac    300
gactcctccc agtaccgcct gatcaactgc aacacctccg ccatcaccca ggccggcctg    360
aacgacatct tcgaggccca gaagatcgag tggcacgagc tggaggtgct gttccagggc    420
cccggccacc atcaccatca ccactaggga tcctctaga                           459
```

<210> SEQ ID NO 169
<211> LENGTH: 453
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 169

```
aagcttgtcg acaccatgga gaccgacacc ctgctgctgt gggtgctgct gctgtgggtg      60
cccggctcca ccggcgacca ggtgaagctg accccctgt gcgtgaccct gaactgcacc     120
gacgtgacca acgccaccaa catcaacgcc accaacatca caactcctc cggcggcgtg     180
gagtccggcg agatcaagaa ctgctccttc aacatcacca cctccgtgcg cgacaaggtg    240
cagaaggagt acgccctgtt ctacaagctg gacatcgtgc ccatcaccaa cgagtcctcc    300
aagtaccgcc tgatctcctg caacacctcc gtgctgaccc aggccggcct gaacgacatc    360
ttcgaggccc agaagatcga gtggcacgag ctggaggtgc tgttccaggg ccccggccac    420
caccatcacc atcaccacta gggatcctct aga                                 453
```

<210> SEQ ID NO 170
<211> LENGTH: 441
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 170

```
aagcttgtcg acaccatgga gaccgacacc ctgctgctgt gggtgctgct gctgtgggtg      60
cccggctcca ccggcgacca ggtgaagctg accccctgt gcgtgaccct gaactgcacc     120
accaactcca caacttcgc caactccacc ggcaaggaca tcgagatgca ggactgctcc     180
ttcaacatca ccaccgagat ccgcgacaag cagaagaagg tgcacgccct gttctacaag    240
ctggacatcg tgcagatcga caacaacacc gaggccaacg ccaactacac ctcctaccgc    300
ctgatcaact gcaacacctc cgccatcacc caggccggcc tgaacgacat cttcgaggcc    360
cagaagatcg agtggcacga gctggaggtg ctgttccagg gccccggcca ccatcaccat    420
caccactagg gatcctctag a                                               441
```

<210> SEQ ID NO 171
<211> LENGTH: 420

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 171
aagcttgtcg acaccatgga gaccgacacc ctgctgctgt gggtgctgct gctgtgggtg      60
cccggctcca ccggcgacca ggtgaagctg accccctgt gcgtgaccct gcactgcacc     120
aacgtgacct ccgtgaacac caccggcgac cgcgagggcc tgaagaactg ctccttcaac     180
atgaccaccg agctgcgcga caagcgccag aaggtgtact ccctgttcta ccgcctggac     240
atcgtgccca tcaacgagaa ccagggctcc gagtaccgcc tgatcaactg caacacctcc     300
gccatcaccc aggccggcct gaacgacatc ttcgaggccc agaagatcga gtggcacgag     360
ctggaggtgc tgttccaggg ccccggccac catcaccatc accactaggg atcctctaga     420

<210> SEQ ID NO 172
<211> LENGTH: 468
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
aagcttgtcg acaccatgga gaccgacacc ctgctgctgt gggtgctgct gctgtgggtg      60
cccggctcca ccggcgacca ggtgaagctg acccccccct gcgtgaccct gcactgcacc    120
aacgccaacc tgaccaaggc caacctgacc aacgtgaaca accgcaccaa cgtgtccaac     180
atcatcggca acatcaccga cgaggtgcgc aactgctcct tcaacatgac caccgagctg     240
cgcgacaaga agcagaaggt gcacgccctg ttctacaagc tggacatcgt gcccatcgag     300
gacaacaacg actcctccga gtaccgcctg atcaactgca cacctccgt gatcaagcag      360 cccggcctga cgacatcttc gaggcccag aagatcgagt ggcacgagct ggaggtgctg      420
ttccagggcc ccggccacca tcaccatcac cactagggat cctctaga                  468

<210> SEQ ID NO 173
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
aagcttgtcg acaccatgga gaccgacacc ctgctgctgt gggtgctgct gctgtgggtg      60
cccggctcca ccggcgacca ggtgaagctg acccccctgt gcgtgaccct gaactgcatc     120
gacctgcgca acgccaccaa cgccacctcc aactccaaca ccaccaacac cacctcctcc     180
tccggcggcc tgatgatgga gcagggcgag atcaagaact gctccttcaa catcaccacc     240
tccatccgcg acaaggtgca gaaggagtac gccctgttct acaagctgga catcgtgccc     300
atcgacaacc ccaagaactc caccaactac cgcctgatct cctgcaacac ctccgtgatc     360
acccaggccg gcctgaacga catcttcgag gcccagaaga tcgagtggca cgagctggag     420
gtgctgttcc agggccccgg ccaccaccat caccatcacc actagggatc ctctaga       477

<210> SEQ ID NO 174
<211> LENGTH: 441
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
aagcttgtcg acaccatgga gaccgacacc ctgctgctgt gggtgctgct gctgtgggtg      60
cccggctcca ccggcgacca ggtgaagctg acccccctgt gcgtgtccct gaagtgcacc     120
gacctgaaga cgacaccaa caccaactcc tcctccggcc gcatgatcat ggagaagggc     180
gagatcaaga actgctcctt caacatctcc acctccatcc gcggcaaggt gcagaaggag     240
tacgccttct tctacaagct ggacatcatc cccatcgaca cgacaccac ctcctacaag     300 ctgacctcct gcaacacctc cgtgatcacc caggccggcc tgaacgacat cttcgaggcc     360
cagaagatcg agtggcacga gctggaggtg ctgttccagg gccccggcca ccatcaccat     420
caccactagg gatcctctag a                                               441

<210> SEQ ID NO 175
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
aagcttgtcg acaccatgga gaccgacacc ctgctgctgt gggtgctgct gctgtgggtg      60
cccggctcca ccggcgacca ggtgaagctg acccccctgt gcgtgaccct gaactgcacc     120
gacctgcgca acaccaccaa caccaacaac tccaccgaca caacaactc caagtccgag     180 ggcaccatca agggcggcga gatgaagaac tgctccttca acatcaccac ctccatcggc     240
gacaagatgc agaaggagta cgccctgctg tacaagctgg acatcgagcc catcgacaac     300
gactccacct cctaccgcct gatctcctgc aacacctccg tgatcaccca ggccggcctg     360
aacgacatct tcgaggccca gaagatcgag tggcacgagc tggaggtgct gttccagggc     420
cccggccacc accaccacca ccactaggga tcctctaga                            459

<210> SEQ ID NO 176
<211> LENGTH: 453
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
aagcttgtcg acaccatgga gaccgacacc ctgctgctgt gggtgctgct gctgtgggtg      60
cccggctcca ccggcgacca ggtgaagctg acccccctgt gcgtgaccct gaactgcacc     120
aacgccaacg tgaccaacgt gaagaacatc accaacgtgc ccaacatcat cggcaacatc     180
accgacgagg tgcgcaactg ctccttcaac atgaccaccg agctgcgcga caagaagcag     240
aaggtgcacg ccctgttcta caagctggac atcgtgccca tcgaggacaa cacctcctcc     300
tccgagtacc gcctgatcaa ctgcaacacc tccgtgatca agcaggccgg cctgaacgac     360
atcttcgagg cccagaagat cgagtggcac gagctggagg tgctgttcca gggccccggc     420
caccaccacc accaccacta gggatcctct aga                                  453
```

<210> SEQ ID NO 177
<211> LENGTH: 441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177

```
aagcttgtcg acaccatgga gaccgacacc ctgctgctgt gggtgctgct gctgtgggtg     60
cccggctcca ccggcgacca ggtgaagctg accccctgt gcgtgaccct ggagtgcacc     120
aacgccaacc tgaaggagga caacaagacc accgactccc ccatccgcat cggcaacatc    180
tccgacgagg tgcgcaactg ctccttcaac atcaccaccg agatcaagga caagaagcag    240
caggtgcagg ccctgttcta ccgcctggac atcgtgcaga tgggcaacga ctcccgctac    300
cgcctgatca actgcaacac ctccgtgatc aagcagggcc tgaacgacat cttcgaggcc    360
cagaagatcg agtggcacga gctggaggtg ctgttccagg cccccggcca ccaccaccac    420
caccactagg gatcctctag a                                              441
```

<210> SEQ ID NO 178
<211> LENGTH: 462
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178

```
aagcttgtcg acaccatgga gaccgacacc ctgctgctgt gggtgctgct gctgtgggtg     60
cccggctcca ccggcgacca ggtgaagctg accccctgt gcgtgaccct gaagtgcacc     120
gccaacatca ccatcaccaa cgccaccacc cgcaccgaga caccaccaa ggagaacctg    180
atcggcaaca tcaccgacga gctgcgcaac tgctccttca cgtgaccac cgagctgcgc    240
gaccgccagc gcaaggccta cgccctgttc tacaagctgg acatcgtgcc catcaacaac    300
gaggccaact cctccgagta ccgcctgatc aactgcaaca cctccgtgat caagcagggc    360
ctgaacgaca tcttcgaggc ccagaagatc gagtggcacg agctggaggt gctgttccag    420
ggccccggcc accaccacca ccaccactag ggatcctcta ga                       462
```

<210> SEQ ID NO 179
<211> LENGTH: 101
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

```
Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asn Val Lys Gly Asn Glu Ser Asp Thr Ser Glu Val Met
        35                  40                  45

Lys Asn Cys Ser Phe Lys Ala Thr Thr Glu Leu Lys Asp Lys Lys His
    50                  55                  60

Lys Val His Ala Leu Phe Tyr Lys Leu Asp Val Val Pro Leu Asn Gly
65                  70                  75                  80
```

Asn Ser Ser Ser Ser Gly Glu Tyr Arg Leu Ile Asn Cys Asn Thr Ser
                85                  90                  95

Ala Ile Thr Gln Ala
            100

<210> SEQ ID NO 180
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Ser Gln Tyr Val Ser Ser His Val Asn Asn His Asn Ser
        35                  40                  45

Ser His Asn Val Ser Ser His Ser Gly Asn Ile Thr Ser Asp Met Lys
    50                  55                  60

Ile Cys Ser Phe Asn Thr Thr Thr Glu Val Arg Asp Lys Lys Gln Lys
65                  70                  75                  80

Val Tyr Ser Leu Phe Tyr Lys Leu Asp Val Val Pro Ile Ser Asn Asp
                85                  90                  95

Ser Ser Gln Tyr Arg Leu Ile Asn Cys Asn Thr Ser Ala Ile Thr Gln
            100                 105                 110

Ala

<210> SEQ ID NO 181
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asp Val Thr Asn Ala Thr Asn Ile Asn Ala Thr Asn Ile
        35                  40                  45

Asn Asn Ser Ser Gly Gly Val Glu Ser Gly Glu Ile Lys Asn Cys Ser
    50                  55                  60

Phe Asn Ile Thr Thr Ser Val Arg Asp Lys Val Gln Lys Glu Tyr Ala
65                  70                  75                  80

Leu Phe Tyr Lys Leu Asp Ile Val Pro Ile Thr Asn Glu Ser Ser Lys
                85                  90                  95

Tyr Arg Leu Ile Ser Cys Asn Thr Ser Val Leu Thr Gln Ala
            100                 105                 110

<210> SEQ ID NO 182
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 182

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Thr Asn Ser Thr Asn Phe Ala Asn Ser Thr Gly Lys Asp
        35                  40                  45

Ile Glu Met Gln Asp Cys Ser Phe Asn Ile Thr Thr Glu Ile Arg Asp
    50                  55                  60

Lys Gln Lys Lys Val His Ala Leu Phe Tyr Lys Leu Asp Ile Val Gln
65                  70                  75                  80

Ile Asp Asn Asn Thr Glu Ala Asn Ala Asn Tyr Thr Ser Tyr Arg Leu
                85                  90                  95

Ile Asn Cys Asn Thr Ser Ala Ile Thr Gln Ala
            100                 105

<210> SEQ ID NO 183
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

His Cys Thr Asn Val Thr Ser Val Asn Thr Thr Gly Asp Arg Glu Gly
        35                  40                  45

Leu Lys Asn Cys Ser Phe Asn Met Thr Thr Glu Leu Arg Asp Lys Arg
    50                  55                  60

Gln Lys Val Tyr Ser Leu Phe Tyr Arg Leu Asp Ile Val Pro Ile Asn
65                  70                  75                  80

Glu Asn Gln Gly Ser Glu Tyr Arg Leu Ile Asn Cys Asn Thr Ser Ala
                85                  90                  95

Ile Thr Gln Ala
            100

<210> SEQ ID NO 184
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asn Leu Thr Lys Ala Asn Leu Thr Asn Val Asn
        35                  40                  45

Asn Arg Thr Asn Val Ser Asn Ile Ile Gly Asn Ile Thr Asp Glu Val
    50                  55                  60

Arg Asn Cys Ser Phe Asn Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asn Asp Ser Ser Glu Tyr Arg Leu Ile Asn Cys Asn Thr Ser Val
            100                 105                 110

Ile Lys Gln Pro
        115

<210> SEQ ID NO 185
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Met Glu Thr Asp Thr Leu Leu Leu Trp Val Leu Leu Trp Val Pro
1               5                   10                  15

Gly Ser Thr Gly Asp Gln Val Lys Leu Thr Pro Leu Cys Val Thr Leu
            20                  25                  30

Asn Cys Ile Asp Leu Arg Asn Ala Thr Asn Ala Thr Ser Asn Ser Asn
        35                  40                  45

Thr Thr Asn Thr Thr Ser Ser Ser Gly Gly Leu Met Met Glu Gln Gly
    50                  55                  60

Glu Ile Lys Asn Cys Ser Phe Asn Ile Thr Thr Ser Ile Arg Asp Lys
65                  70                  75                  80

Val Gln Lys Glu Tyr Ala Leu Phe Tyr Lys Leu Asp Ile Val Pro Ile
                85                  90                  95

Asp Asn Pro Lys Asn Ser Thr Asn Tyr Arg Leu Ile Ser Cys Asn Thr
            100                 105                 110

Ser Val Ile Thr Gln Ala
        115

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Met Glu Thr Asp Thr Leu Leu Leu Trp Val Leu Leu Trp Val Pro
1               5                   10                  15

Gly Ser Thr Gly Asp Gln Val Lys Leu Thr Pro Leu Cys Val Ser Leu
            20                  25                  30

Lys Cys Thr Asp Leu Lys Asn Asp Thr Asn Thr Asn Ser Ser Ser Gly
        35                  40                  45

Arg Met Ile Met Glu Lys Gly Glu Ile Lys Asn Cys Ser Phe Asn Ile
    50                  55                  60

Ser Thr Ser Ile Arg Gly Lys Val Gln Lys Glu Tyr Ala Phe Phe Tyr
65                  70                  75                  80

Lys Leu Asp Ile Ile Pro Ile Asp Asn Asp Thr Thr Ser Tyr Lys Leu
                85                  90                  95

Thr Ser Cys Asn Thr Ser Val Ile Thr Gln Ala
            100                 105

<210> SEQ ID NO 187
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Glu Thr Asp Thr Leu Leu Leu Trp Val Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asp Leu Arg Asn Thr Thr Asn Thr Asn Asn Ser Thr Asp
        35                  40                  45

Asn Asn Asn Ser Lys Ser Glu Gly Thr Ile Lys Gly Gly Glu Met Lys
    50                  55                  60

Asn Cys Ser Phe Asn Ile Thr Ser Ile Gly Asp Lys Met Gln Lys
65                  70                  75                  80

Glu Tyr Ala Leu Leu Tyr Lys Leu Asp Ile Glu Pro Ile Asp Asn Asp
                85                  90                  95

Ser Thr Ser Tyr Arg Leu Ile Ser Cys Asn Thr Ser Val Ile Thr Gln
            100                 105                 110

Ala

<210> SEQ ID NO 188
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Met Glu Thr Asp Thr Leu Leu Leu Trp Val Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asn Ala Asn Val Thr Asn Val Lys Asn Ile Thr Asn Val
        35                  40                  45

Pro Asn Ile Ile Gly Asn Ile Thr Asp Glu Val Arg Asn Cys Ser Phe
    50                  55                  60

Asn Met Thr Thr Glu Leu Arg Asp Lys Lys Gln Lys Val His Ala Leu
65                  70                  75                  80

Phe Tyr Lys Leu Asp Ile Val Pro Ile Glu Asp Asn Thr Ser Ser
                85                  90                  95

Glu Tyr Arg Leu Ile Asn Cys Asn Thr Ser Val Ile Lys Gln Ala
            100                 105                 110

<210> SEQ ID NO 189
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Met Glu Thr Asp Thr Leu Leu Leu Trp Val Leu Leu Trp Val Pro

-continued

```
                1               5                  10                  15
Gly Ser Thr Gly Asp Gln Val Lys Leu Thr Pro Leu Cys Val Thr Leu
                20                  25                  30

Glu Cys Thr Asn Ala Asn Leu Lys Glu Asp Asn Lys Thr Thr Asp Ser
            35                  40                  45

Pro Ile Arg Ile Gly Asn Ile Ser Asp Glu Val Arg Asn Cys Ser Phe
        50                  55                  60

Asn Ile Thr Thr Glu Ile Lys Asp Lys Gln Gln Val Gln Ala Leu
 65                  70                  75                  80

Phe Tyr Arg Leu Asp Ile Val Gln Met Gly Asn Asp Ser Arg Tyr Arg
                85                  90                  95

Leu Ile Asn Cys Asn Thr Ser Val Ile Lys Gln
            100                 105
```

<210> SEQ ID NO 190
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 190

```
Met Glu Thr Asp Thr Leu Leu Leu Trp Val Leu Leu Leu Trp Val Pro
 1               5                  10                  15

Gly Ser Thr Gly Asp Gln Val Lys Leu Thr Pro Leu Cys Val Thr Leu
                20                  25                  30

Lys Cys Thr Ala Asn Ile Thr Ile Thr Asn Ala Thr Thr Arg Thr Glu
            35                  40                  45

Asn Thr Thr Lys Glu Asn Leu Ile Gly Asn Ile Thr Asp Glu Leu Arg
        50                  55                  60

Asn Cys Ser Phe Asn Val Thr Thr Glu Leu Arg Asp Arg Gln Arg Lys
 65                  70                  75                  80

Ala Tyr Ala Leu Phe Tyr Lys Leu Asp Ile Val Pro Ile Asn Asn Glu
                85                  90                  95

Ala Asn Ser Ser Glu Tyr Arg Leu Ile Asn Cys Asn Thr Ser Val Ile
            100                 105                 110

Lys Gln
```

<210> SEQ ID NO 191
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

```
Met Glu Thr Asp Thr Leu Leu Leu Trp Val Leu Leu Leu Trp Val Pro
 1               5                  10                  15

Gly Ser Thr Gly Asp Gln Val Lys Leu Thr Pro Leu Cys Val Thr Leu
                20                  25                  30

Asn Cys Thr Asn Val Lys Gly Asn Glu Ser Asp Thr Ser Glu Val Met
            35                  40                  45

Lys Asn Cys Ser Phe Lys Ala Thr Thr Glu Leu Lys Asp Lys His
        50                  55                  60

Lys Val His Ala Leu Phe Tyr Lys Leu Asp Val Val Pro Leu Asn Gly
 65                  70                  75                  80
```

Asn Ser Ser Ser Gly Glu Tyr Arg Leu Ile Asn Cys Asn Thr Ser
            85                  90                  95

Ala Ile Thr Gln Ala Gly Leu Asn Asp Ile Phe Glu Ala Gln Lys Ile
        100                 105                 110

Glu Trp His Glu Leu Glu Val Leu Phe Gln Gly Pro Gly His His His
    115                 120                 125

His His His
    130

<210> SEQ ID NO 192
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Ser Gln Tyr Val Ser Ser His Val Asn Asn His Asn Asn Ser
        35                  40                  45

Ser His Asn Val Ser Ser His Ser Gly Asn Ile Thr Ser Asp Met Lys
    50                  55                  60

Ile Cys Ser Phe Asn Thr Thr Thr Glu Val Arg Asp Lys Lys Gln Lys
65                  70                  75                  80

Val Tyr Ser Leu Phe Tyr Lys Leu Asp Val Val Pro Ile Ser Asn Asp
                85                  90                  95

Ser Ser Gln Tyr Arg Leu Ile Asn Cys Asn Thr Ser Ala Ile Thr Gln
            100                 105                 110

Ala Gly Leu Asn Asp Ile Phe Glu Ala Gln Lys Ile Glu Trp His Glu
        115                 120                 125

Leu Glu Val Leu Phe Gln Gly Pro Gly His His His His His His
    130                 135                 140

<210> SEQ ID NO 193
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asp Val Thr Asn Ala Thr Asn Ile Asn Ala Thr Asn Ile
        35                  40                  45

Asn Asn Ser Ser Gly Gly Val Glu Ser Gly Glu Ile Lys Asn Cys Ser
    50                  55                  60

Phe Asn Ile Thr Thr Ser Val Arg Asp Lys Val Gln Lys Glu Tyr Ala
65                  70                  75                  80

Leu Phe Tyr Lys Leu Asp Ile Val Pro Ile Thr Asn Glu Ser Ser Lys
                85                  90                  95

Tyr Arg Leu Ile Ser Cys Asn Thr Ser Val Leu Thr Gln Ala Gly Leu
            100                 105                 110

Asn Asp Ile Phe Glu Ala Gln Lys Ile Glu Trp His Glu Leu Glu Val
        115                 120                 125

Leu Phe Gln Gly Pro Gly His His His His His
    130                 135                 140

<210> SEQ ID NO 194
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Thr Asn Ser Thr Asn Phe Ala Asn Ser Thr Gly Lys Asp
        35                  40                  45

Ile Glu Met Gln Asp Cys Ser Phe Asn Ile Thr Thr Glu Ile Arg Asp
50                  55                  60

Lys Gln Lys Lys Val His Ala Leu Phe Tyr Lys Leu Asp Ile Val Gln
65                  70                  75                  80

Ile Asp Asn Asn Thr Glu Ala Asn Ala Asn Tyr Thr Ser Tyr Arg Leu
                85                  90                  95

Ile Asn Cys Asn Thr Ser Ala Ile Thr Gln Ala Gly Leu Asn Asp Ile
            100                 105                 110

Phe Glu Ala Gln Lys Ile Glu Trp His Glu Leu Glu Val Leu Phe Gln
        115                 120                 125

Gly Pro Gly His His His His His
    130                 135

<210> SEQ ID NO 195
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

His Cys Thr Asn Val Thr Ser Val Asn Thr Thr Gly Asp Arg Glu Gly
        35                  40                  45

Leu Lys Asn Cys Ser Phe Asn Met Thr Thr Glu Leu Arg Asp Lys Arg
50                  55                  60

Gln Lys Val Tyr Ser Leu Phe Tyr Arg Leu Asp Ile Val Pro Ile Asn
65                  70                  75                  80

Glu Asn Gln Gly Ser Glu Tyr Arg Leu Ile Asn Cys Asn Thr Ser Ala
                85                  90                  95

Ile Thr Gln Ala Gly Leu Asn Asp Ile Phe Glu Ala Gln Lys Ile Glu
            100                 105                 110

-continued

```
Trp His Glu Leu Glu Val Leu Phe Gln Gly Pro Gly His His His
        115                 120                 125

His His
    130

<210> SEQ ID NO 196
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asn Leu Thr Lys Ala Asn Leu Thr Asn Val Asn
        35                  40                  45

Asn Arg Thr Asn Val Ser Asn Ile Ile Gly Asn Ile Thr Asp Glu Val
50                  55                  60

Arg Asn Cys Ser Phe Asn Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asn Asp Ser Ser Glu Tyr Arg Leu Ile Asn Cys Asn Thr Ser Val
            100                 105                 110

Ile Lys Gln Pro Gly Leu Asn Asp Ile Phe Glu Ala Gln Lys Ile Glu
        115                 120                 125

Trp His Glu Leu Glu Val Leu Phe Gln Gly Pro Gly His His His His
    130                 135                 140

His His
145

<210> SEQ ID NO 197
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Ile Asp Leu Arg Asn Ala Thr Asn Ala Thr Ser Asn Ser Asn
        35                  40                  45

Thr Thr Asn Thr Thr Ser Ser Ser Gly Gly Leu Met Met Glu Gln Gly
    50                  55                  60

Glu Ile Lys Asn Cys Ser Phe Asn Ile Thr Thr Ser Ile Arg Asp Lys
65                  70                  75                  80

Val Gln Lys Glu Tyr Ala Leu Phe Tyr Lys Leu Asp Ile Val Pro Ile
                85                  90                  95

Asp Asn Pro Lys Asn Ser Thr Asn Tyr Arg Leu Ile Ser Cys Asn Thr
            100                 105                 110
```

Ser Val Ile Thr Gln Ala Gly Leu Asn Asp Ile Phe Glu Ala Gln Lys
          115                 120                 125

Ile Glu Trp His Glu Leu Glu Val Leu Phe Gln Gly Pro Gly His His
    130                 135                 140

His His His His
145

<210> SEQ ID NO 198
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Ser Leu
            20                  25                  30

Lys Cys Thr Asp Leu Lys Asn Asp Thr Asn Thr Asn Ser Ser Ser Gly
        35                  40                  45

Arg Met Ile Met Glu Lys Gly Glu Ile Lys Asn Cys Ser Phe Asn Ile
    50                  55                  60

Ser Thr Ser Ile Arg Gly Lys Val Gln Lys Glu Tyr Ala Phe Phe Tyr
65                  70                  75                  80

Lys Leu Asp Ile Ile Pro Ile Asp Asn Asp Thr Thr Ser Tyr Lys Leu
                85                  90                  95

Thr Ser Cys Asn Thr Ser Val Ile Thr Gln Ala Gly Leu Asn Asp Ile
            100                 105                 110

Phe Glu Ala Gln Lys Ile Glu Trp His Glu Leu Glu Val Leu Phe Gln
        115                 120                 125

Gly Pro Gly His His His His His His
    130                 135

<210> SEQ ID NO 199
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asp Leu Arg Asn Thr Thr Asn Thr Asn Asn Ser Thr Asp
        35                  40                  45

Asn Asn Asn Ser Lys Ser Glu Gly Thr Ile Lys Gly Gly Glu Met Lys
    50                  55                  60

Asn Cys Ser Phe Asn Ile Thr Thr Ser Ile Gly Asp Lys Met Gln Lys
65                  70                  75                  80

Glu Tyr Ala Leu Leu Tyr Lys Leu Asp Ile Glu Pro Ile Asp Asn Asp
                85                  90                  95

Ser Thr Ser Tyr Arg Leu Ile Ser Cys Asn Thr Ser Val Ile Thr Gln
            100                 105                 110

Ala Gly Leu Asn Asp Ile Phe Glu Ala Gln Lys Ile Glu Trp His Glu
        115                 120                 125

Leu Glu Val Leu Phe Gln Gly Pro Gly His His His His His His
    130                 135                 140

<210> SEQ ID NO 200
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Asn Cys Thr Asn Ala Asn Val Thr Asn Val Lys Asn Ile Thr Asn Val
        35                  40                  45

Pro Asn Ile Ile Gly Asn Ile Thr Asp Glu Val Arg Asn Cys Ser Phe
    50                  55                  60

Asn Met Thr Thr Glu Leu Arg Asp Lys Lys Gln Lys Val His Ala Leu
65                  70                  75                  80

Phe Tyr Lys Leu Asp Ile Val Pro Ile Glu Asp Asn Thr Ser Ser Ser
                85                  90                  95

Glu Tyr Arg Leu Ile Asn Cys Asn Thr Ser Val Ile Lys Gln Ala Gly
            100                 105                 110

Leu Asn Asp Ile Phe Glu Ala Gln Lys Ile Glu Trp His Glu Leu Glu
        115                 120                 125

Val Leu Phe Gln Gly Pro Gly His His His His His His
    130                 135                 140

<210> SEQ ID NO 201
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Glu Cys Thr Asn Ala Asn Leu Lys Glu Asp Asn Lys Thr Thr Asp Ser
        35                  40                  45

Pro Ile Arg Ile Gly Asn Ile Ser Asp Glu Val Arg Asn Cys Ser Phe
    50                  55                  60

Asn Ile Thr Thr Glu Ile Lys Asp Lys Lys Gln Gln Val Gln Ala Leu
65                  70                  75                  80

Phe Tyr Arg Leu Asp Ile Val Gln Met Gly Asn Asp Ser Arg Tyr Arg
                85                  90                  95

Leu Ile Asn Cys Asn Thr Ser Val Ile Lys Gln Gly Leu Asn Asp Ile
            100                 105                 110

Phe Glu Ala Gln Lys Ile Glu Trp His Glu Leu Glu Val Leu Phe Gln
        115                 120                 125

```
Gly Pro Gly His His His His His
        130                 135
```

<210> SEQ ID NO 202
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

```
Met Glu Thr Asp Thr Leu Leu Leu Trp Val Leu Leu Leu Trp Val Pro
1               5                   10                  15

Gly Ser Thr Gly Asp Gln Val Lys Leu Thr Pro Leu Cys Val Thr Leu
            20                  25                  30

Lys Cys Thr Ala Asn Ile Thr Ile Thr Asn Ala Thr Thr Arg Thr Glu
        35                  40                  45

Asn Thr Thr Lys Glu Asn Leu Ile Gly Asn Ile Thr Asp Glu Leu Arg
    50                  55                  60

Asn Cys Ser Phe Asn Val Thr Thr Glu Leu Arg Asp Arg Gln Arg Lys
65                  70                  75                  80

Ala Tyr Ala Leu Phe Tyr Lys Leu Asp Ile Val Pro Ile Asn Asn Glu
                85                  90                  95

Ala Asn Ser Ser Glu Tyr Arg Leu Ile Asn Cys Asn Thr Ser Val Ile
            100                 105                 110

Lys Gln Gly Leu Asn Asp Ile Phe Glu Ala Gln Lys Ile Glu Trp His
        115                 120                 125

Glu Leu Glu Val Leu Phe Gln Gly Pro Gly His His His His His His
    130                 135                 140
```

<210> SEQ ID NO 203
<211> LENGTH: 468
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203

```
aagcttgtcg acaccatgga gaccgacacc ctgctgctgt gggtgctgct gctgtgggtg    60
cccggctcca ccggcgacca ggtgaagctg accccccccct gcgtgaccct gcactgcacc   120
aacgccgacc tgaccaaggc cgacctgacc aacgtgaacg accgcaccga cgtgtccaac   180
atcatcggcg acatcaccga cgaggtgcgc aactgctcct tcaacatgac caccgagctg   240
cgcgacaaga agcagaaggt gcacgccctg ttctacaagc tggacatcgt gcccatcgag   300
gacaacgacg actcctccga gtaccgcctg atcaactgcg acacctccgt gatcaagcag   360
cccggcctga cgacatcctt cgaggcccag aagatcgagt ggcacgagct ggaggtgctg   420
ttccagggcc ccggccacca tcaccatcac cactagggat cctctaga                468
```

<210> SEQ ID NO 204
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asp Leu Thr Lys Ala Asp Leu Thr Asn Val Asn
        35                  40                  45

Asp Arg Thr Asp Val Ser Asn Ile Ile Gly Asp Ile Thr Asp Glu Val
    50                  55                  60

Arg Asn Cys Ser Phe Asn Met Thr Thr Glu Leu Arg Asp Lys Lys Gln
65                  70                  75                  80

Lys Val His Ala Leu Phe Tyr Lys Leu Asp Ile Val Pro Ile Glu Asp
                85                  90                  95

Asn Asp Asp Ser Ser Glu Tyr Arg Leu Ile Asn Cys Asp Thr Ser Val
            100                 105                 110

Ile Lys Gln Pro Gly Leu Asn Asp Ile Phe Glu Ala Gln Lys Ile Glu
        115                 120                 125

Trp His Glu Leu Glu Val Leu Phe Gln Gly Pro Gly His His His His
    130                 135                 140

His His
145

<210> SEQ ID NO 205
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
aagcttgtcg acaccatgga gaccgacacc ctgctgctgt gggtgctgct gctgtgggtg    60
cccggctcca ccggcgacca ggtgaagctg accccccccT gcgtgaccct gcactgcacc   120
aacgccgacc tgaccaaggc cgacctgacc aacgtgaacg accgcaccga cgtgtccaac   180
atcatcggcg acatcaccga cgaggtgcgc aactgctcct tcaacatgac caccgagctg   240
cgcgacaaga agcagaaggt gcacgccctg ttctacaagc tggacatcgt gcccatcgag   300
gacaacgacg actcctccga gtaccgcctg atcaactgcg acacctccgt gatcaagcag   360
ccctagggat cctctaga                                                 378

<210> SEQ ID NO 206
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Met Glu Thr Asp Thr Leu Leu Leu Trp Val Leu Leu Leu Trp Val Pro
1               5                   10                  15

Gly Ser Thr Gly Asp Gln Val Lys Leu Thr Pro Pro Cys Val Thr Leu
            20                  25                  30

His Cys Thr Asn Ala Asp Leu Thr Lys Ala Asp Leu Thr Asn Val Asn
        35                  40                  45

Asp Arg Thr Asp Val Ser Asn Ile Ile Gly Asp Ile Thr Asp Glu Val
    50                  55                  60

```
Arg Asn Cys Ser Phe Asn Met Thr Thr Glu Leu Arg Asp Lys Lys Gln
 65                  70                  75                  80

Lys Val His Ala Leu Phe Tyr Lys Leu Asp Ile Val Pro Ile Glu Asp
                 85                  90                  95

Asn Asp Asp Ser Ser Glu Tyr Arg Leu Ile Asn Cys Asp Thr Ser Val
            100                 105                 110

Ile Lys Gln Pro
        115
```

```
<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asp Lys Lys Gln Lys Val His Ala Leu Phe Tyr
1               5                   10
```

```
<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asp Lys Lys Gln Lys Ala Tyr Ala Leu Phe Tyr
1               5                   10
```

```
<210> SEQ ID NO 209
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Glu Ala Gly Gly Pro Ile Trp His Asp Asp Val Lys Tyr Tyr Asp Phe
1               5                   10                  15

Asn Asp Gly Tyr Tyr Asn Tyr His Tyr Met Asp Val
            20                  25
```

```
<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Leu Gly Gly Arg Tyr Tyr His Asp Ser Ser Gly Tyr Tyr Leu Asp
1               5                   10                  15

Tyr
```

```
<210> SEQ ID NO 211
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 211

Asp Ser Pro Arg Gly Glu Leu Pro Leu Asn Tyr
1               5                   10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Thr Ser Gly Val Gly Leu His Phe Gly Tyr Phe Asp Tyr
1               5                   10

<210> SEQ ID NO 213
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Thr Asp Tyr Thr Ile Asp Asp Ala Gly Ile His Tyr Gln Gly Ser
1               5                   10                  15

Gly Thr Phe Trp Tyr Phe Asp Leu
            20

<210> SEQ ID NO 214
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Glu Ala Gly Gly Pro Asp Tyr Arg Asn Gly Tyr Asn Tyr Tyr Asp Phe
1               5                   10                  15

Trp Ser Gly Tyr Tyr Asn Tyr Tyr Tyr Met Asp Val
            20                  25

<210> SEQ ID NO 215
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Glu Ala Gly Gly Pro Ile Trp His Asp Asp Val Lys Tyr Tyr Asp Phe
1               5                   10                  15

Asn Asp Gly Tyr Tyr Tyr Tyr Tyr Met Asp Val
            20                  25

<210> SEQ ID NO 216
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 216

Leu Gly Gly Arg Tyr Tyr Tyr Asp Ser Ser Gly Tyr Tyr Tyr Phe Asp
1               5                   10                  15

Tyr

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Asp Ser Pro Arg Gly Glu Leu Pro Phe Asp Tyr
1               5                   10

<210> SEQ ID NO 218
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Thr Asp Tyr Thr Ile Asp Asp Gln Gly Ile Arg Tyr Gln Gly Ser
1               5                   10                  15

Gly Thr Phe Trp Tyr Phe Asp Leu
            20

<210> SEQ ID NO 219
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Val Arg Glu Ala Gly Gly Pro Asp Tyr Arg Asn Gly Tyr Asn Tyr Tyr
1               5                   10                  15

Asp Phe Tyr Asp Gly Tyr Tyr Asn Tyr His Tyr Met Asp Val
            20                  25                  30

<210> SEQ ID NO 220
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Ala Arg Glu Ala Gly Gly Pro Ile Trp His Asp Asp Val Lys Tyr Tyr
1               5                   10                  15

Asp Phe Asn Asp Gly Tyr Tyr Asn Tyr His Tyr Met Asp Val
            20                  25                  30

<210> SEQ ID NO 221
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 221

Ala Arg Leu Gly Gly Arg Tyr Tyr His Asp Ser Ser Gly Tyr Tyr Tyr
1               5                   10                  15

Leu Asp Tyr

<210> SEQ ID NO 222
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Lys Asp Ser Pro Arg Gly Glu Leu Pro Leu Asn Tyr
1               5                   10

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ala Thr Thr Ser Gly Val Gly Leu His Phe Gly Tyr Phe Asp Tyr
1               5                   10                  15

<210> SEQ ID NO 224
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Arg Gly Thr Asp Tyr Thr Ile Asp Ala Gly Ile His Tyr Gln
1               5                   10                  15

Gly Ser Gly Thr Phe Trp Tyr Phe Asp Leu
            20                  25

<210> SEQ ID NO 225
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Ala Arg Glu Ala Gly Gly Pro Asp Tyr Arg Asn Gly Tyr Asn Tyr Tyr
1               5                   10                  15

Asp Phe Trp Ser Gly Tyr Tyr Asn Tyr Tyr Met Asp Val
            20                  25                  30

<210> SEQ ID NO 226
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 226

Ala Arg Glu Ala Gly Gly Pro Ile Trp His Asp Asp Val Lys Tyr Tyr
1               5                   10                  15

Asp Phe Asn Asp Gly Tyr Tyr Tyr Tyr Tyr Met Asp Val
            20                  25                  30

<210> SEQ ID NO 227
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ala Arg Leu Gly Gly Arg Tyr Tyr Tyr Asp Ser Ser Gly Tyr Tyr Tyr
1               5                   10                  15

Phe Asp Tyr

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ala Lys Asp Ser Pro Arg Gly Glu Leu Pro Phe Asp Tyr
1               5                   10

<210> SEQ ID NO 229
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ala Arg Gly Thr Asp Tyr Thr Ile Asp Asp Gln Gly Ile His Tyr Tyr
1               5                   10                  15

Gly Ser Gly Thr Tyr Trp Tyr Phe Asp Leu
            20                  25

<210> SEQ ID NO 230
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gaggtgcagc tggtggagtc tgggggagac ttggtacagc ctggcaggtc cctgagactc      60
tcctgtgcag cctctggatt cacctttgat gattatgcca tgcactgggt ccggcaagct     120
ccagggaagg gcctggagtg gatctcaggt attagtggga atagtggtag cagaggctat     180
gcggactctg tgaagggccg attcaccatc tccagagaca cgccaagaa ctccctgtat     240 ctgcaaatga acagtctgag agctgaggac acggccttgt attactgtgc aacagatgga     300
```

```
gacagatctg gcactacgcc tcttgaccat tggggccagg aacccgggt caccgtctcc    360 tca                                                                 363

<210> SEQ ID NO 231
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 231
tcctatgagc tgacacagcc accctcggtg tcagtgtccc caggacaaac ggccaggatc    60
acctgctctg gagatgcatt gccaaaaaat tatgcttatt ggtaccagca gaagtcaggc   120
caggcccctg cgttggtcat ctatgaggac agcaaacgac cctccgggat ccctgagaga   180
ttctctggct ccagctcagg gacaatggcc accttgacta tcagtggggc ccaggtggag   240
gatgaagctg actactactg ttactcaaca gacagcagtg gtactccctc cttcggaact   300
gggaccaagg tcaccgtcct a                                              321

<210> SEQ ID NO 232
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232
gaggtgcagc tggtggagtc tgggggaggc ttggtacagc ctgggggtc cctgagactc     60 tcctgtgcag cctctggatt caccttttagc agttatgcca tgaggtgggt ccgccaggct   120
ccagggaagg ggctggagtg ggtctcaggt attagtggta gtggtggtag cacatactac    180
gcagactccg tgaagggccg gttcaccatc tccagagaca attccaagat cacgctgtat    240
ctgcaaatgg acagcctgag agtcgaggac acggccgtat attactgtgc gacagcgccc    300
ctcagctatg attcctccac ggactactgg ggccagggaa ccctggtcac cgtctcctca    360

<210> SEQ ID NO 233
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
tcctatgagc tgacacagcc accctcggtg tcagtgtccc caggacaaac ggccaggatc    60
acctgctctg gagatgcatt gccaaaaaaa tatgcttatt ggtaccagca gaagtcaggc   120
caggcccctg tgctggtcat ctatgaggac agcaaacgac cctccgggat ccctgagaga   180
ttctctggct ccagctcagg gacaatggcc accttgacta tcagtggggc ccaggtggag    240
gatgaagctg actactactg ttactcaaca gacagcagtg gtaatccccg attcggcaga   300
gggaccaagc tgaccgtcct a                                              321

<210> SEQ ID NO 234
<211> LENGTH: 107
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 234

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Asn Tyr Ala
            20                  25                  30

Tyr Trp Tyr Gln Gln Lys Ser Gly Gln Ala Pro Ala Leu Val Ile Tyr
        35                  40                  45

Glu Asp Ser Lys Arg Pro Ser Gly Ile Pro Glu Arg Phe Ser Gly Ser
50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Thr Pro
                85                  90                  95

Ser Phe Gly Thr Gly Thr Lys Val Thr Val Leu
            100                 105

<210> SEQ ID NO 235
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly Asn Pro
                85                  90                  95

Arg Phe Gly Arg Gly Thr Lys Leu Thr Val Leu
            100                 105

<210> SEQ ID NO 236
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala His
            20                  25                  30

Tyr Asp Trp Tyr Gln Gln Leu Pro Gly Thr Ala Pro Lys Leu Leu Ile
        35                  40                  45

Tyr Gly Asn Ser Asn Arg Pro Ser Gly Val Pro Asp Arg Phe Ser Gly
            50                  55                  60

Ser Lys Ser Gly Thr Ser Ala Ser Leu Ala Ile Thr Gly Leu Gln Ala
65                  70                  75                  80

Glu Asp Glu Ala Asp Tyr Tyr Cys Gln Ser Tyr Asp Ser Ser Leu Ser
                85                  90                  95

Gly Tyr Val Phe Gly Thr Gly Thr Lys Val Thr Val Leu
            100                 105

<210> SEQ ID NO 237
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Trp Tyr Gln Gln Leu Pro Gly Thr Ala Pro Lys Leu Leu Ile
        35                  40                  45

Tyr Gly Asn Ser Asn Arg Pro Ser Gly Val Pro Asp Arg Phe Ser Gly
            50                  55                  60

Ser Lys Ser Gly Thr Ser Ala Ser Leu Ala Ile Thr Gly Leu Gln Ala
65                  70                  75                  80

Glu Asp Glu Ala Asp Tyr Tyr Cys Gln Ser Tyr Asp Ser Ser Leu Ser
                85                  90                  95

Gly Tyr Val Phe Gly Thr Gly Thr Lys Val Thr Val Leu
            100                 105

<210> SEQ ID NO 238
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Glu Ile Val Leu Ala Gln Ser Pro Gly Thr Leu Ser Leu Ser Pro Gly
1               5                   10                  15

Glu Arg Ala Thr Leu Ser Cys Arg Ala Ser His Asn Pro Lys Tyr Phe
            20                  25                  30

Ala Trp Tyr Gln Gln Lys Pro Gly Gln Ser Pro Arg Leu Leu Ile Tyr
        35                  40                  45

Gly Gly Ser Thr Arg Ala Ala Gly Ile Pro Gly Lys Phe Ser Gly Ser
            50                  55                  60

Gly Ser Gly Thr Asp Phe Thr Leu Thr Ile Ser Arg Val Asp Pro Glu
65                  70                  75                  80

Asp Phe Ala Val Tyr Tyr Cys Gln Gln Tyr Gly Gly Ser Pro Tyr Thr
                85                  90                  95

Phe Gly Gln Gly Thr Lys Val Glu Ile Lys
            100                 105

<210> SEQ ID NO 239
<211> LENGTH: 107

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ser Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Tyr
                85                  90                  95

Thr Phe Gly Gln Gly Thr Lys Val Glu Ile Lys
            100                 105

<210> SEQ ID NO 240
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
            20                  25                  30

Glu Ser Val Ser Trp Tyr Gln Gln His Pro Gly Lys Ala Pro Lys Val
        35                  40                  45

Val Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
            100                 105                 110

<210> SEQ ID NO 241
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Ser Ala Leu Thr Gln Pro Ala Ser Val Ser Gly Ser Pro Gly Gln
1               5                   10                  15

Thr Ile Thr Ile Ser Cys Asn Gly Thr Ser Ser Asp Val Gly Gly Phe
            20                  25                  30

Asp Ser Val Ser Trp Tyr Gln Gln Ser Pro Gly Lys Ala Pro Lys Val

```
                35                  40                  45
Met Val Phe Asp Val Ser His Arg Pro Ser Gly Ile Ser Asn Arg Phe
         50                  55                  60

Ser Gly Ser Lys Ser Gly Asn Thr Ala Ser Leu Thr Ile Ser Gly Leu
 65                  70                  75                  80

His Ile Glu Asp Glu Gly Asp Tyr Phe Cys Ser Ser Leu Thr Asp Arg
                 85                  90                  95

Ser His Arg Ile Phe Gly Gly Gly Thr Lys Val Thr Val Leu
            100                 105                 110

<210> SEQ ID NO 242
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
             20                  25                  30

Asn Leu Val Ser Trp Tyr Gln Gln His Pro Gly Lys Ala Pro Lys Leu
         35                  40                  45

Met Ile Tyr Glu Val Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Leu Thr Ser Thr
                 85                  90                  95

Arg Arg Trp Val Phe Gly Gly Gly Thr Lys Leu Thr Val Leu
            100                 105                 110

<210> SEQ ID NO 243
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
             20                  25                  30

Asn Leu Val Ser Trp Tyr Gln Gln His Pro Gly Lys Ala Pro Lys Leu
         35                  40                  45

Met Ile Tyr Glu Val Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Cys Ser Leu Thr Asp Arg
                 85                  90                  95

Ser His Arg Ile Phe Gly Gly Gly Thr Lys Leu Thr Val Leu
            100                 105                 110
```

IMMUNOGENS COMPRISING HUMAN IMMUNODEFICIENCY VIRUS V1/V2 POLYPEPTIDES

This application is a U.S. National Phase of International Application No. PCT/US2012/000570, which designated the U.S. and claims priority from U.S. Provisional Application No. 61/566,884, filed Dec. 5, 2011, U.S. Provisional Application No. 61/580,475, filed Dec. 27, 2011 and U.S. Provisional Application No. 61/613,222, filed Mar. 20, 2012, the entire contents of each of which are incorporated herein by reference.

This invention was made with government support under Grant Nos. A1067854 and A1100645 awarded by the National Institutes of Health, Bethesda, Md., and support from the intramural program of the NIAID to the Vaccine Research Center. The government has certain rights in this invention.

SEQUENCE LISTING

The instant application contains a Sequence Listing which has been submitted electronically in ASCII format and is hereby incorporated by reference in its entirety. Said ASCII copy, created on Jun. 10, 2016, is named 2933311-19.US4_SL.txt and is 378,035 bytes in size.

TECHNICAL FIELD

The present invention relates, in general, to human immunodeficiency virus (HIV), and, in particular, to a vaccine for HIV-1 and to methods of making and using same.

BACKGROUND

Development of a safe, practical and effective HIV-1 vaccine is one of the highest priorities of the global scientific community (Klausner et al, Science 5628:2036-2039 (2003); Esparza et al, Science Strategic Plan, DOI: 10.1371/journal.pmed.0020025, Policy Forum Vol. 2, February 2005)). While anti-retroviral treatment (ART) has dramatically prolonged the lives of HIV-1 infected patients, anti-retroviral therapy is not yet routinely available in developing countries, and the global rate of spread of HIV-1 continues unabated.

A recent study of the immune correlates of the RV144 vaccine trial (Rerks-Ngarm et al, N. Eng. J. Med. 361: 2209-20 (2009)) demonstrated that plasma V1V2 antibodies against a scaffolded V1V2-gp70 construct (Pinter et al, Vaccine 16:1803-11 (1998)), was associated with decrease risk of infection in vaccines (Haynes et al, Immune Correlates Analysis of the ALVAC-AIDSVAX HIV-1 Vaccine Efficacy Trial. N. Eng. J. Med., Submitted (2011)). This vaccine trial, however, induced only modest efficacy with an estimated 31.2% vaccine efficacy (Rerks-Ngarm et al, N. Eng. J. Med. 361: 2209-20 (2009)). To design immunogens with the capacity to induce better immune responses to an immunogen, it is critical to design immunogens capable of binding to the unmutated ancestors and the intermediate clonal lineage antibodies of the mature mutated types of antibodies to be induced (Dal Porto et al, J Exp Med 195:1215-1221 (2002); Shih et al, Nat Immunol 3:570-575 (2002); Schwickert et al, J Exp Med 208:1243-1252 (2011); Bonsignori et al, J Virol 85:9998-10009 (2011); Ma et al, PLoS Pathog 7(9): e1002200 (2011); Liao et al, J Exp Med 208:2237-49 (2011); and Alam et al, J Virol 85: 11725-31 (2011)).

In 2012 an immune correlates study of the RV144 trial revealed that antibodies against the Env gp120 V1/V2 region presented on a gp70-V1/V2 fusion protein were associated with lower risk of infection (Haynes et al, TNew Engl. J. Med. 366:1275-1286 (2012)). Epitope mapping of plasma V1/V2 antibody responses showed that within V2, vaccine-induced antibodies targeted a region of HIV-1 Env, amino acid (aa) residues at positions 163-178 (Karasavvas et al; AIDS Research and Human Retroviruses, doi:10.1089/aid.2012.0103 (2012), Zolla-Pazner et al, AIDS Vaccine. Bangkok, Thailand Abstract No.: OA09.03, 77 (2011)). There is considerable sequence variability in V1/V2, ~75% of the residues are conserved or demonstrated to be only conservative changes (Zolla-Pazner & Cardozo, Nat Rev Immunol 10, 527-535 (2010)). While the demonstration that of V1/V2 antibody responses directly correlated with decreased infection risk was suggestive of their protective role in the trial, this association was not sufficient for proving causation of protection (Plotkin & Gilbert, Clinical infectious diseases: an official publication of the Infectious Diseases Society of America 54:1615-1617 doi:10.1093/cid/cis238 (2012)). Indeed further studies are needed to evaluate the ability of such responses to mediate immune pressure on HIV-1. Viral genetic (sieve) analyses, isolation of V1/V2 antibodies and understanding their effector function in vitro and in vivo, and validation of correlates of infection risk in future vaccine trials are some potential studies.

A genetic or sieve analysis of sequences of viruses that caused breakthrough infections in a vaccine trial can demonstrate vaccine effects (Rolland et al, Nature Medicine 17:366-371 (2011)). By comparing sequences of breakthrough infections that occur in vaccines versus placebo recipients, sites of vaccine-induced immune pressure can be identified (Rolland et al, Nature Medicine 17:366-371 (2011)). A recent genetic analysis of breakthrough HIV-1 infections in the RV144 trial demonstrated 48% (CI: 18 to 68%, p=0.0036) vaccine efficacy against viruses matching the CRF_01AE vaccine immunogens with a lysine (K) at position 169 (Rolland et al, Nature 490:417-420 (2012)). Thus, it is critical to determine the binding site and effector functions of RV144-induced V1/V2 antibodies. Effector functions considered for antibody mediated-protection from HIV-1 transmission include the ability of V1/V2 antibodies to neutralize those virus strains involved in HIV-1 transmission (i.e. transmitted/founder viruses) (Keele et al, Proc Natl Acad Sci USA. 105:7552-7557 (2008)), and/or to mediate other antibody effector functions such as antibody-dependent cellular cytotoxicity (ADCC) (Haynes et al, New Engl. J. Med. 366:1275-1286 (2012)).

The present invention results, at least in part, from studies associated with the isolation of V2 neutralizing antibodies from RV144 vaccines blood mononuclear memory B cells (mAbs CH58 and CH59) as well as the isolation of a clonal lineage of HIV-1 broad neutralizing V1V2 conformational gp120 envelope monoclonal antibodies (CH01-CH04) (Bonsignori et al, J Virol 85:9998-10009 (2011)). The present invention provides, at least in part, new vaccine immunogens that induce high titers of vaccine responses to V1V2 of HIV-1 envelope gp120. The invention also results, at least in part, from studies involving the probing of the specificities and effector functions of four V2 monoclonal antibodies (mAbs) isolated from RV144 ALVAC/AIDSVAX vaccine recipients, and the determination of crystal structures of two of these mAbs with V2 peptides containing position 169.

SUMMARY OF THE INVENTION

The present invention relates generally to HIV. More specifically, the invention relates to a vaccine for HIV-1 and to methods of making and using same.

Objects and advantages of the present invention will be clear from the description that follows.

BRIEF DESCRIPTION OF THE DRAWINGS

Copies of drawings executed in color presented in the files of Provisional Application Nos. 61/566,884, Application No. 61/580,475, and/or 61/613,222 are incorporated herein by reference.

FIG. 1 discloses the hairpin structure as SEQ ID NO: 53, the "His6 tag" as SEQ ID NO: 10 and the sequence as SEQ ID NO: 53.

FIG. 2. AE.A244 V1V2. FIG. 2 discloses the hairpin structure as SEQ ID NO: 47 and the sequence as SEQ ID NO: 129.

FIG. 3 discloses the hairpin structure as SEQ ID NO: 131, "His6" as SEQ ID NO: 10 and the sequence as SEQ ID NO: 130.

FIG. 4 discloses the hairpin structure as SEQ ID NO: 133, "His6" as SEQ ID NO: 10 and the sequence as SEQ ID NO: 132.

FIG. 5 discloses the hairpin structure as SEQ ID NO: 133 and the sequence as SEQ ID NO: 134.

FIG. 6. Alignment of V1V2 loops of different HIV-1 Envs. FIG. 6 discloses SEQ ID NOS: 135-137, 47, 138, 42 and 139-142, respectively, in order of appearance.

FIG. 10. HCDR3 alignment of PG9 (SEQ ID NO: 143), CH58 (SEQ ID NO: 144) and CH59 (SEQ ID NO: 145).

FIG. 11. Variable region sequences of CH58, CH59, CH58_RUA and CH59RUA heavy and light chain genes. FIG. 11 discloses SEQ ID NOS: 146-153, respectively, in order of appearance.

FIG. 12 discloses SEQ ID NOS: 137, 154-155, 137, 154-155, 137 and 154-155, respectively, in order of appearance.

FIG. 13. Footprints of mabs CH58 and CH59. FIG. 13 discloses SEQ ID NOS: 11 and 11, respectively, in order of appearance.

FIG. 14. RV144 V2 human mabs. FIG. 14 discloses SEQ ID NOS: 156 and 156, respectively, in order of appearance.

FIG. 17. Codon-optimized DNA sequences of HIV-1 Env V1V2 tags designs; amino acid sequences of the V1V2 designs; amino acid sequences of the V1V2 Tags designs; and codon optimized nucleotide sequences of mutated V1V2 designs. FIG. 17 discloses SEQ ID NOS: 157-206, respectively, in order of appearance.

FIG. 19. Boxplots showing the distribution of the 6 primary immune response variables (lower edge of box=$25^{th}$ percentile; horizontal line in box=$50^{th}$ percentile, upper edge of box=$75^{th}$ percentile). Low, Medium, and High are defined as the tertiles of response readout for the vaccine group, and are divided by horizontal lines.

FIG. 20. Estimated cumulative HIV incidence curves by Low, Medium, and High vaccine responding subgroups for the 6 primary variables and for the entire placebo group HIV-1 negative at week 24. Low, Medium, and High are defined by tertiles of response for the vaccine group.

FIG. 25. Plasma IgA Binding Antibody Score (Primary) Blinded to infection status (top panel) Surfact Plasmon Resonance IgG Avidity (Primary) Blinded to infection status (bottom panel).

FIG. 26. ADCC Infected Target (Primary) Blinded to infection status (top panel) Neutralization Score (Primary) Blinded to infection status (bottom panel).

FIG. 27 Scaffolded gp70-V1V2 ELISA Binding (Primary) Blinded to infection status (top panel) CD4+ T Cells Score (Primary) Blinded to infection status (bottom panel).

FIG. 28. IgA E.A244 gD-Delta11 293T gp120 (Sensitivity) Blinded to infection status (top panel) IgG Avidity B.MN gD-gp120 293T (Sensitivity) Blinded to infection status (bottom panel).

FIG. 29. ADCC gp120-coated E.244 gD-gp120 293T AUC (Sensitivity) Blinded to infection status (top panel) Nab TZM-bl 92TH023.AE (Sensitivity) Blinded to infection status (bottom panel).

FIG. 30. Nab Score TZM-bl Subtype B (Sensitivity) Blinded to infection status (top panel) Nab Score A3R5 Subtype E (Sensitivity) Blinded to infection status (bottom panel).

FIG. 31. V2 Cyclic Peptide 42aa (Sensitivity) Blinded to infection status (top panel) PBMC Luminex Cytokine Score (Sensitivity) Blinded to infection status (bottom panel).

FIG. 32A. Serial dilutions ranging from 100 µg/ml to 0.001 µg/ml of CH58 and CH59mAbs were tested in ELISA for binding to A244 K178 V2 linear peptide (KKKVHALFYKLDIVPIEDKKK) (SEQ ID NO: 1) (in red) and 92TH023 V2 cyclic peptides (CSF-NMTTELRDKKQKVHALFYKLDIVPIEDNTSSSEYR-LINC) (SEQ ID NO: 2) (in blue). Binding is expressed as OD450. FIG. 32B. Effect of alanine point mutations in the V2 region (residues 169 to 190) for binding of CH58 (in blue) and CH59 (in red) to the series of alanine substituted peptides. For each mutation (y axis), results are normalized as EC50 relative to wild type (WT). FIG. 32B discloses SEQ ID NO: 11.

FIG. 33A. Ribbon representation of the unbound CH58 antigen-binding fragment (Fab). The crystal structure was determined to 2.4 Å resolution. Seven residues of the CDRH3 were disordered. FIG. 33B. Ribbon (left) and molecular surface (right) representation of CH58 Fab in complex with a peptide corresponding to residues 164-182 from HIV-1 gp120 A244 (and 92TH023). The crystal structure was determined to 1.7 Å resolution. Some residues on the N- and C-termini of the peptide were disordered. FIG. 33C. Side-chain interactions between CH58 and the V2 peptide. Side-chains are shown as sticks, and hydrogen bonds are depicted as dashed lines. FIG. 33D. Ribbon representation of the variable domains of CH58 (left) and PG9 (right) bound to a V2 peptide and scaffolded V1/V2, respectively. Residues 167-177 are colored green and shown in the sequence alignment. The PG9 structure is from McLellan et al, Nature 480 (2011). FIG. 33D discloses SEQ ID NOS 207-208, respectively, in order of appearance.

FIG. 34. Binding of sera of RV144 ALVAC-AIDSVAX B/E vaccine recipients to wild-type or mutated forms of the V2 region of HIV-1 Env. Serum samples of 80 RV144 ALVAC-AIDSVAX B/E vaccine recipients were tested in ELISA for binding to a panel of 14 constructs expressing the V2 region of HIV-1 gp120 envelope glycoprotein. Serum was collected post vaccination and tested at a 1:50 dilution. V2 sequences in either J08-scaffolded V1V2 constructs or in gp70-scaffold V1V2 constructs are in Table 19. Gp70 carrier protein was also assayed to control for non-HIV-specific binding to these constructs, and gp70 V1V2 scaffold binding results shown are with gp70 carrier protein subtracted. For each construct, a mutated form containing two point mutations at positions 156 and 160 (N156Q and N160Q) were also tested. Statistical significance of the differences in the binding levels among the wild-type and the mutant forms was evaluated using ANOVA with Bonferroni correction.

FIGS. 35A and 35B. FIG. 35A. Binding of anti-V2 mAb CH58 and CH59 to infected cells. The histograms report the staining of activated PB CD4+ T cells infected with Infectious Molecular Clone CM235 using the CH58 (left), CH59 (middle), and A32 (right) mAb. One-two hundred thousand CD4+ T cells were stained with 10 µg/ml of each mAb. The gating strategy included identification of p24+ cells out of the singlets and viable cell population. The Synagis® and A32 mAbs were used as negative and positive controls, respectively. The overlaying histograms represent the staining of HIV-1 infected CD4+ T cells after incubation with no Ab (unstained; gray area), with the secondary Ab alone (Secondary Ab Alone; black curve), and with primary and secondary Ab (primary Ab+ secondary Ab; green curve). Under each histogram, the table report the Median Fluorescence Intensity (MFI) of the staining of each mAb and the percentage of p24+ cells recognized by each mAb (% positive cells). The MFI of the Synagis is reported as reference, and the background staining for this mAb was 11% of p24+ cells. FIG. 35B. ADCC activity mediated by anti-V2 mAbs CH58 and CH59. The percentage of specific killing mediated by the CH358 (red line) and CH59 (blue line) using IMCCM235-infected CEM.NKRCCR5 is reported. Each mAb was tested starting at 40 µg/ml in a 4 fold dilution series. The Synagis® (orange line) mAbs were used as positive and negative controls, respectively. The green line represents the cut-off for positivity. The curves represent the average of three independent experiments; the error bars represent the standard deviations. The maximum % Specific Killing and the Endpoint Concentration for the CH58 and CH59 mAbs are reported in the table below the graph.

FIGS. 36A-36C. Binding of conformational V2 (697D) and V2V3 mAbs (PG9, PG16, CH01) but not of A32 (C1) or b12 (CD4 bs) to A244 gp120 is blocked by mAbs CH58 (FIG. 36A) and CH59 (FIG. 36B). Binding of the Env gp120 to V3 mAb 19b (FIG. 36C) did not block binding of any of the tested mAbs. Inset in FIG. 36C shows binding data from FIG. 36C resealed for the binding of CH01, PG9 and PG16 (on 19b surface) and overlayed with curves for the same mAbs showing no binding to gp120 captured on CH58 and CH59 immobilized surfaces. Equivalent amounts of A244 gp120 proteins were captured on each mAb immobilized surfaces and each of the mAbs were injected at 50 µg/mL, with Synagis as a negative control mAb.

FIG. 37. Alignment of the HCDR3 sequence of mAbs PG9, PG16, CH58, CH59, CH01 and 697D and their RUAs. The amino acid sequences of the CDR H3 regions of mAbs PG16, CH58, CH59, 697D and CH01 and their RUSAs were aligned to that of mAb PG9. Each sequence was aligned independently to PG9 (paired alignment) using Clustal W and final adjustment was made manually. Gaps are indicated with dots. Amino acids conserved between PG9 and either CH58 or CH59 sequences are highlighted in red. The number of amino acids shared with PG9 over the total is reported on the right for each mAb. FIG. 37 discloses SEQ ID NOS 143 and 209-218, respectively, in order of appearance.

FIGS. 38A and 38B. Coomassie and Western Blot for sulfation detection of CH58 and CH59 mAbs. mAbs identified on the top of the individual lans were fractionated on 4-12% SDS-PAGE and stained by Coomassie blue (FIG. 38A) or Western blotted using an anti-sulfation specific antibody (FIG. 38B).

FIG. 39. Binding of 697D mAb to V2 constructs. Serial dilutions ranging from 100 µg/ml to 0.001 µg/ml of mAb 697D were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

FIG. 40. Binding of CH58 mAb to V2 constructs. Serial dilutions ranging from 100 µg/ml to 0.001 µg/ml of mAb CH58 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

FIG. 41. Binding of CH59 mAb to V2 constructs. Serial dilutions ranging from 100 µg/ml to 0.001 µg/ml of mAb CH159 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

FIG. 42. Binding of PG9 mAb to V2 constructs. Serial dilutions ranging from 100 µg/ml to 0.001 µg/ml of mAb PG9 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

FIG. 43. Binding of PG16 mAb to V2 constructs. Serial dilutions ranging from 100 µg/ml to 0.001 µg/ml of mAb PG9 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

FIG. 44. Binding of CH01 mAb to V2 constructs. Serial dilutions ranging from 100 µg/ml to 0.001 µg/ml of mAb CH01 were tested in ELISA for binding to HIV-1 clades A (92RW020), B (HXB2/BAL) and C (97ZA012) as well as subtype B (CaseA)2 V1V2 proteins scaffold on either gp70 and J08 and V1V2 mutant proteins with N156Q and N160Q mutations.

FIGS. 45A and 45B. Anti-HIV-1 V1V2 responses in rhesus macaques raised by immunization with E.A244 gp120 protein. Plasma samples from rhesus macaques immunized with E.A44 gp120 were tested for binding to recombinant HIV-1 clade A (92RW020 V1V2 protein scaffold on either gp70 (FIG. 45A) and J08 (FIG. 45B) and the same V1V2 mutant proteins with N156Q and N160Q mutations. The reactivity of the plasma plotted as area under curve is shown on the y axis.

FIGS. 46A-46B. Binding of RV144 mAbs CH58 and CH58_RUA to HIV-1 Envs. Serial dilutions ranging from 100 μg/ml to 0.001 μg/ml of mAb CH58 and CH58_RUA were tested for binding to a panel of 43 HIV-1 Envs indicted on the y axis in ELISA. Shown is the binding of mAbs CH58 and CGH58_RUA (indicated on the top of the graphs) expressed as OD405 nm reading at 10 μg/ml (x axis). Data shown are the representative of three experiments. FIGS. 46C-46D. Binding of RV144 mAbs CH59 and CH59_RUA to HIV-1 Envs. Serial dilutions ranging from 100 μg/ml to 0.001 μg/ml of mAb CH59 and CH59_RUA were tested for binding to a panel of 43 HIV-1 Envs indicted on the y axis in ELISA. Shown is the binding of mAbs CH59 and CH59_RUA (indicated on the top of the graphs) expressed as OD405 nm reading at 10 ug/ml (x axis). Data shown are the representative of three experiments. FIGS. 46E-46G. Binding of RV144 mAbs CH01 and CH01_RUAs to HIV-1 Envs. Serial dilutions ranging from 100 μg/ml to 0.001 μg/ml of mAbs CH01 and CH01_RUAs were tested for binding to a panel of 43 HIV-1 Envs indicted on the y axis in ELISA. Shown is the binding of mAbs CH01 and CH01_RUAs (indicated on the top of the graphs) expressed as OD405 nm reading at 10 ug/ml (x axis). Data shown are the representative of three experiments. FIGS. 46H-46I. Binding of RV144 mAbs PG9 and PG9_RUA to HIV-1 Envs. Serial dilutions ranging from 100 μg/ml to 0.001 μg/ml of mAbs PG19 and PG9_RUA were tested for binding to a panel of 43 HIV-1 Envs indicted on the y axis in ELISA. Shown is the binding of mAbs PG19 and PG9_RUA (indicated on the top of the graphs) expressed as OD405 nm reading at 10 ug/ml (x axis). Data shown are the representative of three experiments. FIGS. 46J-46K. Binding of RV144 mAbs PG16 and PG116_RUA to HIV-1 Envs. Serial dilutions ranging from 100 μg/ml to 0.001 μg/ml of mAbs PG16 and PG16_RUA were tested for binding to a panel of 43 HIV-1 Envs indicted on the y axis in ELISA. Shown is the binding of mAbs PG16 and PG16_RUA (indicated on the top of the graphs) expressed as OD405 nm reading at 10 ug/ml (x axis). Data shown are the representative of three experiments. FIGS. 46L-46M. Binding of RV144 mAbs 697D and 697D_RUA to HIV-1 Envs. Serial dilutions ranging from 100 μg/ml to 0.001 μg/ml of mAb 697D and 697D_RUA were tested for binding to a panel of 43 HIV-1 Envs indicted on the y axis in ELISA. Shown is the binding of mAbs 697D and 697D_RUA (indicated on the top of the graphs) expressed as OD405 nm reading at 10 ug/ml (x axis). Data shown are the representative of three experiments.

FIG. 47. Schematic representation of the design of HIV-1 Env V1V2_Tags. Gene constructs of HIV-1 V1V2-Tags were made with an Ig leader N-terminal to the HIV-1 V1V2 loop region sequence followed by avi-tag and His6 tag (SEQ ID NO: 10) as indicated. FIG. 47 discloses SEQ ID NO: 53.

FIGS. 48A-48L. FIGS. 48A-48B. Binding of V2 and V2V3 conformational mAbs PG9 and CH58 to AE.A244 V1V2 Tags protein. Each of the mAbs was captured on an anti-Fe antibody immobilized sensor surface to about 100-125 RU. AE.A244 V1V2 tags protein was injected as analyte at concentrations ranging from 0.5-3 ug/mL (CH58), or 10-50 ug/mL (PG9). A negative control mAb (Synagis) was used with each mAb to subtract non-specific binding. Curve fitting to a 1:1 Langmuir model included binding data from two independent flow cells with the same mAb captured. FIGS. 48C-48D. Binding of mAbs 697D and CH01 to AE.A244 V1V2 Tags protein. Each of the mAbs was captured on an anti-Fc antibody immobilized sensor surface to about 100-125 RU. AE.A244 V1V2 tags protein was injected as analyte at concentrations ranging from 0.5-3 ug/mL (CH58), or 10-50 ug/mL (CH01). A negative control mAb (Synagis) was used with each mAb to subtract non-specific binding. Curve fitting to a 1:1 Langmuir model included binding data from two independent flow cells with the same mAb captured. FIGS. 48E-48F. Binding of mAb CH58 to J08 A.92RW020V1V2 and J08 A.92RW020V1V2 N156QN160Q proteins. mAb CH58 was captured on an anti-Fe antibody immobilized sensor surface to about 100-125 RU. J08 A.92RW020V1 V2 and J08 A.92RW020V1V2 N156QN160Q proteins were injected as analyte at concentrations ranging from 0.5-3 μg/mL. A negative control mAb (Synagis) was used with each mAb to subtract non-specific binding. Curve fitting to a 1:1 Langmuir model included binding data from two independent flow cells with the same mAb captured. FIGS. 48G-48H. Binding of V2 mAb CH58 to gp70 A.92RW020V1V2 and gp70 A.92RW020V1V2 N156QN160Q proteins. CH58 was captured on an anti-Fc antibody immobilized sensor surface to about 100-125 RU. gp70 A.92RW020V1 V2 and gp70 A.92RW020V1V2N156QN160Q proteins were injected as analyte at concentrations ranging from 0.5-3 ug/mL. A negative control mAb (Synagis) was used with each mAb to subtract non-specific binding. Curve fitting to a 1:1 Langmuir model included binding data from two independent flow cells with the same mAb captured. FIGS. 48I-48J. Binding of V2 mAb 697D to J08 A.92RW020V1V2 and gp70 CaseA2 mAb697D was captured on an anti-Fe antibody immobilized sensor surface to about 100-125 RU. J08 A.92RW020V1V2 proteins were injected as analyte at concentrations ranging from 5-50 ug/mL. A negative control mAb (Synagis) was used with each mAb to subtract non-specific binding. Curve fitting to a 1:1 Langmuir model included binding data from two independent flow cells with the same mAb captured. FIGS. 48K-48L. Binding of mAb CH58 to J08.A.92RW020V1V2 and J08.A.92RW020V1V2 N156N160Q Tags proteins. mAb CH58 was captured on an anti-Fe antibody immobilized sensor surface to about 100-125 RU. J08.A.92RW020V1V2 and J08.A.92RW020V1V2 N156N160Q Tags were injected as analyte at concentrations ranging from 0.5-3 ug/mL. negative control mAb (Synagis) was used to subtract non-specific binding. Curve fitting to a 1:1 Langmuir model included binding data from two independent flow cells with the same mAb captured.

FIGS. 51A and 51B. Binding of RV44 mAbs CH58 and CH59 to HIV-1-infected cells and to HIV-1 V2 peptides. FIG. 51A. Effect of alanine point substituted mutations using alanine scanning V2 peptides with the sequence of AE.CM244 Env from positions 165 to 186 in the V2 region on the binding of CH58 (in blue) and CH59 (in red) to the HIV-1 V2 peptide. For each mutation (y axis), results were normalized as EC50 relative to wildtype V2 peptide. FIG. 51A discloses SEQ ID NO: 11. FIG. 51B. Shown is the flow cytometric analysis of binding of mAbs CH58 (upper left), CH59 (middle left), and A32 (lower left) to the activated PB CD4+ T cells infected with infectious molecular clone AE.CM235. Synagis (anti-respiratory syncytial virus mAb) and HIV-1 A32 mAbs were used as negative and positive controls, respectively. Mean fluorescence intensity (MFI) and % of positive cells are indicated next to the histograms. Data shown are representative of 3 independent experiments.

FIGS. 53A-53C. Structures of antibodies CH58 and CH59 bound to an HIV-1 gp120 V2 peptide. Vaccine-elicited antibodies CH58 and CH59 recognize alternative conformations of V2 compared to the broadly neutralizing antibody PG9. FIG. 53A. top: Ribbon representation of the CH58 antigen-binding fragment in complex with an A244 V2 peptide. Heavy chain is colored orange, light chain is blue, and peptide is green. The sequence of the peptide is shown, with modeled residues in green; bottom: Close-up of the top panel rotated 90° about a horizontal axis. The side-chains of residues involved in hydrogen bonds or salt bridges are shown as sticks, with the interactions depicted as dashed lines. FIG. 53A discloses SEQ ID NO: 12. FIG. 53B, Structure of CH59 in complex with peptide, depicted as in FIG. 53A. The heavy chain is tan, and the light chain is light blue. FIG. 53B discloses SEQ ID NO: 12. FIG. 53C, Structure of broadly neutralizing antibody PG9 in complex with the V1/V2 domain from HIV-1 strain CAP45 (PDB ID: 3U4E) (McLellan et al, Nature 480:336-343 (2011)). The PG9 structure is shown as ribbons with heavy and light chains (colored yellow and blue, respectively) in the same orientation as in FIG. 53A and FIG. 53B. The V1/V2 domain is shown as a grey ribbon with residues 168-176 colored green, and N-linked glycans attached to residues Asn156 and Asn160 shown as sticks.

FIG. 55A. Serial dilutions ranging from 100 μg/ml to 0.001 μg/ml of mAbs CH58 (graph on the left) and CH59 (graph on the right) were tested in ELISA for binding to AE.CM244 K178 V2 linear peptide (KKKVHALFYKL-DIVPIEDKKK) (SEQ ID NO: 1) (in red) and AE.92TH023 V2 cyclic peptide (CSFNMTTELRDKKQKVHALFYKL-DIVPIEDNTSSSEYRLINC) (SEQ ID NO: 2) (in blue). Binding is expressed as absorbance OD450 nm. FIG. 55B. The percentage of specific killing mediated by the CH58 (red line) and CH59 (blue line) using IMC AE.CM235-infected CEM.NKRCCR5 is reported. Each mAb was tested starting at 40 μg/ml in a 4 fold dilution series. The Synagis (orange line) mAb was used as negative control. The green line represents the cut-off for positivity. The curves represent the average of three independent experiments; the error bars represent the standard deviations. The maximum % specific killing and the endpoint concentration for the CH58 and CH59 mAbs are reported in the table below the graph. FIG. 55C. Gene constructs of HIV-1 V1/V2 Tags were made with an Ig leader at the N-terminal end of the A244 V1/V2 loop region sequence and the C-terminal sequence with by Avi-tag and His6 tag (SEQ ID NO: 10) as shown in FIG. 55A. FIG. 55C discloses SEQ ID NO: 53. FIG. 55D and FIG. 55E. Binding to the indicated mAbs (FIG. 55D) and their Uas (FIG. 55E) in serial dilutions of mAbs ranging from 100 μg to 0.001 μg/ml (x axis) were assayed in ELISA for binding to AE.A244 V1/V2 Tags and AE.A244 V1/V2Tags N156Q/N160Q mutant Envs (reflected as ELISA OD 405 nm on the y axis. Data are a representative of three independent experiments.

FIG. 56A shows ribbon representation of the CH58 antigen-binding fragment (Fab). The heavy chain is colored orange and the light chain is colored blue. Disordered residues in the CDRH3 are depicted as a dashed line. FIG. 56B shows data collection and refinement statistics (molecular replacement).

FIG. 57A. mAbs indicated on the top of the individual lanes were fractionated on 4-12% SDS-PAGE and stained by Coomassie blue (shown on the left-hand side panel) or by Western blotted using an anti-sulfation specific antibody (shown on the right hand side panel), Known sulfation antibodies, 4.12D, E51, PG9 and PG16 were used as positive controls. FIG. 57B. The amino acid sequences of the CDR H3 regions of mAbs PG16, CH58, CH59, 697D and CH01 and their RUSAs were aligned to that of mAb PG9. Each sequence was aligned independently to PG9 (paired alignment) using Clustal W and final adjustment was made manually. Gaps are indicated with dots. Amino acids conserved between the sequences of PG9 and the other mAb are highlighted in red. The number of amino acids shared with PG9 over the total is reported on the right for each mAb. FIG. 57B discloses SEQ ID NOS 219-228, 223 and 229, respectively, in order of appearance.

FIG. 58A. Plasma samples tested at 1:90 dilution of 40 plasma samples from RV144 ALVAC-AIDSVAX B/E vaccine recipients were tested in ELISA for binding to the wild-type (WT) and mutant Envs* of HIV-1 vaccine Env AE.A244 gp120, RV144 breakthrough Envs (AE. 703359 gp120, and AE.427299 gp120) and gp70 B.CaseA2 V1V2. Statistical significance of the differences in the binding levels among the wild-type and the mutant forms was evaluated using the pairwise Student's t test. FIG. 58B. Blocking of binding of biotinylated CH58 or CH59 to A244 gp120 was determined by incubation of 3-fold dilutions ranging from 1:10 to 1:270 of plasma samples of RV144 vaccine recipients (n=40) followed by incubation with biotinylated sub-saturated CH58 or CH59. The amounts (µg/ml) of antibodies in plasma equivalent to mAb CH58 or CH59 were converted from the % inhibition by plasma samples against the predetermined standard cure generated with unlabeled mAb CH58 or CH59. The levels of CH59 and CH58 blocking antibodies in 3 RV144 vaccines from whom CH58, CH59 (subject ID347759), HG107 (subject ID200134) and HG120 (Subject ID 302689) was identified with arrows.

FIG. 60A. V(D)J rearrangements (FIG. 60A) and VH and VL sequences (SEQ ID NOS 230-233, respectively, in order of appearance) (FIG. 60B) of V2 mAbs isolated from RV144 vaccine-recipients and alignment of VL sequences of CH59 (SEQ ID NO: 149), HG107 (SEQ ID NO: 234), HG120 (SEQ ID NO: 235) and CH58 (SEQ ID NO: 147) with the ED motif highlighted in yellow (FIG. 60C). Effect of alanine substitution scanning of A244 Env V2 peptide (LRDKK169QKVHALFYKLDIVPIED) (SEQ ID NO: 11) on the binding of mAbs, CH59 (FIG. 60D), HG107 (FIG. 60E) and HG120 (FIG. 60F) was analyzed by ELISA. FIGS. 60D-60F disclose SEQ ID NO: 11. Data shows the plot of EC50 values of mAb binding to each mutant peptide with single amino acid substitution relative to the EC50 of binding to the WT peptide. EC50 was calculated by curve fitting analysis to a four parametric sigmoidal equation and are representative of at least two independent measurements. Results show the involvement of K169 and sharing of the same V2 residues critical for CH59 binding. FIG. 60G and FIG. 60H show conserved glutamate-aspartate (ED) motif in the LCDR2 of CH58, CH59, HG107 and HG120. FIG. 60G. Crystal structures of CH58 and CH59 in complex with V2 peptides show remarkable conservation of the interaction between the LCDR2 and V2. Salt bridges between the ED motif and V2 lysines including K169 are critical to V2 recognition. FIG. 60H. Molecular models of the light chains of HG107 and HG120, which also share the LCDR2 ED motif and like CH59 have Vλ3-10 light chains, suggesting, but not proving that HG107 and HG120 may recognize V2 in a similar manner. The light chains of CH58, CH59, HG107 and HG120 are colored magenta, green, blue, and red, respectively. V2 peptides from CH58 and CH59 are colored orange and cyan, respectively. The ED motif and lysines are shown as stick representations and dashed lines denote salt bridges.

DETAILED DESCRIPTION OF THE INVENTION

The efficacy seen in the RV144 ALVAC prime gp120 B/E boost Thai clinical trial demonstrated that a protective HIV-1 vaccine could be made (Rerks-Ngarm, S et al NEJM 361: 2209-30 (2009)). However, the efficacy was modest at 31% and the duration of protection short, demonstrating the need for improvement in level of protection. A recent correlates of infection risk study demonstrated that antibodies to the HIV-1 Env V1V2 region inversely correlated with protection from HIV-1 acquisition (Haynes et al, New Engl. J. Med. 366:1275-1286 (2012)). To improve on the efficacy of RV144 results, it is critical to understand the nature of the immunogens in RV144 and to understand why the trial worked, and to define any immune correlates of protection in the trial.

The present invention results, at least in part, from studies involving the design of V1V2 constructs of a number of subtype HIV-1 Env sequences. The A244 V1V2 Tag design, described below, has superior antigencity for the V2 antibodies seen in RV144 vaccines plasma and made by RV144 memory B cells, and that can bind to both RV144 vaccine V2 mabs and their B cell precursors, and, as well, can bind to broad neutralizing V1V2 conformational monoclonal antibodies and their precursors. Broad neutralizing antibodies to V1V2, though not induced in plasma by the RV144 ALVAC/AIDSVAX vaccine, are highly desired to be induced by an HIV vaccine.

Figure 1:
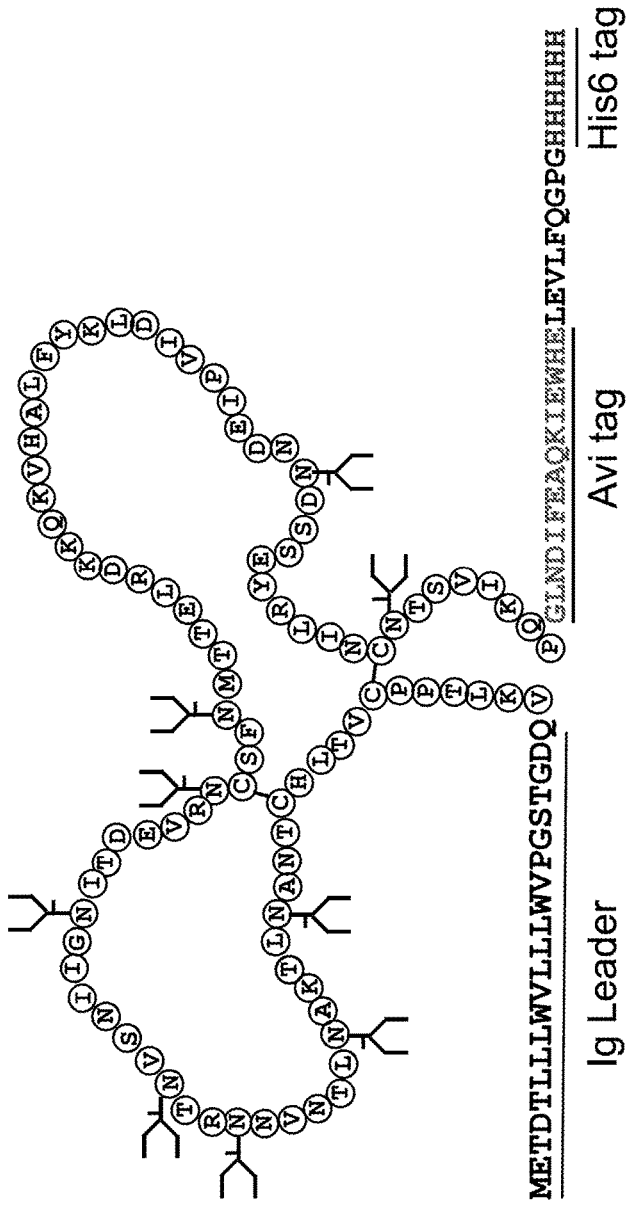
FIG. 1. AE.A244 V1V2_Tags.
Figure 3:
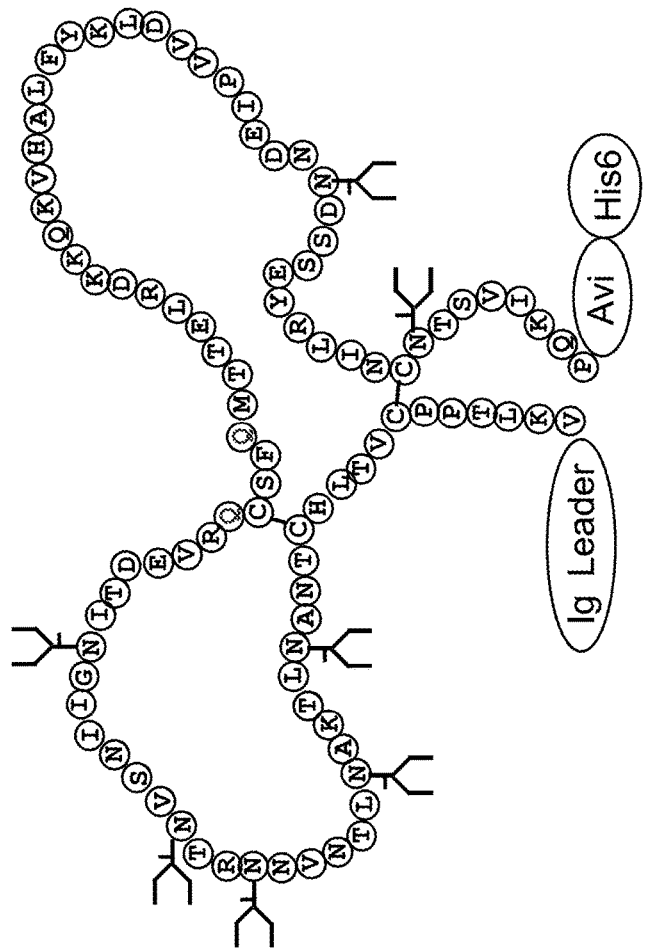
FIG. 3. AE.A244 V1V2_Tags_N156QN160Q.

Alternative designs of the AE. V1V2 tags immunogen are described in FIGS. 1-5. FIG. 1 shows a preferred design with the Ig leader sequence, an AVI tag and a HIS tag. For human use, the AVI and HIS tags can be deleted (FIG. 2).

Figure 4:
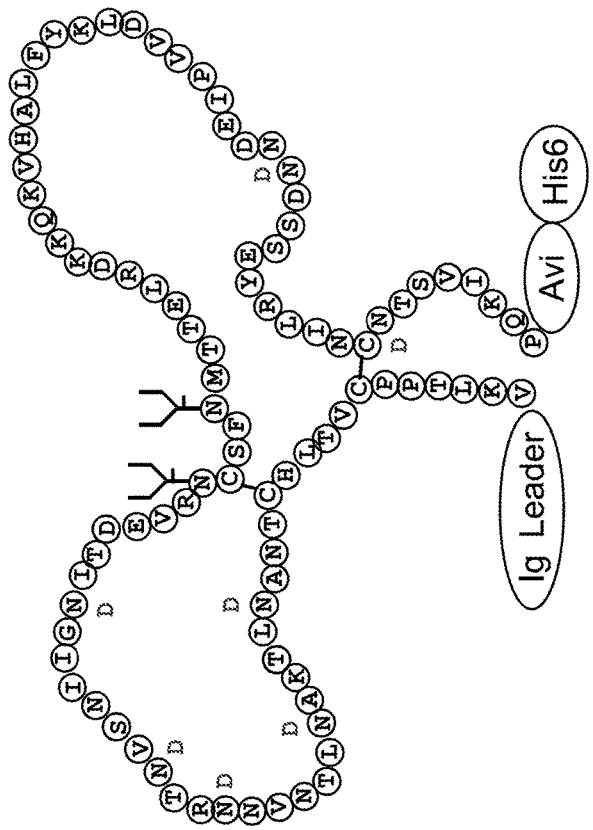
FIG. 4. AE.A244 V1V2_Tags_deltaN7D.
Figure 5:
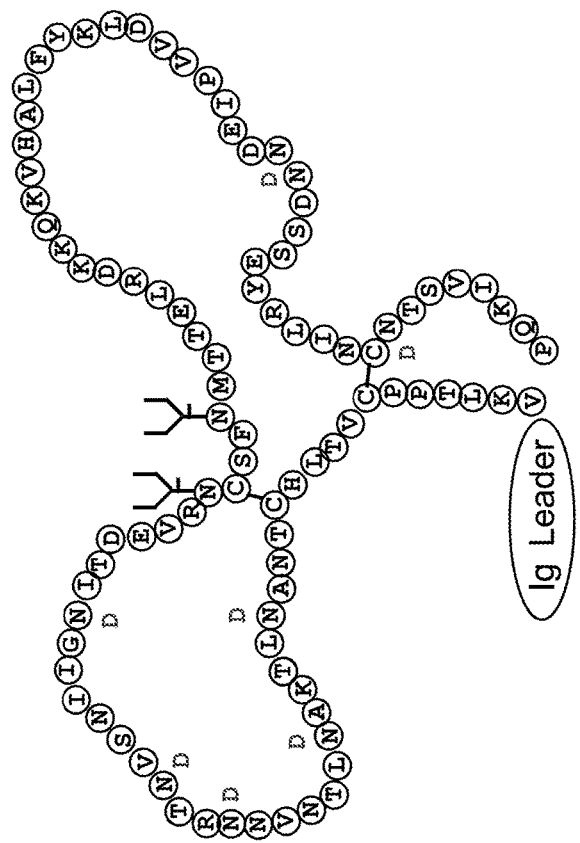
FIG. 5. AE.A244 V1V2_deltaN7D.

Alternative designs that can be used to focus the immune response on N160 and N, 156 glycans for the induction of V1V2 conformational antibodies (McLellan et al, Nature Nov. 23, 2011 Epub ahead of print) are shown in FIGS. 4 and 5 with all V1 V2 asparagines (N) mutated to remove all glycans except those at N160 and N156.

Examples of V1V2 sequences of transmitted founder or other viruses of interest from which V1V2 tags with the Ig leader sequence can be produced for use in a multivalent immunogen are shown in FIG. 6. (See also FIG. 17.)

Previously, Pinter (U.S. Appln. Publication No. US2003/0105282) described V1V2 recombinant proteins from clade B (Pinter et al, Vaccine 16:1803-11 (1998)), or with V1 V2 expressed alone (Granados-Gonzolez et al, AIDS Res. Human Retrovirol. 24:289-299 (2008)). The difference in these constructs and those described herein (or Granados-Gonzolez et al, AIDS Res. Human Retrovirol. 24:289-299 (2008)), are the primary nucleotide sequences and the use of transmitted founder virus sequences in many of the constructs, the use of clade AE sequences and the use of an Ig leader sequence.

Figure 7:
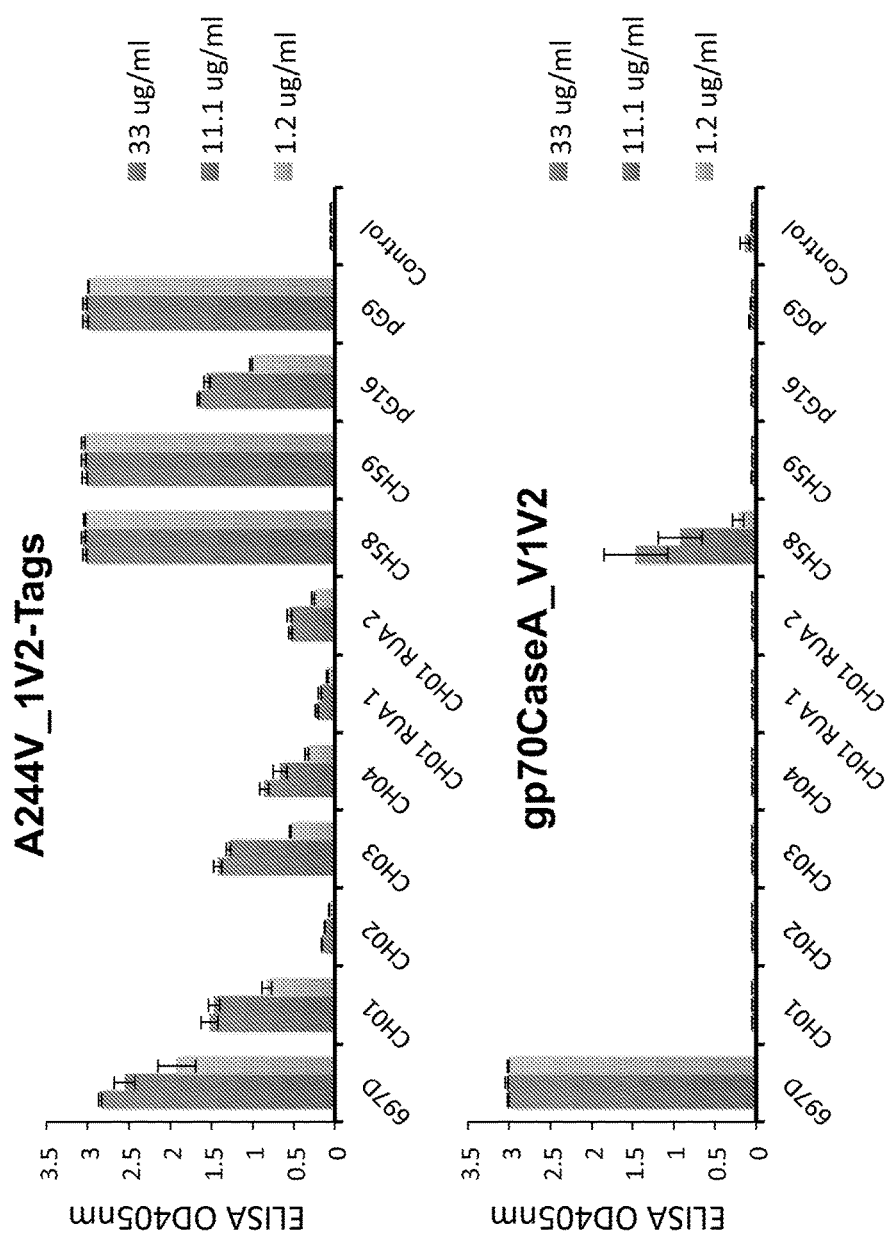
FIG. 7. Reactivity of HIV-1 antibodies to A244 V1V2_Tags vs. gp70Case A_V1V2.
Figure 8:
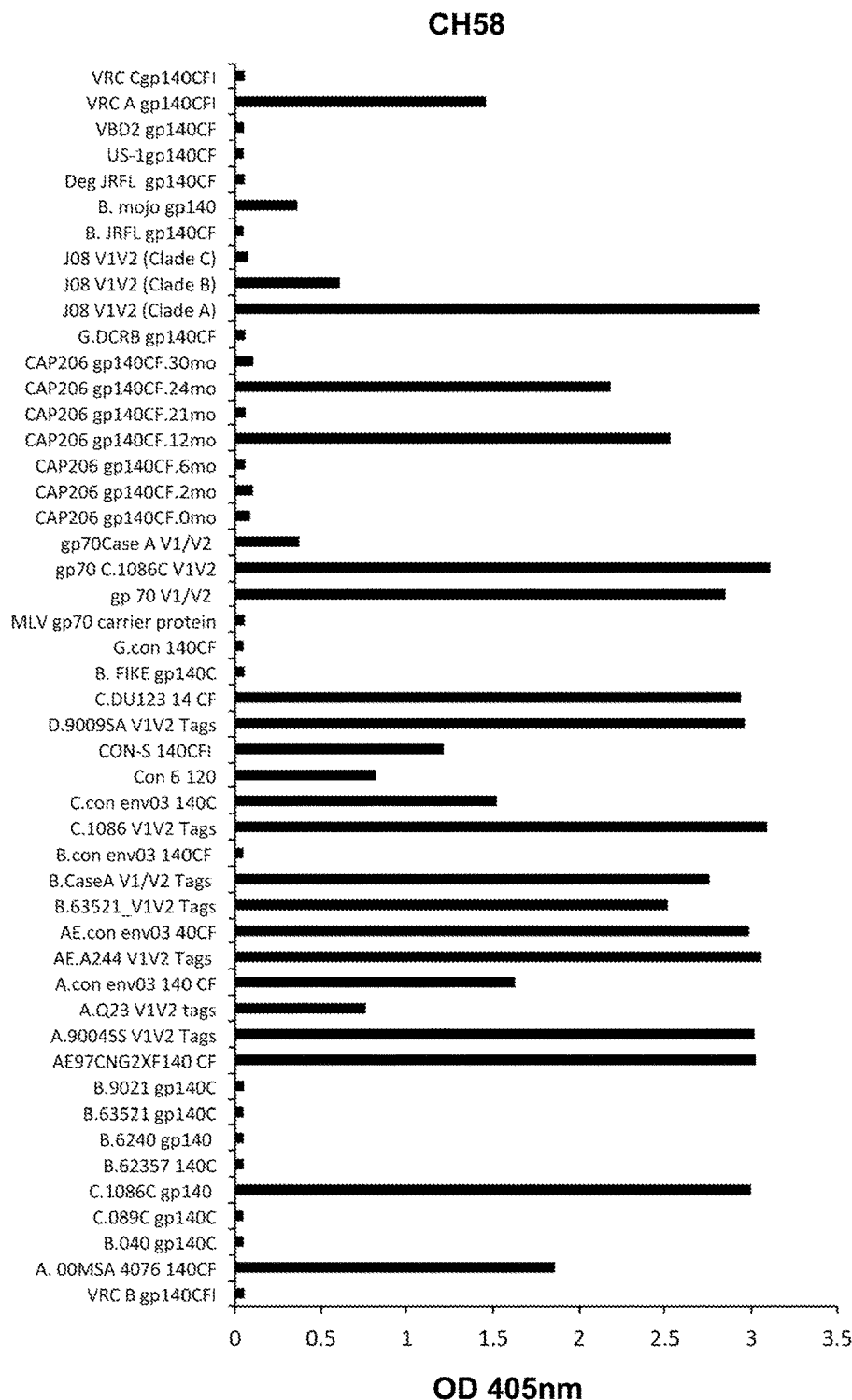
FIG. 8. Reactivity of CH58 and RUA antibodies to various HIV-1 Envs (48).
Figure 8:
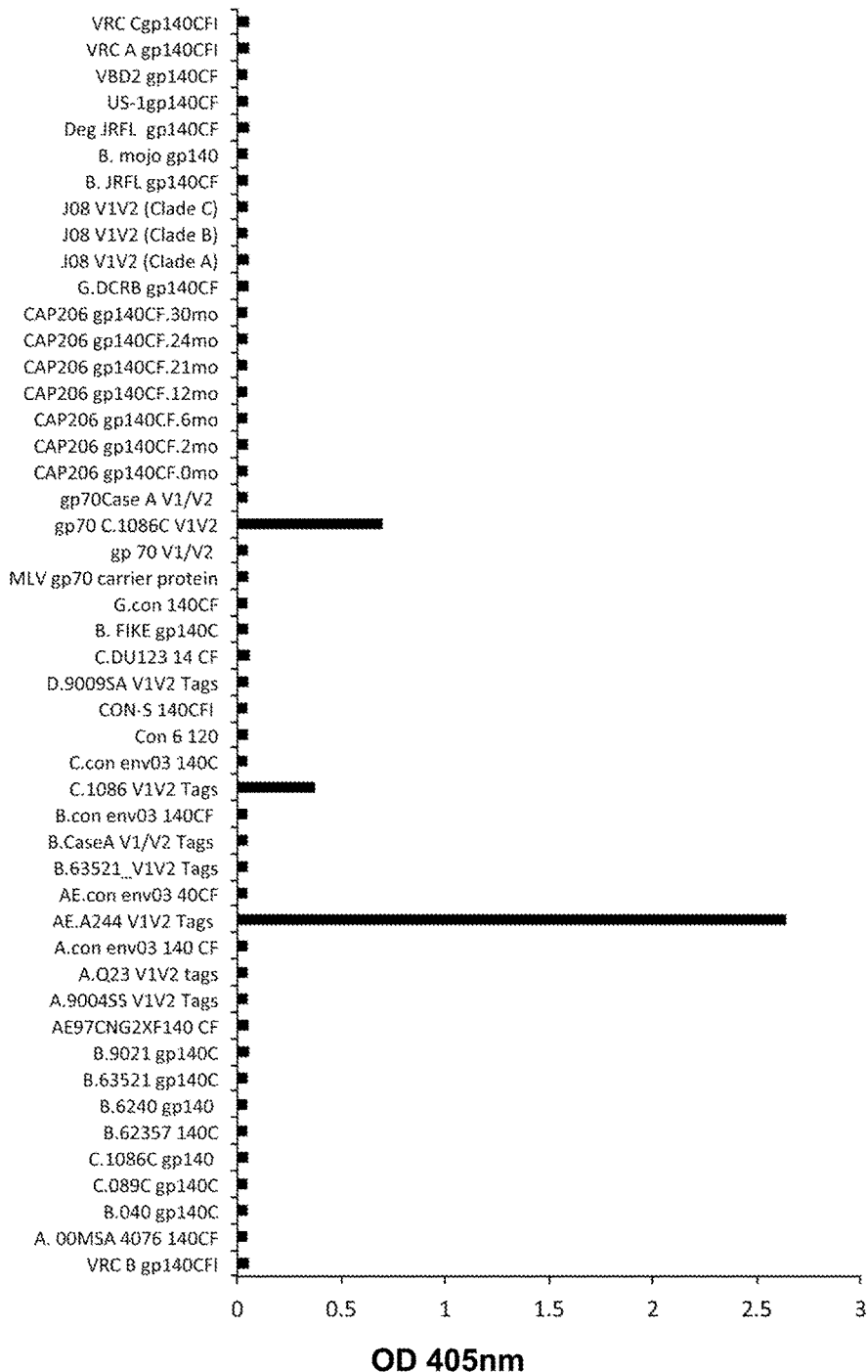
Figure 9:
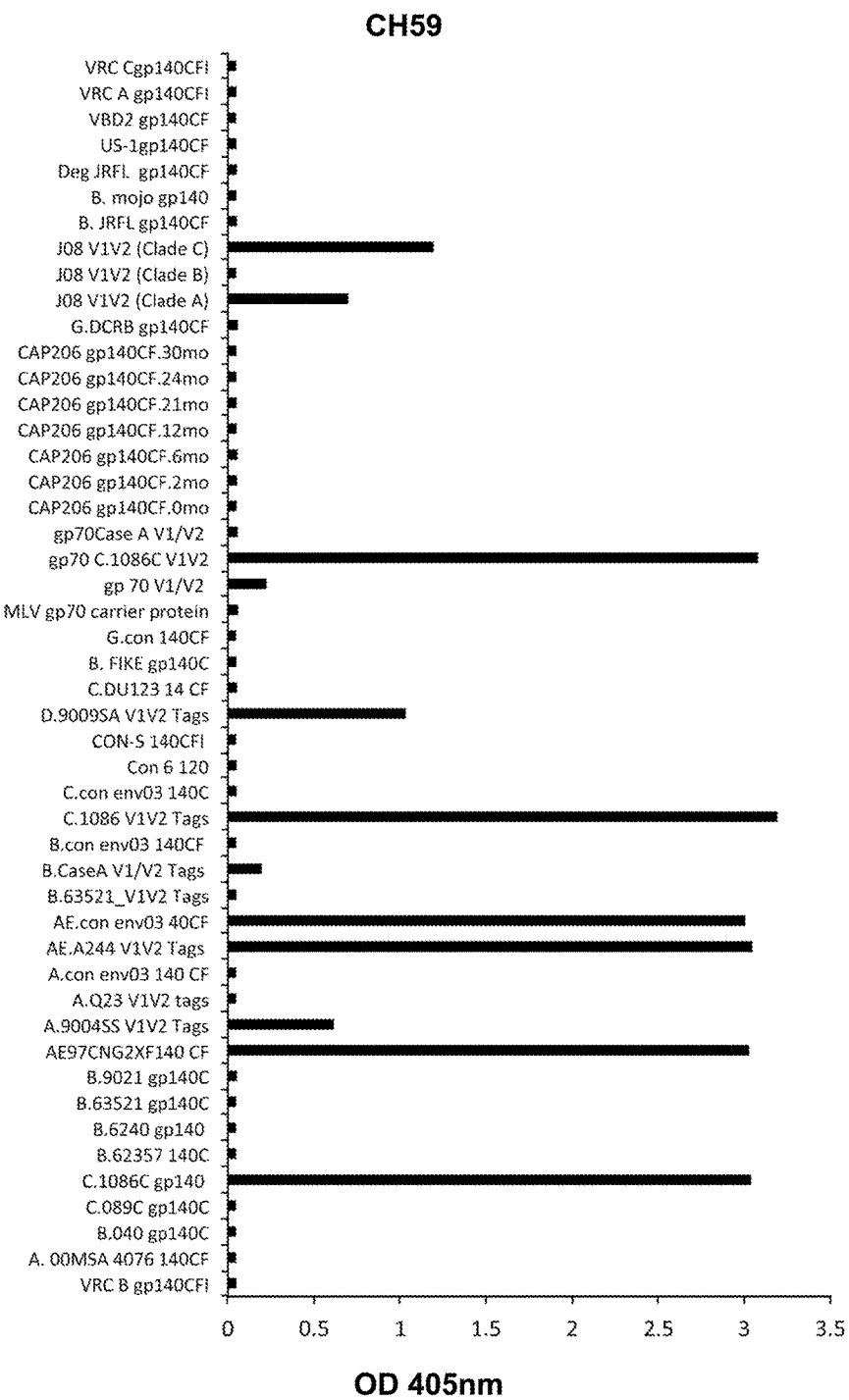
FIG. 9. Reactivity of CH59 and RUA antibodies to various HIV-1 Envs (48).
Figure 9:
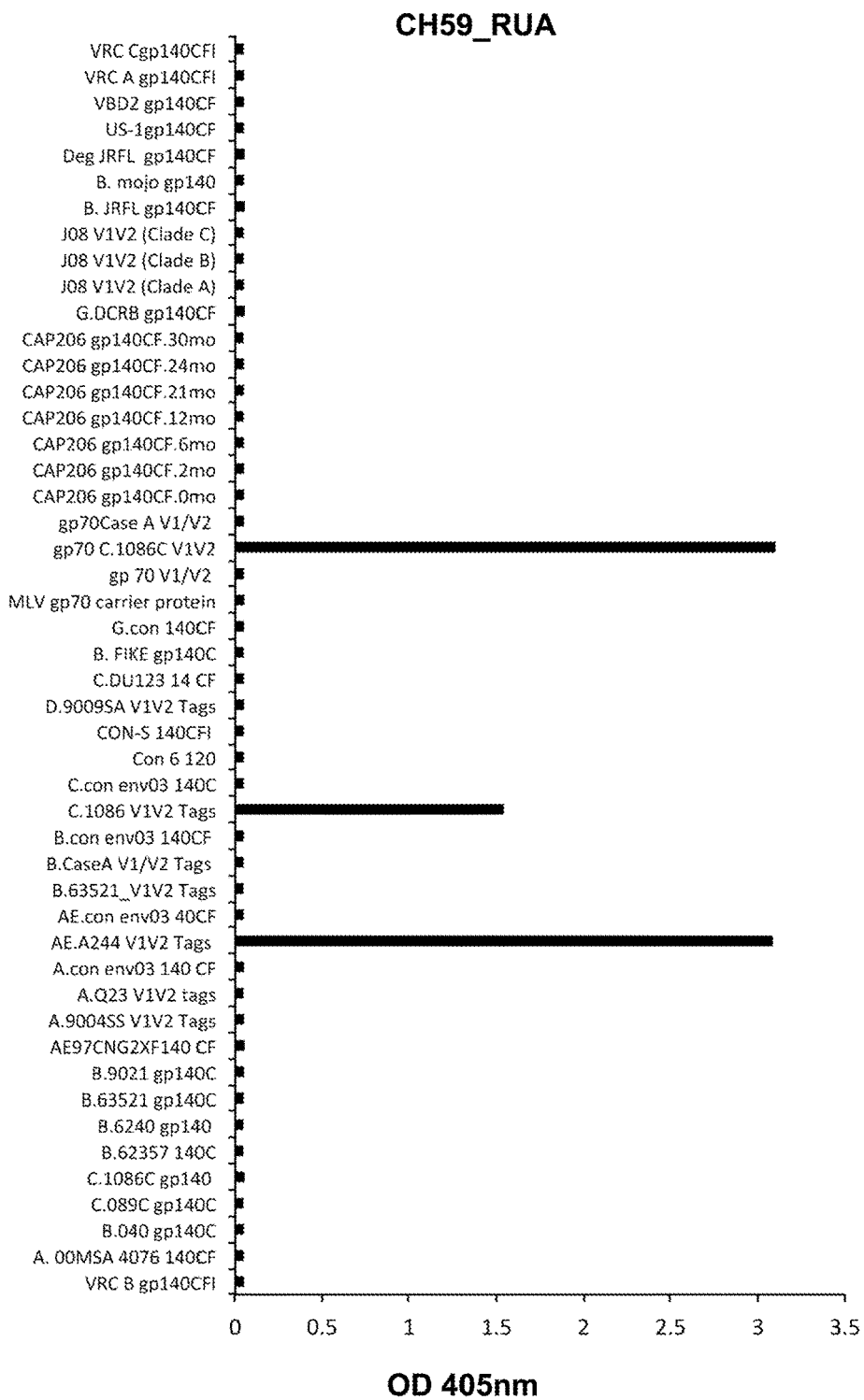

FIG. 7 shows that the A244 V1V2 tags construct of the present invention is superior to the gp70 CASE A V1V2 (Pinter et al, Vaccine 16:1803-11 (1998)) (see also U.S. Appln. Publication No. US2003/0105282) for expressing epitopes that react with conformational V1V2 antibodies (697D, CH01-CH04, PG9, PG16) and with RV144 antibodies CH58, CH59. (See also FIGS. 10-12.) FIG. 8 shows RV144 mab CH58 and its reverted unmutated ancestor antibody (RUA) assayed against a panel of 48 recombinant HIV-1 Envelopes or V1V2 constructs. Whereas the mature CH58 antibody reacted with many Envs, the RUA reacted only with three Env constructs and importantly, reacted best with the V1V2 A244AE tug protein. FIG. 9 similarly shows the same for RV144 mAb CH59 and its RUA but with equal reactivity of the RUA with the V1V2 A244 AE tag protein and with a gp70 Env V1V2 1086C protein.

FIG. 10 shows the similarities in the VH H CDR3 regions of the RV144 CH58 mab and the CH59 mab with the broad neutralizing mab PG9 (Walker et al, Science 326:285-9 (2009)). FIG. 11 shows variable region sequences of VH VL of immunoglobulin of mabs CH58, CH59, and their RUAs.

Figure 12:
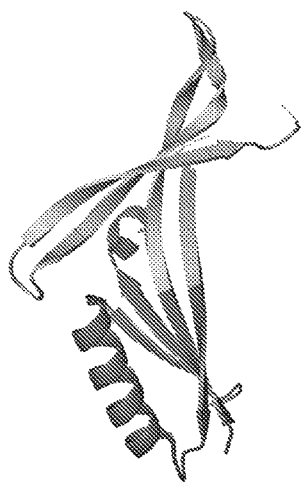
FIG. 12. Binding sites of CH58 and CH59.

Using the V1V2 sequences of CAP 45 and ZM109 of McLellan et al (Nature Nov. 23, 2011 Epub ahead of print), as well as of the AE.92TH023 V1V2 sequence, FIG. 12 shows that the binding sites of CH58 and CH59 on the gp120 C beta strand of V2 are overlapping that of the PG9 mab binding. Using an alanine substituted peptide panel of V2 peptides (glutamine substituted for native alanines), the footprints of mabs CH58 and CH59 are shown in FIG. 13.

Both CH58 and CH59 neutralize the Tier 1 AE strain of HIV-1 AE.92TH023 in the TZMbl neutralization assay (12-14 ug/ml IC50) but not the Tier 2 strain CM244 HIV strain (not shown) (see FIG. 14). Also, both mabs mediate antibody dependent cellular cytotoxicity against the CM235 AE strain infected CD4 T cells in a 6 hour granzyme release assay (not shown). In addition, both mabs capture both AE 92TH023 and CM235 virions (not shown).

Figure 15:
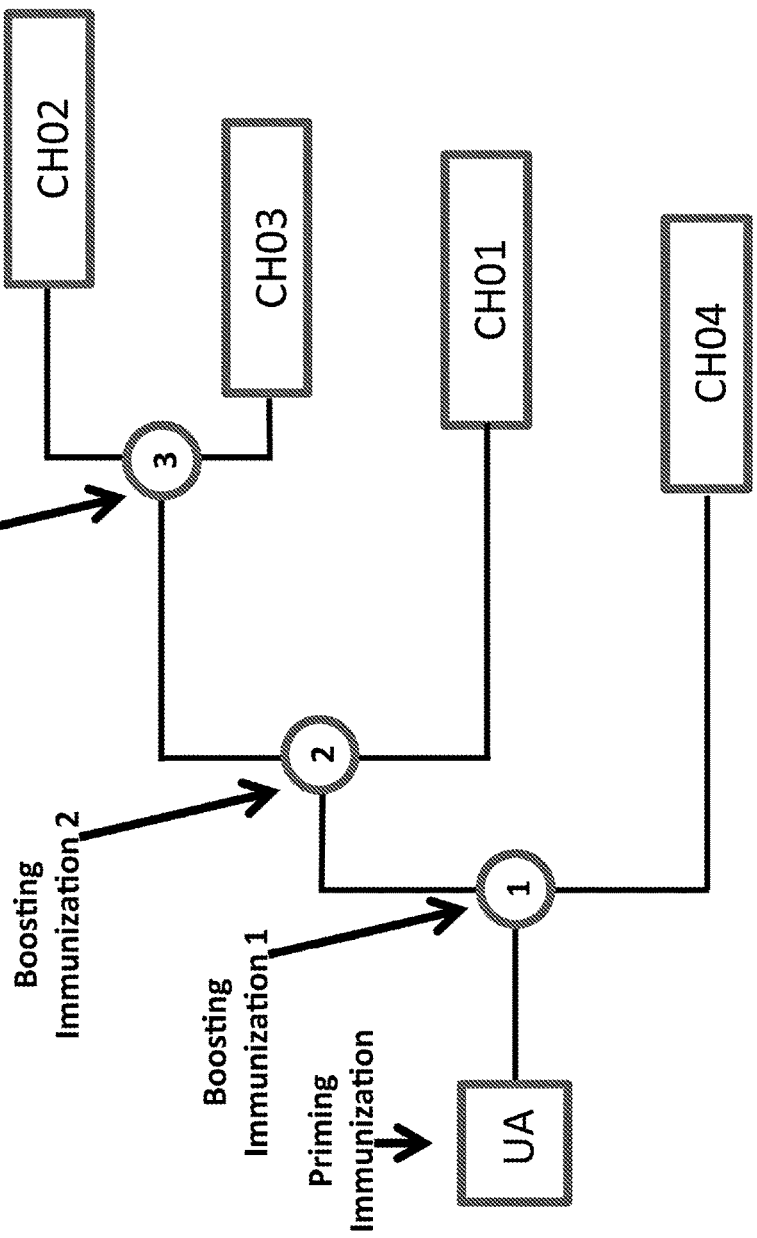
FIG. 15. B cell lineage-based immunogen design.
Figure 16:
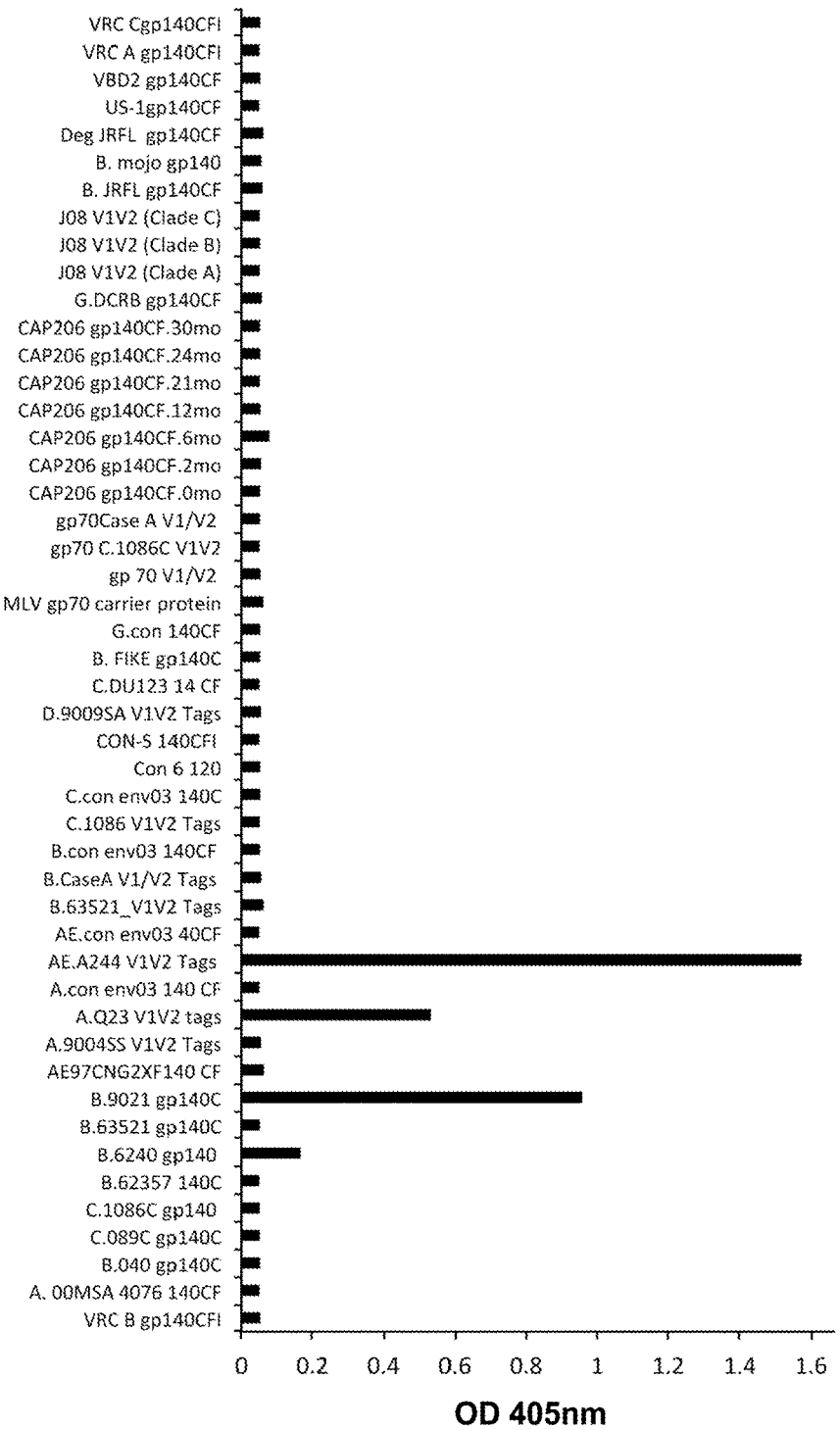
FIG. 16. Reactivity of CH01 and RUA antibodies to various HIV-1 envs.
Figure 16:
Figure 16:
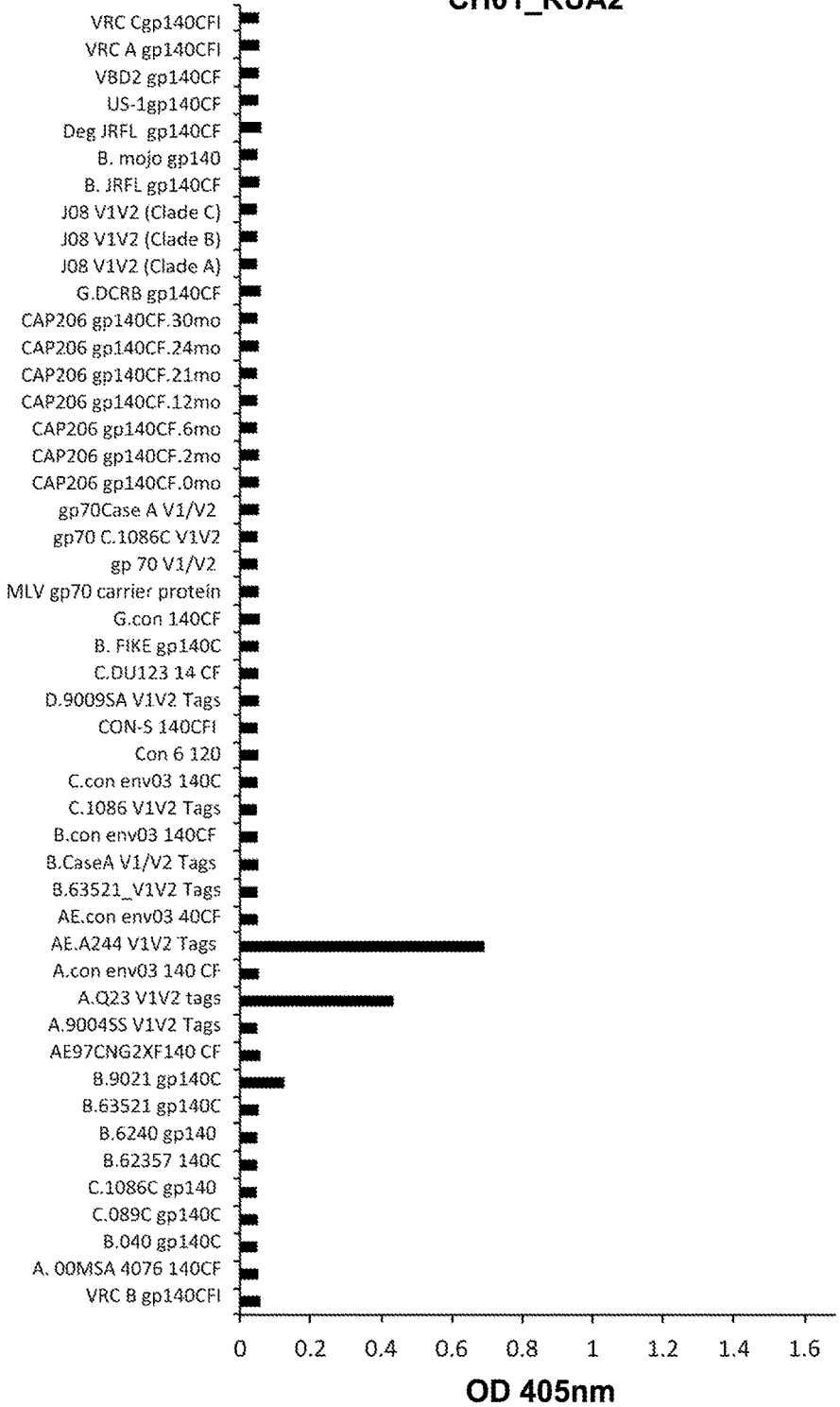

The B cell lineage immunogen design strategy that can be applied to inducing various types of V1V2 antibodies is shown in FIG. 15. For example, the V1V2 AE A244 tag molecule can be used as a prime and/or boost for inducing high levels of CH58 and CH59 types of V2 antibodies and as well for inducing high levels of CH01-CH04 like antibodies. For the latter, it is shown in FIG. 16 that the V1V2 AEA244 tags protein reacts with both the CH01 V1V2 conformational broad neutralizing mutated antibody and as well with the unmutated ancestor antibody for this broad neutralizing antibody. Thus, in the schema in FIG. 15, the V1V2 AE A244 tag molecule can prime both RUAs and intermediate antibodies for driving more mutated broad neutralizing antibodies like CH01. (See also U.S. Prov. Appln. 61/542,469, filed Oct. 3, 2011.)

The immunogens of the invention can be formulated as DNAs (Santra et al, Nature Med. 16:324-8 (2010)) and as inserts in vectors including rAdenovirus (Barouch et al, Nature Med. 16:319-23 (2010)), recombinant mycobacteria (i.e., BCG or *M smegmatis*) (Yu et al, Clinical Vaccine Immunol. 14:886-093 (2007; ibid 13: 1204-11 (2006)), and recombinant vaccinia type of vectors (Santra, Nature Med. 16: 324-8 (2010)). The immunogens can also be administered as a protein boost in combination with a variety of vectored Env primes (i.e., HIV-1 Envs expressed in non-HIV viral or bacterial vectors) (Barefoot et al. Vaccine 26:6108-18 (2008)), or as protein alone (Liao et al, Virology 353:268-82 (2006)). The protein can be administered with an adjuvant such as MF59, AS01B, polyI, polyC or alum and administered, for example, subcutaneously or intramuscularly. Alternatively, the protein or vectored immunogen can be administered mucosally such as via intranasal immunization or by other mucosal route (Torrieri D L et al Mol. Ther. Oct. 19, 2010, E put ahead of print).

Immunogens of the invention are suitable for use in generating an immune response in a patient (e.g., a human patient) to HIV-1. The mode of administration of the HIV-1 protein/polypeptide/peptide, or encoding sequence, can vary with the immunogen, the patient and the effect sought, similarly, the dose administered. As noted above, typically, the administration route will be intramuscular or subcutaneous injection (intravenous and intraperitoneal can also be used). Additionally, the formulations can be administered via the intranasal route, or intrarectally or vaginally as a suppository-like vehicle. Optimum dosing regimens can be readily determined by one skilled in the art. The immunogens are preferred for use prophylactically, however, their administration to infected individuals may reduce viral load.

In addition to the above-described immunogen designed for induction of V1V2 HIV envelope gp120 antibodies, the invention also includes the above-referenced CH58 and CH59 monoclonal antibodies, as well as antibodies having the binding specificity (characteristics) of CH58 and CH59 (e.g., see FIG. 33), and fragments thereof, and the use thereof in methods of treating or preventing HIV-1 in a subject (e.g., a human subject). One can see that since the CH58 and CH59 antibodies bind to the V2 region and bind to the gp70 V1V2 CASEA2 protein, they are candidates for being protective and have potential for use as antibodies to prevent the acquisition of HIV-1, either systemically or locally. The invention further includes compositions comprising such antibodies (e.g., antibodies having the binding specificity/characteristics of CH58 or CH59) or fragments thereof, and a carrier.

As indicated above, either the intact antibody or fragment (e.g., antigen binding fragment) thereof can be used in the method of the present invention. Exemplary functional fragments (regions) include scFv, Fv, Fab', Fab and F(ab')$_2$ fragments. Single chain antibodies can also be used. Techniques for preparing suitable fragments and single chain antibodies are well known in the art. (See, for example, U.S. Pat. Nos. 5,855,866; 5,877,289; 5,965,132; 6,093,399; 6,261,535; 6,004,555; 7,417,125 and 7,078,491 and WO 98/45331.) The invention also includes variants of the antibodies (and fragments) disclosed herein, including variants that retain the binding properties of the antibodies (and fragments) specifically disclosed, and methods of using same in the present method. Moreover, human antibodies CH58 or CH59, or antibodies with their characteristics, can be combined with other antibodies such as A32 or A32-like antibodies (Ferrari et al, J. Virol. 85:7029-36 (2011)) that would potentiate the effect of CH58 or CH59 or synergize with the effects of CH58 or CH59. A32-like antibodies are antibodies whose binding to HIV-1 Env can be blocked by mAb A32.

The antibodies, and fragments thereof, described above can be formulated as a composition (e.g., a pharmaceutical composition). Suitable compositions can comprise the antibody (or antibody fragment) dissolved or dispersed in a pharmaceutically acceptable carrier (e.g., an aqueous medium). The compositions can be sterile and can in an injectable form. The antibodies (and fragments thereof) can also be formulated as a composition appropriate for topical administration to the skin or mucosa. Such compositions can take the form of liquids, ointments, creams, gels and pastes. Standard formulation techniques can be used in preparing suitable compositions. The antibodies can be formulated so as to be administered as a post-coital douche or with a condom.

Suitable dose ranges can depend on the antibody and on the nature of the formulation and route of administration. Optimum doses can be determined by one skilled in the art without undue experimentation. Doses of antibodies in the range of 10 ng to 20 µg/ml can be suitable (both administered and induced).

Certain aspects of the present invention are described in greater detail in the Examples that follow. (See also Haynes et al, N. Engl. Med. 366:1275-1278 (2012), Karasavvas et al, AIDS Vaccine, Bangkok, Thailand, Abstract No. OA07.8LB (2011), Zolla-Pazner et al, AIDS Vaccine, Bangkok, Thailand, Abstract No. OA09.03, 77 (2011).)

Example 1

Figure 18:
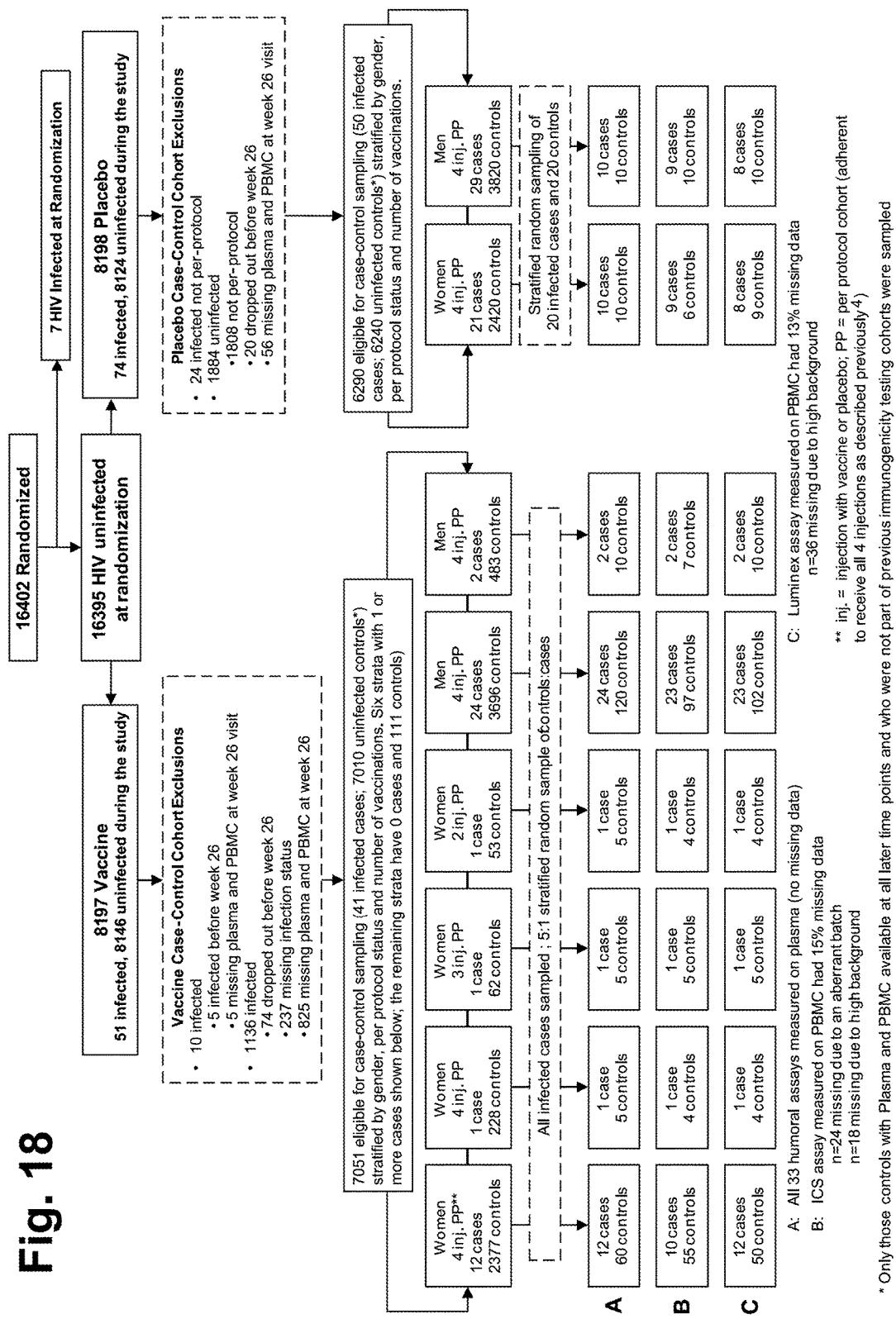
FIG. 18. Sampling of RV144 study participants into the case-control study.

Experimental Details
Study Procedures
  Case-Control Sampling Design.
  Subjects enrolled in the RV144 trial were vaccinated at weeks 0, 4, 12, and 24, and immune responses at week 26 evaluated as immune correlates of infection risk (Rerks-Ngarm et al, N Engl J Med 361:2209-20 (2009)) (FIG. 18). The vaccine-induced immune responses were assessed at peak immunogenicity (week 26, 2 weeks following the final immunization) in vaccines who acquired HIV-1 infection after week 26 (n=41 vaccine cases), in comparison to responses in vaccines who did not acquire infection over 42 month follow-up (n=205 vaccine controls). The vaccine cases were documented to be HIV-1 uninfected at week 24 and were later diagnosed with infection (Rerks-Ngarm et al, N Engl J Med 361:2209-20 (2009)). The vaccines who served as controls were selected from a stratified random sample of vaccine recipients who were documented to be HIV-1 uninfected at the terminal study visit at 42 months. Sampling strata were defined by the cross-classification of gender, the number of four planned vaccinations received, and per-protocol status as previously defined (Rerks-Ngarm et al, N Engl J Med 361:2209-20 (2009)). For each of the 8 strata the number of vaccine cases was noted, and five times this number of vaccine controls sampled. The assays were also performed on random samples of infected placebo recipients (n=20) and uninfected placebo recipient controls (n=20) (FIG. 18).

Process for Immune Variable Selection and Tiered Structure of the Correlates Analysis.

Figure 22:
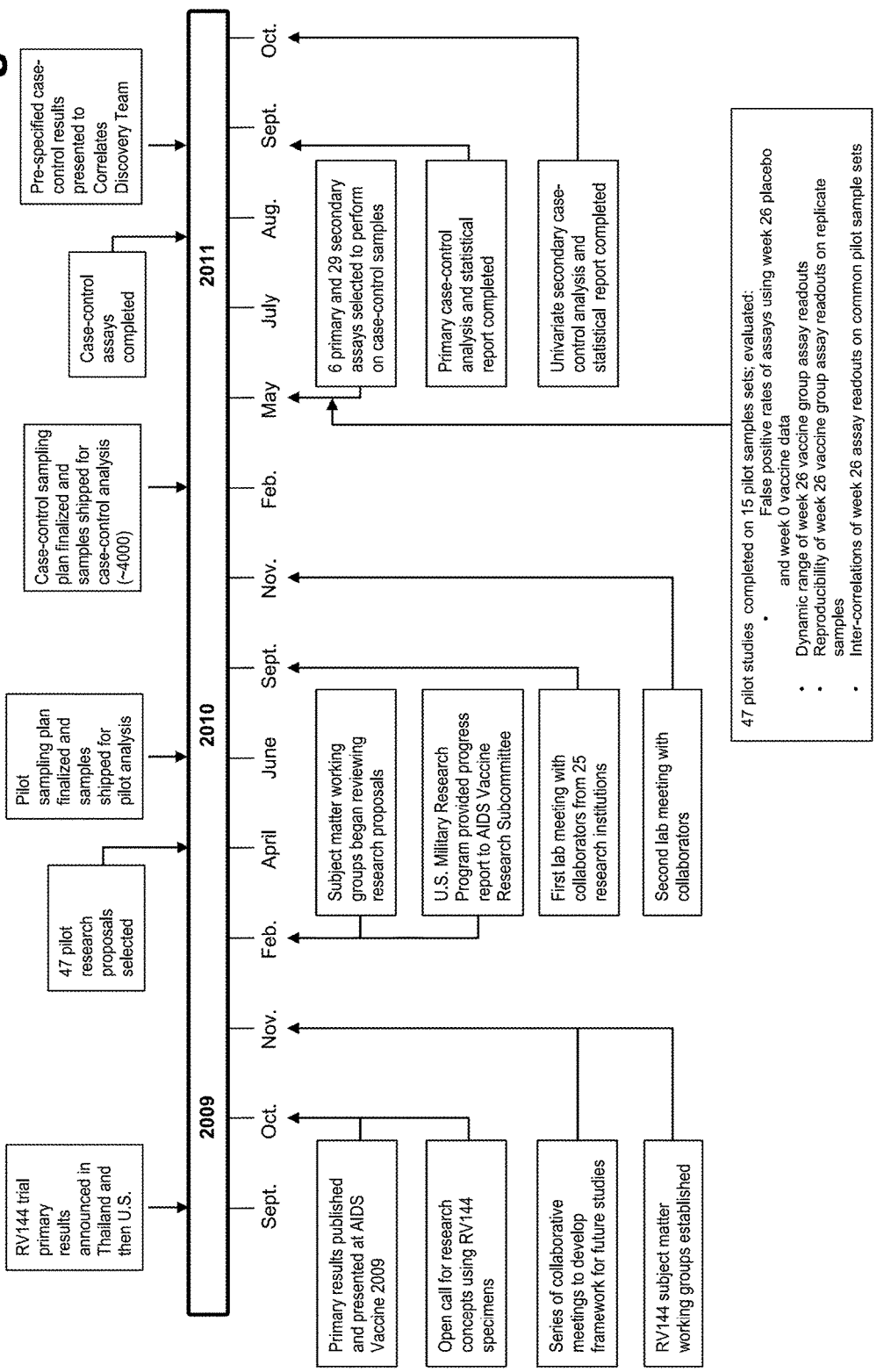
FIG. 22. Time-line for the pilot studies and the case-control study.

The correlates study was preceded by pilot studies from November 2009 to July 2011, that were used to down-select primary and secondary assays for the case-control study (Rolland and Gilbert, AIDS Res Hum Retroviruses Sep. 27 (2011)) (FIG. 22). Pilot assays were performed on baseline and week 26 samples from 50-100 uninfected RV144 participants (80 vaccine and 20 placebo recipients) and were scored by four statistical criteria: low false positive rate based on samples from placebo and vaccine recipients at baseline, large dynamic range of vaccine-induced immune responses, non-redundancy of responses as measured by low correlations, and high reproducibility.

Of the 32 assay types evaluated in pilot studies, 17 passed these criteria and were candidates for the 6 primary assays, from which 6 primary immune variables were chosen to assess as correlates of infection risk. The primary variables evaluated Env-specific antibody (n=5) and cellular (n=1) responses and included: IgA Env binding, IgG Env antibody avidity, ADCC, HIV-1 neutralization, gp120 Env V1V2 antibody binding, and Env-specific CD4+ T cell levels. All of the 17 immune assay types and their component variables were included in the correlates analysis and were classified into either the secondary sensitivity analysis or exploratory analysis tiers.

The purpose was to restrict the primary analysis to 6 variables to optimize statistical power. Secondary variables were evaluated to help interpret the primary analysis and to generate additional hypotheses. For sensitivity analysis, immune variables closely related to the six primary variables (within the same assay type) were substituted for each of the primary immune variables into the multivariable model (n=8 variables, with 3 individual variables paired to the primary neutralization variable). All assays were performed blinded to treatment assignment and case-control status.

A more detailed description of the Study Procedures is provided below.

Immune Biomarker Case-Control Sampling Design.

The objective of the correlates study was to assess vaccine-induced immune responses at the time of peak immunogenicity of the vaccine (week 26) (Rerks-Ngarm et al, N Engl J Med 361:2209-20 (2009)), 2 weeks following the final immunization in vaccine recipients who did not become infected over a 42 month follow-up, versus responses in vaccines who did become infected. Thus, week 26 immune responses were measured from all vaccine recipients documented to be HIV-1 uninfected by HIV-1 RNA PCR analysis at week 24 and who were later diagnosed with HIV-1 infection, using the algorithm previously described (Rerks-Ngarm et al, N Engl J Med 361:2209-20 (2009)) (n=41 vaccine cases with week 26 specimens available). In addition, week 26 immune responses were measured from a stratified random sample of vaccine recipients who were documented to be HIV-1 uninfected at the terminal study visit at 42 months (n=205 vaccine controls with week 26 specimens available and completed the study HIV negative). The sampling strata were defined by the cross-classification of gender, the number of the four planned vaccinations received, and per-protocol status as previously defined (Rerks-Ngarm et al, N Engl J Med 361:2209-20 (2009)). For each stratum the number of vaccine cases was noted, and five times this number of vaccine controls sampled. To determine if the immune responses were related to receipt of vaccine, the assays were performed on random samples of placebo recipient cases (n=20 with week 26 specimens available) and placebo recipient controls (n=20 with week 26 specimens available and completed the study HIV negative).

Process for Immune Variable Selection and Tiered Structure of the Correlates Analysis.

Given the large number of immunological assays and associated immunological variables that could potentially be evaluated as correlates, the limited specimen volumes, and the lack of clear rationale for preferring certain immunological assays, the correlates study was preceded by a series of pilot studies from November 2009 to July 2011, to form the basis for selecting assays for the case-control study (Rolland and Gilbert, AIDS Res Hum Retroviruses Sep. 27 (2011)). Each candidate assay was performed on baseline and week 26 samples from 100 uninfected RV144 participants (80 vaccine and 20 placebo recipients), and was scored by three statistical criteria: low false positive rate based on samples from placebo recipients and vaccine recipients at baseline, large dynamic range of vaccine-induced immune responses, and high reproducibility on replicate samples.

Of the 32 assay types evaluated in pilot studies, 17 assay types passed these criteria and their components were candidates for the 6 variables chosen for study in the primary analyses. All of the assay variables not chosen for the primary analysis were also performed on the case-control samples, and were considered in secondary analyses. From the 17 assay types there were 154 individual secondary variables (Table 1). The primary variables evaluated Env-specific antibody (n=5) and cellular (n=1) responses, and consisted of the six best-performing assays selected from each of six primary variable types: IgA binding, IgG avidity, antibody-dependent cellular cytotoxicity (ADCC), neutralization, gp120 Env V1V2 binding, and Env-specific CD4 T cell levels. All other immune assays and their variables were deemed secondary and were classified into either the sensitivity analysis or exploratory analysis tiers. The purpose or the staged analysis structure was to restrict the primary analysis to 6 priority variables, in order to maximize the chance to discover correlates by restricting the formal statistical testing (with multiplicity adjustment) to a small set of immune variables with the strongest biological and statistical rationale. The use of secondary variables was to help interpret the primary analysis results and to generate additional hypotheses for further testing. For the sensitivity secondary analysis, eight immune variables closely related to the six primary variables were substituted for each of the primary immune variables into the multivariate model with 3 individual assays paired to the primary neutralization variable (Tables 2 and 3).

TABLE 1

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively, in order of appearance

| Assay | Investigator | Institution | Quantitative | | | Categorical | | | | |
|---|---|---|---|---|---|---|---|---|---|---|
| | | | $OR^1$ | P value | Q value | Contrast | $OR^2$ | P value | Global P value | Global Q value |
| 1. gp120 V2 Env Binding | | | | | | | | | | |
| V2 cyclic peptide ELISA | Nicos Karasavva | AFRIMS | | | | | | | | |
| Cyclic V2 ELISA sites 157-198 | | | NA | NA | NA | Med vs. Low | 0.85 | 0.67 | 0.87 | 0.44 |
| | | | | | | High vs. Low | 0.82 | 0.63 | | |
| Cyclic V2 scrambled crown ELISA | | | NA | NA | NA | Pos vs. Neg | NA | NA | NA | NA |
| Cyclic V2 scrambled flanks ELISA | | | 0.76 | 0.10 | 0.95 | Med vs. Low | 0.6 | 0.23 | 0.49 | 0.35 |
| | | | | | | High vs. Low | 0.84 | 0.66 | | |
| V2 cyclic peptide-SPR | Mangala Rao | USMHRP | | | | | | | | |
| Cyclic scrambled crown V2 Biacore | | | 0.79 | 0.18 | 0.95 | Med vs. Low | 0.46 | 0.09 | 0.20 | 0.30 |
| | | | | | | High vs. Low | 0.9 | 0.8 | | |
| Cyclic V2 Biacore sites 157-198 | | | 0.81 | 0.24 | 0.95 | Med vs. Low | 0.53 | 0.15 | 0.35 | 0.34 |
| | | | | | | High vs. Low | 0.84 | 0.66 | | |
| V2 peptide Luminex | Georgia Tomaras | Duke University | | | | | | | | |
| IgGV2 A244 K178 KKKVHALFYKLDIVPIEDKKK-Biotin | | | 0.74 | 0.05 | 0.95 | Med vs. Low | 0.57 | 0.22 | 0.36 | 0.34 |
| | | | | | | High vs. Low | 1.02 | 0.95 | | |
| IgA V2 A244 K178 KKKVHALFYKLDIVPIEDKKK-Biotin | | | NA | NA | NA | Pos vs. Neg | 0.79 | 0.77 | 0.77 | 0.42 |
| V2 cyclic peptide ELISA | Susan Zolla-Pazner | New York University | | | | | | | | |

TABLE 1-continued

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively, in order of appearance)

| | | | Quantitative | | | | Categorical | | Global | Global |
|---|---|---|---|---|---|---|---|---|---|---|
| Assay | Investigator | Institution | OR[1] | P value | Q value | Contrast | OR[2] | P value | P value | Q value |
| V2 cyclic peptide 42aa CSFNMTTELRDKKQKVHALFYKLDIV PIEDNTSSSEYRLINC | | | 0.82 | 0.26 | 0.95 | Med vs. Low High vs. Low | 0.73 0.65 | 0.45 0.31 | 0.57 | 0.38 |
| biotin V2 peptide 6 (aa 165-178) LRDKKQRVYSLFYK | | | 0.95 | 0.8 | 0.98 | Med vs. Neg High vs. Neg | 0.71 0.85 | 0.46 0.71 | 0.76 | 0.42 |
| V2 linear peptides | Philip Berman | University of California, Santa Cruz | | | | | | | | |
| V2 MNELISA ITTSIGDKMQKEYALLYKLDIEP | | | NA | NA | NA | Pos vs. Neg | 0.41 | 0.25 | 0.25 | 0.31 |
| V2 A244-TH023 ELISA SFNMTTELRDKKQKVHALFYK | | | 0.9 | 0.57 | 0.98 | Med vs. Low High vs. Low | 0.37 0.88 | 0.04 0.74 | 0.09 | 0.28 |
| 2. gp120 V3 Env Binding | | | | | | | | | | |
| Scaffold gp70-V3 | Susan Zolla-Pazner | New York University | NA | NA | NA | Pos vs. Neg | 0.8 | 0.57 | 0.57 | 0.38 |
| 3. HIV-1 Neutralization | | | | | | | | | | |
| TZM-bl Assay Nab TZM-bl 92TH023.AE* | Ruengpueng Sutthent | Siriraj Hospital | 1.2 | 0.29 | 0.95 | Med vs. Low High vs. Low | 0.63 1.32 | 0.32 0.49 | 0.34 | 0.34 |
| Nab source TZM-bl subtype B* | Chitraporn Karnasuta | AFRIMS | 1.02 | 0.91 | 0.98 | Med vs. Low High vs. Low | 0.53 0.72 | 0.14 0.43 | 0.34 | 0.34 |
| NAb TZM-bl MN.3.B | | | 0.92 | 0.65 | 0.98 | Med vs. Low High vs. Low | 0.51 1.05 | 0.14 0.9 | 0.23 | 0.30 |
| NAb TZM-bl MW965.26.C | | | 1.12 | 0.5 | 0.98 | Med vs. Neg High vs. Neg | 0.57 1.16 | 0.22 0.72 | 0.34 | 0.34 |
| NAb TZM-bl SF162.LS.B | | | NA | NA | NA | Pos vs. Neg | 1.01 | 0.98 | 0.98 | 0.47 |
| A3R5 Assay | David Montefiori | Duke University | | | | | | | | |
| Nab score A3R5 subtype E* | | | 1.02 | 0.92 | 0.98 | Med vs. Low High vs. Low | 0.58 1.11 | 0.23 0.79 | 0.30 | 0.34 |
| NAb A3R5 C1080.c03.LucR.T2A.ecto.AE | | | 1.07 | 0.69 | 0.98 | Med vs. Neg High vs. Neg | 0.9 1.1 | 0.82 0.82 | 0.88 | 0.44 |
| NAb A3R5 C3347.c11.LucR.T2A.ecto.AE | | | 0.95 | 0.79 | 0.98 | Med vs. Neg High vs. Neg | 0.48 0.8 | 0.13 0.64 | 0.26 | 0.31 |
| 4. CD4 Inducible Epitope Antibody Env Binding | | | | | | | | | | |
| ELISA | George Lewis | University of Maryland | NA | NA | NA | Pos vs. Neg | 1.1 | 0.78 | 0.78 | 0.42 |
| 5. IgA Env Binging-Luminex | Georgia Tomaras | Duke University | | | | | | | | |
| IgA A.00MSA gp140CF | | | NA | NA | NA | Pos vs. Neg | 2.63 | 0.02 | 0.02 | 0.27 |
| IgA E.92TH023 gD-293T gp120 | | | 1.21 | 0.3 | 0.95 | Med vs. Neg High vs. Neg | 0.72 1.95 | 0.49 0.09 | 0.07 | 0.28 |
| IgA E.92TH023 gD+ 293T gp120 | | | 1.08 | 0.69 | 0.98 | Med vs. Low High vs. Low | 0.72 1.99 | 0.5 0.1 | 0.05 | 0.27 |
| IgA B.MN gD+ CHOGSID gp120 | | | 1.27 | 0.26 | 0.95 | Med vs. Low High vs. Low | 1.27 1.84 | 0.59 0.16 | 0.35 | 0.34 |

TABLE 1-continued

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively, in order of appearance)

| Assay | Investi-gator | Institution | Quantitative | | | Contrast | Categorical | | Global P value | Global Q value |
|---|---|---|---|---|---|---|---|---|---|---|
| | | | $OR^1$ | P value | Q value | | $OR^2$ | P value | | |
| IgA E.97CNGX2F gp140CF | | | NA | NA | NA | Pos vs. Neg | 1.64 | 0.18 | 0.18 | 0.30 |
| IgA A.con.env03 gp140CF | | | NA | NA | NA | Pos vs. Neg | 3.71 | <0.002 | <0.01 | 0.1 |
| IgA E.A244 gD- 293T gp120 | | | NA | NA | NA | Pos vs. Neg | 1.49 | 0.26 | 0.26 | 0.31 |
| IgA E.A244 gD- Delta 11 293T gp120 | | | 1.25 | 0.25 | 0.95 | Med vs. Neg | 0.85 | 0.75 | 0.09 | 0.28 |
| | | | | | | High vs.Neg | 1.92 | 0.15 | | |
| IgA E.A244 gD+ 293T gp120 | | | 1.19 | 0.36 | 0.95 | Med vs. Low | 1.16 | 0.74 | 0.25 | 0.31 |
| | | | | | | High vs. Low | 1.94 | 0.13 | | |
| IgA E.A244 gD+ CHOGSID gp120 | | | 1.18 | 0.37 | 0.95 | Med vs. Neg | 1.0 | 1.0 | 0.36 | 0.34 |
| | | | | | | High vs. Neg | 1.65 | 0.28 | | |
| IgA B.con.env gp140CF | | | 1.25 | 0.25 | 0.95 | Med vs. Neg | 1.37 | 0.5 | 0.59 | 0.40 |
| | | | | | | High vs. Neg | 1.59 | 0.31 | | |
| IgA C1 peptide MQEDVISLWDQSLKPCVKLTPLCV | | | NA | NA | NA | Pos vs. Neg | 3.15 | <0.004 | <0.01 | 0.13 |
| IgA C.con.env03 gp140CF | | | 1.25 | 0.23 | 0.95 | Med vs. Neg | 1.45 | 0.4 | 0.59 | 0.39 |
| | | | | | | High vs. Neg | 1.5 | 0.35 | | |
| IgA CON6 gp120 | | | 1.01 | 0.96 | 0.98 | Med vs. Neg | 0.4 | 0.07 | 0.07 | 0.27 |
| | | | | | | High vs. Neg | 1.14 | 0.76 | | |
| IgA CON-S gp140CFI | | | 1.19 | 0.35 | 0.95 | Med vs. Neg | 0.99 | 0.98 | 0.53 | 0.36 |
| | | | | | | High vs. Neg | 1.48 | 0.39 | | |
| IgA G.con.env03 gp140CF | | | NA | NA | NA | Pos vs. Neg | 1.77 | 0.14 | 0.14 | 0.29 |
| IgA HSV gD peptide KYALVDASLKMADPNFTFGKDLPVL DQLTDPP | | | 1.01 | 0.94 | 0.98 | Med vs. Neg | 0.5 | 0.15 | 0.13 | 0.29 |
| | | | | | | High vs. Neg | 1.17 | 0.71 | | |
| IgA GNEB gD+, CHOGSID gp120 | | | 1.13 | 0.53 | 0.98 | Med vs. Low | 0.72 | 0.48 | 0.2 | 0.30 |
| | | | | | | High vs. Low | 1.54 | 0.3 | | |
| IgA AE.con.env03 gp140CF | | | NA | NA | NA | Pos vs. Neg | 1.17 | 0.65 | 0.65 | 0.40 |
| IgA G.DRCBL gp140CF | | | NA | NA | NA | Pos vs. Neg | 2.02 | 0.05 | 0.05 | 0.27 |
| IgA B.JRFL gp140CF | | | 1.1 | 0.59 | 0.98 | Med vs. Neg | 0.82 | 0.67 | 0.54 | 0.47 |
| | | | | | | High vs. Neg | 1.39 | 0.42 | | |
| IgA V2 A244 K178 KKKVHALFYKLDIVPIEDKKK-Biotin | | | NA | NA | NA | Pos vs. Neg | 0.79 | 0.77 | 0.77 | 0.42 |
| IgA A244 K198 KKKEYRLINCNTSVIKQAKKK-Biotin | | | NA | NA | NA | Pos vs. Neg | NA | NA | NA | NA |
| IgA breadth non-vaccine Envs | | | 1.43 | 0.03 | 0.95 | Med vs. Low | 0.78 | 0.59 | 0.28 | 0.33 |
| | | | | | | High vs. Low | 1.51 | 0.32 | | |
| IgA vaccine Envs | | | 1.26 | 0.18 | 0.95 | Med vs. Low | 0.86 | 0.75 | 0.44 | 0.34 |
| | | | | | | High vs. Low | 1.48 | 0.32 | | |
| IgA US1 $SIV_{cpz}$ gp140CF | | | NA | NA | NA | Pos vs. Neg | 3.29 | 0.07 | 0.07 | 0.28 |
| 6. IgG Env Binding | | | | | | | | | | |
| IgG A.00MSA gp140cf | | | 0.92 | 0.63 | 0.98 | Med vs. Neg | 0.7 | 0.41 | 0.7 | 0.42 |
| | | | | | | High vs. Neg | 0.9 | 0.79 | | |
| IgG E.A244 gD- 293T gp120 | | | 0.71 | 0.03 | 0.95 | Med vs. Low | 0.4 | 0.04 | 0.13 | 0.29 |
| | | | | | | High vs. Low | 0.72 | 0.42 | | |
| IgG E.92TH023 gD- 293T gp120 | | | 0.76 | 0.1 | 0.95 | Med vs. Low | 0.6 | 0.27 | 0.26 | 0.31 |
| | | | | | | High vs. Low | 1.22 | 0.63 | | |
| IgG E.92TH023 gD+ 293T | | | 0.95 | 0.76 | 0.98 | Med vs. Low | 0.7 | 0.45 | 0.15 | 0.29 |
| | | | | | | High vs. Low | 1.61 | 0.25 | | |
| IgG B.MN gD+ CHOGSID | | | 0.98 | 0.91 | 0.98 | Med vs. Low | 0.81 | 0.64 | 0.72 | 0.42 |
| | | | | | | High vs. Low | 1.14 | 0.75 | | |

TABLE 1-continued

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively, in order of appearance)

| Assay | Investigator | Institution | Quantitative | | | Categorical | | | Global P value | Global Q value |
|---|---|---|---|---|---|---|---|---|---|---|
| | | | OR[1] | P value | Q value | Contrast | OR[2] | P value | | |
| IgG E.97CNGX2F gp140CF | | | 0.75 | 0.08 | 0.95 | Med vs. Low | 0.54 | 0.16 | 0.36 | 0.34 |
| | | | | | | High vs. Low | 0.72 | 0.43 | | |
| IgG A.con.env03.140CF | | | 0.87 | 0.42 | 0.95 | Med vs. Neg | 0.49 | 0.12 | 0.26 | 0.31 |
| | | | | | | High vs. Neg | 0.86 | 0.71 | | |
| IgG E.A244 gD- Delta 11 293T gp120 | | | 0.82 | 0.26 | 0.95 | Med vs. Low | 0.56 | 0.23 | 0.22 | 0.30 |
| | | | | | | High vs. Low | 1.21 | 0.64 | | |
| IgG E.A244 gD- N160 minus N160K gp120 | | | 0.74 | 0.09 | 0.95 | Med vs. Low | 0.68 | 0.35 | 0.37 | 0.34 |
| | | | | | | High vs. Low | 0.56 | 0.17 | | |
| IgG E.A244 gD+ 293T gp120 | | | 0.94 | 0.75 | 0.98 | Med vs. Low | 0.77 | 0.55 | 0.64 | 0.39 |
| | | | | | | High vs. Low | 1.15 | 0.74 | | |
| IgG E.A244 gD+ CHOGSID gp120 | | | 0.87 | 0.44 | 0.95 | Med vs. Low | 0.42 | 0.07 | 0.1 | 0.29 |
| | | | | | | High vs. Low | 1.07 | 0.87 | | |
| IgG E.A244 gD+ N160 minus N160K gp120 | | | 0.84 | 0.3 | 0.95 | Med vs. Low | 0.83 | 0.65 | 0.67 | 0.4 |
| | | | | | | High vs. Low | 0.69 | 0.37 | | |
| IgG B.con.env03 gp140CF | | | 0.9 | 0.59 | 0.98 | Med vs. Low | 1.14 | 0.77 | 0.79 | 0.42 |
| | | | | | | High vs. Low | 1.35 | 0.49 | | |
| IgG C1 peptide MQESVISLWDQSLKPCVKLTPLCV | | | 0.85 | 0.35 | 0.95 | Med vs. Low | 0.41 | 0.06 | 0.09 | 0.28 |
| | | | | | | High vs. Low | 1.06 | 0.88 | | |
| IgG C.con.env03 gp140CF | | | 0.85 | 0.37 | 0.95 | Med vs. Low | 1.12 | 0.8 | | 0.42 |
| | | | | | | High vs. Low | 1.35 | 0.49 | | |
| IgG Con6 gp120 | | | 0.9 | 0.59 | 0.98 | Med vs. Low | 0.95 | 0.91 | 0.41 | 0.34 |
| | | | | | | High vs. Low | 1.57 | 0.3 | | |
| IgG CON-S gp140CFI | | | 0.88 | 0.51 | 0.98 | Med vs. Low | 1.32 | 0.54 | 0.66 | 0.4 |
| | | | | | | High vs. Low | 1.5 | 0.36 | | |
| IgG G.con.env03 gp140CF | | | 0.81 | 0.21 | 0.95 | Med vs. Low | 0.59 | 0.24 | 0.38 | 0.34 |
| | | | | | | High vs. Low | 1.04 | 0.93 | | |
| IgG HSV gD peptide KYALVDASLKMADPNRFRGKDLPVLDQLTDPP | | | 1.02 | 0.93 | 0.98 | Med vs. Low | 1.39 | 0.47 | 0.45 | 0.35 |
| | | | | | | High vs. Low | 1.73 | 0.21 | | |
| IgG GNE8 gD+ CHO GSID gp120 | | | 0.97 | 0.88 | 0.98 | Med vs. Low | 1.0 | 1.0 | 0.56 | 0.38 |
| | | | | | | High vs. Low | 1.47 | 0.37 | | |
| IgG AE.con.env03 gp140CF | | | 0.78 | 0.14 | 0.95 | Med vs. Low | 0.7 | 0.43 | 0.71 | 0.42 |
| | | | | | | High vs. Low | 0.92 | 0.85 | | |
| IgG G.DRCBL gp140 | | | 1.01 | 0.97 | 0.98 | Med vs. Neg | 0.54 | 0.2 | 0.12 | 0.29 |
| | | | | | | High vs. Neg | 1.31 | 0.53 | | |
| IgG HxB2new8bcore minus HxB2new8bcore1420R | | | 0.75 | 0.18 | 0.95 | Med vs. Low | 0.63 | 0.26 | 0.42 | 0.34 |
| | | | | | | High vs. Low | 0.62 | 0.26 | | |
| IgG B.JRFL gp140 | | | 0.85 | 0.35 | 0.95 | Med vs. Low | 1.04 | 0.93 | 0.61 | 0.39 |
| | | | | | | High vs. Low | 1.46 | 0.38 | | |
| IgG V2 A244 K178 KKKVHALFYKLDIVPIEDKKK-Biotin | | | NA | NA | NA | Med vs. Low | 0.57 | 0.22 | 0.36 | 0.34 |
| | | | | | | High vs. Low | 1.02 | 0.95 | | |
| IgG A244 K198C KKKEYRLINCNTSVIKQAKKK-Biotin | | | NA | NA | NA | Pos vs. Neg | NA | NA | NA | NA |
| IgG total binding score | | | 0.85 | 0.39 | 0.95 | Med vs. Low | 0.92 | 0.86 | 0.81 | 0.42 |
| | | | | | | High vs. Low | 1.2 | 0.67 | | |
| IgG breadth non-vaccine Envs | | | 0.86 | 0.41 | 0.95 | Med vs. Low | 0.79 | 0.59 | 0.83 | 0.43 |
| | | | | | | High vs. Low | 0.99 | 0.97 | | |

TABLE 1-continued

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively, in order of appearance)

| Assay | Investigator | Institution | Quantitative | | | Categorical | | | Global P value | Global Q value |
|---|---|---|---|---|---|---|---|---|---|---|
| | | | $OR^1$ | P value | Q value | Contrast | $OR^2$ | P value | | |
| IgG vaccine Envs | | | 0.86 | 0.42 | 0.95 | Med vs. Low | 0.65 | 0.34 | 0.38 | 0.34 |
| | | | | | | High vs. Low | 1.18 | 0.69 | | |
| IgG B.p24 | | | 0.8 | 0.18 | 0.95 | Med vs. Neg | 0.7 | 0.39 | 0.38 | 0.34 |
| | | | | | | High vs. Neg | 0.56 | 0.17 | | |
| IgG RSC3 minus RSC3delta371L | | | 1.13 | 0.43 | 0.95 | High vs. Low | 0.81 | 0.61 | 0.61 | 0.39 |
| IgG A244 gD- Delta11 gp120 | | | 0.84 | 0.31 | 0.95 | Med vs. Low | 0.56 | 0.23 | 0.22 | 0.30 |
| | | | | | | High vs. Low | 1.21 | 0.64 | | |
| IgG US1 $SIV_{cpz}$ gp140CF | | | 1.1 | NA | NA | Pos vs. Neg | 1.44 | 0.51 | 0.51 | 0.36 |
| IgG YU2gp120oldcore minus YU2gp120oldcoreD368R | | | 0.76 | 0.16 | 0.95 | Med vs. Low | 0.59 | 0.21 | 0.41 | 0.34 |
| | | | | | | High vs. Low | 0.66 | 0.33 | | |
| 7. IgG Avidity | S. Munir Alam | Duke University | | | | | | | | |
| IgG Avidity B.MN gD- gp120 293T | | | 0.91 | 0.61 | 0.98 | Med vs. Low | 0.71 | 0.43 | 0.69 | 0.4 |
| | | | | | | High vs. Low | 0.97 | 0.94 | | |
| IgG Avidity C.1086 gp120 gD- CHO | | | 1.02 | 0.91 | 0.98 | Med vs. Low | 1.18 | 0.72 | 0.53 | 0.36 |
| | | | | | | High vs. Low | 1.61 | 0.28 | | |
| IgG Avidity C.1086 gp120 gD- Delta 7 CHO | | | 1 | 0.99 | 0.98 | Med vs. Low | 1.53 | 0.36 | 0.5 | 0.36 |
| | | | | | | High vs. Low | 1.68 | 0.25 | | |
| IgG Avidity E.A244 gD- 293T gp120 | | | 1.01 | 0.96 | 0.98 | Med vs. Low | 0.61 | 0.26 | 0.51 | 0.36 |
| | | | | | | High vs. Low | 0.9 | 0.8 | | |
| IgG Avidity E.A244 gD+ N160 293T gp120 | | | 0.87 | 0.44 | 0.95 | Med vs. Low | 0.66 | 0.34 | 0.63 | 0.39 |
| | | | | | | High vs. Low | 0.82 | 0.63 | | |
| IgG Avidity E.A244 gD+ N160 minus A244 gD+ N160K gp120 | | | 0.91 | 0.65 | 0.98 | Med vs. Low | 2.55 | 0.03 | 0.03 | 0.27 |
| | | | | | | High vs. Low | 1.0 | 1.0 | | |
| IgG Avidity E.A244 gD+ CHO GSID gp120 | | | 1.03 | 0.88 | 0.98 | Med vs. Low | 1.01 | 0.98 | 0.79 | 0.42 |
| | | | | | | High vs. Low | 1.29 | 0.55 | | |
| IgG Avidity E.92Th023 gp120 gDneg 293T | | | 0.96 | 0.83 | 0.98 | Med vs. Low | 0.71 | 0.47 | 0.29 | 0.33 |
| | | | | | | High vs. Low | 1.41 | 0.41 | | |
| IgG Avidity B.MN gD+ 293T gp120 | | | 0.84 | 0.33 | 0.95 | Med vs. Low | 0.84 | 0.68 | 0.91 | 0.45 |
| | | | | | | High vs. Low | 0.88 | 0.77 | | |
| IgG Avidity B.MN gD+ CHO GSID gp120 | | | 0.97 | 0.89 | 0.98 | Med vs. Low | 0.9 | 0.81 | 0.95 | 0.46 |
| | | | | | | High vs. Low | 1.03 | 0.94 | | |
| IgG Avidity E.A244 gD+ N160K 293T gp120 | | | 0.98 | 0.91 | 0.98 | Med vs. Low | 0.79 | 0.6 | 0.66 | 0.4 |
| | | | | | | High vs. Low | 1.16 | 0.72 | | |
| IgG Avidity A.OOMSA gp140CF 293T | | | 1.03 | 0.87 | 0.98 | Med vs. Low | 1.05 | 0.06 | 0.13 | 0.29 |
| | | | | | | High vs. Low | 1.05 | 0.91 | | |
| 8. Overlapping Peptide Array Assay | Richard Koup, David Montefiori | Duke University | | | | | | | | |
| C1 hotspot | | | 1.15 | 0.43 | 0.95 | Med vs. Low | 1.51 | 0.35 | 0.64 | 0.39 |
| | | | | | | High vs. Low | 1.25 | 0.63 | | |
| C5 hotspot | | | 1.3 | 0.12 | 0.95 | Med vs. Low | 1.13 | 0.8 | 0.07 | 0.28 |
| | | | | | | High vs. Low | 2.4 | 0.05 | | |
| V2 hotspot | | | 0.64 | 0.03 | 0.98 | Med vs. Low | 0.95 | 0.89 | 0.04 | 0.27 |
| | | | | | | High vs. Low | 0.32 | 0.02 | | |

TABLE 1-continued

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively,
in order of appearance)

|  |  |  | Quantitative | | | Categorical | | Global | Global |
|---|---|---|---|---|---|---|---|---|---|
| Assay | Investigator | Institution | OR[1] | P value | Q value | Contrast | OR[2] | P value | P value | Q value |
| V3 hotspot |  |  | 0.88 | 0.48 | 0.98 | Med vs. Low | 0.94 | 0.88 | 0.71 | 0.42 |
|  |  |  |  |  |  | High vs. Low | 0.71 | 0.43 |  |  |
| 9. Blocking of CD4 Binding to Envelope | | | | | | | | | |
| sCD4 blocking on E.A244 gD+ CHO GSID gp120 | Barton Haynes | Duke University | NA | NA | NA | Pos vs. Neg | 1.31 | 0.44 | 0.44 | 0.34 |
| sCD4 blocking on E.A244 gD+ CHO GSID baseline adjusted |  |  | NA | NA | NA | Pos vs. Neg | 1.12 | 0.77 | 0.77 | 0.42 |
| CD4 blocking on B.MN gp120 | Philip Berman | Uni. of California, Santa Cruz | NA | NA | NA | Pos vs. Neg | 1.35 | 0.46 | 0.46 | 0.35 |
| CD4 blocking 92THO23.AE gp120 |  |  | NA | NA | NA | Pos vs. Neg | 1.41 | 0.33 | 0.33 | 0.34 |
| 10. Blocking of MAb A32 | | | | | | | | | |
| mAb A32 blocking on B.BaL Env gp120 ELISA | Anthony DeVico | University of Maryland | 1.17 | 0.38 | 0.95 | Med vs. Neg | 0.59 | 0.29 | 0.29 | 0.33 |
|  |  |  |  |  |  | High vs. Neg | 1.09 | 0.85 |  |  |
| mAb A32 blocking on E.A244 Delta 11 293T gp120 ELISA | Barton Haynes | Duke University | 1.11 | 0.59 | 0.98 | Med vs. Low | 1.08 | 0.87 | 0.08 | 0.28 |
|  |  |  |  |  |  | High vs. Low | 2.33 | 0.06 |  |  |
| mAb A32 blocking on E.A244 Delta 11 293T gp120 ELISA baseline adj |  |  | 1.03 | 0.87 | 0.98 | Med vs. Low | 1.18 | 0.72 | 0.39 | 0.34 |
|  |  |  |  |  |  | High vs. Low | 1.76 | 0.2 |  |  |
| mAb A32 blocking on E.A244 gD+ CHO GSID gp120 ELISA |  |  | NA | NA | NA | Med vs. Low | 1.16 | 0.75 | 0.41 | 0.34 |
|  |  |  |  |  |  | High vs. Low | 1.72 | 0.22 |  |  |
| mAb A32 E.A244 gD+ CHO GSID gp120 baseline adj ELISA |  |  | 1.18 | 0.4 | 0.95 | Med vs. Low | 1.0 | 1.0 | 0.44 | 0.34 |
|  |  |  |  |  |  | High vs. Low | 1.57 | 0.29 |  |  |
| 11. ADCC | | | | | | | | | |
| E.CM243gp120-coated CD4 T cells | Guido Ferrari | Duke University |  |  |  |  |  |  |  |  |
| ADCC gp120-coated E.A244 gD- gp120 293T AUC |  |  | 1.11 | 0.53 | 0.98 | Med vs. Low | 0.98 | 0.96 | 0.38 | 0.34 |
|  |  |  |  |  |  | High vs. Low | 1.62 | 0.26 |  |  |
| ADCC gp120-coated E.A244 gD- gp120 293T Peak |  |  | 1.06 | 0.72 | 0.98 | Med vs. Neg | 1.28 | 0.55 | 0.83 | 0.43 |
|  |  |  |  |  |  | High vs. Neg | 1.07 | 0.87 |  |  |
| ADCC gp120-coated E.A244 gD+ gp120 293T AUC |  |  | 1.07 | 0.7 | 0.98 | Med vs. Low | 0.27 | 0.01 | 0.02 | 0.27 |
|  |  |  |  |  |  | High vs. Low | 0.96 | 0.91 |  |  |
| ADCC gp120-coated E.A244 gD+ gp120 293T Peak |  |  | 0.94 | 0.71 | 0.98 | Med vs. Low | 0.48 | 0.11 | 0.17 | 0.30 |
|  |  |  |  |  |  | High vs. Low | 1.06 | 0.89 |  |  |
| 12. IgG3 Env Binding | Georgia Tomaras | Duke University | | | | | | | | |
| IgG3 A.OOMSA gp140CF |  |  | 1.12 | NA | NA | Pos vs. Neg | 1.38 | 0.44 | 0.44 | 0.34 |
| IgG3 E.92TH023 gD- 293T gp120 |  |  | 1 | NA | NA | Pos vs. Neg | 0.93 | 0.85 | 0.85 | 0.43 |
| IgG3 E.92TH023 gD+ 293T gp120 |  |  | 1.09 | 0.64 | 0.98 | Med vs. Neg | 1.03 | 0.95 | 0.95 | 0.46 |
|  |  |  |  |  |  | High vs. Neg | 1.14 | 0.79 |  |  |
| IgG3 E.A244 gD- Delta 11 293T gp120 |  |  | 1.05 | NA | NA | Pos vs. Neg | 1.04 | 0.91 | 0.91 | 0.45 |
| IgG3 E.A244 gD- N160 minus A244 gD- N160K |  |  | 0.77 | 0.16 | 0.95 | High vs. Low | 1.02 | 0.96 | 0.96 | 0.46 |
| IgG3 E.A244 gD+ N160 minus A244 gD+ N160K |  |  | 1.08 | 0.69 | 0.98 | Med vs. Low | 0.35 | 0.04 | 0.03 | 0.27 |
|  |  |  |  |  |  | High vs. Low | 1.19 | 0.67 |  |  |

TABLE 1-continued

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively, in order of appearance

| Assay | Investigator | Institution | Quantitative | | | | Categorical | | Global P value | Global Q value |
|---|---|---|---|---|---|---|---|---|---|---|
| | | | OR[1] | P value | Q value | Contrast | OR[2] | P value | | |
| IgG3 CON-S gp140CFI | | | 1.31 | 0.14 | 0.95 | Med vs. Neg | 1.35 | 0.5 | 0.37 | 0.34 |
| | | | | | | High vs. Neg | 1.81 | 0.16 | | |
| IgG3 B.GNE8 gp120 CHO GSID | | | 1.18 | 0.38 | 0.95 | Med vs. Neg | 1.03 | 0.94 | 0.57 | 0.38 |
| | | | | | | High vs. Neg | 1.49 | 0.37 | | |
| IgG3 AE.con.env03 gp140CF | | | 1.1 | NA | NA | Pos vs. Neg | 1.26 | 0.53 | 0.53 | 0.27 |
| IgG3 B.p24 | | | 0.87 | NA | NA | Pos vs. Neg | 0.84 | 0.64 | 0.64 | 0.39 |
| IgG3 E.A244 gD+ CHOGSID gp120 | | | 1.2 | 0.34 | 0.95 | Med vs. Neg | 1.35 | 0.52 | 0.62 | 0.39 |
| | | | | | | High vs. Neg | 1.56 | 0.33 | | |
| IgG3 B.MN gD+ CHOGSID gp120 | | | 1.02 | 0.9 | 0.98 | Med vs. Neg | 0.43 | 0.11 | 0.13 | 0.29 |
| | | | | | | High vs. Neg | 0.92 | 0.87 | | |
| 13. Env-specific CD4 T Cell Intracellular Cytokines | M. Juliana McElrath | FHCRC | | | | | | | | |
| E.92TH023 peptide stimulated CD4+ CD154+ T Cells | | | 1.11 | 0.51 | 0.93 | Med vs. Neg | 0.7 | 0.41 | 0.4 | 0.34 |
| | | | | | | High vs. Neg | 0.55 | 0.19 | | |
| E.92TH023 peptide stimulated CD4+ T, IFNγ+ | | | NA | NA | NA | Pos vs. Neg | 0.52 | 0.14 | 0.14 | 0.29 |
| E.92TH023 peptide stimulated CD4+, IL2+ | | | NA | NA | NA | Positive | 0.6 | 0.18 | 0.18 | 0.3 |
| E.92TH023 peptide stimulated CD4+ T, TNFα+ | | | NA | NA | NA | Positive | 1.22 | 0.7 | 0.7 | 0.41 |
| E.92TH023 peptide stimulated CD4+ T, average no. cytokines | | | 1.09 | 0.58 | 0.98 | Med vs. Low | 0.72 | 0.44 | 0.24 | 0.31 |
| | | | | | | High vs. Low | 0.46 | 0.09 | | |
| E.92TH023 peptide stimulated CD4+ T, at least 2 cytokines | | | 1.07 | 0.71 | 0.98 | Med vs. Low | 0.59 | 0.22 | 0.14 | 0.29 |
| | | | | | | High vs. Low | 0.41 | 0.06 | | |
| E.92TH023 peptide stimulated CD4+ T, at least 3 cytokines | | | 1.14 | 0.41 | 0.95 | Med vs. Low | 0.35 | 0.02 | 0.04 | 0.27 |
| | | | | | | High vs. Low | 0.45 | 0.07 | | |
| E.92TH023 peptide stimulated CD4+ T, all 4 cytokines | | | 1.18 | 0.29 | 0.95 | Med vs. Low | 0.55 | 0.18 | 0.37 | 0.34 |
| | | | | | | High vs. Low | 0.65 | 0.32 | | |
| 14. Env Stimulated PBMC Supernatant Cytokines | M. Juliana McElrath | FHCRC | | | | | | | | |
| PBMC Luminex cytokine score* | | | 0.75 | 0.21 | 0.95 | Med vs. Low | 0.42 | 0.04 | 0.02 | 0.27 |
| | | | | | | High vs. Low | 0.31 | 0.01 | | |
| Luminex GM-CSF | | | NA | NA | NA | Pos vs. Neg | 0.59 | 0.19 | 0.19 | 0.30 |
| Luminex IFNγ | | | NA | NA | NA | Pos vs. Neg | 0.5 | 0.18 | 0.18 | 0.30 |
| Luninex IL10 | | | NA | NA | NA | Pos vs. Neg | 0.29 | 0.03 | 0.03 | 0.27 |
| Luminex IL13 | | | 0.71 | 0.18 | 0.95 | Med vs. Neg | 0.44 | 0.07 | 0.02 | 0.27 |
| | | | | | | High vs. Neg | 0.26 | 0.01 | | |
| Luminex IL2 | | | 0.75 | 0.23 | 0.95 | Med vs. Neg | 1.01 | 0.99 | 0.08 | 0.28 |
| | | | | | | High vs. Neg | 0.28 | 0.03 | | |
| Luminex IL4 | | | NA | NA | NA | Pos vs. Neg | 0.62 | 0.41 | 0.41 | 0.34 |
| Luminex IL5 | | | NA | NA | NA | Pos vs. Neg | 0.41 | 0.05 | 0.05 | 0.27 |
| Luminex IL9 | | | NA | NA | NA | Pos vs. Neg | 0.61 | 0.28 | 0.28 | 0.33 |
| Luminex MIP-1β | | | NA | NA | NA | Pos vs. Neg | 0.79 | 0.77 | 0.77 | 0.42 |
| Luminex TNFα | | | NA | NA | NA | Pos vs. Neg | 0.47 | 0.18 | 0.18 | 0.30 |
| Luminex TNFβ | | | NA | NA | NA | Pos vs. Neg | 0.73 | 0.49 | 0.49 | 0.35 |

TABLE 1-continued

Secondary Assays performed on RV144 Case control Samples (17 Assay Types, 154 Immune Variables)
(Tables 1 discloses SEQ ID NOS 1, 1, 2-7, 1, 8, 6-7, 1 and 8, respectively, in order of appearance)

|  |  |  | Quantitative |  |  |  | Categorical |  | Global | Global |
|---|---|---|---|---|---|---|---|---|---|---|
| Assay | Investigator | Institution | OR[1] | P value | Q value | Contrast | OR[2] | P value | P value | Q value |
| 15. Env Stimulated CFSE | M. Juliana McElrath |  |  |  |  |  |  |  |  |  |
| CFSE-CD4+ E.92TH023.AE-Env stimulated |  |  | NA | NA | NA | Pos vs. Neg | 2.46 | 0.11 | 0.11 | 0.29 |
| CFSE-CD8+ E.92TH023.AE-Env stimulated |  |  | NA | NA | NA | Pos vs. Neg | 5.7 | 0.22 | 0.22 | 0.30 |
| 16. Env Stimulated B Cell ELISpot | M. Juliana McElrath |  |  |  |  |  |  |  |  |  |
| gDneg E.A244 gp120 293T |  |  | 0.97 | 0.88 | 0.98 | Med vs. Low | 0.24 | 0.01 | 0.03 | 0.27 |
|  |  |  |  |  |  | High vs. Low | 0.86 | 0.71 |  |  |
| gDneg B.MN gp120 293T |  |  | 1.14 | 0.4 | 0.95 | Med vs. Low | 0.24 | 0.01 | 0.03 | 0.27 |
|  |  |  |  |  |  | High vs. Low | 0.77 | 0.54 |  |  |
| Group M CON-S gp140CF |  |  | 1.07 | 0.72 | 0.98 | Med vs. Low | 0.58 | 0.25 | 0.48 | 0.35 |
|  |  |  |  |  |  | High vs. Low | 0.93 | 0.86 |  |  |
| 17. NK cell phenotyping | M. Juliana McElrath |  |  |  |  |  |  |  |  |  |
| CD16 expression |  |  | 0.88 | 0.45 | 0.95 | Med vs. Low | 0.51 | 0.12 | 0.15 | 0.29 |
|  |  |  |  |  |  | High vs. Low | 0.48 | 0.1 |  |  |
| CD16-CD56dim NK |  |  | 1.17 | 0.33 | 0.95 | Med vs. Low | 1.79 | 0.19 | 0.42 | 0.34 |
|  |  |  |  |  |  | High vs. Low | 1.39 | 0.49 |  |  |
| CD89 expression |  |  | 1.02 | 0.9 | 0.98 | Med vs. Low | 0.78 | 0.56 | 0.74 | 0.42 |
|  |  |  |  |  |  | High vs. Low | 0.73 | 0.47 |  |  |
| Myeloid dendritic cells |  |  | 0.82 | 0.3 | 0.98 | Med vs. Low | 0.74 | 0.48 | 0.57 | 0.38 |
|  |  |  |  |  |  | High vs. Low | 0.62 | 0.3 |  |  |
| NKG2A expression |  |  | 0.98 | 0.9 | 0.98 | Med vs. Low | 0.89 | 0.8 | 0.96 | 0.46 |
|  |  |  |  |  |  | High vs. Low | 0.9 | 0.81 |  |  |
| NKp46 expression |  |  | 0.91 | 0.61 | 0.98 | Med vs. Low | 0.47 | 0.12 | 0.15 | 0.29 |
|  |  |  |  |  |  | High vs. Low | 1.16 | 0.72 |  |  |

[1]Estimated odds ratio per one standard deviation increment in the immune biomaker; not available (NA) if response rates, when applicable, are less than 50%.
[2]Estimated odds ratio comparing different subgroups defined by Negative (Neg), Low, Medium (Med) or High response. Negative means a vaccine recipient was deemed by a statistical criterion to not have a vaccine-induced immune. Low, Medium and High are subgroups with the lower third, middle third of response values among vaccine recipients; not available (NA) when data are not sufficient to render stable estimates.
*Sensitivity variables assessed as alternates to the primary variables in the multivariate models

TABLE 2

Primary Immune Response Variable Assays and Their Secondary Sensitivity Assay Variables

| Primary Assay | Investigator | Institution | Secondary Assay for Sensitivity Analysis | Investigator | Institution |
|---|---|---|---|---|---|
| 1. Env IgA binding score [14 Envs]* | Georgia Tomaras | Duke University | Plasma IgA binding to Δ11AE A244gD | Georgia Tomaras | Duke University |
| 2 IgG Avidity to AE.Δ1 A244gD- | S. Munir Alam, | Duke University | IgG Avidity to B.MN gp120gD- | S. Munir Alam | Duke University |
| 3. ADCC AE.92TH023-infected CD4 T cells | David Evans, Mark Aipert | Harvard | ADCC E.CM243 gp120-coated CD4 T cells | Guido Ferrari | Duke University |

TABLE 2-continued

Primary Immune Response Variable Assays and Their Secondary Sensitivity Assay Variables

| Primary Assay | Investigator | Institution | Secondary Assay for Sensitivity Analysis | Investigator | Institution |
|---|---|---|---|---|---|
| 4. Neutralizing antibody panel score of both T2Mb1 + A3R5 neutralizing assays [n = 6]** 5. Scaffolded V1V2*** 6. Env-specific CD4 T cells (IFN-γ, IL-2, TNF-γ, CD154) | David Montefiori, Chitraporn Karnasuta, Ruengpueng Sutthent Susan Zolla-Pazner M. Juliana McElrath, Nicole Frahm | Duke University AFRIMS+ Siriraj Hospital New York Univ FHCRC# | A3R5 assay (2 isolates) T2Mb1 assay (3 isolates) T2Mb1 assay (1 isolate) V2 42aa cyclic peptideΩ PBMC Env peptide stimulated supernatant cytokines (IL-2, TNF-, IL-10, IL-13, MIP-1β, GM-CSF, IL-4, TNFβ) | David Montefiori Chitraporn Karnasuta Ruengpueng Sutthent Susan Zolla-Pazner M. Juliana McElrath Nicole Frahm | Duke University AFRIMS Siriraj Hospital New York Univ FHCRC |

*A244 gD-gp120, AE.92TH023 gD-gp120, A.00MSA gp140CF AE.97CNGX 140CF, A1.CON03 140CF, B.CON.03140CF, C.CON.03 140CF, G.CON.03 gp140CF, AE.CON.03gp140CF, G.DRCBL gp140, B.JRFLgp140, US1 gp140 SIV CPZ, B.
**MN.3, B.SF162.LS, C.MW965.26, TH023.6, C.1080.c03.LucR, C.3347.c11.LucR.
***Case A2 gp70.V1V2 sequence described in Pinter, A. et al., Vaccine 16:1803-11, 1998.
ΨAFRIMS = Air Force Research Institute Medical Sciences
FHCRC = Fred Hutchinson Cancer Research Center
+42aa V2 peptide - get sequence from M. Rao (G. Tomaras)

TABLE 3

Summary of multivariate logistic regression results for the 8 secondary variables used for sensitivity analysis. For each variable, the odds ratio (OR) is reported per standard deviation (sd) and comparing Medium and High responses to Low responses. Low/Medium/High are determined by tertiles of response in the vaccine group

| Variable | OR scale | Multivariate Logistic Regression | | | Corresponding Primary Variable | | |
|---|---|---|---|---|---|---|---|
| | | OR | 95% CI | P (Q) | OR | 95% CI | P (Q) |
| IgA Binding A244 | per 1-sd | 1.15 | (0.75, 1.75) | 0.53 (0.66) | 1.54 | (1.05, 2.25) | 0.03 (0.08) |
| IgG Avidity MN | per 1-sd | 0.76 | (0.48, 1.20) | 0.24 (0.36) | 0.81 | (0.50, 1.30) | 0.37 (0.56) |
| ADCC gp120-coated | per 1-sd | 1.22 | (0.80, 1.86) | 0.35 (0.43) | 0.92 | (0.62, 1.37) | 0.68 (0.68) |
| NAb TZM-bl Clade B | per 1-sd | 1.12 | (0.71, 1.75) | 0.62 (0.75) | 1.37 | (0.82, 2.27) | 0.23 (0.45) |
| NAb TZM-bl TH023.6 | per 1-sd | 1.46 | (0.95, 2.25) | 0.08 (0.17) | 1.37 | (0.82, 2.27) | 0.23 (0.45) |
| NAb A3R5 Clade E | per 1-sd | 1.17 | (0.75, 1.83) | 0.49 (0.65) | 1.37 | (0.82, 2.27) | 0.23 (0.45) |
| Cyclic V2 Binding | per 1-sd | 0.74 | (0.48, 1.15) | 0.18 (0.54) | 0.57 | (0.36, 0.90) | 0.02 (0.08) |
| PBMC Cytokines | per 1-sd | 0.79 | (0.51, 1.22) | 0.29 (0.40) | 1.09 | (0.79, 1.49) | 0.61 (0.68) |
| IgA Binding A244 | Med vs Low | 1.0 | (0.34, 2.93) | 0.99 | 0.68 | (0.25, 1.83) | 0.45 |
| | High vs Low | 2.58 | (0.93, 7.16) | 0.07 | 1.89 | (0.75, 4.74) | 0.17 |
| | Overall | — | — | 0.05 (0.25) | — | — | 0.07 (0.23) |
| IgG Avidity MN | Med vs Low | 0.75 | (0.30, 1.88) | 0.54 | 0.67 | (0.26, 1.75) | 0.42 |
| | High vs Low | 0.95 | (0.36, 2.53) | 0.92 | 0.83 | (0.30, 2.30) | 0.72 |
| | Overall | — | — | 0.80 (0.81) | — | — | 0.71 (0.84) |
| ADCC gp120-coated | Med vs Low | 1.23 | (0.47, 3.24) | 0.68 | 0.93 | (0.39, 2.19) | 0.86 |
| | High vs Low | 2.00 | (0.69, 5.78) | 0.20 | 0.59 | (0.22, 1.59) | 0.30 |
| | Overall | — | — | 0.41 (0.67) | — | — | 0.57 (0.84) |
| NAb TZM-bl Clade B | Med vs Low | 0.68 | (0.27, 1.71) | 0.41 | 2.08 | (0.78, 5.57) | 0.14 |
| | High vs Low | 0.80 | (0.29, 2.16) | 0.65 | 2.43 | (0.77, 7.67) | 0.13 |
| | Overall | — | — | 0.71 (0.89) | — | — | 0.26 (0.52) |
| NAb TZM-bl TH023.6 | Med vs Low | 0.93 | (0.36, 2.42) | 0.88 | 2.08 | (0.78, 5.57) | 0.14 |
| | High vs Low | 3.10 | (1.06, 9.05) | 0.04 | 2.43 | (0.77, 7.67) | 0.13 |
| | Overall | — | — | 0.07 (0.17) | — | — | 0.26 (0.52) |
| NAb A3R5 Clade E | Med vs Low | 0.61 | (0.23, 1.60) | 0.31 | 2.08 | (0.78, 5.57) | 0.14 |
| | High vs Low | 1.86 | (0.72, 4.78) | 0.20 | 2.43 | (0.77, 7.67) | 0.13 |
| | Overall | — | — | 0.08 (0.15) | — | — | 0.26 (0.52) |
| Cyclic V2 | Med vs Low | 0.54 | (0.22, 1.34) | 0.18 | 0.68 | (0.28, 1.62) | 0.38 |
| | High vs Low | 0.51 | (0.19, 1.36) | 0.18 | 0.29 | (0.10, 0.86) | 0.02 |
| | Overall | — | — | 0.31 (0.62) | — | — | 0.08 (0.23) |
| PBMC Cytokines | Med vs Low | 0.42 | (0.18, 1.00) | 0.05 | 0.84 | (0.35, 2.02) | 0.69 |
| | Hi vs Low | 0.41 | (0.15, 1.12) | 0.08 | 0.77 | (0.31, 1.91) | 0.57 |
| | Overall | — | — | 0.09 (0.19) | — | — | 0.84 (0.84) |

Primary Variable Assay Methods.

All assays were performed blinded to treatment assignment and case-control status.

Assays for Binding of Plasma IgA Antibodies to HIV-1 Env Proteins.

Binding Antibody Multiplex Assays for IgA were performed as previously described (Tomaras et al, J. Virol. 82:12449-63 (2008)) with the following modifications. IgA assays were performed as pre-specified in an assay Study Plan (USMHRP RV144 Case Control Assay, Anti-Env IgA Binding Breadth), was assessed as part of an "in process audit" by Duke-CFAR GAP QAU and was performed under routine GCLP conditions. Briefly, serum specimens were centrifuged (10,000×g) for 10 min and filtered in a 1.2-um-pore-size filter plate (Pall AcroPrep). The filtered and diluted samples were depleted of IgG using protein G high-performance MultiTrap plates (GE, Inc.) according to the manufacturer's instructions with minor modifications and were utilized to measure IgA specific responses. A total of 5×10⁶ carboxylated fluorescent beads (Luminex Corp, Austin, Tex.) were covalently coupled to 25 ag of one of the purified HIV antigens and incubated with the vaccine plasma. HIV-specific antibody isotypes were detected with goat anti-human IgA (Jackson Immunoresearch, West Grove, Pa.) (and mouse anti-human IgG (Southern Biotech, Birmingham, Ala.) for detection of HIVIG) each conjugated to biotin, at 4 µg/ml, followed by washing and incubation with streptavidin-PE (BD Pharmingen). Antibody measurements were acquired on a Bio-Plex instrument (Bio-Rad) and the readout was expressed as mean fluorescent intensity (MFI). Positive and negative controls were included in each assay to ensure specificity and for maintaining consistency and reproducibility between assays. Positive controls included purified IgG (HIVIG) and b12 mAb IgA (kindly provided by Drs. Burton and Hessell). Negative controls included in every assay were blank beads, HIV-1 negative sera, and baseline (pre-vaccination) samples. The preset assay criteria for sample reporting were: coefficient of variation (CV) per duplicate values for each sample were ≤15% and >100 beads counted per sample. To control for Env protein performance, use was made of the preset criteria that the positive control titer (HIVIG) included on each assay had to be within +/−3 standard deviations of the mean for each antigen (tracked with a Levy-Jennings plot with preset acceptance of titer (calculated with a four-parameter logistic equation, Sigma-Plot, Systat Software).

Assay validation for the HIV-1 binding antibody multi-plex assay (Duke CFAR GCLP-Compliant AIDS Program) reported the following parameters of the assay; Specificity (Determination of negative and positive criteria), Accuracy (Detection of a range of concentrations of plasma specimens spiked with 2F5 IgA and 1b12 IgA), Precision (Repeatability, including sample replicates and Intermediate Precision, including inter-operator, inter-instrument, inter-day precision), Linearity, Range, Robustness (Coupling consistency, Coupling Incubation Time, Primary Antibody Incubation Time, Secondary Antibody Incubation Time, Pre-Read Incubation Time, Sample Freeze-Thaw Cycles) and Limits of Detection and Quantification. All parameters passed the assay validation and two examples of the data generated from the assay validation are discussed here. For "Precision", the following results were obtained: inter-instrument variation was <3.0% CV, inter-operator variation was <12% CV and the inter-day variation was <13% CV. For "Limit of Detection (LLOD) and Quantitation (LLOQ)", the following results were obtained for IgA: LLOD was between 1.9 to 3.1 ng/ml for HIV Env gp120/gp140 proteins and the LLOQ was between 18.5 to 19.3 ng/ml for gp120/gp140 proteins.

The primary variable (IgA binding score) was a weighted average of the binding of purified IgA to 14 recombinant gp120 and gp140 Env proteins measured by Luminex, that included A244 gD-293T gp120, 92TH023 gD-293T gp120, 00MSA4076 gp140, 97CNGX2F gp140CF, A1.con.env03.gp140CF, B.con.env03 gp140CF, C.con.env03 gp140CF, CON6 gp120, CON-S gp140CFI, G.con.env03 gp140CF, AE.con.env03 gp140CF, DRCBL gp140, JRFL gp140, and USISIV$_{cpz}$ gp140 that were produced as described (Ma et al, PLoS Pathog. 7:e1002200 (2011), Liao et al, Virology 353:268-82 (2006), Liao et al, J. Exp. Med. 208:2237-49 (2011)) (Table 4). For each Env, four fluorescence intensity readouts were measured: 1) week 0 binding to blank bead, denoted by y00, 2) week 0 binding to Env-coated bead, denoted by y01, 3) week 26 binding to blank bread, denoted by y260, and 4) week 26 binding to Env-coated bead, denoted by y261. A sample was called positive if both y261−y260>100 and (y261−y260)/(y01−y00)>3. Binding activity to each Env is defined as 0 if it fails the positivity call and log (max(y261−y260.0)+1) otherwise. To compute the weights for the 14 Envs, first a bottom-up hierarchical clustering tree with average linkage for all Env but A244 gD−, 92TH023 gD− and US1gp140 was constructed based on a distance measured as 1 minus the Spearman correlation coefficient between pairs of binding activities. Relative weights were computed based on the tree using the Gerstein-Sonnhammer-Chothia method (Durbin et al, Biological sequence analysis, Cambridge University Press 1998; New York). Average weighting across 10 bootstrap samples (within vaccine recipients) was taken. Second, US1gp140 was given the same relative weight as the highest relative weight among the 11 non-vaccine strain Envs. Together the 12 non-vaccine strain Envs were assigned two-thirds of the total weight. Finally, gD-A244 and gD-92TH023 were each assigned one-sixth of the total weight. The weights were selected to give greatest influence to the two vaccine Envs (MN.B and A244.AE) and to the non-vaccine Envs that were least redundant based on cluster analysis (Table 4).

TABLE 4

Plasma IgA binding antibody score construction:
Weights for the 14 Envs used in calculating the IgA score

| Env target | Weight |
| --- | --- |
| G.conenv03 gp140CF | 0.082 |
| A.00MSA gp140CF | 0.086 |
| A.conenv03 gp140CF | 0.090 |
| AE.conenv03140CF | 0.054 |
| E.97CNGX2F gp140CF | 0.054 |
| G.DRCBL gp140CF | 0.069 |
| C.conenv03 gp140CF | 0.026 |
| CON-S gp140CFI | 0.026 |
| B.JRFL gp140 | 0.026 |
| B.conenv03 gp140CF | 0.026 |
| CON6 gp120 | 0.039 |
| E.92TH023 gD- | 0.167 |
| E.A244 gD- | 0.167 |
| US1SIV$_{cpz}$ gp140 | 0.090 |

Surface Plasmon Resonance (SPR) Measurements of Plasma IgG Avidity.

IgG avidity was measured on a BIAcore 4000 instrument (BIAcore/GE Healthcare) using the multiplex array format (1×16) in which purified plasma IgG samples were flowed over duplicate spots of the RV144 A244 clade E Δ11 gp120 Env for primary analysis (Δ11 signifies gp120 with deletion of the first 11 aa of the mature Env protein). Using a Series S CM5 chip (BIAcore/GE Healthcare) gp120 proteins were amine coupled in duplicate on 16 different spots on four flow channels of the chip. The negative control respiratory syncytial virus (RSV) mAb Synagis was flowed over each surface and the signal was used to subtract out non-specific interactions with each individual spot. The Env was immobilized to 6000-8000 RU using amine coupling chemistry as described (Alam et al, J. Immunol. 178:4424-35 (2007), Alam et al, Proc. Natl. Acad. Sci. USA 106:20234-9 (2009), Alam et al, J. Virol. 82:115-25 (2008)). Antigen surface activity was monitored using the gp120 C1 mAb A32 as positive control. A random selection of IgG samples collected at visit 0 from 20 vaccines were also included. Following each binding cycle, surfaces were regenerated with a short injection (20s) of Glycine, pH2.5. Each surface activity was monitored by including A32 mAb (20 µg/mL) injection at regular interval of every 20 cycles of samples and surface decay of A32 binding over the entire experimental run was used to normalize binding signal of plasma IgG samples. Non-specific binding of the negative control mAb was subtracted from each IgG sample binding data. Data analyses were performed with BIAevaluation 4000 and BIAevaluation 4.1 software (BIAcore/GE Healthcare) as described earlier for Biacore 3000 (Alam et al, Proc. Natl. Acad. Sci. USA 106:20234-9 (2009)) and Biacore A100 (Safsten et al, Anal. Biochem. 353:181-90 (2006)) data analysis respectively. Kinetic binding responses were measured by averaging post-injection response unit (RU) over a 20s window and dissociation rate constant, kd (s−1) was measured during the post-injection/buffer wash phase (after the first 20s to allow stabilization of signal) following curve fitting to a Langmuir dissociation equation. The majority of IgG bound with a relatively slow dissociation rate ($<10^{-3}$ $s^{-1}$), and the previously described method for BIAcore A100 ranking of dissociation rates in complex or polyclonal samples as a ratio of response units measured as binding late and stability late (Safsten et al, Anal. Biochem. 353:181-90 (2006), Kasturi et al, Nature 470:543-7 (2011)) was modified to include binding response and dissociation rate constant measurements and as described (Alam et al, Proc. Natl. Acad. Sci. USA 106:20234-9 (2009)). The primary variable was a relative avidity binding score based on the week 26 sample, calculated as follows: Avidity score (RU·s)=Binding Response (RU)/kd (s−1), with higher binding responses and slower dissociation constant kd as an indicator of higher affinity interaction (Fkynn et al, (Alam et al, Proc. Natl. Acad. Sci. USA 108:7131-6 (2011)).

HIV-1 Neutralization Assays.

Neutralization was measured in 96-well culture plates by using Tat-regulated Luc reporter gene expression to quantify reductions in virus infection in either TZM-bl or A3R5 cells. Assays in TZM-bl cells were performed with Env-pseudotyped viruses MN.B, SF162.B, MW965.0 and 92Th023.AE as described previously (Li et al, J. Virol. 79:10108-25 (2005)), TZM-bl is a genetically engineered HeLa cell line (also known as JC53-BL) that expresses the CD4 receptor and the CCR5 and CXCR4 coreceptors (Platt et al, J. Virol. 72:2855-64 (1998)) and contains Tat-regulated reporter genes for firefly Luc and *Escherichia coli*-galactosidase under regulatory control of an HIV-1 long terminal repeat sequence (Wei et al, Antimicrob. Agents Chemother. 46:1896-905 (2002)). The cells were obtained from the NIH AIDS Research and Reference Reagent Program, as contributed by John Kappes and Xiaoyun Wu. A3R5 (A3.01/R5.6) is a derivative of the CEM human lymphoblastoid cell line that naturally expresses CD4 and CXCR4 (Folks et al, Proc. Natl. Acad. Sci. USA 82:4539-43 (1985)) and was engineered to express CCR5 (McLinden et al, Novel CD4+/CCR5+/CXCR4+ human T-cell line shows enhanced sensitivity of HIV-1 to neutralization by sCD4, mAbs and HIV-1-positive sera; In preparation (2011)). The A3R5 assay was performed with the Env.IMC.LucR viruses C1080.c03.lucR and C3347.c11.LucR because multiple rounds of replication are needed to achieve an adequate infection signal in this assay (McLinden et al, Novel CD4+/CCR5+/CXCR4+ human T-cell line shows enhanced sensitivity of HIV-1 to neutralization by sCD4, mAbs and HIV-1-positive sera; In preparation (2011)). Neutralization assays were performed with heat-inactivated (56° C., 1 hr) samples, tested at 3-fold dilutions ranging from 1:20 to 1:43,740. Neutralization titers are the sample dilution at which relative luminescence units (RLU) were reduced by 50% compared to RLU in virus control wells after subtraction of background RLU in cell control wells. The primary variable was the area under the magnitude-breadth curve (Huang et al, Development. Stat. Biopyharm. Res. 1:81-91 (2009)) based on the week 26 sample, calculated using the log-transformed neutralization titers for the six evaluated pseudo-viruses.

Antibody-Dependent Cellular Cytotoxicity (ADCC).

ADCC against cells infected by HIV-1 AE.92TH023 was measured in an assay that employs a natural killer (NK) cell line as effectors and a T cell line as targets. The NK cell line was derived from KHYG-1 cells (Japan Health Sciences Foundation) by transduction with a retroviral vector that expresses the V158 variant of human CD16a (FCGR3A) (Yagita et al, Leukemia 14:922-30 (2000)). The target cells were derived from NKR.CEM-CCR5 cells (AIDS Research and Reference Reagent Program, Division of AIDS, NIAID, NIH, contributed by Dr. Alexandra Trkola). These were transduced with a pLNSX-derived retroviral vector to express Luciferase under the transcriptional control of a Tat-inducible promoter. Target cells were infected with HIV-1 AE.92TH023 4 days prior to each assay by spinoculation (O'Doherty et al, J. Virol. 74:10074-80 (2000)). Assays were conducted in 96-well plates, with each well containing $10^5$ effector cells and $10^4$ target cells, ADCC activity was measured as the loss of Luciferase after an 8-hour incubation in the presence of triplicate serial 2-fold dilutions beginning at a 1/32 dilution of heat-inactivated plasma. Wells containing NK cells and uninfected targets without plasma defined 0% relative light units (RLU), and wells with NK cells plus infected targets without plasma defined 100% RLU. The assays were run over 10 days, each in parallel with a positive control plasma sample from a Thai HIV-1 patient. The average 50% ADCC titer for the positive control sample was 51,577, with a range of 31,237 to 81,954. The primary variable was the partial area between the curves (pABC) for baseline minus week 26 luciferase activity at the four lowest plasma dilutions tested.

Binding ELISA to Scaffolded HIV-1 Envelope V1V2.

Immulon 4HBX plates (Thermo Scientific) were coated with 1 µg/ml scaffolded V1V2 (murine leukemia virus gp70-V1V2 or the control gp70 alone) (Pinter et al, Vaccine 16:1803-11 (1998)), for 1.5 h at 37° C. and then washed 6 times with PBS containing 0.05% Tween-20, pH 7.4, before incubation for 1.5 h at 37° C. with RV144 plasma diluted 1:100 in 15% RPMI media. The plates were washed again 6 times. For detection of bound Abs, alkaline phosphatase-conjugated goat anti-human IgG (Southern Biotech 1:2000) was added for 1.5 h at 37° C. After washing, 10% diethanolamine substrate was added for 30 min to develop color, and the plates were read at 405 nm. At each step, every well contained 50 µl; specimens were run in duplicate in each experiment, and three experiments were performed (Wang et al, Eur. J. Immunol. 22:1749-55 (1992)). The primary variable was the optical density based on the week 26 sample.

CD4+ T Cell Potency by Multiparameter Flow Cytometry.

Multiparameter flow cytometry was employed to detect Env-specific CD4+ T cell responses as previously described (Horton et al, J. Immunol. Methods 323:39-54 (2007)) with a few modifications. Peptides of 15 amino acids spanning the Env 92TH023 sequence expressed in vCP1521 and overlapping by 11 amino acids (Biosynthesis, Lewisville, Tex.) were combined into one pool at a final concentration of 1 µg/ml and used to stimulate $10^6$ PBMC ex vivo. Staphylococcal enterotoxin B and 0.5% DMSO in peptide diluent served as positive and negative controls, respectively. The following monoclonal antibodies were used to identify antigen-specific responses: IL-2 PE, IFN-γ V450, TNF-α FITC, CD154 PE-Cy5, IL-4 APC, MIP1-β Alexa700

(all Becton Dickinson Biosciences (BD), San Jose, Calif.); fixable Aqua Dead Cell Stain (Invitrogen; Eugene, Oreg.); CD4 PerCP Cy5.5, CD8 APC e780 (eBioscience; San Diego, Calif.); and CD3 ECD (Beckman Coulter, Miami, Fla.). The BD Cytofix/Cytoperm kit protocol was used for cell fixation and permeabilization. Samples were acquired on a LSRII flow cytometer, FlowJo® software was used to perform all analyses (Treestar, Inc; OR). The primary variable was the negative control-subtracted percentage of those live CD3+CD4+ T cells expressing any of surface CD154 or intracellular IL-2, IFN-γ or TNF-α, based on the week 26 sample.

Antigens and Media for the CD4+ T Cell Secondary Assays.

Antigen-specific T-cell responses were assessed using peptide pools of 15-mers overlapping by 11 amino acids (Biosynthesis, Lewisville, Tex.) representing the Env 92TH023 insert sequences of the ALVAC vector, at a final concentration of 1 µg/ml per peptide. For the B-cell ELISpot, Env ConS gp140 protein was kindly provided by Dr. Hua-Xin Liao, Duke University. Env A244 gp120 and MN gp120 proteins were kindly provided by Dr. Hua-Xin Liao, Duke University. Stimulations were carried out in R10 media [RPMI 1640 media with 25 mM HEPES buffer and 2.05 mM L-glutamine (Invitrogen, Carlsbad, Calif.) supplemented with L-glutamine (final concentration 3.6 mM, Invitrogen), 88.5 units/ml Penicillin, 88.5 mg/ml Streptomycin (both Invitrogen), and 10% heat-inactivated FBS (Gemini Bio-Products, West Sacramento, Calif.)] unless otherwise noted, with additional supplements as described for each assay.

Multiplex Cytokine Bead Array.

Cryopreserved PBMC were thawed and rested overnight. $5 \times 10^3$ PBMC each were stimulated with Env 92TH023 peptides at 37° C.; 1 µg/ml SEB and 0.5% DMSO served as positive and negative controls, respectively. After 48 hours, supernatants were harvested and frozen at −80° C. until analysis. Analyte concentrations were measured using a MILLIPLEX MAP Human Cytokine/Chemokine—Custom-12-Plex kit (Millipore, Billerica, Mass.) following instructions provided by the manufacturer; analytes are summarized in Table 5:

TABLE 5

Analytes in Multiplex Cytokine Bead Array

| $T_h1$/Pro-inflammatory | $T_h2$ | Chemokines/Growth Factors |
|---|---|---|
| IFN-γ | IL-4 | MIP-1β |
| IL-2 | IL-5 | GM-CSF |
| TNF-α | IL-10 | IL-3 |
| TNF-β | IL-13 | IL-9 |

All samples were acquired on a Luminex 200 instrument (Millipore) and data analyses were performed using MasterPlex software or using the Ruminex package (http://labs.fhcrc.org/fong/Ruminex/index.html) available on the R statistical programming system (Ritz and Streibig, Journal of Statistical Software 12:1-22 (2005)). The concentration-response data of the standard samples of each analyte was modeled by a five-parameter log-logistic curve (5PL) (Finney, International Statistical Review/Revue Internationale de Statistique 47:1-12 (1979)). The 5PL curve was fit to log-transformed median fluorescence intensity (MFI) versus concentrations. Observations with MFI>24,000 were removed prior to fitting the standard curves. Curve fitting was carried out using the maximum likelihood method, which produced the point estimates and standard errors of the five parameters. For each unknown sample measurement, the MFI values were log-transformed and the inverse function of the 5PL function was used to find a point estimate for the unknown concentration. For each analyte, three positivity criteria were defined aimed at controlling the false positive rate to below 2%: i) an analyte-specific threshold is determined for the DMSO-stimulated (background) response, and data from participants with high background are excluded; ii) antigen-specific responses after background subtraction need to be above a minimum concentration defined for each analyte; and iii) antigen-specific responses need to exceed the background response by x-fold, where x is defined separately for each analyte. Positivity criteria are summarized for the analyzed markers in Table 6:

TABLE 6

Positivity Criteria for Multiplex Cytokine Bead Array

| Analyte | Minimum concentration | Minimum fold over background | Maximum background |
|---|---|---|---|
| IL-2 | 40 | 3 | 40 |
| IFN-γ | 75 | 5 | 40 |
| TNF-α | 30 | 3 | 20 |
| TNF-β | 10 | 4 | 10 |
| IL-3 | 5 | 3 | 5 |
| IL-4 | 15 | 3 | 20 |
| IL-5 | 20 | 5 | 20 |
| IL-9 | 10 | 3 | 5 |
| IL-10 | 50 | 4 | 40 |
| IL-13 | 50 | 3 | 120 |
| MIP-1β | 100 | 3 | 250 |
| GM-CSF | 50 | 3 | 50 |

CFSE Proliferation Assay.

For the CFSE assay, normal human serum (Gemini Bio-Products) was used instead of FBS in all media. PBMC were thawed and rested overnight, then labeled with 50/1 Vybrant CFDA SE Cell Tracer Kit (Molecular Probes, Invitrogen) for eight minutes and quenched for one minute. $10^6$ PBMC each were stimulated with Env peptides, anti-CD3 (0.3 µg/ml) and anti-CD28 (1 µg/ml) monoclonal antibodies (BD) as a positive control, or 0.5% DMSO as a negative control. PBMC were cultured for six days at 37° C./5% $CO_2$, labeled with LIVE/DEAD Fixable Aqua Dead Cell Stain (Invitrogen), and stained with CD3-APC, CD8-PE (BD) and CD4 ECD (Beckman Coulter). Samples were analyzed on a LSRII flow cytometer and analyzed using FlowJo. Precursor frequencies were used to measure the magnitude of the response, with generation gates identified for the positive control and then applied to antigen-specific stimulations. Precursor frequencies were calculated from these gates for cells that divided at least two times.

B-Cell ELISpot.

PBMC were thawed, resuspended at $1 \times 10^6$ cells/ml in stimulation media [R10 media with 0.5 µg/ml 8848 (Mabtech, Cincinnati, Ohio) and 5 ng/ml IL-2 (Mabtech)] and incubated at 37° C. for five days. Following incubation, individual wells of Millipore MAIPSWU10 plates (Millipore, Billerica, Mass.) were coated at 4° C. overnight with one of the following: anti-human-IgG Capture mAb (15 µg/ml, Mabtech), KLH (2.5 µg/ml, Thermo Scientific), gp140 ConS, gp120 MN or gp120 A244 (all 10 µg/ml). Plates were then washed and blocked with R10 media at room temperature. Stimulated PBMC were washed, resuspended in R10 media and plated at $5 \times 10^3$/well for total IgG; $2.5 \times 10^5$/well for gp120 MN, gp120 A244 and KLH; and 1×10⁵/well for ConS. Plates were incubated at 37° C./5% $CO_2$ for 16-24 hours, and developed using biotinylated mouse anti-human-IgG detection mAb (1 µg/ml, 2 h, Mabtech) followed by streptavidin-HRP antibody (1:1000, 1 h, Mabtech) and TMB (Mabtech). Plates were counted on a CTL ELISpot reader (Cellular Technology Ltd, Shaker Heights, Ohio).

ELISA for Cyclic Peptides and Recombinant gp120.

Briefly, U-bottom 2HB plates were coated with either 1 µg/ml of cyclic peptide or with 3 µg/ml of recombinant gp120 in D-PBS at 4° C. overnight. Wells were washed 3× with wash buffer (PBS, 0.1% Tween 20 and 0.01% Thimerosal, pH 7.4) using Microplate Washer ELX405, Bio Tek, Winooski, Vt., USA and blocked with blocking buffer (D-PBS, 5% skim milk) for 2 hours at room temperature. Plasma was initially diluted 1:100 in blocking buffer and then two-fold serial dilutions were performed and samples were added to wells for 2 hours at room temperature. Wells were washed 5× with wash buffer and HRP conjugated goat anti-human IgG (1:25000) was added to wells for 1 hour at room temperature. Plates were washed 5× with wash buffer, 100 µl/well of substrate was added and color was allowed to develop at room temperature for 1 hour in the dark. Plates were read at A405 using ELISA reader Spectramax 340 PC, Molecular Devices. The data are expressed as end point titers, with the titers being defined as the reciprocal of the highest dilution that yielded an absorbance value above 2.5 times the background value (wells that did not contain recombinant protein or capturing peptides).

Biotinylated Linear Peptide ELISAs.

Briefly, StreptaWell plates (Roche) were coated with 1 µg/ml biotinylated linear V2 peptides for 1.5 h at 37° C. and then washed 6× with PBS containing 0.05% Tween-20, pH 7.4, before incubation for 1.5 h at 37° C. with RV144 plasma diluted 1:100 in RPMI media containing 15% fetal bovine serum. The plates were washed 6× and alkaline phosphatase-conjugated goat anti-human IgG (1:2000) was added for 1.5 h at 37° C. After washing, 10% diethanolamine substrate was added for 30 min to develop color, and the plates were read at A 405 nm. At each step, every well contained 50 µl; specimens were run in duplicate in each experiment, and three experiments were performed.

V2 Linear Peptide ELISA.

A solution of 5 µg/ml peptide PBS was used to coat plates with 100 µl/well and incubate overnight at 4° C. Plates were washed 2 times with wash buffer (200 µl/well). 200 µl/well of blocking solution was added and incubated for 1 hr at 37° C., then washed twice. Test sera was diluted in duplicate: 3-fold serial dilutions made, starting with a 1:30 dilution and incubated RT×2 hrs. Plates were washed ×4 with wash buffer (200 µl/well). Anti-human HRP antibody diluted 1:10 000 (American Qualex Antibodies), 100 µl/well was incubated for 1 hr at room temperature. Plates were was 4 times with wash buffer (200 µl/well). 100 µl/well of the substrate (OPD) was added ×20 minutes. The reaction was stopped by adding 100 µl/well of 3 M $H_2SO_4$. Plates read at 490 nm in a plate reader: Spectra Max 190 (Molecular devices). Data were analyzed with the plate reader software, SoftMax.

Surface Plasmon Resonance.

To confirm the findings of the ELISA studies, surface plasmon resonance (SPR) measurements were conducted with a Biacore T100 using CM5 or SA chips. Lysozyme was immobilized onto a CM5 chip using the amine coupling kit. Unbound free amines were quenched with ethanolamine. All immobilization steps used a flow rate of 10 µl/min and all experiments were performed at 25° C. The immobilization wizard packaged within the T100 control software was used to immobilize 500 nM lysozyme in 20 mM sodium phosphate, pH 7.4 (5 min contact time) in flow cell 1. Cyc V2 biotinylated peptides were prepared at 0.1 to 1 µM in Tris buffered saline, pH 7.4 and allowed to flow for 2 to 10 min over the streptavidin coated surface of the SA chip, which resulted in immobilization of approximately 895, 1401, and 2073 response units (RU), respectively for the 16, 25, and 42 amino acid cyclic V2 peptides. Similarly, 1900 RU of cyclic V2 peptide with scrambled crown (CucV2 Scr Cr) and 1850 RU of cyclic V2 peptide with scrambled glanks (CycV2 ScrF1) were immobilized to their respective flow cells.

Plasma samples were heat inactivated (56° C., 45 min), centrifuged (5 min, 4° C., 14,500 rpm), and the supernatant filtered prior to use. The plasma was diluted 50-fold in Tris buffered saline, pH 7.4. The diluted plasma samples were passed over the chip surface at 30 µl/min for 3 min followed by a 5 min dissociation period. At the end of the 5 min period, a 50 nM solution of affinity-purified gamma chain-specific sheep anti-human IgG antibody was passed over the peptide coated-Ig bound surface for 2 min at a flow rate of 10 µl/min. After a 70 s dissociation period, the chip surface was regenerated using a 30 second pulse of 50 mM HCl, a 30 second pulse of 100 mM EDTA in 20 mM Tris, pH=7.4, another 30 second pulse of 50 mM HCl and a 1 minute injection of Tris-buffered saline, pH=7.4. Non-specific binding was subtracted and data analysis was performed using the BIAevaluation 4.1 software. The reported response units (RU) for the IgG specific values are the difference between the average value of a 5 second window taken 60 seconds after the end of the anti-IgG injection and the average value of a 5 second window taken 10 seconds before the beginning of the anti-IgG injection.

CD4 Inducible Epitope Antibody Env Binding.

CD4 inducible epitope antibodies were measured as previously described (DeVico et al, Proc. Natl. Acad. Sci. USA 104:17477-82 (2007)).

Overlapping Peptide Array Assay.

Each array consisted of 1423 tiled Env peptides arranged in three identical sub-arrays, allowing for triplicate evaluation of the entire set of peptides. Peptide sequences were provided by LANL to cover the entire gp160 HIV Env from 6 HIV-1 Group M subtypes (A, B, C, D, CRF01 and CRF02) for a total of 1423 peptides (15-mers with 3 amino-acid overlaps). The specific peptides were determined by LANL's method for generating the mosaic peptide set (Ngo et al, J. Immunol. Methods 343:68-78 (2009)). Microarray development was performed using the HS4800 Pro Hybridization Station (Tecan). All arrays were blocked with Superblock T20 PBS blocking buffer for 0.5 hour at 30° C., followed by 2 hour incubation at 30° C. with heat inactivated plasma diluted 1:100 in Superblock T20. Arrays were then incubated for 45 minutes at 30° C. with a secondary antibody, 1.5 mg/ml anti-IgG Cy5 antibody diluted 1:1000 with Superblock T20. Washes between all steps were with PBS containing 0.1% Tween. Arrays were scanned at a wavelength of 635 nm using an Axon Genepix 4300 Scanner (Molecular Devices, Sunnyvale, Calif., USA) at a PMT setting of 600, 50% laser power. Images were analyzed using Genepix Pro 7 software (Molecular Devices) and the Genepix Array List supplied by JPT.

Peptide microarray spot intensities were extracted from the raw images using the GenePix® software, and peptide intensities calculated as follows: 1) Spot intensities are defined as foreground median intensity minus background median intensity. 2) Resulting intensities are log 2 transformed and centered by subtracting the average (log 2) intensities of the empty (control) spots on the slide. 3) For each unique peptide, a single intensity is defined as the median of the triplicate intensities on the slide for that peptide. In order to remove effects unrelated to true peptide binding activity, such as non-specific binding of primary antibody in the sample, array normalization was performed in an attempt to remove such effects (especially helpful when no good baseline samples are available). Based on the notion that non-specific binding may be related to physiochemical properties of the peptide, use was made of the z-scales to correct for non-specific binding biases (Sandberg et al, J. Med. Chem. 41:2481-91 (1998)). To arrive at a summary z-scale score for each peptide, the z-scale values of the individual amino acids comprising that peptide are summed. Here, the normalization is done in two stages: (i) regression model for the probe intensities is derived from their overall z-scores and (ii) each probe is normalized by subtracting its predicted intensity (representing the bias) from the observed intensity. Instead of using a typical Gaussian linear model, use is made of a linear model with $t_4$ distributed errors, which provide more robustness against probe outliers as described previously (Droit et al, Bioinformatics 26:678-9 (2010)). This normalization is performed on each array separately. Once the data have been normalized, the next step consists in smoothing probe intensities and calculating a score for each peptide that will be used to detect binding regions. Based on the assumption that an antibody will bind a region of approximately 9 aa or more, normalized peptide intensities were smoothed using a sliding window mean statistics of size 9 aa, i.e. peptides with HBX2 positions within 9 aa of one another are grouped together. This smoothing step can be made sub-type specific (e.g. for sub-type A) or across all sub-types to borrow strength across multiple peptides.

Baseline correction: Samples were corrected for baseline by subtracting, for each sample, the peptide intensities measured pre-vaccination for that sample. For the HIV+ data, no paired baseline samples (i.e. before infection) were available. In this case, the average of 10 HIV− samples was used as baseline for all 72 HIV+ samples.

Detecting binding regions: Once scores have been calculated and corrected for baseline, the score cutoff to call positive peptides can be set arbitrarily, determined based on simple validation, or based on a FDR cutoff. Here, the placebo group from the RV144 data was used to estimate the FDR and set an appropriate threshold. Peptides with log 2 fold change greater than 1.2 (with respect to baseline) were called positive, which lead to an FDR of approximately 5%. Even though no control groups were available for the naturally infected data, the same threshold was applied for consistency.

Four secondary immune variables were used based on the peptide microarray data, one for each of the four reactivity hotspots identified in the pilot data analysis (in the C1, V2, V3, and C5 regions). For each hotspot, an immune variable was defined as the average of the normalized intensities for all peptides on the array centered on the hotspot-region summit, and evaluated as a correlate of risk. These immune variables measure depth by aggregating scores over several peptides from the 7 sub-types represented in the arrays.

Blocking of Antibody Blocking and CD4 Blocking Binding Assays.

384 well ELISA plates (Costar #3700) were coated with 30 ng/well env overnight at 4° C. and blocked with assay diluent (PBS containing 4% (w/v) whey protein/15% Normal Goat Serum/0.5% Tween20/0.05% Sodium Azide) for 1 hour at room temp. All assay steps, were conducted in assay diluent (except substrate step) and incubated for 1 hour at room temp followed by washing with PBS/0.1% Tween-20. Sera were diluted 1:50 and incubated in quadruplicate wells. For CD4 (binding site) blocking assays, 10 μl of a saturating concentration soluble CD4 (Progenies Pharm Inc.) was added following serum incubation step. 10 μl biotinylated target Mab was added at the EC50 (determined by a direct binding of biotinylated-Mab to, JRFL). Biotin-Mab binding was detected with streptavidin-alkaline phosphatase at 1:1000 (Promega V5591) followed by substrate (CBC buffer+2 mM $MgCl_2$+1 mg/ml p-npp [4-Nitrophenyl phosphate di(2-amino-2-ethyl-1,3-propanediol)salt]). Plates were read with a plate reader at 405 nm at 45 minutes. Quadruplicate wells were background subtracted and averaged. Percent inhibition was calculated as follows: 100−(sera triplicate mean/no inhibition control mean)×100.

Blocking of mAb A32 to Env.

Assays to define blocking of mAb A32 by RV144 plasma antibodies was performed as described (DeVico et al, Proc. Natl. Acad. Sci. USA 104:17477-82 (2007)).

Blocking of CD4 Binding to Env.

Assays to define blocking of soluble CD4 to HIV-1 Env were performed as described (Gilbert et al, J. Infect. Dis. 181:666-77 (2005), Pitisutihum et al, J. Acquir. Immune Defic. Syndr. 37:1160-5 (2004)).

ADCC Using gp120-Coated CD4 T Cells.

ADCC assays using the gp120-coated target cells were performed as described (Horton et al, J. Immunol. Meth. 323:39-54 (2007)). The recombinant gp120 proteins represented the sequence of the HIV-1 A244 isolate with or without the gD tag peptide sequence.

Binding Antibody Multiplex Assays.

Binding antibody multiplex assays for IgG, IgG3 and IgA were performed as previously described (Tomaras et al, J. Virol. 82:12449-63 (2008), Yates et al, AIDS 25:2089-97 (2011)) and as described in the methods for the primary analysis above. HIV-specific antibody isotypes were detected with goat anti-human IgA (Jackson Immunoresearch, West Grove, Pa.), mouse anti-human IgG (Southern Biotech, Birmingham, Ala.) and mouse anti-human IgG3 (Calbiochem, Gibbstown, N.J.). The following Env antigens were included in the binding assay: C.con.env03 140 CF, B.con.env03 140 CF, JRFL gp140,G.con.env03 140 CF, HV 13700 AE.con.env03 140 CF, HV 14000 (DRCBL) gp140, 00MSA 4076 gp140, US-1 gp140,97CNGX2F 140 CF, A1.con.env03 140 CF, Con S gp140 CFI, Con 6 gp120B, A244 gp120 gD+/293T/monomer, A244 gp120 gDneg/293T/monomer, A244 gp120 gDneg delta 11/293T, 92TH023 gp120 gDneg/293T mon (all provided by Drs. Liao and Haynes) and r.gp120 MN (gD+/CHO/GSID), r.gp120 A244 (gD+/CHO/GSID), GNE8 rgp120 Q pool (provided by GSID) and (92) TH023 gp120 (gD+/293T/Berman) (provided by Dr. Berman) and binding responses to p24 Gag protein was also determined. Proteins for assessing conformational epitopes for CD4BS (RSC, RSC delta 368, RSC delta 371) and CD4i antibodies (HxB2 new8bcore 1420R) were provided by Dr. John Mascola (Vaccine Research Center, NIH). Proteins for assessing conformational epitopes for CD4BS (RSC, RSC delta 368, RSC delta 371) and CD4i antibodies (HxB2 new8bcore 1420R) were provided by Dr. John Mascola (Vaccine Research Center, NIH). Peptides specific for HIV-1 Env V2 (KKKVHAL-FYKLDIVPIEDKKK-Biotin, A244 sequence) (SEQ ID NO: 1), HIV-1 Env C1 (CSFNMTTELRDKKQKVHAL-FYKLDIVPIEDNTSSSEYRLINC CRF1AE sequence) (SEQ ID NO: 2), and HSV gD (KYALVDASLKMADPN-RFRGKDLPVLDQLTDPP) (SEQ ID NO: 7) were also included in the analysis.

Statistical Methods

The statistical analysis plan (SAP) was finalized before data analysis, and the primary results were confirmed by an independent statistical group (EMMES Corporation, Rockville, Md., USA). This SAP prescribed the immune variable definitions and statistical methods. In the primary analysis, logistic regression and Cox proportional hazards models accounting for the sampling design were used (Breslow et al, Journal of the Royal Statistical Society Series B, Statistical Methodology 59:447-61 (1997), Borgan et al, Lifetime Data Anal. 6:39-58 (2000)). The analyses controlled for gender and baseline behavioral risk as defined previously (Rerks-Ngarm et al, N. Engl. J. Med. 361:2209-20 (2009)). The 6 primary variables were evaluated in multivariate as well as univariate models. For each type of model, the immune variables were modeled quantitatively as well as using Low/Medium/High categories defined based on tertiles of response in the vaccine group. Q-values were used for multiplicity correction with significance threshold set as $q<0.2$, indicating any detected correlate can have up to 20% chance of false positivity. This approach was designed to optimize correlates discovery at the expense of an acceptable risk of false positives. Because of the small number of infected vaccines, this study had statistical power to detect only strong correlates of infection risk, with 80% power to detect a 50% reduction in infection rate per standard deviation increment in normally distributed immune responses.

The 17 groups of secondary assays were assessed with the same univariate regression analyses as the primary variables, to generate exploratory hypotheses for further study.

The goals of this analysis were to identify correlates of infection risk. An identified correlate of infection risk could be a cause of vaccine protection, a surrogate for another unidentified but linked immune response(s) actually responsible for protection, or a marker of HIV-1 exposure or intrinsic susceptibility to HIV-1 (Plotkin, Clin. Infec. Dis. 47:401-9 (2008), Plotkin, Clin. Vaccine Immunol. 17:1055-65 (2010), Qin et al, J. Infect. Dis. 196:1304-12 (2007)). To determine if a correlate of infection risk is a cause of vaccine protection, it must be tested in additional clinical vaccine efficacy trials and tested in animal models (Plotkin, Clin. Infec, Dis. 47:401-9 (2008), Plotkin, Clin. Vaccine Immunol. 17:1055-65 (2010), Qin et al, J. Infect. Dis. 196:1304-12 (2007)).

Certain aspects of the statistical methods are described in greater detail below.

The design and statistical analysis plan (SAP) for this correlates study was not specified in the original protocol (Rerks-Ngarm et al, N. Eng. J. Med. 361: 2209-20 (2009)). For statistical integrity the SAP was finalized before data analysis, and the primary results were confirmed by an independent statistical group (EMMES Corporation, Rockville, Md., USA). This SAP prescribed the immune variable definitions and statistical methods (the SAP is provided below). The one exception to pre-specified analysis is the follow-up association modeling of variable interactions.

Descriptive Plots.

Boxplots describe the distribution of each immune variable for subgroups of subjects defined by treatment group cross-classified with infection status. Cumulative HIV-1 incidence curves were plotted for the three subgroups of vaccine recipients defined by the lower, middle, and upper third of response values (Low, Medium, High subgroups), as well as for the entire placebo group HIV negative at week 24 (n=6267 subjects) for reference. These curves were estimated via the Kaplan-Meier method with inverse probability weighting that accounted for the sampling design.

Relative Risk Estimation.

Logistic regression and Cox proportional hazards models were used for evaluating whether and how the week 26 immune biomarkers affect the subsequent rate of HIV-1 infection. The fitting methods accommodate the outcome-dependent stratified biomarker sampling design via maximum likelihood estimation (Griffiss et al, J. Immunol. 130:2882-5 (1983)) and inverse probability weighted maximum partial likelihood estimation (estimator 11 in) (Jarvis et al, J. Immunol. 147:1962-7 (1991)), respectively. Two regression methods were used to assess consistency of results, with relative advantages of theoretical efficiency and accommodation of the failure time, respectively. The right-censored failure time was defined as the time between the week 26 sample date and the estimated date of HIV-1 infection or the last contact date, as defined previously (Rerks-Ngarm at al, N. Eng. J. Med. 361: 2209-20 (2009)). All regression analyses adjusted for gender and baseline risk behavior (divided into three categories as defined previously (Rerks-Ngarm et al, N. Eng. J. Med. 361: 2209-20 (2009))).

Primary Analysis Tier.

The primary analysis applied the models in four ways: in multivariate and univariate analyses of the 6 primary variables, crossed with entering the variables as quantitative readouts or as Low, Medium, High variables as defined above. The quantitative variables were mean-centered and scaled to have standard deviation one. The multivariate models included all 6 variables, and for the quantitative variable models a generalized Wald statistic was used to test the overall null hypothesis that none of the variables associated with infection. For each of the four modeling approaches separately, Holm-Bonferroni adjusted p-values (Quan et al, Eur. J. Immunol. 28:4001-9 (1998)) and q-values (Mathew et al, Int. J. Cancer 27:175-80 (1981)) (Plotkin, Clin. Infec. Dis. 47:401-9 (2008), Plotkin, Clin. Vaccine Immunol. 17:1055-65 (2010), Qin et al, J. Infect. Dis. 196:1304-12 (2007)) were applied to the six individual immune assay primary variables. These q-values are conservative in that they pre-assume that all of the null hypotheses are true (computed using the p adjust function R, with method="BH"). Q-values<0.20 were deemed to provide statistical evidence for association.

Secondary Sensitivity Analysis Tier.

The sensitivity analysis was conducted with both logistic and Cox regression models. For each model type, 8 multivariate models were fit, one for each alternate variable. These models contained an alternate variable together with the original 5 primary variables of the other immunological classes or assay subtypes. The results for the alternate variable are informally compared to those for the primary model, to evaluate if and how the result changes.

Secondary Exploratory Analysis Tier.

The univariate logistic regression and Cox regression results are presented for all secondary immune variables. Q values are reported for multiplicity correction. The details of these analyses are described in the statistical analysis plan below, in the section Exploratory analyses.

Accommodating Missing Data.

The immune variables measured on plasma samples had 100% complete data (n=286 samples). The CD4+ T cell ICS assay had 85% complete data [missing due to an aberrant batch (n=24) or high background (n=18)]. The T cell multiplex assay (Luminex) had 87% complete data (n=36 high background). Univariate analyses used all available data-points (complete-case). Multivariate analyses used a complete filled-in data-set obtained by singly imputing the missing data-points based on linear regression with gender and infection status as predictors. Multiple imputation-inference with 20 imputed data-sets (Rubin, Journal of the American Statistical Association 434:473-89 (1996)) gave nearly identical results (results not shown). All p-values and q-values are 2-sided.

Description of Case-Control Study Objectives, Sampling Plan, and Statistical Analysis Plan Provided below is an expanded description of the objectives and sampling design of the case-control study, and the statistical analysis plan (SAP). The SAP describes in detail the pre-specified set of analyses to perform for the primary analysis of correlates of HIV-1 infection risk for the vaccine group.

Structure of the Case-Control Correlates Analysis.

Assays were evaluated in the case-control study in three tiers. The first tier [primary analysis tier] consisted of a limited set of 6 priority assays, each of which was representative of an immunological class of assays (IgA binding, IgG avidity, ADCC, neutralization, V2 binding, CD4+ T cell potency). The second tier [sensitivity analysis tier] consists of alternates to the primary variables that were toggled into the primary multivariable analysis, to assess if and how changes in the primary variables altered the correlate of risk results (Table 2). The third tier [exploratory tier] consisted of all other assays that qualified for the case-control study and that could be conducted within the constraints of the available specimen volumes (Table 1). The primary analysis evaluated the 6 primary analysis tier variables whereas the secondary analysis evaluates the two other tiers of assay variables.

The case-control study first evaluated week 26 correlates (the exclusive focus of the primary report), and later evaluated time-dependent correlates. Accordingly, for the week 26 correlates analysis, the assays were performed on week 26 samples (and for some assays additionally on week 0 samples), for all four groups vaccine cases, vaccine controls, placebo cases, placebo controls (case=HIV-1 infected after week 26 and control=never diagnosed with HIV-1 infection).

Objectives of the Case-Control Study

Primary Objectives:

1. (Week 26 Primary Analysis). To assess in vaccine recipients the 6 primary immune response variables measured at week 26 as predictors of the rate of HIV infection over the subsequent period of study follow-up.

2. (Week 26 Sensitivity Analysis). To assess sensitivity of the primary analysis results to toggling/substituting the primary immune response variables with alternate immune response variables within immunological classes.

Secondary Objectives:

1. (Week 26 Secondary Analysis). To identify models based on all immune response variables measured at week 26 that best-classify vaccine recipients by their status of whether they become HIV infected over the subsequent period of study follow-up.

The primary report will report the results of the first and second primary objectives; as well as of the univariate descriptive and inferential results for the first secondary objective. The results for secondary assays should be interpreted with caution, given that no multivariate analyses are being reported (the presence of multiple immunological variables in the analysis may affect the correlation results).

Summary of the Analysis Plan for Addressing the Primary and Secondary Objectives (Week 26 Primary Analysis). Based on regression models accounting for the sampling design, univariate and multivariate analyses were conducted to assess the 6 primary immune variables measured at month 26 as significant predictors of the subsequent rate of HIV-1 infection during the study. The multivariate analysis (with all 6 primary variables in the same model) was considered to be the priority analysis, because it allowed multiple immune response variables to co-predicted HIV infection. In addition to the univariate and multivariate analyses, an all-subsets model selection procedure will be used to identify the best combination of the 6 primary variables that predict infection rate, with cross-validation applied to assess the accuracy with which the selected models predict infection outcomes for vaccine recipients left out of the model-building.

(Week 26 Sensitivity Analysis). The multivariate analyses conducted for the week 26 Primary Analysis was repeated for each alternate sensitivity variable, to informally assess if and how the correlation results changed.

(Week 26 Secondary Analysis). Machine learning model selection methods designed to handle a high-dimensional set of potential predictor variables were used to identify models that best classified infection status, with cross-validation applied to assess the accuracy with which the selected models predict infection outcomes for vaccine recipients left out of the model-building.

All of the analyses use pre-specified procedures for controlling the rate of false positive findings or for estimating the prediction accuracy on data left out of the model-building, as detailed below in the SAP.

Case-Control Sampling Plan.

HIV-1 diagnostic testing time-points subjects were tested for HIV infection at the scheduled visits at week 0, 24, 52, 78, 104, 130, 156, 182.

Sampling Time-Points.

Plasma samples were collected at the visits at week 0, 24, 26, 52, 78, 104, 130, 156, 182, whereas PBMC samples were collected at the visits at week 0, 26, 52, 182. For plasma samples, the blood volumes were larger at the week 0, 26, 52, 182 visits than the other visits (where blood was collected for purposes of HIV diagnostics).

Week 26 and time-dependent correlates of HIV infection rate.

The main analysis cohort is modified intention-to-treat (MITT) vaccine group subjects who have a negative HIV test result at the week 24 visit and who have a plasma or PBMC sample available at the week 26 visit (we refer to this as the "vaccine case-control cohort"). This cohort was analyzed to evaluate immunological measurements at the week 26 visit as predictors of HIV-1 infection over the remainder of the follow-up period (about 3 years).

Sampling Cohorts.

Before SCHARP began work on RV144, Don Stablein at EMMES Corporation drew a random sample of control subjects (i.e., subjects never diagnosed with HIV-1 infection), matched to infected subjects by gender×age×baseline behavioral risk level×Number of vaccinations received prior to infection diagnosis×treatment group. Age was categorized into the three levels≤20, 21-25, and ≥26, whereas baseline behavioral risk level was categorized into the three levels Low, Medium and High (Rerks-Ngarm et al, N. Eng. J. Med. 361: 2209-20 (2009)). In this document we refer to this control set as Control Set A.

For each infected subject, the stratum was noted, and, if available, 10 never-infected subjects were randomly sampled from the stratum. If fewer than 10 such subjects were available, all available subjects were sampled. The matched control sampling was done prior to selecting several hundred (approximately 600) subjects whose samples were used for immunogenicity testing, which we refer to as Control Set B.

In late 2010 and January 2011, SCHARP statisticians evaluated different potential sampling designs for the case-control study. The main designs considered were an individually-matched design (wherein the analysis would be conducted by conditional logistic regression), which could use Control Set A previously developed, and a non-matched stratified sampling design, which would be based on a newly constructed sampling list. SCHARP sought to identify the approach that would provide the greatest statistical power for identifying immunological correlates of HIV-1 infection risk. The literature on matched nested case-control studies suggests that individual-matching can be more efficient if the matching variables are confounders (correlated with both the immune biomarker of interest and the infection outcome), but that matching on non-confounders may lose efficiency compared to the non-matched approach.

Of the 4 individual matching factors gender, age, baseline behavioral risk level, and number of vaccinations received prior to infection diagnosis, the data do not support age and baseline behavioral risk as confounders, and it is unclear whether gender and the number of prior vaccinations are confounders, such that we conclude that the non-matched analysis is more likely to have greater efficiency. Furthermore, the non-matched approach allows evaluation of the effect of immune biomarkers on infection rate in the whole vaccinated population that is infection-free through week 26. Below the non-matched sampling plan is described, which provides the algorithm for which RV144 subjects are randomly sampled for inclusion into the case-control study. Note that in the future it would be possible to also implement the matched analysis using Control Set A, as a complementary analysis, which would be advantageous if the initial case-control studies reveal correlates.

Sample Availability.

Figure 24:
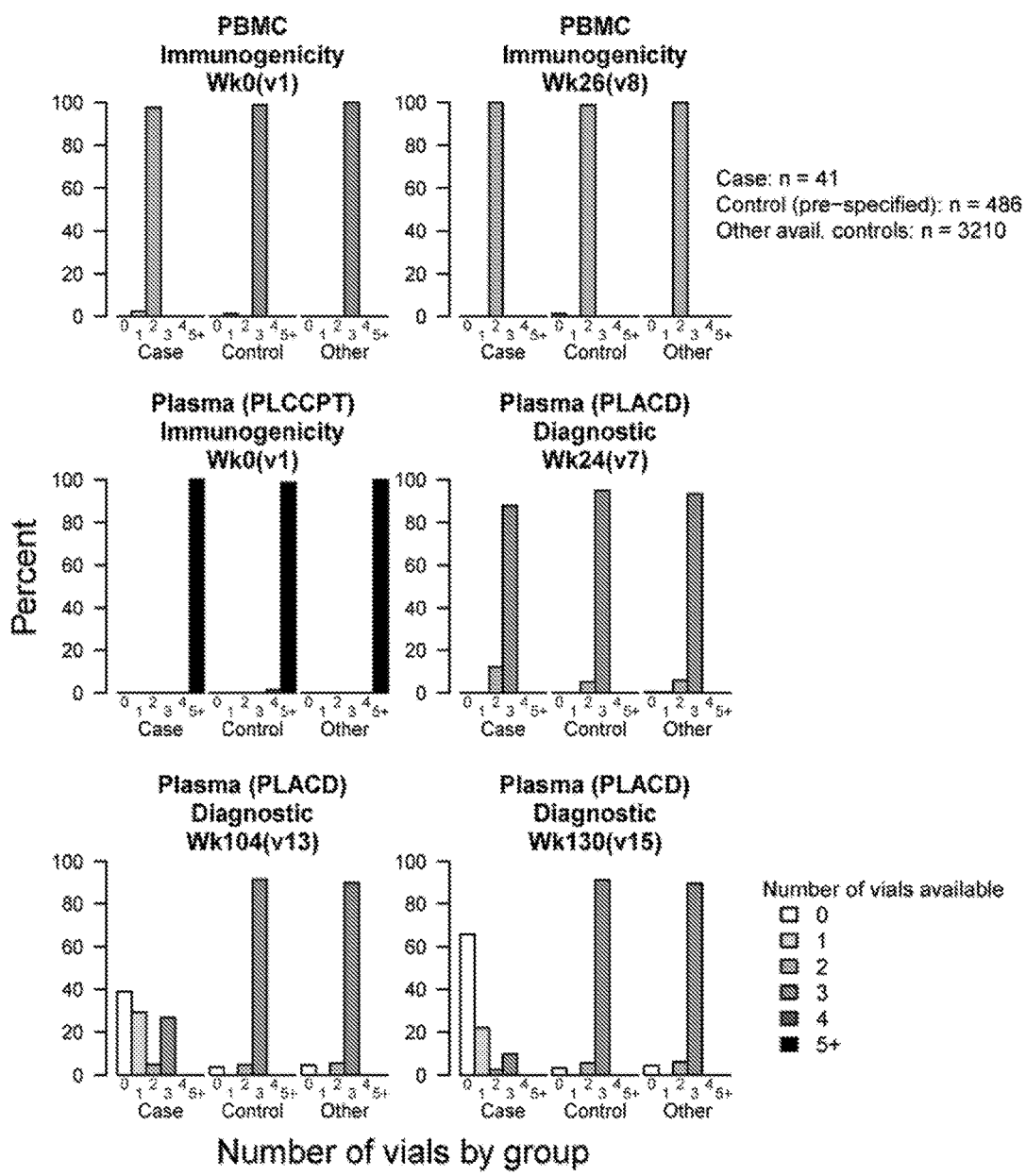
FIG. 24. Plasma and PBMC availability by sampling time point for cases (diagnosed with HIV infection after the Week 26 visit, defined by an estimated date of infection at or after the left-edge of the Week 26 visit window [23 weeks minus 2 days], n=41 subjects); Control Set A (n=486 subjects); and other available controls (never-infected subjects not previously sampled into Control Set A, into Control Set B, nor into any of the immunogenicity pilot studies, n=4169 subjects).
Figure 24:
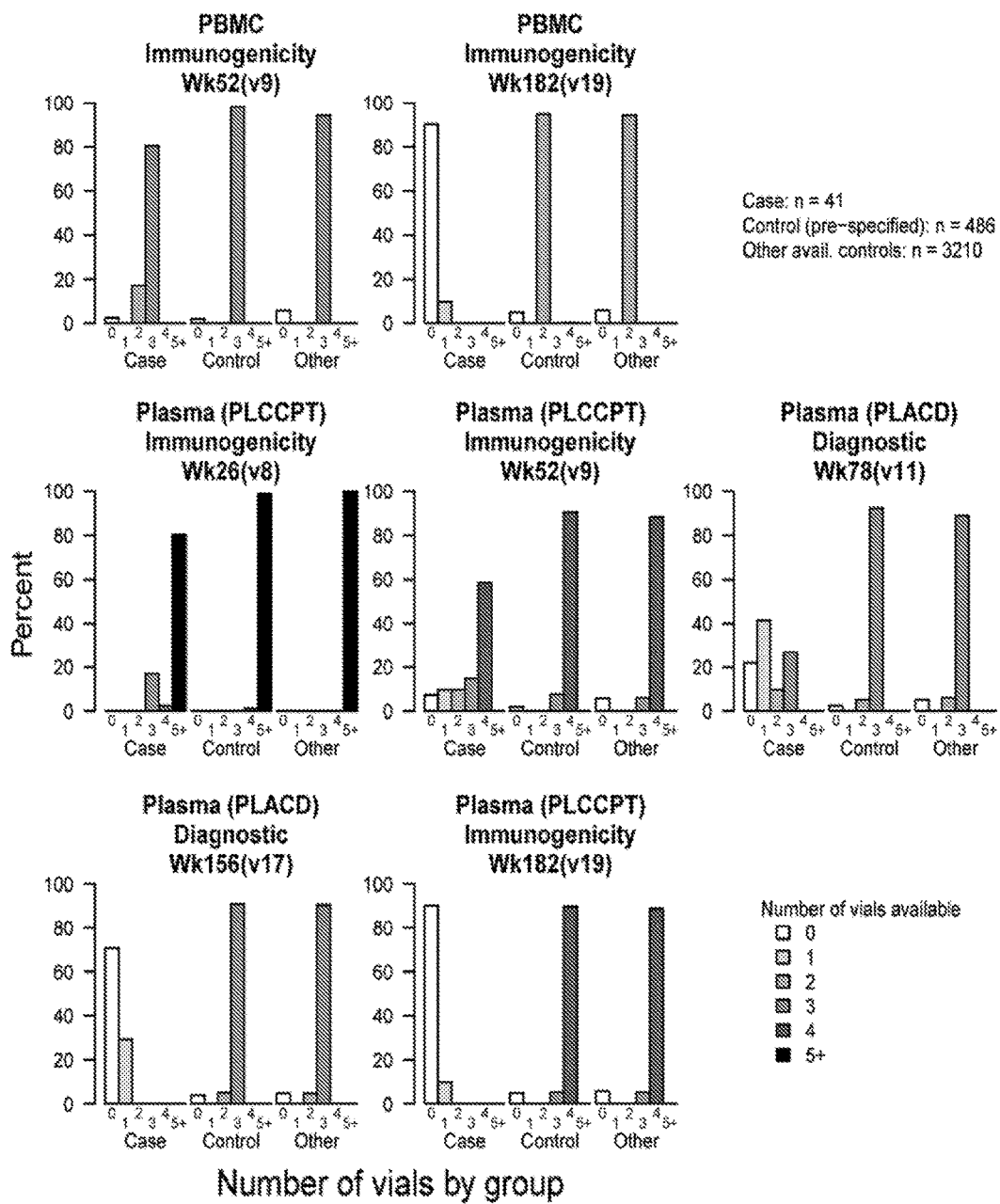

For subjects in the vaccine case-control cohort, FIG. 24 describes the distribution of the number of plasma and PBMC vials available at the sampling time-points. The distribution is described separately for three groups: cases (diagnosed with HIV-1 infection after the week 26 visit, defined by an estimated date of infection at or after the left-edge of the week 26 visit window [23 weeks minus 2 days], n=41 subjects); Control Set A (n=486 subjects); and other available controls (never-infected subjects not previously sampled into Control Set A, into Control Set B, nor into any of the immunogenicity pilot studies, n=4169 subjects). Note that the number of individually matched controls selected into Control Set A (n=486) exceeds 10-fold the number of vaccine cases (n=41), because controls were matched to cases irrespective of whether a sample was available at the week 26 visit and an HIV negative test result was available at the week 24 visit. In addition, note that there are 5 other vaccine cases who are HIV negative at the week 24 visit but missing a week 26 visit. While some interesting information could potentially be obtained from these subjects, they are excluded from the sampling lists, because three of the subjects received only one immunization, one received two immunizations and only had samples available at the week 0 and week 156 visits, and one received three immunizations and only had samples available at the week 0, 130, 156, and 182 visits.

Three hundred and one of the 486 Control Set A controls had "complete plasma sample availability," defined as at least 5 plasma vials at the Week 0 and 26 visits, at least 4 plasma vials at the Week 52 and 182 visits, and at least 3 plasma vials at each of the other 5 sampling visits (Week 24, 78, 104, 130, 156). In addition, 450 of 486 Control Set controls had "complete PBMC sample availability," defined as at least 3 PBMC vials at the Week 0 and 52 visits and at least 2 PBMC vials at the week 26 and 182 visits. In addition, 2546 of the 4169 other available controls had complete plasma sample availability and 3816 of the 4169 other available controls had complete PBMC sample availability. Moreover, 301 of the 486 Control Set A controls had complete plasma and PBMC sample availability, while 2546 of the 4169 other available controls have complete plasma and PBMC sample availability; therefore complete plasma sample availability implies complete PBMC sample availability for both the pre-specified and other controls. Based on this assessment, vaccine controls were drawn from the pool of 2546 vaccine controls that had complete sampling available. This minimized missing data, and maximize the ability to assess time-dependent correlates of HIV-1 infection rate as well as maximized the ability to assess temporal dynamics of vaccine induced immune responses.

Of the 41 vaccine cases, 39 had all 4 immunizations prior to infection diagnosis, and 1 each had 2 and 3 immunizations. Thirty-six of the 41 vaccine cases qualified for the per-protocol (PP) population as pre-specified in the RV144 protocol. Table 7 shows the distribution of gender, the number of immunizations, and per protocol status of the 41 vaccine cases.

TABLE 7

Distribution of the 41 vaccine cases in the vaccine case-control cohort

| | Women | | Men | |
|---|---|---|---|---|
| Number of Vaccinations | Per Protocol | Not Per Protocol | Per Protocol | Not Per Protocol |
| 2 | 0 | 1 | 0 | 0 |
| 3 | 0 | 1 | 0 | 0 |
| 4 | 12 | 1 | 24 | 2 |
| Total | 12 | 3 | 24 | 2 |

Stratified Sampling Plan.

The assays were performed for all subjects in the vaccine case-control cohort who were diagnosed with HIV-1 infection after the week 26 visit (vaccine cases). In addition, the assays were performed on a 5:1 random sample of subjects in the vaccine case-control cohort who were never diagnosed with HIV infection and have complete specimen sampling as described above (vaccine controls). This random sample was stratified by gender, number of vaccinations received, and PP status; in other words, for each case, 5 subjects were randomly sampled from the subset of vaccine controls that have the same gender, number of vaccinations, and PP status. This sampling was done after excluding all three sets of the approximately 600 subjects pre-selected for immunogenicity testing, the matched control set, and subjects previously sampled for immunogenicity pilot studies. From Table 7, the 41 vaccine cases divide into the following 6 strata, with the number of cases and controls listed:

1. Women, 4 vaccinations, PP (n=12 cases; n=60 controls)
 2. Women, 4 vaccinations, not PP (n=1 case; n=5 controls)
 3. Women, 3 vaccinations, not PP (n=1 case; n=5 controls)
 4. Women, 2 vaccinations, not PP (n=1 case; n=5 controls)
 5. Men, 4 vaccinations, PP (n=24 cases; n=120 controls)
 6. Men, 4 vaccinations, not PP (n=2 cases; n=10 controls)

Furthermore, the assays were performed on a random sample of PP placebo subjects who have a negative HIV test result at the week 24 visit and who have samples available at the week 26 visit (the placebo case-control cohort). In particular, the assays were performed on a random sample of 20 PP subjects in the placebo case-control cohort who were diagnosed with HIV infection after the week 26 visit (placebo cases), and on a random sample of 20 PP subjects in the placebo case-control cohort who were never diagnosed with HIV infection and have complete specimen sampling as described above (placebo controls), with gender-balance compared to the cases.

In addition, an extra set of 5:1 never-infected subjects from the vaccine case-control cohort with complete longitudinal plasma and PBMC samples available were sampled, balanced within each of the strata defined by the same three factors used for the first set. The extra samples may optionally be used by investigators who wish to conduct their assay on an expanded set of control samples. The extra samples were augmented with 20 additional PP placebo cases and 20 additional PP controls, selected using the same criteria as used for selecting the main set.

Note that the assays were performed blinded to both case/control and vaccine/placebo status, so that all batches will contain a subset of each. This ensured that a) not all cases were lost if there is any problem with an assay on a certain day, and that b) labs conduct the assays in an unbiased manner. For the analysis of extra control samples, the analyses were blinded to vaccine/placebo status.

Statistical Analysis Plan

Descriptive Analyses.

For each primary variable and each alternate variable used for sensitivity analysis (collectively referred to below as the "assay variables"), boxplots were used to display the week 26 readouts, first blinded to case/control status and stratified by vaccine/placebo group and men/women (4 strata); and second stratified by case/control status, vaccine/placebo group, and men/women (8 strata). Readouts for the two vaccine cases who received fewer than 4 immunizations (both women) were distinguished in the plots with an asterisk.

For each assay variable, the "blinded" descriptive analyses (pooled over cases and controls) will be used to determine low, medium, and high responses. The week 26 placebo readouts were used to ensure that the medium responses are clearly above placebo responses. For assays with almost all vaccine recipient responses positive (and thus above the placebo responses), the default categories were tertiles. For assays with substantial numbers of vaccine recipients with a negative responses, the default was for the low response category were to be negative response, and the medium and high response categories to be below and above the median among the subset of positive responses, respectively. Based on the descriptive analyses the low, medium, and high categories were defined differently than these defaults; however in all instances the categories were determined without respect to case/control status and were fixed before conducting any descriptive or inferential analyses that were unblinded to case/control status.

For some of the assay variables, Week 0 readouts were available and were used in the analysis. For these assay variables and for the vaccine and placebo groups separately, boxplots and line plots were used to display the within-subject contrasts in readouts (week 26 versus Week 0).

For the set of primary and alternate sensitivity analysis assay variables, for the vaccine and placebo groups separately, inter-correlations of the week 26 readouts were evaluated by pairwise scatterplots and Spearman rank correlations, as well as a summary heat map displaying the Spearman rank correlations. These analyses were repeated for secondary assays, for various combinations of assays of interest.

Inferential Analyses.

Univariate and multivariate analyses were performed to assess the week 26 assay readouts individually and jointly as correlates of infection rate in the vaccine group. The multivariate analyses of week 26 immune biomarkers included both antibody and T-cell measurements. All statistical models described below adjusted for gender and baseline behavioral risk score (divided into categories low risk, medium risk, and high risk, as defined in the model (Rerks-Ngarm et al, N. Eng. J. Med. 361: 2209-20 (2009)).

Vaccine Recipient Cohorts for Analysis.

All vaccine recipient cases (n=41) and their set of 5:1 vaccine recipient controls were used in the analysis. A sensitivity analysis was conducted that excluded the two vaccine recipient cases that received fewer than 4 vaccinations prior to infection; for this analysis the same set of control subjects as for the main analysis was used.

Missing Immunological Measurements.

When the probability of missing immunological measurements depended on either the unobserved missing value or other unobserved covariates or observed covariates not included in the modeling, ignoring these missing data in the methods described below could yield biased results. If at least 15% of data was missing for a given assay variable, then multiple imputation was used to fill in the missing data. The Mice package in R was used to perform linear-regression-based imputation with infection status and gender as predictors. A total of 20 imputed datasets were generated and results were combined across imputed datasets using standard multiple imputation rules (Rubin, Journal of the American Statistical Association 434:473-89 (1996)). For comparison, "complete-case" analyses was performed, whereby subjects missing relevant immunological variables were excluded from the analyses. If the two analyses provide highly similar results, then for simplicity the primary report will focus on reporting the results for the complete-case analysis of univariate models and single-imputation analysis of multivariate models.

Primary Analysis for Week 26 Correlates.

The primary analysis of week 26 correlates used maximum likelihood estimation in a logistic regression model (Breslow and Holubkov, Journal of the Royal Statistical Society Series B, Statittical Methodology 59:447-61 (1997)) for estimation and inferences on relative risks of infection per increment of immunological variables. A version of this method designed specifically to accommodate the 2-phase sampling design was applied, as implemented in the R package tpsDesign. While the method actually estimated odds ratios, the low event rate implied the odds ratios closely approximate relative risks. Moreover, the low event rate implies that this dichotomous-endpoint method has negligible power loss compared to a time-to-event method (i.e., that assesses the time from the week 26 sampling date to the estimated date of HIV-1 infection, described below). The advantage of the 2-phase logistic regression method was that maximum likelihood estimation was fully efficient (providing maximum precision and statistical power in large samples), whereas the inverse probability weighted partial likelihood method used in the Cox proportional hazards model (described below) was not efficient.

Primary Analysis: Fixed Modeling Approach.

For the primary analysis, the 6 primary immunological variables was first evaluated as quantitative variables, and secondly as trichotomous variables (with categories defined as described above). The quantitative variables were mean-centered and scaled to have standard deviation 1. Univariate analyses were performed using the 2-phase logistic regression model, and Holm-Bonferroni adjusted p-values (Holm, Scandinavian Journal of Statistics 6:65-70 (1979)) and q-values Benjamini and Hochberg, Journal of the Royal Statistical Society Series B, Statistical Methodology 57:4289-300 (1995)) applied to judge significance after correction for 6 tests. In addition, a multivariable regression model was fit using all 6 variables in the analysis, and a generalized Wald test applied to test the global null hypothesis that the set of variables does not predict infection rate versus the complement alternative that one or more variables predict infection rate. The multivariate analyses with the 6 primary variables were considered to be the main/primary analyses.

For each assay variable, cumulative HIV incidence curves for the low, medium, and high biomarker categories were calculated using the inverse-sampling-probability-weighted Kaplan-Meier method, and are presented in plots. The curve for the entire placebo group HIV negative at the Week 24 visit was included for reference.

Primary Analysis: Model Selection Approach.

Logistic regression all-subsets model selection was used to select the immune variables among the 6 primary variables that best classify vaccinated subjects by HIV infection status. Two-way interactions among the 6 variables were included in the model selection. In addition, gender was forced in all models to control for the two-phase sampling and the sampling weights was ignored; per-protocol status and number of vaccinations was not included due to the sparse categories defined by these variables. In addition, risk category was included in all models to control for potential confounding. The model search was limited to models with 15 predictors or less, to avoid unstable parameter estimates. This method was limited by the fact that main effect terms are not forced into the model building.

ROC analysis was used to evaluate classification accuracy. Specifically, the all-subsets model selection used the AIC criterion for selecting the best logistic regression model. This model was re-estimated using the tpsDesign function that adjusted for the sampling weights. Based on this best model, vaccine recipients were classified as infected or uninfected using their predicted probabilities of infection. The ROC curve for these predicted probabilities were used to summarize the classification accuracy of the model. Cross-validation were used to evaluate classification accuracy for vaccine recipients left out of the model building.

Specifically, vaccine subjects were randomly split with two-thirds in the training set and one-thirds in the holdout set. The all-subsets model selection procedure described above were used to pick the best model for the training data, which were applied to the holdout data to estimate the ROC curve. This procedure was repeated 1000 times, and the distribution of the areas-under-the-ROC curves (AUCs) were used to summarize the ability of the models to classify infection status for left-out vaccine recipients. The immunological variables were deemed to have some ability to classify infection status if the 5th percentile of the distribution of these AUCs exceeds 0.5.

The all-subsets model selection was performed using both quantitative immunological variables and using dichotomized (low or medium vs high) immunological variables. The analyses were performed using a single imputed dataset for variables with imputed missing values.

In order to interpret the models, which may include interactions among the immunological variables, plots were used to show the estimated odds ratio as a function of each variable in the model. Where there were interactions, this function depend on the values of the other variables.

Complementary Method for the Primary Analysis of Week 26 Correlates.

Cox Proportional Hazards Model (Fixed Modeling Approach).

To ensure the results were not overly sensitive to the method employed, the proportional hazards model was used to assess correlates, with outcome the time between the week 26 visit and the estimated date of HIV infection. Borgan et al.'s estimator II was used, accounting for the stratified sampling (Borgan et al, Lifetime Data Anal. 6:39-58 (2000)). Analyses parallel to those with the logistic regression model were conducted, except the model-selection exercise was not performed. In particular, univariate analyses of the 6 primary variables were performed using Holm-Bonferroni adjusted p-values and q-values applied to judge significance after correction for 6 tests. In addition, a multivariable regression model was fit using all 6 variables in the analysis, and a generalized Wald test applied to test the global null hypothesis that the set of variables does not predict infection rate versus the complement alternative that one or more variables predict infection rate. Interactions were assessed using the same methods described in the logistic regression section.

The analysis yielded estimates of hazard ratios of HIV infection for different levels or increments in immune biomarkers, along with 95% confidence intervals and p-values for testing null hypotheses of no correlation. As for the two-phase logistic regression model, the analysis were done both using quantitative immunological variables and using categorized (low, medium, high) immunological variables. Complete-case and multiple-imputation versions of the analyses were done. As for the logistic regression analysis, since the two sets of results were very similar, for simplicity the primary report focused on reporting the results for the complete-case analysis of univariate models and single-imputation analysis of multivariate models.

Sensitivity Analysis of Week 26 Correlates.

A single alternate closely related variable was associated with 5 of the 6 primary variables, and three closely related alternates were associated with the neutralization primary variable. The sensitivity analysis proceeded as follows, first based on the two-phase logistic regression model and second based on the two-phase Cox model. The full multivariable model (with 6 variables) was fit using 5 of the primary variables and one alternate variable for sensitivity analysis. The estimated relative risk, 95% confidence interval, and p-value for the alternate variable was compared to those of the corresponding primary variable, to evaluate if and how the result changed (no formal statistics are involved in this comparison). The resulting 8 multivariable models with one alternate variable toggled in was reported. In addition, for the best logistic regression model selected by all-subsets model selection (as described above), each variable in this model was replaced with the alternate variable toggled in (one at a time) and the result reported. Similar to the above, the sensitivity analysis was done both using quantitative immunological variables and using categorized (Low, Medium, High) immunological variables.

All p-values are 2-sided. In the univariate analyses, adjusted p-values<0.05 were considered to constitute strong evidence for a real correlation. Q-values<0.20 were considered to constitute evidence for a real correlation that merits further investigation.

Exploratory Analyses.

The set of immune variables to evaluate as potential correlates of infection rate (both primary and secondary variables) are listed in the Table 1 and Table 8. For each immune variable, univariate two-phase logistic regression and Cox regression analyses (as described above, which control for gender and baseline behavioral risk) was used to estimate the relative risk of infection with 95% confidence interval and 2-sided p-value. The analyses were done for quantitative variables (pre-scaled to have mean zero and standard deviation 1), as well as for categorical variables. For the assays with a positivity response criterion, the rate of vaccine recipients with a positive response affects the approach to the categorical variable analysis. In particular, the following rules were followed to determine the categorical analysis used for each secondary variable:

Assess the relative risk for positive versus negative responders if the positive response rate is less than 50%
   Assess the relative risk for Medium versus Negative and for High versus Negative if the positive response rate is between 50% and 85%, where Medium and High are defined by below and above the median of the responders, respectively.
   Assess the relative risk for Medium versus Low and for High versus Low if the positive response rate is greater than 85%, where Low, Medium, and High are defined as the tertiles for vaccine recipients.

were summarized by grouping sets of immune variables into rational sets (e.g., all variables measuring IgA binding, or all variables measuring V2 binding antibodies). Plots were presented showing estimated relative risks with 95% confidence intervals. In addition, in future analyses machine learning variable selection methods were applied to identify potential correlates of infection rate.

Results of the Binded Analysis used to Define Low, Medium, High for the 6 Primary and 8 Sensitivity Variables.

Boxplots of Individual Biomarkers: Blinded to Case-Control Status.

FIGS. 25-31 show the distributions of the primary and sensitivity variable assay readouts, pooling over cases and controls. Based on these figures and related analyses, the low, medium, and high response categories were defined as follows. The category definition is described for each of the 14 primary and alternate sensitivity variables, and for associated secondary variables.

Plasma IgA Binding Variables.

For the primary IgA binding score variable, Low/Medium/High were defined as the tertiles for the vaccine group. For the alternate variable (IgA binding A244 gD-Delta11), Low was defined as a negative response based on the positivity call method that takes into account the Week 0 value, and Medium/High are defined by the median in the vaccine group responders.

Plasma IgG Avidity.

For the primary (IgG avidity A244 gD-Delta11) and alternate (IgG avidity MN) variables, Low/Medium/High were defined as the tertiles for the vaccine group.

TABLE 8

Univariate and multivariate logistic regression results for the 6 primary variables

| Assay | OR scale | Multivariate Logistic Regression | | | Univariate Logistic Regression | | |
|---|---|---|---|---|---|---|---|
| | | OR | 95% CI | P (Q) | OR | 95% CI | P (Q) |
| IgA Binding | per 1-SD | 1.54 | (1.05, 2.25) | 0.03 (0.08) | 1.39 | (1.00, 1.93) | 0.05 (0.19) |
| IgG Avidity | per 1-SD | 0.81 | (0.50, 1.30) | 0.37 (0.56) | 0.93 | (0.65, 1.34) | 0.70 (0.81) |
| ADCC | per 1-SD | 0.92 | (0.62, 1.37) | 0.68 (0.68) | 0.96 | (0.68, 1.35) | 0.81 (0.81) |
| NAb | per 1-SD | 1.37 | (0.82, 2.27) | 0.23 (0.45) | 1.08 | (0.76, 1.54) | 0.67 (0.81) |
| gp70-V1V2 Binding | per 1-SD | 0.57 | (0.36, 0.90) | 0.02 (0.08) | 0.70 | (0.49, 1.02) | 0.06 (0.19) |
| CD4+ T Cells | per 1-SD | 1.09 | (0.79, 1.49) | 0.61 (0.68) | 1.08 | (0.79, 1.47) | 0.64 (0.81) |
| IgA Binding | Med vs Low | 0.68 | (0.25, 1.83) | 0.45 | 0.71 | (0.28, 1.77) | 0.46 |
| | High vs Low | 1.89 | (0.75, 4.74) | 0.17 | 1.55 | (0.69, 3.48) | 0.29 |
| | Overall[1] | — | — | 0.07 (0.23) | — | — | 0.18 (0.54) |
| IgG Avidity | Med vs Low | 0.67 | (0.26, 1.75) | 0.42 | 0.79 | (0.34, 1.84) | 0.59 |
| | High vs Low | 0.83 | (0.30, 2.30) | 0.72 | 0.87 | (0.38, 2.01) | 0.75 |
| | Overall | — | — | 0.71 (0.84) | — | — | 0.86 (0.86) |
| ADCC | Med vs Low | 0.93 | (0.39, 2.19) | 0.86 | 0.96 | (0.43, 2.14) | 0.92 |
| | High vs Low | 0.59 | (0.22, 1.59) | 0.30 | 0.60 | (0.24, 1.48) | 0.27 |
| | Overall | — | — | 0.57 (0.84) | — | — | 0.53 (0.71) |
| NAb | Med vs Low | 2.08 | (0.78, 5.57) | 0.14 | 1.58 | (0.66, 3.76) | 0.31 |
| | High vs Low | 2.43 | (0.77, 7.67) | 0.13 | 1.29 | (0.53, 3.14) | 0.57 |
| | Overall | — | — | 0.26 (0.52) | — | — | 0.59 (0.71) |
| gp70-V1V2 Binding | Med vs Low | 0.68 | (0.28, 1.62) | 0.38 | 0.84 | (0.38, 1.84) | 0.67 |
| | High vs Low | 0.29 | (0.10, 0.86) | 0.02 | 0.43 | (0.18, 1.05) | 0.06 |
| | Overall | — | — | 0.08 (0.23) | — | — | 0.16 (0.54) |
| CD4+ T Cells | Med vs Low | 0.84 | (0.35, 2.02) | 0.69 | 0.62 | (0.27, 1.45) | 0.27 |
| | High vs Low | 0.77 | (0.31, 1.91) | 0.57 | 0.51 | (0.21, 1.23) | 0.13 |
| | Overall | — | — | 0.84 (0.84) | — | — | 0.28 (0.57) |

[1]2-sided p-value from a Wald test of the null hypothesis of an equal infection rate in the Low, Medium, and High vaccine responding subgroups.

Given the large number of secondary variables, these univariate secondary analyses are largely descriptive. Unadjusted p-values<0.05 and <0.01 were used as informal screens for flagging variables as potential correlates. Results Antibody-Dependent Cellular Cytotoxicity (ADCC).

For the primary (ADCC luciferase 92TH023 infected target cells) and alternate (ADCC gp120-coated A244 target cells) variables, Low/Medium/High were defined as the tertiles for the vaccine group.

Neutralization (NAb).

For the primary variate (NAb score to the n=6 pseudoviruses) and the three alternate variables (NAb score to the n=3 subtype B viruses with TZM-bl cells; NAb to 92T1-1023 with TZM-bl cells; NAb score to the n=2 subtype E viruses with A3R5 cells), Low/Medium/High were defined as the tertiles for the vaccine group.

V2 Binding ELISAs.

For the primary (scaffolded V1V2) and alternate (Cyclic C2 peptide 42aa sites 157-198) variables, Low/Medium/High were defined as the tertiles for the vaccine group.

T Cell Response Magnitude.

For the primary variable (CD4+ T cells measured by ICS), Low/Medium/High are defined as the tertiles for the vaccine group. For the alternate variable (PBMC production of cytokines measured by Luminex), Low was defined as a negative response and Medium/High are defined by below and above the median among vaccine group responders, respectively.

Results

Primary Case Control Analyses.

Figure 23:
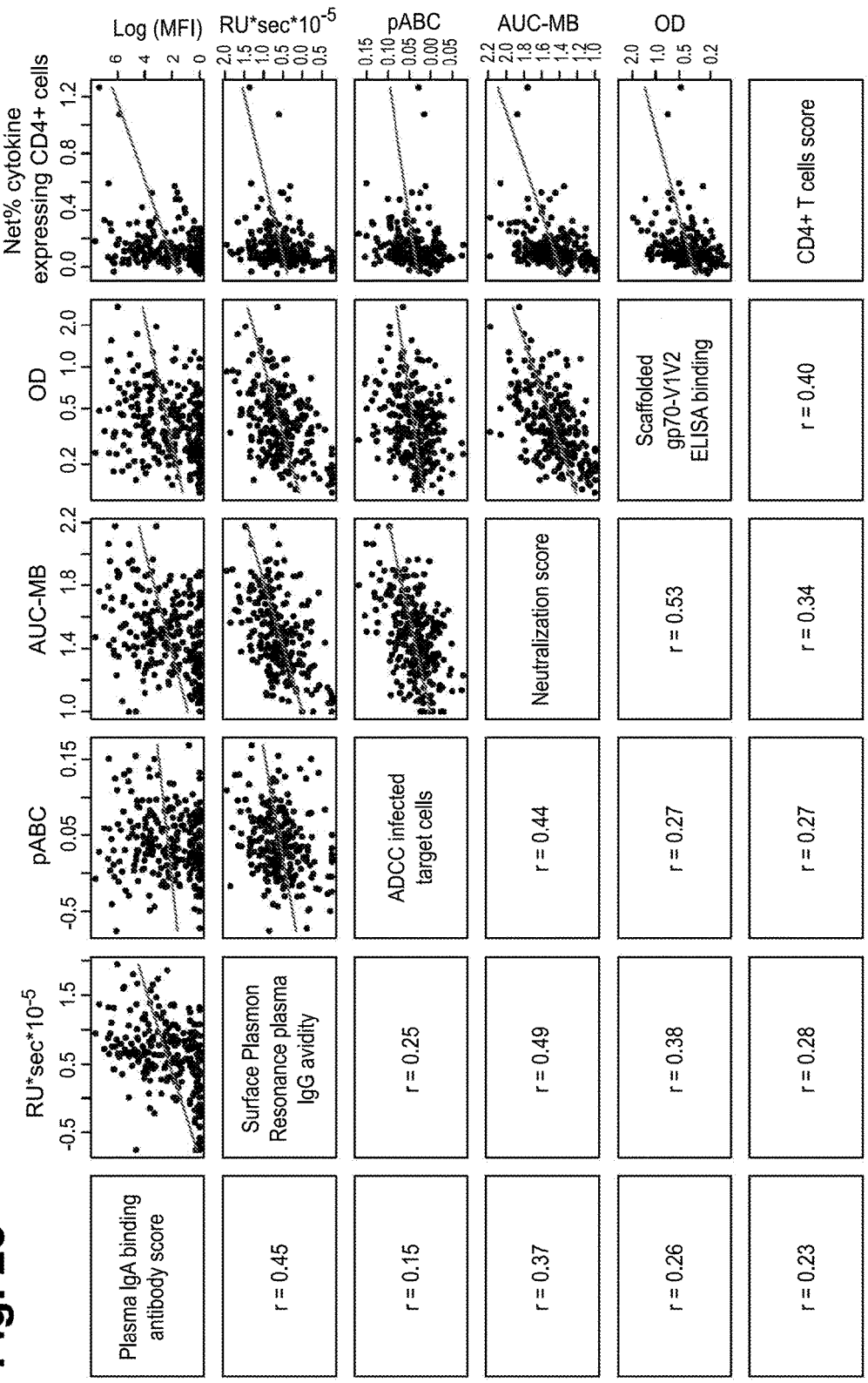
FIG. 23. Scatterplots and Spearman rank correlation values (r) for all pairs of the 6 primary variables.

Vaccine-induced immune responses were detected with all primary assay variables, with sufficient dynamic ranges to support regression analyses (FIG. 19). FIG. 23 shows that the 6 primary variables were only weakly correlated with each other, verifying that the process for selecting the primary variables yielded non-redundant primary immune response variables.

First, when the 6 quantitative variables were analyzed together in multivariate logistic regression models, there was a trend that the variables together predicted the risk of infection (overall p=0.08). In this model, the IgG avidity, ADCC, neutralizing antibodies, and CD4 intracellular cytokine variables did not significantly predict HIV infection rate (q-values>0.2). However, IgG binding to a scaffolded V1V2 antigen inversely correlated with infection (estimated OR=0.57 per sd increase, p=0.02, q=0.08), and composite Env IgA binding antibodies directly correlated with infection (estimated OR=1.54 per sd increase, p=0.03, q=0.08) (Table 8). The univariate analyses of individual variables yielded OR estimates of 0.70 and 1.39, respectively, for V1V2 and IgA responses with slightly reduced significance (p=0.06, 0.05; q=0.19, 0.19), respectively (Table 8).

Parallel multivariate analyses with the Cox model yielded similar results with overall multivariate p=0.06 and multivariate hazard ratio estimates of 0.57 for V1V2 (p=0.01, q=0.06) and 1.58 for IgA responses (p=0.02, q=0.06) (Table 9). When the multivariate analysis was repeated with only the V1V2 and IgA immune variables, the overall p-value was 0.01 for both logistic and Cox regression.

TABLE 9

Univariate and multivariate Cox regression results for the 6 primary variables. For each variable, the hazard ratio (HR) is reported per standard deviation (sd) and comparing Medium and High responses to Low responses. Low/Medium/High are determined by tertiles of response in the vaccine group

| Variable | OR scale | Multivariate Cox Regression | | | Univariate Cox Regression | | |
|---|---|---|---|---|---|---|---|
| | | HR | 95% CI | P (Q) | HR | 95% CI | P (Q) |
| IgA Binding | per 1-sd | 1.58 | (1.07, 2.32) | 0.02 (0.06) | 1.43 | (1.02, 2.02) | 0.04 (0.22) |
| IgG Avidity | per 1-sd | 0.83 | (0.50, 1.36) | 0.46 (0.55) | 0.95 | (0.65, 1.38) | 0.77 (0.77) |
| ADCC | per 1-sd | 0.92 | (0.62, 1.37) | 0.69 (0.69) | 0.94 | (0.67, 1.33) | 0.74 (0.77) |
| Nab | per 1-sd | 1.39 | (0.83, 2.35) | 0.21 (0.43) | 1.11 | (0.77, 1.60) | 0.59 (0.77) |
| gp70-V1V2 Binding | per 1-sd | 0.57 | (0.36, 0.89) | 0.01 (0.06) | 0.72 | (0.50, 1.03) | 0.07 (0.22) |
| CD4+ T Cells | per 1-sd | 1.17 | (0.83, 1.64) | 0.38 (0.55) | 1.11 | (0.77, 1.61) | 0.56 (0.77) |
| IgA Binding | Med vs Low | 0.73 | (0.27, 1.96) | 0.53 | 0.71 | (0.29, 1.77) | 0.47 |
| | High vs Low | 2.01 | (0.79, 5.15) | 0.14 | 1.58 | (0.70, 3.55) | 0.27 |
| | Overall | — | — | 0.07 (0.32) | — | — | 0.17 (0.50) |
| IgG Avidity | Med vs Low | 0.60 | (0.23, 1.58) | 0.30 | 0.78 | (0.34, 1.81) | 0.57 |
| | High vs Low | 0.91 | (0.33, 2.48) | 0.85 | 0.90 | (0.39, 2.05) | 0.80 |
| | Overall | — | — | 0.53 (0.71) | — | — | 0.85 (0.85) |
| ADCC | Med vs Low | 0.93 | (0.38, 2.23) | 0.87 | 0.93 | (0.42, 2.09) | 0.87 |
| | High vs Low | 0.61 | (0.23, 1.62) | 0.32 | 0.60 | (0.24, 1.46) | 0.26 |
| | Overall | — | — | 0.59 (0.71) | — | — | 0.52 (0.62) |
| NAb | Med vs Low | 1.94 | (0.73, 5.14) | 0.18 | 1.65 | (0.70, 3.88) | 0.25 |
| | High vs Low | 2.22 | (0.74, 6.70) | 0.16 | 1.32 | (0.54, 3.18) | 0.54 |
| | Overall | — | — | 0.31 (0.61) | — | — | 0.52 (0.62) |
| gp70-V1V2 Binding | Med vs Low | 0.73 | (0.31, 1.74) | 0.48 | 0.85 | (0.39, 1.87) | 0.68 |
| | High vs Low | 0.32 | (0.11, 0.93) | 0.04 | 0.45 | (0.18, 1.08) | 0.07 |
| | Overall | — | — | 0.11 (0.32) | — | — | 0.19 (0.50) |
| CD4+ T Cells | Med vs Low | 0.71 | (0.28, 1.80) | 0.48 | 0.58 | (0.24, 1.39) | 0.22 |
| | High vs Low | 0.73 | (0.29, 1.80) | 0.49 | 0.49 | (0.20, 1.20) | 0.12 |
| | Overall | — | — | 0.71 (0.71) | — | — | 0.25 (0.50) |

The logistic regression analyses for the 6 primary variables broken down into Low/Medium/High tertiles yielded OR estimates consistent with the quantitative variable analysis. There was no evidence that IgG avidity, ADCC, NAb, or Env-specific CD4 T cells were associated with infection risk (q-values>0.20). Comparison of high to low tertiles showed V1V2 antibody levels inversely correlated with infection (estimated OR=0.29, p=0.02) and IgA antibody levels trended toward direct correlation with infection (estimated OR=1.89, p=0.17) (Table 8). However, these categorical model results had reduced significance levels for testing equal infection rate across low, medium and high groups (q=0.23, q=0.23), which may be related to the division of responses into tertiles, which can reduce statistical power.

FIG. 20 shows the cumulative HIV-1 incidence curves for each primary variable by Low/Medium/High response and for the entire placebo group which was HIV-1-negative at Week 24. These curves emphasize the increased rate of infection in vaccine recipients with high Env IgA antibodies compared to other vaccine recipients, and the decreased rate of infection in vaccine recipients with high V1V2 antibody levels.

Comparison of Infection Rates of Vaccinees with Low, Medium or High V1V2 or Env IgA with Infection Rates in the Placebo Group.

antibodies with V1V2 antibodies, but did show significant interactions of Env IgA with IgG Env avidity, ADCC, neutralizing antibodies and CD4+ T cells (q<0.2). Thus, in the presence of high Env IgA none of these four variables correlated with risk of infection, whereas with low Env IgA, all four variables had borderline significant inverse correlations with risk of infection (Table 10).

TABLE 10

Summary of logistic and Cox regression results of interaction analyses. For each two-way interaction between quantitative variables with Q-value <0.20, the odds ratio (hazard ratio) per standard deviation in one variable is reported as a function of the percentile of the other variable. Percentiles are calculated among vaccine recipients

| Variable | Interacting Assay Percentile | Univariate Logistic Regression Interaction | | | Univariate Cox Regression Interaction | | |
|---|---|---|---|---|---|---|---|
| | | OR[1] | 95% CI | P (Q) | HR[1] | 95% CI | P (Q) |
| IgA Binding | 20% IgG Avidity | 1.11 | (0.68, 1.81) | 0.68 | 1.09 | (0.66, 1.79) | 0.74 |
| | 50% IgG Avidity | 1.54 | (1.54, 1.04) | 0.03 | 1.58 | (1.05, 2.35) | 0.03 |
| | 80% IgG Avidity | 1.93 | (1.25, 2.98) | <0.01 | 2.04 | (1.30, 3.19) | <0.01 |
| | Interaction | — | — | 0.02 (0.10) | — | — | 0.01 (0.04) |
| IgG Avidity | 20% IgA Binding | 0.54 | (0.33, 0.88) | 0.01 | 0.57 | (0.35, 0.91) | 0.02 |
| | 50% IgA Binding | 0.74 | (0.49, 1.12) | 0.15 | 0.82 | (0.53, 1.28) | 0.38 |
| | 80% IgA Binding | 1.12 | (0.65, 1.94) | 0.69 | 1.06 | (0.63, 1.79) | 0.82 |
| | Interaction | — | — | 0.02 (0.10) | — | — | 0.01 (0.04) |
| IgA Binding | 20% ADCC | 1.11 | (0.71, 1.67) | 0.60 | 1.14 | (0.75, 1.73) | 0.54 |
| | 50% ADCC | 1.43 | (1.01, 2.02) | 0.05 | 1.49 | (1.04, 2.15) | 0.03 |
| | 80% ADCC | 1.96 | (1.22, 3.14) | 0.01 | 2.11 | (1.27, 3.51) | <0.01 |
| | Interaction | — | — | 0.03 (0.10) | — | — | 0.03 (0.07) |
| ADCC | 20% IgA Binding | 0.55 | (0.31, 1.00) | 0.05 | 0.58 | (0.34, 0.99) | 0.05 |
| | 50% IgA Binding | 0.74 | (0.49, 1.11) | 0.14 | 0.76 | (0.52, 1.13) | 0.17 |
| | 80% IgA Binding | 1.06 | (0.73, 1.55) | 0.75 | 1.08 | (0.73, 1.61) | 0.70 |
| | Interaction | — | — | 0.03 (0.10) | — | — | 0.03 (0.07) |
| IgA Binding | 20% NAb | 1.00 | (0.63, 1.59) | 0.99 | 0.96 | (0.57, 1.59) | 0.86 |
| | 50% NAb | 1.36 | (0.93, 1.99) | 0.12 | 1.35 | (0.90, 2.02) | 0.14 |
| | 80% NAb | 1.94 | (1.22, 3.09) | 0.01 | 2.01 | (1.24, 3.27) | <0.01 |
| | Interaction | — | — | 0.01 (0.10) | — | — | 0.01 (0.04) |
| NAb | 20% IgA Binding | 0.55 | (0.30, 0.99) | 0.05 | 0.58 | (0.33, 1.03) | 0.06 |
| | 50% IgA Binding | 0.75 | (0.49, 1.16) | 0.20 | 0.82 | (0.53, 1.27) | 0.37 |
| | 80% IgA Binding | 1.15 | (0.75, 1.75) | 0.52 | 1.22 | (0.76, 1.96) | 0.41 |
| | Interaction | — | — | 0.01 (0.10) | — | — | 0.01 (0.04) |
| IgA Binding | 20% CD4+ T Cells | 1.16 | (0.80, 1.69) | 0.43 | 1.16 | (0.80, 1.67) | 0.43 |
| | 50% CD4+ T Cells | 1.30 | (0.92, 1.84) | 0.14 | 1.34 | (0.94, 1.91) | 0.11 |
| | 80% CD4+ T Cells | 1.60 | (1.08, 2.39) | 0.02 | 1.74 | (1.17, 2.59) | 0.01 |
| | Interaction | — | — | 0.06 (0.14) | — | — | <0.01 (0.03) |
| CD4+ T Cells | 20% IgA Binding | 0.47 | (0.20, 1.13) | 0.09 | 0.47 | (0.22, 0.99) | 0.05 |
| | 50% IgA Binding | 0.62 | (0.33, 1.16) | 0.13 | 0.54 | (0.28, 1.04) | 0.07 |
| | 80% IgA Binding | 0.87 | (0.59, 1.30) | 0.51 | 0.70 | (0.42, 1.15) | 0.16 |
| | Interaction | — | — | 0.06 (0.14) | — | — | <0.01 (0.03) |

[1]OR/HR per 1-sd

Figure 21:
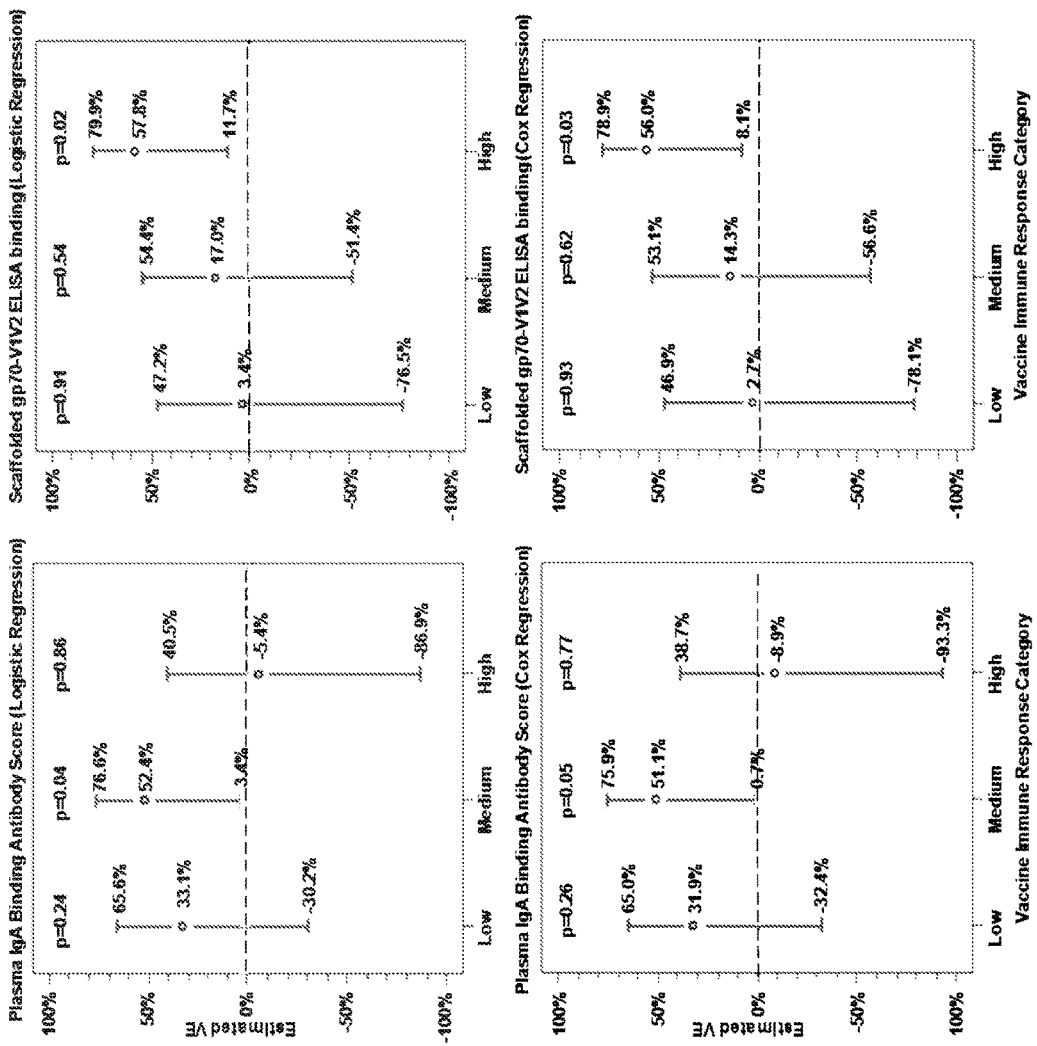
FIG. 21. Estimated vaccine efficacy (VE) for Low, Medium, and High responding vaccine subgroups versus the entire placebo group for the two primary immune response variables with evidence of association with HIV infection. For logistic (Cox) regression, VE is estimated as one minus the odds (hazard) of infection in vaccine recipients with Low/Medium/High response divided by the odds (hazard) of infection in the entire placebo group HIV-1 negative at week 24. Points show the estimated VE values and vertical lines delineate 95% confidence interval. Two-sided p-values are from Wald tests.

Env IgA responses were directly associated with infection risk in the vaccine group, raising the possibility that a vaccine-elicited plasma Env IgA response enhanced infection in the trial. In order to evaluate this possibility, vaccine efficacy (VE) was estimated using logistic and Cox regression as 1 minus the odds (hazard) of infection among vaccines with Low/Medium/High Env IgA responses relative to the entire placebo group that was HIV-1-negative at Week 24 (FIG. 21). It was found that neither low V1V2 nor high Env-specific plasma IgA levels in vaccines were associated with infection rates higher than placebo recipients (FIG. 21). These data suggest that vaccine-induced IgA levels did not confer added risk relative to placebo, and therefore were not enhancing antibodies.

Interaction analyses were performed with logistic and Cox regression models to test for interactions of IgA Env and V1V2 antibodies with the other 5 primary variables. The analysis demonstrated no interaction of Env IgA binding Secondary and Exploratory Analyses.

In the sensitivity analysis that toggled each of the eight secondary analysis variables into the primary variable slot, the significance levels tended to be similar or weaker, with exceptions that neutralization of TH023.6, neutralization of clade AE viruses in the A3R5 assay (NAb A3R5 Clade E), and cytokines magnitude measured in PBMCS (PBMC cytokines) had q-values<0.20 although with p values>0.05) (Tables 2 and 3).

Of the 152 exploratory variables analyzed, only two had q values<0.2. These two variables were IgA binding antibody responses to group A consensus envelope gp140 (OR=3.71 for positive versus negative responses, p=0.001, q=0.10), and IgA binding antibody to a gp120 envelope first constant (C1) region peptide (MQEDVISLWDQSLKP-CVKLTPLCV) (SEQ ID NO: (OR=3.15 for positive versus negative responses, p=0.003, q=0.13) (Table 1).

In summary, described above are the results of an immune correlates analysis of the RV144 HIVOP-1 vaccine efficacy trial. This correlates study was designed to be hypothesis-generating and sensitive for discovering strong correlates of infection risk (Rothman, Epidemiology 1:43-6 (1990)). Extensive pilot immunogenicity studies yielded informative immune assays that were prioritized into pre-specified primary and secondary/exploratory analyses in order to maximize statistical power in the primary analysis to detect correlates of infection risk. Of the six assay variables chosen for the primary analysis, two demonstrated significant correlations with infection among vaccine recipients: IgG antibody binding to scaffolded V1V2 Env correlated inversely with infection, and composite IgA binding antibodies correlated directly with infection. These two correlates of risk, taken together, were highly correlated with infection rate and may either be causally related to protection from infection or may represent surrogate markers for an as yet unmeasured factor mechanistically responsible for protection (Qin et al, J. Infect. Dis. 196:1304-12 (2007)). Nonetheless, these results generate important hypotheses about immune responses needed for protection from HIV-1 (Plotkin, Clin. Infec. Dis. 47:401-9 (2008), Plotkin, Clin. Vaccine Immunol. 17:1055-65 (2010), Qin et al, J. Infect. Dis. 196:1304-12 (2007)), which may improve the selection of primary endpoints in subsequent HIV-1 vaccine trials (Gilbert et al, International Journal of Biostatistics; Judea Pearl: in press).

Several lines of evidence suggest that vaccine-induced antibodies recognize conformational epitopes in the scaffolded V1V2 reagent, which has been shown to detect conformational V1V2 antibodies (Pinter et al, Vaccine 16:1803-11 (1998)). A dominant V1V2 antibody response in RV144 was to amino acids 165-178 encompassing the N terminal and crown of V2 (Zolla-Paznerd et al, AIDS Research and Human Retroviruses, Abstract No. 27:A21 (2011)), and analysis of breakthrough viruses from RV144 subjects was consistent with selective vaccine protection against HIV-1 genotypes with amino acid patterns in and flanking this region (Edlefsen et al, AIDS Vaccine 2011, Abstract No. S07.04:47 Bangkok, Thailand, Sep. 12-14 (2011)). The V1V2 region of HIV-1 Env serves several critical functions, including participation in CD4 and chemokine receptor binding, the binding through a tripeptide motif to α4β7 integrin (Newaz et al, PLoS Pathogens 7:e1001301 (2011)), and the binding site of broadly neutralizing antibodies recognizing conformational epitopes (Gormy et al, J. Virol. 79:5232-7 (2005), Walker et al, k Science 326:285-9 (2009), Changela et al, J. Virol. 85:2524-35 (2011), McLellan et al, Nature 2011, in press)). There also appear to be functional constraints on V1V2 length, particularly in transmitted-founder viruses (Zolla-Pazner and Cardozo, Nat. Rev. Immunol. 10:527-35 (2010), Chohan et al, J. Virol. 79:6528-31 (2005)).

No vaccine-enhancement of acquisition risk was seen in the RV144 trial, and, in comparative analyses of infection rates between vaccine recipient subgroups and the placebo group, no enhancement associated with high vaccine-induced Env plasma IgA antibody levels was seen (FIG. 21). However, a limitation of the analyses comparing infection risk between vaccine and placebo recipients is that the comparator groups could not be randomized, and there could be residual confounding because the analysis controlled for gender and baseline behavioral risk only.

The significant interactions of Env-specific IgA with other primary variables further support the importance of IgA binding antibodies in predicting infection (Table 10). For vaccines with low levels of Env IgA, IgG Env antibody avidity, ADCC, neutralizing antibodies, and Env-specific CD4+ T cell primary variables were inversely correlated with infection, whereas for vaccines with high levels of IgA, these responses did not correlate with infection (Table 10). These interactions generated the hypothesis that plasma IgA antibody levels interfered with protective IgG effector functions, a phenomenon that has been observed with other pathogens (Griffiss and Goroff, J. Immunol. 130:2882-5 (1983), Jarvis and Griffiss, J. Immunol. 147:1962-7 (1991)), in regulation of autoantibody function (Quan et al, Eur. J. Immunol. 28:4001-9 (1998)), and immune responses to malignancy (Mathew et al, Int. J. Cancer 27:175-80 (1981)). It was found that vaccines with IgA antibodies to the first conserved region (C1) of gp120 had an elevated infection risk compared to vaccines without these antibodies (OR=3.15, p=0.003, q=0.13). The gp120 C1 region contains an epitope that can be a target on the surface of virus-infected cells for antibodies mediating ADCC (Ferrari et al, J. Virol. 85:7029-36 (2011)). Another scenario may be that high Env IgA is a surrogate marker for HIV-1 exposure that was not fully accounted for by adjusting for baseline self-reported behavioral risk in the regression models. The primary Env IgA antibody variable was not significantly associated with baseline behavioral risk (p=0.28), nor did IgA to the individual Envs comprising the primary IgA variable correlate with baseline behavorial risk (Table 11). Of note, plasma IgA is primarily monomeric IgA, while mucosal fluid IgA is primarily dimeric (Mestecky et al, Elsevier Academic Press, Chapter 9 (2005)). Thus, any protective role of mucosal dimeric IgA in the setting of HIV-1 vaccination could not be evaluated in RV144 because mucosal samples were not collected.

TABLE 11

Vaccine recipient association of Week 26 IgA binding with HIV-1 infection rate and baseline behavioral risk by Envelope antigen*

| Envelope | Association of IgA Env binding with infection P value** | Association of IgA Env binding with baseline behavioral risk P value+ |
|---|---|---|
| 00MSA4076gp140 | 0.031 | 0.71 |
| 92TH023gp120gDneg293T | 0.30 | 0.034 |
| A1conenv03140CF | 0.002 | 0.46 |
| HV14000DRCBLgp140 | 0.071 | 0.61 |
| US1gp140 | 0.063 | 0.98 |

*Each row shows the results of a two-phase logistic regression model with outcome HIV infection after Week 26 and independent variables gender, baseline behavioral risk (Low/Medium/High), and quantitative Week 26 IgA binding to the specific Envelope (scaled to have standard deviation 1).
**P value from a Wald test of the null hypothesis that the IgA Env binding does not affect infection risk adjusting for gender and behavioral risk.
+P value from a Kruskal-Wallis test of the null hypothesis that the IgA Env binding and the baseline behavioral risk are independent.
The Wilcoxon test comparing the primary IgA variable among the low, medium and high baseline behavioral risk groups yielded a p = 0.28.

The relevance of these findings to different HIV-1 risk populations receiving ALVAC-HIV and AIDSVAX B/E or to other future HIV-1 vaccine regimens cannot be inferred and must be prospectively determined. Moreover, further studies are required to determine causality—whether V1V2 antibodies mediate vaccine induced protection from infection or IgA antibodies interfere with protection. Nonetheless, the identification of immune correlates of risk of HIV-1 infection in RV 144 lends credence to the original clinical observation of vaccine efficacy (Rerks-Ngarm et al, N. Engl. Med. 361:2209-20 (2009)) and may accelerate the clinical development of future similar vaccine candidates.

Example 2

In the study described below. V1V2 antibody specificities induced by the ALVAC-VAXGEN B/E gp120 vaccines were probed by studying human mAbs isolated from clonal memory B cell cultures (Seaman et al, J, Virol. 84:1439-1452 (2010)) of vaccine recipients.

Experimental Details

Monoclonal antibodies CH58 and CH59 were produced by culturing, screening and rescue of memory B cells in near-clonal cultures as described (Seaman et al, J. Virol. 84:1439-1452 (2010)). Crystallographic analysis of CH58 and V2 peptide were performed as previously reported (McLellan et al, Nature 480:336-343 (2011)). Anti-HIV functional studies of virion binding, neutralization and ADCC were as described (Bonsignori et al, J. Virol. 85:9998-10009 (2011), Ferrari et al, J. Virol. 85:7029-7036 (2011), Liao et al, J. Exp. Med. 208:237-2249 (2011)). Surface plasmon reasonance and ELBA were performed as described previously (Bonsignori et al, J. Virol. 85:9998-10009 (2011)). Unmutated ancestors of antibodies were inferred for RV144 V2, conformational V2 and V2V3 BnAbs using the methods described previously (Ma et al, PLoS Pathog, 7:e1002200 (2011), Alam et al, J. Virol. 85:11725-11731 (2011), Liao et al, J. Exp. Med. 208:237-2249 (2011)).

Production of Recombinant HIV-1 Proteins and Antibodies.

RV144 vaccine immunogen proteins E.A244 gp120 and MN gp120 were produced, purified and supplied by GSID (Global Solutions for Infectious Diseases, South San Francisco, Calif.). Recombinant HIV-1 gp120 proteins including E.A244 gD+Δ11, E.A244gDneg, E.A244 gDneg☐gp120Δ11, E.A244 gD p120N160K, B.MN gD+gp120 and B.MN gDneg p120, C.1086 gp120 were expressed in 293T cells by transfection and purified by using lectin-affinity columns (Liao et al, Virology 353:268-282 (2006)) followed by size exclusion chromatography on a Superdex 200 FPLC (GE Healthcare) to homogeneity for monomeric gp120. Recombinant Envs including 7 Consensus Envs-group M Con-S gp140CFI, Con6 gp120, A.con gp140CF, B.con gp140CF, C.con gp140CF, AE.con gp140CF, G.con gp140CF, 8 chronic Envs, A. 00MASA gp140, A.92RW020 gp140CFI, B.JRFL gp140CF, HXB/BAL gp140CFI, C.CAP206 gp140CF.12, C.DU123 gp140CF, C.97ZA012 gp140CFI, G.DCRB gp140CF, and SIV-Env US-1 SIVCPZ gp140CF were produced in 293T cells by recombinant vaccinia (Liao et al, Virology 353:268-282 (2006)). HIV-1 Envs, B.62357 gp140C, B.6240 gp140C, B.63521 gp140C, B.040 gp140C, B. 684-6 gp140C, B.681-7, C.1086, C.089 gp140C were produced in 293T cells by either transient or stable transfection. J08 A.92RW020 V1V2, J08 A.92RW020 V1V2 N156QN160Q, J08 B.HXB/BAL V1V2, J08 B.HXB/BAL V1V2 N156QN160Q and J08 C.97ZA012 V1V2 and J08 C.97ZA012 V1V2 N156QN160Q, J08 C.ZM109.V1V2, J08 C.ZM109 V1V2 N173D were scaffold on J08 protein (McLellan et al, Nature 480:336-343 (2011)), and gp70 A.92RW020V1V2, gp70 A.92RW020V1V2 N156QN160Q, gp70 B.HXB2/BALV1V2, gp70 B.HXB2/BALV1V2N156QN160Q, gp70 C.97ZA012V1V2, gp70 C.97ZA012V1V2 N156QN160Q were scaffold on MuLV gp70 were produced as described previously (Pinter et al, Vaccine 16:1803-1811 (2998)). MLV gp70 carrier protein without V1V2 sequence produced in 293F cells and purified by nickel columns was used as negative control for gp70 scaffold proteins. A.9004SS V1V2 Tags, A.Q23 V1V2 tags, E.A244 V1V2 Tags, B.63521_V1V2 Tags, B.Case A2 V1/V2 Tags, C.1086 V1V2 Tags and D.9009SA V1V2 Tags were designed with Ig leader (METDTLLLWVLLLWVPG-STGD) (SEQ ID NO: 9) serving as a mature protein cleavage and secretion signal at the N-terminus and Avi-tag followed by His6-tag (SEQ ID NO: 10) for purification and produced in 293F cells and purified by nickel columns. Natively deglycosylated B.JRFL gp140CF and C.CAP206 gp140CF proteins was prepared as described (Ma et al, PLoS Pathog. 7:e1002200 (2011)).

Production of Recombinant Antibodies.

CH58 and CH59 were identified by screening memory B cells near-clonal cultures as described (Seaman et al, J. Virol. 84:1439-1452 (2010)). VH and VL genes of 697D were obtained from Gorny, Miroslaw and Susan Zolla-Pazner. VH and VL genes of CH58 and CH59 were isolated by RT/PCR and used to generate full-length heavy and light Ig gene expression plasmids using the methods as described. The VH and VL sequences of CH58, CH59, 697D, PG9 and PG16 were analyzed using SoDA computational program (Volpe et al, Bioinformatics 22:438-444 (2006)) to infer reverted unmutated ancestor (RUA). Recombinant CH58, CH59, 697D, and their RUA antibodies were produced in 293T cells by transient transfection using the methods as described. CH01 mAb and its unmutated ancestor antibodies were derived from IgG+ memory B cells of a broad neutralizer subject as previously described (Bonsignori et al, J. Virol. 85:9998-10009 (2011)). V2 mAb 697D was provided by S. Zolla-Pazner (New York University, NY) and described previously (Gomy, Virology in press (2012)). V2V3 quaternary mAbs PG9 and PG16 were provided by D. Burton (IAVI, NY). mAb 7B2 were supplied by James Robinson (Tulane University, LA). Synagis, human anti-RSV mAb, mouse mAb P3X63 were used as a negative control.

HIV-1 Env V1V2 peptides. HIV-1 Env E.A244 gp120 V2 peptide A244 V2-171 (LRDKKQKVHALFYKLDIVPIED) (SEQ ID NO: 11) spanning from L165 to D186 and a panel of 22 Alanine-scanning mutant peptides (Table 12) were designed and produced (CPC Scientific Inc., San Jose, Calif.) for epitope mapping of CH58 and CH59.

TABLE 12

Comparison of binding kinetics of PG9 and CH58 to HIV-1 V1V2 proteins.

| HIV-1 Env V1V2 | mAb | Ka, M-1s-1 | Kd, s-1 | Kd, nM |
|---|---|---|---|---|
| E.A244 V1V2 Tags | PG9 | $6.0 \times 10^3$ | $5 \times 10^{-4}$ | 83.3 |
| E.A244 V1V2 Tags | CH58 | $270 \times 10^3$ | $9 \times 10^{-5}$ | 0.33 |
| J08 C.ZM109 | PG9 | $7.96 \times 10^3$ | $2.53 \times 10^{-3}$ | 318 |
| 1C.FD6-ZM109 | PG9 | $4.59 \times 10^3$ | $2.49 \times 10^{-2}$ | 4820 |
| J08 A.92RW020 V1V2 | CH58 | $460 \times 10^3$ | $5.5 \times 10^{-2}$ | 117 |
| gp70 C.97ZA012 V1V2 | CH58 | $83 \times 10^3$ | $2.5 \times 10^{-2}$ | 304 |
| J08 B.HXB2/BAL V1V2 | CH58 | $37.4 \times 10^3$ | $1.2 \times 10^{-2}$ | 323 |

Surface Plasmon Resonance (SPR) Kinetics Measurements.

Env gp120 binding Kd and rate constant measurements were carried out on BIAcore 3000 instruments as described earlier (Alam et al, J. Immunol. 178:4424-4435 (2007), Alam et al, J. Virol. 82:115-125 (2008), Alam et al, Proc. Natl. Acad. Sci. USA 106:20234-20239 (2009)). Anti-human IgG Fc antibody (Sigma Chemicals) was immobilized on a CM5 sensor chip to about 15000 Response Unit (RU) and each antibody was captured to about 50-100 RU on three individual flow cells for replicate analysis, in addition to one flow cell with the control Synagis mAb on the same sensor chip. Non-specific binding of Env gp120 to the control surface and/or blank buffer flow was subtracted for each mAb-gp120 binding interactions. Antibody capture level, which ranged from 50-100 RU, on the sensor surface was optimized for each mAb to minimize rebinding and any associated avidity effects. 697D Fab was directly coupled via amine coupling chemistry to the sensor surfaces and Env gp120 was flowed and data collected as above. All curve fitting analysis were performed using global fit of multiple titrations to the 1:1 Langmuir model. Mean and s.d. of rate constants and Kd were calculated from at least three measurements on individual sensor surfaces with equivalent amounts of captured antibody. All data analysis was performed using the BIAevaluation 4.1 analysis software (GE Healthcare).

Isolation and Purification of IgG from Plasma.

Total IgG was isolated from RV144 Vaccinee plasma using Protein G resin pre-packed into 96-well depletion plates (GE Healthcare). Plasma was diluted 2-fold with TBS, pH 7.5, and 200 µl of the diluted sample was added per well. The plates were incubated at room temperature, with shaking, for one hour. The unbound fractions were removed by centrifugation at 700×g for 3 minutes. Wells were then washed 3 times with 200 µl of TBS to remove loosely bound material. The IgG bound to the resin was eluted with 200 µl of 2.5% glacial acetic acid, pH 2.53, and immediately neutralized with 120 µl of 1M Tris-HCL pH 9.0. The eluted IgG fractions were concentrated using Amicon Ultra centrifugal filters (Millipore) with a 30K cut-off. The sample volume was reduced to 50 µl by centrifugation at 14,000×g in a microcentrifuge pre-cooled to 4° C. A buffer exchange was then performed using 2.5 volumes of PBS, pH 7.5. The concentrated IgG was diluted to the desired volume with PBS and assayed for protein concentration using a Nano-Drop 8000 Spectrophotometer (Thermo Fisher Scientific) using the IgG reference setting.

Surface Plasmon Resonance (SPR) measurements of Plasma IgG Avidity.

RV144 Vaccinee IgG avidity was measured on an upgraded BIAcore 4000 instrument (BIAcore/GE Healthcare) using the multiplex array format (1×16) in which each IgG samples were flowed over duplicate spots of 8 different Env gp120 antigen surfaces. Using a Series S CM5 chip (BIAcore/GE Healthcare) gp120 proteins were amine coupled in duplicate on 16 different spots on four flow channels of the chip. The negative control mAb Synagis was flowed over each surface and the signal was used to subtract out non-specific interactions with each individual spot. Each of the above listed gp120 Env proteins, including the vaccine immunogen E.A244gp120 and B.MN g120, were immobilized to about 6000-8000 RU using amine coupling chemistry as described earlier (Alam et al, J. Immunol. 178:4424-4435 (2007), Alam et al, J. Virol. 82:115-125 (2008), Alam et al, Proc. Natl. Acad. Sci. USA 106:20234-20239 (2009)). Antigen surface activity was monitored using the C1 mAb A32 as positive control and an irrelevant anti-RSV (Synagis) mAb as negative control. V1 V2 mAb CH01, which is sensitive to N160K substitution, was used as a negative control for antigen spots with E.A244gD/N160K gp120. An anti-gD Fab was used to monitor binding to the gD peptide tag in Env gp120 with gD and to select IgG samples with low gD reactivity for mAb blocking studies. The IgG samples from placebo (n=40), infected (n=41) and protected (n=205) groups were diluted in PBS to 200 µg/mL and injected over each of the flow cells with replicate spots (2×) at 10:L/min for an association time of 120 s and a dissociation time of 600s. A random selection of IgG samples collected at visit 0 from 20 vaccines was also included. Following each binding cycle, surfaces were regenerated with a short injection (20s) of Glycine, pH2.5. Each surface activity was monitored by including A32 mAb (20:g/mL) injection at regular interval of every 20 cycles of samples and surface decay of A32 binding over the entire experimental run was used to normalize binding signal of plasma IgG samples. Non-specific binding of the negative control mAb was subtracted from each IgG sample binding data. Data analyses were performed with BIAevaluation 4000 and BIAevaluation 4.1 software (BIAcore/GE Healthcare) as described earlier for Biacore 3000 (Alam et al, Proc. Natl. Acad. Sci. USA 106:20234-20239 (2009)) and Biacore A100 (Safsten et al, Anal. Biochem. 353:181-190 (2006)) data analysis, respectively. Kinetic binding responses were measured by averaging post-injection response unit (RU) over a 20s window and dissociation rate constant, kd (s−1) was measured during the post-injection/buffer wash phase (after the first 20s to allow stabilization of signal) following curve fitting to a Langmuir dissociation equation. The majority of IgG bound with a relatively slow dissociation rate ($<10^{-3}$ $s^{-1}$), and the previously described method for BIAcore A100 ranking of dissociation rates in complex or polyclonal samples as a ratio of response units measured as binding late and stability late (Safsten et al, Anal. Biochem. 353:181-190 (2006), Kasturi et al, Nature 470:543-547 (2011) was modified to include binding response and dissociation rate constant measurements and as described earlier (Flynn et al, Proc. Natl. Acad. Sci. USA 108:7131-7136 (2011)). A relative avidity binding score was calculated for each IgG sample as follows, Avidity score (RU.s)=Binding Response (RU)/kd, s−1, with higher binding responses and slower kd as an indicator of higher affinity interaction (Flynn et al, Proc. Natl. Acad. Sci. USA 108:7131-7136 (2011)).

Infectious Molecular Clones (IMC).

HIV-1 reporter virus used were replication-competent infectious molecular clones (IMC) designed to encode the CM235 (subtype A/E) env genes in cis within an isogenic backbone that also expresses the Renilla luciferase reporter gene and preserves all viral open reading frames (Edmonds et al, Virology 408:1-13 (2010)). The Env-IMC-LucR viruses used was the NL-LucR.T2A-AE.CM235-ecto (IM-$C_{CM235}$) (GenBank No. AF259954.1; plasmid provided by Dr. Jerome Kim, US Military HIV Research Program). Reporter virus stocks were generated by transfection of 293T cells with proviral IMC plasmid DNA and tittered on TZM-bl cells for quality contro (Adachi et al, J. Virol. 59:284-291 (1986)).

Infection of CEM.NKR$_{CCR5}$ Cell Line and Primary CD4$^+$ T Cells with HIV-1 IMC.

The staining of infected CD4$^+$ T cells was performed as modification of the previously published procedure (Ferrari et al, J. Virol. 85:7029-7036 (2011)) that allows incubation of the primary mAb with the infected cells for 2 hours instead of 1 hour. For ADCC assay, IMC$_{CM235}$ was titrated in order to achieve maximum expression within 36 hours post-infection by detection of Luciferase activity and intracellular p24 expression. 2×10$^6$ cells were infected with IMC$_{CM235}$ by incubation with 1 TCID50/cell dose of IMC for 0.5 hour at 37° C. and 5% CO$_2$ in presence of DEAE-Dextran (7.5 µg/ml). The cells were subsequently resuspended at 0.5×10$^6$/ml and cultured for 36 hours in complete medium containing 7.5 µg/ml DEAE-Dextran. On ADCC assay day, the infection of target cells was monitored by measuring the frequency of cells expressing intracellular p24. The assays performed using the IMC-infected target cells were considered reliable if the percentage of viable p24$^+$ target cells on assay day was ≥20%.

Luciferase ADCC Assay.

The HIV-1 IMC$_{CM235}$ infected CEM.NKR$_{CCR5}$ cell line (NIH AIDS Research and Reference Reagent Repository)

were used as target cells. The cells were incubated in the presence of 4-fold serial concentrations of mAbs starting at 40 µg/ml. Purified CD3-CD16+ NK cells obtained from a HIV seronegative donor with the F/F Fc-gamma Receptor (FcRγ) IIIa phenotype. The cells were isolated from the cryopreserved PBMCs by negative selection with magnetic beads (Miltenyi Biotec GmbH, Germany). After overnight resting, the NK cells were used as effector cells at an effector to target ratio of 5:1. The cells were incubated for 6 hours at 37° C. in 5% $CO_2$. The final read-out was the luminescence intensity generated by the presence of residual intact target cells that have not been lysed by the effector population in presence of ADCC-mediating mAb. The % of killing was calculated using the formula:

$$\% \text{ killing} = \frac{(RLU \text{ of Target} + \text{Effector well}) + (RLU \text{ of test well})}{RLU \text{ of Target} + \text{Effector well}} ! \, 100$$

In this analysis, the RLU of the target plus effector wells represents spontaneous lysis in absence of any source of Ab. The humanized monoclonal antibody (IgG1$_k$) directed to an epitope in the A antigenic site of the F protein of respiratory syncytial virus, Synagis® (palivizumab; MedImmune, LLC; Gaithersburg, Md.) was purchased from the manufacturer and used as a control.

Immunization of Rhesus Macaques.

This study involved in the use of rhesus macaques was carried out in strict accordance with the recommendations in the Guide for the Care and Use of Laboratory Animals of the National Institutes of Health in BIOQUAL (Rockville, Md.) BIOQUAL is fully accredited by AAALAC and through OLAW, assurance number A-3086. The protocol was approved by the BIOQUAL IACUC. All physical procedures associated with this work were done under anesthesia to minimize pain and distress. Four rhesus macaques per group were immunized intramuscularly 4 times with 100 ug/dose of variants of recombinant E.A244 gp120 Env proteins including E.A244 1 gp120 gD+)11 (3 macaques), E.A244 gp120 gDneg (3 macaques) and E.A244gp120 gDneg)11 (4 macaques). Env proteins were adjuvanted with a squalene-based adjuvant supplemented with Lipid A, R848 and oCpGs. Blood samples were collected at day 0 and week 2 weeks post-4$^{th}$ immunization for isolation of plasma.

CH58 Fab Fragment Preparation.

Purified CH58 IgG was Digested with Lys-C (1:2000 w/w) for 2 hours at 37° C. The reaction was quenched by the addition of Complete protease inhibitors. To remove the Fe fragment, the digested proteins were passed over Protein A agarose. The Fab was further purified over a Superdex 200 gel filtration column and concentrated aliquots were stored frozen at −80° C.

Protein Crystallization and Data Collection.

The CH58 Fab at a concentration of 12.4 mg/ml was screened against 576 crystallization conditions using a Cartesian Honeybee crystallization robot. Initial crystals were grown by the vapor diffusion method in sitting drops at 20° C. by mixing 0.2 µl of protein complex with 0.2 µl of reservoir solution (38% (w/v) PEG 8000, 0.2 M NaCl, 0.1 M sodium phosphate-citrate pH 4.2). These crystals were manually reproduced in hanging drops by mixing 1.0 µl protein complex with 1.0 µl of the initial reservoir solution containing a range of PEG 8000 concentrations. Crystals were flash frozen in liquid nitrogen in a cryoprotectant containing 15% (v/v) 2R,3R-butanediol. Data to 2.4 Å were collected at a wavelength of 1.00 Å at the SER-CAT beamline BM-22 (Advanced Photon Source, Argonne National Laboratory).

To obtain crystals of CH58 Fab in complex with peptide, American Peptide Company synthesized a peptide with an acetylated N-terminus and an amidated C-terminus containing the amino acid sequence ELRDKKQKVHALFYKLDIV (SEQ ID NO: 12), corresponding to HIV-1 gp120 residues 164-182. A 2-fold molar excess of peptide was mixed with CH58 Fab and the mixture was concentrated to an A280=26.0 and then screened against 576 crystallization conditions using a Cartesian Honeybee crystallization robot. A crystal was grown by the vapor diffusion method in a sitting drop at 20° C. by mixing 0.2 µl of protein complex with 0.2 µl of reservoir solution (14% (w/v) PEG 8000, 2% (v/v) MPD, 0.1 M imidazole pH 6.5). This crystal was taken from the 192-well plate and flash frozen in liquid nitrogen in a cryoprotectant containing 15% (v/v) 2R,3R-butanediol. Data to 1.7 Å were collected remotely at a wavelength of 1.00 Å at the SER-CAT beamline BM-22 (Advanced Photon Source, Argonne National Laboratory).

Structure Determination, Model Building and Refinement.

Diffraction data for the unbound CH58 Fab were processed with the HKL2000 suite and a molecular replacement solution consisting of one Fab molecule per asymmetric unit was obtained using PHASER. The search model consisted of the constant domains and light chain variable domain from PDB ID 3H0T and the heavy chain variable domain from PDB ID 3UJJ. Model building was carried out using COOT, and refinement was performed with PHENIX.

The diffraction data for CH58 Fab bound to peptide were processed with the HKL2000 suite and a molecular replacement solution consisting of one complex per asymmetric unit was obtained using PHASER with the CH58 Fab as a search model. Model building was done in COOT, and the structure was refined with PHENIX.

Results

Vaccine-Induced Antibodies and Structure

Figure 32:
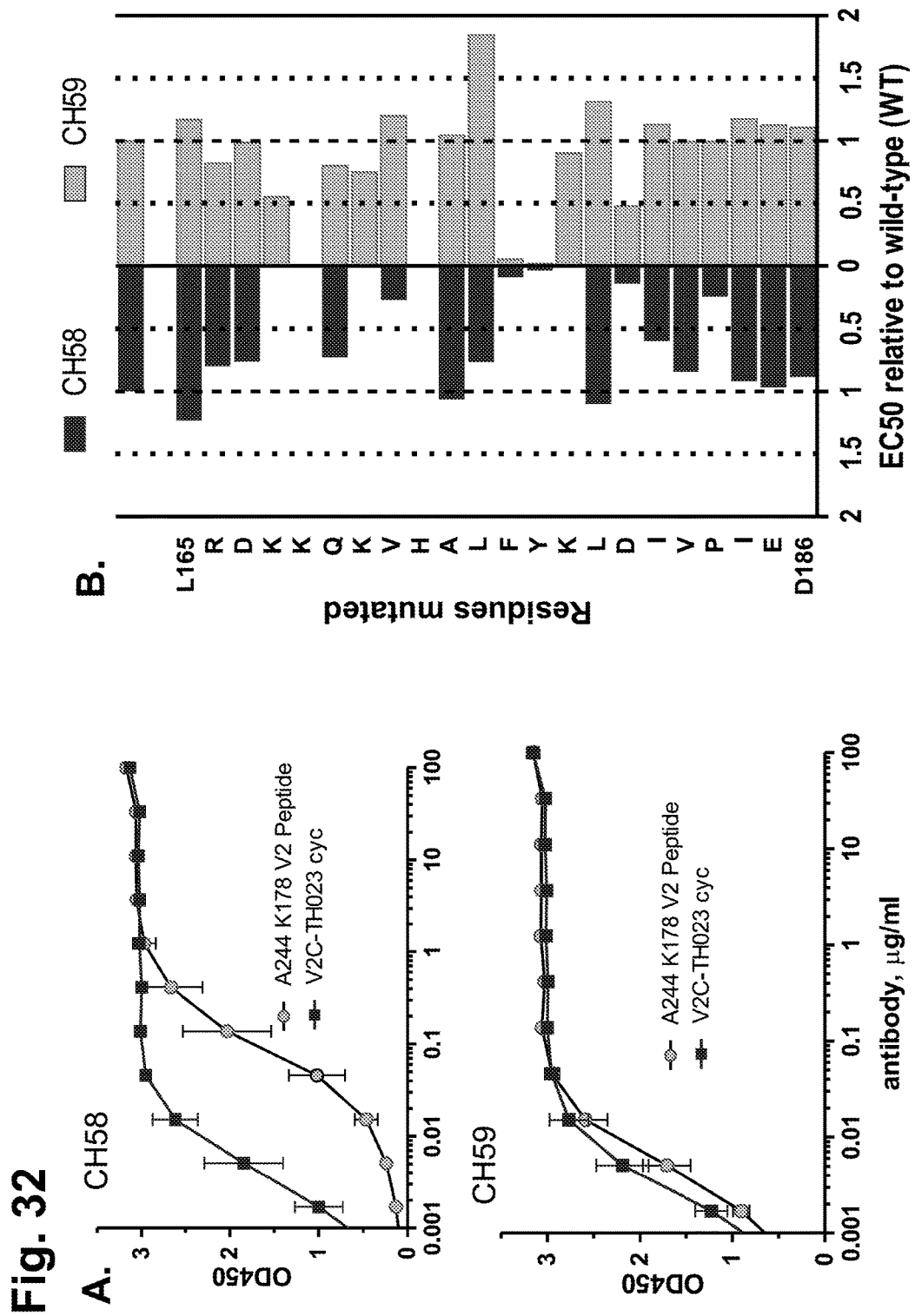
FIGS. 32A and 32B. Binding of RV44 mAbs CH58 and CH59 to HIV-1 V2 peptides.

Two V2 monoclonal antibodies (mAbs) (CH58, CH59) were isolated that bound to E.A244 gp120 Env and to a V2 aa 168-182 peptide (KKKVHALFYKLDIV) (SEQ ID NO: 13) (Table 13, FIG. 32A). Tier 1 HIV-1 strains are relatively neutralization sensitive whereas Tier 2 HIV-1 strains are more neutralization resistant (Seaman et al, J. Virol 84:1439-1452 (2010)). Both mAbs neutralized the Tier 1 RV144 ALVAC vaccine strain AE.92TH023 Env pseudovirus and a Tier 1 clade C simian human immunodeficiency virus (SHIV), but not the Tier 2 AE.CM244 RV144 vaccine AE gp120 protein strain with the same V1V2 sequences as Tier 1 isolate HIV-1 AE.92TH023 (Table 14). Both antibodies bound to Tier 2 AE.CM235 infectious molecular clone-infected CD4 T cells and mediated antibody dependent cellular cytotoxicity (ADCC) with these cells as targets (FIG. 35). HIV-1 gp120 has been demonstrated to interact with the α4β7 molecule on CD4+ T cells using a tripeptide motif in V2 (Arthos et al, Nat. Immunol. 9:301-309 (2008), Nawaz et al, PLoS Pathog. 7:31001301 (2011)). Both CH58 and CH59 mAbs inhibited V2 peptide interactions with α4β7 (Table 15). Both CH58 and CH59 mAbs captured Tier 1 and Tier 2 HIV-1 CRF01_AE virions (Table 16).

TABLE 13

Characteristics of the V(D)J rearrangements of RV144 mAbs CH58 and CH59 that bind to the V2 region of the HIV-1 gp120 envelope glycoprotein compared with V2V3 conformational bnAbs (PG9, PG16, CH01 and the V2 conformational antibody 697D.

| | V-Heavy Chain | | | | | | V-Light Chain | | | | Binding to gp120 Env glycoproteins[c] | | |
|---|---|---|---|---|---|---|---|---|---|---|---|---|---|
| mAb ID | V | D | J | Mutation frequency | HCDR3 length[a] | Isotype | V | J | Mutation frequency | LCDR3 length[b] | A244 gp120 | 92TH023 gp120 | MN gp120 |
| CH58 | 5-51 | 3-22 | 4 | 1.8% | 19 | IgG1 | 6-57 | 3 | 1.8% | 9 | +++ | +++ | − |
| CH59 | 3-9 | 1-26 | 4 | 2.8% | 13 | IgG1 | 3-10 | 3 | 0.9% | 11 | +++ | +++ | ++ |
| PG9 | 3-33 | 1-1 | 6 | 14.9% | 28 | IgG1 | 2-14 | 3 | 10.1% | 8 | ++ | + | ++ |
| PG16 | 3-33 | 1-1 | 6 | 14.5% | 28 | IgG1 | 2-14 | 3 | 12.5% | 8 | ++ | ++ | − |
| CH01 | 3-20 | 3-10 | 2 | 13.3% | 24 | IgG1 | 3-20 | 1 | 10.0% | 9 | ++ | − | − |
| 697D | 1-69 | 4-11 | 4 | 5.5% | 14 | IgG1 | 1-40 | 1 | 1.0% | 11 | +++ | +++ | +++ |

[a]HCDR3 = Heavy chain Complementarity Region 3. Length is expressed in amino acids according to the Kabat numbering system (Kabat E.A. et al., 1991).
[b]LCDR3 = Light chain Complementarity Region 3. Length is expressed in amino acids according to the Kabat numbering system (Kabat E.A. et al., 1991).
[c]+++ = IC50 <10 nM; ++ = IC50 between 10 and 100 nM; + = IC50 between 0.1 and 1 µM; − = negative >CH58VH
GAGGTGCAGCTGGTGCAGTCTGGAGCAGAGGTGAAAAAGCCCGGGGAGTCTCTGAAGATCTCCTGTAAGGGTTCTGGATACAGGTTTACCAGTTACTGGATCGTCTGGGTGCGCCAGAT
GCCCGGGAAAGGCCTGGAGTGGATGGGGATCATCTATCCTGGTGACTTTGATACCAAATACAGCCCGTCCTTCCAAGGCCAGGTCACCATCTCAGCCGACAAGTCCATCAGCACCGCCT
ACCTACAGTGGAGCAGCCTGAAGGCCTCGGACACCGCCATGTATTACTGTGCGAGACTTGGCGGCAGATATTACCATGATAGTAGTGGTTATTACTACCTTGACTACTGGGGCCAGGGA
ACCCTGGTCACCGTCTCCTCA
(SEQ ID NO: 17)
>CH58VL
AATTTTATGCTGACTCAGCCCCACTCTGTGTCGGAGTCTCCGGGGAAGACGGTAACCATCTCCTGCACCCGCAGCAGTGGCAGCGTTGCCAGCGACTATGTGCAGTGGTACCAGCAGCG
CCCGGGCAGTGCCCCCACCACTGTGGTCTATGAGGATAACAAAGACCCTCTGGGGTCCCTGATCGATTCTCTGGCTCCATCGACAGCTCCTCCAACTCTGCCTCCCTCACCATCTCTG
GACTCAAGACTGAGGACGAGGCTGACTACTACTGTCAGTCTTATGATAACAGCTCTTGGGTGTTCGGCGGAGGGACCAAGCTGACCGTCCTA
(SEQ ID NO: 15)
>CH59VH
GAAGTGCAGCTGGTGGAGTCTGGGGGAGGCTTGGTACAGCCTGGCAGGTCCCTGAGACTCTCCTGTGCAGCCTCTGGATTCACCTTTGATGATGGTGCCATGCACTGGGTCCGGCAAGC
TCCAGGGAAGGGCCTGGAGTGGGTCTCAGGTATTAGTTGGAATAGTAATATCATAGCCTATGCGGACTCTGTGAAGGGCCGATTCACCATCTCCAGAGACAACGCCAAGAACTCCCTGT
ATTTAGAAATGAACAGTCTGAGAGTTGAGGACACGGCCTTGTATTACTGTGCAAAAGATTCTCCGCGGGGGGAGCTACCCTTGAACTACTGGGGCCAGGGAACCCTGGTCACCGTCTCC
TCA
(SEQ ID NO: 16)
>CH59VL
TCCTATGAGCTGACACAGCCACCCTCGGTGTCAGTGTCCCCAGGACAAACGGCCAGGATCACCTGCTCTGGAGATGCATTGCCAAAAAACTATGCTTATTGGTACCAGCAGAAGTCAGG
CCAGGCCCCTGTGTTGGTCATCTATGAGGACAGCAAACGACCCTCCGGGATCCCTGAGAGATTCTCTGGCTCCAGCTCAGGGACAATGGCCACCTTGACTATCAGTGGGGCCCAGGTTG
AGGATGAAGCTGACTACTACTGTTACTCAACAGACAGCAGTGGTAATCATAGGGTGTTCGGCGGAGGGACCAAGCTGACCGTCCTA
(SEQ ID NO: 17)

TABLE 14

Neutralization of tier 1 and tier 2 HIV-1 strains by CH58, CH59, CH01, PG9, PG16 and 697D mAbs

A.

| | EC50, ug/ml | | | |
|---|---|---|---|---|
| mAb | B.MN | AE.CM244 | AE.TH023 | SVA |
| CH58 | >50 | >50 | 18.78 | >50 |
| CH59 | >50 | >50 | 12.07 | >50 |

B.

| | EC50, ug/ml | | | | |
|---|---|---|---|---|---|
| mAb | SHIV SF162P3 | SHIV-SF162P4 | SHIV-BaL | SHIV-1157ipEL-p | SHIV-1157ipd3N4 |
| CH58 | >50 | >50 | >50 | 37.6 | >50 |
| CH59 | >50 | >50 | >50 | 24.6 | >50 |

TABLE 15

Inhibition of RPMI 8866 cell binding to cyclic V2 92TH023 peptide#

| Antibody | Concentration (µg/ml) | % inhibition (mean ± SD)* |
|---|---|---|
| CH58 | 5 | 2.9 ± 4.1 |
| | 10 | 8.3 ± 7.3 |
| | 20 | 37.1 ± 11.3 |
| CH59 | 5 | 19.4 ± 7.8 |
| | 10 | 36.7 ± 8.6 |
| | 20 | 44.8 ± 5.2 |
| CH01 | 10 | −11.2 ± 11.8 |
| 697D | 10 | −13.1 ± 9.5 |
| Controls: | | |
| MADCAM-ACT-1 | 2 | 71.3 ± 17.8 |
| TH023-ACT-1 | 5 | 53.3 ± 10.1 |

Triplicate wells were performed in each experiment and each experiment was repeated 2 to 4 times.
CSFNMTTELRDKKQKVHALFYKLDIVPIEDNTSSSEYRLINC (SEQ ID NO: 2)

TABLE 16

Ability to capture HIV-1 viruses by Anti-HIV-1 Env antibodies.

|  | C.CAP45 (p24 ng/ml) | | AE.92TH023 (p24 ng/ml) | | AE.CM244 (p24 ng/ml) | |
|---|---|---|---|---|---|---|
|  | sCD4− | sCD4+ | sCD4− | sCD4+ | sCD4− | sCD4+ |
| 697D | 6.88 | 6.05 | 1.05 | 1.20 | 0.98 | 0.63 |
| CH58 | 3.18 | 3.70 | 6.15 | 8.77 | 6.88 | 7.66 |
| CH59 | 2.29 | 2.90 | 5.51 | 12.12 | 7.00 | 9.41 |
| CH01 | 14.42 | 9.89 | 1.14 | 1.05 | 1.72 | 1.80 |
| PG16 | 210.5 | 158.23 | 7.66 | 2.57 | 9.06 | 8.61 |
| PG9 | 159.8 | 119.72 | 7.94 | 4.48 | 7.78 | 6.17 |
| P3X63 (neg control) | 2.48 | 2.0 | 0.90 | 0.68 | 0.43 | 0.59 |
| 7B2 (pos control) | 63.49 | 94.0 | 16.18 | 22.47 | 12.24 | 12.69 |

Data shown are representative of 3 experiments performed.
Numbers in bold face are positive values over background and controls.

CH58 mAb bound to two and CH59 bound to all three Envs in the ALVAC vCP1521 and AIDSVAX B/E prime-boost vaccine expressed as recombinant proteins (Table 13), as well as bound to V2 linear and cyclic peptides (FIG. 32A). Alanine-substituted V2 peptide analysis across the A244 V2 peptide sequence aa 165-186 LRDKKQKVHALFYKL-DIVPIED (SEQ ID NO: 11) (Table 17, FIG. 32B) showed that the footprint for mAb CH58 involved 10 aa (K168, K169, K171, V172, H173, F176, Y177, K178, D180, F183) and for mab CH59 involved only 4 aa that overlapped CH58 (K169, H173, F176, Y177).

TABLE 17

Amino acid sequences of A244V2 peptide and A244V2 mutant peptides.

| Peptide ID | a.a sequence | SEQ ID NO: |
|---|---|---|
| A244V2-171 | LRDKKQKVHALFYKLDIVPIED | 11 |
| A244V2-171_mut1 | ARDKKQKVHALFYKLDIVPIED | 18 |
| A244V2-171_mut2 | LADKKQKVHALFYKLDIVPIED | 19 |
| A244V2-171_mut3 | LRAKKQKVHALFYKLDIVPIED | 20 |
| A244V2-171_mut4 | LRDAKQKVHALFYKLDIVPIED | 21 |
| A244V2-171_mut5 | LRDKAQKVHALFYKLDIVPIED | 22 |
| A244V2-171_mut6 | LRDKKAKVHALFYKLDIVPIED | 23 |
| A244V2-171_mut7 | LRDKKQAVHALFYKLDIVPIED | 24 |
| A244V2-171_mut8 | LRDKKQKAHALFYKLDIVPIED | 25 |
| A244V2-171_mut9 | LRDKKQKVAALFYKLDIVPIED | 26 |
| A244V2-171_mut10 | LRDKKQKVHELFYKLDIVPIED | 27 |
| A244V2-171_mut11 | LRDKKQKVHAAFYKLDIVPIED | 28 |
| A244V2-171_mut12 | LRDKKQKVHALAYKLDIVPIED | 29 |
| A244V2-171_mut13 | LRDKKQKVHALFAKLDIVPIED | 30 |
| A244V2-171_mut14 | LRDKKQKVHALFYALDIVPIED | 31 |
| A244V2-171_mut15 | LRDKKQKVHALFYKADIVPIED | 32 |
| A244V2-171_mut16 | LRDKKQKVHALFYKLAIVPIED | 33 |
| A244V2-171_mut17 | LRDKKQKVHALFYKLDAVPIED | 34 |
| A244V2-171_mut18 | LRDKKQKVHALFYKLDIAPIED | 35 |
| A244V2-171_mut19 | LRDKKQKVHALFYKLDIVAIED | 36 |
| A244V2-171_mut20 | LRDKKQKVHALFYKLDIVPAED | 37 |
| A244V2-171_mut21 | LRDKKQKVHALFYKLDIVPIAD | 38 |
| A244V2-171_mut22 | LRDKKQKVHALFYKLDIVPIEA | 39 |

The mapping data of CH58 and CH59 suggested these antibodies may bind at or near the PG9 (McLellan et al, Nature 480:336-343 (2011)) binding site. An evaluation was made of their ability to block these and V2 conformational mAb 697D binding to recombinant Envs. It was found that found CH58 and CH59 blocked the binding of V2V3 conformational BnAbs CH01, PG9, PG16, as well as the weak neutralizing 697D (Gorny, Virology in press (2012)) to monomeric Env)244 gp120 (FIGS. 36A-36C) that provides additional evidence for the co-localization of RV144 V2 abs with conformational V2 mAb binding epitopes.

Figure 33:
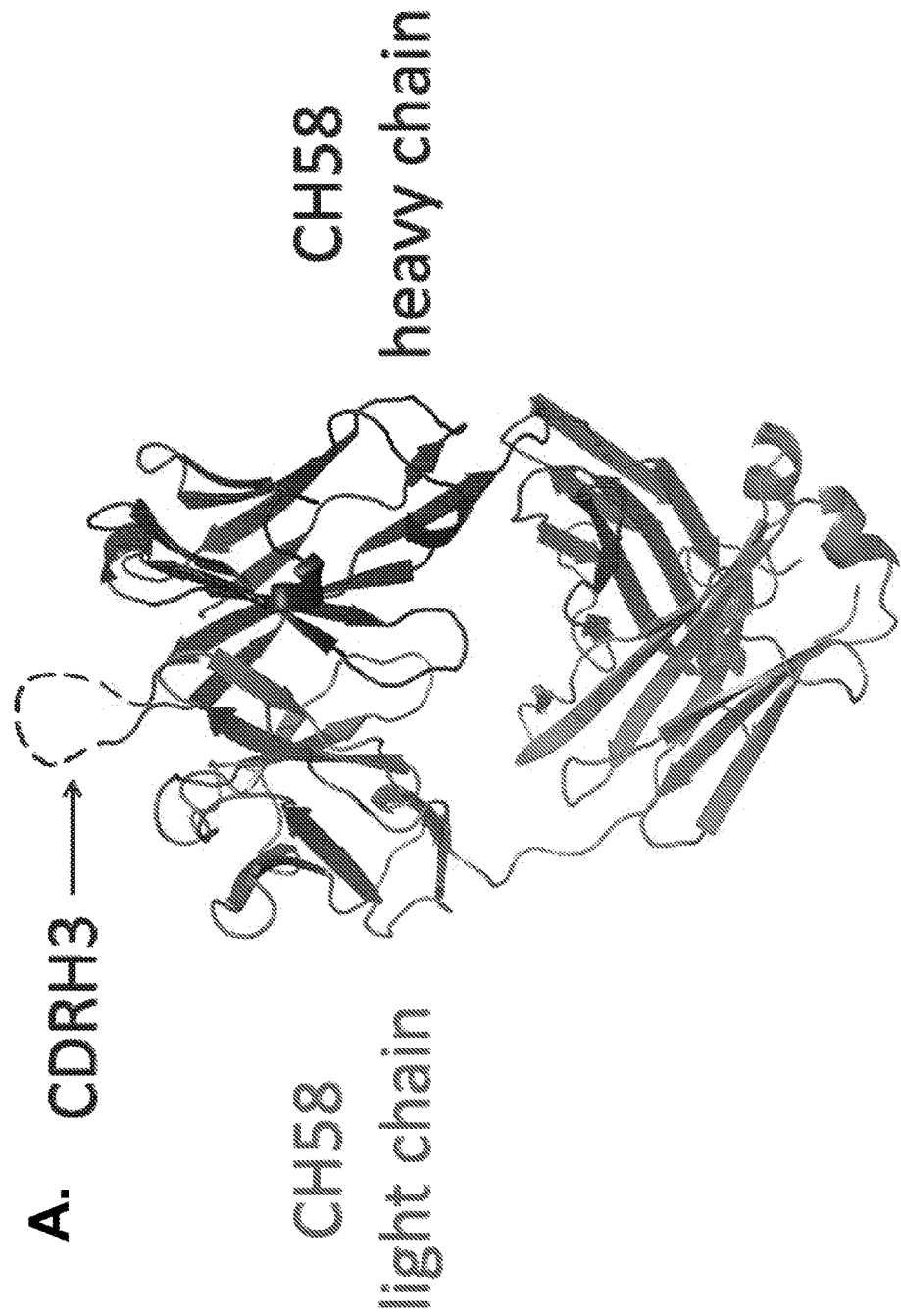
FIGS. 33A-33D.
Figure 33:
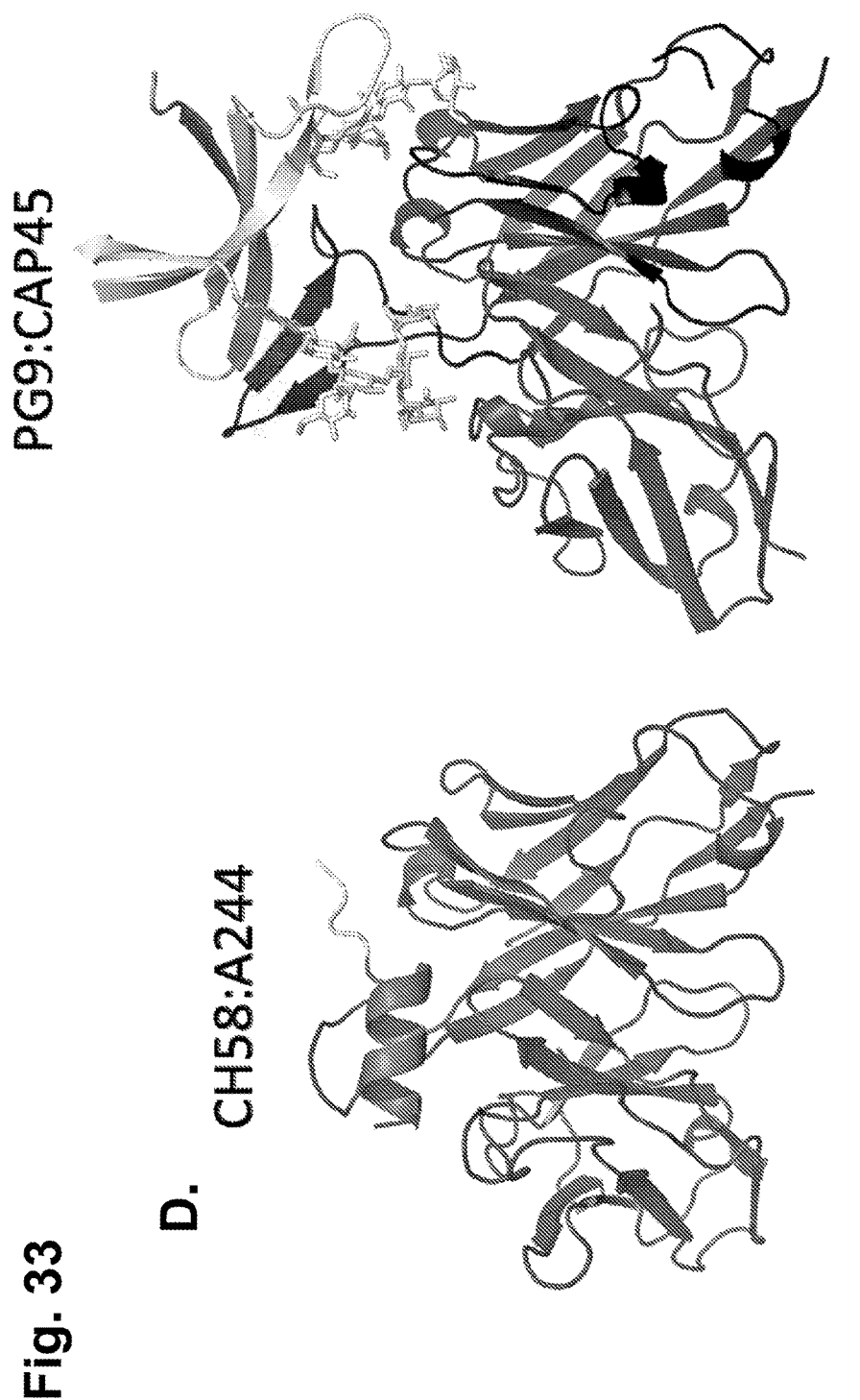
Figure 46:
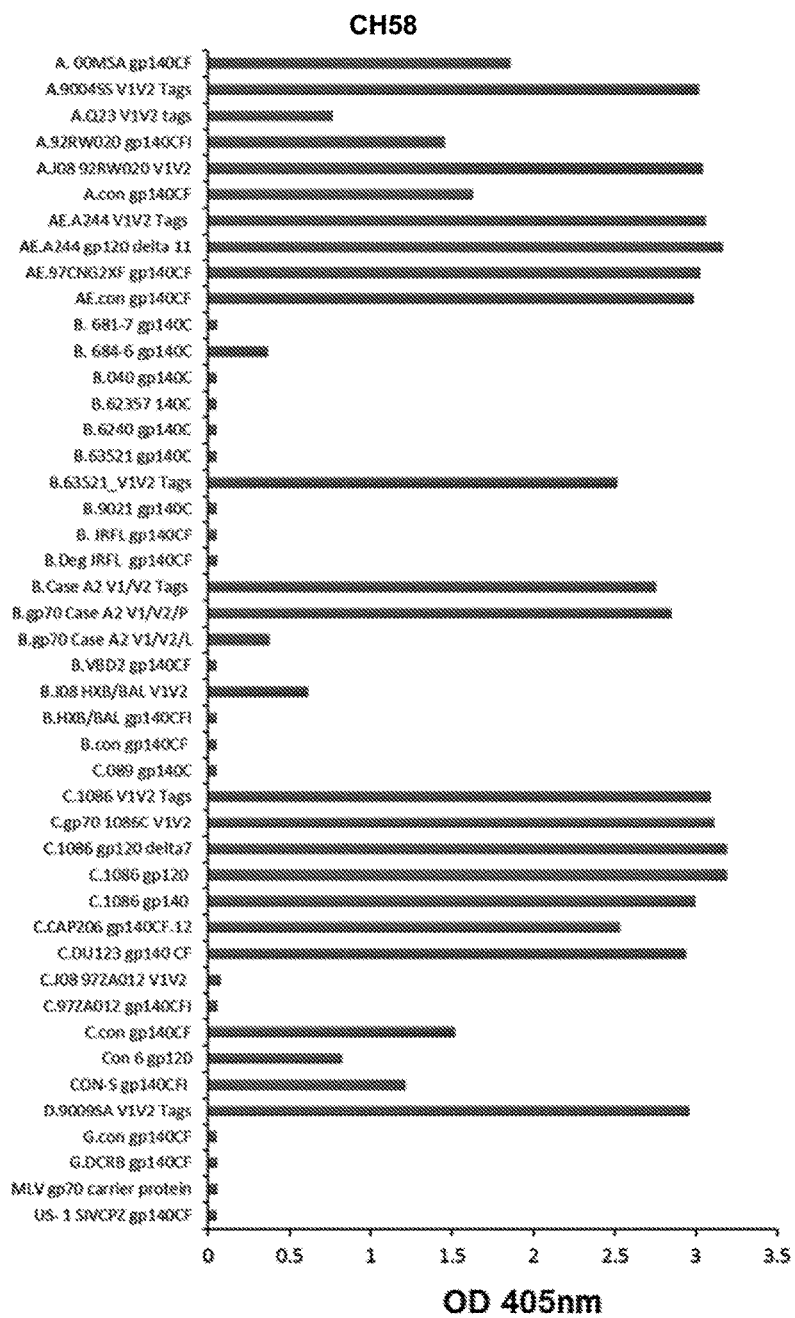
FIGS. 46A-46M.
Figure 46:
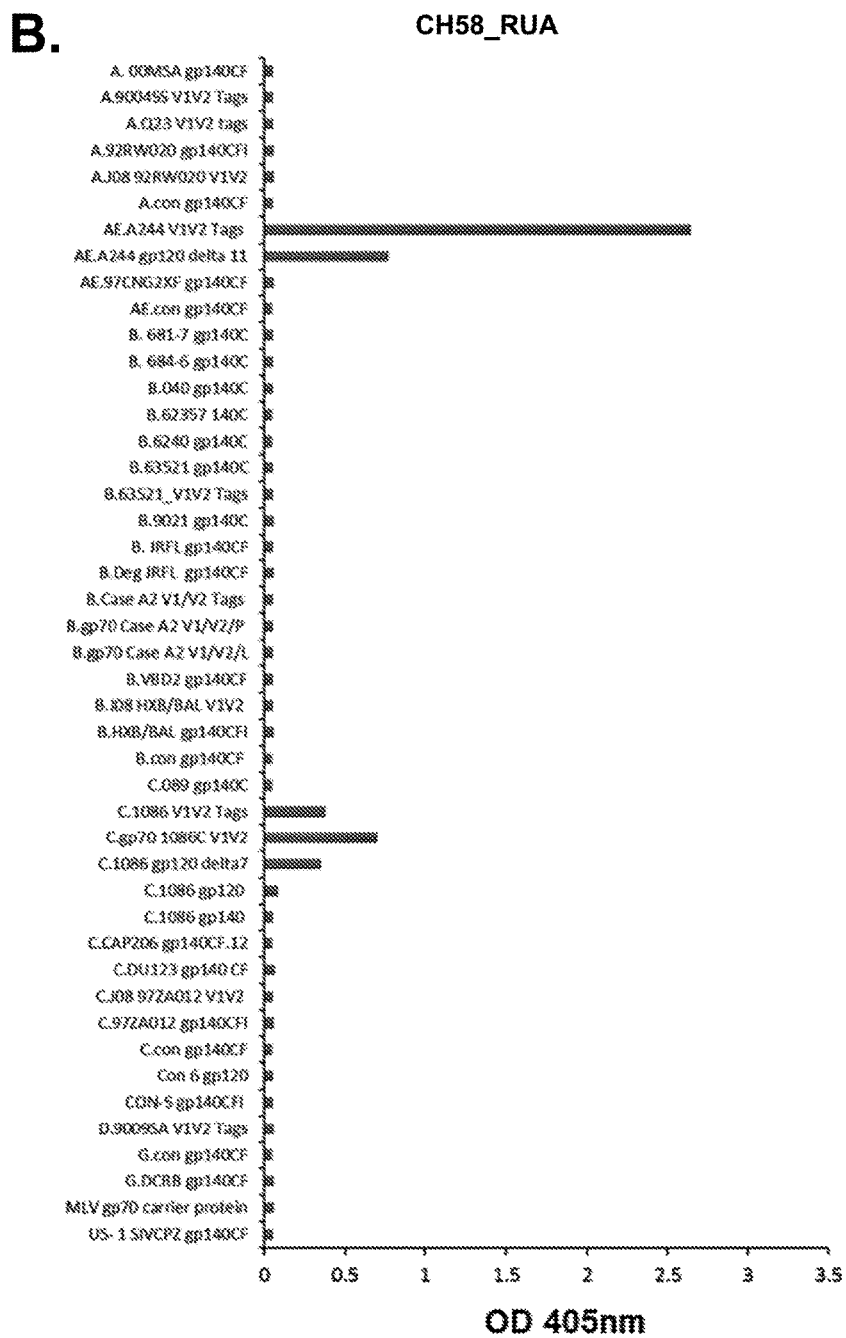
Figure 46:
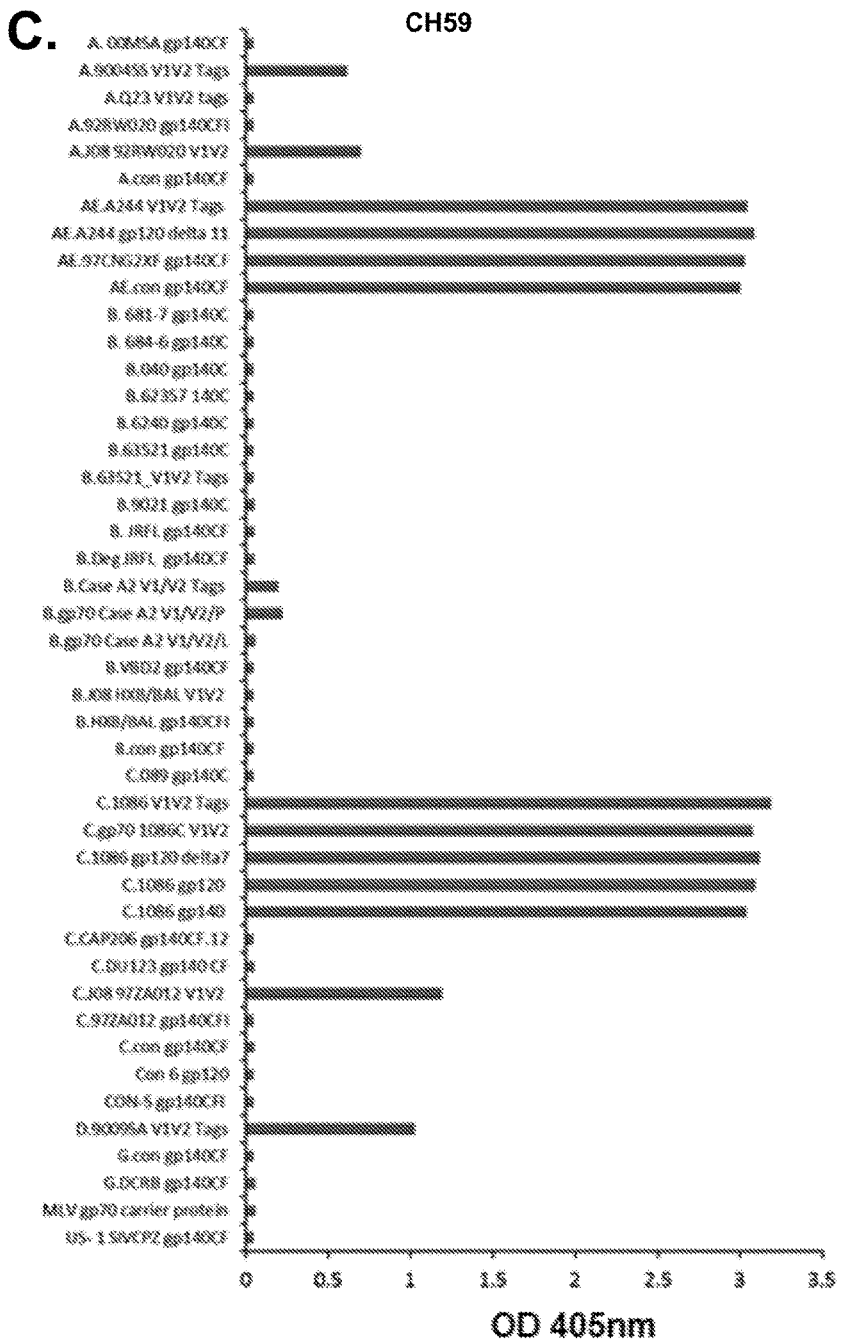
Figure 46:
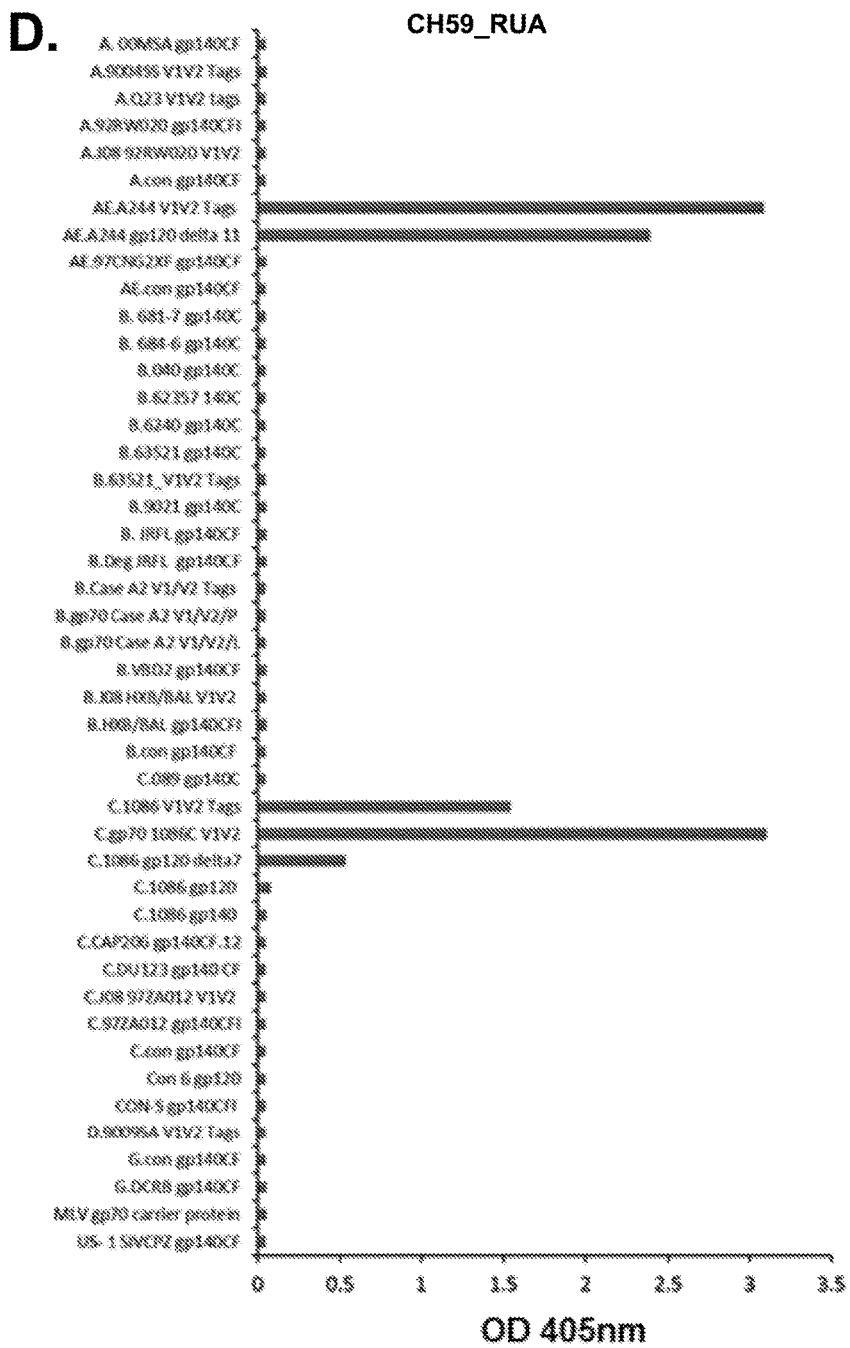
Figure 46:
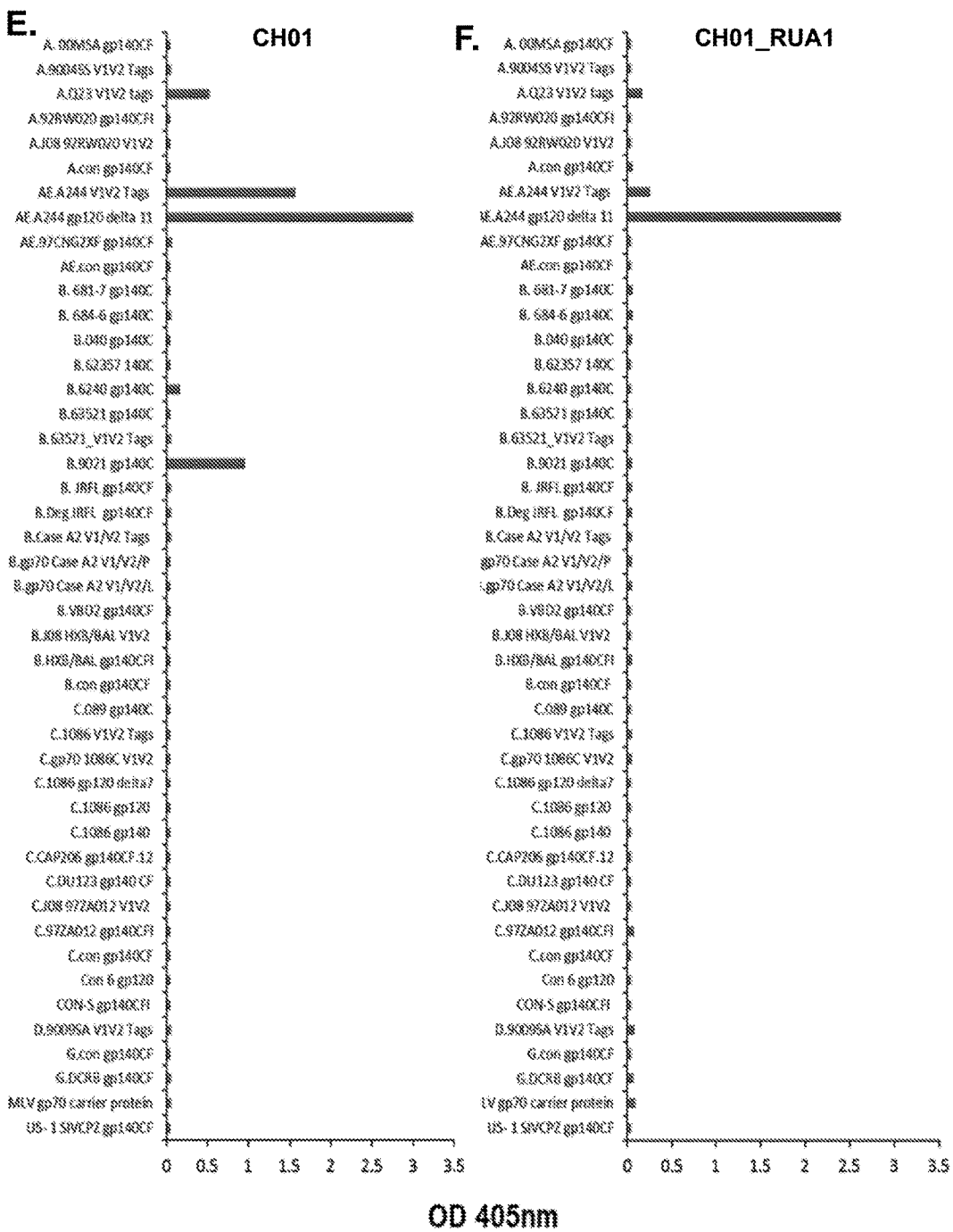
Figure 46:
Figure 46:
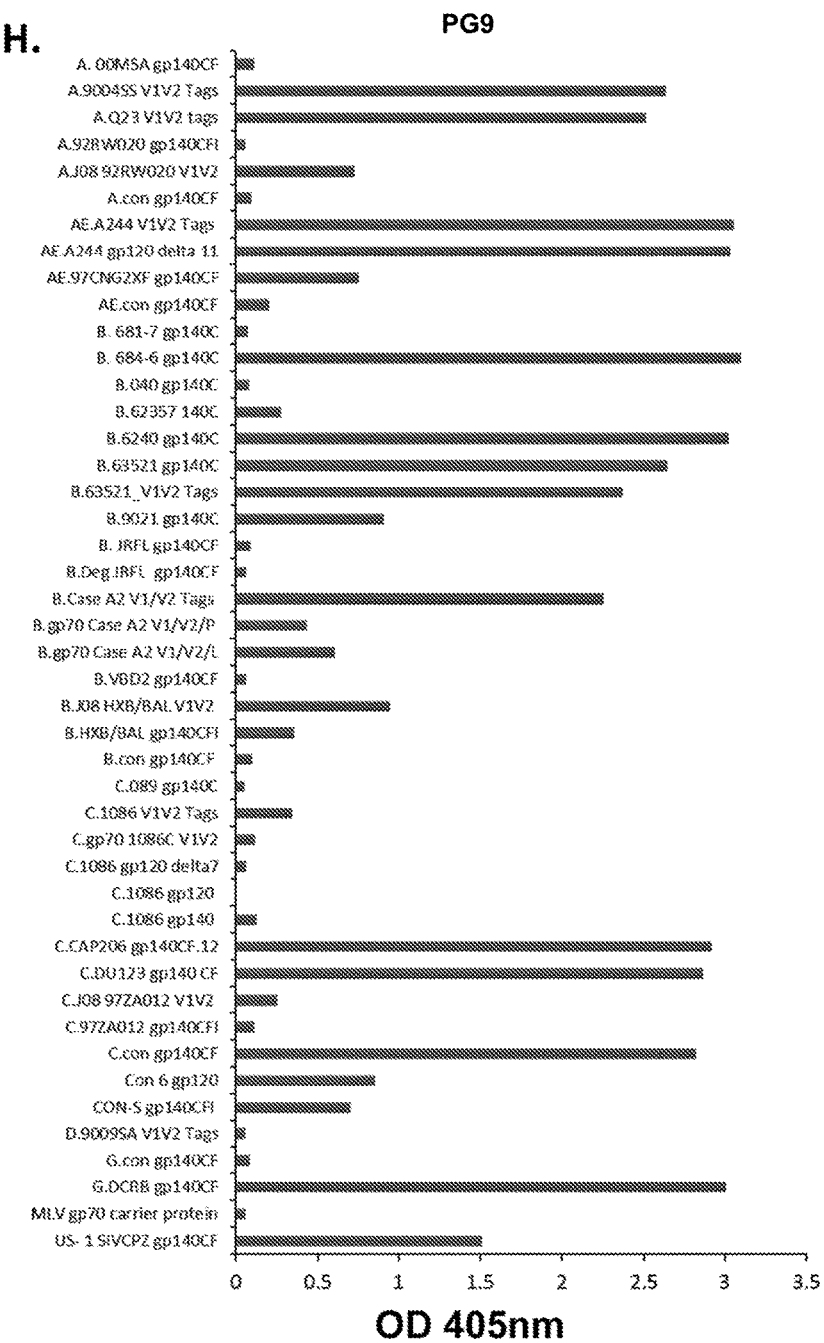
Figure 46:
Figure 46:
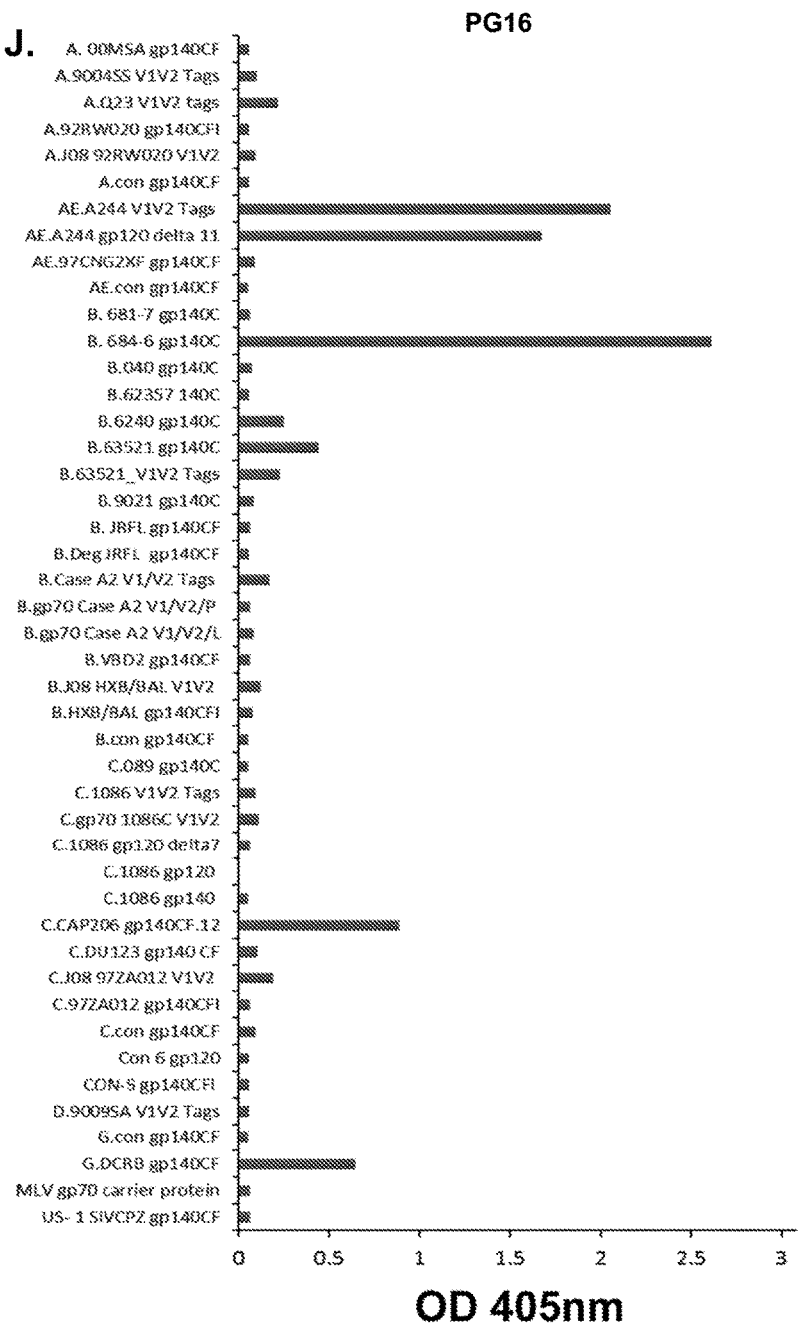
Figure 46:
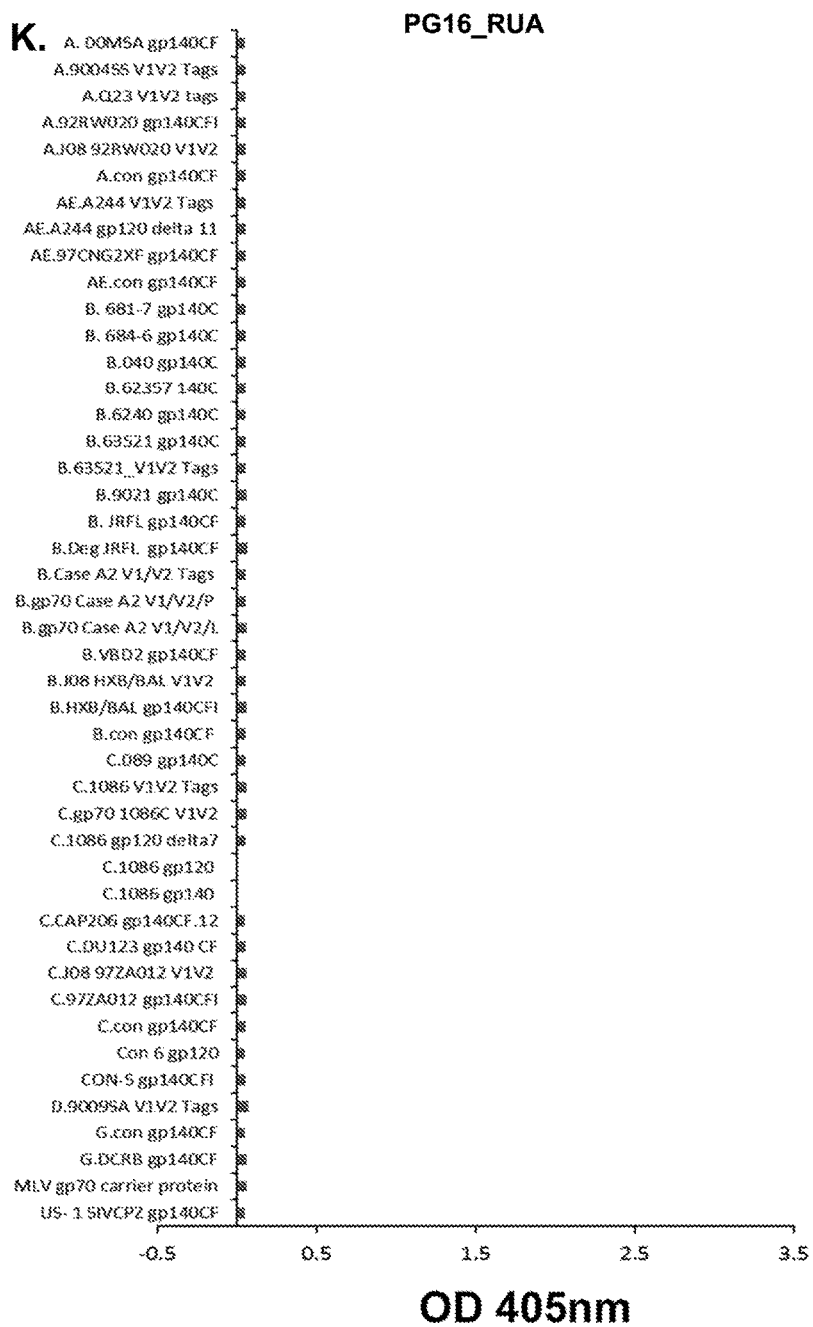
Figure 46:
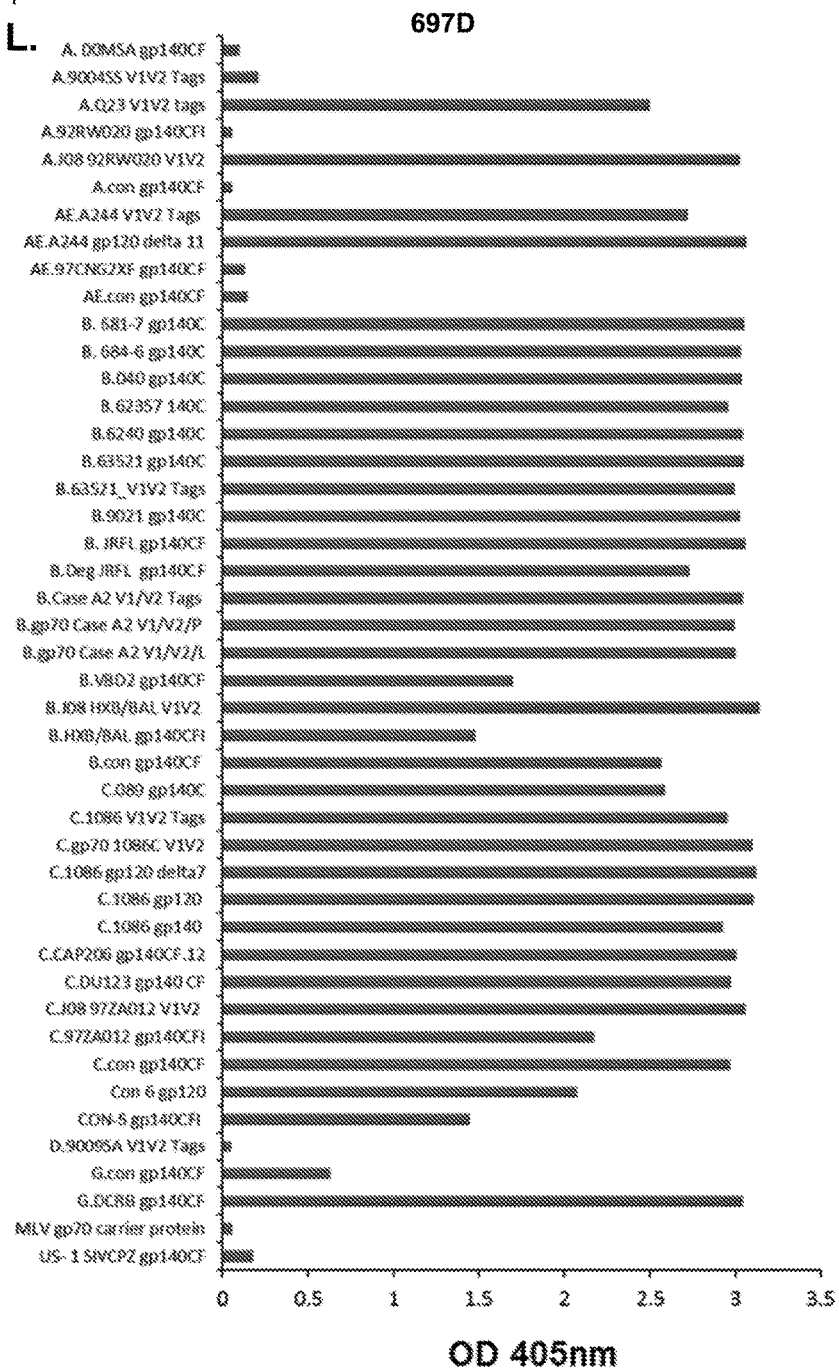
Figure 46:
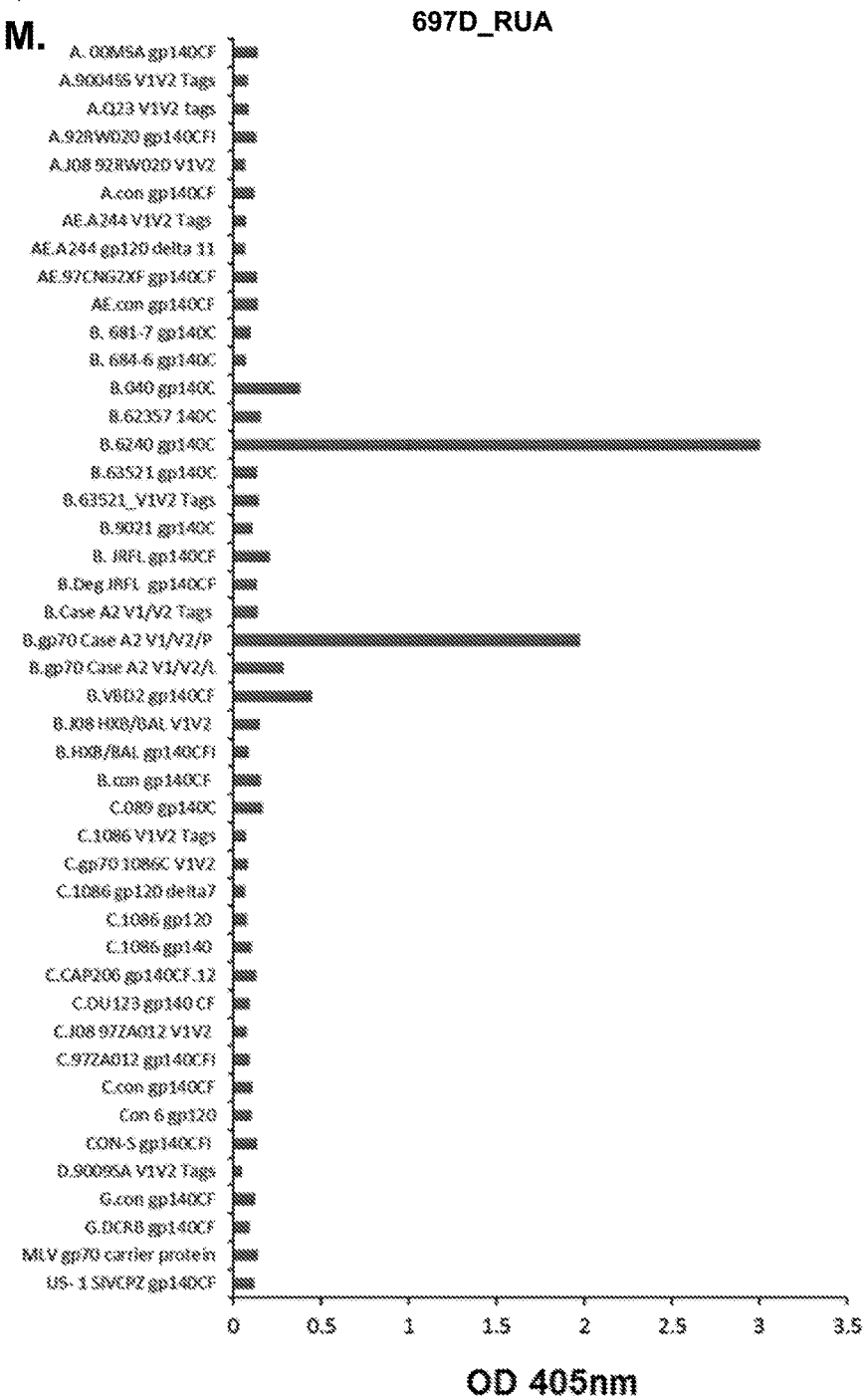
Figure 49:
FIG. 49. Impact of ALVAC gp 120AE/B immunogenicity and correlates.
Figure 49:
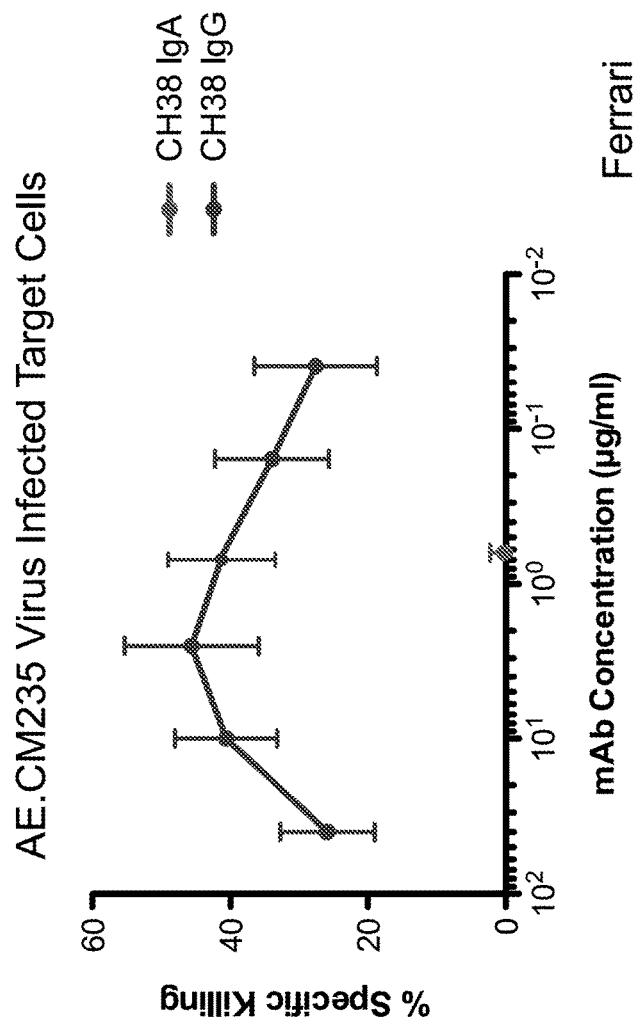
Figure 49:
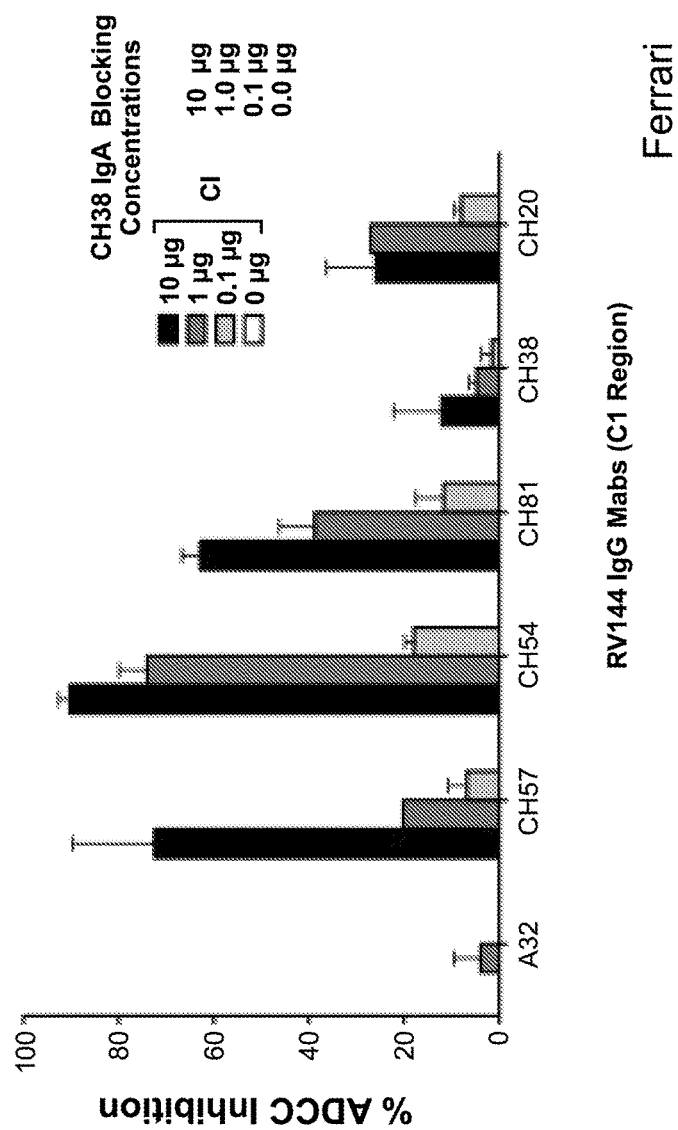
Figure 49:
Figure 49:
Figure 49:
Figure 49:
Figure 50:
FIG. 50. V1V2 IgG and IgA Breadth in HVTN 204.
Figure 50:
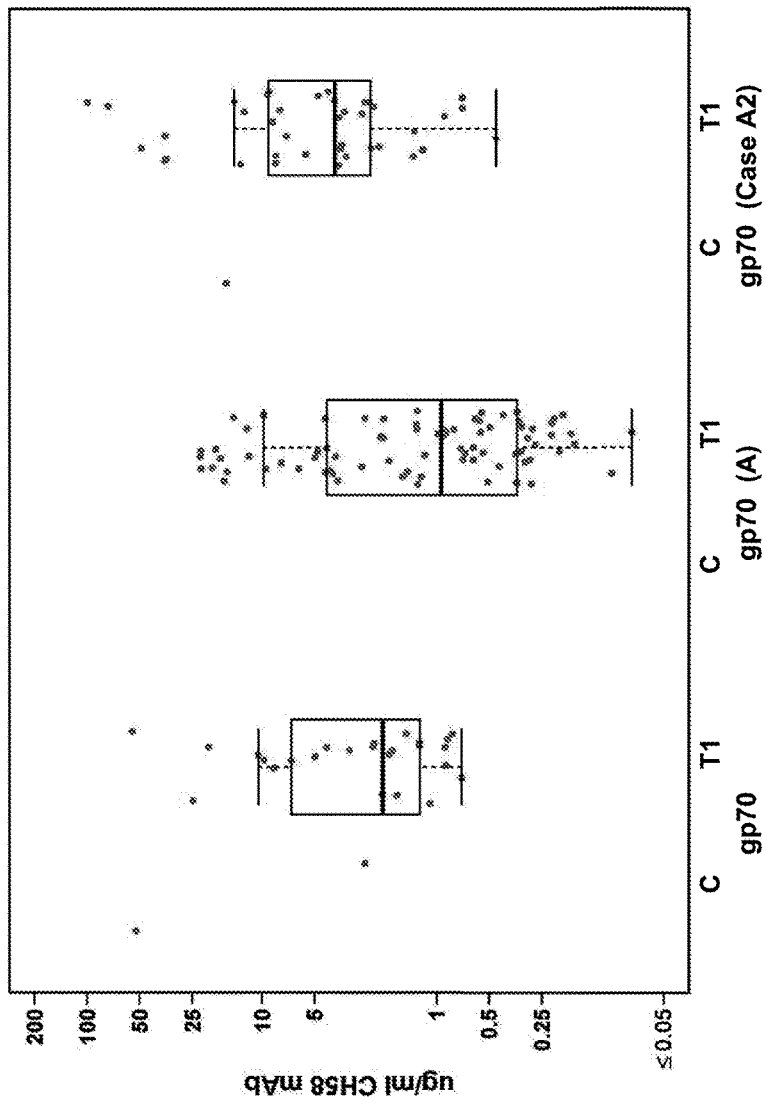
Figure 50:
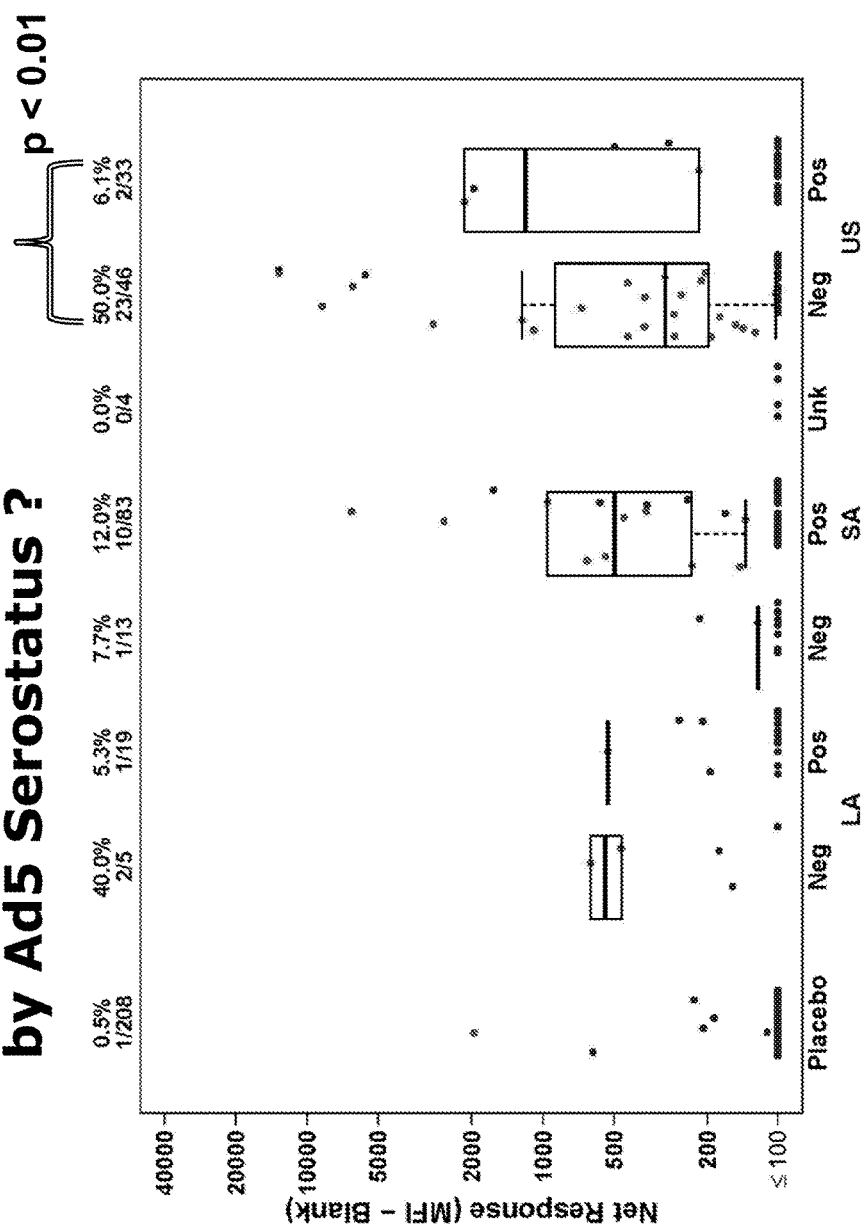
Figure 50:
Figure 50:
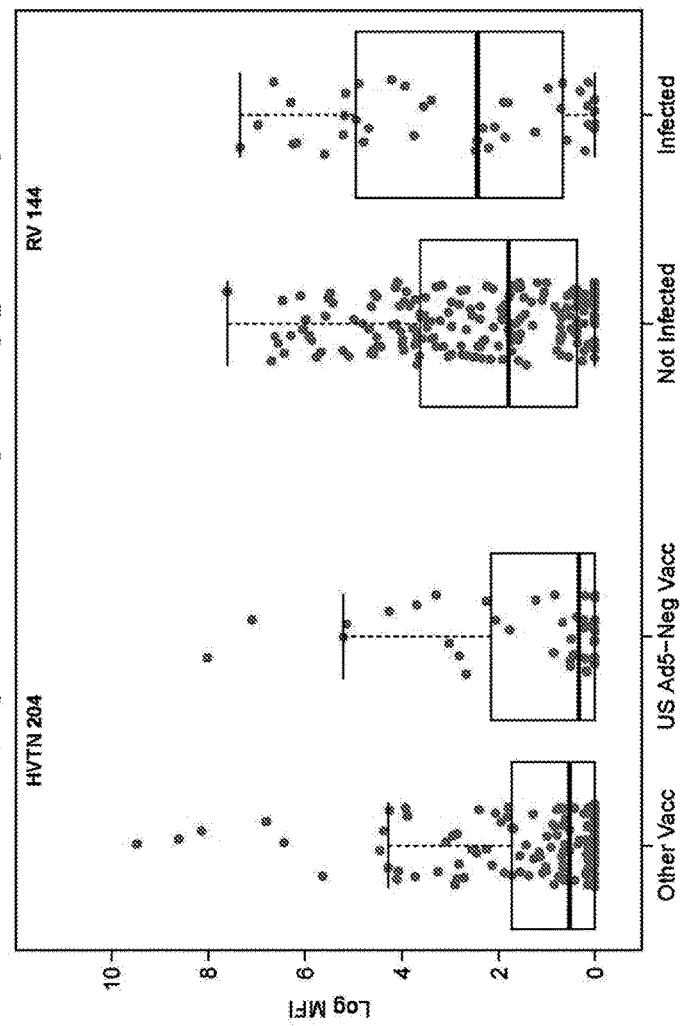
Figure 50:
Figure 50:
Figure 50:
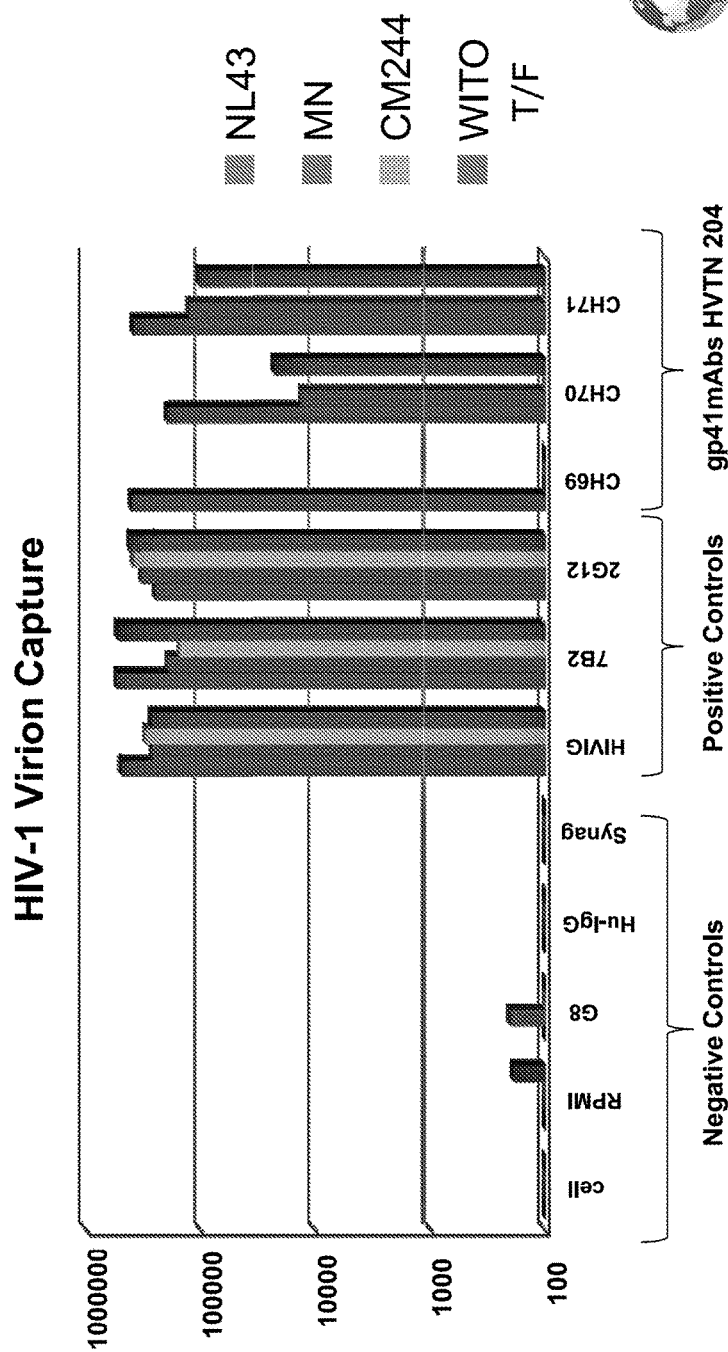

Crystal structure of mAb CH58 Fab with the AE.92TH023 peptide DKKQKVHALFYKLD (SEQ ID NO: 40) demonstrated polar contacts of the CH58 VH with H173, K178, D180 and non-polar contacts with V172, L175, and F176. Interestingly, the CH58 Fab VL had polar interactions with K168 and K169 (FIG. 33). In addition, although the Y177 side chain did not pack well with adjacent hydrophobic surfaces, it can be seen why alanine substitution at Y177 disrupted mAb CH58 binding, since this substitution would be predicted to disrupt the C-terminal portion of the peptide in the CH58 complex. Thus, there was concordance of the alanine-scanning mapped CH58 footprint with the observed crystal structure of the CH58-V2 peptide complex.

Rolland et al. have demonstrated that within the Env gp120 V1V2 region, sieve analysis of breakthrough viruses demonstrated immune pressure on K169 in Env V2 (Rolland et al, Nature submitted (2011)). Both CH58 and CH59 binding were abrogated by alanine substitution at K169 (FIG. 32B), and the CH58 Fab VL formed a polar contact with K169 in the crystal structure (FIG. 33). Thus, both the CH58 crystal structure of mAb CH58 and the alanine scanning analysis of mAb CH59 demonstrated antibody binding sites at the position of imputed immune pressure (K169) induced by ALVAC/AIDSVAX B/E vaccination (Rolland et al, Nature submitted (2011)).

Comparison of CH58-V2 and PG9-V1V2 Crystal Structures

Interestingly, both CH58 and CH59 mAb binding sites also involved key residues that make up the cationic and hydrophobic segments within aa168-178 of V1V2 that are components of the binding site of the V2V3 bnAb PG9 in the context of a scaffolded V1V2 recombinant protein (McLellan et al, Nature 480:336-343 (2011)) (FIG. 33). In addition to binding to aa within 168-178 of V1V2, mAb PG9 binds to N-linked glycans at N160 and N156 (McLellan et al, Nature 480:336-343 (2011)), Walker et al, Science 326: 285-289 (2009), Pancera et al, J. Virol. 84:8098-8110 (2010)). This similarity of CH58 to P09 mAb for binding to cationic and hydrophobic residues within aa 168-180 of V1V2 suggests that the presence of acidic residues in both mAbs would most likely allow specific electrostatic interactions with the cationic residues of this V1V2 region, as is the case for the conformational V1V2 mAb PG9 (McLellan et al, Nature 480:336-343 (2011)). Indeed the CDRH3 domain of CH58 includes six Tyr residues. It is notable that the collection of Tyr residues interspersed with charged amino acids on CH58 and the CH58 reverted unmutated ancestor antibody resembles that of the P09 CDRH3 (Pancera et al, J. Virol. 84:8098-8110 (2010)), although the HCDR3 of CH58 is shorter than that of PG9 (FIG. 37). The V2 168K residue interacts with the sulfated tyrosine at PG9 position 100H, and when 168K is replaced by an acidic residue, resistance to PG9 neutralization is seen (Pancera et al, J. Virol. 84:8098-8110 (2010)). Similarly, binding of CH58 to and it was found that whereas the binding of PG9, PG16 and CH01 to E.A244 was abrogated by the N160K mutation, the binding of CH58 and CH59 mAbs was not affected by this mutation (Table 8). In addition, native deglycosylation (Ma et al, PLoS Pathog. 7:e1002200 (2011)) of the C.CAP206 gp140 Env (that removes all V1V2 glycans) did not affect CH58 and CH59 Env binding, but did affect the binding of both PG9 and PG16. Thus, on these Envs tested, glycans are not required for mAb CH58 and CH59 binding to HIV-1 envelope gp120.

TABLE 18

Effect of N160K mutation and glycosylation of HIV-1 Env gp120 on binding of anti-HIV-1 Env mAbs.

| HIV-Env | | EC50 (nM) | | | | | |
|---|---|---|---|---|---|---|---|
| | | PG9 | PG16 | CH58 | CH59 | CH01 | 697D |
| E.A244 gp120 | wt | 0.7 | 22 | 0.02 | 0.03 | 1.3 | 0.8 |
| | N160K | >667 | — | 0.02 | 0.04 | — | 0.8 |
| E.A244 gD+ gp120 | wt | 0.7 | 15 | 0.02 | 0.04 | 0.9 | 0.3 |
| | N160K | >667 | — | 0.02 | 0.03 | — | 0.2 |
| B.JRFL gp140 | wt | 273 | — | >667 | — | — | 0.2 |
| | degly | — | >667 | >667 | — | — | 1.1 |
| C.CAP206 gp140 | wt | 0.8 | 16 | 1 | >667 | — | 0.1 |
| | degly | 279 | — | 1 | >667 | — | 12 |

Table shows the effect of N160K mutation (E.A244gp120 and E.A244 gD+ gp120 envelope glycoproteins) and deglycosylation (B.JRFL gp120 and C.CAP206 gp140 envelope glycoproteins) on the ability of PG9, PG16, CH58, CH59, CH01 and 697D to bind in ELISA. Results are expressed as EC50 nM. Positive results with EC50 above the highest tested concentration (667 nM) are indicated as >667 nM. Negative results are indicated with a "—".

V2 peptide is abrogated by alanine substitution at K168 (FIG. 32B). MAb CH58 (like CH04, a member of the CH01-CH04 V2V3 BnAb clonal lineage (Bonsignori et al, J. Viral. 85:9998-10009 (2011)) demonstrated no tyrosine sulfation (FIG. 38).

Although CH58 and PG9 share binding to the same gp120 V2 amino acids (aa 168-171 KKQK (SEQ ID NO: 41)), the most dramatic difference between the crystal structures of CH58 and PG9 regarding aa interactions are that when bound to CH58, aa168-171 is in a short alpha helix, whereas this region in the PG9 structure is in a beta strand conformation (McLellan et al, Nature 480:336-343 (2011)). While PG9 is broadly neutralizing for Tier 2 HIV-1 strains, PG9 and the related V2V3 PG16 and CH01-CH04, do not neutralize Tier 1 strains (Walker et al, Science 326:285-289 (2009), Pancera et al, J. Virol. 84:8098-8110 (2010), Bonsignori et al, J. Virol. 85:9998-10009 (2011)). Conversely, CH58 neutralizes only select Tier 1 HIV-1 strains. That PG9 binds to V1V2 in a β strand conformation and CH58 binds in an α helix, raises the hypothesis that the conformation of V2 aa 168-171 may take on alternate conformations in Tier 1 versus Tier 2 HIV-1 strains, a notion that will require structural analyses of the V2 region in the context of Tier 1 and Tier 2 native envelope trimers.

A series of peptides and recombinant Envs were next used to determine CH58 and CH59 mAb binding dependence on adjacent N160, N156 and N173 glycan sites compared to that of known conformational V1V2 mAbs (PG9, PG16, CH01, 697D). Whereas none of the conformational V1V2 mAbs (PG9, PG16, CH01, 697D) bound to linear and cyclic V2 peptides, both CH58 and CH59 bound well to V2 peptides with EC50s from 0.06 µg/ml to 0.003 µg/ml (FIG. 32A). It has been previously described that PG9, PG16 and CH01 V2V3 bnAbs bound well to the E.A244 gp120 recombinant Env (Bonsignori et al, J. Virol. 85:9998-10009 (2011)). N160K mutants of E.A244 gp120 were constructed Next, two designs of V1V2 scaffolds (Table 19) with sequences from clades A (A.92RW020), B (B.HXB2/BaLV3, B.CaseA2) and C (C.97ZA012) strains were expressed as described (McLellan et al, Nature 480:336-343 (2011), Pinter et al, Vaccine 16:1803-1811 (1998)). For clades A, B and C V1V2, a small scaffolding protein J08 was used (Table 19) (McLellan et al, Nature 480:336-343 (2011). For clades A and B V1V2, a murine leukemia virus gp70 scaffold was used (Pinter et al, Vaccine 16:1803-1811 (1998)). The gp70-clade B CaseA2 scaffold was used in the RV144 immune correlates analysis where reactivity to B.CaseA2 V1V2 correlated inversely with risk of infection in the trial (Haynes et al, N. Engl. Med. In press (Apr. 4, 2012)). These scaffolds were tested in ELISA for reactivity with mAbs CH58, CH59 compared to reactivity with mAbs 697D, CH01, PG9 and PG16 (Table 20, FIGS. 39-44). As expected, mAb PG9, PG16, CH01 and 697D binding was consistently dependent on N160/N156 glycans (Walker et al, Science 326:285-289 (2009), Bonsignori et al, J. Virol. 85:9998-10009 (2011)). In contrast, it was found that RV144 V2 mAb CH58 and CH59 binding to clade A, B, and C scaffolds (gp70 A.9ZRW020 V1V2, JO8 A.9ZRW020 V1V2, B.CaseA2 gp70 V1V2, JO8 C.97ZA012 V1V2) were affected by N160Q, N156Q mutations, and CH59 binding to the J08 C.ZM109 V1V2 scaffold was decreased by an N173D mutation (mAb CH58 did not bind to C.ZM109 due to the F to D change at aa D178). Thus, since CH58 and CH59 bind to non-glycosylated V2 peptides, and neither native deglycosylation nor N160K mutations of Env had any effect on CH58 and CH59 Env binding (Table 18), it is likely that the N160Q, N156Q and N173D mutations in V1V2 scaffolds most likely perturbed the conformation of the binding epitopes of CH58 and CH59, rather than glycan moieties binding to CH58 or CH59 mAbs.

TABLE 19

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| E.92TH023 V2 cyclic peptide | CSFNMTTELRDKKQKVHALFYKLDIVPIEDNTSSEYRLINC | 2 |
| E.A244 K178 V2 peptide | KKKVHALFYKLDIVPIEDKKK | 1 |
| B. Case A2.V1V2 | VKLTPLDVTLNCIDLRNATNATSNSNTTNTTSSSGGLMMEQGEIKNCSFNITTSIRDKVQKEYALFYK LDIVPIDNPKNSTNYRLISCNTSVITQA | 42 |
| A.92RW020V1V2 | LKPCVKLTPLCVTLDCNATASNVTNEMRNCSFNITTELKDKKQQVYSLFYKLDVVQINEKNETDKYRL INCNTSAITQA | 43 |
| B.HXB2/BALV1V2 | LKPCVKLTPLCVSLKCTDLKNDTNTNSSSGRMIMEKGEIKNCSFNISTSIRGKVQKEYAFFYKLDIIP IDNDTTSYSLTSCNTSVITQA | 44 |
| C.97ZA012V1V2 | LKPCVKLTPLCVTLHCTNATFKNNVTNDMNKEIRNCSFNTTTEIRDKKQQGYALFYRPDIVLLKENRN NSNNSEYILINCNASTITQA | 45 |
| C.ZM109 V1V2 | CVTLNCTSPAAHNESETRVKHCSFNITTDVKDRKQKVNATFYDLDIVPLSSSDNSSNSSLYRLISC | 46 |
| E.A244 V1V2 | VKLTPPCVTLHCTNANLTKANLTNVNNRTNVSNIIGNITDEVRNCSFNMTTELRDKKQKVHALFYKLD IVPIEDNNDSSEYRLINCNTSVIKQP | 47 |
| B.gp70CaseA2 V1/V2 | MACSTLPKSPKDKIDPRDLLIPLILFLSLKGARSAAPGSSPHHHHHQVYNITWEVTNGDRETVWAIS GNHPLWTWWPVLTPDLCMLALSGPPHWGLEYQAPYSSPPGPPCCSGSSGSSAGCSRDCDEPLTSLTPR CNTAWNRLKLDQVTHKSSEGFYVCPGSHRPREAKSCGGPDSFYCASWGCETTGRVYWKPSSSWDYITV DNNLTTSQAVQVCKDNKWCNPLAIQFTNAGKQVTSWTTGHYWGLRLYVSGRDPGLTFGIRLRYQNLGP RVPIGPNPVLADQLSLPRPNPLPKPAKSPPASVKLTPLCVTLNCIDLRNATNATSNSNTTNTTSSSGG LMMEQGEIKNCSFNITTSIRDKVQKEYALFYKLDIVPIDNPKNSTNYRLISCNTSVITQA | 48 |
| C.gp70 1086C V1V2 | MACSTLPKSPKDKIDPRDLLIPLILFLSLKGARSAAPGSSPHHHHHQVYNITWEVTNGDRETVWAIS GNHPLWTWWPVLTPDLCMLALSGPPHWGLEYQAPYSSPPGPPCCSGSSGSSAGCSRDCDEPLTSLTPR CNTAWNRLKLDQVTHKSSEGFYVCPGSHRPREAKSCGGPDSFYCASWGCETTGRVYWKPSSSWDYITV DNNLTTSQAVQVCKDNKWCNPLAIQFTNAGKQVTSWTTGHYWGLRLYVSGRDPGLTFGIRLRYQNLGP RVPIGPNPVLADQLSLPRPNPLPKPAKSPPASVKLTPLCVTLNCTNVKGNESDTSEVMKNCSFKATTE LKDKKHKVHALFYKLDVVPLNGNSSSSGEYRLINCNTSAITQA | 49 |
| MLV gp70 carrier protein | MACSTLPKSPKDKIDPRDLLIPLILFLSLKGARSAAPGSSPHHHHHQVYNITWEVTNGDRETVWAIS GNHPLWTWWPVLTPDLCMLALSGPPHWGLEYQAPYSSPPGPPCCSGSSGSSAGCSRDCDEPLTSLTPR CNTAWNRLKLDQVTHKSSEGFYVCPGSHRPREAKSCGGPDSFYCASWGCETTGRVYWKPESSWDYITV DNNLTTSQAVQVCKDNKWCNPLAIQFTNAGKQVTSWTTGHYWGLRLYVSGRDPGLTFGIRLRYQNLGP RVPIGPNPVLADQLSLPRPNPLPKPAKSPPAS | 50 |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| A.9004SS V1V2 Tags | METDTLLLWVLLLWVPGSTGDQVKLTPLCVTLNCSQYVSSHVNNHNNSSHNVSSHSGNITSDMKICSF NTTTEVRDKKQKVYSLFYKLDVVPISNDSSQYRLINCNTSAITQAGLNDIFEAQKIEWHELEVLFQGP GHHHHHH | 51 |
| A.Q23 V1V2 tags | METDTLLLWVLLLWVPGSTGDQVKLTPLCVTLHCTNVTSVNTTGDREGLKNCSFNMTTELRDKRQKVY SLFYRLDIVPINENQGSEYRLINCNTSAITQAGLNDIFEAQKIEWHELEVLFQGPGHHHHHH | 52 |
| AE.A244 V1V2 Tags | METDTLLLWVLLLWVPGSTGDQVKLTPPCVTLHCTNANLTKANLTNVNNRTNVSNIIGNITDEVRNCS FNMTTELRDKKQKVHALFYKLDIVPIEDNNDSSEYRLINCNTSVIKQPGLNDIFEAQKIEWHELEVLF QGPGHHHHHH | 53 |
| B.63521_V1V2 Tags | METDTLLLWVLLLWVPGSTGDQVKLTPLCVTLNCTDVTNATNINATNINNSSGGVESGEIKNCSFNIT TSVRDKVQKEYALFYKLDIVPITNESSKYRLISCNTSVLTQAGLNDIFEAQKIEWHELEVLFQGPGHH HHHH | 54 |
| B.Case A2 V1/V2 Tags | METDTLLLWVLLLWVPGSTGDQVKLTPLCVTLNCIDLRNATNATSNSNTTNTTSSSGGLMMEQGEIKN CSFNITTSIRDKVQKEYALFYKLDIVPIDNPKNSTNYRLISCNTSVITQAGLNDIFEAQKIEWHELEV LFQGPGHHHHHH | 55 |
| D.9009SA V1V2 Tags | METDTLLLWVLLLWVPGSTGDQVKLTPLCVTLNCTTNSTNFANSTGKDIEMQDCSFNITTEIRDKQKK VHALFYKLDIVQIDNNTEANANYTSYRLINCNTSAITQAGLNDIFEAQKIEWHELEVLFQGPGHHHHH H | 56 |
| A. 00MSA gp140CF | MGAMGIQMNWQNLWRWGTMILGMLIICSVAEKSWVTVUUGVPVWRDAETTLFCASDAKAHDKEVHNVW ATHACVPTDPNPQEMILENVTEDFNMWKNSMVEQMHTDIISLWDQSLKPCVKLTPLCVTLNCSDSNIT SNSTSNSTKDSATLDMKSEIQNCSFNMTTELRDKKQKVYSLFYRLDVVQINENSSDYRLINCNTSAIT QACPKVTFEPIPIHYCAPAGFAILKCNDKKFNGTGPCTNVSTVQCTHGIKPVVTTQLLLNGSLAEEEV MIRSENITENAKNIIVQFKEPVQIICIRPGNNTRKSVHIGPGQAFYATGDIIGDIRQAHCNVSRELWN KTLQEVATWLRKHFRNNTKIIFTNSSGGDVEITTHSFNCGGEFFYCDTSGLFNSSWTASNDSMQEAHS TESNITLQCRIKQIINMWQRAGQAMYAPPIPGIIRCESNITGLILTRDGGEGNNSTNETFRPVGGNMR DNWRSELYKYKVVKVEPLGVAPTKSRTLTVQARQLLSGIVQQQSNLLRAIEAQQHLLKLTVWGIKQLQ ARVLAVERYLRDQQLLGIWGCSGKLICTTNVPWNSSWSNKSLDEIWENMTWMQWDKEVSNYTQMIYNL LEESQNQQEKNEQELLALDKWANLWNWFNISNWLW | 57 |
| A.92RW020 gp140CF1 | MRVRGIQTSWQNLWRWGTMILGMLVIYSAAENLWVAVYYGVPVWKDAETTLGCASDAKAYDTEVHNVW ETHACVPTDPNPQEIHLENVTEDFNMWRNNMVEQMHTDIISLWDQSLKPCVKLTPLCVTLDCNATASN VTNEMRNCSFNITTELKDKKQQVYSLFYKLDVVQINEKNETDKYRLINCNTSAITQACPKVSFEPIPI HYCAPAGFAILKCKDTEFNGTGPCKNVSTVQCTHGIRPVISTQLLLNGSLAEEGIQIRSENITNNAKT IIVQLDKAVKINCTRPNNNTRKGVRIGPGQAFYATGGIIGDIRQAHCHVSRAKWNDTLRGVAKKLREH FKNKTIIFEKSSGGDIEITTHSFICGGEFFYCNTSGLFNSTWESNSTESNNTTSNDTITLTCRIKQII NMWQKVGQAMYPPPIQGNIRCESNITGLLLTRDGGNNSTNEIFRPGGGNMRDNWRSELYLYLVVKIEP | 58 |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| | LGVAPSRAKLTAQARQLLSGIVQQQSNLLRAIEAQQHMLKLTVWGIKQLQARVLAVERYLKDQQLEIW | |
| | DNMTWLQWDKEISNYTQIIYNLIEESQNQQEKNEQDLLALDKWASLWNWFDISRWLW | |
| A.con gp140CF | MRVMGIQRNCQHLLRWGTMILGMIIICSAAENLWVTVYYGVPVWKDAETTLFCASDAKAYETEMHNVW | 59 |
| | ATHACVPTDPNPQEIHLENVTEEFNMWKNNMVEQMHTDIISLWDQSLKPCVKLTPLCVTLNCSNVNVT | |
| | NNTTNTHEEEIKNCSFNMTTELRDKKQKVYSLFYRLDVVQINENNSNSSYRLINCNTSAITQACPKVS | |
| | FEPIPIHYCAPAGFAILKCKDKEFNGTGPCKNVSTVQCTHGIKPVVSTQLLLNGSLAEEEVIIRSENI | |
| | TNNAKTIIVQLTKPVKINCTRPNNNTRKSIRIGPGQAFYATGDIIGDIRQAHCNVSRSEWNKTLQKVA | |
| | KQLRKYFKNKTIIFTNSSGGDLEITTHSFNCGGEFFYCNTSGLFNSTWNNGTMKNTITLPCRIKQIIN | |
| | MWQRAGQAMYAPPIQGVIRCESNITGLLLTRDGGNNNTNETFRPGGGDMRDNWRSELYCYCVVKIEPL | |
| | GVAPTRAKTLTVQARQLLSGIVQQQSNLLRAIEAQQHLLKLTVWGIKQLQARVLAVERYLKDQQLLGI | |
| | WGCSGKLICTTNVPWNSSWSNKSWNEIWDNMTWLQWDKIESNYTHIITNLIEESQNQQEKNEQDLLAL | |
| | DKWANLWNWFDISNWLW | |
| AE.97CNG2XF gp140CF | MRVKETQMNWPNLWKWGTLILGLVIICSASDNLWVTVYYGVPVWRDADTTLFCASDAKAHETEVHNVW | 60 |
| | ATHACVPTDPNPQEIHLENVTENFNMWRNNMVEQMQEDVISLWDQSLKPCVKLTPLCVTLNCTNANWT | |
| | NSNNTTNGPNKIGNITDEVKNCTFNMTTELKDKKQKVHALFYKLDIVQINSSEYRLINCNTSVIKQAC | |
| | PKISFDPIPIHYCTPAGYAILKCNDKNFNGTGPCKNVSSVQCTHGIKPVVSTQLLLNGSLAEEEIIIR | |
| | SENLTNNAKTIIVHLNKSVEINCTRPSNNTRTSITMGPGQVFYRTGDIIGDIRKAYCEINGIKWNEVL | |
| | VQVTGKLKEHFNKTIIFQPPSGGDLEIITHHFSCRGEFFYCNTTKLFNNTCIGNTSMEGCNNTIILPC | |
| | KIKQIINMWQGVGQAMYAPPISGRINCVSNITGILLTRDGGADNNTTNETFRPGGGNIKDNWRSELYK | |
| | YKVVEIEPLGIAFTRARTLTVQARQLLSGIVQQQSNLLRAIEAQQHLLQLTVWGIKQLQARVLAVERY | |
| | LKDQKFLGLWGCSGKIICTTAVPWNSSWSNKSFEEIWDNMTWIEWEREISNYTSQIYEILTESQNQQD | |
| | RNEKDLLELDKWASLWNW | |
| AE.A244 gp120 delta 11 | MRVKETQMNWPNLWKWGTLILGLVIICSAVPVWKEADTTLFCASDAKAHETEVHNVWATHACVPTDPN | 61 |
| | PQEIDLENVTENFNMWKNNMVEQMQEDVISLWDQSLKFCVKLTPPCVTLHCTNANLTKANLTNVNNRT | |
| | NVSNIIGNITDEVRNCSFNMTTELRDKKQKVHALFYKLDIVPIEDNNDSSEYRLINCNTSVIKQPCPK | |
| | ISFDPIPIHYCTPAGYAILKCNDKNFNGTGPCKNVSSVQCTHGIKPVVSTQLLLNGSLAEEEIIIRSE | |
| | NLTNNAKTIIVHLNKSVVINCTRPSNNTRTSITIGPGQVFYRTGDIIGDIRKAYCEINGTEWNKALKC | |
| | VTEKLKEHFNNKPIIFQPPSGGDLEITMHHFNCRGEFFYCNTTRLFNNTCIANGTIEGCNGNITPLCK | |
| | IKQIINMWQGAGQAMYAPPISGTINCVSNITGILLTRDGGATNNTNNETFRPGGGNIKDNWRNELYKY | |
| | KVVQIEPLGVAPTRAKRRVVEREKR | |
| AE.A244 gD-gp120 | MRVKETQMNWPNLWKWGTLILGLVIICSASDNLWVTVYYGVPVWKEADTTLFCASDAKAHETEVHNVW | 62 |
| | ATHACVPTDPNPQEIDLENVTENFNMWKNNMVEQMQEDVISLWDQSLKFCVKLTPPCVTLHCTNANLT | |
| | KANLTNVNNRTNVSNIIGNITDEVRNCSFNMTTELRDKKQKVHALFYKLDIVPIEDNNDSSEYRLINC | |
| | NTSVIKQPCPKISFDPIPIHYCTPAGYAILKCNDKNFNGTGPCKNVSSVQCTHGIKPVVSTQLLLNGS | |
| | LAEEEIIIRSENLTNNAKTIIVHLNKSVVINCTRPSNNTRTSITIGPGQVFYRTGDIIGDIRKAYCEI | |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| | NGTEWNKALKCVTEKLKEHFNNKPIIFQPPSGGDLEITMHHFNCRGEFFYCNTTRLFNNTCIANGTIE GCNGNITPLCKIKQIINMWQGAGQAMYAPPISGTINCVSNITGILLTRDGGATNNTNNETFRPGGGNI KDNWRNELYKYKVVQIEPLGVAPTRAKRRVVEREKR | |
| AE.con gp 140CF | MRVKETQMNWPNLWKWGTLILGLVIICSASDNLWVTVYYGVPVWRDADTTLFCASDAKAHETEVHNVW ATHACVPTDPNPQEIHLENVTENFNMWRNNMVEQMQEDVISLWDQSLKPCVKLTPLCVTLNCTNANWT NVNNTTNVSNIIGNITNEVRNCSFNMTTELRDKKQKVHALFYKLDIVQIEDNNSYRLINCNTSVIKQA CPKISFDPIPIHYCTPAGYAILKCNDKNFNGTGPCKNVSSVQCTHGIKPVVSTQLLLNGSLAEEEIII RSENLTNNAKTIIVHLNKSVEINCTRPSNNTRTSITMGPGQVFYRTGDIIGDIRKAYCEINGIKWNEV LKQVTEKLKEHFNNYTIIFQPPSGGDLEITMHHFNCRGEFFYCNTTKLFNNTCIGNETMEGCNGTIIL PCKIKQIINMWQGAGQAMYAPPISGRINCVSNITGILLTRDGGANNTNETFRPGGGNIKDNWRSELYK YKVVEIEPLGIAFTRARTLTVQARQLLSGIVQQQSNLLRAIEAQQHLLQLTVWGIKQLQARVLAVERY LKDQKFLGLWGCSGKIICTTAVPWNSSWSNKSFEEIWDNMTWIEWEREISNYTSQIYEILTESQNQQD RNEKDLLELDKWASLWNWFDITNWLW* | 63 |
| B. 681-7 gp140C | MRVMGTRRNCQHLWKWGIMLLGLMICSATEQLWVTVYYGVPVWKDATTTLFCASDAKAYDTEAHNVW ATHACVPTDPNPQEVPLVNVTEKFDIWKNNMVDQMHEDIISLWDQSLKPCVKLTPLCVTLNCTNATIT NEVTATVATATSSKTISPAISPEMKNCSFNTNAILQDKVSKDYALFYNLDIVQIEDKDNKTNNDSKTY DSYRLISCNTSVITQACPKTSFKPIPIHYCAPAGFAILKCNDRNFNGTEPCKNVSTVWCTHGIRPVVS TQLLLNGSLAEDEVVIRSSNFSNNARTILVQLKDPVTINCTRPNNNTRRSINIGPGRAFYATGEIIGN IRQAHCNISMANWTNTLKQIAGKLGKQFDHKTIVFNHSSGGDPEIVMHTFNCGGEFFYCNTSGLFNST WTWNSTGNYYSSNSSGSGTNNNTIILQCRIKQIINMWQTVGKAMYAPPIRGKISVNSNITGLLLVRDG GDNNSSEEIFRPAGGDMRDNWRSELYKYKVVKIEPLGIAPTKARERVVQREKEAVGIGALFLGFLGAA GSTMGAASIALTVQARQLLSGIVQQQNNLLRAIEAQQHMLQLTVWGIKQLQARVLAVERYLRDQQLLG IWGCSGKHICTTNVPWNASWSNNRNLSQIWDNLTWMQWEKEIDNYTSLIYSLIEESQIQQEKNEQDLL ALDKWDSLWNWFNITHWLWYIK | 64 |
| B. 684-6 gp140C | MKVKGIMKNCQNSWSGGILLLGMLMICSAAEDKWVTVYYGVPVWKEATTTLFCASDAKAYSTERHNIW ATHACVPTDPSPQEIVMGNVTEDFNMWKNEMAVQMHEDVISLWDQSLKPCVKLTPLCVSLDCTNVNIT NHNSTNPEEQMKEGEIKNCSFNFTTNIKDKIQKTYALFYKLDLVPIDDENNTNTSYRLISCNTSVITQ ACPKVTFEPIPIHYCAPAGFAILKCNNKTFNGTGPCTNVSTVQCTHGIKPVVSTQLLLNGSLAEEEII IRSENITDNTKNIIVHLNKSVQINCIRPNNNTRKGIHIGPGAFWATGEIIGDIRQAHCNVSREDWNKT LRRISKKLRDIFNKTINFTSSSGGDPEIVMHSFNCGGEFFYCNSTPLFNSSWYGNETDVSNSTENSTR GEITLPCRIKQIINMWQEVGKAMYAPPISGPISCSSNITGLILTRDGGNNSSNTEIFRPGGGNMMDNW RSELYKYKVVQLEPLGIAPSRARERVVQREKEAVGFGALLLGFLGTAGSTMGAVSLTLTVQARQLLSG IVQQQNNLLRAIEAQQHMLQLTVWGIKQLQARVLAVERYLKDQQLLGIWGCSGKLICTTAVPWNDSWS NRSLTDIWDNMTWMQWEKEIDNYTGLIYTLIEESQFQQEKNEQDLLALDKWASLWNWFDITKWLWYIK | 65 |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| B. JRFL gp140CF | MPMGSLQPLATLYLLGMLVASVLAVEKLWVTVYYGVPVWKEATTTLFCASDAKAYDTEVHNVWATHAC VPTDPNPQEVVLENVTEHFNMWKNNMVEQMQEDIISLWDQSLKPCVKLTPLCVTLNCKDVNATNTTND SEGTMERGEIKNCSFNITTSIRDEVQKEYALFYKLDVVPIDNNNTSYRLISCDTSVITQACPKISFEP IPIHYCAPAGFAILKCNDKTFNGKGPCKNVSTVQCTHGIRPVVSTQLLLNGSLAEEEVVIRSDNFTNN AKTIIVQLKESVEINCTRPNNNTRKSIHIGPGRAFYTTGEIIGDIRQAHCNISRAKWNDTLKQIVIKL REQFENKTIVFNHSSGGDPEIVMHSFNCGGEFFYCNSTQLFNSTWNNNTEGSNNTEGNTITLPCRIKQ IINMWQEVGKAMYAPPIRGQIRCSSNITGLLLTRDGGINENGTEIFRPGGGDMRDNWRSELYKYKVVK IEPLGVAPTKAKTLTVQARLLLSGIVQQQNNLLRAIEAQQRMLQLTVWGIKQLQARVLAVERYLGDQQ LLSIWGCSGKLICTTAVPWNASWSNKSLDRIWNNMTWMEWEREIDNYTSEIYTLIEESQNQQEKNEQE LLELDKWASLWNWFDITKWLW | 66 |
| B.040 gp140C | MRVMGIRKNYQHLWREGILLLGTLMICSAADNLWVTVYYGVPVWREATTTLFCASDAKAYDTEAHNVW ATHACVPTDPNPQEVELKNVTENFNMWENNNMVEQMHEDIISLWDQSLKPCVKLTPLCVTLNCTDLGNV TNTTNSNGEMMEKGEVKNCSFKITTDIKDRTRKEYALFYKLDVVPINDTRYRLVSCNTSVITQACPKV SFEPIPIHYCAPAGFAILKCNDKQFIGTGPCTNVSTVQCTHGIRPVVSTQLLLNGSLAEEEVVIRSVN FSDNAKTIIVQLNKSVEITCTRPNNNTRKSIPMGPGKAFYARGDITGDIRKAYCEINGTEWHSTLKLV VEKLREQYNKTIVFNRSSGGDPEIVMYSFNCGGEFFYCNSTKLFNSTWPWNDTKGSHDTNGTLILPCK IKQIINMWQGVGKAMYAPPIEGKIRCSSNITGLLLTRDGGYESNETDEIFRPGGGDMRDNWRSELYKY KVVKIEPLGVAPTKAKERVVQREKEAFGLGAVFLGFLFAAGSTMGAASITLTVQARQLLSGIVQQQNN LLRAIEAQQHLLGLTVWGIKQLQARVLAVERYLKDQQLLGIWGCSGKLICTTTVPWNTSWSNKSLEQI WDNMTWMEWEREIDNYTGYIYQLIEESQNQQEKNEQELLALDKWASLWNWFDITNWLWYIK | 67 |
| B.62357 140C | MRVREIRRNYQHLWKWGIMLLGILMICSATEKLWVTVYYGVPVWKEATTTLFCASDAKAYDTEVHNVW ATHACVPTDPNPQEVDLENVTENFNMWKNNMVEQMHEDIISLWDESLKPCVKLTPLCVTLNCTNATST NFTAKNEGGIKNCSFNITTERRGRKKTEYATFYETDLVLINDDNTTSYRLISCNTSVIKQACPKVTFE PIPIHYCAPAGFAILKCKDKKFNGTGACTNVSTVQCTHGIRPVVSTQLLLNGSLAEEEVVVRSEKFAN NAKIIIVQLNEWVEINCTRPNNNTRKSIHIGPGQAFYTTGAIIGDIRQAYCNISRAKWNDTLKQIAIK LREKFNGGKTIVFNQSSGGDPEVVMIHSNCHHEFFYCNTTKLFNNTWNSNDTWTNTEESNETEIRLPC RIKQIINMWQEVGKAMYAPPIQGQIRCSSNITGLLLTRDGGNNTNNTEVFRPGGGDMRDNWRSELYKY KVVKIEPLGVAPTKAKERVVQREKEAVGLGALFLGFLGAAGSTMGAASVTLTVQARQLLSGIVQQQSN LLRAIEAQQHLLQLTVWGIKQLQARVLAVERYLKDQQLLGIWGCSGKLICTTAVPWNASWSNKSLNDI WNNMTWMEWEREINNYTSLIYNLIEESQNQQEKNELELLELDKWASLWNWFDITNWLWYIK | 68 |
| B.6240 gp140C | MRVKGIRKNYQHLWRWGIWRWGIMLLGTLMICSATEKLWVTVYYGVPVWKEATTTLFCASDAKAYSPE KHNIWATHACVPTDPNPQELVLGNVTEDFNMWKNNMVEQMHEDIISLWDQSLKPCVKLTPLCVTLNCT DLKNSATDTNGTSGTNNRTVEQGMETEIKNCSFNITTGIGNKMQKEYALFYKLDVVPIDSNNNSDNTS YRILSCNTSVVTQACPKTSFEPIPIHYCAPAGFAILKCNNKTFSGKGPCKNVSTVQCTHGIRPVVSTQ LLLNGSLAEEEIVIRSENFTNNAKTIIVQLNESVIINCTRPNNNTRKGIHIGLGRALYATGDIIGDIR | 69 |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
|  | QAHCNLSSKSWNKTLQQVVRKLREQFGNKTIAFNQSSGGDQEIVKHSFNCGGEFFYCDTTQLFNSTWS SNDTWNSTGVQDNNITLPCRIKQIINMWQEVGKAMYAPPIQGLISCSSNITGLLLTRDGGTNNTNATE LFRPGGGDMRDNWRSELYKYYVVKIEPLGIAPTKAKERVVQREKEAVGLGAVFIGFLGAAGSTMGAAS VTLTVWARQLLSGIVQQQNNLLRAIEAQQHMLQLTVWGIKQLQARILAVERYLKDQQILGIWGCSGKL ICPTAVPWNASWSNKSLTAIWNNMTWMEWEREIDNYTGLIYSLIEESQIQQEQNEKELLELDKWASLW NWFKITKWLWYIK |  |
| B.63521 gp140C | MRVKGIRKNYQHLWRWGTMLLGILMICSAAAQLWVTVYYGVPVWKEATTTLFCASDAKAYDTEVHNVW ATHACVPTDPNPQELVLANVTENFNMWNNTMVEQMHEDIISLWDQSLKPCVKLTPLCVTLNCTDVTNA TNINATNINNSSGGVESGEIKNCSFNITTSVRDKVQKEYALFYKLDIVPITNESSKYRLISCNTSVLT QACPKVSFEPIPIHYCAPAGFAILKCNNETFNGKGPCINVSTVQCTHGIRPVVSTQLLLNGSLAEKEV IIRSDNFSDNAKNIIVQLKEYVKINSTRPNNNTRKSIHIGPGRAFYATGEIIGNIRQAHCNISRWKWN DTLKQIAAKLGEQFRNKTIVFNPSSGGDLEIVTHSFNCGGEFFYCNTTKLFNSTWIREGNNGTWNGTI GLNDTAGNDTIILPCKIKQIINMWQEVGKAMYAPPIRGQIRCSSNITGLILTRKDDKDDSNGSEILEI FRPGGGDMRDNWRSELYKYKVVRIEPLGVAPTRARERVVQKEKEAVGLGAMFLGFLGAAGSAMGAASM TLTVQARQLLSGIVQQQNNLLRAIEAQQHMLTLTVWGIKQLQARVLAVERYLKDQQLLGIWGCSGKLI CTTDVPWDTSWSNKTLDDIWGSNMTWMEWEREIDNYTSTIYTLLEEAQYWWEKNEKELLELDKWASLW NWFDITNWLWYIR | 70 |
| B.9021 gp140C | MRVKGIRKNCQQHLWRWGTMLLGILMICSAAENLWVTVYYGVPVWKEATTTLFCASDAKAYDTEVHNV WATHACVPTDPNPQEMVLENVTEYFNMWKNNMVEQMHEDIISLWDQSLKPCVKLTPLCVTLTCTDYEW NCTGIRNSICKYNNMTNNSSSGNYTGWERGEIKNCSFNSTISGIRDKVRKEYALLYKIDLVSIDGSNT SYRMISCNTSVITQSCPKISFEPIPLHYCTPAGFALLKCNDKKFNGTGLCHNVSTVQCTHGIKPVVST QLLLNGSLAEEEVVIRSKNFTDNAKIIIVQLNETVEINCTRPGNNTRKSIHIAPGRTFYATGEIIGDI RRAHCNISREKWNTTLHRIATKLREQYNKTIVFNQSSGGDPEIVMHSVNCGGEFFYCNTSKLFNSTWN STGGSISEDSENITLPCRIKQIVNMWQEVGKAMYAPPIRGQIRCSSNITGLLLTRDGGINQSISETFR PGGGDMRDNWRSELYKYKVVKIEPLGIAPTKARERVVQREKEAVGIGAVFLGFLGAAGSTMGAASLTL TVQARLLLSGIVQQQNNLLRAIEAQQHMLQLTVWGIKQLQARVLALERYLRDQQLMGIWGCSGKLICT TAVPWNASWSNKSLNDIWNNMTWMQWEREIDNYTGLIYSLLEESQNQQEKNEQDLLALDKWANLWTWF DISNWLWYIK | 71 |
| B.con gp140CF | MRVKGIRKNYQHLWRWGTMLLGMLMICSAAEKLWVTVYYGVPVWKEATTTLFCASDAKAYDTEVHNVW ATHACVPTDPNPQEVVLENVTENFNMWKNNMVEQMHEDIISLWDQSLKPCVKLTPLCVTLNCTDLMNA TNTNTTIIYRWRGEIKNCSFNITTSIRKDVQKEYALFYKLDVVPIDNDNTSYRLISCNTSVITQACPK VSFEPIPIHYCAPAGFAILKCNDKKFNGTGPCTNVSTVQCTHFIRPVVSTQLLLNGSLAEEEVVIRSE NFTDNAKTIIVQLNESVEINCTRPNNNTRKSIHIGPGRAFYTTGEIIGDIRQAHCNISRAKWNNTLKQ IVKKLREQFGNKTIVFNQSSGGDPEIVMHSFNCGGEFFYCNTTQLFNSTWNGTNWWTEGNITLPCRIK | 72 |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| | QIINMWQEVGKAMYAPPIRGQIRCSSNITGLLLTRDGGNNETEIFRPGGGDMRDNWRSELYKYKVVKI | |
| | EPLGVAPTKAKTLTVQARQLLSGIVQQQNNLLRAIEAQQHLLQLTVWGIKQLQARVLAVERYLKDQQL | |
| | LGIWGCSGKLICTTAVPWNASWSNKSLDEIWDNMTWMEWEREIDNYTSLIYTLIEESQNQQEKNEQEL | |
| | LELDKWASLWNWFDITNWLW | |
| B.Deg JRFL gp140CF | MPMGSLQPLATLYLLGMLVASVLAVEKLWVTVYYGVPVWKEATTTLFCASDAKAYDTEVHNVWATHAC | 73 |
| | VPTDPNPQEVVLENVTEHFNMWKNNMVEQMQEDIISLWDQSLKPCVKLTPLCVTLNCKDVNATNTTND | |
| | SEGTMERGEIKNCSFNITTSIRDEVQKEYALFYKLDVVPIDNNNTSYRLISCDTSVITQACPKISFEP | |
| | IPIHYCAPAGFAILKCNDKTFNGKGPCKNVSTVQCTHGIRPVVSTQLLLNGSLAEEEVVIRSDNFTNN | |
| | AKTIIVQLKESVEINCTRPNNNTRKSIHIGPGRAFYTTGEIIGDIRQAHCNISRAKWNDTLKQIVIKL | |
| | REQFENKTIVFNHSSGGDPEIVMHSFNCGGEFFYCNSTQLFNSTWNNNTEGSNNTEGNTITLPCRIKQ | |
| | IINMWQEVGKAMYAPPIRGQIRCSSNITGLLLTRDGGINENGTEIFRPGGGDMRDNWRSELYKYKVVK | |
| | IEPLGVAPTKAKTLTVQARLLLSGIVQQQNNLLRAIEAQQRMLQLTVWGIKQLQARVLAVERYLGDQQ | |
| | LLGIWGCSGKLICTTAVPWNASWSNKSLDRIWNNMTWMEWEREIDNYTSEIYTLIEESQNQQEKNEQE | |
| | LLELDKWASLWNWFDITKWLW | |
| B.HXB/BAL gp140CF1 | MRVKEKYQHLRWGWRWGTMLLGMLMICSATEKLWVTVYYGVPVWKEATTTLLCASDAKAYDTEVHNV | 74 |
| | WATHACVPTDPNPQEVVLVNVTENFDMWKNDMVEQMHEDIISLWDQSLKPCVKLTPLCVSLKCTDLKN | |
| | DTNTNSSSGRMIMEKGEIKNCSFNISTSIRGKVQKEYAFFYKLDIIPIDNDTTSYSLTSCNTSVITQA | |
| | CPKVSFEPIPNHYCAPAGFAILKCKDKKFNGKGPCTNVSTVQCTHFIRPVVSTQLLVTGNLAEEEVVI | |
| | RSANFADNAKVIIVQLNESVEINCTRPNNNTRKSIHIGPGRAFYTTGEIIGDIRQAHCNLSRAKWNDT | |
| | LNKIVIKLREQFGNKTIVFKHSSGGDPEIVTHSFNCGGEFFYCNSTQLFNSTWFNSTWSTEGSNNTEG | |
| | SDTITLPCRIKQIINMWQKVGKAMYAPPISGQIRCSSNITGLLLTRDGGNSNNESEIFRLGGGDMRDN | |
| | WRSELYKYKVVKIEPLGVAPTKAKLTVQARQLLSGIVQQQNNLLRAIEAQQHLLQLTVWGIKQLQART | |
| | LAVERYLKDQQLLEQIWNHTTWMEWDREINNYTSLIHSLIEESQNQHEKNEQELLELDKWASLWNWFN | |
| | ITNWLW | |
| C.089 gp140C | MRVRGMLRNCQQWWIWGILGFWMLMICSVVGNLWVTVYYGVPVWKEAKTTLFCASDARAYEREVHNVW | 75 |
| | ATHACVPTDPNPQEMVLVNVTENFNMWKNDMVDQMHEDIISLWDQSLKPCVKLTPLCVILECNNANGT | |
| | TNNGSVIVVNENSTMYGEIQNCSFKVNSEIKGKKQDVYALFNSLDIVKLYNNGTSQYRLINCNTSTLT | |
| | QACPKVSFDPIPIHYCAPAGYAILKCNNKTFNGTGPCNNVSTVQCTHGIKPVVSTQLLLNGSLAEGEI | |
| | IIRSKNLTDNTKTIIVHLNESIKINCIRPNNNTRRSIRIGPGQAFYAANGIVGNIRQAHCNISEGEWN | |
| | KTLYRVSRKLAEHFPGKEIKFKPHSGGDLEITTHSFNCRGEFFYCNTSKLFNGTYNGTYTNNDTNSTI | |
| | ILPCRIKQIINMWQEVGKAMYAPPIEGIIACNSTITGLLLTRDGGDKNGSKPEIFRPGGGDMRDNWRS | |
| | ELYKYKVVEIKPLGIAPTKAKERVVEKEKTIQKEAVGIGAVFLGFLGAAGSTMGAASITLTVQARQLL | |
| | SGIVQQQSNLLRAIEAQQHMLQLTVWGIKQLQARVLAMERYLQDQQLLGIWGCSGKLICTTAVPWNSS | |
| | WSNKTLEYIWGNMTWMQWDREIDNYTGIIYDLLEDSQIQQEKNEKDLLALDSWKNLWSWFSITNWLWY | |
| | IK | |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| C.1086 gp120 | MRVRGIWKNWPQWLIWSILGFWIGNMEGSWVTVYYGVPVWKEAKTTLFCASDAKAYEKEVHNVWATHA CVPTDPNPQEMVLANVTENFNMWKNDMVEQMHEDIISLWDESLKPCVKLTPLCVTLNCTNVKGNESDT SEVMKNCSFKATTELKDKKHKVHALFYKLDVVPLNGNSSSGEYRLINCNTSAITQACPKVSFDPIPL HYCAPAGFAILKCNNKTFNGTGPCRNVSTVQCTHGIKPVVSTQLLLNGSLAEEEIIIRSENLTNNAKT IIVHLNESVNIVCTRPNNNTRKSIRIGPGQTFYATGDIIGNIRQAHCNINESKWNNTLQKVGEELAKH FPSKTIKFEPSSGGDELITTHSFNCRGEFFYCNTSDLFNGTYRNGTYNHTGRSSNGTITLQCKIKQII NMWQEVGRAIYAPPIEGEITCNSNITGLLLLRDGGQSNETNDTETFRPGGGDMRDNWRSELYKYKVVE IKPLGVAPTEAKERVVEREKE | 76 |
| C.1086 gp120 Δ7 | MRVRGIWKNWPQWLIWSILGFWIGNMEGSVPVWKEAKTTLFCASDAKAYEKEVHNVWATHACVPTDPN PQEMVLANVTENFNMWKNDMVEQMHEDIISLWDESLKPCVKLTPLCVTLNCTNVKGNESDTSEVMKNC SFKATTELKDKKHKVHALFYKLDVVPLNGNSSSGEYRLINCNTSAITQACPKVSFDPIPLHYCAPAG FAILKCNNKTFNGTGPCRNVSTVQCTHGIKPVVSTQLLLNGSLAEEEIIIRSENLTNNAKTIIVHLNE SVNIVCTRPNNNTRKSIRIGPGQTFYATGDIIGNIRQAHCNINESKWNNTLQKVGEELAKHFPSKTIK FEPSSGGDLEITTHSFNCRGEFFYCNTSDLFNGTYRNGTYNHTGRSSNGTITLQCKIKQIINMWQEVG RAIYAPPIEGEITCNSNITGLLLLRDGGQSNETNDTETFRPGGGDMRDNWRSELYKYKVVEIKPLGVA PTEAKRRVVEREKR | 77 |
| C.1086 gp140 | MRVRGIWKNWPQWLIWSILGFWIGNMEGSWVTVYYGVPVWKEAKTTLFCASDAKAYEKEVHNVWATHA CVPTDPNPQEMVLANVTENFNMWKNDMVEQMHEDIISLWDESLKPCVKLTPLCVTLNCTNVKGNESDT SEVMKNCSFKATTELKDKKHKVHALFYKLDVVPLNGNSSSGEYRLINCNTSAITQACPKVSFDPIPL HYCAPAGFAILKCNNKTNFGTGPCRNVSTVQCTHGIKPVVSTQLLLNGLSAEEEIIIRSENLTNNAKT IIVHLNESVNIVCTRPNNNTRKSIRIGPGQTFYATGDIIGNIRQAHCNINESKWNNTLQKVGEELAKH FPSKTIKFEPSSGGDLEITTHSFNCRGEFFYCNTSDLFNGTYRNGTYNHTGRSSNGTITLQCKIKQII NMWQEVGRAIYAPPIEGEITCNSNITGLLLLRDGGQSNETNDTETFRPGGGDMRDNWRSELYKYKVVE IKPLGVAPTEAKERVVEREKEAVGIGAVFLGFLGAAGSTMGAASMTLTVQARQLLSGIVQQQSNLLRA IEAQQHNLQLTVWGIKQLQARVLAIERYLKDQQLLGMWGCSGKLICTTAVPWNSSWSNKSQNEIWGNM TWMQWDREINNYTNTIYRLLEDSQNQQEKNEKDLLALDSWKNLWNWFKISKWLWYIK | 78 |
| C.1086 V1V2 Tags | METDTLLLWVLLLWVPGSTGDQVKLTPLCVTLNCTNVKGNESDTSEVMKNCSFKATTELKDKKHKVHA LFYKLDVVPLNGNSSSGEYRLINCNTSAITQAGLNDIFEAQKIEWHELEVLFQGPGHHHHHH | 79 |
| C.97ZA012 gp140CF1 | MRVRGIPRNWPQWWMWGILGFWMIIICRVVGNMWVTVYYGVPVWTKADTTLFCASDTKAYDREVHNVW ATHACVPTDPNPQEIVLENVTENFNMWKNDMVDQMHEDIISLWDQSLKPCVKLTPLGVTLHCTNATFK NNVTNDMNKEIRNCSFNTTTEIRDKKQQGYALFYRPDIVLLKENRNNSNNSEYILINCNASTITQACP KVNFDPIPIHYCAPAGYAILKCNNKTFSGKGPCNNVSTVQCTHGIKPVVSTQLLLNGSLAEKEIIIRS ENLTDNVKTIIVHLNKSVEIVCTRPNNNTRKSMRIGPGQTFYATGDIIGDIRQAYCNISGSKWNETLK RVKEKLQENYNNNKTIKFAPSSGGDLEITTHSFNCRGEFFYCNTTRLFNNNATEDETITLPCRIKQII | 80 |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| | NMWQGVGRAMYAPPIAGNITCKSNITGLLLVRDGGEDNKTEEIFRPGGGNMKDNWRSELYKYKVIELK PLGIAPTGAKLTVQARQLLSSIVQQQSNLLRAIEAQQHMLQLTVWGIKQLQTRVLAIERYLKDQQLEI WNNMTWMEWDREISNYTDTIYRLLEDSQTQQEKNEKDLLALDSWKNLWSWFDISNWLW | |
| C.CAP206 gp140CF.12 | MRVRGIPRNWPQWWIWGLLGFWVIITCRVVGQLWVTVYYGVPVWTEAKTTLFCASDAKAYDKEVHNVW ATHACVPTDPNPQEIVLENITENFNMWKNDMVDQMHEDIISLWDQSLKPCVKLTPLCVTLNCTNANIN VTSVSNDSRIMNEEIKNCSFNTTTEIRDKKQRVYALFYRSDVVPLNSSEYILINCNTSTITQACPKVT FDPIPLHYCAPAGYAILKCNNKTFNGAGPCLNVSTVQCTHGIKPVVSTQLLLNGSLAEEEIIIKSKNL TDDTNTIIVHLNKSIEIVCTRPGNNTRKSIRIGPGQTFFATGDIIGDIREAHCNLSKDAWNKTLEQIK GKLKEHGSGKEIKFAPSSGGDPEVATHSFNCRGEFFYCNTTKLFNETYTRSNNSNETIILPCRIKQII NMWQEVGRAMYAPPIAGNITCNSSITGLLLTRDPGHNNTETFRPTGGNMKDNWRNELYKYKVVEIKPL GVAPTNAKERVVEREKEAVGIGAVLLGFLGAAGSTMGAASITLTVQARQLLSGIVQQQSNLLRAIEAQ QHMLQLTVWGIKQLQTRVLAIERYLKDQQLLGLWGCSGRLICTTNVPWNSSWSNKSQEDIWGNMTWMQ WDREISNYTSTIYRLLEDSQNQQEKNEKDLLALDSWKNLWNWFDITKWLWYIR | 81 |
| C.con gp140CF | MRVRGILRNCQQWWIWGILGFWMLMICNVVGNLWVTVYYGVPVWKEAKTTLFCASDAKAYEKEVHNVW ATHACVPTDPNPQEIVLENVTENFNMWKNDMVDQMHEDIISLWDQSLKPCVKLTPLCVTLNCTNATNA TNTMGEIKNCSFNITTELRDKKQKVYALFYRLDIVPLNENNSYRLINCNTSAITQACPKVSFDPIPIH YCAPAGYAILKCNNKTFNGTGPCNNVSTVQCTHGIKPVVSTQLLLNGSLAEEEIIIRSENLTNNAKTI IVHLNEWVEIVCTRPNNNTRKSIRIGPGQTFYATGDIIGDIRQAHCNISEDKWNKTLQKVSKKLKEHF PNKTIKFEPSSGGDLEITTHSFNCRGEFFYCNTSKLFNSTYNSTNSTITLPCRIKQIINMWQEVGRAM YAPPIAGNITCKSNITGLLLTRDGGKNNTETFRPGGGDMRDNWRSELYKYKVVEIKPLGIAPTKAKTL TVQARQLLSGIVQQQSNLLRAIEAQQHMLQLTVWGIKQLQTRVLAIERYLKDQQLLGIWGCSGKLICT TAVPWNSSWSNKSQEDIWDNMTWMQWDREISNYTDTIYRLLEDSQNQQEKNEKDLLALDSWKNLWNWF DITNWLW | 82 |
| C.DU123 gp140 CF | MRVKGIQRNWPQWWIWGILGFWMIIICRVVGNLWVTVYYGVPVWTEAKTTLFCASDAKAYEREVHNVW ATHACVPTDPNPQEIVLGNVTENFNMWKNDMVDQMHEDIISIWDQSLKPCVKLTPLCVTLNCTDVKVN ATSNGTTTYNNSIDSMNGEIKNCSFNITTEIRDKKQKVYALFYRPDVVPLNENSSSYILINCNTSTTT QACPKVSFDPIPIHYCAPAGYAILKCNNKTFNGTGPCHNVSTVQCTHGIKPVVSTQLLLNGSLAEEEI IIRSENLTNNAKTIIVHLNESIEIVCTRPNNNTRKSIRIGPGQTVYATNDIIGDIRQAHCNISKTKWN TTLEKVKEKLKEHFPSKAITFQPHSGGDLEVTTHSFNCRGEFFYCDTTKLFNESNLNTTNTTTLTLPC RIKQIVNMWQGVGRAMYAPPVEGNITCNSSITGLLLVRDGGNTSNSTPEIFRPGGGNMKDNWRSELYK YKVVEIKPLGVAPTKAKTLTVQARQLLSGIVQQQSNLLRAIEAQQHMLQLTVWGIKQLQARVLAIERY LKDQQLLGLWGCSGKLICPTTVPWNSSWSNKSQTDIWDNMTWMQWDREISNYTGTIYKLLEESQNQQE KNEKDLLALDSWKNLWSWFDITNWLW* | 83 |
| Con 6 gp120 | MRVMGIQRNCQHLWRWGTMILGLMLICSAAENLWVTVYYGVPVWKEANTTLFCASDAKAYDTEVHNVW ATHACVPTDPNPQEIVLENVTENFNMWKNNMVEQMHEDIISLWDQSLKPCVKLTPLCVTLNCTNVRNV | 84 |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| | SSNGTETDNEEIKNCSFNITTELRDKKQKVYALFYRLDVVPIDDKNSSEISGKNSSEYYRLINCNTSA | |
| | ITQACPKVSFEPIPIHYCAPAGFAILKCNDKKFNGTGPCKNVSTVQCTHGIKPVVSTQLLLNGSLAEE | |
| | EIIIRSENITNNAKTIIVQLNESVEINCTRPNNNTRKSIGIGPGQAFYATGEIIGDIRQAHCNISRTK | |
| | WNKTLQQVAKKLREHFNNKTIIFKPSSGGDLEITTHSFNCGGEFFYCNTSGLFNSTWMFNGTYMFNGT | |
| | KDNSETITLPCEIKQIINMWQGVGQAMYAPPIEGKITCKSNITGLLLTRDGGNNSNKNKTETFRPGGG | |
| | DMRDNWRSELYKYKVVKIEPLGVAPTKAKRRVVEREKR | |
| CON-S gp140CF1 | MRVRGIQRNCQHLWRWGTLILGMLMICSAAENLWVTVYYGVPVWKEANTTLFCASDAKAYDTEVHNVW | 85 |
| | ATHACVPTDPNPQEIVLENVTENFNMWKNNMVEQMHEDIISLWDQSLKPCVKLTPLCVTLNCTNVNVT | |
| | NTTNNTEEKGEIKNCSFNITTEIRDKKQKVYALFYRLDVVPIDDNNNNSSNYRLINCNTSAITQACPK | |
| | VSFEPIPIHYCAPAGFAILKCNDKKFNGTGPCKNVSTVQCTHGIKPVVSTQLLLNGSLAEEEIIIRSE | |
| | NITNNAKTIIVQLNESVEINCTRPNNNTRKSIRIGPGQAFYATGDIIGDIRQAHCNISGTKWNKTLQQ | |
| | VAKKLREHFNNKTIIFKPSSGGDLEITTHSFNCRGEFFYCNTSGLFNSTWIGNGTKNNNNTNDTITLP | |
| | CRIKQIINMWQGVGQAMYAPPIEGKITCKSNITGLLLTRDGGNNNTNETEIFRPGGGDMRDNWRSELY | |
| | KYKVVKIEPLGVAPTKAKLTVQARQLLSGIVQQQSNLLRAIEAQQHLLQLTVWGIKQLQARVLAVERY | |
| | LKDQQLEIWDNMTWMEWEREINNYTDIIYSLIEESQNQQEKNEQELLALDKWASLWNWFDITNWLW | |
| G.con gp140CF | MRVKGIQRNWQHLWKWGTLILGLVIICSASNNLWVTVYYGVPVWEDADTTLFCASDAKAYSTERHNVW | 86 |
| | ATHACVPTDPNPQEITLENVTENFNMWKNNMVEQMHEDIISLWDESLKPCVKLTPLCVTLNCTDVNVT | |
| | NNNTNNNTKKEIKNCSFNITTEIRDKKKKEYALFYRLDVVPINDNGNSSIYRLINCNVSTIKQACPKVT | |
| | FDPIPIHYCAPAGFAILKCRDKKFNGTGPCKNVSTVQCTHGIKPVVSTQLLLNGSLAEEEIIIRSENI | |
| | TDNTKVIIVQLNETIEINCTRPNNNTRKSIRIGPGQAFYATGDIIGDIRQAHCNVSRTKWNEMLQKVK | |
| | AQLKKIFNKSITFNSSSGGDLEITTHSFNCRGEFFYCNTSGLFNNSLLNSTNSTITLPCKIKQIVRMW | |
| | QRVGQAMYAPPIAGNITCRSNITGLLLTRDGGNNNTETFRPGGGDMRDNWRSELYKYKIVKIKPLGVA | |
| | PTRARTLTVQVRQLLSGIVQQQSNLLRAIEAQQHLLQLTVWGIKQLQARVLAVERYLKDQQLLGIWGC | |
| | SGKLICTTNVPWNTSWSNKSYNEIWDNMTWIEWEREISNYTQQIYSLIEESQNQQEKNEQDLLALDKW | |
| | ASLWNWFDITKWLW | |
| G.DCRB gp140CF | MRVKGIQRNWQHLWNWGILILGLVIICSAEKLWVTVYYGVPVWEDANAPLFCASDAKAHSTESHNIWA | 87 |
| | THACVPTDPSPQEINMRNVTENFNMWKNNMVEQMHEDIISLWDESLKPCVKLTPLCVTLNCTEINNS | |
| | TRNITEEYRMTNCSFNMTTELRDKKKAEYALFYRTDVVPINEMNNENNGTNSTWYRLTNCNVSTIKQA | |
| | CPKVTFEPIPIHYCAPAGFAILKCVDKKFNGTGTCNNVSTVQCTHGIKPVVSTQLLLNGSLAEKDIII | |
| | SSENISDNAKVIIVHLNRSVEINCTRPNNNTRRSVAIGPGQAFYTTGEVIGDIRKAHCNVSWTKWNET | |
| | LRDVQAKLQEYFINKSIEFNSSSGGDLEITTHSFNCGGEFFYCNTSGLFNNSILKSNISENNDTITLN | |
| | CKIKQIVRMWQRVGQAMYAPPIAGNITCRSNITGLILTRDGGDNNSTSEIFRPGGGDMKNNWRSELYK | |

TABLE 19-continued

Amino acid sequences of peptides and envelope glycoproteins tested
For Case A2, A.92RW020, B.HXB2/BAL, C.97ZA012 and ZM109 V1V2 constructs were scaffold with
JO8 protein (McLellan et al, Nature 480:336:343 (2011) or with MuLV gp70 protein (Pinter et al,
Vaccine 16:1803-1811 (1998)). For E. A244 V1V2-Tags design, V1V2 construct was made with an n-
terminal Ig VH leader sequence as well as an AVI tag and HIS tag at the C-terminal end for
labeling and purification respectively (see SOM methods).

| HIV-1 Env | a.a sequence | SEQ ID NO: |
|---|---|---|
| | YKTVKIKSLGIAPTRARTLTVQVRQLLSGIVQQQSNLLRAIEAQQHLLQLTVWGIKQLRARVLALERY | |
| | LKDQQLLGIWGCSGKLICTTNVPWNTSWSNKSYNEIWENMTWIEWEREIDNYTYHIYSLIEQSQIQQE | |
| | KNEQDLLALDQWASLWSW | |
| US-1 SIVCPZ gp140CF | MKVMEKKKRLWLSYCLLSSLIIPGLSSLWATVYYGVPVWRDVETTLFCASDAKAYKQEAHNIWATQAC | 88 |
| | VPTDPNPQEVHLPNVTEKFDMWENNMAEQMQEDIISLWDQSLKPCIKLTPLCVTMTCLNPDSNSSAVN | |
| | TTDIMRNCSFNITTELRDKKKQVYSLFYVDDLAHINNNTYRLINCNTTAITQACPKTSFEPIPIHYCA | |
| | PPGFAILKCNEKDFKGKGECKNVSTVQCTHGIKPVVTTQLIINGSLATNKVTVRSKNFADIILVQFSE | |
| | GVNMTCIRPGNNTVGNVQLGPGMTFYNIPKIVGDVREAHCNISKLTWEKQRKYTLEIIKKEANLTKVE | |
| | LIPNAGGDPEVVNMMLNCGGEFFYCNTIPLFNMTYNNTDNTTITLKCRIRQIVNQWMRVGKGIFAPPI | |
| | KGVLSCNSNITGMILDISISAVNNDSRNITVMPTGGDMTALWKNELHKYKVVSIEPIGVAPGKAKVLT | |
| | VQARQLLSGIVQQQNNLLRAIEAQQGLLQLSVWGIKQLQARVLAVERYLKDQQILGLWGCSGKTICYT | |
| | TVPWNDTWSNNLSYDAIWGNLTWQEWDRKVRNYSGTIFSLIEQAQEQQNTNEKSLLELDQWSSLWNWF | |
| | DITNWLW | |

TABLE 20

Binding of Anti-HIV-1 Env mAbs to scaffold V1V2
recombinant proteins and linear V1V2peptides.

| Scaffold | EC50 (nM) | | | | | |
|---|---|---|---|---|---|---|
| | CH58 | CH59 | PG9 | PG16 | CH01 | 697D |
| gp70 A.92RW020V1V2 | 0.03 | 235 | — | — | — | 14 |
| gp70 A.92RW020V1V2/N156QN160Q | 0.64 | — | — | — | — | 94 |
| J08 A.92RW020V1V2 | 0.22 | 377 | 64 | — | — | 0.07 |
| J08 A.92RW020VV1V2/N156QN160Q | 3 | — | — | — | — | 661 |
| gp70 B.HXB2/BALV1V2 | >667 | — | 157 | — | — | 0.64 |
| gp70 B.HXB2/BALV1V2/N156QN160Q | 146 | — | — | — | — | >667 |
| gp70 B.CaseAV1V2 | 72 | — | — | — | — | 0.05 |
| gp70 B.CaseA2V1V2/N156QN160Q | >667 | — | — | — | — | 9 |
| J08 B.HXB2/BALV1V2 | >667 | — | 149 | — | — | 0.12 |
| J08 B.HXB2/BALV1V2N156QN160Q | >667 | — | — | — | — | 66 |
| J08 C.97ZA012V1V2 | — | 107 | — | — | — | 0.06 |
| J08 C.97ZA012V1V2N156QN160Q | — | >667 | — | — | — | 2 |
| J08 C.ZM109.V1V2 | — | 1.16 | 0.23 | 0.24 | — | 3 |
| J08 C.ZM109V1V2 N173D | — | 22 | 3 | >667 | — | 0.41 |

*A., B. and C. represent the clades of HIV-1 V1V2 Env. Positive results with EC50 above the highest tested concentration (>667 nM) are indicated as >667 nM. Negative results are indicated with a "—".

Reactivity of RV144 Vaccinee Plasma with V1V2 Scaffold Proteins

Figure 34:
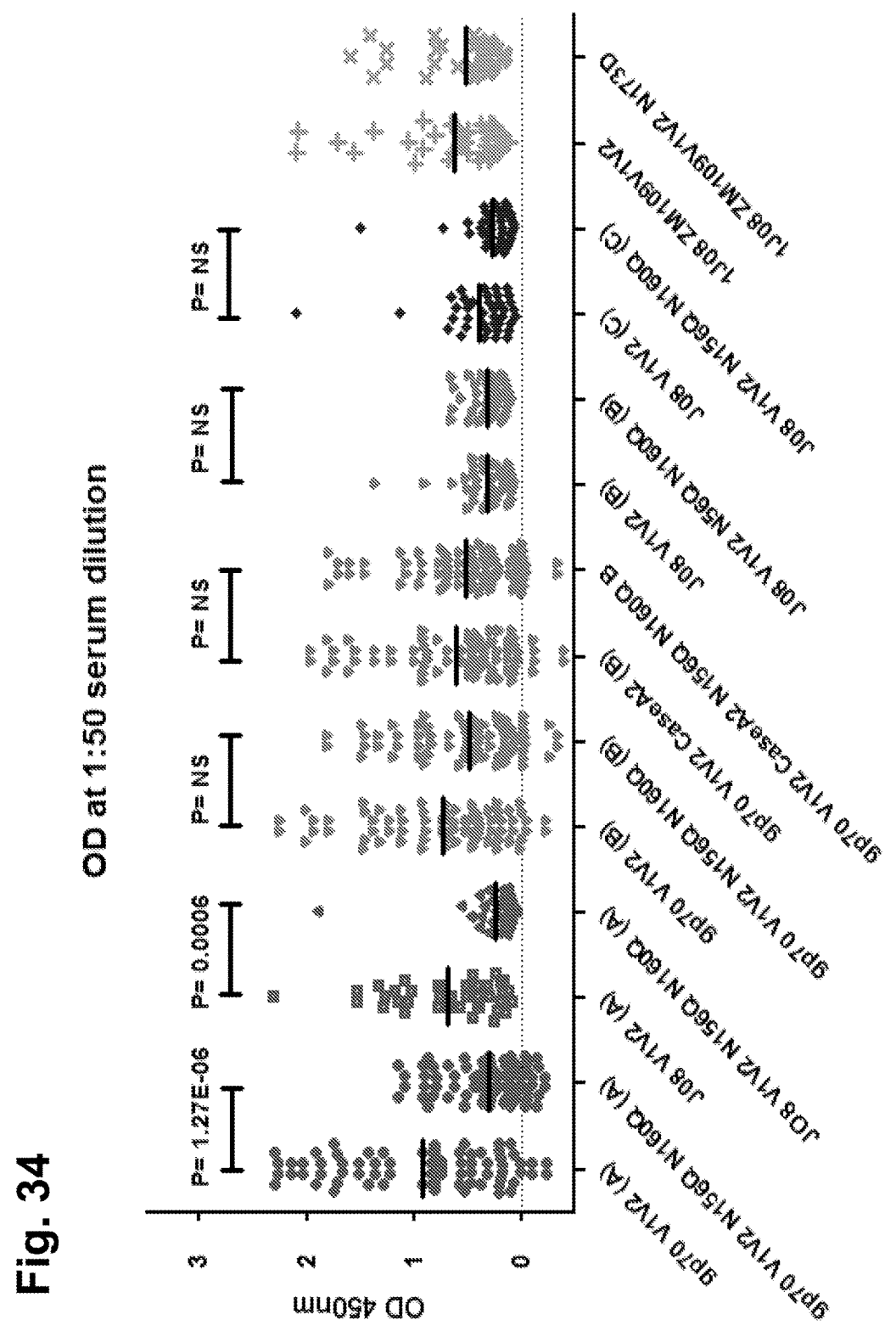

A determination was next made with whether the RV144 vaccines immunized with ALVAC/AIDSVAX B/E vaccine or rhesus macaques immunized with A244 gp120 reacted with V1V2 scaffolds in a manner similar to CH58 and CH59 antibodies. FIG. 34 shows reactivity of 80 RV144 vaccine plasma with V1V2 scaffolds and demonstrated significant binding dependence on the clade A V1V2 scaffolds on N160, N156, but not for N160, N156-mutated clade B or C V1V2 scaffolds. Similarly, immunization of rhesus macaques with A244 gp120 recombinant Env demonstrated the same dependence on N160, N156 for optimal induced antibody binding. While macaques had a robust plasma antibody response to the V2 aa 168-182 peptide (KKKVHALFYKL-DIV) (SEQ ID NO: 13) (FIG. 45). Thus, humans and rhesus macaques made similar RV144 E.Env-induced CH58 and CH59-like plasma V2 antibodies.

Reactivity of Unmutated Ancestor Antibodies of RV144 V2 and V2 V3 BbAbs

Finally, reverted unmutated ancestor antibodies (RUA) were constructed as models for nave B cell receptors for CH58, CH59, PG9/PG16, CH01-CH04 and 697D mAbs, and their reactivity was compared to 43 recombinant Envs or V1V2 scaffold constructs (FIGS. 46A-46F). A new V1V2 construct is the gp120 V1V2 region expressed with the Ig leader sequence and avi-tag and His6-tag (SEQ ID NO: 10) (V1V2 tags) (FIG. 47). It was found that whereas the mature CH58 and CH59 antibodies reacted with 27/43 and 15/43 of the Env constructs, respectively, their RUAs reacted with only 5/43 (FIGS. 46A, 46B). Remarkably, although CH58 and CH59 are from different VH families, their RUAs reacted with the same Env constructs (E.A244 gp120 A 11, E.A244 V1V2 tag, C.1086 gp120Δ7, C.1086 gp70 V1V2 scaffold and C.1086 V1V2 tag proteins (FIGS. 46A-46D, Table 21).

Potential Protective Roles of RV144 V2 Antibodies

Eighty-nine percent of infections in the RV144 efficacy trial were circulating recombinant form (CRF) AE_01 HIV-1 strains (Rerks-Ngarm, N. Engl. J. Med. 361:2209-2220 (2009)). That Env analysis of these infections demonstrated a signature in V1V2 at K169 suggests the hypothesis that RV144 V2 antibodies such as CH58 and CH59 may have mediated, in as yet undefined manner, immune pressure at that site (Rolland et al, Nature submitted (2011)). Based on effector functions that can be mediated in vitro by mAbs, CH58 and CH59, three potential mechanisms of protection are: a) inhibition of mAb virion traversing mucosal barriers by virion binding, b) neutralization of susceptible CRF AE_01 HIV-1 strains, and c) binding to CRF AE_01 virus-infected CD4 T cells and mediation of ADCC. Virus capture by CH58 and CH59 was relatively weak compared to V2V3 BnAbs capture of C.CAP45 virus (Table 16). Most transmitted/founder viruses are Tier 2 in neutralization sensitivity, yet CH58 and CH159 neutralized only Tier 1 strains. However, CH58 and CH59 mAbs did bind to Env on Tier 2 infected CD4 T cells and mediated ADCC (FIGS. 35A, 35B). In the correlates of risk analysis of immune effector functions that predicted risk of infection, two correlates or infection risk were found: plasma IgA Env levels that directly correlated with infection risk, and plasma Env V1V2 IgG levels that inversely correlated with infection risk (Haynes et al, N. Engl. Med. In press (Apr. 4, 2012)). While as single variables, neutralizing antibodies and ADCC were not significant correlates of risk of infection, interaction analyses with IgA Env levels demonstrated that, in the presence of low IgA Env antibodies, both neutralizing antibodies and ADCC correlated with low risk of infection, while in the presence of high IgA Env antibodies, there were no correlations (Haynes et al, N. Engl. Med. In press (Apr. 4, 2012)). Direct conformation of protective roles of V2 antibody neutralization and ADCC will require passive protection studies with R5 AE SHIVs, and correlates analyses of future efficacy trials.

TABLE 21

Binding of recombinant HIV-1 Envs and select V1V2 recombinant constructs by mature mutated RV144 V2, V2V3 BnAbs and V2 conformational mAb and their reverted unmutated ancestor antibodies (RUAs) in ELISA.

| | EC50, nM | | | | | | | | | | | |
|---|---|---|---|---|---|---|---|---|---|---|---|---|
| HIV-1 Env* | CH58 | CH59A | CH01 | 697D | PG9 | PG16 | CH5 RUA | CH59 RUA | CH01 RUA | 697D RUA | PG9 RUA | PG16 RUA |
| E. A244 V1V2 Tags | 0.02 | 0.014 | 8.9 | 0.1 | 1.1 | 3.7 | 4.9 | 0.13 | >667 | NB | NB | NB |
| E.A244gp12Δ11 | 0.07 | 0.087 | 0.47 | 0.23 | 0.53 | 37.6 | >667 | 15.5 | 8.33 | >667 | NB | NB |
| C.1086V1V2 Tags | 0.08 | 0.1 | NB | 0.23 | >667 | NB | >667 | 50.1 | NB | NB | NB | NB |
| C.1086gp70V1V2 | 0.05 | 0.067 | NB | 0.067 | NB | NB | >66.7 | 11.3 | NB | NB | NB | NB |
| C.1086C gp120Δ7 | 0.055 | 0.07 | NB | 0.02 | NB | NB | >667 | 66.7 | NB | NB | NB | NB |
| A.Q23V1V2 Tags | >66.7 | NB | >66.7 | >66.7 | 14.94 | >66.7 | NB | NB | NB | >667 | NB | NB |
| B.6240 gp140C | NB | NB | >667 | 0.016 | 0.3 | 10.3 | NB | NB | NB | 0.19 | NB | NB |
| gp70 B.CaseA2 V1V2 | >667 | NB | NB | 0.33 | NB | NB | NB | NB | NB | >667 | NB | NB |

*E., B. and C. represent the clades of HIV-1 Env.

Positive results with EC50 above the highest tested concentration (100 ug/ml) are indicated as >667 nM; NB = no detectable binding.

Interestingly the RV144 mutated V2 Abs (CH58, CH59), the mutated V2V3 bnAbs (CHO1, PG9, PG16) and the mutated V2 conformational mAb (697D) all reacted with the E.A244 V1V2 tags construct that contains the full V1V2 region of HIV-1 RV144 vaccine component Env E.A244 gp120 with only C terminal avi-tag and His6-tag (SEQ ID NO: 10) (FIGS. 47 and 48). PG9 bound to E.A244 tags protein with a Kd of 83.3 nM while CH58 bound to E.A244 V1V2 tags with a Kd of 0.33 nM (FIGS. 48A, 48B, Table 12). The slower on-rate for binding to E.A244 V1V2 tags protein of PG9 (~40-fold) is hypothesized to be due to additional requirement of glycan interactions. That both CH58 and P69 (with two different V2 crystal structures recognized) reacted with the E.A244 V1V2 tags recombinant protein suggested that the E.A244 V1V2 tags protein can exist in alternate conformations. This question will be resolved by crystal structures of each mAb with this A244 V1V2 protein.

Finally, ⅔ of the Env constructs that reacted with the RUAs of CH58 and CH59 (A244 gp120)11, A244 V1V2 tag scaffold) also reacted with the RUAs of CH01-CH04 V2V3 bnAb clonal lineage (FIGS. 46E-46G, Table 21). In contrast, in spite of similarities of RUA HCDR3s of CH58, CH59 and PG9 and PG16 (FIG. 37) none of the 43 Envs tested reacted with RUAs of PG9 (FIGS. 46H-46I) or PG16 (FIGS. 46J-46K, Table 21). Similarly, the RUA of mAb 697D did not react with any of Env constructs bound by the RUAs of CH01-04, PG9/PG16, CH58 or CH59, but did bind with B.6240 gp140 and B.gp70V1V2 CaseA2 protein ( ) Pinter et al, Vaccine 16:1803-1811 (1998)) (FIGS. 46H-46I, Table 21).

A Common Pathway Vaccine V2 and Broad Neutralizing V2V3 Antibodies?

That RV144 mature V2 mAbs bind to the same gp 120 region as mature V2V3 BnAbs, that CH58 has HCDR3 similarities with PG9/PG16, and the CH58 and CH59 inferred RUAs bind the same V1V2 constructs as the CH01-CH04 V2V3 bnAb lineage, raise the hypothesis that the RV144 vaccine-induced V1V2 antibodies may share early stages of a maturation pathway similar to that followed by some antibodies targeting the V2V3 BnAb epitope. However, it is critical to note that in the RV144 trial, the ALVAC/AIDSVAX vaccine only induced serum Tier 1 neutralizing antibodies with no Tier 2 BnAb activity seen (Montefiori, J. Infect. Dig. In press (2012)). Moreover, vaccine-induced V2 antibodies lacked the degree of somatic mutation to achieve broadly-neutralizing, glycan-dependent binding to V1V2 PG9 epitope, and the RV144-induced antibodies arose from naïve B cells with B cell receptor HCDR3s that are shorter (13-19 aa) than for PG9/PG16 or CH01-CH04 bnAb lineages (28/25 aa). The lack of CH58 and CH59 mAbs to interact with glycans likely represents a hurdle for CH58 or CH59 to penetrate past the glycans and interact well with the aa 168-181 of V1V2 on Tier 2 HIV-1 native trimers, a feat that is well suited for glycan-dependent antibodies like PG9 that completely engulf glycans associated with N160 and N156 (McLellan et al, Nature 480:336-343 (2011)). Alternatively, the conformations of V1V2 may differ on Tier 1 versus Tier 2 native trimers. In either case, RV144 CH58 and CH59 V2 mAbs are not fully adapted for the property of immune recognition of glycans that might be acquired under immune selection.

A key task for the HIV-1 vaccine development field is to improve on level of vaccine efficacy seen in the RV144 clinical trial with subsequent vaccine designs. One approach may be to determine if continued boosting of subjects with the RV144 B/E Envs plus ALVAC (or their variations) will result in antibodies with greater somatic mutations than CH58 and CH59 that lead to glycan binding. Alternatively, to achieve greater somatic mutations in vaccine-induced antibodies, it may be necessary to target unmutated common ancestor and intermediate forms of V2 antibodies (e.g. with new constructs such as E.A244 V1V2 tags) to drive otherwise unusual and subdominant antibody development pathways to mature into robust germinal center clonal lineages (Bonsignori et al, J. Virol. 85:9998-10009 (2011), Ma et al, PLoS Pathog. 7:e1002200 (2011), Xiao et al, Viruses 1:802-817 (2009), Alam et al, J. Virol. 85:11725-11731 (2011), Wu et al, Science 333:1593-1602 (2011)).

Example 3

In the studies described below, the specificities and effector functions of four V2 monoclonal antibodies (mAbs) isolated from RV144 ALVAC/AIDSVAX vaccine recipients have been probed, and the crystal structures determined of two of these mAbs with V2 peptides containing position 169.

It is shown that V2 residue 169 is in a structurally polymorphic region of HIV-1, thus revealing that immune responses to such regions of HIV-1 Env correlated with decreased transmission. It is also shown that the V2 antibodies isolated from RV144 vaccines mediated ADCC against RV144 trial breakthrough Env-target cells, and this ADCC activity was dependent on position 169 in breakthrough Envs. These data directly demonstrate the ability of the isolated V2 antibodies to mediate immune pressure targeted at position 169 of Env V2.

Experimental Details

Production of Recombinant Antibodies.

Three RV144 vaccine-recipients 347759, 200134, and 302689 were studied for isolation of HIV-1 antibodies. Twenty-six weeks after RV144 vaccination, all these 3 vaccine recipients developed antibodies to vaccine immunogens, MN, A244 and 92TH023 gp120 (Table 31). MAbs CH58 and CH59 were isolated from RV144 vaccine-recipient 347759, mAb HG107 was isolated from RV144 vaccine-recipient 200134, and mAb HG120 was isolated from RV144 vaccine-recipient 302689 (Table 31) by screening clonal cultures of memory B cells as described (Bonsignori et al, J. Virol. 85:9998-10009 (2011)). VH and VL genes of 697D (Gorny et al, J. Virol. 68:8312-8320 (1994)) were obtained from M. Gorny, and S. Zolla-Pazner (New York University, NY). VH and VL genes of mAbs CH58, CH59, HG107 and HG120 were isolated by RT/PCR, annotated by using SoDa, and used to generate full-length heavy and light Ig gene expression plasmids using the methods as described (Liao et al, J Exp Med 208:2237-2249 (2011), Liao et al, J Virol Methods 158, 171-179 (2009), Volpe et al, Bioinformatics 22:438-444 (2006)).

TABLE 31

Comparison of the binding of a broad panel of HIV-1 Envs to the plasma IgG purified from three RV144 vaccinees from whom CH58, CH59, HG107 and HG120 were isolated.

| | EC50, ug/ml purified plasma IgG | | | EC50, ug/ml mAb | | | |
|---|---|---|---|---|---|---|---|
| HIV-1 Envs | 200134 | 302869 | 347759 | CH58 | CH59 | HG107 | HG120 |
| AE.A244 gp120gD+ | 18.6 | 98.7 | 49.4 | 0.027 | 0.01 | 0.03 | 0.02 |
| AE.92TH023 gp12 gD+ | 10.5 | 17.8 | 7.9 | 0.036 | 0.023 | 0.04 | 0.02 |
| AE.97CNG2XF gp140CF | 42.2 | >200 | 194.2 | 0.07 | 0.066 | 0.055 | 0.06 |
| A.92RW020 gp140CFI | 91.8 | >200 | >200 | 0.2 | NB | NB | NB |
| A1.con_env03 gp140CF | 93.6 | >200 | 194.9 | 0.8 | NB | NB | NB |
| B.MN gp120 gD | 12.6 | 12.9 | 7.5 | NB | NB | NB | NB |
| B.9021V1/V2 tags | >200 | >200 | >200 | NB | NB | NB | NB |
| B.1059 gp120 | 47.7 | 59.7 | 51 | NB | NB | NB | NB |
| B.HxB/Ba gp140 CFI | 210.4 | 132.5 | >200 | NB | NB | NB | NB |
| B.63521 gp120 | 30.6 | 42.3 | 35 | NB | NB | NB | NB |
| B.9021 GP140C | 164.5 | 129.3 | >100 | NB | NB | NB | NB |
| B.JRFL gp140CF | 90.4 | 125.3 | >100 | NB | NB | NB | NB |
| B.Yu2 gp140i | 69.6 | >200 | >200 | NB | NB | NB | NB |
| C.97ZA012 gp140CFI | 77.9 | >200 | >200 | NB | NB | NB | NB |
| C.089C gp140C | 44.4 | >200 | 74.2 | NB | NB | NB | NB |
| C.1086 gp120 | 8.7 | 18.6 | 8.1 | 0.027 | 0.02 | 0.03 | 0.02 |
| C.DU123 gp140C | 119.8 | >200 | >100 | 0.14 | NB | NB | NB |
| G.DRCBL gp140CF | 74.7 | >200 | >200 | NB | NB | NB | NB |
| SIV CPZ US-1 gp140CF | >200 | 124.6 | >200 | NB | NB | NB | NB |

It should be noted that because of few frozen vials peripheral blood mononuclear cells from the RV144 trial were available, studies could not be performed to determine the frequency of V2-reactive B cells in fresh peripheral blood memory B cells. However, in the memory B cell culture system used to isolate CH58 and CH59 (Bonsignori et al, J. Virol. 85:9998-10009 (2011)), of 5,232 IgG+ memory B cell cultures, 5 cultures were scored as positive for V2 reactivity in the initial 20 culture screen. This yielded a frequency of V2-reactive memory B cells of 0.096%. This frequency of V2 antibody producing B cells is comparable to the frequency of immunodominant V3 antibody producing B cells (0.13%) induced in the VAX004 HIV vaccine clinical trial (Bonsignori et al, J Immunol 183:2708-2717 (2009)).

The reverted unmutated ancestor antibodies (UAs) of the VH and VL sequences of CH58, CH59, CH01, 697D, PG9 and PG16 (Table 29) were inferred as described (Bonsignori et al, J. Virol. 85:9998-10009 (2011), Ma et al, PLoS Pathog 7:e1002200 (2011), Liao et al, J Exp Med 208:2237-2249 (2011), Haynes et al, Nat Biotechnol 30, 423-433, doi: 10.1038/nbt.2197 (2012)). Where there were ambiguous nucleotides due to uncertainty regarding allele variants, n-additions and somatic mutations, each UA candidate was produced. Recombinant CH58, CH59, 697D, and their UA antibodies as well as UA antibodies of PG9 and PG16 were produced as described (Liao et al, J Exp Med 208:2237-2249 (2011)). CH01 mAb and its UA antibodies were produced as described (Bonsignori et al, J. Virol. 85:9998-10009 (2011)). V1/V2-directed quaternary mAbs PG9 and PG16 (Walker et al, Science 326:285-289 (2009)) were provided by D. Burton (Scripps Institute, La Jolla, Calif. and IAVI, New York, N.Y.). MAb 7B2 (James Robinson, Tulane University, LA) and Synagis (MedImmune, LLC; Gaithersburg, Md.), a human anti-respiratory syncytial virus mAb, were used as negative controls.

TABLE 29A

Variable regions of heavy-(VH) and light-chain (VL) gene sequences of
UAs of mAbs CH58, CH59, 697D, PG9 and PG16.
Table 29A discloses SEQ ID NOS 89-102, respectively, in order of appearance.

```
>CH58VH_UA
GAGGTGCAGCTGGTGCAGTCTGGAGCAGAGGTGAAAAAGCCGGGGGAGTCTCTGAAGATCTCCTGTAAGGGTTCTGGATACA
GCTTTACCAGCTACTGGATCGGCTGGGTGCGCCAGATGCCCGGGAAAGGCCTGGAGTGGATGGGGATCATCTATCCTGGTGA
CTCTGATACCAGATACAGCCCGTCCTTCCAAGGCCAGGTCACCATCTCAGCCGACAAGTCCATCAGCACCGCCTACCTGCAG
TGGAGGAGCCTGAAGGCCTCGGACACCGCCATGTATTACTGTGCGAGACTTGGCGGCAGGTATTACTATGATAGTAGTGGTT
ATTACTACTTTGACTACTGGGGCCAGGGAACCCTGGTCACCGTCTCCTCA

>CH58VL_UA
AATTTTAZGCTGACTCAGCCCCACTCTGTGTCGGAGTCTCCGGGGAAGACGGTAACCATCTCCTGCACCCGCAGCAGTGGCA
GCATTGCCAGCAACTATGTGCAGTGGTACCAGGAGCGCCCGGGCAGTTCCCCCACCACTGTGATCTATGAGGATAACCAAAG
ACCCTCTGGGGTCCCTGATCGGTTCTCTGGCTCCATCGACAGCTCCTCCAACTCTGCCTCCCTCACCATCTCTGGACTGAAG
ACTGAGGACGAGGCTGACTACTACTGTCAGTCTTATGATAGCAGCTCTTGGGTGTTCGGCGGAGGGACCAAGCTGACCGTCC
TA

>CH59VH_UA
GAAGTGCAGCTGGTGGAGTCTGGGGGAGGCTTGGTACAGCCTGGCAGGTCCCTGAGACTCTCCTGTGCAGCCTCTGGATTCA
CCTTTGATGATTATGCCATGCACTGGGTCCGGCAAGCTCCAGGGAAGGGCCTGGAGTGGGTCTCAGGTATTAGTTGGAATAG
TGGTAGCATAGGCTATGCGGACTCTGTGAAGGGCCGATTCACCATCTCCAGAGACAACGCCAAGAACTCCCTGTATCTGCAA
ATGAACAGTCTGAGAGCTGAGGACACGGCCTTGTATTACTGTGCAAAAGATTCTCCGCGGGGGGAGCTACCCTTTGACTACT
GGGGCCAGGGAACCCTGGTCACCGTCTCCTCA

>CH59L_UA
TCCTATEAGCTGACACAGCCACCCTCGGTGTCAGTGTCCCCAGGACAAACGGCCAGGATCACCTGCTCTGGAGATGCATTGC
CAAAAAAATATGCTTATTGGTACCAGCAGAAGTCAGGCCAGGCCCCTGTGCTGGTCATCTATGAGGACAGCAAACGACCCTC
CGGGATCCCTGAGAGATTCTCTGGCTCCAGCTCAGGGACAATGGCCACCTTGACTATCAGTGGGGCCCAGGTGGAGGATGAA
GCTGACTACTACTGTTACTCAACAGACAGCAGTGGTAATCATAGGGTGTTCGGCGGAGGGACCAAGCTGACCGTCCTA

>697DVH_UA
CAGGTCCAGCTGGTGCAATCTGGGGCTGAGGTGAAGAAGCCTGGGTCCTCGGTGAAGGTCTCCTGCAAGGCTTCTGGAGGCA
CCTTCAGCAGCTATACTATCAGCTGGGTGCGACAGGCCCCTGGACAAGGGCTTGAGTGGATGGGAAGGATCATCCCTATCCT
TGGTATAGCAAACTACGCACAGAAGTTCCAGGGCAGAGTCACGATTACCGCGGACAAATCCACGAGCACAGCCTACATGGAG
CTGAGGAGCCTGAGATCTGAGGACACGGCCGTGTATTACTGTGCGACATCTGGGGTGGGACTACACTTCGGCTACTTTGACT
ACTGGGGCCAGGGAACCCTGGTCACCGTCTCCTCA

>697D_VL_UA
CAGTCTGT6CTGACGCAGCCGCCCTCAGTGTCTGGGGCCCAGGGCAGAGGGTCACCATCTCCTGCACTGGGAGGAGCTCCA
ACATCGGGGCAggTTATGATGTaCACTGGTACCAGCAGCTTCCAGGAACAGCCCCCAAACTCCTCATCTATGGTAACAGCAA
TCGGCCCTCAGGGGTCCCTGACCGATTCTCTGGCTCCAAGTCTGGCACCTCAGCCTCCCTGGCCATCACTGGGCTCCAGGCT
GAGGATGAGGCTGATTATTACTGCCAGTCCTATGACAGCAGCCTGAGTGGTTATGTCTTCGGAACTGGGACCAAGGTCACCG
TCCTA

>CH01VH_UA1
GAGGTGCAGCTGGTGGAGTCTGGGGGAGGTGTGGTACGGCCTGGGGGGTCCCTGAGACTCTCCTGTGCAGCCTCTGGATTCA
CCTTTGATGATTATGGCATGAGCTGGGTCCGCCAAGCTCCAGGGAAGGGGCTGGAGTGGGTCTCTGGTATTAATTGGAATGG
TGGTAGCACAGGTTATGCAGACTCTGTGAAGGGCCGATTCACCATCTCCAGAGACAACGCCAAGAACTCCCTGTATCTGCAA
ATGAACAGTCTGAGAGCCGAGGACACGGCCTTgTATTACTGTGCGAGAGGGACCGATTACACTATTGACGACCAGGGGATCC
GTTATCAAGGTTCGGGGACCTTCTGGTACTTCGATCTCTGGGGCCGTGGCACCCTGGTCACTGTCTCCTCA
```

TABLE 29A-continued

Variable regions of heavy-(VH) and light-chain (VL) gene sequences of UAs of mAbs CH58, CH59, 697D, PG9 and PG16.
Table 29A discloses SEQ ID NOS 89-102, respectively, in order of appearance.

>CH01VH_UA2
GAGGTGCAGCTGGTGGAGTCTGGGGGAGGTGTGGTACGCCTGGGGGGTCCCTGAGACTCTCCTGTGCAGCCTCTGGATTCA
CCTTTGATGATTATGGCATGAGCTGGGTCCGCCAAGCTCCAGGGAAGGGGCTGGAGTGGGTCTCTGGTATTAATTGGAATGG
TGGTAGCACAGGTTATGCAGACTCTGTGAAGGGCCGATTCACCATCTCCAGAGACAACGCCAAGAACTCCCTGTATCTGCAA
ATGAACAGTCTGAGAGCCGAGGACACGGCCTTgTATTACTGTGCGAGAGGGACCGATTACACTATTGACGACCAGGGGATCC
TTTATCAAGGTTCGGGGACCTTCTGGTACTTCGATCTCTGGGGCCGTGGCACCCTGGTCACTGTCTCCTCA

>CH01VH_UA3
GAGGTGCAGCTGGTGGAGTCTGGGGGAGGTGTGGTACGGCCTGGGGGGTCCCTGAGACTCTCCTGTGCAGCCTCTGGATTCA
CCTTTGATGATTATGGCATGAGCTGGGTCCGCCAAGCTCCAGGGAAGGGGCTGGAGTGGGTCTCTGGTATTAATTGGAATGG
TGGTAGCACAGGTTATGCAGACTCTGTGAAGGGCCGATTCACCATCTCCAGAGACAACGCCAAGAACTCCCTGTATCTGCAA
ATGAACAGTCTGAGAGCCGAGGACACGGCCTTGTATCACTGTGCGAGAGGGACCGATTACACTATTGACGACCAGGGGATCC
ATTACTATGGTTCGGGGACCTACTGGTACTTCGATCTCTGGGGCCGTGGCACCCTGGTCACTGTCTCCTCA

>CH-1VK_UA
GAAATTGTGTTGACGCAGTCTCCAGGCACCCTGTCTTTGTCTCCAGGGGAAAGAGCCACCCTCTCCTGCAGGGCCAGTCAGA
GTGTTAGCAGCAGCTACTTAGCCTGGTACCAGCAGAAACCTGGCCAGGCTCCCAGGCTCCTCATCTATGGTGCATCCAGGAG
GGCCACTGGCATCCCAGACAGGTTCAGTGGCAGTGGGTCTGGGACAGACTTCACTCTCACCATCAGCAGACTGGAGCCTGAA
GATTTTGCAGTGTATTACTGTCAGCAGTATGGTAGCTCCCCGTACACGTTCGGCCAAGGGACCAAGGTGGAAATCaaa >PG9VH_UA
CAGGTGCAGCTGGTGGAGTCTGGGGGAGGCGTGGTCCAGCCTGGGAGGTCCCTGAGACTCTCCTGTGCAGCGTCTGGATTCA
CCTTCAGTAGCTATGGCATGCACTGGGTCCGCCAGGCTCCAGGCAAGGGGCTGGAGTGGGTGGCAGTTATATCATATGATGG
AAGTAATAAATACTATGCAGACTCCGTGAAGGGCCGATTCACCATCTCCAGAGACAATTCCAAGAACACGCTGTATCTGCAA
ATGAACAGCCTGAGAGCCGAGGACACGGCTGTGTATTACTGTGCGAGAGAGGCTGGTGGGCCCGACTACGTAATGGGTACA
ACTATTACGATTTTTGGAGTGGTTATTATAACTACTACTACATGGACGTCTGGGGCAAAGGGACCACGGTCACCGTCTCCTCA >PG9VL_UA
CAGTCTGCCCTGACTCAGCCTGCCTCCGTGTCTGGGTCTCCTGGACAGTCGATCACCATCTCCTGCACTGGAACCAGCAGTG
ATGTTGGGAGTTATAACCTTGTCTCCTGGTACCAACAGCACCCAGGCAAAGCCCCCAAACTCATGATTTATGAGGTCAGTAA
GCGGCCCTCAGGGGTTTCTAATCGCTTCTCTGGCTCCAAGTCTGGCAACACGGCCTCCCTGACAATCTCTGGGCTCCAGGCT
GAGGACGAGGCTGATTATTACTGCTGCTCTCTGACAAGCACGAGACGTTGGGTGTTCGGCGGAGGGACCAAGCTGACCGTCCTA >PG16VH_UA
CAGGTGCAGCTGGTGGAGTCTGGGGGAGGCGTGGTCCAGCCTGGGAGGTCCCTGAGACTCTCCTGTGCAGCGTCTGGATTCA
CCTTCAGTAGCTATGGCATGCACTGGGTCCGCCAGGCTCCAGGCAAGGGGCTGGAGTGGGTGGCAGTTATATCATATGATGG
AAGTAATAAATACTATGCAGACTCCGTGAAGGGCCGATTCACCATCTCCAGAGACAATTCCAAGAACACGCTGTATCTGCAA
ATGAACAGCCTGAGAGCCGAGGACACGGCTGTGTATTACTGTGCGAGAGAGGCTGGTGGGCCAATCTGGCATGACGACGTCA
AATATTACGATTTTAATGACGGCTACTACTACTACTACATGGACGTCTGGGGCAAAGGGACCACGGTCACCGTCTCCTCA >PG16VL_UA
CAGTCTGCCCTGACTCAGCCTGCCTCCGTGTCTGGGTCTCCTGGACAGTCGATCACCATCTCCTGCACTGGAACCAGCAGTG
ATGTTGGGAGTTATAACCTTGTCTCCTGGTACCAACAGCACCCAGGCAAAGCCCCCAAACTCATGATTTATGAGGTCAGTAA
GCGGCCCTCAGGGGTTTCTAATCGCTTCTCTGGCTCCAAGTCTGGCAACACGGCCTCCCTGACAATCTCTGGGTCCAGGCT
GAGGACGAGGCTGATTATTACTGCTGCTCACTGACAGACAGAAGCCATCGCATATTCGGCGGAGGGACCAAGCTGACCGTCCTA

TABLE 29B

Amino acid sequence alignments of CH58, CH59, 697D, PG9 and PG16 with UA antibodies (VH and VLsequences are separated by ~~~ and VH sequences in bold). Table 29B discloses "CH58" VH and VL sequences as SEQ ID NOS 103 and 147, respectively; "CH58UA" VH and VL sequences as SEQ ID NOS 104 and 151, respectively; "CH59" VH and VL sequences as SEQ ID NOS 105 and 149, respectively; "CH59UA" VH and VL sequences as SEQ ID NOS 106 and 153, respectively; "697D" VH and VL sequences as SEQ ID NOS 107 and 236, respectively; "697DVUA" VH and VL sequences as SEQ ID NOS 108 and 237, respectively; "CH01" VH and VL sequences as SEQ ID NOS 109 and 238, respectively; "CH01 UA 1" VH and VL sequences as SEQ ID NOS 110 and 239, respectively; "CH01 UA 2" VH and VL sequences as SEQ ID NOS 111 and 239, respectively; "CH01 UA 3" VH and VL sequences as SEQ ID NOS 112 and 239, respectively; "PG9VH" VH and VL sequences as SEQ ID NOS 113 and 240, respectively; "PG16VH" VH and VL sequences as SEQ ID NOS 114 and 241, respectively; "PG9VH UA" VH and VL sequences as SEQ ID NOS 115 and 242, respectively; "PG16VH UA" VH and VL sequences as SEQ ID NOS 116 and 243, respectively.

```
CH58       EVQLVQSGAE VKKPGESLKI SCKGSGYRFT SYWIVWVRQM PGKGLEWMGI IYPGDFDTKY
CH58UA     ---------- ---------- -------S-- ----G----- ---------- -----S--R-    60
CH58       SPSFQGQVTI SADKSISTAY LQWSSLKASD TAMYYCARLG GRYYHDSSGY YYLDYWGQGT
CH58UA     ---------- ---------- ---------- ---------- ----Y----- ---F------   120
CH58       LVTVSS~~~N FMLTQPHSVS ESPGKTVTIS CTRSSGSVAS DYVQWYQQRP GSAPTTVVYE
CH58UA     ---------- ---------- ---------- -------I-- N--------- --S----I--   180
CH58       DNQRPSGVPD RFSGSIDSSS NSASLTISGL KTEDEADYYC QSYDNSSWVF GGGTKLTVL
CH58UA     ---------- ---------- ---------- ---------- ----S----- ---------    240

CH59       EVQLVESGGG LVQPGRSLRL SCAASGFTFD DGAMHWVRQA PGKGLEWVSG ISWNSNIIAY
CH59UA     ---------- ---------- ---------- -Y-------- ---------- -----GS-G-    60
CH59       ADSVKGRFTI SRDNAKNSLY LEMNSLRVED TALYYCAKDS PRGELPLNYW GQGTLVTVSS
CH59UA     ---------- ---------- -Q-----A-- ---------- ------FD-- ----------   120
CH59       ~~~SYELTQP PSVSVSPGQT ARITCSGDAL PKNYAYWYQQ KSGQAPVLVI YEDSKRPSGI
CH59UA     ~~~------- ---------- ---------- --K------- ---------- ----------   180
CH59       PERFSGSSSG TMATLTISGA QVEDEADYYC YSTDSSGNHR VFGGGTKLTV L
CH59UA     ---------- ---------- ---------- ---------- ---------- -            231

697D       QVQLVQSGAE VKKPGSSVKV SCKASGGNFN TYTISWVRQA PGQGLEWMGR IIPIFGIVNP
697DVUA    ---------- ---------- -------T-S S--------- ---------- ----L--A-Y    60
697D       AQKFPGRVTI NVDKSTNTAY MELSSLRSED TAVYYCATSG VGLHFGYFDY WGQGTQVTVS
697DVUA    ----Q----- TA----S--- ---------- ---------- ---------- -----L----   120
697D       S~~~QSVLTQ PPSVSGAPGQ RVTISCTGSS SNIGAHYD   WYQQLPGTAP KLLIYGNSNR
697DVUA    -~~~------ ---------- ---------- -----G---- ---------- ----------   180
697D       PSGVPDRFSG SKSGTSASLA ITGLQAEDEA DYYCQSYDSS LSGYVFGTGT KVTVL
697DVUA    ---------- ---------- ---------- ---------- ---------- -----         235

CH01       EVQLVESGAN VVRPGGSLRL SCKASGFIFE NFGFSWVRQA PGKGLQWVAG LNWNGGDTRY
CH01_UA 1  --------GG ---------- --A----T-D DY-M------ -----E--S- I-----S-G-
CH01_UA 2  --------GG ---------- --A----T-D DY-M------ -----E--S- I-----S-G-
CH01_UA 3  --------GG ---------- --A----T-D DY-M------ -----E--S- I-----S-G-    60
CH01       ADSVKGRFRM SRDNSRNFVY LDMDKVGVDD TAFYYCARGT DYTIDDAGIH YQGSGTFWYF
CH01_UA 1  --------TI ----AK-SL- -Q-NSLRAE- --L------- ------Q--R ----------
CH01_UA 2  --------TI ----AK-SL- -Q-NSLRAE- --L------- ------Q--R ----------
CH01_UA 3  --------TI ----AK-SL- -Q-NSLRAE- --L-H----- ------Q--- -Y----Y---   120
CH01       DLWGRGTLVS VSS~~~EIVL AQSPGTLSLS PGERATLSCR ASHN  PKYF AWYQQKPGQS
CH01_UA 1  ---------T --~~~~---- T--------- ---------- --QS-SSS-L ---------A
CH01_UA 2  ---------T --~~~~---- T--------- ---------- --QS-SSS-L ---------A
CH01_UA 3  ---------T --~~~~---- T--------- ---------- --QS-SSS-L ---------A   180
CH01       PRLLIYGGST RAAGIPGKFS GSGSGTDFTL TISRVDPEDF AVYYCQQYGG SPYTFGQGTK
CH01_UA 1  -------A-S --T---DR-- ---------- ----LE---- ---------S ----------
CH01_UA 2  -------A-S --T---DR-- ---------- ----LE---- ---------S ----------
CH01_UA 3  -------A-S --T---DR-- ---------- ----LE---- ---------S ----------   240
CH01       VEIK
CH01_UA 1  ----
CH01_UA 2  ----
CH01_UA 3  ----                                                                244

PG9VH      QR~LVESGGG VVQPGSSLRL SCAASGFDFS RQGMHWVRQA PGQGLEWVAF IKYDGSEKYH
PG16VH     -EQ------- -----G---- --L----T-H KY-------- --K------L -SD--MR---
PG9VH_UA   -VQ------- -----R---- -------T-- SY-------- --K------V -S----N--Y
PG16VH_UA  -VQ------- -----R---- -------T-- SY-------- --K------V -S----N--Y    60
```

TABLE 29B-continued

Amino acid sequence alignments of CH58, CH59, 697D, PG9 and PG16 with UA
antibodies (VH and VLsequences are separated by ~~~ and VH sequences in bold).
Table 29B discloses "CH58" VH and VL sequences as SEQ ID NOS 103 and 147,
respectively; "CH58UA" VH and VL sequences as SEQ ID NOS 104 and 151,
respectively; "CH59" VH and VL sequences as SEQ ID NOS 105 and 149,
respectively; "CH59UA" VH and VL sequences as SEQ ID NOS 106 and 153,
respectively; "697D" VH and VL sequences as SEQ ID NOS 107 and 236,
respectively; "697DVUA" VH and VL sequences as SEQ ID NOS 108 and 237,
respectively; "CH01" VH and VL sequences as SEQ ID NOS 109 and 238,
respectively; "CH01 UA 1" VH and VL sequences as SEQ ID NOS 110 and 239,
respectively; "CH01 UA 2" VH and VL sequences as SEQ ID NOS 111 and 239,
respectively; "CH01 UA 3" VH and VL sequences as SEQ ID NOS 112 and 239,
respectively; "PG9VH" VH and VL sequences as SEQ ID NOS 113 and 240,
respectively; "PG16VH" VH and VL sequences as SEQ ID NOS 114 and 241,
respectively; "PG9VH UA" VH and VL sequences as SEQ ID NOS 115 and 242,
respectively; "PG16VH UA" VH and VL sequences as SEQ ID NOS 116 and 243,
respectively.

```
PG9VH      ADSVWGRLSI  SRDNSKDTLY  LQMNSLRVED  TATYFCVREA  GGPDYRNGYN  YYDFYDGYYN
PG16VH     S--M---VT-  ------N---  --FS--K---  --MF--A---  ---IWHDDVK  ----N-----
PG9VH_UA   ----K--FT-  ------N---  -------A--  --V-Y-A---  ----------  ----WS----
PG16VH_UA  ----K--FT-  ------N---  -------A--  --V-Y-A---  ---IWHDDVK  ----N----Y  120

PG9VH      YHYMDVWGKG  TTVTVSS~~~  QSALTQPASV  SGSPGPSITI  SCNGTSNDVG  GYESVSWYQQ
PG16VH     ----------  ----------  ----------  ------T---  ------S---  -FD-------
PG9VH_UA   -Y--------  ----------  ----------  ----------  --T---S---  S-NL------
PG16VH_UA  -Y--------  ----------  ----------  ----------  --T---S---  S-NL------  180

PG9VH      HPGKAPKVVI  YDVSKRPSGV  SNRFSGSKSG  NTASLTISGL  QAEDEGDYYC  KSLTSTRRRV
PG16VH     S-------MV  F---H----I  ----------  ----------  HI------F-  S---DRSH-I
PG9VH_UA   -------LM-  -E--------  ----------  ----------  -----A----  C-------W-
PG16VH_UA  -------LM-  -E--------  ----------  ----------  -----A----  C---DRSH-I  240

PG9VH      FGTGTKLTVL
PG16VH     --G---V---
PG9VH_UA   --G-------
PG16VH_UA  --G-------                                                               250
```

Production of Recombinant HIV-1 Proteins.

Figure 61:
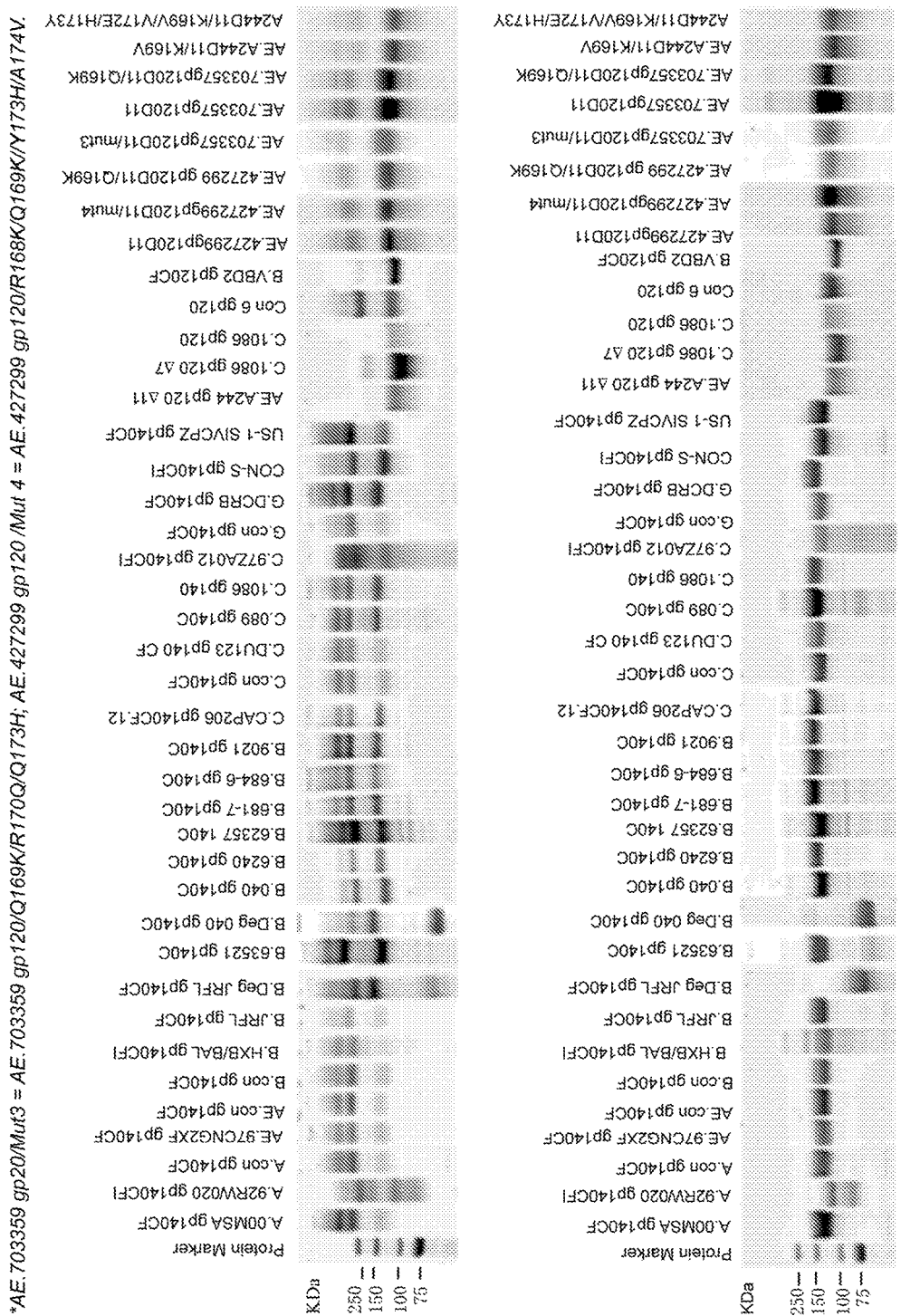
FIG. 61. SDS-PAGE analysis of recombinant HIV-1 Env gp140, gp120 and V1/V2 proteins*. HIV-1 Env gp140, gp120 and V1/V2 proteins as indicated on the tope of gels were produced as described in Example 3, loaded at 1 µg per lane, fractionated on 4-20% gradient SDS_PAGE under non-educing (Top panel) and reducing condition (lower panel) and stained with Coomassie blue.
Figure 61:
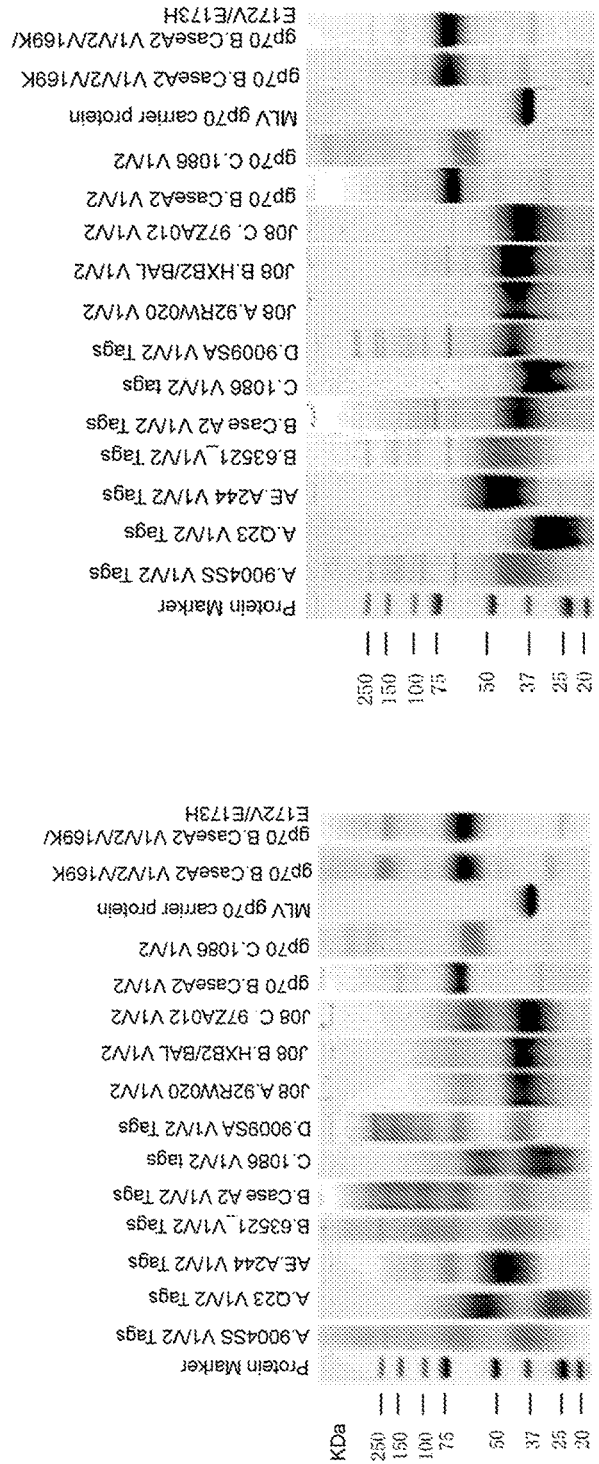

RV144 vaccine immunogen proteins AE.A244 gp120 and B.MN gp120 were produced, purified and supplied by GSID (Global Solutions for Infectious Diseases, South San Francisco, Calif.). Recombinant HIV-1 gp120 proteins including AE.A244 gD+Δ11, AE.A244gDneg, AE.A244 gDneg gp120Δ11, AE.A244 gD gp120N160K, B.MN gD+gp120 and B.MN gDneg gp120, C.1086 gp120 were expressed in 293F cells by transfection and purified by using lectin-affinity columns (Liao et al, Virology 353:268-282 (2006)) followed by size exclusion chromatography on a Superdex 200 FPLC (GE Healthcare) to homogeneity for monomeric gp120. Recombinant Envs including 7 consensus Envs—group M CON-S gp140CFI, Con6 gp120, A.con gp140CF, B.con gp140CF, C.con gp140CF, AE.con gp140CF, G.con gp140CF, 7 chronic Envs, A. 00MASA gp140CF, A.92RW020 gp140CFI, B.JRFL gp140CF, HXB/BAL gp140CFI, C.DU123 gp140CF, C.97ZA012 gp140CFI, G.DCRB gp140CF, and SIV-Env, US-1 SIVCPZ gp140CF, were produced in 293T cells by recombinant vaccinia viruses (Liao et al, Virology 353:268-282 (2006)). HIV-1 Envs, B.62357 gp140C, B.6240 gp140C, B.63521 gp140C, B.040 gp140C, B. 684-6 gp140C, B.681-7, C.CAP206 gp140C.12, C.1086gp140C and C.089 gp140C were produced in 293T cells by either transient or stable transfection (Ma et al, PLoS Pathog 7:e1002200 (2011)). J08 A.92RW020 V1/V2, J08 B.HXB/BAL V1/V2, and J08 C.97ZA012 V1/V2 and were scaffolded on J08 protein (McLellan et al, Nature 480:336-343 (2011)), and gp70 CaseA2 V1/V2, gp70 A.92RW020V1/V2, gp70 B.HXB2/BALV1/V2 and gp70 C.97ZA012V1/V2 were made as fusion proteins with murine leukemia virus (MLV) gp70 and produced as described (Pinter et al, Vaccine 16:1803-1811 (1998)). Sequences of HIV-1 Envs, AE.703357 and AE.427299, were derived from RV144 subjects in the placebo arm and represent breakthrough infection Envs with wildtype (WT) V2 sequences that do not match the AE vaccine strains A244 and 92TH023 (Table 26). AE.A244 gp120/K169V and AE.A244 gp120/K169V/V172E/H173Y, AE.703359 gp120/Q169K and AE.703359 gp120/Q169K/R170Q/Q173H Env mutants were constructed (Table 26). Similarly, AE.427299 gp120/Q169K and AE.427299 gp120/R168K/Q169K/Y173H/A174V mutant Envs were constructed as shown in Table 30. Finally, gp70 B.CaseA2 V1/V2/V169K and gp70 B.CaseA2 V1/V2/V169K/E172V/E173H Env mutants were constructed (Table 26). MLV gp70 carrier protein without V1/V2 sequence was produced in 293F cells, purified by nickel columns and used as negative control for gp70 scaffold proteins. A.9004SS V1/V2 tags, 22 A.Q23 V1/V2 tags, AE.A244 V1/V2 tags, B.63521 V1/V2 tags, B.CaseA2 V1/V2 tags, C.1086 V1/V2 tags and D.9009SA V1/V2 tags were designed with Ig leader (MET-DTLLLWVLLLWVPGSTGD) (SEQ ID NO: 9) serving as a mature protein cleavage and secretion signal at the N-terminus and with the C-terminal avi-tag followed by His6-tag (SEQ ID NO: 10) for purification, produced in 293F cells by transfection and purified by nickel columns. Natively deglycosylated B.JRFL gp140CF (Deg B.JRFL gp140CF) and AE.A244 V1/V2 tags proteins were as described (Ma et al, PLoS Pathog 7:e1002200 (2011)). FIG. 61 shows SDS-PAGE analyses of all recombinant Env proteins used in this study.

TABLE 26

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
| AE.92TH023 V2 cyclic peptide | CSFNMTTELRDKKQKVHALFYKLDIVPIEDNTSSSEYRLINC |
| AE.A244 K178 V2 peptide | KKKVHALFYKLDIVPIEDKKK |
| AE.A244V2 peptide and AE.A244V2 mutant peptides | LRDKKQKVHALFYKLDIVPIED<br>ARDKKQKVHALFYKLDIVPIED<br>LADKKQKVHALFYKLDIVPIED<br>LRAKKQKVHALFYKLDIVPIED<br>LRDAKQKVHALFYKLDIVPIED<br>LRDKAQKVHALFYKLDIVPIED<br>LRDKKAKVHALFYKLDIVPIED<br>LRDKKQAVHALFYKLDIVPIED<br>LRDKKQKAHALFYKLDIVPIED<br>LRDKKQKVAALFYKLDIVPIED<br>LRDKKQKVHELFYKLDIVPIED<br>LRDKKQKVHAAFYKLDIVPIED<br>LRDKKQKVHALAYKLDIVPIED<br>LRDKKQKVHALFAKLDIVPIED<br>LRDKKQKVHALFYALDIVPIED<br>LRDKKQKVHALFYKLDIVPIED<br>LRDKKQKVHALFYKLAIVPIED<br>LRDKKQKVHALFYKLDIVPIED<br>LRDKKQKVHALFYKLDTAPIED<br>LRDKKQKVHALFYKLDIVAIED<br>LRDKKQKVHALFYKLDIVPAED<br>LRDKKQKVHALFYKLDIVPIAD<br>LRDKKQKVHALFYKLDIVPIEA |
| B.CaseA2 V1/V2 | VKLTPLCVTLNCIDLRNATNATSNSNTTNTTSSSGGLMMEQGEIKNCSENITTSIRDKVQKEYALF<br>YKLDIVPIDNPKNSTNYRLISCNTSVITQA |
| A.92RW020 V1N2 | LKPCVKLTPLCVTLDCNATASNVINEMRNCSFNITTELKDKKQQVYSLEYKLDVVQINEKNETDKY<br>RLINCNTSAITQA |
| B.HXB2/BALV1/V2 | LKPCVKLTPLCVSLKCTDLKNDTNINSSSGRMIMEKGEIKNCSFNISTSIRGKVQKEYAFFYKLDI<br>IPIDNDTTSYSLTSCNTSVITQA |
| C.ZM109 V1N2 | CVTLNCTSPAAHNESETRVKHCSFNITTDVKDRKQKVNATFYDLDIVPLSSSDNSSNSSLYRLISC |
| AE.A244 V1N2 | VKLTPPCVTLHCTNANLTKANLTNVNNRTNVSNIIGNITDEVRNCSFNMTTELRDKKQKVHALFYK<br>LDIVPIEDNNDSSEYRLTNCTSVIKQP |
| gp70 B.CaseA2 V1/V2 | MACSTLPKSPKDKIDPRDLLIPLILFLSLKGARSAAPGSSPHHHHHHQVYNITWEVINGDRETVWA<br>ISGNHPLWTWWPVLTPDLCMLALSGPPHWGLEYQAPYSSPPGPPCCSGSSGSSAGCSRDCDEPLTS<br>LTPRCNTAWNRLKLDQVTHKSSEGFYVCPGSHRPREAKSCGGPDSFYCASWGCETTGRVYWKPSSS<br>WDYITVDNNLTTSQAVQVCKDNKWCNPLAIQFTNAGKQVISWTTGHYWGLRLRYVSGRDPGLTEGIR<br>LRYQNLGPRVPIGPNPVLADQLSLPRPNPLPKPAKSPPASVKLTPLCVTLNCIDLRNATNATSNSN<br>TTNTTSSSGGLMMEQGEIKNCSFNITTSIRDKVQKEYALFYKLDIVPIDNPKNSTNYRLISCNTSV<br>ITQA |
| gp70 C.1086 V1N2 | MACSTLPKSPKDKIDPRDLLIPLILFLSLKGARSAAPGSSPHHHHHHQVYNITWEVINGDRETVWA<br>ISGNHPLWTWWPVLTPDLCMLALSGPPHWGLEYQAPYSSPPGPPCCSGSSGSSAGCSRDCDEPLTS<br>LTPRCNTAWNRLKLDQVTHKSSEGFYVCPGSHRPREAKSCGGPDSFYCASWGCETTGRVYWKPSSS<br>WDYITVDNNLTTSQAVQVCKDNKWCNPLAIQFTNAGKQVTSWTTGHYWGLRLRYVSGRDPGLTEGIR<br>LRYQNLGPRVPIGPNPVLADQLSLPRPNPLPKPAKSPPASVKLTPLCVTLNCTNVKGNESDTSEVM<br>KNCSFKATTELKDKKHKVHALFYKLDVVPLNGNSSSSGEYRLINCNTSAITQA |
| MLV gp70 Carrier protein | MACSTLPKSPKDKIDPRDLLIPLILELSLKGARSAAPGSSPHHHHHHQVYNITWEVINGDRETVWA<br>ISGNHPLWTWWPVLTPDLCMLALSGPPHWGLEYQAPYSSPPGPPCCSGSSGSSAGCSRDCDEPLTS<br>LTPRCNTAWNRLKLDQVTHKSSEGFYVCPGSHRPREAKSCGGPDSFYCASWGCETTGRVYWKPSSS<br>WDYITVDNNLTTSQAVQVCKDNKWCNPLAIQFTNAGKQVTSWTTGHYWGLRLRYVSGRDPGLTFGIR<br>LRYQNLGPRVPIGPNPVLADQLSLPRPNPLPKPAKSPPAS |
| A.9004SSV1N2 tags | METDTLLLWVLLLWVPGSTGDQVKLTPLCVTLNCSQYVSSHVNNHNNSSHNVSSHSGNITSDMKIC<br>SENTTTEVRDKKQKVYSLEYKLDVVPISNDSSYQRLINCNTSAITQAGLNDIFEAQKIEWHELEVL<br>FQGPGHHHHHH |

TABLE 26-continued

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
| A.Q23 V1N2 tags | METDTLLLWVLLLWVPGSTGDQVKLTPLCVTLHCTNVTSVNTTGDREGLKNCSFNMTTELRDKRQK<br>VYSLFYRLDIVPINENQGSEYRLINCNTSAITQAGLNDIFEAQKIEWHELEVLFQGPGHHHHHH |
| AE.A244 V1N2 tags | METDTLLLWVLLLWVPGSTGDQVKLTPPCVTLHCTNANLTKANLTNVNNRTNVSNIIGNITDEVRN<br>CSFNMTTELRDKKQKVHALFYKLDIVPIEDNNDSSEYRLINCNTSVIKQPGLNDIFEAQKIEWHEL<br>EVLFQGPGHHHHHH |
| B.63521 V1 N2 tags | METDTLLLWVLLLWVPGSTGDQVKLTPLCVTLNCTDVTNATNINATNINNSSGGVESGEIKNCSFN<br>ITTSVRDKVQKEYALFYKLDIVPITNESSKYRLISCNTSVLTQAGLNDIFEAQKIEWHELEVLFQG<br>PGHHHHHH |
| B.CaseA2 V1N2 tags | METDTLLLWVLLLWVPGSTGDQVKLTPLCVTLNCIDLRNATNATSNSNTTNTTSSSGGLMMEQGEI<br>KNCSENTTTSIRDKVQKEYALFYKLDIVPIDNPKNSTNYRLISCNTSVITQAGLNDIFEAQKIEWH<br>ELEVLFQGPGHHHHHH |
| D.9009SA V1N2 tags | METDTLLLWVLLLWVPGSTGDQVKLTPLCVTLNCTTNSTNFANSTGKDIEMQDCSFNITTEIRDKQ<br>KKVHALFYKLDIVQIDNNTEANANYTSYRLINCNTSAITQAGLNDIFEAQKIEWHELEVLFQGPGH<br>HHHHH |
| A. 00MSA gp140CF | MGAMGIQMNWQNLWRWGTMILGMLIICSVAEKSWVTVYYGVPVWRDAETTLFCASDAKAHDKEVHN<br>VWATHACVPTDPNPQEMILENVTEDFNMWKNSMVEQMHTDIISLWDQSLKPCVKLTPLCVTLNCSD<br>SNITSNSTSNSTKDSATLDMKSEIQNCSFNMTTELRDKKQKVYSLFYRLDVVQINENSSDYRLINC<br>NTSAITQACPKVTFEPIPIHYCAPAGFAILKCNDKKENGTGPCTNVSTVQCTHGIKPVVTTQLLLN<br>GSLAEEEVMIRSENITENAKNIIVQFKEPVQIICIRPGNNTRKSVHIGPGQAFYATGDIIGDIRQA<br>HCNVSRELWNKTLQEVATQLRKHFRNNTKIIFTNSSGGDVEITTHSFNCGGEFFYCDTSGLFNSSW<br>TASNDSMQEAHSTESNITLQCRIKQIINMWQRAGQAMYAPPIPGIIRCESNITGLILTRDGGEGNN<br>STNETFRPVGGNMRDNWRSELYKYKVVKVEPLGVAPTKSRTLTVQARQLLSGIVQQQSNLLRAIEA<br>QQHLLKLTVWGIKQLQARVLAVERYLRDQQLLGIWGCSGKLICTTNVPWNSSWSNKSLDEIWENMT<br>WMQWDKEVSNYTQMIYNLLEESQNQQEKNEQELLALDKWANLWNWFNISNWLW |
| A.92RW020 gp140CFI | MRVRGIQTSWQNLWRWGTMILGMLVIYSAAENLWVAVYYGVPVWKDAETTLFCASDAKAYDTEVHN<br>VWETHACVPTDPNPQEIHLENVTEDFNMWRNNEVEQMHTDIISLWDQSLKPCVKLTPLCVTLDCNA<br>TASNVTNEMRNCSFNITTELKDKKQQVYSLEYKLDVVQINEKNETDKYRLINCNTSAITQACPKVS<br>FEPIPIHYCAPAGFAILKCKDTEENGTGPCKNVSTVQCTHGIRPVISTQLLLNGSLAEEEGIQIRSE<br>NITNNAKTIIVQLDKAVKINCTRPNNNTRKGVRIGPGQAFYATGGIIGDIRQAHCVSRAKWNDTL<br>RGVAKKLREHEKNKTI+32KSSGGDIEITTHSFICGGEFFYCNTSGLENSTWESNSTESNNTTSND<br>TITLTCRIKQIINMWQKVGQAMYPPPIQGVIRCESNITGLLLTRDGGNNSTNEIFRPGGGNMRDNW<br>RSELYKYKVVKIEPLGVAPSRAKLTAQARQLLSGIVQQQSNLLRAIEAQQHMLKLTVWGIKQLQAR<br>VLAVERYLKDQQLEIWDNMTWLQWDKEISNYTQIIYNLIEESQNQQEKNEQDLLALDKWASLWNWF<br>DISRWLW |
| A.con gp140CF | MRVMGIQRNCQHLLRWGTMILGMIIICSAAENLWVTVYYGVPVWKDAETTLFCASDAKAYETEMHN<br>VWATHACVPTDPNPQEIHLENVTEEFNMWKNNMVEQMHTDIISLWDQSLKPCVKLTPLCVTLNCSN<br>VNVTNNTTNTHEEEIKNCSFNMTTELRDKKQKVYSLFYRLDVVQINENNSNSSYRLINCNTSAITQ<br>ACPKVSFEPIPIHYCAPAGFAILKCKDKEENGTGPCKNVSTVQCTHGIKPVVSTQLLLNGSLAEEE<br>VIIRSENITNNAKTIIVQLTKPVKINCTRPNNNTRKSIRIGPGQAFYATGDIIGDIRQAHCNVSRS<br>EWNKTLQKVAKQLRKYFKNKTIIFTNSSGGDLEITTHSFNCGGEFFYCNTSGLENSTWNNGTMKNT<br>ITLPCRIKQIINMWQRAGQAMYAPPIQGVIRCESNITGLLLTRDGGNNNTNETFRPGGGDMRDNWR<br>SELYKYKVVKIEPLGVAPTRAKTLTVQARQLLSGIVQQQSNLLRAIEAQQHLLKLTVWGIKQLQAR<br>VLAVERYLKDQQLLGIWGCSGKLICTTNVPWNSSWSNKSQNEIWDNMTWLQWDKEISNYTHIIYNL<br>TEESQNQQEKNEQDLLALDKWANLWNWFDISNWLW |
| AE.97CNG2XF gp140CF | MRVKETQMNWPNLWKWGTLILGLVIICSASDNLWVTVYYGVPVWRDADTTLFCASDAKAHETEVHN<br>VWATHACVPTDPNPQEIHLENVTENFNMWRNNMVEQMQEDVISLWDQSLKPCVKLTPLCVTLHCTN<br>ANWTNSNNTTNGPNKIGNITDEVKNCTFNETTELKDKKQKVHALFYKLDIVQINSSEYRLINCNTS<br>VIKQACPKISFDPIPIHYCTPAGYAILKCNDKNENGTGPCKNVSSVQCTHGIKPVVSTQLLLNGSL<br>AEEEIIIRSENLTNNAKTIIVHLNKSVEINCTRPSNNTRTSITMGPGQVFYRTGDIIGDIRKAYCE<br>INGIKWNEVLVQVTGKLKEHFNKTIIFQPPSSGDLEIITHHFSCRGEFFYCNTTKLENNTCIGNTS<br>MEGCNNTIILPCKIKQIINMWQGVGQAMYAPPISGRINCVSNITGILLTRDGGADNNTTNETERPG<br>GGNIKDNWRSELYKYKVVEIEPLGIAPTRARTLTVQARQLLSGIVQQQSNLLRAIEAQQHLLQLTV<br>WGIKQLQARVLAVERYLKDQKFLGLWGCSGKIICTTAVPWNSSWSNKSFEEIWDNMTWIEWEREIS<br>NYTSQIYEILTESQNQQDRNEKDLLELDKWASLWNW |
| AE.A244 gp120 D11 | MRVKETQMNWPNLWKWGTLILGLVIICSAVPVWKEADTTLFCASDAKAHETEVHNVWATHACVPTD<br>PNPQEIDLENVTENFNMWKNNMVEQMQEDVISLWDQSLKPCVKLTPPCVTLHCTNANLTKANLTNV<br>NNRTNVSNIIGNITDEVRNCSFNMTTELRDKKQKVHALFYKLDIVPIEDNNDSSEYRLINCNTSVI<br>KQPCPKISFDPIPIHYCTPAGYAILKCNDKNENGTGPCKNVSSVQCTHGIKPVVSTQLLLNGSLAE |

TABLE 26-continued

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
|  | EEIIIRSENLTNNAKTIIVHLNKSVVINCTRPSNNTRTSITIGPGQVFYRTGDIIGDIRKAYCEIN<br>GTEWNKALKQVTEKLKEHENNKPIIFQPPSGGDLEITMHHENCRGEFFYCNTTRLENNTCIANGTI<br>EGCNGNITLPCKIKQIINMWQGAGQAMYAPPISGTINCVSNITGILLTRDGGATNNTNNETFRPGG<br>GNIKDNWRNELYKYKVVQIEPLGVAPTRAKRRVVEREKR |
| AE.A244 gD-gp120 | MRVKETQMNWPNLWKWGTLILGLVIICSASDNLWVTVYYGVPVWKEADTTLFCASDAKAHETEVHN<br>VWATHACVPTDPNPQEIDLENVTENFNMWKNNMVEQMQEDVISLWDQSLKPCVKLTPPCVTLHCTN<br>ANLTKANLTNVNNRTNVSNIIGNITDEVRNCSFNMTTELRDKKQKVHALFYKLDIVPIEDNNDSSE<br>YRLINCNTSVIKQPCPKISFDPIPIHYCTPAGYAILKCNDKNENGTGPCKNVSSVQCTHGIKPVVS<br>TQLLLNGSLAEEEIIRSENLTNNAKTIIVHLNKSVVINCTRPSNNTRTSITIGPGQVFYRTGDII<br>GDIRKAYCEINGTEWNKALKQVTEKLKEHFNNKPIIFQPPSGGDLEITMEHENCRGEFFYCNTTRL<br>FNNTCIANGTIEGCNGNITLPCKIKQIINMWQGAGQAMYAPPISGTINCVSNITGILLTRDGGATN<br>NTNNETFRPGGGNIKDNWRNELYKYKVVQIEPLGVAPTRAKRRVVEREKR_ |
| AE.con gp140CF | MRVKETQMNWPNLWKWGTLILGLVIICSASDNLWVTVYYGVPVWRDADTTLFCASDAKAHETEVHN<br>VWATHACVPTDPNPQEIHLENVTENFNMWKNNMVEQMQEDVISLWDQSLKPCVKLTPLCVTLNCTN<br>ANLTNVNNITNVSNIIGNITNEVRNCSFNMTTELRDKKQKVHALFYKLDIVQIEDNNSYRLINCNT<br>SVIKQACPKISFDPIPIHYCTPAGYAILKCNDKNFNGTGPCKNVSSVQCTHGIKPVVSTQLLLNGS<br>LAEEEIIIRSENLTNNAKTIIVHLNKSVEINCTRPSNNTRTSITIGPGQVFYRTGDIIGDIRKAYC<br>EINGTKWNEVLKQVTEKLKEHENNKTIIFQPPSGGDLEITMHHENCRGEFFYCNTTKLENNTCIGN<br>ETMEGCNGTIILPCKIKQIINMWQGAGQAMYAPPISGRINCVSNITGILLTRDGGANNTNETFRPG<br>GGNIKDNWRSELYKYKVVQIEPLGIAPTRAKTLTVQARQLLSGIVQQQSNLLRAIEAQQHLLQLTV<br>WGIKQLQARVLAVERYLKDQKFLGLWGCSGKIICTTAVPWNSTWSNRSFEEIWNNMTWIEWEREIS<br>NYTNQIYEILTESQNQQDRNEKDLLELDKWASLWNWFDITNWLW* |
| B. 681-7 gp140C | MRVMGTRRNCQHLWKWGIMLLGMLMICSATEQLWVTVYYGVPVWKDATTTLFCASDAKAYDTEAHN<br>VWATHACVPTDPNPQEVPLVNVTEKFDIWKNNMVDQMHEDIISLWDQSLKPCVKLTPLCVTLNCTN<br>ATITNEVTATVATATSSKTISPAISPEMKNCSENTNAILQDKVSKDYALFYNLDIVQIEDKDNKTN<br>NDSKTYDSYRLISCNTSVITQACPKTSFKPIPIHYCAPAGFAILKCNDRNFNGTEPCKNVSTVQCT<br>HGIRPVVSTQLLLNGSLAEDEVVIRSSNESNNARTILVQLKDPVTINCTRPNNNTRRSINIGPGRA<br>FYATGEIIGNIRQAHCNISMANWTNTLKQIAGKLGKQEDHKTIVENHSSGGDPEIVMHTFNCGGEF<br>FYCNTSGLFNSTWTWNSTGNYYSSNSSGSGTNNNTIILQCRIKQIINMWQTVGKAMYAPPIRGKIS<br>CVSNITGLLLVRDGGDNNSSEEIFRPAGGGDMRDNWRSELYKYKVVKIEPLGIAPTKARERVVQREK<br>EAVGIGALFLGELGAAGSTMGAASIALTVQARQLLSGIVQQQNNLLRAIEAQQHMLQLTVWGIKQL<br>QARVLAVERYLRDQQLLGIWGCSGKHICTTNVPWNASWSNNRNLSQIWDNLTWMQWEKEIDNYTSL<br>IYSLIEESSQIQQEKNEQDLLALDKWDSLWNWFNITHWLWYIK |
| B. 684-6 gp140C | MKVKGIMKNCQNSWGGILLLGMLMICSAAEDKWVTVYYGVPVWKEATTTLECASDAKAYSTERHN<br>IWATHACVPTDPSPQEIVMGNVTEDFNMWKNENAVQMHEDVISLWDQSLKPCVKLTPLCVSLDCTN<br>VNITNHNSTNPEEQMKEGEIKNCSFNETTNIKDKIQKTYALFYKLDLVPIDDENNTNTSYRLISCN<br>TSVITQACPKVTFEPIPIHYCAPAGFAILKCNNKTENGTGPCINVSTVQCTHGIKPVVSTQLLLNG<br>SLAEEEIIRSENITDNTKNIIVHLNKSVQINCIRPNNNTRKGIHIGPGAFWATGEIIGDIRQAHC<br>NVSREDWNKTLRRISKKLRDIENKTINFTSSSGGDPEIVMHSENCGGEFFYCNSTPLENSSWYGNE<br>TDVSNSTENSTRGEITEPCRIKQIINMWQEVGKANYAPPISGPISCSSNITGLILTRDGGNNSSNT<br>EIFRPGGGNMMDNWRSELYKYKVVQLEPLGIAPSRARERVVQREKEAVGFGALLLGFLGTAGSTMG<br>AVSLTLTVQARQLLSGIVQQQNNLLRAIEAQQHMLQLTVWGIKQLQARVLAVERYLKDQQLLGIWG<br>CSGKLICTTAVPWNDSWSNRSLTDIWDNMTWMQWEKEIDNYTGLIYTLIEESQFQQEKNEQDLLAL<br>DKWASLWNWFDITKWLWYIK |
| B. JRFL gp140CF | MPMGSLQPLATLYLLGMLVASVLAVEKLWVTVYYGVPVWKEATTTLFCASDAKAYDTEVHNVWATH<br>ACVPTDPNPQEVVLENVTEHENNWKNNMVEQMQEDIISLWDQSLKPCVKLTPLCVTLNCKDVNATN<br>TTNDSEGTMERGEIKNCSENITTSIRDEVQKEYALFYKLDVVPIDNNNTSYRLISCDTSVITQACP<br>KISEEPIPIHYCAPAGFAILKCNDKTENGKGPCKNVSTVQCTHGIRPVVSTQLLLNGSLAEEEVVI<br>RSDNFTNNAKTIIVQLKESVEINCTRPNNNTRKSIHIGPGRAFYTTGEIIGDIRQAHCNISRAKWN<br>DTLKQIVIKLREQFENKTIVEHHSSGGDPEIVMHSREQFFYCNSTQLENSTWNNNTEGSNNTE<br>GNTITLPCRIKQIINMWQEVGKAMYAPPIRGQIRCSSNITGLLLTRDGGINENGTEIFRPGGGDMR<br>DNWRSELYKYKVVKIEPLGVAPTKAKTLTVQARLLLSGIVQQQNNLLRAIEAQQRMLQLTVWGIKQ<br>LQARVLAVERYLGDQQLLGIWGCSGKLICTTAVPWNASWSNKSLDRIWNNMTWMEWEREIDNYTSE<br>IYTLIEESQNQQEKNEQELLELDKWASLWNWFDITKWLW |
| B.040 gp140C | MRVMGIRKNYOHLWREGILLLGILMICSAADNLWVTVYYGVPVWREATTTLFCASDAKAYDTEAHN<br>VWATHACVPTDPNPQEVELKNVTENFNMWENNMVEQMHEDIISLWDQSLKPCVKLTPLCVTLNCTD<br>LGNVTNTTNSNGEMMEKGEVKNCSFKITTDIKDRTRKEYALFYKLDVVPINDTRYRLVSCNTSVIT<br>QACPKVSFEPIPIHYCAPAGFAILKCNDKOFIGTGPCTNVSTVQCTHGIRPVVSTQLLLNGSLAEE<br>EVVIRSVNFSDNAKTIIVQLNKSVEITCTRPNNNTRKSIPMGPGKAFYARGDITGDIRKAYCEING<br>TEWHSTLKLVVEKLREQYNKTIVFNRSSGGDPEIVMYSFNCGGEFFYCNSTKLFNSTWPWNDTKGS<br>HDTNGTLILPCKIKQIINMWQGVGKAMYAPPIEGKIRCSSNITGLLLTRDGGYESNETDEIFRPGG<br>GDMRDNWRSELYKYKVVKIEPLGVAPTKAKERVVQREKEAFGLGAVFLGELGAAGSTMGAASITLT |

TABLE 26-continued

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
| | VQARQLLSGIVQQQNNLLRAIEAQQHLLQLTVWGIKQLQARVLAVERYLKDQQLLGIWGCSGKLIC TTTVPWNTSWSNKSLEQIWDNMTWMEWEREIDNYTGYIYQLIEESQNQQEKNEQELLALDKWASLW NWFDITNWLWYIK |
| B.62357 140C | MRVREIRRNYQHLWKWGIMLLGILMICSATEKLWVTVYYGVPVWKEATTTLECASDAKAYDTEVHN VWATHACVPTDPNPQEVDLENVTENFNMWKNNMVEQMHEDIISLWDESLKPCVKLTPLCVTLNCTN ATSTNETAKNEGGIKNCSFNITTERRGRKKTEYATFYEIDLVLINDDNTTSYRLISCNTSVIKQAC PKVTFEPIPIHYCAPAGFAILKCKDKKENGTGACTNVSTVQCTHGIRPVVSTQLLLNGSLAEEEVV VRSEKFANNAKIIIVQLNESVEINCTRPNNNTRKSIHIGPGQAFYTTGAIIGDIRQAYCNISRAKW NDILKQIAIKLREKEGNNKTIVENQSSGGDPEVVMHISNCGGEFFYCNTTKLENNTWNSNDTWTNT EESNETEIRLPCRIKQIINMWQEVGKANYAPPIQGQIRCSSNITGLLLTRDGGNNTNNTEVERPGG GDMRDNWRSELYKYKVVKIEPLGVAPTKAKERVVQREKEAVGLGALFLGFLGAAGSTMGAASVTLT VQARQLLSGIVQQQSNLLRAIEAQQHLLQLTVWGIKQLQARVLAVERYLKDQQLLGIWGCSGKLIC TTAVPWNASWSNKSLNDIWNNMTWNEWEREINNYTSLIYNLIEESQNQQEKNELELLELDKWASLW NWFDITNWLWYIK |
| B.6240 gp140C | MRVKGIRKNYQHLWRWGIWRWGIMLLGTLMICSATEKLWVTVYYGVPVWKEATTTLFCASDAKAYS PEKHNIWATHACVPTDPNPQELVLGNVTEDFNMWKNNMVEQMHEDIISLWDQSLKPCVKLTPLCVT LNCTDLKNSATDTNGTSGTNNRTVEQGMETEIKNCSFNITTGIGNKMQKEYALFYKLDVVPIDSNN NSDNTSYRLISCNTSVVTQACPKTSEEPIPIHYCAPAGFAILKCNNKTFSGKGPCKNVSTVQCTHG IRPVVSTQLLLNGSLAEEEIVIRSENFTNNAKTIIVQLNESVIINCTRPNNNTRKGIHIGLGRALY ATGDIIGDIRQAHCNLSSKSWNKTLQQVVRKLREQFGNKTIAFNQSSGGDQEIVKHSENCGGEFFY CDTTQLFNSTWSSNDTWNSTGVQDNNITLPCRIKQIINMWQEVGKAMYAPPIQGLISCSSNITGLL LTRDGGINNTNATEIENPGGGDMRDNWRSELYKYNVVKIEPLGIAPTKAKERVVQREKEAVGLGAV FIGELGAAGSTMGAASVTLTVQARQLLSGIVQQQNNLLRAIEAQQHMLQLTVWGIKQLQARILAVE RYLKDQQILGIWGCSGKLICPTAVPWNASWSNKSLTAIWNNMTWMEWEREIDNYTGLIYSLIEESQ IQQEQNEKELLELDKWASLWNWFDITKWLWYIK |
| B.63521 gp140C | MRVKGIRKNYQHLWRWGTMLLGILMICSAAAQLWVTVYYGVPVWKEATTTLFCASDAKAYDTEVHN VWATHACVPTDPNPQELVLANVTENFNMWNNTMVEQMHEDIISLWDQSLKPCVKLTPLCVTLNCTD VTNATNINATNINNSSGGVESGEIKNCSFNITTSVRDKVQKEYALFYKLDIVPITNESSKYRLISC NTSVLIQACPKVSFEPIPIHYCAPAGFAILKCNNETENGKGPCINVSTVQCTHGIRPVVSTQLLLN GSLAEKEVIIRSDNFSDNAKNIIVQLKEYVKINCTRPNNNTRKSIHIGPGRAFYATGEIIGNIRQA HCNISRSKWNDTLKQIAAKLGEQFRNKTIVFNPSSGGDLEIVTHSENCGGEFFYCNTTKLENSTWI REGNNGTWNGTIGLNDTAGNDTIILPCKIKQIINMWQEVGKAMYAPPIRGQIRCSSNITGLILTRD GGKDDSNGSEILEIFRPGGGDMRDNWRSELYKYKVVRIEPLGVAPTRARERVVQKEKEAVGLGAMF LGFLGAAGSAMGAASMTLTVQARQLLSGIVQQQNNLLRAIEAQQHMLQLTVWGIKQLQARVLAVER YLKDQQLLGIWGCSGKLICTTDVPWDTSWSNKTLDDIWGSNMTWMEWEREIDNYTSTIYTLLEEAQ YQQEKNEKELLELDKWASLWNWFDITNWLWYIR |
| B.9021 gp140C | MRVKGIRKNCQQHLWRWGTMLLGILMICSAAENLWVTVYYGVPVWKEATTTLFCASDAKAYDTEVH NVWATHACVPTDPNPQEMVLENVTEYFNMWKNNMVEQMHEDIISLWDQSLKPCVKLTPLCVTLTCT DYEWNCTGIRNSICKYNNMTNNSSSGNYTGWERGEIKNCSENSTISGIRDKVRKEYALLYKIDLVS IDGSNTSYRNISCNTSVITQSCPKISFEPIPLHYCTPAGFALLKCNDKKENGTGLCHNVSTVQCTH GIKPVVSTQLLLNGSLAEEEVVIRSKNFTDNAKIIIVQLNETVEINCTRPNGNTRKSIHIAPGRTF YATGEIIGDIRRAHCNISREKWNTTLHRIATKLREQYNKTIVENQSSGGDPEIVMHSVNCGGEFFY CNTSKLENSTWNSIGGSISEDSENITLPCRIKQIVNMWQEVGKAMYAPPIRGQIRCSSNITGLLLT RDGGINQSISETFRPGGGDMRDNWRSELYKYKVVKIEFLGIAPTKARERVVQREKEAVGIGAVFLG FLGAAGSTMGAASLTLTVQARLLLSGIVQQQNNLLRAIEAQQHMLQLTVWGIKQLQARVLALERYL RDQQLMGIWGCSGKLICTTAVPWNASWSNKSLNDIWNNMTWMQWEREIDNYTGLIYSLLEESQNQQ EKNEQDLLALDKWANLWTWFDISNWLWYIK |
| B.con gp140CF | MRVKGIRKNYQHLWRWGTMLLGMLMICSAAEKLWVTVYYGVPVWKEATTTLFCASDAKAYDTEVHN VWATHACVPTDPNPQEVVLENVTENFNMWKNNMVEQMHEDIISLWDQSLKPCVKLTPLCVTLNCTD LMNATNTNTTIIYRWRGEIKNCSFNITTSIRDKVQKEYALFYKLDVVPIDNDNTSYRLISCNTSVI TQACPKVSFEPIPIHYCAPAGFAILKCNDKKENGTGPCINVSTVQCTHGIRPVVSTQLLLNGSLAE EEVVIRSENFTDNAKTIIVQLNESVEINCTRPNNNTRKSIHIGPGRAFYTTGEIIGDIRQAHCNIS RAKWNNTLKQIVKKLREQFGNKTIVENQSSGGDPEIVMHSENCGGEFFYCNTTQLENSTWNGTWNN TEGNITLACRIKQIINMWQEVGKANYAPPIRGQIRCSSNITGLLLTRDGGNNETEIFRPGGGDMRD NWRSELYKYKVVKIEPLGVAPTKAKTLTVQARQLLSGIVQQQNNLLRAIEAQQHLLQLTVWGIKQL QARVLAVERYLKDQQLLGIWGCSGKLICTTAVPWNASWSNKSLDEIWDNMTWMEWEREIDNYTSLI YTLIEESQNQQEKNEQELLELDKWASLWNWFDITNWLW |
| B.Deg JRFL gp140CF | MPMGSLQPLATLYLLGMLVASVLAVEKLWVTVYYGVPVWKEATTTLECASDAKAYDTEVHNVWATH ACVPTDPNPQEVVLENVTEHFNMWKNNMVEQMQEDIISLWDQSLKPCVKLTPLCVTLNCKDVNATN TTNDSEGTMERGEIKNCSFNITTSIRDEVONEYALFYKLDVVPIDNNNTSYRLISCDTSVITQACP KISEEPIPIHYCAPAGFAILKCNDKTFNGKGPCKNVSTVQCTHGIRPVVSTQLLLNGSLAEEEVVI RSDNFTNNAKTIIVQLKESVEINCTRPNNNTRKSIHIGPGRAFYTTGEIIGDIRQAHCNISRAKWN |

TABLE 26-continued

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
|  | DTLKQIVIKLREQFENKTIVFNHSSGGDPEIVMHSENCGGEFFYCNSTQLENSTWNNNTEGSNNTE GNTITLPCRIKQIINMWQEVGKAMYAPPIRGQIRCSSNITGLLLTRDGGINENGTEIFRPGGGDMR DNWRSELYKYKVVKIEPLGVAPTKAKTLTVQARLLLSGIVQQQNNLLRAIEAQQRMLQLTVWGIKQ LQARVLAVERYLGDQQLLGIWGCSGKLICTTAVPWNASWSNKSLDRIWNNMTWMEWEREIDNYTSE IYTLIEESQNQQEKNEQELLELDKWASLWNWFDITKWLW |
| B.HXB/BALgp140CFI | MRVKEKYQHLWRWGWRWGTMLLGMLNICSATEKLWVTVYYGVPVWKEATTILLCASDAKAYDTEVH NVWATHACVPTDPNPQEVVLVNVIENEDMWKNDMVEQMHEDIISLWDQSLKPCVKLTPLCVSLKCT DLKNDTNTNSSSGRMIMEKGEIKNCSFNISTSIRGKVQKEYAFFYKLDIIPIDNDTTSYSLTSCNT SVITQACPKVSFEPIPNHYCAPAGFAILKCKDKKENGKGPCINVSTVQCTHGIRPVVSTQLLVTGN LAEEEVVIRSANFADNAKVIIVQLNESVEINCTRPNNNTRKSIHIGPGRAFYTTGEIIGDIRQAHC NLSRAKWNDTLNKIVIKLREQFGNKTIVEKHSSGGDPEIVTHSENCGGEFFYCNSTQLENSTWENS TWSTEGSNNTEGSDTITLPCRIKQIINMWQKVGKAMYAPPISGQIRCSSNITGLLLTRDGGNSNNE SEIFRLGGGDMRDNWRSELYKYKVVKIEPLGVAPTKAKLTVQARQLLSGIVQQQNNLLRAIEAQQH LLQLTVWGIKQLQARTLAVERYLKDQQLLEQIWNHTTWMEWDREINNYTSLIHSLIEESQNQHEKN EQELLELDKWASLWNWFNITNWLW |
| C.089 gp140C | MRVRGMLRNCQQWWIWGILGEWNLMICSVVGNLWVTVYYGVPVWKEAKTTLFCASDARAYEREVHN VWATHACVPTDPNPQEMVLVNVTENFNMWKNDMVDQMHEDIISLWDQSLKPCVKLTPLCVILECNN ANGTTNNGSVIVVNENSTMYGEIQNCSEKVNSEIKGKKQDVYALFNSLDIVKLYNNGTSQYRLINC NTSTLTQACPKVSFDPIPIHYCAPAGYAILKCNNKTFNGTGPCNNVSTVQCTHGIRPVVSTQLLIN GSLAEGEIIIRSKNLTDNTKTIIVHLNESIKINCIRPNNNTRRSIRIGPGQAFYAANGIVGNIRQA HCNISEGEWNKTLYRVSRKLAEHPPGKEIKFKRHSGGDLEITTHSENCRGETTYCNTSKLENGTYN GTYTNNDTNSTIILPCRIKQIINMWQEVGQAMYAPPIEGIIACNSTITGLLLTRDGGDKNGSKPEI FRPGGGDMRDNWRSELYKYKVVEIKPLGIAPTKAKERVVEKEKTIQKEAVGIGAVFLGELGAAGST MGAASITLTVQARQLLSGIVQQQSNLLRAIEAQQHMLQLTVWGIKQLQARVLAMERYLQDQQLLGI WGCSGKLICTTAVPWNSSWSNKTLEYIWGNMTWMQWDREIDNYTGIIYDLLEDSQIQQEKNEKDLL ALDSWKNLWSWFSITNWLWYIK |
| C.1086 gp120 | MRVRGIWKNWPQWLIWSILGFWIGNMEGSWVTVYYGVPVWKEAKTTLFCASDAKAYEKEVHNVWAT HACVPTDPNPQEMVLANVTENFNMWKNDMVEQMHEDIISLWDESLKPCVKLTPLCVTLNCTNVKGN ESDTSEVMKNCSFKATTELKDKKHKVHALFYKLDVVPLNGNSSSSGEYRLINCNTSAITQACPKVS FDPIPLHYCAPAGFAILKCNNKTFNGTGPCRNVSTVQCTHGIKPVVSTQLLLNGSLAEEEIIIRSE NLTNNAKTIIVHLNESVNIVCTRPNNNTRKSIRIGPGQTFYATGDIIGNIRQAHCNINESKWNNTL QKVGEELAKHEPSKTIKEEPSSGGDLEITTHSENCRGEFFYCNTSDLENGTYRNGTYNHTGRSSNG TITLQCKIKQIINMWQEVGRAIYAPPIEGEITCNSNITGLLLLRDGGQSNETNDTETFRPGGGDMR DNWRSELYKYKVVEIKPLGVAPTEAKERVVEREKE |
| C.1086 gp120 D7 | MRVRGIWKNWPQWLIWSILGFWIGNMEGSVPVWKEAKTTLFCASDAKAYEKEVHNVWATHACVPTD PNPQEMVLANVTENFNMWKNDMVEQMHEDIISLWDESLKPCVKLTPLCVTLNCTNVKGNESDTSEV MKNCSFKATTELKDKKHKVHALFYKLDVVPLNGNSSSSGEYRLINCNTSAITQACPKVSFDPIPLH YCAPAGFAILKCNNKTENGTGPCRNVSTVQCTHGIKPVVSTQLLLNGSLAEEEIIRSENLTNNAK TIIVHLNESVNIVCTRPNNNTRKSIRIGPGQTFYATGDIIGNIRQAHCNINESKWNNTLQKVGEEL AKHFPSKTIKFEPSSGGDLEITTHSENCRGEFFYCNTSDLENGTYRNGTYNHTGRSSNGTITLQCK IKQIINMWQEVGRAIYAPPIEGEITCNSNITGLLLLRDGGQSNETNDTETFRPGGGDMRDNWRSEL YKYKVVEIKPLGVAPTEAKRRVVEREKR |
| C.1086 gp140 | MRVRGIWKNWPQWLIWSILGFWIGNMEGSWVTVYYGVPVWKEAKTTLFCASDAKAYEKEVHNVWAT HACVPTDPNPQEMVLANVTENFNMWKNDMVEQMHEDIISLWDESLKPCVKLTPLCVTLNCTNVKGN ESDTSEVMKNCSFKATTELKDKKHKVHALFYKLDVVPLNGNSSSSGEYRLINCNTSAITQACPKVS FDPIPLHYCAPAGFAILKCNNKTFNGTGPCRNVSTVQCTHGIKPVVSTQLLLNGSLAEEEIIIRSE NLTNNAKTIIVHLNESVNIVCTRPNNNTRKSIRIGPGQTFYATGDIIGNIRQAHCNINESKWNNTL QKVGEELAKHFPSKTIKFEPSSGGDLEITTHSENCRGEFFYCNTSDLENGTYRNGTYNHTGRSSNG TITLQCKIKQIINMWQEVGRAIYAPPIEGEITCNSNITGLLLLRDGGQSNETNDTETFRPGGGDMR DNWRSELYKYKVVEIKPLGVAPTEAKERVVEREKEAVGIGAVFLGELGAAGSTMGAASMTLTVQAR QLLSGIVQQQSNLLRAIEAQQHMLQLTVWGIKQLQARVLAIERYLKDQQLLGMWGCSGKLICTTAV PWNSSWSNKSQNEIWGNMTWMQWDREINNYTNTIYRLLEDSQNQQEKNEKDLLALDSWKNLWNWFD ISKWLWYIK |
| C.1086 V1/V2 Tags | METDTLLLWVLLLWVPGSTGDQVKLTPLCVTLNCTNVKGNESDTSEVMKNCSFKATTELKDKKHKV HALFYKLDVVPLNGNSSSSGEYRLINCNTSAITQAGLNDIFEAQKIEWHELEVLFQGPGHHHHHH |
| C.97ZA012 gp140CF1 | MRVRGIPRNWPQWWMWGILGFWMIIICRVVGNMWVTVYYGVPVWTDAKTTLECASDTKAYDREVHN VWATHACVPTDPNRQEIVLENVTENFNMWKNDMVDQMHEDIISLWDQSLKPCVKLTPLCVLHCTN ATEKNNVTNDMNKEIRNCSENTTTEIRDKKQQGYALITRPDIVLLKENRNNSNNSEYILINCNAST ITQACPKVNFDPIPIHYCAPAGYAILKCNNKTFSGKGPCNNVSTVQCTHGIKPVVSTQLLLNGSLA EKEEIIIRSENLTDNVKTIIVHLNKSVEIVCTRPNNNTRKSMRIGPGQTFYATGDIIGDIRQAYCNI SGSKWNETLKIWKEKLQENYNNNKTIKFAPSSGGDLEIITHSENCRGEFFYCNTTRLENNATEDE |

TABLE 26-continued

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
|  | TITLPCRIKQIINMWQGVGRAMYAPPIAGNITCKSNITGLLLVRDGGEDNKTEEIFRPGGGNMKDN WRSELYKYKVIELKPLGIAPTGAKLTVQARQLLSSIVQQQSNLLRAIEAQQHMLQLTVWGIKQLQT RVLAIERYLKDQQLEIWNNMTWNEWDREISNYTDTIYRLLEDSQTQQEKNEKDLLALDSWKNLWSW FDISNWLW |
| C.CAP206 gp140CF.12 | MRVRGIPRNWPQWWIWGLLGFWVIITCRVVGQLWVTVYYGVPVWTEAKTTLFCASDAKAYDKEVHN VWATHACVPTDPNPQEIVLENITENFNMWKNDMVDQMHEDIISLWDQSLKPCVKLTPLCVTLNCTN ANINVTSVSNDSRIMNEEIKNCSENTTTEIRDKKQRVYALFYRSDVVPLNSSEYILINCNTSTITQ ACPKVTFDPIPLHYCAPAGYAILKCNNKTENGAGPCLNVSTVQCTHGIKPVVSTQLLLNGSLAEEE IIIKSKNLIDDINTIIVHLNKSIEIVCIRPGNNTRKSIRIGPGQIFFATGDIIGDIREAHCNLSKD AWNKTLEQIKGKLKEHFSGKEIKFAPSSGGDPEVATHSENCRGEFFYCNTTKLENETYTRSNNSNE TIILPCRIKQIINMWQEVGRAMYAPPIAGNITCNSSITGLLLTRDPGHNNTETFRPTGGNMKDNWR NELYKYKVVEIKPLGVAPTNAKERVVEREKEAVGIGAVLLGFLGAAGSTMGAASITLTVQARQLLS GIVQQQSNLLRAIEAQQHMLQLTVWGIKQLQTRVLAIERYLKDQQLLGLWGCSGRLICTTNVPWNS SWSNKSQEDIWGNMTWMQWDREISNYTSTIYRLLEDSQNQQEKNEKDLLALDSWKNLNWFDITKW LWYIR |
| C.con gp140CF | MRVRGILRNCQQWWIWGILGEWMLMICNVVGNLWVTVYYGVPVWKEAKTTLFCASDAKAYEKEVHN VWATHACVPTDPNPQEIVLENVTENFNMWKNDMVDQMHEDIISLWDQSLKPCVKLTPLCVTLNCTN ATNATNTMGEIKNCSFNITTELRDKKQKVYALFYRLDIVPLNENNSYRLINCNTSAITQACPKVSF DPIPIHYCAPAGYAILKCNNKTENGTGPCNNVSTVQCTHGIKPVVSTQLLLNGSLAEEEIIIRSEN LTNNAKTIIVHLNESVEIVCTRPNNNTRKSIRIGPGQTFYATGDIIGDIRQAHCNISEDKWNKTLQ KVSKKLKEHFPNKTIKEEPSSGGDLEITTHSFNCRGEFFYCNTSKLENSTYNSTNSTITLPCRIKQ IINMWQEVGRAMYAPPIAGNITCKSNITGLLLTRDGGKNNTETFRPGGGDMRDNWRSELYKYKVVE IKPLGIAPTKAKTLTVQARQLLSGIVQQQSNLLRAIEAQQHMLQLTVWGIKQLQTRVLAIERYLKD QQLLGIWGCSGKLICTTAVPWNSSWSNKSQEDIWDNMTWMQWDREISNYTDTIYRLLEDSQNQQEK NEKDLLALDSWKNLNWFDITNWLW |
| C.DU123 gp140 CF | MRVKGIQRNWPQWWIWGILGEWMIIICRVVGNLWVTVYYGVPVWTEAKTTLFCASDAKAYEREVHN VWATHACVPTDPNPQEIVLGNVTENFNMWKNDINDQMHEDIISLWDQSLKPCVKLTPLCVTLNCTD VKVNATSNGTTTYNNSIDSMNGEIKNCSFNITTEIRDKKQKVYALFYRPDVVPLNENSSSYILINC NTSTTTQACPKVSFDPIPIHYCAPAGYAILKCNNKTENGTGPCHNVSTVQCTHGIKPVVSTQLLLN GSLAEEEIIIRSENLTNNAKTIIVHLNESIEIVCTRPNNNTRKSIRIGPGQTVYATNDIIGDIRQA HCNISKTKWNTTLEKVKEKLKEHEPSKAITFQPHSGGDLEVITHSENCRGEFFYCDTTKLENESNL NTTNITTLTLPCRIKQIVNMWQGVGRAMYAPPVEGNITCNSSITGLLLVRDGGNTSNSTPEIFRPG GGNMKDNWRSELYKYKVVEIKPLGVAPTKAKTLIVQARQLLSGIVQQQSNLLRAIEAQQHMLQLTV WGIKQLQARVLAIERYLKDQQLLGLWGCSGKLICPTTVPWNSSWSNKSQTDIWDNMTWMQWDREIS NYTGTIYKLLEESQNQQEKNEKDLLALDSWKNLWSWFDITNWLW* |
| Con 6 gp120 | MRVMGIQRNCQHLWRWGTMILGMLMICSAAENLWVTVYYGVPVWKEANTTLFCASDAKAYDTEVHN VWATHACVPTDPNPQEIVLENVTENFNMWKNNMVEQMHEDIISLWDQSLKPCVKLTPLCVTLNCTN VRNVSSNGTETDNEEIKNCSENITTELRDKKQKVYALFYRLDVVPIDDKNSSEISGKNSSEYRLI NCNTSAITQACPKVSFEPIPIHYCAPAGFAILKCNDKKENGTGPCKNVSTVQCTHGIKPVVSTQLL LNGSLAEEEIIRSENITNNAKTIIVQLNESVEINCTRPNNNTRKSIHIGPGQAFYATGEIIGDIR QAHCNISRTKWNKTLQQVAKKLREHFNNKTIIFKPSSGGDLEITTHSENCGGEFFYCNTSGLENST WMENGTYMENGTKDNSETITLPCRIKQIINMWQGVGQAMYAPPIEGKITCKSNITGLLLTRDGGNN SNKNKTETFRPGGGDMRDNWRSELYKYKVVKIEPLGVAPTKAKRRVVEREKR |
| CON-Sgp140CFI | MRVRGIQRNCQHLWRWGTLILGMLMICSAAENLWVTVYYGVPVWKEANTTLFCASDAKAYDTEVHN VWATHACVPTDPNPQEIVLENVTENFNMWKNNMVEQMHEDIISLWDQSLKPCVKLTPLCVTLNCTN VNVTNTTNNTEEKGEIKNCSFNITTEIRDKKQKVYALFYRLDVVPIDDNNNNSSNYRLINCNTSAI TQACPKVSFEPIPIHYCAPAGFAILKCNDKKENGTGPCKNVSTVQCTHGIKPVVSTQLLLNGSLAE EEIIIRSENITNNAKTIIVQLNESVEINCTRPNNNTRKSIRIGPGQAFYATGDIIGDIRQAHCNIS GTKWNKTLQQVAKKLREHENNKTIIFKPSSGGDLEITTHSFNCRGEFFYCNTSGLENSTWIGNGTK NNNNTNDTITLPCRIKQIINMWQGVGQAMYAPPIEGKITCKSNITGLLLTRDGGNNNTETEIFRP GGGDMRDNWRSELYKYKVVKIEPLGVAPTKAKLTVQARQLLSGIVQQQSNLLRAIEAQQHLLQLTV WGIKQLQARVLAVERYLKDQQLEIWDNMTWMEWEREINNYTDIIYSLIEESQNQQEKNEQELLALD KWASLWNWFDITNWLW |
| G.con gp140CF | MRVKGIQRNWQHLWKWGTLILGLVIICSASNNLWVTVYYGVPVWEDADTTLFCASDAKAYSTERHN VWATHACVPTDPNPQEITLENVTENFNMWKNNMVEQMHEDIISLWDESLKPCVKLTPLCVTLNCTD VNVINNNTNNTKKEIKNCSENITTEIRDKKKKEYALFYRLDVVPINDNGNSSIYRLINCNVSTIKQ ACPKVIFDPIPIHYCAPAGFAILKCRDKKENGTGPCKNVSTVQCTRGIKPVVSTQLLLNGSLAEEE IIIRSENITDNTKVIIVQLNETIEINCTRPNNNTRKSIRIGPGQAFYATGDIIGDIRQAHCNVSRT KWNEMLQKVKAQLKKIFNKSITENSSSGGDLEITTHSFNCRGEFFYCNTSGLENNSLLNSINSTIT LPCKIKQIVRMWQRVGQAMYAPPIAGNITCRSNITGLLLTRDGGNNNTETFRPGGGDMRDNWRSEL |

TABLE 26-continued

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
| | YKYKIVKIKPLGVAPTRARTLTVQVRQLLSGIVQQQSNLLRAIEAQQHLLQLTVWGIKQLQARVLA<br>VERYLKDQQLLGIWGCSGKLICTTNVPWNTSWSNKSYNEINDNKTWIFWEREISNYTQQIYSLIEE<br>SQNQQEKNEQDLLALDKWASLWNWFDITKWLW |
| G.DCRB gp140CF | MRVKGIQRNWQHLWNWGILILGLVIICSAEKLWVTVYYGVPVWEDANAPLFCASDAKAHSTESHNI<br>WATHACVPTDPSPQEINMRNVTENFNMWKNNMVEQMHEDIISLWDESLKPCVKLTPLCVTLNCTEI<br>NNNSTRNITEEYRMTNCSFNMTTELRDKKKAEYALFYRTDVVPINEMNNENNGTNSTWYRLTNCNV<br>STIKQACPKVIFEPIPIHYCAPAGFAILKCVDKKENGTGTCNNVSTVQCTHGIKPVVSTQLLLNGS<br>LABKDIISSENISDNAKVIIVHLNRSVEINCTRPNNNTRRSVAIGPGQAFYTTGEVIGDIRKAHC<br>NVSWTKWNETLRDVQAKLQEYFINKSIEENSSSGGDLEITTHSENCGGEFFYCNTSGLENNSILKS<br>NISENNDTITLNCKIKQIVRMWQRVGQAMYAPPIAGNITCRSNITGLILTRDGGDNNSTSEIFRPG<br>GGDMKNNWRSELYKYKTVKIKSLGIAPTRARTLTVQVRQLLSGIVQQQSNLLRAIEAQQHLLQLTV<br>WGIKQLRARVLALERYLKDQQLLGIWGCSGKLICTINVPWNTSWSNKSYNEIWENNTWIEWEREID<br>NYTYHIYSLIEQSQIQQEKNEQDLLALDQWASLWSW |
| US-1 SIVCPZ<br>gp140CF | MKVMEKKKRLWLSYCLLSSLIIPGLSSLWATVYYGVPVWRDVETTLFCASDAKAYKQEAHNIWATQ<br>ACVPTDPNPQEVHLPNVTEKEDMWENNMAEQMQEDIISLWDQSLKPCIKLTPLCVTLNPDSNS<br>SAVNTTDIMRNCSFNITTELRDKKKQVYSLEYVDDLAHINNNTYRLINCNTTAITQACPKTSFEPI<br>PIHYCAPPGFAILKCNEKDFKGKGECKNVSTVQCTHGIKPVVITQLIINGSLATKNVIVRSKNFAD<br>IILVQFSEGVNNICIRPGNNTVGNVQLGPGMTFYNIPKIVGDVREAHCNISKLTWEKQRKYTLEII<br>KKEANLTKVELIPNAGGDPEVVNMMLNCGGEFFYCNTIPLENMTYNNTDNITITLKCRIQIVNQW<br>MRVGKGIFAPPIKGVLSCNSNITGMILDISISAVNNDSRNITVMPTGGDMTALWKNELHKYKVVSI<br>EPIGVAPGKAKVLTVQARQLLSGIVQQQNNLLRAIEAQQHLLQLSVWGIKQLQARVLAVERYLKDQ<br>QILGLWGCSGKTICYTTVPWNDTWSNNLSYDAIWGNLTWQEWDRKVRNYSGTIFSLIEQAQEQQNT<br>NEKSLLELDQWSSLWNWFDITNWLW |
| AE.A244 gp120D11/<br>K169V | MRVKETQMNWPNLWKWGTLILGLVIICSAVPVWKEADTTLFCASDAKAHETEVHNVWATHACVPTD<br>PNPQEIDLENVTENFNMWKNNMVEQMQEDVISLWDQSLKPCVKLTPPCVTLHCTNANLTKANLTNV<br>NNRTNVSNIIGNITDEVRNCSFNMTTELRDKVQKVHALFYKLDIVPIEDNNDSSEYRLINCNTSVI<br>KQPCPKISFDPIPIHYCTPAGYAILKCNDKNENGTGPCKNVSSVQCTHGIKPVVSTQLLLNGSLAE<br>EEIIIRSENLTNNAKTIIVHLNKSVVINCTRPSNNTRTSITIGPGQVFYRTGDIIGDIRKAYCEIN<br>GTEWNKALKQVTEKLKEHENNKPIIFQPPSGGDLEITMHHENCRGEFFYCNTTRLENNTCIANGTI<br>EGCNGNITLPCKIKQIINMWQGAGQAMYAPPISGTINCVSNITGILLTRDGGATNNTNNETFRPGG<br>GNIKDNWRNELYKYKVVQIEPLGVAPTRAKRRVVEREKR |
| AE.A244 gp120<br>D11/K169VN172E/H17<br>3Y | MRVKETQMNWPNLWKWGTLILGLVIICSAVPVWKEADTTLFCASDAKAHETEVHNVWATHACVPTD<br>PNPQEIDLENVTENFNMWKNNMVEQMQEDVISLWDQSLKPCVKLTPPCVTLHCTNANLTKANLTNV<br>NNRTNVSNIIGNITDEVRNCSFNMTTELRDKVQKEYALFYKLDIVPIEDNNDSSEYRLINCNTSVI<br>KQPCPKISFDPIPIHYCTPAGYAILKCNDKNENGTGPCKNVSVQCTHGIKPVVSTQLLLNGSLAE<br>EEIIIRSENLTNNAKTIIVHLNKSVVINCTRPSNNTRTSITIGPGQVFYRTGDIIGDIRKAYCEIN<br>GTEWNKALKQVTEKLKEHENNKPIIFQPPSGGDLEITMHHENCRGEFFYCNTTRLENNTCIANGTI<br>EGCNGNITLPCKIKQIINMWQGAGQAMYAPPISGTINCVSNITGILLTRDGGATNNTNNETFRPGG<br>GNIKDNWRNELYKYKVVQIEPLGVAPTRAKRRVVEREKR |
| AE.703359 gp120D11 | MRVKETQRNWPNLWKWGTLILGLVIICSAVPVWKDANTTLFCAADAKAHETEVENVWATHTCVPTD<br>PNPQEIHMENVTENFNMWKNNMVEQMHEDVISLWDQSLKPCIKVTPLCVTLNCIDAKEDSNKTYAN<br>STVENITIENITDEVRNCSFNITTELRDKQRKVQALFYRLDIIQTENRSSGINGSFQEYRLINCNT<br>SVIKQACPKISFDPIPIHYCTPAGYAILKCNDKKENGTGPCKNVSSVQCTHGIKPVISTQLLLNGS<br>IAEEKIIIRSENITNNAKTIIVHLNRTIINCTRPSNNTRTSINIGPGQMLFYKPGDIIGDIRKAY<br>CEINGTKWKKTLDQVKRELEEHFPNKTITFQPSSGGDPEITMHHENCRGEFFYCNITQLFNMTQLN<br>ETLNETIILPCRIKQIINMWQRVGQAMYNPPVQGHINCVSNITGILLTRDGGANETNGTETFRPEG<br>GNIKDNWRSELYKYKVVQIEPLGVAPTRAKERVVERQE |
| AE.703359<br>gp120D11/Q169K | MRVKETQRNWPNLWKWGTLILGLVIICSAVPVWKDANTTLFCAADAKAHETEVHNVWATHTCVPTD<br>PNPQEIHMENVTENFNMWKNNMVEQMHEDVISLWDQSLKPCIKVTPLCVTLNCIDAKEDSNKTYAN<br>STVENITIENITDEVRNCSFNITTELRDKKRKVQALFYRLDIIQTENRSSGINGSFQEYRLINCNT<br>SVIKQACPKISFDPIPIHYCTPAGYAILKCNDKKFNGTGPCKNVSSVQCTHGIKPVISTQLLLNGS<br>IAEEKIIIRSENITNNAKTIIVHLNRTIINCTRPSNNTRTSINIGPGQMLFYKPGDIIGDIRKAY<br>CEINGTKWEKTLDQVKRELEEHFPNKTITFQPSSGGDPEITMHHENCRGEFFYCNITQLFNMTQLN<br>ETLNETIILPCRIKQIINMWQRVGQAMYNPPVQGHINCVSNITGILLTRDGGANETNGTETERPEG<br>GNIKDNWRSELYKYKVVQIEPLGVAPTRAKERVVERQE |
| AE.703359<br>gp120D11/Q169K/R170<br>Q./Q173H | MRVKETQRNWPNLWKWGTLILGLVIICSAVPVWKDANTTLFCAADAKAHETEVHNVWATHTCVPTD<br>PNPQEIHMENVTENFNMWKNNMVEQMHEDVISLWDQSLKPCIKVTPLCVTLNCTDAKFDSNKTYAN<br>STVENITIENITDEVRNCSFNITTELRDKKQKVHALFYRLDIIQTENRSSGINGSFQEYRLINCNT<br>SVIKQACPKISFDPIPIHYCTPAGYAILKCNDKKFNGTGPCKNVSSVQCTHGIKPVISTQLLLNGS<br>IAEEKIIIRSENITNNAKTIIVHLNRTIINCTRPSNNTRTSINIGPGQMLFYKPGDIIGDIRKAY<br>CEINGTKWKKTLDQVKRELEEHFPNKTITFQPSSGGDPEITMHHENCRGEFFYCNTTQLFNMTQLN |

TABLE 26-continued

Amino acid sequences of peptides and envelope glycoproteins tested.
Table 26 discloses SEQ ID NOS 2, 1, 11, 18-39, 42-44, 46-49, 117, 51-88 and
118-127, respectively, in order of appearance, "His6" disclosed as SEQ ID NO: 10.
For CaseA2, A.92RW020, B.HXB2/BAL, C.97ZA012 and ZM109, V1/V2
constructs were scaffolded with J08 protein[3] or with MuLV gp70 protein[4]. For
AE.A244 V1/V2 tags design, V1N2 constructs were made with an N-terminal Ig
VH leader sequence, and an Avi tag as well as His6 tag at the C-terminal end for
labeling and purification, respectively. Sequence region target by mAbs CH58
and CH59 are highlighted in red.

| HIV-1. Env | a.a sequence |
|---|---|
|  | ETLNETIILPCRIKQIINMWQRVGQAMYNPPVQGHINCVSNITGILLTRDGGANETNGTETFRPEG GNIKDNWRSELYKYKVVQIEPLGVAPTRAKERVVERQE |
| AE.427299 gp120D11 | MRVKETQRSWPNLWKWGTLILGLVIMCNAVPVWRDADTTLFCASDAQAHVTEVHNIWATHACVPTD PNPQEIHLENVTENFNMWKNNMAEQMQEDVISLWDQSLKPCVKLTPLCVTLKCIANITITNATTRT ENTTKENLIGNITDELRNCSENVITELRDRQRKAYALFYKLDIVPINNEANSSEYRLINCNTSVIK QACPKVSFDPIPIHYCIPAGYAILKCNDKNENGTGPCKNVSSVQCTHGIKPVVSTQLLLNGSLAED EIIIRSENLTDNSKNIIVHLNESVVINCTRPSNNTVKSIRIGPGQTFYRTGDIIGDIRQAYCNVNG TKWYEVLRNVIKKLKEHENNKTIVFQQPPPGGDLEITTHHENCRGEFFYCNTTELENNTCVNETIN NGTEGWCKGDIILPCRIKQIINLWQEVGQAMYAPPVSGQIRCISNITGIILTRDGGNGKNGTLNNE TFRPGGGNMKDNWRSELYKYKVVEIEPLGIAPSRAKERVVEMKREKE |
| AE.427299 gp120D11/Q169K | MRVKETQRSWPNLWKWGTLILGLVIMCNAVPVWRDADTTLFCASDAQAHVTEVHNIWATHACVPTD PNPQEIHLENVTENFNMWKNNMAEQMQEDVISLWDQSLKPCVKLTPLCVTLKCTANITITNATTRT ENTTKENLIGNITDELRNCSFNVTTELRDRKRKAYALFYKLDIVPINNEANSSEYRLINCNTSVIK QACPKVSFDPIPIHYCTPAGYAILKCNDKNENGTGPCKNVSSVQCTHGIKPVVSTQLLLNGSLAED EIIIRSENLTDNSKNIIVHLNESVVINCTRPSNNTVKSIRIGPGQTFYRTGDIIGDIRQAYCNVNG TKWYEVLRNVTKKLKEHENNKTIVFQQPPPGGDLEITTHHENCRGEFFYCNTTELENNTCVNETIN NGTEGWCKGDIILPCRIKQIINLWQEVGQAMYAPPVSGQIRCISNITGIILTRDGGNGKNGTLNNE TFRPGGGNMKDNWRSELYKYKVVEIEPLGIAPSRAKERVVEMKREKE* |
| AE.427299 gp120/R168K/Q169K1Y 173H/A174V | MRVKETQRSWPNLWKWGTLILGLVIMCNAVPVWRDADTTLFCASDAQAHVTEVHNIWATHACVPTD PNPQEIHLENVTENFNMWKNNMAEQMQEDVISLWDQSLKPCVKLTPLCVTLKCIANITITNATTRT ENTIKENLIGNITDELRNCSENVITELRDKKRKAHVLEYKLDIVPINNEANSSEYRLINCNTSVIK QACPKVSFDPIPIHYCTPAGYAILKCNDKNENGTGPCKNVSSVQCTHGIKPVVSTQLLLNGSLAED EIIIRSENLTDNSKNIIVHLNESVVINCTRPSNNTVKSIRIGPGQTFYRTGDIIGDIRQAYCNVNG TKWYEVLRNVTKKLKEHENNKTIVFQQPPPGGDLEITTHHENCRGEFFYCNTTELFNNTCVNETIN NGTEGWCKGDIILPCRIKQIINLWQEVGQAMYAPPVSGQIRCISNITGIILTRDGGNGKNGTLNNE TFRPGGGNMKDNWRSELYKYKVVEIEPLGIAPSRAKERVVEMKREKE |
| gp70 B.CaseA2 V1/V2V169K | MACSTLPKSPKDKIDPRDLLIPLILFLSLKGARSAAPGSSPHHHHHHQVYNITWEVTNGDRETVWA ISGNHPLWTWWPVLTPDLCMLALSGPPHWGLEYQAPYSSPPGPPCCSGSSGSSAGCSRDCDEPLTS LTPRCNTAWNRLKLDQVTHKSSEGFYVCPGSHRPREAKSCGGPDSFYCASWGCETTGRVYWKPSSS WDYITVDNNLTTSQAVQVCKDNKWCNPLAIQFTNAGKQVTSWITGHYWGLRLYVSGRDPGLTEGIR LRYQNLGPRVPIGPNPVLADQLSLPRPNPLPKPAKSPPASVKLTPLCVTLNCIDLRNATNATSNSN TTNTTSSSGGLMMEQGEIKNCSETITTSIRDKKQKEYALFYKLDIVPIDNPKNSTNYRLISCNTSV ITQA* |
| gp70 B.CaseA2 V1A/2/V169K/E172V/E173H | MACSTLPKSPKDKIDPRDLLIPLILFLSLKGARSAAPGSSPHHHHHHQVYNITWEVTNGDRETVWA ISGNHPLWTWWPVLTPDLCMLALSGPPHWGLEYQAPYSSPPGPPCCSGSSGSSAGCSRDCDEPLIS LTPRCNTAWNRLKLDQVIHKSSEGFYVCPGSHRPREAKSCGGPDSFYCASWGCETTGRVYWKPSSS WDYITVDNNLTTSQAVQVCKDNKWCNPLAIQFTNAGKQVISWITGHYWGLRLYVSGRDPGLTEGIR LRYQNLGPRVPIGPNPVLADQLSLPRPNPLPKPAKSPPASVKLTPLCVTLNCIDLRNATNATSNSN TTNTTSSSGGLMMEQGEIKNCSFNITTSIRDKKOKVHALFYKLDIVPIDNPKNSTNYRLISCNTSV ITQA* |

TABLE 30

Neutralization activity of tier 1 and tier 2
HIV-1 isolates by HG107 and HG120.

| HIV-1 isolate | Tier* | Clade | ID50 assayed in TZM-bl cells, ug/ml | |
|---|---|---|---|---|
| | | | HG107 | HG120 |
| 92TH023 | 2 | AE | 3.47 | 9.26 |
| 92TH023K169Q | 2 | AE | >45 | >50 |
| CM244 | 2 | AE | >50 | >50 |
| MN | 1 | B | >50 | >50 |
| 6535.3 | 1B | B | >50 | >50 |
| QH0692.42 | 2 | B | >50 | >50 |
| C3347.c11 | 2 | AE | >50 | >50 |
| C1080.c03 | 1 | AE | >50 | >50 |
| SHIV 1157ipEL-p/h PBMC | 1A | C | 0.16 | >50 |
| SHIV1157ipd3N4/h PBMC | 2 | C | >45 | >50 |

TABLE 30-continued

Neutralization activity of tier 1 and tier 2
HIV-1 isolates by HG107 and HG120.

| HIV-1 isolate | Tier* | Clade | ID50 assayed in TZM-bl cells, ug/ml | |
|---|---|---|---|---|
| | | | HG107 | HG120 |
| MuLV | Negative control | | >50 | >50 |

Assays were performed in the TZMbl cell-based HIV-1 pseudovirus inhibition assay.
MuLV = murine leukemia virus.
*Clustering analysis by Seaman[5] of the patterns of sensitivity defined four subgroups of viruses: those having very high (tier 1A), above-average (tier 1B), moderate (tier 2), or low (tier 3) sensitivity to antibody-mediated neutralization.

HIV-1 Env V2 Peptides.

HIV-1 Env AE.A244 gp120 and V2 peptide AE.A244 V2-171 (LRDKKQKVHALFYKLDIVPIED) (SEQ ID NO: 11) spanning from L165 to D186 and a panel of 22 alanine-scanning mutant peptides (Table 26) were produced (CPC Scientific Inc., San Jose, Calif.) for epitope mapping of mAbs.

Surface Plasmon Resonance (SPR) Kinetics Measurements.

Binding Kd and rate constant measurements of mAbs to AE.A244 gp120 and AE.A244 V1/V2 tags were carried out on BIAcore 3000 instruments as described (Alam et al, J. Virol. 85: 11725-11731 (2011), Alam et al, J Immunol 178:4424-4435 (2007), Alam et al, J. Virol. 82:115-125 (2008)). All data analysis was performed using the BIAevaluation 4.1 analysis software (GE Healthcare).

Determination of Plasma Levels of CH58- and CH59-Like Antibodies.

The levels of CH58 and CH59-like antibodies in RV144 vaccine plasma (n=43) were determined by blocking of the biotinylated mAbs CH58 and CH59 to recombinant AE.A244 gp120 protein by serial dilutions of plasma of the RV144 vaccines using methods described previously (Alam et al, J. Virol. 82:115-125 (2008)).

Infectious Molecular Clones (IMC).

HIV-1 reporter virus used were replication-competent IMC designed to encode the CM235 (subtype A/E) env genes in cis within an isogenic backbone that also expresses the Renilla luciferase reporter gene and preserves all viral open reading frames (Edmonds et al, Virology 408:1-13 (2010)). The Env-IMC-LucR viruses used was the NLLucR. T2A-AE.CM235-ecto (IMCCM235) (GenBank Accession No. AF259954.1). Reporter virus stocks were generated by transfection of 293T cells with proviral IMC plasmid DNA and tittered on TZM-bl cells for quality control (Adachi et al, J. Virol. 59, 284-291 (1986)).

Infection of CEM.NKRCCR5 Cell Line and Primary CD4+ T Cells with HIV-1 IMC.

The staining of infected CD4+ T cells was performed as described (Ferrari et al, J. Virol. 85:7029-7036 (2011), Pollara et al, Cytometry A 79:603-612 (2011)) with incubation of the primary mAb with the infected cells for 2 hr.

For ADCC assay, $IMC_{CM235}$ was titrated in order to achieve maximum expression within 36 hours post-infection by detection of Luciferase activity and intra-cellular p24 expression. $2 \times 10^6$ cells were infected with $IMC_{CM235}$ by incubation with 1 TCID50/cell dose of IMC for 0.5 hour at 37° C. and 5% $CO_2$ in presence of DEAE-Dextran (7.5 µg/ml). Cells were resuspended ($0.5 \times 10^6$/ml) and cultured for 72 hr. in medium containing 7.5 µg/ml DEAE-Dextran. The assays performed using the IMC-infected target cells were used if the percentage of viable p24+ target cells on assay day was ≥20%.

Luciferase ADCC Assay.

The HIV-1 $IMC_{CM235}$ infected $CEM.NKR_{CCR5}$ cell line (Trkola et al, J. Virol. 73:8966-8974 (1999)) (NIH AIDS Research and Reference Reagent Repository) transfected to express the HIV-1 coreceptor CCR5 to supplement the endogenous expression of CD4 and the CXCR4 coreceptor were used as target cells. The cells were incubated in the presence of 4-fold serial concentrations of mAbs starting at 40 µg/ml. Purified CD3-CD16+ NK cells 24 obtained from a HIV seronegative donor with the F/F Fe-gamma Receptor (FcRγ) IIIa phenotype. The cells were isolated from the cryopreserved PBMCs by negative selection with magnetic beads (Miltenyi Biotec GmbH, Germany). After overnight resting, the NK cells were used as effector cells at an effector to target ratio of 5:1. The cells were incubated for 6 hours at 37° C. in 5% $CO_2$. The final read-out was the luminescence intensity generated by the presence of residual intact target cells that have not been lysed by the effector population in presence of ADCC-mediating mAb. The % of killing was calculated using the formula:

$$\% \text{ killing} = \frac{(RLU \text{ of Target} + \text{Effector well}) + (RLU \text{ of test well})}{RLU \text{ of Target} + \text{Effector well}} \times 100$$

In this analysis, the RLU of the target plus effector wells represents spontaneous lysis in absence of any source of Ab. Palivizumab (MedImmune, LLC; Gaithersburg, Md.) was used as a control.

ADCC-GTL Assay.

Antibody Dependent Cellular Cytotoxic (ADCC) activity was detected as previously described in the ADCC-GranToxiLux (GTL) procedure (Pollara et al, Cytometry A 79:603-612 (2011)). The $CEM.NKR_{CCR5}$ cell line was used to generate target cells (Trkola et al, J. Virol. 73:8966-8974 (1999)) after incubation with gp120 representing the sequence of the previously described wild type and mutated HIV-1 A244, 427299, and 703557 isolates. All the PBMC samples from the seronegative donors used as effector cells were obtained according to the appropriate Institutional Review Board protocol. The effector to target (E:T) ratio of 10:1 was used for purified NK effector cells. The purified IgG preparations were obtained from sera collected from the 347759, 200134, and 302689 vaccine recipients at enrollment (week 0) and two weeks post last immunization (weeks 26). The purified IgG were tested starting as six 5-fold serial dilutions starting concentration of 100 µg/ml. MAb A32 (James Robinson; Tulane University, New Orleans, La.), Palivizumab (MedImmune, LLC; Gaithersburg, Md.; negative control) and vaccine induced mAbs were tested as six 4-fold serial dilutions starting concentration of 40 µg/ml (range 40-0.039 µg/ml). The results were analyzed as previously reported (Pollara et al, Cytometry A 79:603-612 (2011)) and are expressed as % Granzyme (GzB) activity, defined as the percentage of cells positive for proteolytically active GzB out of the total viable target cell population. The final results are expressed after subtracting the background represented by the % GzB activity observed in wells containing effector and target cell populations in absence of mAb, IgG preparation, or plasma. The results were considered positive if % GzB activity after background subtraction was >8% GzB activity. The results are reported as endpoint concentration for both IgG and mAb calculated as the concentration at which the % GzB was greater than the cut-off value.

For IMCs of RV144 breakthrough infections 703359 and 427299 and their mutants that did not sufficiently infect CD4 target cells for CTL assays, recombinant gp120 proteins and coated CD4 cell targets were used with these Envs for ADCC assays.

Plasma IgG Preparation.

Purified IgG obtained at from the week 26 sera of three vaccine recipients, from whom the mAb were isolated, all tested positive for the presence of ADCC Ab directed against the A244 WT gp120-coated target cells. The endpoint concentration of ADCC-mediating IgG in each sample was 0.46±0.06, 1.06±0.15, and 2.53±0.17 (mean±SEM) for 347759, 200134, and 302689, respectively. ADCC Ab responses were not detected in the week 0 IgG preparations.

Flow Cytometric Analysis of the Binding of mAbs to HIV-1-Infected Cells.

The 26 staining of infected PB CD4+ T cells was performed as previously described (Ferrari et al, J. Virol. 85:7029-7036 (2011)) except with a 2 hr. primary antibody incubation.

HIV-1 Virion Capture Assay.

For capture of p24/virions on plates, the ability of mAbs CH58 and CH59 to bind to HIV-1 virions was assayed using the methods as described (Burrer et al, Virology 333:102-113 (2005)).

HIV-1 Infectious Virion Capture Assay.

The capacity of V2 mAbs (10 μg/ml mAb in 300 μl) to capture infectious virions of HIV-1 92TH023 or CM244 (PBMC stock, 2×107 RNA copies/mL) was performed as previously described (Leaman et al, J. Virol. 84:3382-3395 (2010), Liu et al, J. Virol. 85:11196-11207 (2011)). Briefly, The virus particles or infectious virions in the uncaptured and captured fraction were measured by viral RNA with HIV-1 gag real time RT-PCR or TZM-bl infectious virus capture readout, respectively. The captured RNA represents the viral RNA (rVirion) after subtracting the background value (virus only). The percentage of captured infectious virion (iVirion) was calculated as 100−the uncaptured virus infectivity/virus only infectivity×100%.

Neutralization Assays.

Neutralizing antibody assays in TZM-bl cells were performed as described previously (Seaman et al, J. Viral. 84:1439-1452 (2010), Montefiori, D.C., Curr Protoc Immunol Chapter 12, Unit 12 11 (2005)). Assays were also performed on a panel of 12 viruses in the A3R5 neutralization assay (Montefiori et al, J Infect Dis 206:431-441 (2012)). Absorption of AE.92TH023 neutralization by RV144 vaccine plasma 347759 was performed by using titrations of plasma in the TZM/bl assay in which either media, control protein or A244 V1V2 tags protein (50 ug/ml) with either N160, N156 was present or N160Q, N156Q mutations present.

Inhibition of RPMI 8866 Cell Binding to AE.92TH023 Cyclic V2 Peptide.

Ninety six-well microtiter plates were coated with 2 μg/ml of streptavidin followed by the addition of 5 μg/ml of AE.92TH023 biotinylated cyclic V2 peptide or with 2 μg/ml of MADCAM-1 27 (R&D Systems, Inc. (Minneapolis, Minn.) and incubated overnight. The solution from the plates was discarded and the wells were then blocked with blocking buffer (25 mM TRIS-2.7 mM KCl-150 mM NaCl-4 mM MnCl2+0.05% Casien) for 1 hour at 37° C. The mAbs shown in Table 27 were then added in triplicate to the cyclic V2 peptide-coated wells (5-20 μg/ml) for 45 minutes at 37° C. The wells were washed four times with the blocking buffer followed by the addition of RPMI8866 cells (2×105 cells/well). Plates were then incubated at 37° C. (5% $CO_2$) for 1 hour, washed 5 times with blocking buffer followed by the addition of 100 μL of RPMI 1640 containing 1% FBS, pen/strep/glutamine. The adhered cells were detected by the addition of 10 μL of AlamarBlue® (Sigma, St. Louis, Mo.). Plates were incubated at 37° C. (5% $CO_2$) for 8 hours. Fluorescence was measured at 2-hour intervals using a M2 plate reader. The data from the 6-hour time point is shown in Table 27A. The positive cell-binding controls consisted of MADCAM and AE.92TH023 biotinylated cyclic V2 peptide-coated wells followed by the addition of RPMI8866 cells. The wells were washed and cell binding was determined by the addition of AlamarBlue® as described above. The cell binding fluorescence was considered 100% and the inhibition by the mAbs was then calculated. The positive assay controls consisted of the incubation of RPMI8866 cells with α4β7 monoclonal antibody, ACT-1 (obtained through the AIDS Research and Reference Reagent Program, Division of AIDS, NIAID, NIH: (ACT-1 cat#11718) (Lazarovits et al, J Immunol 133:1857-1862 (1984)) ACT-1 is a mouse monoclonal antibody that specifically binds only to the active form of α4β7) at a concentration of 6.7 μg/ml for 45 minutes at 37° C. The cell-antibody mixture was then added to either MADCAM or V2-coated plates. The negative assay control consisted of 28 normal human serum. For each condition a minimum of 2 to 4 independent experiments were performed.

TABLE 27A

Inhibition of RPMI 8866 cell binding to AE.92TH023 cyclic V2 peptide#

| Antibody | Concentration (μg/ml) | % inhibition (mean ± SD)* |
|---|---|---|
| CH58 | 5 | 2.9 ± 4.1 |
|  | 10 | 8.3 ± 7.3 |
|  | 20 | 37.1 ± 11.3 |
| CH59 | 5 | 19.4 ± 7.8 |
|  | 10 | 36.7 ± 8.6 |
|  | 20 | 44.8 ± 5.2 |
| CH01 | 10 | −11.2 ± 11.8 |
| 697D | 10 | −13.1 ± 9.5 |
| Controls: |  |  |
| MADCAM-ACT-1 | 2 | 71.3 ± 17.8 |
| TH023-ACT-1 | 5 | 53.3 ± 10.1 |

CSFNMTTELRDKKQKVHALFYKLDIVPIEDNTSSSEYRLINC

*Triplicate wells were performed in each experiment and each experiment was repeated 2 to 4 times

TABLE 27B

Ability to capture HIV-1 viruses by anti-HIV-1 Env antibodies.

| Antibody | C.CAP45 (p24 ng/ml) | | AE.92TH023 (p24 ng/ml) | | AE.CM244 (p24 ng/ml) | |
|---|---|---|---|---|---|---|
|  | sCD4− | SCD4+ | sCD4− | sCD4+ | sCD4− | SCD4+ |
| 697D | 6.88 | 6.05 | 1.05 | 1.20 | 0.98 | 0.63 |
| CH58 | 3.18 | 3.70 | 6.15 | 8.77 | 6.88 | 7.66 |
| CH59 | 2.29 | 2.90 | 5.51 | 12.12 | 7.00 | 9.41 |
| CH01 | 14.42 | 9.89 | 1.14 | 1.05 | 1.72 | 1.80 |
| PG16 | 210.5 | 158.23 | 7.66 | 2.57 | 9.06 | 8.61 |
| PG9 | 159.8 | 119.72 | 7.94 | 4.48 | 7.78 | 6.17 |
| P3X63 (neg control) | 2.48 | 2.0 | 0.90 | 0.68 | 0.43 | 0.59 |

TABLE 27B-continued

Ability to capture HIV-1 viruses by anti-HIV-1 Env antibodies.

| Antibody | C.CAP45 (p24 ng/ml) | | AE.92TH023 (p24 ng/ml) | | AE.CM244 (p24 ng/ml) | |
|---|---|---|---|---|---|---|
| | sCD4− | SCD4+ | sCD4− | sCD4+ | sCD4− | SCD4+ |
| 7B2 (pos control) | 63.49 | 94.0 | 16.18 | 22.47 | 12.24 | 12.69 |

Data shown are representative of 3 experiments performed.
Numbers in bold are positive values over background and controls.

TABLE 27C

V2 mAb capture of infectious replication competent HIV-1 92TH023.

| | AE.92TH023 | | AE.CM244 | |
|---|---|---|---|---|
| Antibody | Captured total virions (RNA copies) | Captured infectious virons (% virus) | Captured total virions (RNA copies) | Captured infectious virons (% virus) |
| CH58 | 532,800 | 37.5 | 0 | 0 |
| CH59 | 627,200 | 39.7 | 217,800 | 0 |
| CH01 | 494,400 | 39.4 | 1,377,000 | 9.9 |
| 697D | 710,000 | 33.4 | 7,200 | 0 |
| PG9 | 2,152,000 | 99.4 | 3,825,000 | 99.3 |
| HIVIG (Pos. control) | 2,222,800 | 66.3 | 2,343,000 | 2.8 |
| Synagis ® (neg. control) | 40,800 | 2.8 | 33,000 | 0 |

Results were the mean of 3 independent experiments.

Immunization of Rhesus Macaques.

This study involved in the use of rhesus macaques was carried out in accordance with the recommendations in the Guide for the Care and Use of Laboratory Animals of the National Institutes of Health in BIOQUAL (Rockville, Md.) BIOQUAL is fully accredited by AAALAC and through OLAW, assurance number A-3086. The protocol was approved by the BIOQUAL IACUC. All physical procedures associated with this work were performed under anesthesia to minimize pain and distress. Four rhesus macaques per group were immunized intramuscularly 4 times with 100 μg/dose of variants of recombinant AE.A244 gp120 Env proteins including AE.A244 1 gp120 gD+Δ11 (3 macaques), AE.A244 gp120 gDneg (3 macaques) and AE.A244gp120 gDnegΔ11 (4 macaques). Env proteins were adjuvanted with a squalene-based adjuvant supplemented with Lipid A, R848 and oCpGs. Blood samples were collected at day 0 and week 2 weeks post-4th immunization for isolation of plasma. The antibody levels of each group were similar and the data of all 9 animals were combined for analysis.

CH58 and CH59 Fab Crystallization and Data Collection.

For CH58 and CH59 Fab preparation, purified IgG was digested with Lys-C at 37° C. The reaction was quenched by the addition of Complete protease inhibitors. To remove the Fe fragment, the digested proteins were passed over Protein A agarose. The Fab was further purified over a Superdex 200 gel filtration column and concentrated aliquots were stored frozen at −80° C.

CH58 Fab at a concentration of 12.4 mg/ml was screened against 576 crystallization conditions using a Cartesian Honeybee crystallization robot. Initial crystals were grown by the vapor diffusion method in sitting drops at 20° C. by mixing 0.2 μl of protein complex with 0.2 μl of reservoir solution (38% (w/v) PEG 8000, 0.2 M NaCl, 0.1 M sodium phosphate-citrate pH 4.2). These crystals were manually reproduced in hanging drops by mixing 1.0 μl protein complex with 1.0 μl of the initial reservoir solution containing a range of PEG 8000 concentrations. Crystals were flash frozen in liquid nitrogen in a cryoprotectant supplemented with 15% (v/v) 2R,3R-butanediol.

To obtain crystals of CH58 Fab in complex with peptide, a V2 peptide with an acetylated N-terminus and an amidated C-terminus containing the aa sequence ELRDKKQK-VHALFYKLDIV (SEQ ID NO: 12), corresponding to HIV-1 gp120 residues 164-182, was produced by American Peptide Company (Sunnyvale, Calif.). A 2-fold molar excess of peptide was mixed with CH58 Fab and the mixture was concentrated to an A280=26.0 and then screened against 576 crystallization conditions using a Cartesian Honeybee crystallization robot. A crystal was grown by the vapor diffusion method in a sitting drop at 20° C. by mixing 0.2 μl of protein complex with 0.2 μl of reservoir solution (14% (w/v) PEG 8000, 2% (v/v) MPD, 0.1 M imidazole pH 6.5). This crystal was taken from the 192-well plate and flash frozen in liquid nitrogen in a cryoprotectant supplemented with 15% (v/v) 2R,3R-butanediol.

The complex of CH59 Fab with peptide was prepared using the approach same as for CH58, and the complex was concentrated to an $A_{280}$=18.5. Initial crystals were grown using the Cartesian Honeybee robot in a reservoir solution containing 15% (w/v) PEG 8000, 40% (v/v) isopropanol, 0.1M imidazole pH 6.5. Crystals were manually reproduced by combining 0.5 μl of protein with 0.5 μl of reservoir containing 15% (w/v) PEG 8000, 30% (v/v) isopropanol, 0.1M imidazole pH 6.5. Crystals were flash frozen in a cryoprotectant supplemented with 20% (v/v) glycerol. Data for all crystals were collected at a wavelength of 1.00 Å at the SER-CAT beamline BM-22 (Advanced Photon Source, Argonne National Laboratory).

Structure Determination, Model Building and Refinement.

Figure 56:
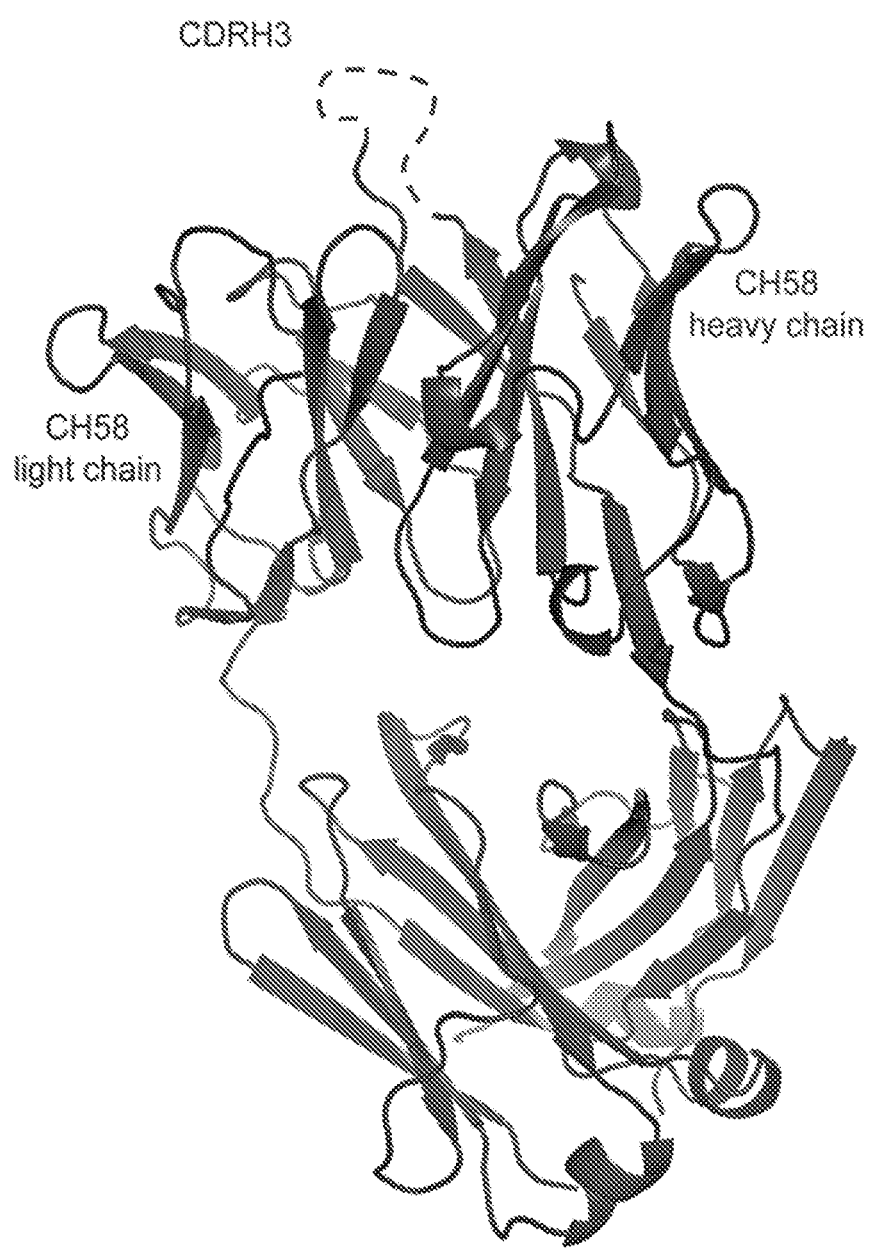
FIGS. 56A and 56B. Structure analysis of CH58, CH59, HG107 and HG120.

All diffraction data were processed with the HKL2000 suite (Otwinowski & Minor, Methods Enzymol 276:307-326 (1997)) and model building and refinement were performed in COOT (Emsley & Cowtan, Acta Crystallogr D Biol Crystallogr 60:2126-2132 (2004)) and PHENIX (Adams et al, Acta Crystallogr D Biol Crystallogr 58:1948-1954 (2002)), respectively. For the unbound CH58 Fab data (FIG. 56), a molecular replacement solution consisting of one Fab molecule per asymmetric unit was obtained using PHASER. The search model consisted of the constant domains and light chain variable domain from PDB ID 3140T and the heavy chain variable domain from PDB ID 3UJJ. For the CH58/peptide complex and the CH59/peptide complex, a molecular replacement solution consisting of one complex per asymmetric unit was obtained using PHASER with the CH58 Fab as a search model. Automatic model building was performed by Arp/wArp (Langer et al, Nat Protoc 3:1171-1179 (2008)) and Phase_and_Build for the CH59/peptide complex before manual building was initiated. Coordinates and structure factors for unbound CH58 Fab, as well as CH58 and CH59 Fabs in complex with a V2 peptide have been deposited with the Protein Data Bank under accession codes 4HQQ, 4HPO and 4HPY, respectively.

Molecular Modeling.

Homology models of the light chains for HG107 and HG120 were constructed using ROSETTA 3.3's threading protocol (Leaver-Fay et al, Methods Enzymol 487:545-574 (2011)) with the light chain of CH59 from the crystal structure of the V2-CH59 complex as the template. The model with the best energy score was selected from 100 models generated for each light chain.

Results

Vaccine-Induced Antibodies and Structure.

Figure 55:
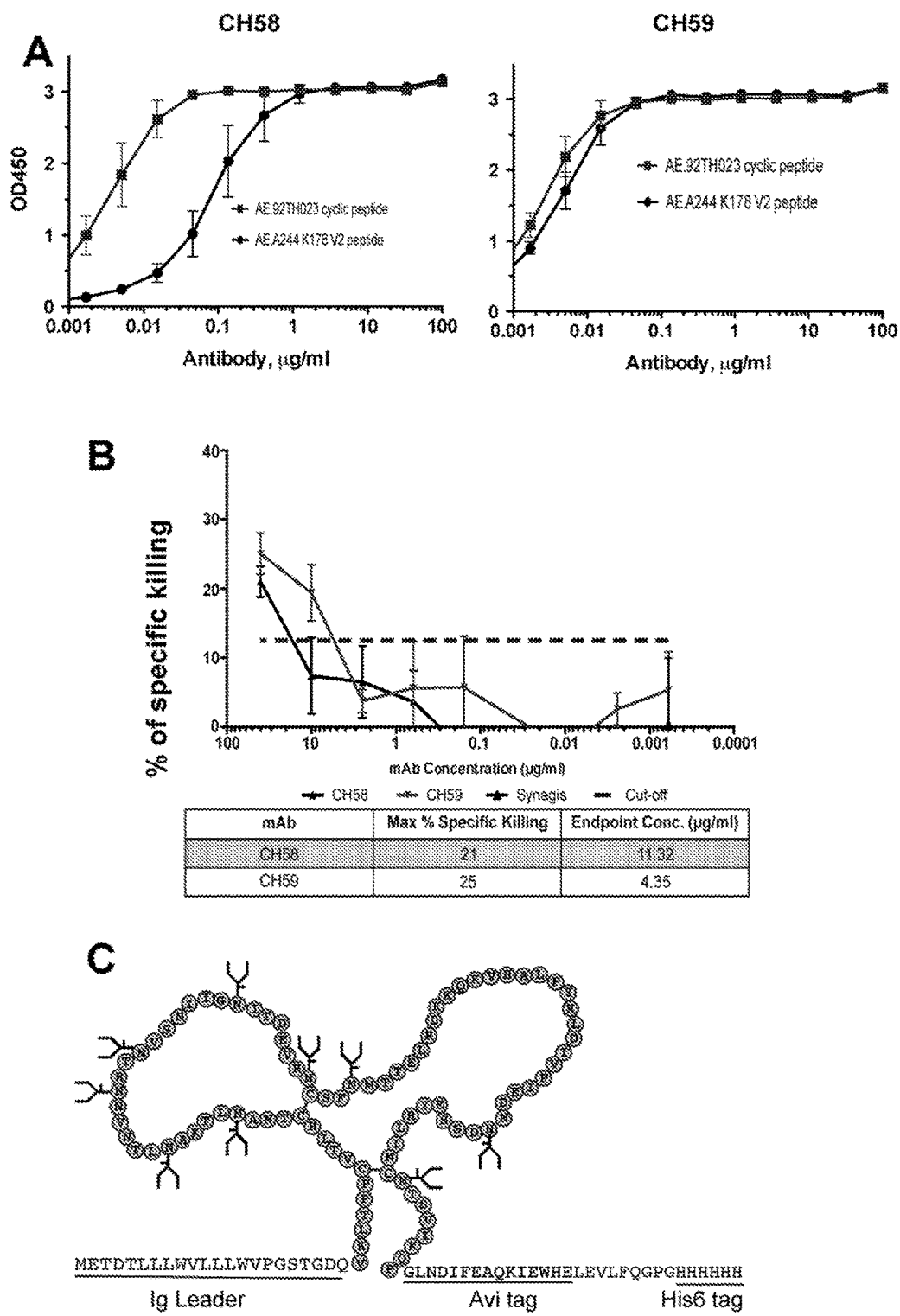
FIGS. 55A-55E. Binding of RV44 mAbs CH58 and CH59 to HIV-1 V2 peptides and ADCC activity mediated by anti-V2 mAbs CH58 and CH59 and binding of mAbs CH58, CH59, PG9, PG16, CH01 and 697D and their to AE.A244 V1/V2 Tags and AE.A244 V1/V2 Tags N156QN160Q mutant.
Figure 55:
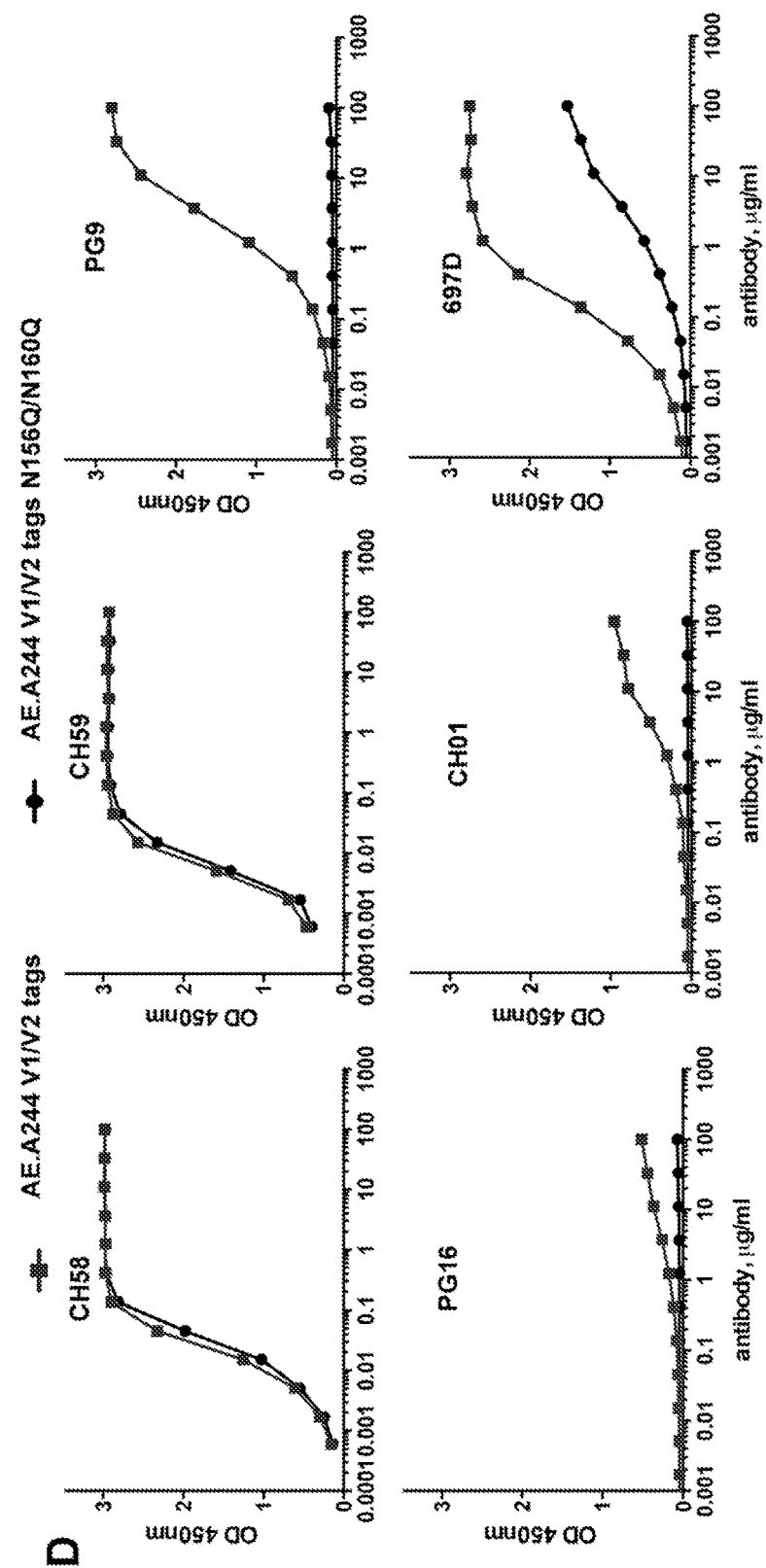
Figure 55:
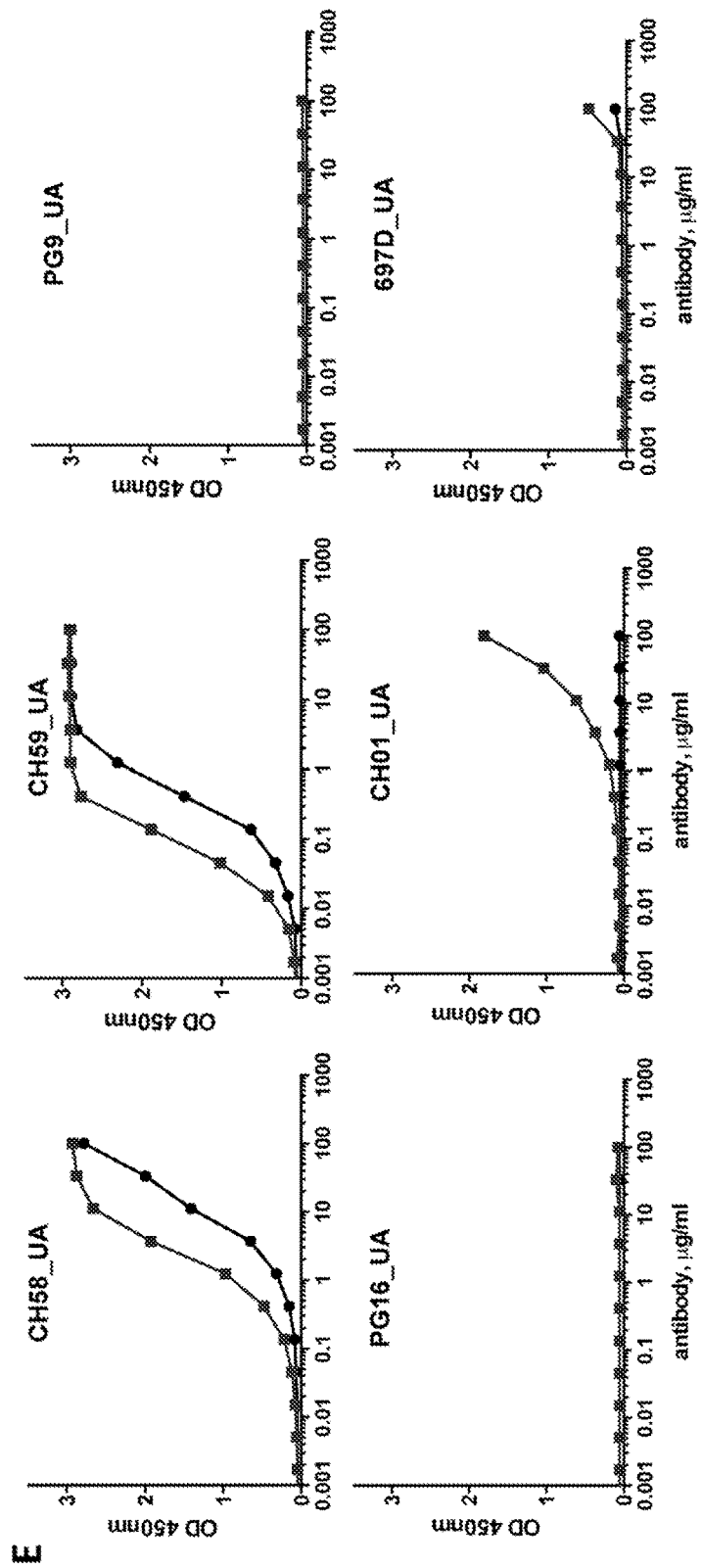

Using clonal memory B cell cultures and high throughput antigen-specific screening assays (Bonsignori et al, J. Virol. 85:9998-10009 (2011)), two V2 monoclonal antibodies (mAbs), CH58 and CH59, were initially isolated that bound to the vaccine immunogen AE.A244 gp120 and to a V2 peptide (residues 169-182, KKKVHALFYKLDIV) (SEQ ID NO: 13) (Table 25; FIG. 55A). Epitope mapping of mAbs CH58 and CH59 using alanine-scanning peptides (Table 26) with the sequence of AE.A244 Env from positions 165 to 186 (LRDKKQKVHALFYKLDIVPIED) (SEQ ID NO: 11) showed that the footprint for binding of mAb CH58 involved 10 residues (K168, K169, K171, V172, H173, F176, Y177, K178, D180, F183), while that of mAb CH59 involved 4 residues (K169, H173, F176, Y177) (FIG. 51A). Recently, HIV Env V1/V2 broadly neutralizing antibodies (bnAbs) have been described that bind both glycans as well as bind V1/V2 aa residues around and including position 169 (Bonsignori et al, J. Virol. 85:9998-10009 (2011), Doria-Rose et al, J. Virol. 86:8319-8323 (2012), McLellan et al, Nature 480:336-343 (2011), Walker et al, Science 326:285-289 (2009)). These results of peptide alanine scan mapping of RV144 V2 antibodies suggested that mAbs CH58 and CH59 may bind at or near the site in V2 to which the HIV-1 V1/V2 bnAbs (e.g. PG9) binds (Doria-Rose et al, J. Virol. 86:8319-8323 (2012), McLellan et al, Nature 480:336-343 (2011)).

TABLE 25

Characteristics of the V(D)J rearrangements of RV144 mAbs CH58 and CH59 that bind to the V2 region of the HIV-1 gp120 envelope glycoprotein compared with V1/V2 conformational bnAbs (PG9, PG16, CH01 and the V2 conformational antibody 697D. Table 25 discloses SEQ ID NOS 14-16 and 28, respectively, in order of appearance.

| | V-Heavy Chain | | | | | V-Light Chain | | | Binding to gp120 Env glycoproteins[c] | | |
|---|---|---|---|---|---|---|---|---|---|---|---|
| mAb ID | V | D | J | Mutation frequency | HCDR3 length[a] | Isotype | V J | Mutation frequency | LCDR3 length[b] | A244 gp120 | 92TH023 gp120 | MN gp120 |
| CH58 | 5-51 | 3-22 | 4 | 1.8% | 19 | IgG1 | 6-57 3 | 1.8% | 9 | +++ | +++ | − |
| CH59 | 3-9 | 1-26 | 4 | 2.8% | 13 | IgG1 | 3-10 3 | 0.9% | 11 | +++ | +++ | − |
| PG9 | 3-33 | 1-1 | 6 | 14.9% | 28 | IgG1 | 2-14 3 | 10.1% | 8 | ++ | + | ++ |
| PG16 | 3-33 | 1-1 | 6 | 14.5% | 28 | IgG1 | 2-14 3 | 12.5% | 8 | ++ | ++ | − |
| CH01 | 3-20 | 3-10 | 2 | 13.3% | 24 | IgG1 | 3-20 1 | 10.0% | 9 | ++ | − | − |
| 697D | 1-69 | 4-11 | 4 | 5.5% | 14 | IgG1 | 1-40 1 | 1.0% | 11 | +++ | +++ | +++ |

[a]HCDR3 = Heavy chain Complementarity Region 3. Length is expressed in amino acids according to the Kabat numbering system (Kabat E. A. et al., 1991).
[b]LCDR3 = Light chain Complementarity Region 3. Length is expressed in amino acids according to the Kabat numbering system (Kabat E. A. et al., 1991).
[c]+++ = 1050 <10 nM; ++ = IC50 between 10 and 100 nM; + = IC50 between 0.1 and 1 μM; − = negative.

>CH5 8VH
GAGGTGCAGCTGGTGCAGTCTGGAGCAGAGGTGAAAAAGCCCGGGGAGTCTCTGAAGATCTCCTGTAAGGGTTCTG
GATACAGGTTTACCAGTTACTGGATCGTCTGGGTGCGCCAGATGCCCGGGAAAGGCCTGGAGTGGATGGGGATCAT
CTATCCTGGTGACTTTGATACCAAATACAGCCCGTCCTTCCAAGGCCAGGTCACCATCTCAGCCGACAAGTCCATC
AGCACCGCCTACCTACAGTGGAGCAGCCTGAAGGCCTCGGACACCGCCATGTATTACTGTGCGAGACTTGGCGGCA
GATATTACCATGATAGTAGTGGTTATTACTACCTTGACTACTGGGGCCAGGGAACCCTGGTCACCGTCTCCTCA
>CH5 8VL
AATTTTATGCTGACTCAGCCCCACTCTGTGTCGGAGTCTCCGGGGAAGACGGTAACCATCTCCTGCACCCGCAGCA
GTGGCAGCGTTGCCAGCGACTATGTGCAGTGGTACCAGCAGCGCCCGGGCAGTGCCCCCACCACTGTGGTCTATGA
GGATAACCAAAGACCCTCTGGGGTCCCTGATCGATTCTCTGGCTCCATCGACAGCTCCTCCAACTCTGCCTCCCTC
ACCATCTCTGGACTCGAAGACTGAGGACGAGGCTGACTACTACTGTCAGTCTTATGATAACAGCTCTTGGGTGTTCG
GCGGAGGGACCAAGCTGACCGTCCTA
>CH5 9VH
GAAGTGCAGCTGGTGGAGTCTGGGGGAGGCTTGGTACAGCCTGGCAGGTCCCTGAGACTCTCCTGTGCAGCCTCTG
GATTCACCTTTGATGATGGTGCCATGCACTGGGTCCGGCAAGCTCCAGGGAAGGGCCTGGAGTGGGTCTCAGGTAT
TAGTTGGAATAGTAATATCATAGCCTATGCGGACTCTGTGAAGGGCCGATTCACCATCTCCAGAGACAACGCCAAG
AACTCCCTGTATTTAGAAATGAACAGTCTGAGAGTTGAGGACACGGCCTTGTATTACTGTGCAAAAGATTCTCCGC
GGGGGGAGCTACCCTTGAACTACTGGGGCCAGGGAACCCTGGTCACCGTCTCCTCA
>CH5 9VL
TCCTATGAGCTGACACAGCCACCCTCGGTGTCAGTGTCCCCAGGACAAACGGCCAGGATCACCTGCTCTGGAGATG
CATTGCCAAAAAACTATGCTTATTGGTACCAGCAGAAGTCAGGCCAGGCCCCTGTGTTGGTCATCTATGAGGACAG
CAAACGACCCTCCGGGATCCCTGAGAGATTCTCTGGCTCCAGCTCAGGGACAATGGCCACCTTGACTATCAGTGGG
GCCCAGGTTGAGGATGAAGCTGACTACTACTGTTACTCAACAGACAGCAGTGGTAATCATAGGGTGTTCGGCGGAG
GGACCAAGCTGACCGTCCT

CH58 and CH59 bound to two Env immunogens used in the ALVAC vCP1521/AIDSVAX B/E vaccine (AE.A244 and AE.92TH023) when the Envs were expressed as recombinant proteins (Table 25). Both antibodies bound to the surface of tier 2 AE.CM235 infectious molecular clone-infected CD4+ T cells (FIG. 51B) and mediated ADCC with CEM.NKR$_{CCR5}$ cells as targets (FIG. 55B). HIV-1 gp120 has been demonstrated to interact with the $α_4β_7$ molecule on CD4+ T cells using a tripeptide (LDI) motif in V2 (Arthos et al, Nat Immunol 9:301-309 (2008), Nawaz et al, PLoS Pathog 7:e1001301 (2011)). Both CH58 and CH59 mAbs inhibited V2 peptide interactions with $\alpha_4\beta_7$ (Table 27A) and weakly captured HIV-1 CRF01_AE virions (Tables 27B). When assayed for infectious virus capture, CH58 and CH59 only captured infectious virions Of AE.92TH023 strain but not of the AE.CM244 HIV-1 strain (Table 27C).

HIV-1 quasispecies or strains can be classified as different tiers according to their relative ease or difficulty by which they are neutralized by Env antibodies (Seaman et al, J. Virol. 84:1439-1452 (2010)). Tier 1 HIV-1 strains are relatively neutralization-sensitive, whereas tier 2 HIV-1 strains are more neutralization-resistant, and no plasma tier 2 neutralizing activity was found in RV144 vaccines (Montefiori et al, J Infect Dis 206:431-441 (2012)). Both CH58 and CH59 mAbs neutralized the tier 1 pseudovirus carrying the Env of strain AE.92TH023 from which the ALVAC prime was constructed (Table 28A); neutralization of this strain by both antibodies was abrogated by a K169Q Env mutation. MAbs CH58 and CH59 also neutralized the tier 1 clade C SHIV1157ipEL-p, but not the tier 1 B.MN or the tier 2 AE.CM244 strains that comprised the gp120 components in AIDSVAX, nor did they neutralize the tier 2 clade C SHIV 1157ipd3N4 nor other tier 1 or 2 HIV-1 strains (Table 28B). Thus, both the tier 2 AE.CM244 and tier 1 AE.92TH023 HIV-1 strains have identical V1/V2 sequences spanning residues 165-184 that contain the CH58/CH59 epitopes, but mAbs C1158 and CH59 neutralized only HIV-1 tier 1 strain, AE.92TH023. The differential neutralization of tier 1 AE.92TH023 but not tier 2 AE.CM244 can be explained by the failure of CH58 and CH59 to capture tier 2 AE.CM244 infectious virions, while both antibodies can capture tier 1 AE.92TH023 infectious virions (Tables 27C and 28C.

TABLE 28

Neutralization of tier 1 and tier 2 HIV-1 strains* by CH58, CH59 and their UA antibodies.

A

| | | ID50 assayed in TZM-bl cells, ug/ml | | | | |
|---|---|---|---|---|---|---|
| HIV isolate | Tier* | CH58 | CH59 | CH58 RUA | CH59 RUA | CH01 |
| TH023.6 | 1 | 10.75 | 1.92 | >50 | >50 | >25 |
| TH023.6.K169Q | 1* | >50 | >50 | >50 | >50 | 22.8 |
| TH023.6.I181L | 1* | 29.89 | 5.33 | >50 | >50 | >25 |
| 703357.c02 | 2 | >50 | >50 | >50 | >50 | >25 |
| 703357.2.Q169K | 2* | >50 | >50 | >50 | >50 | >25 |
| 703357.2.Q169KR170Q | 2* | >50 | >50 | >50 | >50 | >25 |
| 703357.2.I181L | 2* | >50 | >50 | >50 | >50 | >25 |
| 703357.2.Q169KI181L | 2* | >50 | >50 | >50 | >50 | >25 |
| 703357.2.Q169KR170QI181L | 2* | >50 | >50 | >50 | >50 | >25 |
| 427299.c12 | 2 | >50 | >50 | >50 | >50 | 0.09 |
| 427299.c12.Q169K | 2* | >50 | >50 | >50 | >50 | 0.18 |
| 427299.c12.H81L | 2* | >50 | >50 | >50 | >50 | 0.16 |
| 427299.c12.KL.Q169K/I181L | 2* | >50 | >50 | >50 | >50 | 0.15 |
| CM244.ec1 | 2 | >50 | >50 | >50 | >50 | 0.02 |
| CM244NW.4.K169Q | 2* | >50 | >50 | >50 | >50 | 0.05 |
| CM244NW.6.I181L | 2* | >50 | >50 | >50 | >50 | 0.03 |

UA = Unmutated common ancestor of CH58 or CH59.
*Based on the wildtype strain neutralization sensitivity.

B

| | EC50, ug/ml | | | | |
|---|---|---|---|---|---|
| mAb | SHIV B.SF162P3 (tier 2) | SHIV B.SF162P4 (tier 2) | SHIV B.BaL (tier 2) | SHIV C.1157ipEL-p (tier 1A) | SHIVC.1157ipd3N4 (tier 2) |
| CH58 | >50 | >50 | >50 | 37.6 | >50 |
| CH59 | >50 | >50 | >50 | 24.6 | >50 |

C

| | | | ID50 assayed in A3R5.7 cells, ug/ml | | |
|---|---|---|---|---|---|
| HIV-1 Isolate | Tier* | Clade | CH58 | CH59 | CH01 |
| SC22.3C2.LucR.T2A.ecto | 2 | B | >25 | >25 | >25 |
| RHPA.LucR.T2A.ecto | 2 | B | >25 | >25 | 8.2 |
| WITO.LucR.T2A.ecto | 2 | B | >25 | >25 | 0.05 |
| 1051.C22.LucR.T2A.ecto | 2 | B | >25 | >25 | >25 |
| Ce1086_B2.LucR.T2A.ecto | 2 | C | >25 | >25 | >25 |
| Du151.2.LucR.T2A.ecto | 2 | C | >25 | >25 | 1.51 |
| Ce1176_A3.LucR.T2A.ecto | 2 | C | >25 | >25 | 0.04 |
| Du422.1.LucR.T2A.ecto | 2 | C | >25 | >25 | >25 |
| R2184.c04.LucR.T2A.ecto | 2 | AE | >25 | >25 | >25 |
| CM235-2.LucR.T2A.ecto | 2 | AE | >25 | >25 | 0.04 |
| 644039.c01b-CM235LucR.T2A.11 | 2 | AE | >25 | >25 | >25 |
| CM244.c01.ETH2220LucR.T2A.4 | 2 | AE | >25 | >25 | 0.33 |

*Clustering analysis by Seaman[5] of the patterns of sensitivity defined four subgroups of viruses: those having very high (tier 1A), above-average (tier 1B), moderate (tier 2), or low (tier 3) sensitivity to antibody-mediated neutralization.

Since bnAbs that target V1/V2 regions (Bonsignori et al, J. Virol. 85:9998-10009 (2011), Walker et al, Science 326: 285-289 (2009)) (e.g. PG9, PG16 and CH01) and V2 conformational mAbs (e.g. 697D) (Gorny et al, Virology 427:198-207 (2012)) that also target epitopes in V2 are glycan-dependent, used next were peptides, recombinant gp120 and V1/V2 constructs to determine the dependence of CH58 and CH59 binding on adjacent N160, N156 glycan sites. Whereas 697D, PG9, PG16 and CH01 did not bind to linear and cyclic V2 peptides (not shown), both CH58 and CH59 bound well to V2 peptide (KKKVHALFYKLDIV) (SEQ ID NO: 13) with EC50s of 0.06 μg/ml and 0.003 ug/ml, respectively (FIG. 55A). Thus the binding of CH58 and CH59 to V2 is glycan-independent.

It has been previously described that bnAbs PG9, PG16 and CH01 bound well to the AE.A244 gp120 recombinant Env (Bonsignori et al, J. Virol. 85:9998-10009 (2011)). N160K mutants of AE.A244 gp120 were therefore constructed and it was found that whereas the binding of PG9, PG16 and CH01 bnAbs to AE.A244 gp120 was abrogated by the N160K mutation, the binding of CH58 and CH59 mAbs was not (Table 22). In addition, native deglycosylation (Ma et al, PLoS Pathog 7:e1002200 (2011)) (that removes all V1/V2 glycans) of the AE.A244 V1/V2 tags protein (FIG. 51C, Table 26) abrogated the binding of V1/V2 bnAbs CH01, PG9 and PG16 and decreased the binding of mAb 697D six-fold but did not affect CH58 and CH59 Env binding (Table 22). Similarly, the N156Q, N160Q mutations had no effect on CH58 and CH59 binding to A244 V1/V2 tags protein, while the two mutations completely abrogated the binding of PG9, PG16, and CH01 bnAbs and markedly decreased the binding by mAb 697D, thus confirming the glycan independence of CH58 and CH59 V1/V2 binding (FIG. 55D).

A244 V1/V2 tags protein. Initially, a crystal structure was determined of the CH58 antigen-binding fragment (Fab) alone, but several residues in the third complementarity determining region of the heavy chain (CDRH3) were disordered (FIG. 56A). Next crystal structures of the CH58 and CH59 Fabs were determined in complex with an AE.92TH023 Env V2 peptide 164-ELRDKKQKVHAL-FYKLDIV-182 (SEQ ID NO: 12) to 1.7 Å and 1.5 Å, respectively. The CH58:peptide structure was refined to an $R_{cryst}/R_{free}$ of 0.185/0.211 (FIG. 56B) and revealed that CH58 recognizes V2 residues 167-176 as an α-helix and residues 177-181 as an extended coil (FIG. 53A). Surprisingly, the CH59:peptide structure, which was refined to an $R_{cryst}/R_{free}$ of 0.171/0.187 (FIG. 52B), revealed that CH59 recognizes residues 168-173 as coil or turn, and residues 174-176 as a short 310 helix (FIG. 53B). Thus, the two Fabs recognize similar V2 residues in completely different conformations. In general, the interactions observed in the crystal structures agreed well with the peptide mapping studies, and both Fabs made multiple hydrogen bond or salt bridge interactions with K169 and H173. Collectively, these results demonstrate antibody binding sites for both mAbs CH58 and CH59 at the position of imputed immune pressure (K169) induced by ALVAC/AIDSVAX B/E vaccination (Rolland et al, Nature 490:417-420 (2012)).

Comparison of RV144 mAb CH58-V2, CH59-V2 and bnAb PG9-V1/V2 Crystal Structures.

Interestingly, both CH58 and CH59 mAb binding sites also involved key residues that are components of the bnAb PG9 binding site (Doria-Rose et al, J. Virol. 86:8319-8323 (2012), McLellan et al, Nature 480:336-343 (2011)) (FIG. 53C). In addition to binding to aa within 168-178 of a scaffolded-V1/V2 recombinant protein, mAb PG9 binds to N-linked glycans at N160 and N156 (Walker et al, Science

TABLE 22

Effect of N160K mutation and glycosylation of HIV-1 Env gp120 on binding of anti-HIV-1 Env mAbs.

| HIV-Env | | EC50 (nM) | | | | | |
|---|---|---|---|---|---|---|---|
| | | PG9 | PG16 | CH58 | CH59 | CH01 | 697D |
| AE.A244 gp120 | WT | 0.7 | 22 | 0.02 | 0.03 | 1.3 | 0.8 |
| | N160K | >667 | — | 0.02 | 0.04 | — | 0.8 |
| AE.A244 gD+ gp120 | WT | 0.7 | 15 | 0.02 | 0.04 | 0.9 | 0.3 |
| | N160K | >667 | — | 0.02 | 0.03 | — | 0.2 |
| AE.A244V1V2 tags | WT | 0.25 | 5.6 | 0.0015 | 0.0018 | 1.7 | 0.6 |
| | Degly | — | — | 0.0015 | 0.0015 | — | 3.6 |

Table shows the effect of N160K mutation (AE.A244gp120 and AE.A244 gD+gp120 envelope glycoproteins) and deglycosylation C.CAP206 gp140 envelope glycoprotein) on the ability of PG9, PG16, CH58, CH59, CH01 and 697D to bind in ELISA. Results are expressed as EC50 nM. Positive results with EC50 above the highest tested concentration (667 nM) are indicated as >667 nM. No detectable binding are indicated with a (−).

Figure 52:
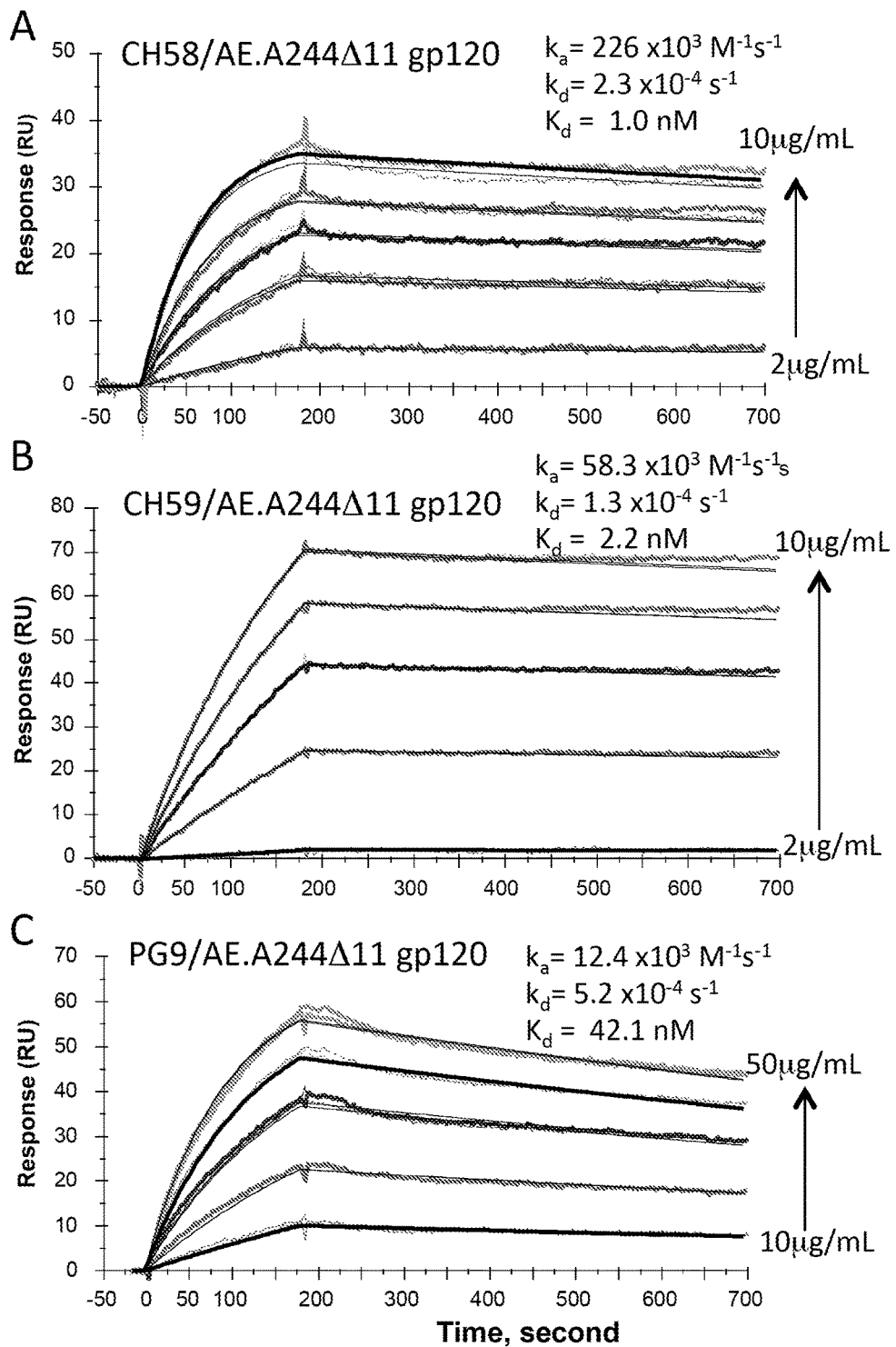
FIGS. 52A-52F. Binding of RV144 V2 and PG9 bnAbs to AE.A244 V1/V2 tags protein and AE.A244 Δ11 gp120. Each of the mAbs was captured on an anti-Fc antibody immobilized sensor surface to about 100-125 RU. For binding to A244Δ11 gp120, 2-10 μg/mL (CH58, FIG. 52A), 2-10 μg/mL (CH59, FIG. 52B), 10-50 μg/mL (PG9, FIG. 52C) of monomeric gp120 were injected over each of the mAbs. AE.A244 V1/V2 tags protein was injected at concentrations ranging from 0.5-5 μg/mL (CH58, FIG. 52D), 0.1-5 μg/mL (CH59, FIG. 52E), 10-100 μg/mL (PG9, FIG. 52F). A negative control mAb (Synagis) was used to subtract non-specific binding. Each plot shows binding curves with increasing concentrations of gp120 or V1/V2 proteins (shown in different colors) injected over two independent flow cells immobilized with the same mAbs. For binding to CH58 and CH59 mAbs, A244 D11gp120 protein was injected at 2, 4, 6, 8, and 10 μg/mL and AE.A244 V1V2 protein at 0.2, 0.5, 1, 2, 3, 4 and 5 μg/mL. For PG9 mAb, A244D11 gp120 and AE.A244 V1V2 proteins were injected at 10, 20, 30, 40 and 50 μg/mL and 10, 25, 50, 75 and 100 μg/mL respectively. Global Curve fitting (shown in black) to a 1:1 Langmuir model was used to derive rate constants and Kd values following simultaneous fitting to binding data from two independent flow cells with the same mAb captured. A third flow cell with each of them Abs gave similar rate constant values.
Figure 52:
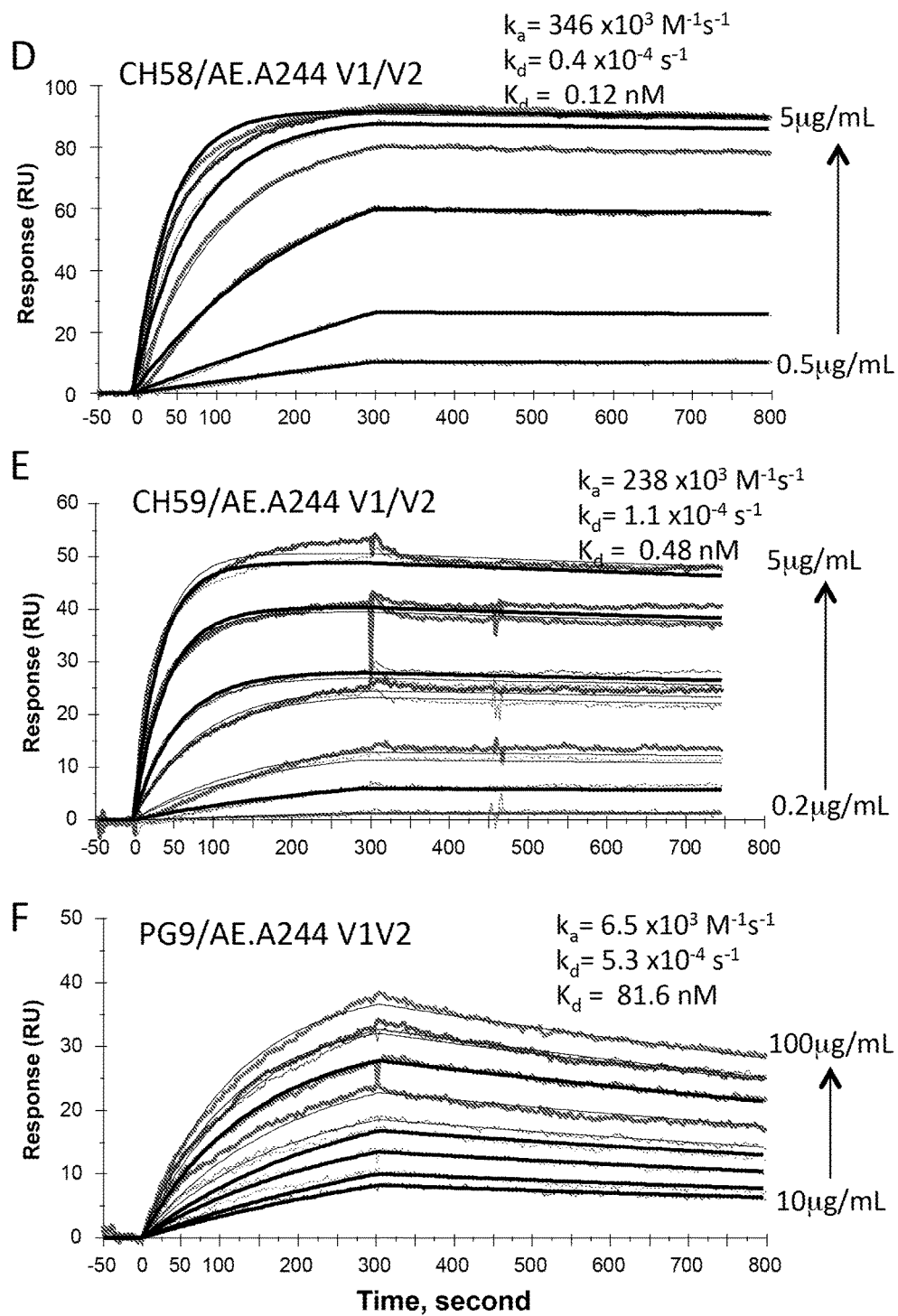
Figure 57:
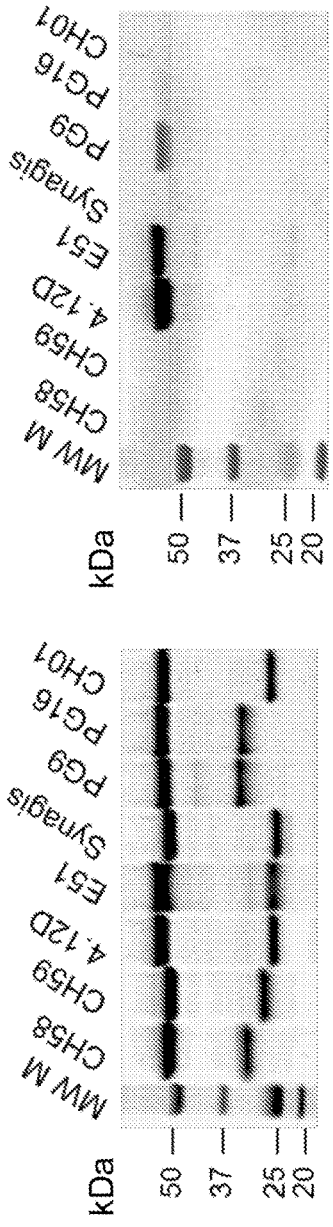
FIGS. 57A and 57B. Sulfation detection of CH58 and CH59 mAbs by Coomassie stain and Western blot, and alignment of the HCDR3 sequence of mAbs PG9, PG16, CH58, CH59, CH01 and 697D and their UAs.

In SPR assays, mAbs CH58, CH59 and PG9 bound well to AE.A244 Δ11gp120 with Kds of 2.3 nM, 2.2 nM and 47.3 nM, respectively (FIGS. 52A-52C). Similarly, CH58, CH59 and PG9 also bound well to AE.A244 V1/V2 tags protein with Kds of 0.33 nM, 1.0 nM and 83.3 nM, respectively (FIGS. 52D-52F). Binding kinetics of PG9 was distinct from CH58 and CH59 in having slower association rates (about 40-fold to AE.A244 V1/V2 11 tags and about 6-15 fold slower to AE.A244 Δ11gp120) (FIG. 52). Thus, both RV144 V2 mabs CH58 and CH59 and V1/V2 bnAbs bound to the 326:285-289 (2009), Pancera et al, J. Virol. 84:8098-8110 (2010)). PG9 also recognizes positively 12 charged V2 residues using a combination of sulfated tyrosines and acidic residues. MAbs CH58 and CH59, however, demonstrated no tyrosine sulfation (FIG. 57A). Although CH58, CH59, and PG9 share binding to some of the same gp120 V2 aa residues (aa 168-171 KKQK) (SEQ ID NO: 41), the most differences among the crystal structures of these three antibodies in complex with their epitopes reveal substantial differences in the conformations of V2 residues 168-176. These residues are bound to CH58 as an alpha helix, to CH59 as a coil and 310 helix, and to PG9 as a beta strand (McLellan et al, Nature 480:336-343 (2011)) (FIG. 53). While PG9 is broadly neutralizing for tier 2 HIV-1 strains, PG9 and the related PG16 and CH01-CH04 bnAbs do not neutralize most tier 1 HIV-1 strains (Bonsignori et al, J. Virol. 85:9998-10009 (2011), Walker et al, Science 326:285-289 (2009), Pancera et al, J. Virol. 84:8098-8110 (2010)).

Conversely, CH58 and CH59 neutralize only select tier 1 HIV-1 and no tier 2 strains. That PG9 binds to V1/V2 in a beta strand conformation whereas CH58 and CH59 recognize alternative V2 conformations raises several hypotheses. First, this V1/V2 region may exist in multiple conformations since CH58, CH59, and PG9 all bind to AE.A244 gp120 and V1/V2 tags proteins (Table 22, FIGS. 52A-52F) despite their binding to different conformations in their respective crystal structures. Alternatively, the predominant conformation of V1/V2 on peptides and recombinant Env constructs may be different from that on virion trimeric Env and on virus infected CD4 T cells. Third, the conformation of V2 aa 168-176 may take on alternate conformations in tier 1 versus tier 2 HIV-1 strains on virions and virus infected cells. Regardless, these data demonstrate differences in the structures recognized by weakly neutralizing vaccine-induced and broadly neutralizing infection induced antibodies that include V2 as part of their conformational epitopes.

Reactivity of RV144 Vaccinee Plasma with RV144 Vaccine Envs, RV144 Placebo Infection Breakthrough AE.Envs and gp70V1/V2 Case A2 Fusion Protein Mutants.

An immune correlates study of RV144 vaccines demonstrated that antibodies to a gp70V1/V2 fusion protein (gp70V1/V2 CaseA2) correlated with lowered infection risk (Haynes et al, New Engl. J. Med. 366:1275-1286 (2012)). Whereas in the RV144 sieve analysis, vaccine efficacy was 48% (p=0.0036, 95% CI:18%, 66%) against viruses that matched the vaccine at V2 aa169K (Rolland et al, Nature 490:417-420 (2012)), the gp70V1/V2 CaseA2 protein has a valine at aa169, and of CH58 and CH59, only CH58 binds to gp70V1/V2 CaseA2 fusion protein. Thus, there are two distinct but related antibody correlates of risk of infection identified in the RV144 trial that are relevant to CH58 and CH59 antibodies described herein: 1) antibodies that bind to gp70V1/V2CaseA2 scaffold (e.g. CH58-like antibodies) and 2) antibodies that bind to K169 and can potentially mediate immune pressure as found in the RV144 sieve analysis (e.g. CH58- and CH59-like antibodies).

It was next determined whether CH58, CH59 and conformational V2 and bnAb V1/V2 mabs reacted with the vaccine Env A244 wildtype (WT), RV144 placebo (i.e. breakthrough) infection Envs (that did not match vaccine Envs), and gp70V1/V2 CaseA2 scaffold WT (V169), and the effect of mutations introduced in the CH58 and CH59 footprints was evaluated (Table 23).

TABLE 23

Effect of amino acid substitutions in the V2 region of HIV-1 Env on ability of HIV-1 V2 mAbs to bind.

| | A244 gp120 | | | AE. 703359 gp120 | | | AE.427299 gp120 | | | gp70 B.CaseA2 V1/V2 | | |
|---|---|---|---|---|---|---|---|---|---|---|---|---|
| mAb | WT | K169V | Mut3 | WT | Q169K | Mut3 | WT | Q169K | Mut4 | WT | V169K | Mut3 |
| RV144V2 antibodies: | | | | | | | | | | | | |
| CH58 | 0.03 | 0.05 | 7 | 0.38 | 0.04 | 0.07 | 22.5 | 3.4 | 0.03 | 1.2 | 0.025 | 0.03 |
| CH59 | 0.029 | 0.58 | NB | NB | 1.2 | 0.05 | NB | NB | 0.03 | NB | NB | 0.02 |
| Other V1V2 antibodies: | | | | | | | | | | | | |
| 697D | 0.1 | 0.06 | 0.08 | 0.21 | 0.51 | 0.12 | 0.07 | 0.13 | NB | 0.04 | 0.14 | 0.04 |
| PG9 | 0.6 | 3 | >100 | >5 | 0.53 | 0.54 | 0.47 | 0.13 | >10 | NB | >100 | >10 |
| PG16 | >10 | >100 | NB | NB | >10 | >10 | >10 | 0.26 | NB | NB | NB | NB |
| CH01 | 0.35 | 0.13 | 0.93 | NB | NB | NB | >10 | >10 | NB | NB | NB | NB |

The indicated HIV-1 Env willdtype (WT), and Env mutants with a single a.a residue substitution at the position 169, 3 a.a. residue substitutions (Mut3) or 4 a.a. residue substitutions (Mut4).
AE.A244 gp120/Mut 3 = K169V/V172E/H173Y.
AE.703359 gp120/Mut 3 = Q169K/R170Q/Q173H.
AE.427299 gp120/Mut 4 = R168K/Q169K//Y173H/A174V.
gp70 B.CaseA2 V1/V2/Mut3 = V169K/E172V/E173H.

It was found that CH58 and CH59 binding was high on WT A244 gp120 and either reduced for CH58 or abrogated for CH59 on A244 gp120 with K169V, V172E and H173Y mutations (mutations away from the sequence of the vaccine Envs) (Table 23). For RV144 placebo breakthrough infection Envs 703357 and 427299 gp120s (that did not match the vaccine in V2) binding of CH58 was low on WT and increased by two logs on R168K, Q169K, Y173H, A174V Env mutants (mutations that changed the breakthrough infection Env sequences to match those of the Env vaccines). Similarly, 14 CH59 did not bind to WT breakthrough infection Envs but did bind well to breakthrough Envs with Q169K, R170Q and Q173H mutations (Table 23). Finally, while CH58 but not CH59 bound to gp70V1/V2 CaseA2 fusion protein, the introduction of V169K, E172V and E173H substitutions (to match the vaccine Envs) within the CH58 and CH59 footprints on the V1/V2 fusion protein resulted in increased binding of CH58 and the appearance of CH59 binding (Table 23). The V2 conformational mAb 697D, and V1/V2 bnAbs CH01, PG9 and PG16 had either little or varying binding patterns to these Envs and their mutants (Table 23). That the binding patterns of CH58 and CH59 to whole gp120 proteins with the same mutations in gp120s and V2 peptides similarly abrogated mAb binding, lends credence to, but do not prove, the relevance of the structures obtained with V2 peptides.

Figure 58:
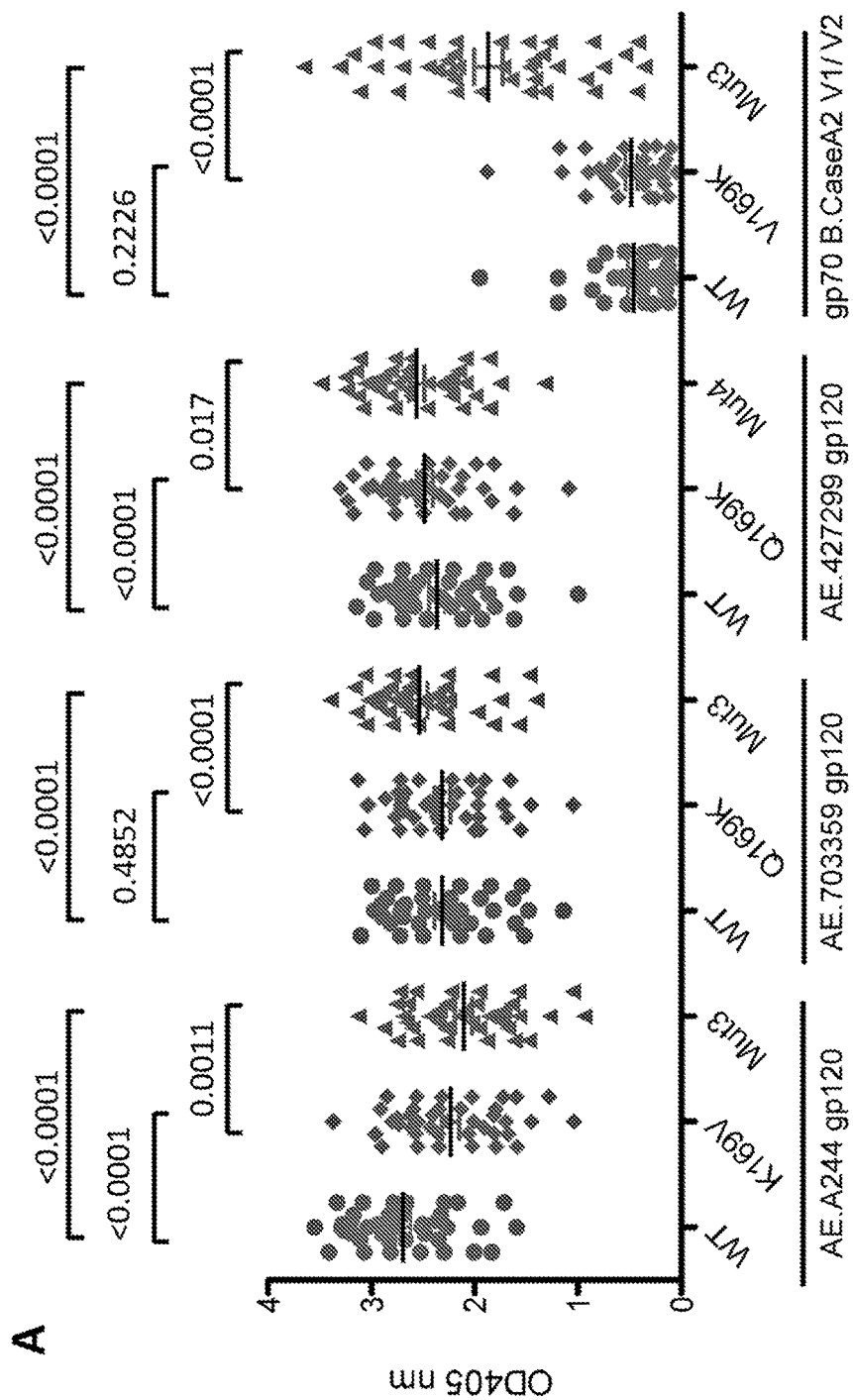
FIGS. 58A and 58B. Binding of plasma antibodies of RV144 ALVAC-AIDSVAX B/E vaccine recipients to wild-type or mutated forms of the V2 region of HIV-1 vaccine Envs and blocking binding of CH58 or CH59 by plasma antibodies of RV144 vaccine recipients.
Figure 58:
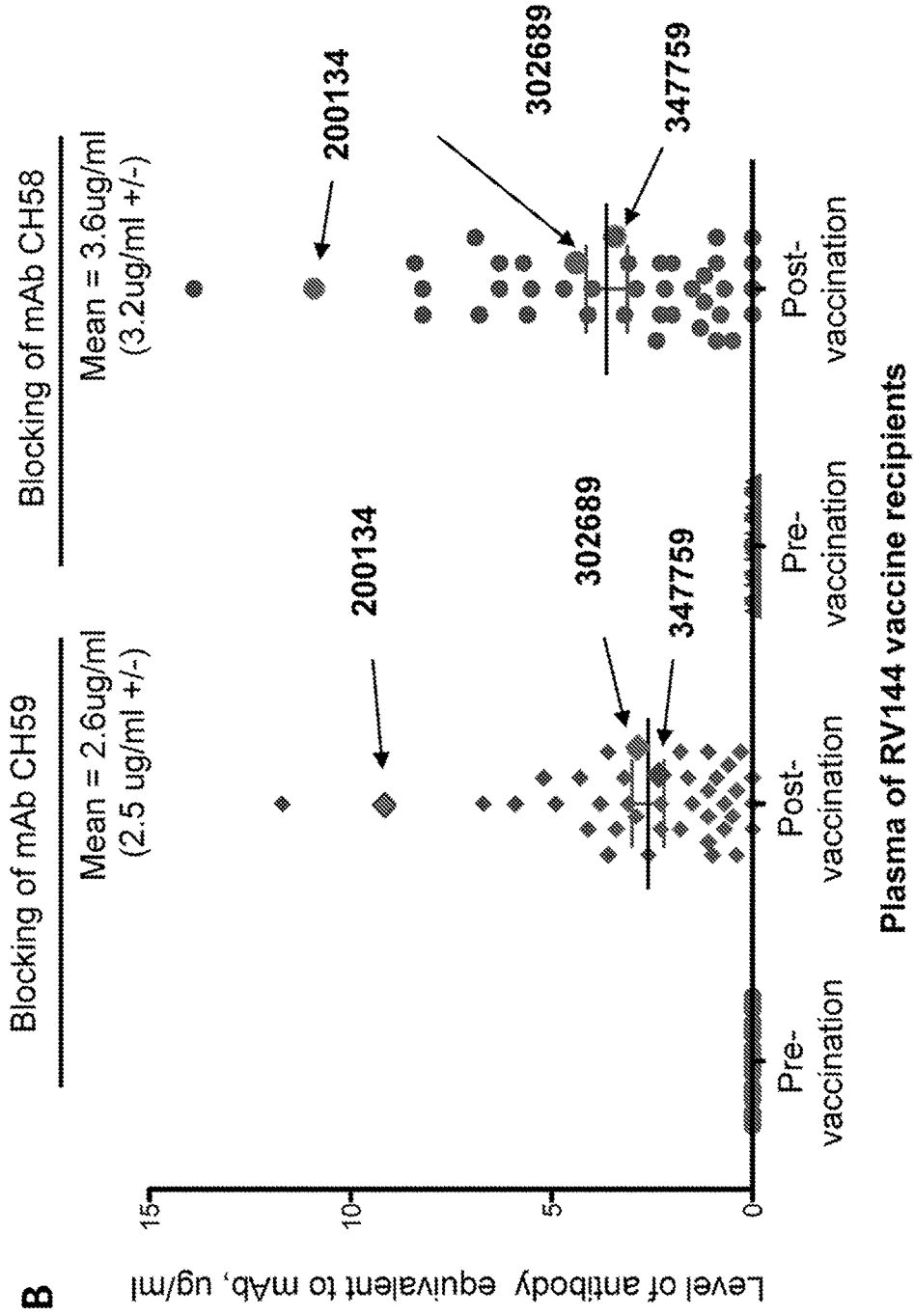

A study was next made of the reactivity of plasma from 40 RV144 vaccines to these Env proteins and their mutants (FIG. 58A). Antibody binding decreased significantly on A244 gp120 K169V compared to WT A244 gp120 (p<0.0001, paired Student's t test), and decreased further with the K169V, V172E and H173Y (mut3) mutant of A244. For RV144 breakthrough Envs AE.703359 and AE.427299, binding was significantly less on WT Env than on the Envs containing mutations necessary for optimal CH58 and CH59 binding (AE703359 mut3 and AE427299 mut4) (p<0.0001 for both Envs, paired Student's t test). Moreover, RV144 plasma antibodies bound AE.427299 Q169K Env significantly better than WT (p<0.0001, paired Student's t test).

RV144 plasma antibodies bound to gp70V1/V2 CaseA2 protein (FIG. 58A), with no significant improvement in binding to the V169K mutant scaffold, but dramatically improved vaccine plasma binding to the gp70V1 V2 CaseA2 protein with 169K, E172V 15 and E173H triple mutations (p<0.0001, paired Student's t test). Thus, the RV144 vaccine clearly induced antibodies dependent on the CH58 and CH59 footprint aa residues found in the vaccine, and used this footprint for recognition of vaccine immunogen Env A244 gp120, and most importantly, for recognition of breakthrough CRF_AE01 infection Envs with CH58 and CH59 footprint mutations.

Reactivity of Unmutated Ancestor Antibodies of RV144 V2 mAbs and PG9, PG16 and CH01 V1/V2 bnAbs.

Figure 59:
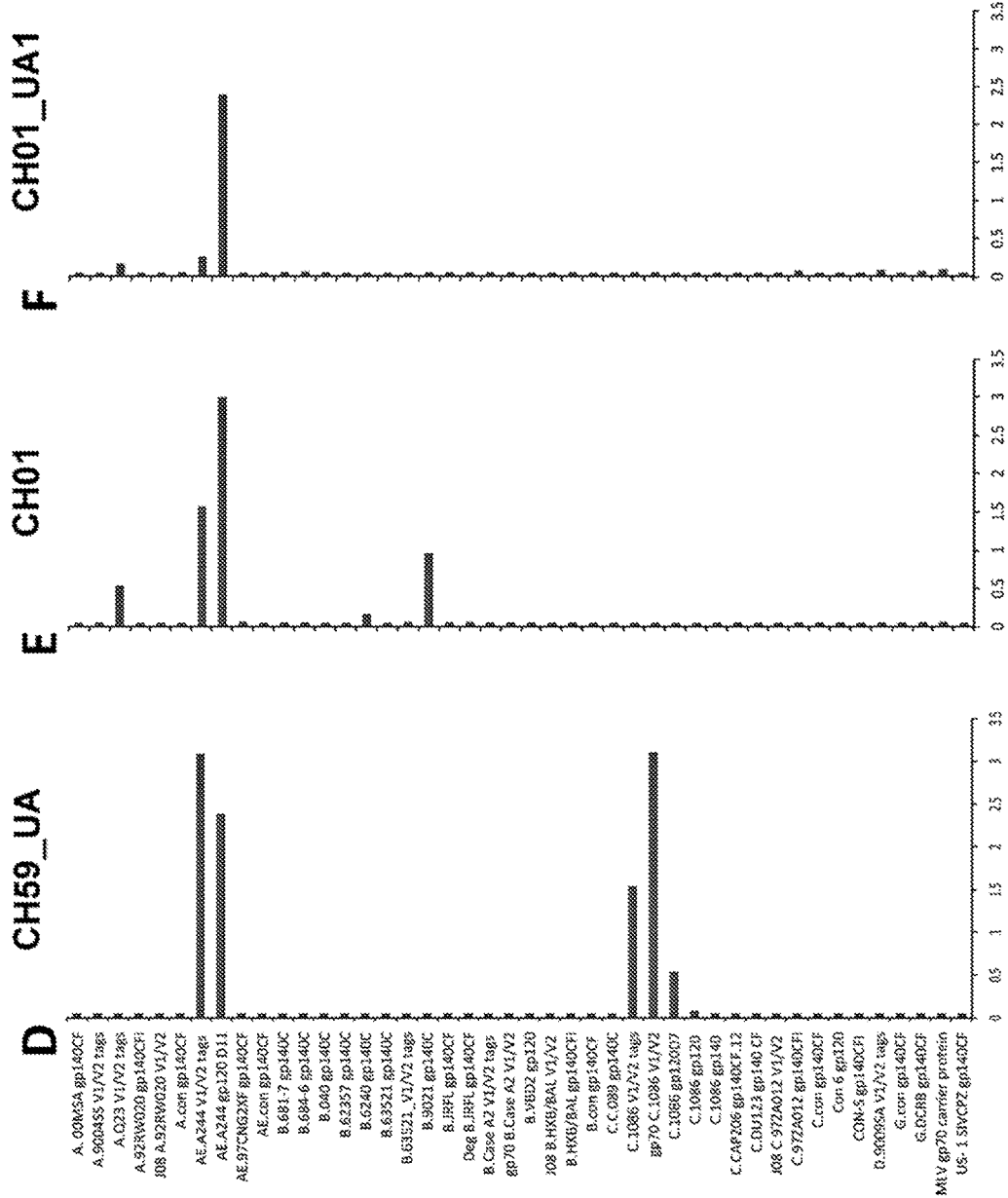
FIGS. 59A-59N. Binding of RV144 mAbs CH58, CH59, CH01, PG9, PG16, and 697D as well as their unmutated ancestors (UAs) to HIV-1 Envs. Serial dilutions ranging from 100 µg/ml to 0.001 µg/ml of mAbs as indicated on the top of each panel were tested in ELISA for binding to a panel of 43 HIV-1 and 1 SIV Envs as well as a negative control protein (MuLV gp70) as indicted on the y axis. Shown is the binding of mAbs to HIV-1 Envs expressed as OD 405 nm reading at 10 µg/ml (x axis). Data shown are a representative of three experiments.
Figure 59:
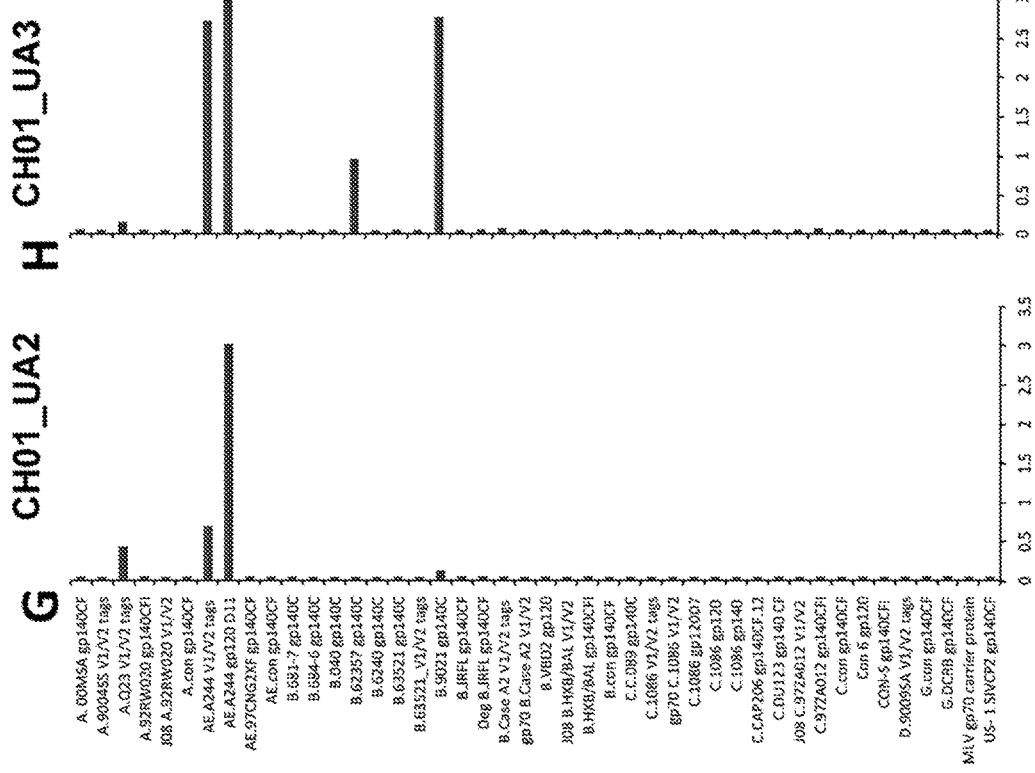
Figure 59:
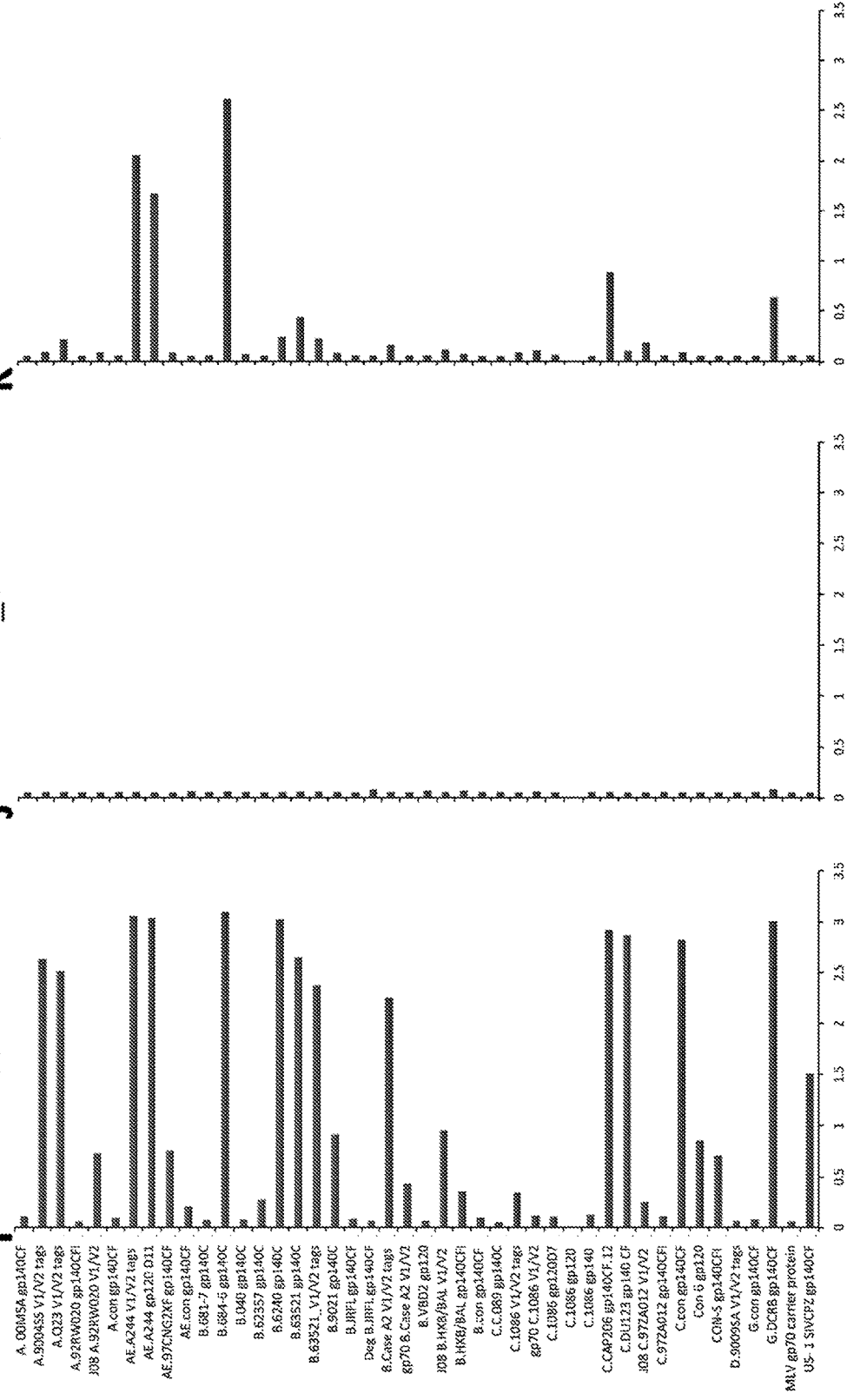

The presence of multiple tyrosines in HCDR3s of CH58, CH01, and PG9 and their unmutated ancestor antibodies (UAs) (FIG. 57B, Table 29) led to the expectation that reactivities of UAs of RV144 V2 mAbs and these bnAbs may be similar. Reverted UAs were constructed as models for naïve B cell receptors for CH58, CH59, PG9/PG16, CH01-CH04 and 697D, and their reactivity compared to 43 recombinant Envs or V1/V2 scaffold constructs (FIGS. 59A-59N, Table 26, Table 24). It was found that whereas the mature CH58 and CH59 antibodies reacted with 26/43 and 15/43 of the Env constructs, respectively, their UAs reacted with only 5/43 (FIGS. 59A-59D). Remarkably, although CH58 and CH59 are from different VH families, their UAs reacted with the same Env constructs (AE.A244 gp120Δ11, AE.A244 V1/V2 tags, C.1086 gp120Δ7, C.1086 gp70 V1/V2 scaffold and C.1086 V1/V2 tags proteins.

CH59-like antibody (FIG. 58B). Thus, 12 of 43 (28%) of RV144 vaccines studied has >5.0 μg/ml of either CH58- or CH59-like plasma antibody levels, and the ranges of induced V2 antibodies is well within the levels required for RV144 V2 mAb-mediated ADCC and tier 1 neutralizing activity.

Figure 54:
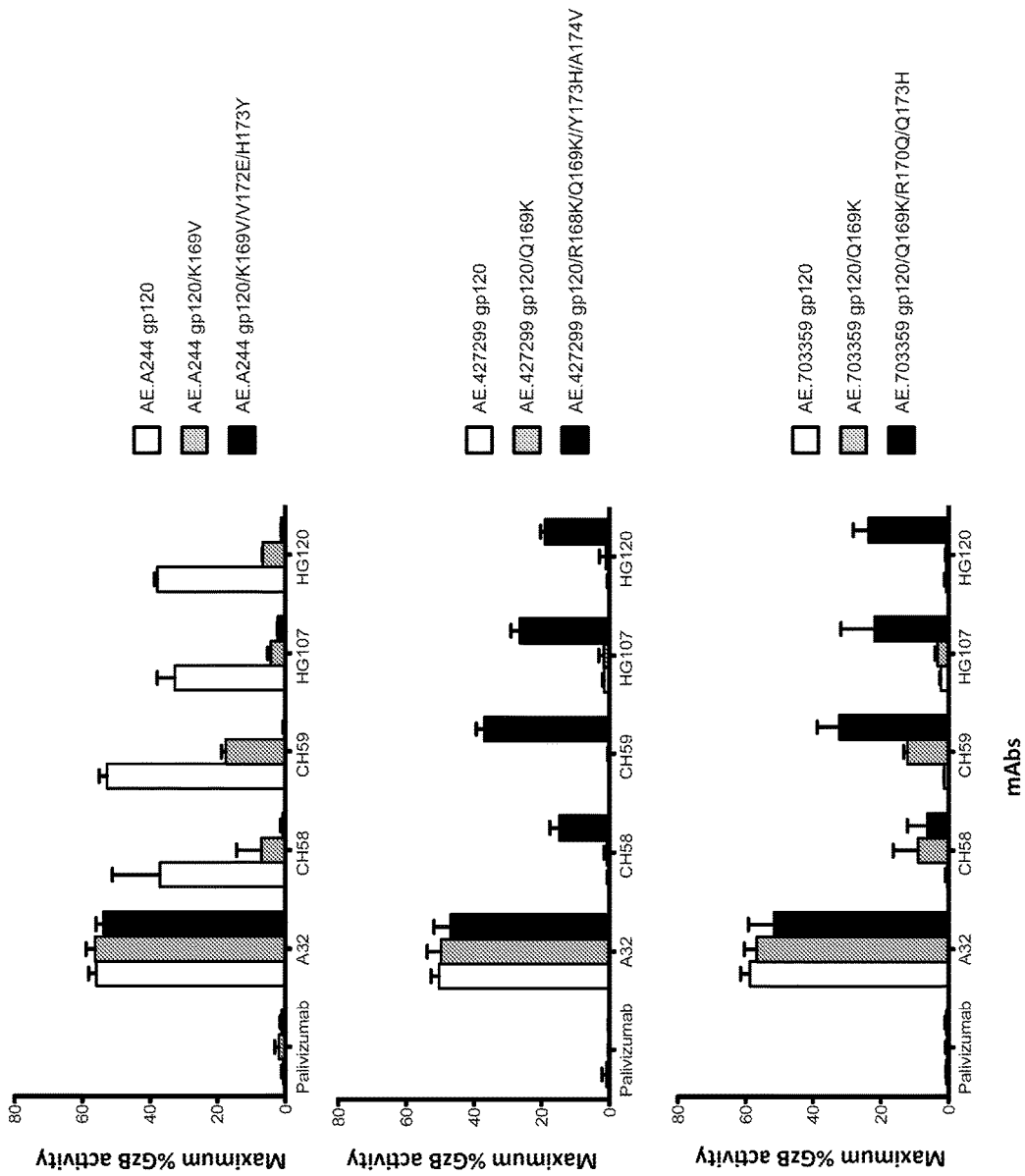
FIG. 54. Effect of V2 mAbs CH58, CH59, HG107, HG120 footprint mutations in HIV-1 vaccine AE.A244 Env and RV144 breakthrough AE.427299 and AE.703357 Envs on ability of V2 mAbs to mediate ADCC. Panels show the ability of mAb A32 and RV144 V2 mAbs CH58, CH59, HG107, HG120 to mediate ADCC against gp120-coated CD4 cell ($CEM_{CCR5}$) target T cells. Data shown is maximum percent granzyme Bactivity from ADCC as described in Example 3. Top panel shows that CH58, CH59, HG107 and HG120 mAbs all mediate high levels of ADCC against AE.244 Env wild type (WT)CD4 T cell targets (white bars), and this killing is mitigated by a single K169V mutation (grey bars), and is abrogated by the full V2 mAb footprint set of mutations (black bars). Middle and lower panels show, in contrast, that none of the CH58, CH59, HG107 and HG120 mAbs mediated ADCC against RV144 breakthrough Env AE.427299 and AE.703357 WT CD4 T cell targets (with V2s that did not match the RV144 vaccine) (white bars), and that ADCC was restored minimally with AE.703357 targets with the Q169K mutation (grey bars), and restored in a pronounced manner in both breakthrough Env targets with the full set of mutations that include Q169K that restored the V2 mAb footprint mutations (black bars). Purified NK cells isolated from a normal donor with Fc-gamma receptor IIIa F/F phenotype were used as effector cells. The effector to target ratio was 10:1. Each antibody was tested in a wide dose curve starting at 40 μg/ml with 4-fold dilutions.
Figure 60:
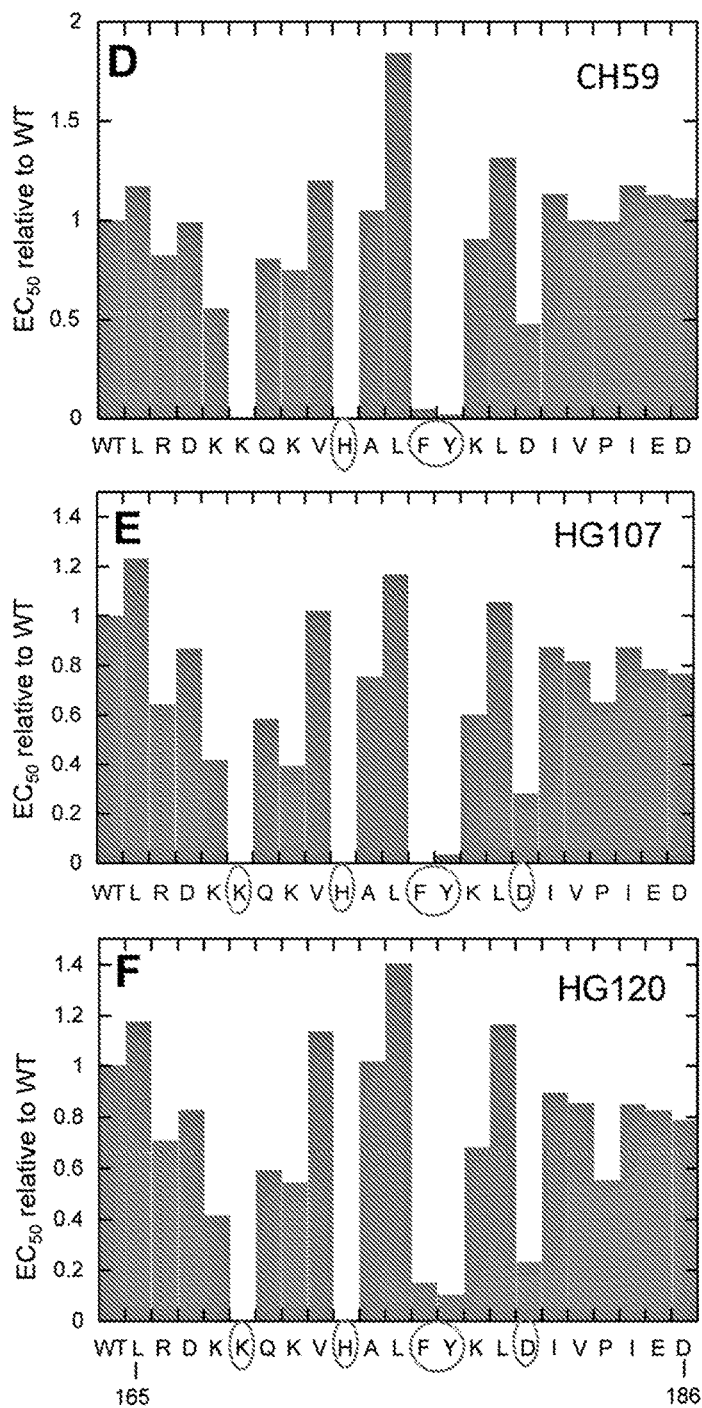
FIGS. 60A-60H. VH and VL genes and epitope mapping of mAbs HG107 and HG120 and molecular modeling.

CH58 and CH59 mAbs were derived from the same RV144 vaccine (347759). To determine the presence of K169 mAbs in other vaccines, two additional subjects (200184 and 302689) were studied and it was possible to isolate two additional V1/V2 antibodies (HG107, HG120) with V2 footprints identical to CH59 (FIG. 60). Moreover, these two V2 antibodies both neutralized AE.92T11023 HIV-1 (Table 30) and mediated ADCC of Tier 2 AE.CM235 infected CD4 CEM.NKRCCR5 T cells in a manner identical to CH59 (FIG. 54). Importantly, when the A244 gp120 and RV144 breakthrough infection 427299 and 703357 Env gp120s were used to coat CD4 CEM.NKRCCR5 T cell targets in ADCC assays, the ability of CH58, CH59, HG107 and HG120 mAbs to mediate ADCC was totally dependent on CH58, CH58, HG107, HG120 mAb footprint mutations that included 169K (FIG. 54).

Remarkably, like CH59, the light chains of HG107 and HG120 were Vλ3-10 with a common aa glutamate-aspartate (ED) residue motif in LCDR2 that is critical for binding to K169 (FIGS. 60A-60C), in that the D of this motif in CH59 forms a salt bridge with V2 17 K169 (FIG. 53, FIGS. 60G, 60H). In CH58, the Ig light chain is Vλ6-57 and also shares the LCDR2 ED motif (FIG. 60C), with the E of the motif binding K169 in the V2-CH58 structure (FIGS. 60G, 60H).

TABLE 24

Binding of recombinant HIV-1 Envs and select V1/V2 recombinant constructs by mature mutated RV144 V2, V2V3 bnAbs and V2 conformational mAb and their reverted unmutated ancestor antibodies (UAs) in ELISA.

| | EC50, nM | | | | | | | | | | | |
|---|---|---|---|---|---|---|---|---|---|---|---|---|
| HIV-1 Env* | CH58 | CH59 | CH01 | 697D | PG9 | PG16 | CH58 UA | CH59 UA | CH01 UA3 | 697D UA | PG9 UA | PG16 UA |
| AE. A244 V1/V2 tags | 0.02 | 0.014 | 8.9 | 0.1 | 1.1 | 3.7 | 4.9 | 0.13 | 18 | NB | NB | NB |
| AE.A244gp120Δ11 | 0.07 | 0.087 | 0.47 | 0.23 | 0.53 | 37.6 | >667 | 15.5 | 9.3 | >667 | NB | NB |
| A.Q23V1/V2 tags | >66.7 | NB | >66.7 | >66.7 | 14.94 | >66.7 | NB | NB | NB | >667 | NB | NB |
| B.6240 gp140C | NB | NB | >667 | 0.016 | 0.3 | 10.3 | NB | NB | NB | 0.19 | NB | NB |
| gp70 B.CaseA2 V1/V2 | 9.3 | NB | NB | 0.08 | NB | NB | NB | NB | NB | >667 | NB | NB |
| gp70 C.1086V1/V2 | 0.05 | 0.067 | NB | 0.067 | NB | NB | >66.7 | 11.3 | NB | NB | NB | NB |
| C.1086V1/V2 tags | 0.08 | 0.1 | NB | 0.23 | >667 | NB | >667 | 50.1 | NB | NB | NB | NB |
| C.1086C gp120D7 | 0.055 | 0.07 | NB | 0.02 | NB | NB | >667 | 66.7 | NB | NB | NB | NB |

*AE., B. and C. represent the CRF or clades of HIV-1 Env.
Positive results in ELISA with EC50 above the highest tested concentration (100 ug/ml) are indicated as >667 nM; NB = no detectable binding.

Finally, 2/3 of the Env constructs that reacted with the UAs of CH58 and CH59 (AE.A244 gp120Δ11, AE.A244 V1/V2 tags) also reacted with the UAs of the CH01-CH04 V1/V2 bnAb clonal lineage (Table 24, FIG. 55E, FIGS. 59E and 59H). In contrast, none of the 43 Envs tested reacted with UAs of PG9 (FIGS. 59I, 59J) or PG16 (Table 24, FIGS. 59K, 59L) and the Env constructs that reacted with the UA of 697D were entirely different than those reacting with the UAs of any of the other mAbs studied (FIGS. 59M, 59N).

CH58- and CH59-Like Antibodies in RV144 Vaccinee Plasma.

To determine the levels of CH58- and CH59-like antibodies present in RV144 vaccine plasma, assays were established wherein vaccine plasma was tested for the ability to block the binding of biotinylated CH58 or CH59 to AE.A244 gp120 Env protein. It was found that vaccine plasma had a mean of 3.2 μg/ml (range 0-13.9 μg/ml) of CH58-like antibody and 2.5 μg/ml (range 0-11.7 μg/ml) of Overlayed VL CDR2 ED motif regions of CH58 and CH59 show striking similarity between the two LC-Env binding regions (FIGS. 60G, 60H). Thus, with four V2 antibodies from three different RV144 vaccines, light chain usage was restricted to Vλ light chains containing an LCDR2 ED motif required for CH58 and CH59 Env V2 K169 binding.

Potential Roles of RV144 V2 Antibodies in Mediation of Immune Pressure.

Eighty-nine percent of infections in the RV144 efficacy trial were with CRF01_AE HIV-1 strains (Rerks-Ngarm et al, New Engl. J. Med. 361:2209-2220 (2009)). One correlate of infection risk from the RV144 trial analysis is the genetic analysis of Env sequences in vaccine compared to placebo recipients that demonstrated increased vaccine efficacy against viruses with a V2 K169 residue among vaccines (Rolland et al, Nature 490:417-420 (2012)). This signature at K169 suggested the hypothesis that RV144 V2 antibodies such as CH58 and CH59 may have mediated, in as yet undefined manners, immune pressure at that site. Based on antibody effector functions shown to be mediated in vitro by mAbs CH58, CH59, HG107 and HG120, the potential mechanisms of antibody-mediated immune pressure include: a) virus neutralization of susceptible CRF01_AE HIV-1 strains, and b) binding HIV-1-infected CD4 T cells and mediation of ADCC, or other as yet undefined effector mechanisms.

A second immune correlate of lowered infection risk is the antibody response to V1/V2 as measured by the clade B gp70V1/V2 CaseA2 fusion protein (Haynes et al, New Engl. J. Med. 366:1275-1286 (2012)). Since gp70V1/V2 CaseA2 has a V169 and only CH58 binds to this protein, there may be at least two types of RV144 V2 antibodies capable of mediating immune pressure, those 18 that bind to gp70V1V2 CaseA2 protein and bind K169 (i.e. CH58-like), and those that do not bind to gp70V1V2 CaseA2 protein and bind K169 (i.e. CH59, HG107, HG120-like). Critical studies going forward will be to perform new efficacy trials in humans and perform passive protection trials in rhesus macaques with RV144 V2 antibodies with R5 SHIVs derived from RV144 trial breakthrough infections to directly explore the protective effect of these two types of V2 monoclonal antibodies. Nonetheless, these studies describe two types of V2 antibodies induced by the RV144 vaccine that recognize K169, define their structures and effector function capabilities, and demonstrate light chain conserved usage for binding to the Env V2 K169.site of immune pressure.

A key task for the HIV-1 vaccine development field is to improve the level of vaccine efficacy seen in the RV144 clinical trial with subsequent vaccine designs. Vaccine designers generally focus on regions of conservation. For RNA viruses such as influenza and HIV-1, which are highly divergent and capable of rapid genetic alteration, conserved regions on Env are generally well-protected from humoral recognition, and it is the divergent regions that may be more susceptible to antibody-mediated neutralization. Indeed, antibodies directed against the variable head region of influenza hemagglutinin are the source of the vaccine protection elicited by the seasonal influenza vaccines (Karlsson et al, Nat Rev Microbiol 6:143-155 (2008)). With the RV144 trial, it also seems a variable region—in this case, around residue 169 of V2—is the site of successful vaccine-induced immune pressure. Virologically, it makes sense that selection and/or immune pressure could be identified by variation. The results with RV144 trial antibodies CH58, CH59, HG107 and HG120 mAbs indicate that this variation may include not only sequence diversity, but also 19 conformational changes in the structure of the same aa sequence. Despite extraordinary variation in both sequence and structure, the humoral immune system appears capable of recognizing V1/V2 in the setting of vaccination with a restricted Ig light chain LCDR2 motif- and Env immunogens that focus the elicited response to this V2 region should be explored.

Additional Results

Implications of mAb Binding Studies.

The binding studies suggest that the mAbs studied here fall into three types: PG9-like (including PG16 and CH01), 697D-like (including other similar mAbs such as 21581 (Gorny et al, Virology 427:198-207 (2012)), and mAbs such as linear V2 mAbs like CH58, CH59, HG107 and HG120. While all bind to AE.A244 gp120, only CH58, CH59, HG107 and HG120 bind to V2 peptides. In addition, CH58, CH59, HG107 and HG120 mAbs are glycan-independent, while PG9-like mAbs are absolutely dependent on glycans at a.a. residue positions 156 and 160, and 697D-like mAbs are affected by glycosylation but do not require the glycan at residue 160 that is required for binding by PG9-like mAbs (Table 22).

Absorption of RV144 Vaccinee Plasma with A244 V1/V2 Tags Protein for Determination of Effects of Glycans on HIV-1 AE.92TH023 Neutralization.

Absorption of AE.92TH023 neutralization by RV144 vaccine plasma 347759 was performed by using titrations of plasma in the TZM/bl assay in which either media, control protein or A244 V1V2 tags protein (50 µg/ml) with either N160/N 156 or N160Q/N156Q mutations. It was found that both A244 V1V2 tags proteins with either N160/N156 or N160Q/N156Q equally absorbed the neutralization activity in vaccine sera for AE.92TH023 pseudovirus (plasma titer as IC50 was 117 for plasma in control assay wells; IC50 in the A244 V1V2 tags N160/N156 assay wells was 63; IC50 in the A244 V1V2 tags N160Q/N156Q assay wells was 53). Thus, the N-linked glycans at positions 3 156 and 160 were not involved in inducing vaccine 347759 antibodies that neutralized AE.92TH023 HIV pseudovirus.

CH58 and CH59-Like Antibodies in AE.A244 Gp120-Immunized Rhesus Monkey Plasma.

Rhesus macaques immunized with recombinant AE.A244 gp120 proteins 5 times induced 10-100× greater levels of antibodies that bind to the CH58 and CH59 epitopes than that found in RV144 vaccine plasma (not shown). Thus, repetitive protein boosting can increase the plasma levels of V2 antibodies.

Comparison of Env Binding of RV144 Vaccinee Sera from Whom V2 mAbs were Isolated with V2 mAb Reactivity.

Purified IgG from the three RV144 vaccines from whom CH58, CH59, HG107 and HG120 were isolated bound a wide range of HIV-1 clade A, B, C, G and one SIVcpz Env while mAbs CH58, CH59, HG107 and HG120 bound only AE and C clade Envs. A large panel of antibodies that bind HIV-1 Envs and mediate ADCC has recently been published (Bonsignori et al, J. Virol. Doi.1128/JVI.01023-12 (2012)). In that study, it is demonstrated that one predominant Env binding type of antibody induced by the RV144 vaccine is a C1-directed conformational antibody that is blockable by mAb A32 (Bonsignori et al, J. Virol. Doi.1128/JVI.01023-12 (2012)). Thus, the majority of the remainder of the specificity of binding antibodies in RV144 plasma is likely this latter type of C1 gp120 antibody (McLellan et al, Nature 480:336-343 (2011)).

All documents and other information sources cited herein are hereby incorporated in their entirety by reference. Also incorporated by reference in their entirety are WO 2011/106100 and US Prov. Applns. 61/542,469, 61/457,906, 61/529,137, 61/566,884 and 61/580,475, and Pinter et al, Vaccine 16:1803-1811 (1998) and Seaman et al, J. Virol. 84:1439-1452 (2010).

What is claimed is:

1. A V1V2 polypeptide, wherein the polypeptide is AE.A244 V1/V2 (SEQ ID NO: 184), AE.A244 V1/V2tag (SEQ ID NO: 196), A.Q23V1/V2 (SEQ ID NO: 183), or A.Q23V1/V2tag (SEQ ID NO: 195).

2. A composition comprising any one of the polypeptides of claim 1 and a carrier.

3. The composition according to claim 2 further comprising an adjuvant.

4. A V1V2 polypeptide, wherein the polypeptide consists essentially of peptide AE.A244 V1/V2 (SEQ ID NO: 184), AE.A244 V1/V2tag (SEQ ID NO: 196), A.Q23V1/V2 (SEQ ID NO: 183), or A.Q23V1/V2tag (SEQ ID NO: 195).

5. The composition of claim 2, wherein the polypeptide is AE.A244 V1/V2 (SEQ ID NO: 184).

6. The composition of claim 2, wherein the polypeptide is AE.A244 V1/V2tag (SEQ ID NO: 196).

7. The composition of claim 2, wherein the polypeptide is A.Q23V1/V2 (SEQ ID NO: 183).

8. The composition of claim 2, wherein the polypeptide is A.Q23V1/V2tag (SEQ ID NO: 195).

9. The composition of claim 5 further comprising an adjuvant.

10. The composition according to claim 6 further comprising an adjuvant.

11. The composition according to claim 7 further comprising an adjuvant.

12. The composition according to claim 8 further comprising an adjuvant.

13. A method of inducing antibodies to the V1V2 region of HIV-1 env gp120 in a subject comprising administering to said subject the composition of claim 2.

14. The method according to claim 13 wherein said subject is a human.

15. The method according to claim 13 further comprising administering an adjuvant.

16. The method according to claim 13, wherein the composition is administered as prime.

17. A method of inducing antibodies to the V1V2 region of HIV-1 env gp120 in a subject comprising administering to said subject a composition comprising the polypeptide of claim 4 and a carrier.

18. The method according to claim 17 further comprising administering an adjuvant.

19. The method according to claim 17, wherein the composition is administered as prime.

20. The method according to claim 17, wherein the polypeptide consists essentially of peptide AE.A244 V1/V2 (SEQ ID NO: 184) or AE.A244 V1/V2tag (SEQ ID NO: 196).

* * * * *